(12) United States Patent
Borriello

(10) Patent No.: US 10,731,128 B2
(45) Date of Patent: Aug. 4, 2020

(54) COMPOSITIONS AND METHODS FOR IN VITRO ACTIVATION AND EXPANSION OF SERIAL KILLER T CELL POPULATIONS AND PASSIVE IMMUNIZATION OF A CANCER PATIENT WITH TUMOR CELL KILLING CELLS

(71) Applicant: ALLOPLEX BIOTHERAPEUTICS, Winchester, MA (US)

(72) Inventor: Frank Borriello, Winchester, MA (US)

(73) Assignee: ALLOPLEX BIOTHERAPEUTICS, INC., Woburn, MA (US)

( * ) Notice: Subject to any disclaimer, the term of this patent is extended or adjusted under 35 U.S.C. 154(b) by 0 days.

(21) Appl. No.: 16/660,442

(22) Filed: Oct. 22, 2019

(65) Prior Publication Data

US 2020/0102538 A1 Apr. 2, 2020

Related U.S. Application Data

(63) Continuation-in-part of application No. 15/821,105, filed on Nov. 22, 2017.

(60) Provisional application No. 62/425,424, filed on Nov. 22, 2016.

(51) Int. Cl.
| | |
|---|---|
| *A61K 35/17* | (2015.01) |
| *A61K 45/06* | (2006.01) |
| *C07K 14/52* | (2006.01) |
| *C12N 5/0783* | (2010.01) |
| *A61P 35/00* | (2006.01) |
| *C07K 16/18* | (2006.01) |
| *A61K 39/395* | (2006.01) |
| *C07K 14/535* | (2006.01) |
| *A61K 38/19* | (2006.01) |
| *C07K 14/705* | (2006.01) |
| *A61K 38/17* | (2006.01) |
| *C07K 14/525* | (2006.01) |

(52) U.S. Cl.
CPC ............ *C12N 5/0638* (2013.01); *A61K 35/17* (2013.01); *A61K 38/177* (2013.01); *A61K 38/19* (2013.01); *A61K 38/191* (2013.01); *A61K 38/193* (2013.01); *A61K 39/39533* (2013.01); *A61K 45/06* (2013.01); *A61P 35/00* (2018.01); *C07K 14/52* (2013.01); *C07K 14/525* (2013.01); *C07K 14/535* (2013.01); *C07K 14/70575* (2013.01); *C07K 14/70578* (2013.01); *C07K 16/18* (2013.01); *C07K 2317/53* (2013.01); *C07K 2317/622* (2013.01); *C07K 2319/00* (2013.01); *C07K 2319/30* (2013.01); *C12N 2502/30* (2013.01); *C12N 2523/00* (2013.01)

(58) Field of Classification Search
CPC ...... A61K 38/17; A61K 38/177; A61K 38/19; A61K 45/06; C07K 14/525

USPC ...................................................... 424/184.1
See application file for complete search history.

(56) References Cited

U.S. PATENT DOCUMENTS

| | | |
|---|---|---|
| 2009/0162404 A1 | 6/2009 | Podack |
| 2010/0297189 A1 | 11/2010 | Dobric et al. |
| 2013/0071403 A1 | 3/2013 | Rolland et al. |
| 2018/0185463 A1 | 7/2018 | Borriello |

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Whiteside, T. L., The tumor microenvironment and its role in promoting tumor growth, Oncogene (2008) 27, 5904-5912.
Wigler, et al., Transfer of purified herpes virus thymidine kinase gene to cultured mouse cells. Cell 1977, 11: 223-232.
Wigler, M., et al., Transformation of mammalian cells with an amplifiable dominant acting gene. Proc Natl Acad Sci USA 1980, 77:3567.
Williams, K.J.,et al., Correlationbetween the Inductionof Heat Shock Protein 70 and Enhanced Viral Reactivation in Mammalian Cells Treated with Ultraviolet Light and Heat Shock. Cancer Res 1989, 49:2735-42.
Woerly, G. et al., CD28 and secretory immunoglobulin A—dependent activation of eosinophils: inhibition of mediator release by the anti-allergic drug, suplatast tosilate. Clin Exp Allergy. (2004) 34:1379-1387.
Wolff, JA., et al., Direct gene transfer into mouse muscle in vivo. Science 247:1465, 1990.
Wolint, Petra, et al. "Immediate Cytotoxicity but Not Degranulation Distinguishes Effector and Memory Subsets of CD8+ T Cells." J. Experimental Medicine, vol. 199, No. 7, Apr. 5, 2004 925-936 (Apr. 5, 2004).

(Continued)

*Primary Examiner* — Lynn A Bristol
(74) *Attorney, Agent, or Firm* — McCarter & English, LLP; Beverly W. Lubit

(57) ABSTRACT

The described invention provides a method for in vitro immunoactivation of mononuclear cells by contact with one or more populations of engineered leukocyte stimulator cells genetically engineered to express a core of 3 essential immunomodulator peptides, and optionally additional R immunomodulator peptides, and use of a cell product comprising the expanded and activated mononuclear cell population comprising one or more subpopulations of cytotoxic serial killer cells for passive immunization of a cancer patient not currently under the influence of an immunosuppressive regimen.

18 Claims, 58 Drawing Sheets
(56 of 58 Drawing Sheet(s) Filed in Color)
Specification includes a Sequence Listing.

(56) References Cited

OTHER PUBLICATIONS

Woodlock, TJ., et al., Active specific immunotherapy for metastatic colorectal carcinoma: phase I study of an allogeneic cell vaccine plus low-dose interleukin-1 alpha. J Immunother 1999, 22:251-259.
Wooten, J. and Federhen, S., Statistics of Local Complexity in Amino Acid Sequences and Sequence Databases. Comput. Chem., 17:149-163 (1993).
Wortham, B. W., et al. TLR and NKG2D Signaling Pathways Mediate CS-Induced Pulmonary Pathologies. PLoS ONE 8(10):e78735. doi:10.1371/journal.pone.0078735 (2013).
Wu YL, et al. Gamma delta T Cells and Their Potential for Immunotherapy. Int J Biol Sci 2014; 10(2):119-135. doi:10.7150/ijbs.7823.
Wu, CH., et al., Targeting Genes: Delivery and Persistent Expression of a Foreign Gene Driven by Mammalian Regulatory Elements in Vivo. Journal of Biological Chemistry, vol. 264, No. 29. pp. 16985-16987, 1989.
Wu, G.Y., et al., Receptor-mediated in Vitro Gene Transformation by a Soluble DNA Carrier System*. J. Biol. Chem. 262, 4429-4432 (1987).
Wu, GY., et al., Receptor-mediated Gene Delivery and Expression in Vivo. Journal of Biological Chemistry 263, No. 29, pp. 14621-14624, 1988.
Xu, L., et al. MMI-0100 inhibits cardiac fibrosis in myocardial infarction by direct actions on cardiomyocytes and fibroblasts via MK2 inhibition. J Mol Cell Cardiol. Dec. 2014; 77: 86-101.
Yao, S. et al., B7-H2 Is a Costimulatory Ligand for CD28 in Human. Immunity (2011) 34:729-740.
Youn B. et al., "Chemokines, chemokine receptors and hematopoiesis", Immunol Rev, vol. 177: 150-174, (2000).
Yu, H., et al Crosstalk between cancer and immune cells: role of STAT3 in the tumour microenvironment. (2007) Nature Rev. Immunol. 7:41-51.
Zhao Y. et al., A unique human blood-derived cell population displays high potential for producing insulin. Biochemical and Biophysical Research Communications 360 (2007) 205-211.
Zhao Y. et al., Identification of stem cells from human umbilical cord blood with embryonic and hematopoietic characteristics. Exp. Cell Res., 312, 2454 (2006).
Zinn, K, et al., Regulated expression of an extrachromosomal human p-interferon gene in mouse cells. Proc Natl Acad Sci USA 1982, 79:4897.
Seaman, W.E. (2000) "Natural Killer Cells and Natural Killer T Cells." Arthritis & Rheumatism 43(6): 1204-1217.
Shani, M., Tissue-specific expression of rat myosin light-chain 2 gene in transgenic mice, Nature 1985, 314:283-286.
Sharma, R, et al. Failure of Immunological Cells to Eradicate Tumor and Cancer Cells: an overview. Turkish Journal of Biology, 38:786-799 (2014).
Sharpe, A.H. and Freeman, G.J, The B7-CD28 superfamily. Nat Rev Immunol. (2002) 2:116-126.
Shi Y et al., Granulocyte-macrophage colony-stimulating factor (GM-CSF) and T-cell responses: what we do and don't know, Cell Research (2006) 16: 126-133.
Shirota, H., et al. CpG-conjugated apoptotic tumor cells elicit potent tumor-specific immunity, Cancer Immunol Immunother (2011) 60:659-669.
Shojaei, F. et al., G-CSF-initiated myeloid cell mobilization and angiogenesis mediate tumor refractoriness to anti-VEGF therapy in mouse models. Proc Natl Acad Sci U S A. (2009) 106: 6742-7.
Shortman, K., et al., Steady-state and inflammatory dendritic-cell development, Nature Reviews Immunology, vol. 7. 19-30 (2007).
Shouval, DS., et al., Interleukin-10 Receptor Signaling in Innate Immune Cells Regulates Mucosal Immune Tolerance and Anti-Inflammatory Macrophage Function. Immunity (2014) 40: 706-719.
Smith and Waterman, Comparison of Biosequences. Adv. Appl. Math. 2:482 (1981).
So T, and Croft M. Cutting Edge: OX40 Inhibits TGF beta- and Antigen-Driven Conversion of Naive CD4 T Cells into CD25+ Foxp3+ T cells. J Immunol. (2007) 179:1427-30.
So, T et al, Immune Regulation and Control of Regulatory T cells by OX40 and 4-1BB. Cytokine Growth Factor Rev. (2008) 19 (3-4): 253-62.
Soghoian, D. Z. and Streeck, H. "Cytolytic CD4+T Cells in Viral Immunity." Expert Rev Vaccines. Dec. 2010 ; 9(12): 1453-1463. doi:10.1586/erv.10.132.www.ncbi.nlm.nih.gov/pmc/articles/PMC3033049/.
Souza-Fonseca-Guimaraes, F., et al. The Emergence of Natural Killer Cells as a Major Target in Cancer Immunotherapy. Trends in Immunology, Feb. 2019, vol. 40, No. 2, 142-158.
Spear, Paul, et al. "NKG2D Ligands as Therapeutic Targets." Cancer Immunity, Academy of Cancer Immunology, May 1, 2013 vol. 13, p. 8. www.ncbi.nlm.nih.gov/pmc/articles/PMC3700746/.
Spickofsky, N., et al., Procedures for constructing cDNA expression libraries in Epstein-Barr virus shuttle vectors capable of stable episomal replication. DNA Prot Eng Tech 1990, 2:14-18.
Sprent J. et al., "The thymus and central tolerance", Philos Trans R Soc Lond B Biol Sci, vol. 356(1409): 609-616, (2001).
Stahl, P.H., et al. Handbook of Pharmaceutical Salts: Properties, Selection, and Use (Wiley VCH, Zurich, Switzerland: 2002).
Stein, PH et al., The Cytoplasmic Domain of CD28 Is both Necessary and Sufficient for Costimulation of Interleukin-2 Secretion and Association with Phosphatidylinositol 3'-Kinase. Mol Cell Biol. (1994) 14: 3392-3402).
Sternberg, N. and Hamilton, D., Bacteriophage P1 site-specific recombination: I. Recombination between IoxP sites. J. Mol. Biol., 150:467-486, 1981.
Straubinger, RM., et al., Liposomes as carriers for intracellular delivery of nucleic acids. Methods in Enzymology 101:512-527, 1983.
Studier, F.W. et al., Use of T7 RNA polymerase to direct expression of cloned genes. Methods Enzymol 1990, 185:60-89.
Swift, G. H., et al., Tissue-specific expression of the rat pancreatic elastase I gene in transgenic mice. Cell 1984, 38:639-646.
Szybalska, E.H., et al, Genetics of Human Cell Lines, IV. Dna-Mediated Heritable Transformation of a Biochemical Trait. Proc Natl Acad Sci USA 1962, 48:2026.
Taams, L. S. et al., "Human anergic/suppressive CD4+CD25+T cells: a highly differentiated and apoptosis-prone population", Eur. J. Immunol. vol. 31: 1122-1131(2001).
Takahashi, H., et al., Induction of CD8+ cytotoxic T cells by immunization with purified HIV-1 envelope protein in ISCOMs. Nature 1990, 344:873-875.
Tartour, E. et al., Angiogenesis and immunity: a bidirectional link potentially relevant for the monitoring of antiangiogenic therapy and the development of novel therapeutic combination with immunotherapy. Cancer Metastasis Rev. (2011) 30: 83-95.
Taub D.D. et al., "Recombinant human interferon-inducible protein 10 is a chemoattractant for human monocytes and T lymphocytes and promotes T cell adhesion to endothelial cells", J Exp Med., vol. 177:1809-1814, (1993).
Taylor, I.C.A, et al., Factor Substitution in a Human HSP70 Gene Promoter: TATA-Dependent and TATA-Independent Interactions. Mol Cell Biol 1990, 10:165-75.
Thompson, CB et al., CD28 activation pathway regulates the production of multiple Tcell- derived lymphokines/cytokines. Proc Natl Acad Sci U S A. (1989) 86:1333-1337.
Torina, A., et al. The Janus Face of NKT Cell Function in Autoimmunity and Infectious Diseases. Int. J. Mol. Sci. 2018, 19, 440; doi:10.3390/ijms19020440.
Ueno H, et al., Harnessing Human Dendritic Cell Subsets for Medicine. Immunol. Rev. (2010) 234: 199-212.
Underwood, K.W., et al., Catalytically Active MAP KAP Kinase 2 Structures in Complex with Staurosporine and ADP Reveal Differences with the Autoinhibited Enzyme. Structure, vol. 11, 627-636, Jun. 2003.
Van Acker, HH, t al., "CD56 in the immune system: more than a marker for cytotoxicity?" Front. Immunol. (2017) 8:892.

(56) References Cited

OTHER PUBLICATIONS

Van Doren, K., et al., Efficient Transformation of Human Fibroblasts by Adenovirus Simian Virus 40 Recombinants. Mol Cell Biol 1984, 4:1653-1656.
Van Kaer, L., et al. Invariant natural killer T cells: bridging innate and adaptive immunity. Cell Tissue Res. Jan. 2011 ; 343(1): 43-55 doi:10.1007/s00441-010-1023-3.
Van Kooten C et al., CD4O-CD40 ligand. J. Leukoc Biol. Jan. 2000; 67(1):2-17.
Venuprasad, K., et al., Human Neutrophil-Expressed CD28 Interacts with Macrophage B7 to Induce Phosphatidylinositol 3-Kinase-Dependent IFN-gamma Secretion and Restriction of Leishmania Growth1. Eur J Immunol. (2001) 31:1536-1543.
Vivier, E., et al. Targeting natural killer cells and natural killer T cells in cancer. Nat Rev Immunol. (2012) 12(4): 239-252. doi:10.1038/nri3174.
Vollmer, J., et al. Immunotherapeutic applications of CpG oligodeoxynucleotide TLR9 agonists. Advanced drug delivery reviews. 61 (3): 195-204.
Voo, KS., et al. Targeting of TLRs Inhibits CD4+ Regulatory T Cell Function and Activates Lymphocytes in Human Peripheral Blood Mononuclear Cells. The Journal of Immunology, 2014, 193: 627-634.
Vu MD, et al. OX40 costimulation turns off Foxp3+ Tregs. Blood. (2007) 110:2501-10.
Wagner, E. et al., Transferrin-polycation conjugates as carriers for DNA uptake into cells. Proc. Natl. Acad. Sci. USA 87, 3410-3414 (1990).
Wakkach, A., et al. Characterization of IL-10-Secreting T Cells Derived from Regulatory CD4+CD25+ Cells by the TIRC7 Surface Marker. The Journal of Immunology, 2008, 180: 6054-6063.
Walunas, TL et al., CTLA-4 can function as a negative regulator of T cell activation. Immunity. (1994) 1:405-413.
Warren, HS., et al., Future prospects for vaccine adjuvants. Critical Reviews in Immunology 1988, 8:83.
Watanabe, R. et al., Grb2 and Gads Exhibit Different Interactions with CD28 and Play Distinct Roles in CD28-Mediated Costimulation. J Immunol. (2006) 177:1085-1091.
Watkins SK, et al. IL-12 rapidly alters the functional profile of tumor-associated and tumor-infiltrating macrophages in vitro and in vivo. J Immunol. (2007) 178:1357-1362.
Weinberg, AD, et al., "OX-40: life beyond the effector T cell stage," Semin. Immunol. (1998) 10(6): 471-80.
Weiss, A. et al., Synergy between the T3/antigen receptor complex and Tp44 in the activation of human T cells. J Immunol. (1986) 137:819-825.
Nocentini, G., et al. Pharmacological modulation of GITRL/GITR system: therapeutic perspectives. British Journal of Pharmacology (2012) 165 2089-2099.
Nunes-Duby, S.E., et al., Similarities and differences among 105 members of the Int family of site-specific recombinases. Nucleic Acids Res. 26:391-406, 1998.
O'Hare, K., et al., Transformation of mouse fibroblasts to methotrexate resistance by a recombinant plasmid expressing a prokaryotic dihydrofolate reductase. Proc Natl Acad Sci USA 1981, 78:1527.
O'Konek, J.J., et al. "Immune Regulation of Tumor Immunity by NKT Cells." in Natural Killer T Cells: Balancing the Regulation of Tumor Immunity. Springer New York, 2012, Ch. 4, 55-70. Terabe and Berzofsky, eds.
O'Sullivan T, et al. Cancer immunoediting by the innate immune system in the absence of adaptive immunity. J Exp Med. (2012) 209: 1869-1882.
Obata, T. et al, MAP kinase pathways activated by stress: The p38 MAPK pathway. Crit. Care Med. 28 (4 Suppl: N67-N77) (2000).
Ohshima, Y. et al., OX40 Costimulation Enhances Interleukin-4 (IL-4) Expression at Priming and Promotes the Differentiation of Naive Human CD4+ T Cells Into High IL-4-Producing Effectors. Blood (1998) 92: 3338-3345.

Okkenhaug, K., et al., Grb2 Forms an Inducible Protein Complex with CD28 through a SRC Homology 3 Domain-Proline Interaction. J Biol Chem. (1998) 273: 21194-21202.
Oliver, K.G., et al. Multiplexed Analysis of Human Cytokines by Use of the FlowMetrix System. Clin Chem 1998;44 (9):2057-2060.
Ono, T., et al., Plasmid DNAs directly injected into mouse brain with lipofectin can be incorporated and expressed by brain cells. Neuroscience Letters vol. 117, Issue 3, :259-263, 1990.
Ornitz, D.M., et al., Elastase I Promoter Directs Expression of Human Growth Hormone and SV40 T Antigen Genes to Pancreatic Acinar Cells in Transgenic Mice. Cold Spring Harbor Symp Quant Biol 1986, 50:399-409.
Pages, F., et al., Binding of phosphatidyl-inositol-3-OH kinase to CD28 is required for T-cell signalling. Nature. (1994) 369:327-329.
Palucka K. et al., Cancer immunotherapy via dendritic cells. Nature Reviews Cancer (Apr. 2012) 12: 265-276.
Panicali. D., et al., Construction of poxviruses as cloning vectors: Insertion of the thymidine kinase gene from herpes simplex virus into the DNA of infectious vaccinia virus. Proc Natl Acad Sci USA 1982, 79:4927-4931.
Pardoll, D. "Cancer Immunotherapy with Vaccines and Checkpoint Blockade" in. The Molecular Basis of Cancer. Chapter 52. pp. 709-738. Mendelsohn, J., et al (eds). Elsevier Health Sciences, 2015.
Pardoll, D., The blockade of immune checkpoints in cancer immunotherapy, Nature Reviews: Cancer, vol. 12, Apr. 2012, 253.
Paterson DJ, et al. Antigens of activated rat T lymphocytes includig a molecule of 50,000 Mr detectde only on CD4 positive T blasts. Mol Immunol. (1987) 24:1281-1290. doi: 10.1016/0161-5890(87)90122-2.
Paul, S. and Girdhari, L. The Molecular Mechanism of Natural Killer Cells Function and Its Importance in Cancer Immunotherapy. Frontiers in Immunology. Sep. 2017, vol. 8, Article 1124.
Pauza, C.D., et al. Gamma Delta T Cell Therapy for Cancer: It is Good to be Local. Frontiers in Immunology. Jun. 2018. vol. 9, Article 1305.
PCT/US2017/063016 International Search Report and Written Opinion, dated Apr. 30, 2018, 13 pgs.
PCT/US2017/63016 International Preliminary Report on Patentability, dated Sep. 25, 2018, 5 pgs.
Pearson W.R. (1994) Using the FASTA Program to Search Protein and DNA Sequence Databases. In: Griffin A.M., Griffin H.G. (eds) Computer Analysis of Sequence Data. Methods in Molecular Biology 24:307-331 1994 Humana Press.
Pearson, W. R., et al, "Improved tools for biological sequence comparison", (1988), Proc. Natl. Acad. Sci. 85:2444-2448.
Peterfalvi, A., et al. "Invariant Valpha7.2-Jalpha33 TCR Is Expressed in Human Kidney and Brain Tumors Indicating Infiltration by Mucosal-Associated Invariant T (MAIT) Cells." International Immunology 20(12), 1517-1525, 2008.
Pinkert, C.A., et al. An albumin enhancer located 10 kb upstream functions along with its promoter to direct efficient, liver-specific expression in transgenic mice. Genes Devel, 1987, 1:268-276.
Plasterk, R.H.A, et al., Resident aliens the Tc1/mariner superfamily of transposable elements. TIG 15:326-332, 1999.
Prasad, KV et al., T-cell antigen CD28 interacts with the lipid kinase phosphatidylinositol 3-kinase by a cytoplasmic Tyr(P)-Met-Xaa-Met motif. Proc Natl Acad Sci U S A. (1994) 91: 2834-2838.
Qian, C. and Cao, X, (2013), "Regulation of Toll-like receptor signaling pathways in innate immune responses," Ann. NY Acad. Sci. 1283: 67-74.
Qian, F., et al. Pivotal Role of Mitogen-Activated Protein Kinase-Activated Protein Kinase 2 in Inflammatory Pulmonary Diseases. Curr Protein Pept Sci. 2016 ; 17(4): 332-342.
Raab, M et al., p56Lck and p59Fyn regulate CD28 binding to phosphatidylinositol 3-kinase, growth factor receptor-bound protein GRB-2, and T cell-specific protein-tyrosine kinase ITK: Implications for T-cell costimulation. Proc Natl Acad Sci U S A. (1995) 92: 8891-8895.
Rabinovitch A. et al., "Roles of cytokines in the pathogenesis and therapy of type 1 diabetes", Cell Biochem Biophys, vol. 48(2-3): 159-63, (2007).

(56) References Cited

OTHER PUBLICATIONS

Raker V. K. et al., "Tolerogenic Dendritic Cells for Regulatory T Cell Induction in Man", Front Immunol, vol., 6(569): 1-11, (2015).
Readhead, C., et al., Expression of a myelin basic protein gene in transgenic shiverer mice: Correction of the dysmyelinating phenotype, Cell 1987, 48:703-712.
Richards, David M, et al. "Monocytes and Macrophages in Cancer: Development and Functions." Cancer Microenvironment (2013) 6:179-191.
Ricklin, Daniel, et al. "Complement: a Key System for Immune Surveillance and Homeostasis." Nature Immunology, U.S. National Library of Medicine, Sep. 2010, www.ncbi.nlm.nih.gov/pmc/articles/PMC2924908/.
Rieger, R., et al., Chimeric form of tumor necrosis factor-alpha has enhanced surface expression and antitumor activity, Cancer Gene Therapy, 2009, 16, 53-64.
Rossi D. et al., "The biology of chemokines and their receptors", Annu Rev Immunol,, vol. 18: 217-242, (2000).
Rossowska, J., et al. Temporary elimination of IL-10 enhanced the effectiveness of cyclophosphamide and BMDC-based therapy by decrease of the suppressor activity of MDSCs and activation of antitumour immune response. Immunobiology 220 (2015) 389-398.
Rozanski, CH et al., Sustained antibody responses depend on CD28 function in bone marrow-resident plasma cells. J Exp Med. (2011) 208:1435-1446.
Rudd, CE and Schneider, H., Unifying concepts in CD28, ICOS and CTLA4 co-receptor signalling. Nat Rev Immunol. (2003) 3: 544-556.
Sadowski, J., Site-Specific Recombinases: Changing Partners and Doing the Twist. Bacteriol., 165:341-357, 1986.
Saenger, Y.M., et al. Immunomodulatory Molecules of the Immune System, H.L. Kaufman and J.D. Wolchok (eds.) General Principles of Tumor Immunotherapy, Chapter 5, 67-121.
Sallusto, F., et al. Two subsets of memory T lymphocytes with distinct homing potentials and effector functions. (1999), Nature 401:708-712.
Salmons, B., et al. Targeting of Retroviral Vectors for Gene Therapy. Human Gene Ther 1993, 4:129-141.
Salomon B. et al., B7/CD28 Costimulation Is Essential for the Homeostasis of the CD4+CD25+ Immunoregulatory T Cells that Control Autoimmune Diabetes. Immunity. 2000;12:431-440.
Santerre, R.F., et al., Expression of prokaryotic genes for hygromycin B and G418 resistance as dominant-selection markers in mouse L cells. Gene 1984, 30:147.
Santiago-Schwarz, F., et al. Distinct Characteristics of Lymphokine-Activated Killer (LAK) Cells Derived From Patients With B-Cell Chronic Lymphocytic Leukemia (B-CLL). A Factor in B-CLL Serum Promotes Natural Killer Cell-Like LAK Cell Growth. Blood, vol. 76, No. 7 (Oct. 1). 1990: pp. 1355-1360.
Saraiva, M., and O'Garra, A. The regulation of IL-10 production by immune cells. Nat. Rev. Immunol. (2010) 10:180-181.
Schrum S. et al., "Synthesis of the CC-chemokines MIP-1alpha, MIP-1beta, and RANTES is associated with a type 1 immune response", J Immunol, vol. 157: 3598-3604, (1996).
Schwartz, R. H., "T cell anergy", Annu. Rev. Immunol., vol. 21: 305-334 (2003).
Clark, R.A., "Resident memory T cells in human health and disease", Sci. Tranl. Med., 7, 269rv1, (2015).
Claverie, J.M. and States, D.J. Information enhancement methods for large scale sequence analysis. Comput. Chem., 17:191-201 (1993).
Colberre-Garapin, F., et al., A new dominant hybrid selective marker for higher eukaryotic cells. J Mol Biol 1981, 150:1-14.
Corpet, F., "Multiple sequence alignment with hierarchical clustering", (1988) Nucleic Acids Research 16:10881-90.
Croci, D. O., Dynamic cross-talk between tumor and immune cells in orchestrating the immunosuppressive network at the tumor microenvironment. Cancer Immunol Immunother (2007) 56:1687-1700.

Curotto De Lafaille, M.A., et al. Natural and Adaptive Foxp3+ Regulatory T Cells: More of the Same or a Division of Labor? Immunity, 30(6): 626-635, (2009).
De Kouchkovsky, D et al., microRNA-17-92 Regulates IL-10 Production by Regulatory T Cells and Control of Experimental Autoimmune Encephalomyelitis. J Immunol. (2013) 191: 1594-1605.
Dematteis, S. et al., "Immunosuppressive Treg cells acquire the phenotype of effector T cells in chronic lymphocytic leukemia patients," J. Translational Medicine (2018) 16: article 172.
Deroost, K. and Langhorne, J. Gamma/Delta T Cells and Their Role in Protection Against Malaria. Frontiers in Immunology. Dec. 2018, vol. 9, Article 2973.
Desai-Mehta, A. et al., "Hyperexpression of CD40 ligand by B and T cells in human lupus and its role in pathogenic autoantibody production," J. Clin. Invest. vol. 97(9), 2063-2073, (1996).
Desmedt, T et al, Ox40 Costimulation Enhances the Development of T Cell Responses Induced by Dendritic Cells in Vivo. J. Immunol (2002) 168: 661-670. doi: 10.4049/jimmunol.168.2.661.
Dolfi, DV, et al., Late Signals from CD27 Prevent Fas-Dependent Apoptosis of Primary CD8+ T Cells1. J. Immunol. (2008) 180(5): 2912-2921.
Dong, C. et al, (2002) "MAP kinases in the immune response," Annu. Rev. Immunol. 20: 55-72.
Drake, C.G., et al. Current status of immunological approaches for the treatment of prostate cancer. Curr Opin Urol. May 2010; 20(3): 241-246.
Dunn, GP et al., The Three Es of Cancer Immunoediting. Ann. Rev. Immunol. (2004): 329-60.
Dyall R., et al., Heteroclitic Immunization Induces Tumor Immunity, J. Exp. Med., vol. 188, No. 9, Nov. 2, 1998.
Eager, R. & Nemunaitis, J., GM-CSF Gene-Transduced Tumor Vaccines, Molecular Therapy, vol. 12, No. 1, 18 (Jul. 2005).
Earley, M.C., et al. Report from a Workshop on Multianalyte Microsphere Arrays. Cytometry 2002;50:239-242.
Ebihara, T., et al. "Induction of NKG2D Ligands on Human Dendritic Cells by TLR Ligand Stimulation and RNA Virus Infection." International Immunology, vol. 19, No. 10, pp. 1145-1155, 2007. doi:10.1093/intimm/dxm073.
Elgueta R et al., Molecular mechanism and function of CD40/CD40L engagement in the immune system. Immunological reviews. 2009; 229(1).
Elgueta R et al., Molecular mechanism and function of CD40/CD40L engagement in the immune system. Immunological Reviews. 2009; 229(1):. 10.1111/j.1600-065X.2009.00782.x.
Elshal, M.F.,et al., Multiplex Bead Array Assays: Performance Evaluation and Comparison of Sensitivity to ELISA. Methods 38(4): 317-323, Apr. 2006.
Evans, EJ et al., Crystal structure of a soluble CD28-Fab complex. Nat Immunol. (2005) 6:271-279.
Faas, M.M., et al. Monocyte intracellular cytokine production during human endotoxaemia with or without a second in vitro LPS challenge: effect of RWJ-67657, a p38 MAP-kinase inhibitor, on LPS-hyporesponsiveness. Clin Exp Immunol 2002; 127:337-343.
Falschlehner, C., et al. "Following TRAIL's Path in the Immune System." Immunology 127, 145-154 Jun. 2009.
Felgner, PL., et al., Lipofection: A highly efficient, lipid-mediated DNA-transfection procedure. Proc. Natl. Acad. Sci. U.S.A. 84:7413, 1987.
Fraser, JD et al., Regulation of interleukin-2 gene enhancer activity by the T cell accessory molecule CD28. Science. (1991) 251:313-316.
Frey, N.V., et al., The Promise of Chimeric Antigen Receptor T-Cell Therapy, Oncology (2016).
Fujiyama, K., et al, IgG H chain [*Homo sapiens*]. NCBI PDB Accession No. BAN63131. Submitted Jan. 13, 2013; downloaded from the internet< https://www.ncbi.nlm.nih.gov/protein/BAN63131> on Feb. 21, 2018; Genbank Supplement pp. 1-2 (cited in PCT/US2017/63016 International Search Report).
Gabrilovich, DE et al, Coordinated regulation of myeloid cells by tumours. Nat Rev Immunol.(2012)12:253-68.
Gabrilovich, DI., "Myeloid-derived suppressor cells," Cancer Immunol. Res. (2017) 5(1): 3-8.

(56) References Cited

OTHER PUBLICATIONS

Galluzzi, L, et al. Classification of Current Anticancer Immunotherapies. Oncotarget, vol. 5, No. 24. 12472-12508 (2014).

Gao, X., et al. "Cytokine-Induced Killer Cells As Pharmacological Tools for Cancer Immunotherapy." Frontiers Immunol. 8:774, 2017.

Gati, A. et al., CD158 Receptor Controls T-Lymphocyte Susceptibility to Tumor-mediated Activation-induced Cell Death by Interfering with Fas signaling. Cancer Res. (2003) 63 (21): 7475-82.

Gati, A., et al. CD158 Receptor Controls Cytotoxic T-Lymphocyte Susceptibility to Tumor-Mediated Activation Induced Cell Death by Interfering with Fas Signaling. Cancer Research, 63, 7475-7482, Nov. 1, 2003.

Girardi, E. and Zajonc, D.M. (2012). "Molecular basis of lipid antigen presentation by CD1d and recognition by natural killer T cells." Immunol Rev. 250(1): 167-179.

Godfrey, D.I. , et al. (2004). "NKT cells: what's in a name?" Immunology, Nature Reviews 4:231-237.

Gorman, C.M., Mammalian cell expression. Curr Op Biotechnol 1990, 1:36-47.

Gottschalk et al. (2015) "The Role of Invariant Natural Killer T Cells in Dendritic Cell Licensing, Cross-Priming, and Memory CD8+ T Cell Generation." Front Immunol 6:379.

Graf D et al., A soluble form of TRAP (CD40 ligand) is rapidly released after T cell activation. Eur J Immunol. Jun. 1995; 25(6):1749-54.

Gray Parkin, K., et al., Expression of CD28 by Bone Marrow Stromal Cells and Its Involvement in B Lymphopoiesis. J. Immunol. (2002) 169:2292-2302.

Grell M. et al., The Transmembrane Form of Tumor Necrosis Factor Is the Prime Activating Ligand of the 80 kDa Tumor Necrosis Factor Receptor, Cell, vol. 83, 793-802 (1995).

Grohmann, U., et al., CTLA-4-lg regulates tryptophan catabolism in vivo. Nat Immunol. (2002) 3:1097-1101.

Grosschedl, R., et al. Introduction of a µ immunoglobulin gene into the mouse germ line: Specific expression in lymphoid cells and synthesis of functional antibody. Cell 1984, 38:647-658.

Grossman, M., et al. Retroviruses: delivery vehicle to the liver. Curr Opin Genet Devel 1993, 3:110-114.

Groth, A.C., et al., Phage Integrases: Biology and Applications. J. Mol. Biol. 335:667-678, 2004.

Guinn, B, et al., 4-1BBL Cooperates with B7-1 and B7-2 in Converting a B Cell Lymphoma Cell Line into a Long-Lasting Antitumor Vaccine1. J. Immuno. (1999) 162: 5003-5010.

Gulley, J.L. et al. Immunotherapy for Prostate Cancer: Recent Advances, Lessons Learned, and Areas for Further Research. Clin Cancer Res; 17(12) Jun. 15, 2011.

Guo, Y and Han, W., Cytokine-induced killer (CIK) cells: from basic research to clinical translation. Chinese Journal of Cancer (2015) 34:6.

Gutegemann, S., et al. (2007). "Cytokine-induced killer cells are type II natural killer T cells." GMS German Medical Science 5: 1-4.

Adams, J.M., et al. The c-myc oncogene driven by immunoglobulin enhancers induces ymphoid malignancy in transgenic mice. Nature 1985, 318:533-538.

Alexander, W., et al., Expression of the c-myc Oncogene under Control of an Immunoglobulin Enhancer in E[L-myc Transgenic Mice. Mol Cell Biol 1987, 7:1436-1444.

Alexandraki K. et al "Inflammatory process in type 2 diabetes: The role of cytokines", Annals of the New York Academy of Sciences, 1084: 89-117, (2006).

Altschul, P., et al. Gapped BLAST and PSI-BLAST: a new generation of protein database search programs. Nucleic Acids Res. 25:3389-3402 (1997).

Ausubel, et al. Current Protocols in Molecular Biology, Chapter 19, Eds., Greene Publishing and Wiley-Interscience, New York (2005).

Battaglia, M. et al., "Rapamycin promotes expansion of functional CD4+CD25+Foxp3+ regulator T cells of both healthy subjects and type 1 diabetic patients", J. Immunol., vol. 177: 8338-8347, (2006).

Bendall, S.C., et al. Single-Cell Mass Cytometry of Differential Immune and Drug Responses Across a Human Hematopoietic Continuum. Science, vol. 332:687-696; May 6, 2011.

Bendall, S.C., et al., From single cells to deep phenotypes in cancer. Nature Biotechnology, vol. 30 No. 7:639-647; Jul. 2012.

Bestor, T.H., Transposons Reanimated in Mice. Cell, 122(3):322-325, 2005.

Bitter, G.A. et al., Expression and secretion vectors for yeast. Meth Enzymol 1987, 153:516-544.

Bode, C., CpG DNA as a vaccine adjuvant, Expert Rev Vaccines. Apr. 2011; 10(4): 499-511).

Boesen, J.J.B., et al., Circumvention of chemotherapy-induced myelosuppression by transfer of themdr1 gene. Biotherapy 1994, 6:291-302.

Bonifant CL, et al., Toxicity and management in CAR T-cell therapy, Molecular Therapy—Oncolytics (2016) 3, 16011; doi:10.1038/mto.2016.11.

Bradley L.M. et al., "Islet-specific Th1, but not Th2, cells secrete multiple chemokines and promote rapid induction of autoimmune diabetes", J Immunol, vol. 162:2511-2520, (1999).

Broach, J.R., et al., Recombination within the yeast plasmid 2µ circle is site-specific. Cell, 29:227-234, 1982.

Browning, M., Antigen presenting cell/tumor cell fusion vaccines for cancer, Human Vaccines & Immunotherapeutics 9:7, 1545-1548; Jul. 2013;DOI: 10.4161/hv.24235.

Butterfield, L., Dendritic Cells in Cancer Immunotherapy Clinical Trials: Are We Making Progress?, Frontiers of Immunology, 2013 4: 454.

Cai, G., The CD160, BTLA, LIGHT/HVEM pathway: a bidirectional switch regulating T-cell activation, Immunol. Rev., May; 229(1):244-58 (2009).

Carbone, E et al. A New Mechanism of NK Cell Cytotoxicity Activation: The CD40-CD40 Ligand Interaction. J Exp Med. Jun. 16, 1997; 185(12):2053-60.

Carmi, Y, et al. Tumor-binding antibodies and tumor immunity. Oncotarget, vol. 6, No. 34, 35129-35130 (2015).

Carmi, Y., et al. Allogeneic IgG combined with dendritic cell stimuli induces anti-tumor T cell immunity. Nature. May 7, 2015; 521(7550): 99-104.

Chang, S., Overview of Prostate-Specific Membrane Antigen, Reviews in Urology, vol. 6 Suppl. 10, S13 (2004).

Choulika, A., et al., Transfer of Single Gene-Containing Long Terminal Repeats into the Genome of Mammalian Cells by a Retroviral Vector Carrying the cre Gene and the loxP Site. J Virol 1996, 70:1792-1798.

Clark, R.A., "Resident memory T cells in human health and disease", Sci. Transl. Med., 7, 269rv1, (2015).

Faas, M.M., et al., Monocyte intacellular cytokine production during human endototoxaemia with or without a second in vitro LPS challenge: effect of RWJ-67657, a p38 MAP-kinase inhibitor, on LPS-hyporesponsiveness. Clin Exp Immunol 2002; 127:337-343.

Hamer, D.H., et al., SV40 recombinants carrying rabbit beta-globin gene coding sequences. Cell 1979, 17:725-735.

Hammer, R.E., et al. Diversity of alpha-fetoprotein gene expression in mice is generated by a combination of separate enhancer elements. Science 1987, 235:53-58.

Hanahan, D. Heritable formation of pancreatic β-cell tumours in transgenic mice expressing recombinant insulin/simian virus 40 oncogenes. Nature 1985, 315:115-122.

Henikoff & Henikoff; "Amino acid substitution matrices from protein blocks"; Proc. Natl. Acad. Sci. USA vol. 89, pp. 10915-10919, Nov. 1992.

Higano C S, et al., Integrated Data From 2 Randomized, Double-Blind, Placebo Controlled, Phase 3 Trials of Active Cellular Immunotherapy With Sipuleucel-T in Advanced Prostate Cancer. Cancer (2009) 115: 3670-3679.

Higgins, D. G., et al, "Fast and sensitive multiple sequence alignments on a microcomputer", (1989) CABIOS 5:151-153.

Higgins, D.G., et al, "Clustal: a package for performing multiple sequence alignment on a microcomputer", (1988), Gene 73:237-244.

(56) References Cited

OTHER PUBLICATIONS

Hoover, HC., et al., Adjuvant active specific immunotherapy for human colorectal cancer: 6.5-year median follow-up of a phase III prospectively randomized trial. J Clin Oncol 1993, 11:390.

Huang, X., et al., "Parallelization of a local similarity algorithm", (1992) Computer Applications in the Biosciences 8:155-165.

Hunter TB, et al., An Agonist Antibody Specific for CD40 Induces Dendritic Cell Maturation and Promotes Autologous Anti-tumour T-cell Responses in an in vitro Mixed Autologous Tumour Cell/Lymph Node Cell Model (2007) Scandanavian J. Immunology 65, 479-486.

Jancey, J., et al., "Effective recruitment and retention of older adults in physical activity research: PALS study", Am J Health Behav, vol. 30(6): 626-635, (2009).

Janeway, CA, Jr., "The priming of helper T cells", Semin. Immunol., vol. 1(1): 13-20 (1989).

Jensen, S.M. et al. Adoptive cellular immunotherapy of cancer: a three-signal paradigm for translating recent developments into improved treatment strategies. Springer Science & Business Media, 2007, Tumor Immunology and Cancer Vaccines, vol. 123, Chapter 13, 293-336.

Jiang T.T., "Regulatory T cells: new keys for further unlocking the enigma of fetal tolerance and pregnancy complications", J Immunol., vol. 192(11): 4949-4956, (2014).

Kantoff P W, et al., Sipuleucel-T Immunotherapy for Castration-Resistant Prostate Cancer. N. Engl. J. Med. (2010) 363: 411-422.

Karlin & Altschul; "Applications and statistics for multiple high-scoring segments in molecular sequences"; Proc. Natl. Acad. Sci. USA, vol. 90, pp. 5873-5877, Jun. 1993.

Karpusas M et al., 2 å crystal structure of an extracellular fragment of human CD40 ligand. Structure. Oct. 15, 1995; 3(10):1031-9.

Kaufman and Wolchok (eds.), General Principles of Tumor Immunotherapy, Chapter 5, 67-121 (2007).

Kelsey, G.D., et al. Species- and tissue-specific expression of human alpha 1-antitrypsin in transgenic mice. Genes Devel 1987, 1:161-171.

Klein L., "Aire gets company for immune tolerance", Cell, vol. 163(4):794-795, (2015).

Kleinnijenhuis, J., et al. Innate Immune Recognition of *Mycobacterium tuberculosis*. (2011) Clin. Dev. Immunol. 405310 (12 pgs.).

Knapinska, A.M., et al. Chaperone Hsp27 Modulates AUF1 Proteolysis and AU-Rich Element-Mediated mRNA Degradation. Molecular and Cellular Biology, Apr. 2011, vol. 31., No. 7, 1419-1431.

Kollias, G., et al., Regulated expression of human a gamma-, beta-, and hybrid gamma beta-globin genes in transgenic mice: manipulation of the developmental expression patterns, Cell 1986, 46:89-94.

Kootstra, N.A., et al., Gene Therapy with Viral Vectors. Ann. Rev. Pharm. Toxicol., 43:413-439, 2003.

Kozlowska, A., et al. Therapeutic gene modified cell based cancer vaccines. Gene 525 (2013) 200-207.

Krieg, AM., et al. (1995). CpG motifs in bacterial DNA trigger direct B-cell activation. Nature. 374 (6522): 546-9.

Kronenberg, M. et al., "Regulation of immunity by self-reactive T cells", Nature, vol. 435: 598-604 (2005).

Krug, A., et al. Identification of CpG oligonucleotide sequences with high induction of IFN-alpha/beta in plasmacytoid dendritic cells . . . Eur. J. Immunol. 2001. 31: 2154-2163.

Krumlauf, R., et al. Developmental regulation of alpha-fetoprotein genes in transgenic mice . . . Mol Cell Biol 1985, 5:1639-1648.

Kumar N.P. et al. 2015. Coincident diabetes mellitus modulates Th1-, Th2-, and Th17-cell responses in latent tuberculosis in an IL-10- and TGF-beta-dependent manner. Eur J Immunol. 2016. 46:390-399. doi: 10.1002/eji.201545973.

Kumar, C, et al., AKT crystal structure and AKT-specific inhibitors. Oncogene (2005) 24, 7493-7501.

Leder, A., et al. Consequences of widespread deregulation of the c-myc gene in transgenic mice: Multiple neoplasms and normal development. Cell 1986, 45:485-495.

Lefebvre, E., et al. Antifibrotic Effects of the Dual CCR2/CCR5 Antagonist Cenicriviroc in Animal Models of Liver and Kidney Fibrosis. PLoS ONE 11(6): e0158156. doi:10.1371/journal.pone.0158156, Jun. 2016.

Liu, Q., et al. Developing irreversible inhibitors of the protein kinase cysteinome. Chem Biol. Feb. 21, 2013; 20(2): 146-159.

Loetscher P. et al., "The ligands of CXC chemokine receptor 3, I-TAC, Mig, and IP10, are natural antagonists for CCR3", J. Biol. Chem., vol. 276: 2986-2991, (2001).

Logan, J., et al, Adenovirus tripartite leader sequence enhances translation of mRNAs late after infection. Proc Natl Acad Sci USA 1984, 81:3655-3659.

Lowy, I., et al., Isolation of transforming DNA: cloning the hamster aprt gene . . . Cell 1980, 22:817.

Macdonald, R.J. Expression of the pancreatic elastase I gene in transgenic mice. Hepatology 1987, 7:425-515.

Macey, Marion G., Flow cytometry: principles and applications, Humana Press, 2007.

Mackay C.R., "Chemokines: immunology's high impact factors", Nat Immunol., vol. 2: 95-101, (2001).

Mackett, M., et al., General Method for Production and Selection of Infectious Vaccinia Virus Recombinants Expressing Foreign Genes. J Virol 1984, 49:857-864.

Mackett, M., et al., Vaccinia virus: A selectable eukaryotic cloning and expression vector. Proc Natl Acad Sci USA 1982, 79:7415-7419.

Magram, J. et al., Developmental regulation of a cloned adult beta-globin gene in transgenic mice, Nature 1985, 315:338-340.

Makaryan, V., et al., TCIRG1 associated Congenital Neutropenia. Hum Mutat. Jul. 2014; 35(7): 824-827.

Makrides, S.C., Strategies for Achieving High-Level Expression of Genes in *Escherichia coli*. Microbiol Rev 1996, 60:512-538.

Mason AJ., et al., A deletion truncating the gonadotropin-releasing hormone gene is responsible for hypogonadism in the hpg mouse. Science 1986, 234:1366-1371.

Matsuzaki,H., et al., Chromosome Engineering in *Saccharomyces cerevisiae* by Using a Site-Specific Recombination System of a Yeast Plasmid. J. Bacteriology, 172:610-618, 1990.

Mazzei GJ et al., Recombinant Soluble Trimeric CD40 Ligand Is Biologically Active. J Biol Chem. Mar. 31, 1995; 270(13):7025-8.

Mclachlin, J.R., et al. Retroviral-Mediated Gene Transfer. Prog Nucleic Acid Res Mol Biol 1990, 38:91-135.

Metzger T.C. et al., "Control of central and peripheral tolerance by Aire", Immunol. Rev. 2011, vol. 241: 89-103, (2011).

Meyers and Miller; "Optimal alignments in linear space"; Computer Applic. Biol. Sci., 4:11-17 (1988).

Morgenstern, J.P., et al., Advanced mammalian gene transfer: high titre retroviral vectors with multiple drug selection markers and a complementary helper-free packaging cell line. Nucleic Acids Res 1990, 18:3587-3596.

Mulligan, R.C., et al, Selection for animal cells that express the *Escherichia coli* gene coding for xanthine-guanine phosphoribosyltransferase. Proc Natl Acad Sci USA 1981, 78:2072.

Murphy, Kenneth. Janeway's Immunobiology: 8th ed. Chapter 15: Garland Science. (2012), pp. 611-668.

Nash, H.A., Purification of Bacteriophage lambda, Int Protein. Nature, 247, 543-545, 1974).

Needleman, S., et al, "A General Method Applicable to the Search for Similarities in the Amino Acid Sequence of Two Proteins", (1970), J. Mol. Biol. 48:443.

Van Kooten C et al., CD40-CD40 ligand. J. Leukoc Biol. Jan. 2000; 67(1):2-17.

Wigler, M., et al., Transfer of purified herpes virus thymidine kinase gene to cultured mouse cells. Cell 1977, 11:223-232.

Abel, A.M., et al. Natural Killer Cells: Development, Maturation, and Clinical Utilization. Frontiers in Immunology. vol. 9, Article 1869, Aug. 2018.

Adams, J.M., et al. The c-myc oncogene driven by immunoglobulin enhancers induces lymphoid malignancy in transgenic mice. Nature 1985, 318:533-538.

Alberts, B. et al, The Adaptive Immune System from Molecular Biology of the Cell, 4th Ed. Chapter 24, 1363-1420 (2002).

(56) References Cited

OTHER PUBLICATIONS

Alter, G., et al. CD107a as a functional marker for the identification of natural killer cell activity. Journal of Immunological Methods 294 (2004) 15-22.

Anderson, M.H., et al. Cytotoxic T Cells. J. Investigative Dermatology, (2006) vol. 126, 32-41.

Appay, V., et al. Memory CD8+ T cells vary in differentiation phenotype in different persistent virus infections. (2002) Nature Med. 8, 349-385.

August, A. and Dupont, B. CD28 of T lymphocytes associates with phosphatidylinositol 3-kinase. Int Immunol. (1994) 6:769-774.

Balato, A., et al. Natural Killer T Cells: An Unconventional T-Cell Subset with Diverse Effector and Regulatory Functions. J. Investigative Dermatology. (2009), vol. 129. 1628-1642.

Benichou, G, and A W Thomson. "Direct versus Indirect Allorecognition Pathways: on the Right Track." American Journal of Transplantation : Official Journal of the American Society of Transplantation and the American Society of Transplant Surgeons, U.S. National Library of Medicine, Apr. 2009, www.ncbi.nlm.nih.gov/pmc/articles/PMC3746751/.

Bennstein, S.B. (2017), "Unraveling Natural Killer T-Cells Development" Front Immunol. 8:1950.

Bhatia, S. et al., Different cell surface oligomeric states of B7-1 and B7-2: Implications for signaling. Proc Natl Acad Sci U S A. (2005) 102:15569-15574.

Bingle, L, et al The role of tumor-associated macrophages in tumor progression: implications for new anticancer therapies. J Pathol. (2002) 196: 254-265.

Bluestone, JA et al., CTLA4Ig: Bridging the Basic Immunology with Clinical Application. Immunity. (2006)24: 233-238.

Boomer, JS and Green, JM, An enigmatic tail of CD28 signaling. Cold Spring Harb Perspect Biol. (2010) 2:a002436.

Bour-Jordan, H. et al., Intrinsic and extrinsic control of peripheral T-cell tolerance by costimulatory molecules of the CD28/B7 family. Immunol Rev. (2011) 241:180-205. doi:10.1111/j.1600-065X.2011. 01011.x.

Bradley L.M. et al., "Islet-specific Th1, but not Th2, cells secrete multiple chemokines and promote rapid induction pf autoimmune diabetes", J Immunol, vol. 162:2511-2520, (1999).

Brigham, KL., et aL., In vivo transfection of expression in murine lungs with a functioning prokaryotic gene using a cationic liposome vehicle. Am. J. Med. Sci. 298:278, 1989.

Brutkiewicz, R.R. "CD1d Ligands: The Good, the Bad, and the Ugly." The Journal of Immunology (2006) 177 (2) 769-775.

Cai, YC et al., Selective CD28pYMNM Mutations Implicate Phosphatidylinositol 3-Kinase in CD86-CD28-Mediated Costimulation. Immunity. (1995) 3: 417-426.

Campbell, J. et al., CCR7 Expression and Memory T Cell Diversity in Humans. J Immunol 2001; 166:877-884.

Campbell, K.S. and Purdy, A.K., "Structure/function of human killer cell immunoglobulin-like receptors: lessons from polymorphisms, evolution, crystal structures and mutations," Immunol. (2011) 132(3): 315-325.

Campbell, K.S. and Purdy, K. Structure/function of human killer cell immunoglobulin-like receptors: lessons from polymorphisms, evolution, crystal structures and mutations. Immunology (2011) 132, 315-325.

Cappuzzello, E., et al. Cytokines for the induction of antitumor effectors: The paradigm of Cytokine-Induced Killer (CIK) cells. Cytokine & Growth Factor Reviews 36 (2017) 99-105.

Carmi, Y., et al. Allogeneic IgG combined with dendritic cell stimuli induces anti-tumor T cell immunity. Nature. 2015 May 7; 521(7550): 99-104.

Carreno and Collins, M., The B7 Family of Ligands and Its Receptors: New Pathways for Costimulation and Inhibition of Immune Responses. Annu Rev Immunol. (2002) 20: 29-53.

Casella, I., et al., Autocrine-paracrine VEGF loops potentiate the maturation of megakaryocytic precursors through Flt1 receptor. Blood. (2003) 101:1316-23.

Chao MP, et al. The CD47-SIRPalpha pathway in cancer immune evasion and potential therapeutic implications. Curr Opin Immunol. (2012) 24: 225-232.

Chapman, TL, et al, "The inhibitory receptor LIR-1 uses a common binding interaction to recognize class I MHC molecues and the viral homolog UL18," Immunity (1999) 11 (5): 603-13.

Chen, L. and Flies, D.B., Molecular mechanisms of T cell co-stimulation and co-inhibition. Nat Rev Immunol. 2013;13:227-242.

Choulika, A., et al., Transfer of Single Gene-Containing Long Terminal Repeats into the Genome of Mammalian Cells by a Retroviral Vector Carrying the cre Gene and the IoxP Site. J Virol 1996, 70:1792-1798.

Chow, K.V., et al. Innate Allorecognition Results in Rapid Accumulation of Monocyte-Derived Dendritic Cells. The Journal of Immunology, 2016, 197: 2000-2008.

Lenschow, DJ et al., Differential up-regulation of the B7-1 and B7-2 costimulatory molecules after Ig receptor engagement by antigen. J Immunol. (1994) 153:1990-1997.

Levine, B., et al., Antiviral Effect and Ex Vivo CD4+ T Cell Proliferation in HIV-Positive Patients as a Result of CD28 Costimulation. 1996, Science 272:1939-1943.

Levine, B., et al., Effects of CD28 costimulation on long-term proliferation of CD4+ T cells in the absence of exogenous feeder cells. 1997, J. Immunol. 159:5921-5930.

Liao, CM et al. (2014) "The Functions of Type I and Type II Natural Killer I (NKT) Cells in Inflammatory Bowel Diseases." Inflamm Bowel Dis. 19(6): 1330-1338.

Liu, J., et al. The Regulation of CD1d+ and CD1d– Tumors by NKT Cells: The Roles of NKT Cells in Regulating CD1d+ and CD1d– Tumor Immunity. "Natural Killer T Cells Balancing the Regulation of Tumor Immunity." Springer New York, 2012, Ch. 5, Terabe and Berzofsky, eds.

Lopez, Jamie A., et al. "Perforin Forms Transient Pores on the Target Cell Plasma Membrane to Facilitate Rapid Access of Granzymes during Killer Cell Attack." Blood Journal, American Society of Hematology, vol. 121, No. 14, 2659-2668, 2013.

Lu, T. et al., Tumor-infiltrating myeloid cells induce tumor cell resistance to cytotoxic T cells in mice. J. Clinical Investigation. (2011) 121: 4015-29.

Lyddane, C et al., Cutting Edge: CD28 Controls Dominant Regulatory T Cell Activity during Active Immunization. J Immunol. (2006) 176: 3306-3310.

Mak,T.W. et al. "NK, yo T and NKT Cells." in Primer to the Immune Response. 2nd Ed. 2014. Chapter 11, 247-268. Elsevier.

Mandal, A and Viswanathan, C (2015). "Natural killer cells: In health and disease." Hematol. Oncol. Stem Cell The. 8(2): 47-55.

Marcus, Assaf, et al. "Recognition of Tumors by the Innate Immune System and Natural Killer Cells." Advances in Immunology, U.S. National Library of Medicine, 2014, www.ncbi.nlm.nih.gov/pmc/articles/PMC4228931.

Martin, PJ et al., A 44 kilodalton cell surface homodimer regulates interleukin 2 production by activated human T lymphocytes . . . J Immunol. (1986) 136: 3282-3287.

McLaughlin, SK et al., Adeno-Associated Virus General Transduction Vectors: Analysis of Proviral Structures. J Virol 1988, 62:1963-9173.

McNamara, DA et al., Tamoxifen inhibits endothelial cell proliferation and attenuates VEGF-mediated angiogenesis and migration in vivo . . . Eur. J. Surg. Oncol. (2001) 27(8): 714-718.

Meng, M., et al. A dynamic transcriptomic atlas of cytokine induced killer cells. J. Biol. Chem. published online Oct. 17, 2018 as Manuscript RA118.003280 (29 pgs).

Metzler, WJ et al., Solution structure of human CTLA-4 and delineation of a CD80/CD86 binding site conserved in CD28. Nat Struct Biol. (1997)4: 527-531.

Molon, B. et al., Chemokine nitration prevents intratumoral infiltration of antigen-specific T cells. J Exp Med. (2011) 208: 1949-62.

Moore, KW, et al., Interleukin-10 and the interleukin-10 receptor. Annu. Rev. Immunol. (2001) 19: 683-765.

Moretta, A. et al., "A Novel surface antigen expressed by a subset of human CD3-CD16+ natural killer cells. Role in cell activation and regulaton of cytolytic function." J. Exptl. Med. (1990) 3: 695-714.

(56) References Cited

OTHER PUBLICATIONS

Moynihan, K.D. and Irvine, D.J., Roles for Innate Immunity in Combination Immunotherapies. Cancer Res; 77(19); 5215-21. (2017).
Murphy, Kenneth M., et al. "T-Cell Mediated Immunity." Janeways Immunobiology. 9th ed., GS, Garland Science, Taylor & Francis Group, 2017. pp. 387-395.
Murphy, Kenneth M., et al. Janeways Immunobiology. 9th ed., GS, Garland Science, Taylor & Francis Group, 2017. p. 129-130.
Murphy, Kenneth. Janeway's Immunobiology: 8th ed. Chapter 9: T Cell-Mediated Immunity. Garland Science. (2012).
Murphy, Kenneth. Janeway's Immunobiology: 8th ed. Chapter 8: Garland Sciences. pp. 275-334.
Nagaraj S, et al. Altered recognition of antigen is a mechanism of CD8+ T cell tolerance in cancer. Nat Med. (2007) 13: 828-35.
Nair, S. and Dhodapkar, M.V. (2017). "Natural Killer T Cells in Cancer Immunotherapy." Frontiers in Immunology 8:1178.
Njau, NM and Jacob, J., The CD28/B7 Pathway: A Novel Regulator of Plasma Cell Function. Adv Exp Med Biol. (2013) 785:67-75.
Hastings, K.T. Innate and Adaptive Immune Responses to Cancer in Fundamentals of Cancer Prevention. Alberts, D.S., and L.M. Hess, (eds.) Springer-Verlag Berlin Heidelberg. 2008. pp. 79-108.
Holdorf, AD et al., Proline Residues in CD28 and the Src Homology (SH)3 Domain of Lck Are Required for T Cell Costimulation. J Exp Med. (1999) 190: 375-384.
Huang, L. et al., OX40L induces helper T cell differentiation during cell immunity of asthma through PI3K/AKT and P38 MAPK signaling pathway. J. Trans. Med. (2018) 16: 74; doi: 10.1186/s12967-018-1436-4.
Huynh, TV.,et al., in "DNA Cloning Techniques, vol. I: A Practical Approach," 1985, (D. Glover, ed.), pp. 49-78, IRL Press, Oxford.
Hwu, P. et al. "Cancer and the Celuular Immune Response" in The Molecular Basis of Cancer. Chapter 51. Mendelsohn, J. et al (eds) Elsevier Health Sciences, 2015, pp. 695-708.
Ito, H. and Seishima, M. (2010), "Regulation of the Induction and Function of Cytotoxic T Lymphocytes by Natural Killer T Cell." J Biomed Biotechnol, 8 pages.
June, CH et al., T-Cell Proliferation Involving the CD28 Pathway Is Associated with Cyclosporine-Resistant Interleukin 2 Gene Expression. Mol Cell Biol. (1987) 7: 4472-4481.
Kaur D. and Brightling C. OX40/OX40 Ligand Interactions in T-Cell Regulation and Asthma. Chest. (2012) 141:494-499. doi: 101378/chest.11-1730.
Kim, HH et al., Growth Factor Receptor-bound Protein 2 SH2/SH3 Domain Binding to CD28 and Its Role in Co-signaling. J Biol Chem. (1998) 273: 296-301.
King, PD et al., Analysis of CD28 cytoplasmic tail tyrosine residues as regulators and substrates for the protein tyrosine kinases, EMT and LCK . . . J Immunol. (1997) 158: 580-590.
Kleiveland, C.R., "Peripheral Blood Monouclear Cells" in: Verhoeckx, K. et al. (eds). The Impact of Food Bioactives on Health (2015), Springer, Cham. Doi.org/10.1007/978-3-319-1610404. Chapter 15, p. 161-167.
Koeh BH, et al. GVHD-associated, inflammasome-mediated loss of function in adoptively transferred myeloid-derived suppressor cells. Blood (2015) 126:1621-8.
Koostra, N.A., et al., Gene Therapy with Viral Vectors. Ann. Rev. Pharm. Toxicol., 43:413-439, 2003.
Krovi, S.H. and Gapin, L. Invariant Natural Killer T Cell Subsets—More Than Just Developmental Intermediates. Frontiers in Immunology. Jun. 2018, vol. 9, Article 1393.
Krummel, MF and Allison, JP., CD28 and CTLA-4 have opposing effects on the response of T cells to stimulation. J Exp Med. 1995;182:459-465.
Kumar, A., et al. Natural Killer T Cells: An Ecological Evolutionary Developmental Biology Perspective. Frontiers in Immunology. Dec. 2017, vol. 8, Article 1858.
Kumar, V. and Delovitch, T.L. (2014) "Different subsets of natural killer T cells may vary in their roles in health and disease." Immunology 142: 321-336.
Lanier, LL, NKG2D Receptor and Its Ligands in Host Defense. Cancer Immunol. Res. (2015) 3(6): 575-82.
Leder, A., et al. Consequences of widespread deregulation of the c-myc gene in transgenic mice: Multiple neoplasm and normal development. Cell 1986, 45:485-495.

* cited by examiner

PARENT LINE

APX/14-18-30 LINE

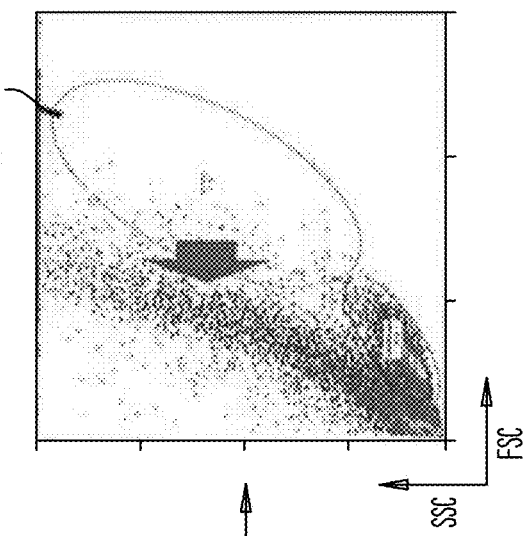
FIG. 54A
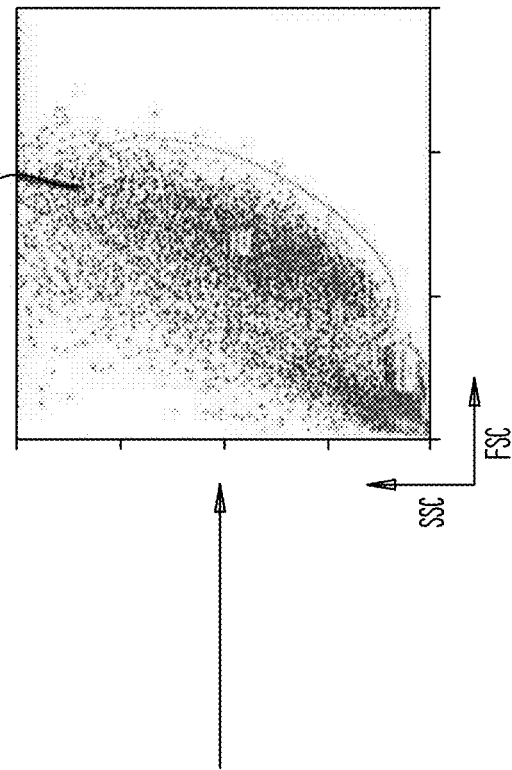
FIG. 54B
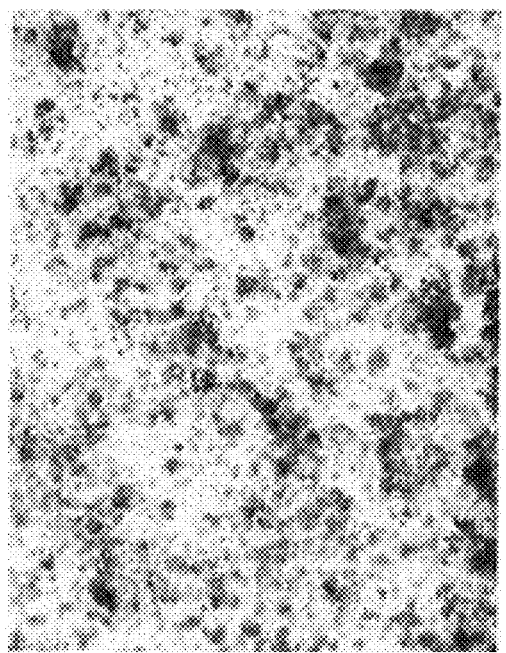
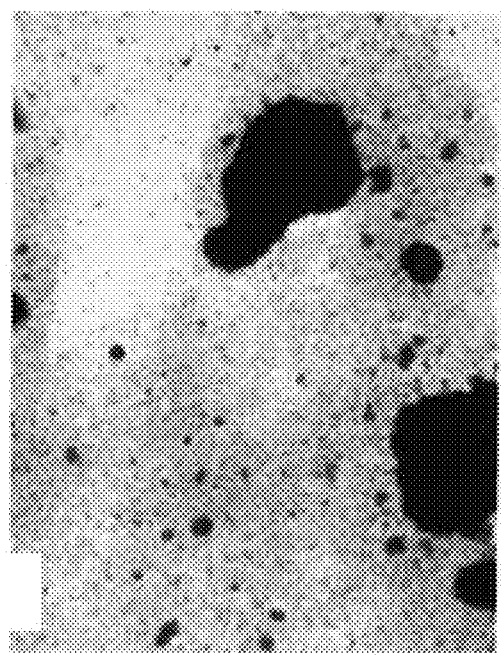

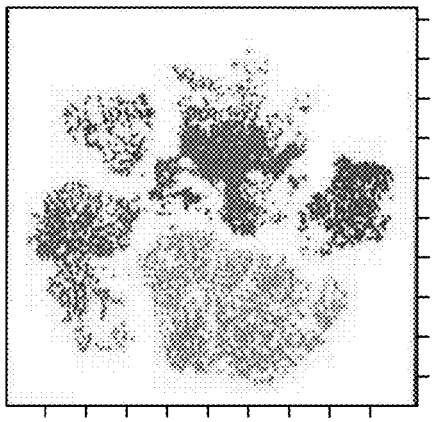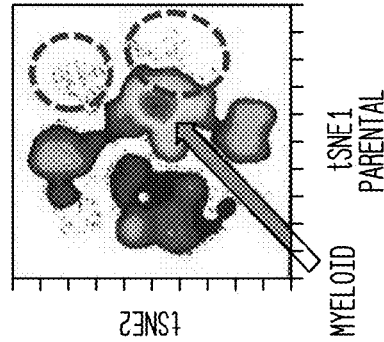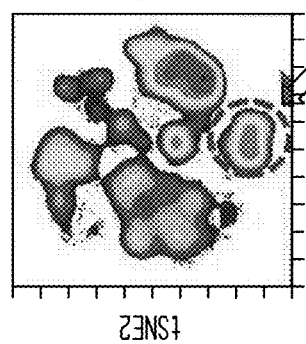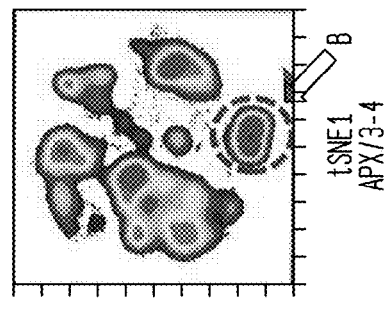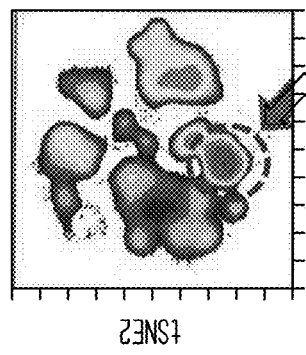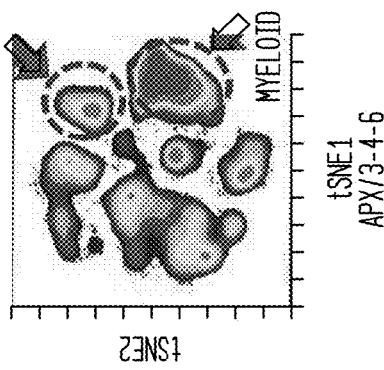

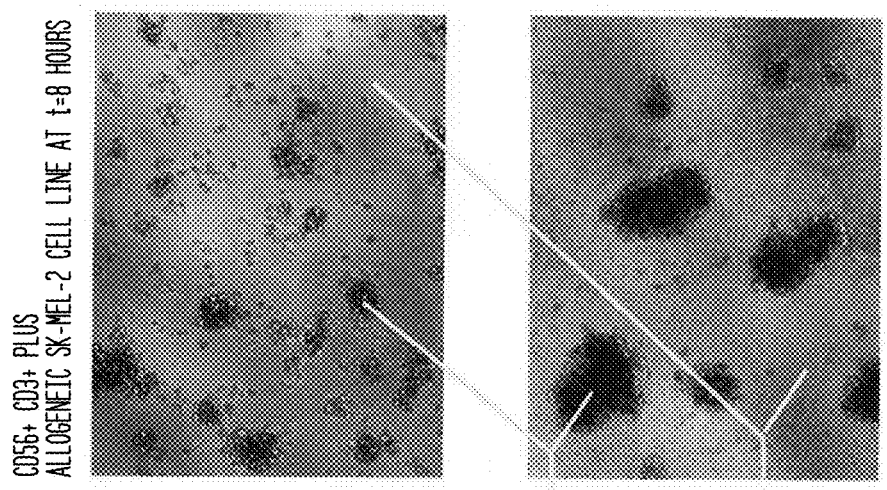
FIG. 57C
CD56+ CD3+ PLUS
ALLOGENEIC SK-MEL-2 CELL LINE AT t=8 HOURS
FIG. 57E
CD56neg CD3+ CD8+ PLUS
ALLOGENEIC SK-MEL-2 CELL LINE AT t=8 HOURS
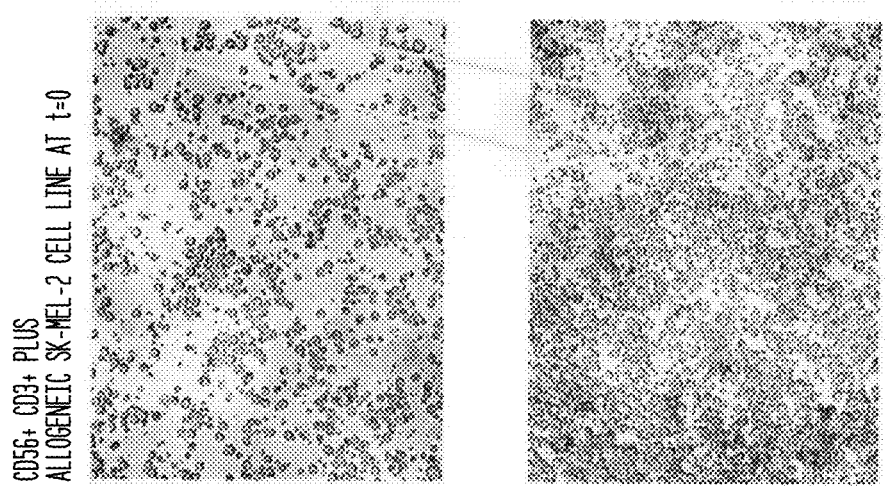
FIG. 57B
CD56+ CD3+ PLUS
ALLOGENEIC SK-MEL-2 CELL LINE AT t=0
FIG. 57D
CD56neg CD3+ CD8+ PLUS
ALLOGENEIC SK-MEL-2 CELL LINE AT t=0
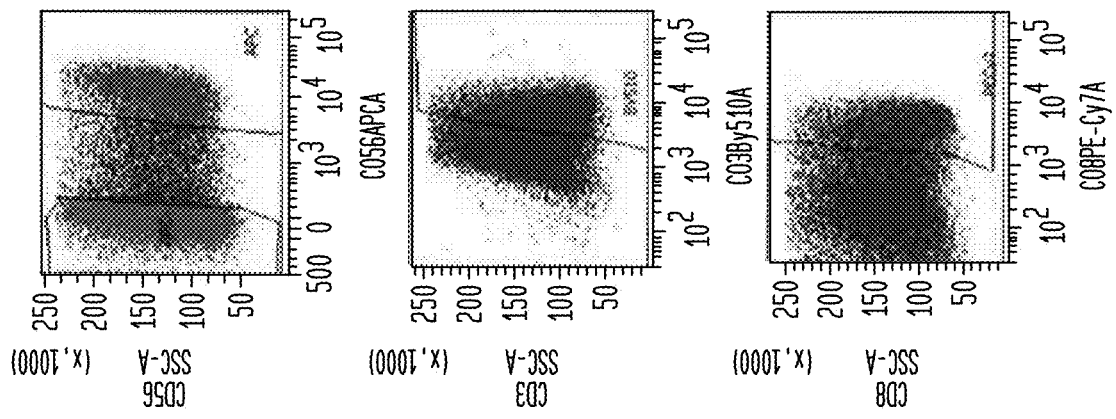
FIG. 57A

COMPOSITIONS AND METHODS FOR IN VITRO ACTIVATION AND EXPANSION OF SERIAL KILLER T CELL POPULATIONS AND PASSIVE IMMUNIZATION OF A CANCER PATIENT WITH TUMOR CELL KILLING CELLS

CROSS-REFERENCE TO RELATED APPLICATIONS

This application is a continuation in part of Ser. No. 15/821,105 (filed Nov. 22, 2017), which claims priority to provisional 62/425,424, filed Nov. 22, 2016, the contents of which are incorporated by reference in their entirety.

SEQUENCE LISTING

The instant application contains a Sequence Listing which has been submitted electronically in ASCII format and is hereby incorporated by reference in its entirety. Said ASCII copy, created on Oct. 17, 2019, is named 128663-00301_SL.txt and is 302,072 bytes in size.

FIELD OF THE INVENTION

The described invention relates generally to immunological approaches to the treatment of cancer, and more particularly to in vitro induction and expansion of serial killer T cell populations followed by passive immunization of a cancer patient with the tumor cell killing activated and expanded serial killer T cells.

BACKGROUND OF THE INVENTION

The human immune system is a complex arrangement of cells and molecules that maintain immune homeostasis to preserve the integrity of the organism by elimination of all elements judged to be dangerous. Responses in the immune system may generally be divided into two arms, referred to as "innate immunity" and "adaptive immunity."

The innate arm of the immune system is a nonspecific fast response to pathogens that are predominantly responsible for an initial inflammatory response via a number of soluble factors, including the complement system and the chemokine/cytokine system; and a number of specialized cell types, including mast cells, macrophages, dendritic cells (DCs), and natural killer cells (NKs).

The adaptive immune arm involves a specific, delayed and longer-lasting response by various types of cells that create long-term immunological memory against a specific antigen. It can be further subdivided into cellular and humoral branches, the former largely mediated by T cells and the latter by B cells. T cells further can be categorized by the expression of CD4+ molecules or the expression of CD8+ molecules, the latter of which allows for the identification of CD8+ cytotoxic T lymphocytes (CTLs).

A third arm of the immune system involves lineage members of the adaptive arm that have effector functions in the inate arm, therefore bridging the gap between the innate and adaptive immune response. These include cells such as γδ T cells and T cells with limited T cell receptor repertoires, such as natural killer T (NKT) cells and mucosal-associated invariant T (MAIT) cells. The third arm will be referred to herein as "innate-like immunity."

The three arms of immunity do not operate independently of each other, but rather work together to elicit effective immune responses. Because the initiation of an adaptive immune response requires some time, innate immunity and innate-like immunity provide the first line of defense during the critical period just after the host's exposure to a pathogen.

Components of the Immune System

The immune system comprises cellular interactions that occur through specific receptor-ligand pairs, which signal in both directions, so that each cell receives instructions based on the temporal and spatial distribution of those signals.

Cells of the immune system include lymphocytes, monocytes/macrophages, dendritic cells, the closely related Langerhans cells, natural killer (NK) cells, mast cells, basophils, and other members of the myeloid lineage of cells. In addition, a series of specialized epithelial and stromal cells provide the anatomic environment in which immunity occurs, often by secreting critical factors that regulate growth and/or gene activation in cells of the immune system, which also play direct roles in the induction and effector phases of the response. (Paul, W. E., "Chapter 1: The immune system: an introduction," Fundamental Immunology, 4th Edition, Ed. Paul, W. E., Lippicott-Raven Publishers, Philadelphia, (1999), at p. 102).

The cells of the immune system are found in peripheral organized tissues, such as the spleen, lymph nodes, Peyer's patches of the intestine and tonsils. Lymphocytes also are found in the central lymphoid organs, the thymus, and bone marrow, where they undergo developmental steps that equip them to mediate the myriad responses of the mature immune system. A substantial portion of lymphocytes and macrophages comprise a recirculating pool of cells found in the blood and lymph, providing the means to deliver immunocompetent cells to sites where they are needed and to allow immunity that is generated locally to become generalized (Id.).

Leukocytes derived from the myeloid or lymphoid lineage provide either innate or specific adaptive immunity. Myeloid cells include highly phagocytic, motile neutrophils, monocytes, and macrophages that provide a first line of defense against most pathogens. Other myeloid cells, including eosinophils, basophils, and their tissue counterparts, mast cells, are involved in defense against parasites and in the genesis of allergic reactions. Lymphocytes regulate the action of other leukocytes and generate specific immune responses that prevent chronic or recurrent infections (Id.).

The Complement System. The complement system, a part of innate immunity, comprises over 30 different proteins that circulate in blood plasma. In the absence of an infection, the complement proteins circulate in an inactive form. In the presence of a pathogen, the complement proteins become activated to kill the pathogen either directly or by facilitating phagocytosis. There are two pathways in which the complement system acts on pathogens: the classical pathway, involving antibody-dependent cell mediated cytotoxicity; and the alternative pathway, involving complement dependent cell cytotoxicity. (Ricklin, Daniel, et al. "Complement: a Key System for Immune Surveillance and Homeostasis." Nature Immunology, U.S. National Library of Medicine, September 2010, www.ncbi.nlm.nih.gov/pmc/articles/PMC2924908/).

Antibody-dependent cell mediated cytotoxicity (ADCC) is a mechanism by which effector cells of the immune system actively lyse target cells that have been bound by antibodies. The ADCC killing mechanism of an antibody-coated target cell by a cytotoxic effector cell is through a nonphagocytic process. This process involves the release of the content of cytotoxic granules or the expression of cell death-inducing molecules. ADCC is triggered through interaction of target-bound antibodies (belonging to IgG or IgA or IgE classes) with certain Fc receptor glycoproteins present on the effector cell surface that bind the Fc region of immunoglobulins (Ig). Effector cells that mediate ADCC include natural killer (NK) cells, monocytes, macrophages, neutrophils, eosinophils and dendritic cells. ADCC is dependent on a number of parameters, such as density and stability of the antigen on the surface of the target cell, antibody affinity, and FcR-binding affinity.

In contrast with ADCC, complement dependent cell cytotoxicity (CDCC) is a process of the immune system that kills pathogens by damaging target cell membrane without the involvement of antibodies. This alternative pathway is initiated by spontaneous hydrolysis and activation of the complement component C3, which binds directly to microbial surfaces. Alternatively, the lectin pathway is initiated by soluble carbohydrate binding proteins that bind to specific carbohydrate molecules on microbial surfaces.

Each of the ADCC and CDCC mechanisms generates a C3 convertase that cleaves C3, leaving behind C3b bound to the pathogen's surface and releasing C3a. This results in a number of cellular activities, including activation of the complement cascade, recruitment of phagocytic cells to the site of an infection, phagocytosis of pathogens by immune cells, and/or formation of a membrane attack complex (MAC) that disrupts pathogen cell membrane and causes cell lysis.

Immune Response

Generally speaking, immune responses are initiated by an encounter between an individual and a foreign substance, e.g., an infectious microorganism. The infected individual rapidly responds with both a humoral immune response with the production of antibody molecules specific for the antigenic determinants/epitopes of the immunogen, and a cell mediated immune response with the expansion and differentiation of antigen-specific regulatory and effector T-lymphocytes, including cells that produce cytokines and killer T cells, capable of lysing infected cells. Primary immunization with a given microorganism evokes antibodies and T cells that are specific for the antigenic determinants/epitopes found on that microorganism, but that usually fail to recognize or recognize only poorly antigenic determinants expressed by unrelated microbes (Paul, W. E., "Chapter 1: The immune system: an introduction," Fundamental Immunology, 4th Edition, Ed. Paul, W. E., Lippicott-Raven Publishers, Philadelphia, (1999), at p. 102).

As a consequence of this initial response, the immunized individual develops a state of immunologic memory. If the same or a closely related microorganism is encountered again, a secondary response ensues. This secondary response generally consists of an antibody response that is more rapid, greater in magnitude and composed of antibodies that bind to the antigen with greater affinity and that are more effective in clearing the microbe from the body, and a similarly enhanced and often more effective T-cell response. However, immune responses against infectious agents do not always lead to elimination of the pathogen (Paul, W. E., "Chapter 1: The immune system: an introduction," Fundamental Immunology, 4th Edition, Ed. Paul, W. E., Lippicott-Raven Publishers, Philadelphia, (1999), at p. 102).

Immune Homeostasis

The immune system is a tightly regulated network that is typically able to maintain homeostasis under normal physiological conditions in that the various actors of the immune system act cooperatively to avoid immune disequilibrium. Normally, when challenged with a foreign antigen, specific appropriate responses are initiated that are aimed at restoring equilibrium. However, under certain circumstances, this balance is not maintained and immune responses either under- or over-react. Cancer is an example of a situation where the immune response can be inefficient or unresponsive, resulting in uncontrolled growth of the cancer cells. Conversely, when the immune response over-reacts, this can result in conditions such as autoimmunity, chronic inflammation, and/or pathology following infection.

Immune Tolerance

The immune system is tolerant of self-antigens, i.e., it can discriminate between antigenic determinants expressed on foreign substances, and antigenic determinants expressed by tissues of the host. The capacity of the system to ignore host antigens, referred to as immune tolerance or immunological tolerance, is an active process involving the elimination or inactivation of cells that could recognize self-antigens through immunologic tolerance (Fundamental immunology, 4th Edn, William E. Paul, Ed. Lippincott-Raven Publishers, Philadelphia, (1999), at p. 2).

Innate immune cells recognize and discriminate between self and non-self through three distinct mechanisms: 1) innate leukocytes can recognize "nonself" from "non-infectious self" by recognizing conserved products not expressed by the host; 2) innate immune cells can recognize "missing self" by recognizing self-proteins that are specific to the host and absent from pathogens; 3) innate immune cells can also recognize "altered self" by recognizing abnormal cell markers that are upregulated due to infection or cellular transformation. (Spear, Paul, et al. "NKG2D Ligands as Therapeutic Targets." *Cancer Immunity*, Academy of Cancer Immunology, 1 May 2013, www.ncbi.nlm.nih.gov/pmc/articles/PMC3700746/).

Immune tolerance is classified into 1) central tolerance or 2) peripheral tolerance, depending on where the state is originally induced, i.e., whether it is in the thymus and bone marrow (central) or in other tissues and lymph nodes (peripheral). The biological mechanisms by which these forms of tolerance are established are distinct, but the resulting effect is similar (Raker V. K. et al. Front Immunol, Vol., 6(569): 1-11, (2015)).

Central tolerance, the principal way in which the immune system is educated to discriminate self-molecules from non-self-molecules, is established by deleting autoreactive lymphocyte clones at a point before they mature into fully immunocompetent cells. It occurs during lymphocyte development in the thymus and bone marrow for T and B lymphocytes, respectively (Sprent J. et al. Philos Trans R Soc Lond B Biol Sci, Vol. 356(1409): 609-616, (2001)). In these tissues, maturing lymphocytes are exposed to self-antigens presented by thymic epithelial cells and thymic dendritic cells, or bone marrow cells. Self-antigens are present due to endogenous expression, importation of antigen from peripheral sites via circulating blood, and in the case of thymic stromal cells, expression of proteins of other non-thymic tissues by the action of the transcription factor AIRE (Murphy, Kenneth. *Janeway's Immunobiology:* 8th ed. Chapter 15: Garland Science. (2012), pp. 611-668; see also, Klein L. Cell, Vol. 163(4):794-795, (2015)). Those lymphocytes that have receptors that bind strongly to self-antigens are removed by means of apoptosis of the autoreactive cells, or by induction of anergy (Id. at pp. 275-334). Weakly autoreactive B cells may also remain in a state of immunological inactivity where they do not respond to stimulation of their B cell receptor. Some weakly self-recognizing T cells are alternatively differentiated into natural regulatory T cells (nTreg cells), which act as sentinels in the periphery to lower potential instances of T cell autoreactivity (Id. at pp. 611-668).

The deletion threshold is more stringent for T cells than for B cells, since T cells are the main populations of cells that can cause direct tissue damage. Furthermore, it is more advantageous for the organism to let its B cells recognize a wider variety of antigens so that they can elicit antibodies against a greater diversity of pathogens. Since B cells can only be fully activated after confirmation by more self-restricted T cells that recognize the same antigen, autoreactivity is held in great check (Id. at pp. 275-334).

This process of negative selection ensures that T and B cells that potentially may initiate a potent immune response to the individual's own tissues are destroyed while preserving the ability to recognize foreign antigens. Lymphocyte development and education is most active in fetal development, but continues throughout life as immature lymphocytes are generated, slowing as the thymus degenerates and the bone marrow shrinks in the adult life (Id. at pp. 275-334; see also Jiang T. T. J Immunol., Vol. 192(11): 4949-4956, (2014)).

Peripheral tolerance develops after T and B cells mature and enter the peripheral tissues and lymph nodes (Murphy, Kenneth. Janeway's Immunobiology: 8th ed. Chapter 8: Garland Sciences. pp. 275-334). It is set forth by a number of overlapping mechanisms that predominantly involve control at the level of T cells, especially CD4+ helper T cells, which orchestrate immune responses and give B cells the confirmatory signals that the B cells need in order to progress to produce antibodies. Inappropriate reactivity toward a normal self-antigen that was not eliminated in the thymus can occur, since the T cells that leave the thymus are relatively, but not completely, safe. Some will have TCRs that can respond to self-antigens that the T cell did not encounter in the thymus (Id.). Those self-reactive T cells that escape intra-thymic negative selection in the thymus can inflict cell injury unless they are deleted in the peripheral tissue chiefly by nTreg cells.

Autoimmune regulator (Aire), usually expressed in thymic medullary epithelial cells, plays a role in immune tolerance by mediating ectopic expression of peripheral self-antigens and mediating the deletion of auto-reactive T cells (Metzger T. C., et al. Immunol. Rev. 2011, 241: 89-103, (2011)).

Appropriate reactivity towards certain antigens can also be suppressed by induction of tolerance after repeated exposure. Naïve CD4+ helper T cells differentiate into induced Treg cells (iTreg cells) in the peripheral tissue, or accordingly, in nearby lymphoid tissue (lymph nodes, mucosal-associated lymphoid tissue, etc.). This differentiation is mediated by IL-2 produced upon T cell-activation, and TGF-β from any of a variety of sources, including tolerizing dendritic cells (DCs) or other antigen presenting cells (Curotto de Lafaille et al. Immunity, 30(6): 626-635, (2009)).

Immunity and Cancer
Immune Tolerance of Cancer

Cancer is characterized by genetic instability of particular cells, but has also been described as a disorder of the immune system, based on the fact that the immune system fails, at least in certain segments of the afflicted human population, to respond optimally to cancerous cells that have taken on a distinctly non-self phenotype that should be recognized as foreign. Several reasons have been advanced to explain the basis of this observation. For example, first, cancer cells consist mainly of self-antigens, in striking contrast to the situation with infectious organisms. Some antigens that are classified as cancer antigens are actually normal antigens that are overexpressed, or normal antigens that have a mutation in only one or two amino acids in the polypeptide chain. Second, cancer cells down-regulate MHCs, and thus do not much present tumor cell-derived peptides by way of MHC. Third, cancer cells, and associated tumor-associated macrophages, express cytokines that dampen the immune response (see, e.g., Yu et al (2007) Nature Rev. Immunol. 7:41-51). This dampening is caused, for example, by the secretion of interleukin-10 (IL-10) by the cancer cells or by the associated macrophages. Fourth, unlike the situation with infections, cancer cells do not provide any immune adjuvant. Pathogens express a variety of naturally-occurring immune adjuvants, which take the form of TLR agonists and NOD agonists (see, e.g., Kleinnijenhuis et al (2011) Clin. Dev. Immunol. 405310 (12 pages)). Generally, optimal activation of dendritic cells requires contact of an immune adjuvant with one or more TLRs expressed by the dendritic cell. Without activation of the dendritic cell, contact between the dendritic cell and T cells (immune synapse) fails to result in optimal activation of the T cell.

Tumor Immune Surveillance and Immune Editing

While a functional cancer immunosurveillance process indeed exists that acts as an extrinsic tumor suppressor, it has become clear that the immune system can facilitate tumor progression, at least in part, by sculpting the immunogenic phenotype of tumors as they develop. This so-called "tumor immune editing" is divided into three phases: an elimination phase, an equilibrium phase, and an escape phase. The elimination phase, also known as immune surveillance, is the process by which the immune system identifies cancerous or pre-cancerous cells and eliminates them before they grow out of control. This phase can be complete when all cancerous or precancerous cells are eliminated. If some tumor cells are not eliminated, a temporary state of equilibrium may be achieved between the immune system and tumor cell growth. In this equilibrium phase, tumors cells can either remain dormant or continue to evolve by accumulating further changes to genomic DNA that can modulate the antigens they present. During this process, the immune system exerts a selective pressure on evolving cells, whereby the tumor cells that are less able to be recognized have a survival advantage. Eventually the immune response is unable to recognize cells of the tumor, resulting in the transition to the escape phase, where tumor cells progressively grow out of control. (Dunn, G P et al., Ann. Rev. Immunol. (2004): 329-60).

Tumor Immunology

Tumors are able to progress and evolve by numerous evasion mechanisms.

For example, tumors are able to evolve under selective pressure from the immune response to selectively lose receptors that activate anti-tumor immune cells. For example, it has been reported that tumors that are NKG2D ligand-deficient in mice that are NKG2D expressing have been able to persist despite the loss of other tumor cells. (Marcus, Assaf, et al. "Recognition of Tumors by the Innate Immune System and Natural Killer Cells." *Advances in Immunology*, U.S. National Library of Medicine, 2014, www.ncbi.nlm.nih.gov/pmc/articles/PMC4228931/).

Tumors also shed ligands that activate anti-tumor immune cells through a variety of techniques, such as alternative splicing, cleavage, proteolytic shedding, or exosome secretion. This can be seen in the increase of soluble ligands, such as MIC (MHC class I-related molecules distantly related to the MHC class I proteins) and UL16-binding proteins (ULBPs) which bind to MICB), that have been identified in the sera of patients with various tumor types, including breast, lung, colon, and obarious carinomal, glioma, neuroblastoma, leukemia, and melanoma. The shedding of ligands and the existence of soluable ligands in the surrounding reaction environment can result in several distinct effects. First, it decreases the level of activating ligands on the cell surface and thus reducing tumor cell susceptibility to attack by lymphocytes. For example, it has been postulated that the shedding of NKG2D ligands from tumor cells reduces their ability to be cytolytic attacked by NKs or T cells. Alternatively, the existence of soluable ligands in the reaction environment may desensitize NKs by binding to ligand receptors on lymphocytes and preventing interactions necessary to induce cytotoxic activity on tumor cells. Id. Soluable ligands are also thought to downregulate the expression of their receptors. For example, cancer patients with elevated soluble MICA in their serum exhibited strongly reduced NKG2D staning of their peripheral blood CD8+ T cells. Id. Soluble ligands along with exosomes have also been postulated to bundle together and act in concert to impact lymphocyte immune responses. Id.

Similarly, tumors can lose the ability to express receptors and/or shed them in an effort to evade cell death. For example, tumors can evade immune recognition through disrupting MHC class I restricted antigen processing through the loss of class I itself or components in the class I pathway. Some melanomas have lost cell surface expression of MHC class I through defective expression of $\beta 2$ microglobulin ($\beta_2 M$), which is required for stable assembly of class I, or defective expression of the transporter associated with tumor antigen processing (TAP). (Alberts, D. S., and L. M. Hess, editors. *FUNDAMENTALS OF CANCER PREVENTION*. SPRINGER NATURE, 2019. Pps. 79-108).

Tumor Microenvironment

The tumor microenvironment provides a consistently effective barrier to immune cell function, because tumors actively downregulate all phases of anti-tumor immune responses using a spectrum of different strategies and mechanisms. Many molecular mechanisms that cause dysfunction of immune cells in the tumor microenvironment have been identified, including those directly mediated by factors produced by tumors, and others resulting from alterations of normal tissue homeostasis in the presence of cancer. Most human tumors appear to be able to interfere with one or more stages of immune cell development, differentiation, migration, cytotoxicity and other effector functions (T L Whiteside, The tumor microenvironment and its role in promoting tumor growth, Oncogene (2008) 27, 5904-5912).

One such mechanism involves accumulation in tumors of regulatory T cells (Tregs) (CD4+CD25bright Foxp3+) and myeloid-derived cells (CD34+CD33+CD13+CD11b+ CD15−), which are common features of human tumors, and have been linked to poor prognosis in patients with cancer (Id.). Under normal conditions, Treg cells are involved in preventing autoimmunity, but in cancer, they expand, migrate to tumors, downregulate autologous effector T-cell proliferation, and suppress anti-tumor responses of both CD4+CD25− and CD8+CD25− T cells using distinct molecular pathways. The Treg cells in the tumor are a heterogeneous population of regulatory CD3+CD4+ T cells, comprising natural Treg, antigen-specific Tr1 cells, and other less well defined subsets of suppressor cells. T regulatory type 1 (Tr1) cells are induced in the tumor microenvironment, which is rich in IL-10, TGF-$\beta$, and prostaglandin E2 (PGE2), all of which have been shown to promote Tr1 generation (Id.).

Myeloid-derived suppressor cells (MDSC's), which are closely related to neutrophils and monocytes, are not present at steady state in healthy individuals, and appear in cancer and pathological conditions associated with chronic inflammation or stress. (Gabrilovich, D I., "Myeloid-derived suppressor cells," Cancer Immunol. Res. (2017) 5(1): 3-8). They are a relatively stable, distinct state of functional activity of neutrophils and monocytes. The main functional characteristic of these cells is their potent ability to suppress various types of immune responses. MDSC consist of two large groups of cells termed granulocytic or polymorphonuclear (PMN-MDSC), which phenotypically and morphologically are similar to neutrophils; and monocytic (M-MDSC), which are phenotypically and morphologically similar to monocytes. Therefore phenotypic criteria alone are not sufficient to identify cells as MDSCs. In most types of cancer, PMN-MDSC represent more than 80% of all MDSC. In addition to these two main populations, MDSCs include a small group (less than 3%) of cells with myeloid colony forming activity representing a mixture of myeloid progenitors and precursors. Among peripheral blood mononuclear cells (PBMCs), PMN-MDSCs are defined as CD11b+CD14−CD15+ or CD11b+CD14−CD66b+, and M-MDSC as CD11b+CD14+HLA-DR−/loCD15−. Lin− (including CD3, CD14, CD15, CD19, CD56) HLA-DR− CD33+ cells contain mixed groups of MDSC comprising more immature progenitors. The term "early-stage MDSC" (e-MDSC) has been proposed for this latter population.

Although MDSCs were implicated in suppression of different cells of the immune system, the main targets of MDSCs are T cells. The main factors implicated in MDSC-mediated immune suppression include arginase (ARG1), iNOS, TGF$\beta$, IL-10, COX2, indoleamine 2,3-dioxygenase (IDO) sequestration of cysteine, decrease of L-selectin expression by T-cells and many others. M-MDSC and PMN-MDSC utilize different mechanisms of immune suppression. M-MDSC suppress T-cell responses both in antigen-specific and non-specific manners utilizing mechanisms associated with production of NO and cytokines (reviewed in (Id., citing Gabrilovich, D E et al, Coordinated regulation of myeloid cells by tumours. Nat Rev Immunol. (2012)12:253-68). PMN-MDSCs, on the other hand, are capable of suppressing immune responses primarily in an antigen-specific manner. Induction of antigen-specific T-cells tolerance is one of the major characteristics of these cells (Id., citing Koehn B H, et al. GVHD-associated, inflammasome-mediated loss of function in adoptively transferred myeloid-derived suppressor cells. Blood (2015) 126:1621-8; Nagaraj S, Gupta K, Pisarev V, Kinarsky L, Sherman S, Kang L, et al. Altered recognition of antigen is a mechanism of CD8+ T cell tolerance in cancer. Nat Med. (2007) 13: 828-35). Reactive oxygen species (ROS) production is essential for this ability. Reaction of NO with superoxide generates peroxynitrite (PNT), which directly inhibits T-cells by nitrating T-cell receptors and reducing their responsiveness to cognate antigen-MHC complexes (Id., citing Nagaraj S, et al. Altered recognition of antigen is a mechanism of CD8+ T cell tolerance in cancer. Nat Med. (2007) 13: 828-35). PNT also reduces the binding of antigenic peptides to MHC molecules on tumor cells (Id., citing Lu, T. et al., Tumor-infiltrating myeloid cells induce tumor cell resistance to cytotoxic T cells in mice. J. Clinical Investigation. (2011) 121: 4015-29) and blocks T-cell migration by nitrating T-cell specific chemokines (Id., citing Molon, B. et al., Chemokine nitration prevents intratumoral infiltration of antigen-specific T cells. J Exp Med. (2011) 208: 1949-62). Besides immune suppressive mechanisms, MDSCs promote tumor progression by affecting the remodeling of the tumor microenvironment and tumor angiogenesis via production of VEGF, bFGF, Bv8, and MMP9 (Id., citing Tartour, E. et al., Angiogenesis and immunity: a bidirectional link potentially relevant for the monitoring of antiangiogenic therapy and the development of novel therapeutic combination with immunotherapy. Cancer Metastasis Rev. (2011) 30: 83-95; Casella, I., et al., Autocrine-paracrine VEGF loops potentiate the maturation of megakaryocytic precursors through FM receptor. Blood. (2003) 101:1316-23; Shojaei, F. et al., G-CSF-initiated myeloid cell mobilization and angiogenesis mediate tumor refractoriness to anti-VEGF therapy in mouse models. Proc Natl Acad Sci USA. (2009) 106: 6742-7).

Mostly, dendritic cells found in the TME are immature and tunable to activate specific T cells. NKTs secrete IL-4 and IFN-γ and further upregulate CD40L, thereby inducing the maturation of DCs. DC maturation leads to increased costimulatory capacity through upregulation of CD80 and CD86, of MHC molecules, and by producing the pro-inflammatory cytokine IL-12 and the chemokine, CCL17. The presence of the chemokine attracts CCR4+ cells including CD8+ T cells, which then can be activated by the "licensed" DC cell. (Gottschalk et al. (2015) "The Role of Invariant Natural Killer T Cells in Dendritic Cell Licensing, Cross-Priming, and Memory CD8+ T Cell Generation." Front Immunol 6:379).

Typically, there are two types of tumor cells in a human tumor mass: one is HLA Class I-positive and the other is HLA Class I-negative. Effective tumor immunity requires that both types of tumor cells are eliminated at once. NKTs are the only cell type that is able both to interact with immature DCs, inducing their maturation, and to augment the function of both NK and CD8+ T cells. NKTs induce maturation of DCs, allowing DCs to present tumor antigens to CD8+ T cells. The activated CD8+ T cells can then eliminate HLA Class I—positive tumor cells. NKTs also produce IFNγ which activates NKs thereby killing HLA Class I—negative tumor targets. (Terabe, M., & Berzofsky, J. A. (2012). Natural killer T cells balancing the regulation of tumor immunity. New York, N.Y.: Springer).

NKTs can form bidirectional interactions with B cells, which can present lipid antigens to some NKTs through CD1d. In return, NKTs can license B cells to effectively prime and activate antitumor CTL responses and provide B call help to enhance and sustain a humoral response. (Nair and Dhodapkar (2017). "Natural Killer T Cells in Cancer Immunotherapy." Frontiers in Immunology 8:1178).

Tumor associated macrophages (TAMs) are prominent immunosuppressive immune cells present in the tumor microenvironment. TAMs contribute to tumor progression by enhancing angiogenesis, tumor cell invasion, suppression of NKs and T cell responses. Some NKTs have been found to o-localize with CD1d-expressing TAMs in neuroblastomas and kill TAMs in an IL-15 and CD1d-restricted manner. (Id.).

NKTs can also alter the effects of CD1d+ myeloid-derived suppressor cell (MDSC)-mediated immune suppression. MDSCs often accumulate during tumor growth and contribute to immune escape and tumor progression. Research has found that NKTs may inhibit the arginate 1 and nitrous oxide synthase-mediated suppressive activity of MDSCs. This ability to inhibit the immunosuppressive activity of MDSCs has been reported to be dependent on CD1d and CD40 interactions. (Id.).

While some NKTs can promote strong antitumor immunity, other types have been known to suppress antitumor immune responses and play more of a regulatory role, similar to Tregs and MDSCs. The balance between immunomodulating and immunosuppressive NKTs can determine whether immune responses to tumors will be activated resulting in tumor elimination, or will be suppressed, allowing the tumor to grow. (Terabe, M., & Berzofsky, J. A. (2012). Natural killer T cells balancing the regulation of tumor immunity. New York, N.Y.: Springer).

Some NKT types have been shown to promote the accumulation of MDSCs in tumor-bearing mice. NKTs have also been shown to inhibit the proinflammatory functions of other NKT cell types, conventional T cells, and DCs. One attribute of immunosuppressive NKTs is their elevated production of IL-13 and IL-4 cytokines, which are capable of skewing the cytokine response predominantly towards the tumor promoting Th2 type. Studies have shown that immunosuppressive type NKTs have been shown to suppress cytotoxic T cells through IL-13 production via an IL4R and STAT6 axis, and also induce MDSCs producing immunosuppressive cytokine TGF-B. (Nair and Dhodapkar (2017). "Natural Killer T Cells in Cancer Immunotherapy." Frontiers in Immunology 8:1178).

It has been hypothesized that immunosuppressive NKTs when stimulated with CpG secrete IFNy instead of IL-13, therefore enhancing the activation and function of CD8+ cells and contributing to an anti-tumor effect. (Id.) Therefore, while the balance of immunosuppressive NKTs and immunomodulating NKTs is important in enhancing anti-tumor activity, another factor is the activating ligand of the NKTs itself.

Tumor Immunotherapy

Traditional chemotherapy works by killing cells that multiply quickly whether normal or cancerous. Targeted therapy works by stopping or slowing the growth or spread of cancer on a cellular level by targeting the cancer's specific genes, proteins, or the tissue environment that contributes to cancer growth and survival.

Monoclonal antibodies, for example, block a specific target on the outside of cancer cells and/or in the area around the cancer. Antibody therapies such as Trastuzumab (Herceptin®), which is effective against tumors that overexpress the HER2/neu protein, and Cetuximab (Erbitux®), an epidermal growth factor receptor inhibitor antineoplastic agent, have yielded considerable improvement in clinical outcome, as measured by, e.g. the recurrence rate, progression free survival and overall survival.

Small molecule drugs have been designed against specific targets. For example, angiogenesis inhibitors keep tissue around the tumor from making blood vessels, thereby starving the tumor (e.g., bevacizumam (Avastin®); imatinib mesylate (GLEEVEC™); tamoxifen attenuates VEGF-mediated angiogenesis (antiangiogenic effect mediated by EGF (McNamara, D A et al., Eur. J. Surg. Oncol. (2001) 27(8): 714-718)

Immunotherapy is a type of therapy that uses substances to stimulate or suppress the immune system to help the body fight cancer, infection and other diseases. Some types of immunotherapy only target certain cells of the immune system. Others affect the immune system more generally.

Anti-cancer immunotherapy has been an unattained goal for many years. One difficulty is that target antigens are often tissue specific molecules found on both cancer cells and normal cells, and either do not elicit immunity or show non-specificity regarding cell killing (Kaufman and Wolchok eds., General Principles of Tumor Immunotherapy, Chpt 5, 67-121 (2007)). Furthermore, tumor cells have features that make immune recognition difficult, such as loss of expression of antigens that elicit immune response, lack of major histocompatibility (MHC) class II, and downregulation of MHC class I expression. These features can lead to non-recognition of tumor cells by both CD4+ and CD8+ T cells (Id.). Tumors may also evade detection through active mechanisms, such as the production of immunosuppressive cytokines (Id.)).

Dendritic cell vaccines are vaccines made of antigens and dendritic antigen-presenting cells (APCs). Vaccination strategies involving DCs to induce tumor-specific effector T cells that can reduce the tumor mass specifically and that can induce immunological memory to control tumor relapse have been developed. For example, DCs generated ex vivo by culturing hematopoietic progenitor cells or monocytes with cytokine combinations have been tested as therapeutic vaccines in cancer patients for more than a decade (Ueno H, et al., Immunol. Rev. (2010) 234: 199-212). Treatment of metastatic prostate cancer with sipuleucel-T (also known as APC 8015), a cellular product based on enriched blood APCs that are briefly cultured with a fusion protein of prostatic acid phosphatase (PAP) and granulocyte macrophage colony-stimulating factor (GM-CSF), resulted in an approximately 4-month-prolonged median survival in Phase III trials (Higano C S, et al., Cancer (2009) 115: 3670-3679; Kantoff P W, et al., N. Engl. J. Med. (2010) 363: 411-422). This study concluded that DC-based vaccines are safe and can induce the expansion of circulating CD4+ T-cells and CD8+ T-cells specific for tumor antigens. As a result of this and similar studies, sipuleucel-T has been approved by the US Food and Drug Administration (FDA) for the treatment of metastatic prostate cancer, thereby paving the clinical development and regulatory path for the next generation of cellular immunotherapy products (Palucka K and Banchereau J, Nature Reviews Cancer (April 2012) 12: 265-276).

DC-tumor cell fusions have been developed to generate hybrid cells that express the relevant tumor associated antigens derived from the parent tumor cells, and that also have the ability to process and present such antigens to appropriate cells of the immune system. Such DC-tumor cell fusions provide a greater variety of tumor antigens, but have met with limited success in human trials, likely due to the autologous components required, the heterogeneity of the product caused by maturation of DC cells, and variations in antigen loading (Browning, M., Antigen presenting cell/tumor cell fusion vaccines for cancer, Human Vaccines & Immunotherapeutics 9:7, 1545-1548; July 2013; Butterfield, L., Dendritic Cells in Cancer Immunotherapy Clinical Trials: Are We Making Progress?, Frontiers of Immunology, 2013 4: 454).

Immune checkpoint inhibitors (e.g., PD-1 and CTLA4 inhibitors) have been reported to block discrete checkpoints in an active host immune response allowing an endogenous anti-cancer immune response to be sustained. As used herein, the term "immune checkpoints" refers to the array of inhibitory pathways necessary for maintaining self-tolerance and that modulate the duration and extent of immune responses to minimize damage to normal tissue. Immune checkpoint molecules such as PD-1, PD-L1, CTLA-4 are cell surface signaling receptors that play a role in modulating the T-cell response in the tumor microenvironment. Tumor cells have been shown to utilize these checkpoints to their benefit by up-regulating their expression and activity. With the tumor cell's ability to commandeer some immune checkpoint pathways as a mechanism of immune resistance, it has been hypothesized that checkpoint inhibitors that bind to molecules of immune cells to activate or inactivate them may relieve the inhibition of an immune response. Recent discoveries have identified immune checkpoints or targets, like PD-1, PD-L1, PD-L2, CTLA4, TIGIT, TIM-3, LAG-3, CCR4, OX40, OX40L, IDO, and A2AR, as proteins responsible for immune evasion. Specific immune checkpoint inhibitors, including antibodies against CTLA-4, PD-1 receptor or its ligand PD-L1 have produced impressive results in the clinic in a range of cancers, leading to FDA approvals for YERVOY™ (Ipilimumab; CTLA-4 antagonist), OPDIVO™ (Nivolumab; PD-1 antagonist) and KEYTRUDA™ (Pembrolizumab; PD-1 antagonist) in multiple tumor indications and with ongoing registration trials in many more.

For example, TIGIT, a member of the Ig super family and an immune inhibitory receptor, is overexpressed on tumor antigen-specific CD8+ T cells and CD8+ TILs and plays a key role in the suppression of T-cell proliferation and activation; it is involved in tumor cell immune evasion, and the inhibition of antiviral immune responses. Anti-TIGIT monoclonal antibody OMP-313M32 targets this immune checkpoint and prevents T cell downregulation. Upon administration, anti-TIGIT monoclonal antibody OMP-313M32 binds to TIGIT expressed on various immune cells, including T cells, and prevents the interaction of TIGIT with its ligands CD112 (nectin-2; poliovirus receptor related-2; PVRL2) and CD155 (poliovirus receptor; PVR; nectin-like protein 5; NECL-5). This leaves CD112 and CD155 free to interact with the costimulatory receptor CD226 (DNAX Accessory molecule-1; DNAM-1), which is expressed on immune cells, such as natural killer (NK) cells and CD8-positive T cells, and leads to CD226 dimerization and CD226-mediated signaling. This activates the immune system to exert a T-cell-mediated immune response against cancer cells.

TIM-3, a transmembrane protein and immune checkpoint receptor, is associated with tumor-mediated immune suppression. Anti-TIM-3 monoclonal antibody TSR-022, a monoclonal antibody against the inhibitory T-cell receptor, T-cell immunoglobulin and mucin domain-containing protein 3 (TIM-3; TIM3; hepatitis A virus cellular receptor 2; HAVCR2), and anti-TIM-3 antibody BMS-986258, an antibody against TIM-3, have potential immune checkpoint inhibitory and antineoplastic activities. Upon administration, the anti-TIM-3 monoclonal antibody TSR-022 binds to TIM-3 expressed on certain T cells, including tumor infiltrating lymphocytes (TILs). This abrogates T-cell inhibition, activates antigen-specific T lymphocytes and enhances cytotoxic T-cell-mediated tumor cell lysis, which results in a reduction in tumor growth.

LAG-3 is a member of the immunoglobulin superfamily (IgSF) and binds to major histocompatibility complex (MHC) class II. LAG-3 expression on TILs is associated with tumor-mediated immune suppression.

Relatlimab (previously known as BMS-986016, Bristol-Myers Squibb) is a monoclonal antibody directed against the inhibitor receptor lymphocyte activation gene-3 (LAG-3), with potential immune checkpoint inhibitory and antineoplastic activities. Upon administration, relatlimab binds to LAG-3 on tumor infiltrating lymphocytes (TILs), which may activate antigen-specific T lymphocytes and enhance cytotoxic T cell-mediated tumor cell lysis, which leads to a reduction in tumor growth.

Anti-LAG-3 monoclonal antibody LAG525 is a humanized monoclonal antibody directed against the inhibitory receptor lymphocyte activation gene-3 (LAG-3), with potential immune checkpoint inhibitory and antineoplastic activities. Upon administration, the anti-LAG-3 monoclonal antibody LAG525 binds to LAG-3 expressed on tumor-infiltrating lymphocytes (TILs) and blocks its binding with major histocompatibility complex (MHC) class II molecules expressed on tumor cells. This activates antigen-specific T-lymphocytes and enhances cytotoxic T-cell-mediated tumor cell lysis, which leads to a reduction in tumor growth. LAG-3, a member of the immunoglobulin superfamily (IgSF) and expressed on various immune cells, negatively regulates cellular proliferation and activation of T-cells. Its expression on TILs is associated with tumor-mediated immune suppression.

Anti-LAG3 monoclonal antibody TSR-033 is a humanized, immunoglobulin G4 (IgG4) monoclonal antibody directed against the inhibitory receptor lymphocyte activation gene 3 protein (LAG3; LAG-3), with potential immune checkpoint inhibitory and antineoplastic activities.

TIGIT targeting agent MK-7684 is an antagonistic agent targeting the co-inhibitory molecule and immune checkpoint inhibitor T-cell immunoglobulin (Ig) and immunoreceptor tyrosine-based inhibitory motif (ITIM) domains (TIGIT; T-cell immunoreceptor with Ig and ITIM domains; T-cell immunoglobulin and ITIM domain), with potential immune checkpoint inhibitory and antineoplastic activities. Upon administration, MK-7684 targets and binds to TIGIT expressed on various immune cells, particularly on tumor-infiltrating T lymphocytes (TILs) and natural killer (NK) cells, thereby preventing the interaction of TIGIT with its ligands CD112 (nectin-2; poliovirus receptor related-2; PVRL2) and CD155 (poliovirus receptor; PVR; nectin-like protein 5; NECL-5), which are expressed on T cells, NK cells and certain cancer cells. This enhances the interaction of CD112 and CD155 with the costimulatory receptor CD226 (DNAX Accessory molecule-1; DNAM-1), which is expressed on immune cells, such as NK cells and CD8+ T cells, and activates CD226-mediated signaling. This activates the immune system to exert a T-cell-mediated immune response against cancer cells.

This method of therapy, however, can only be successful if a pre-existing antitumor immune response is present within a patient (Pardoll, D., The blockade of immune checkpoints in cancer immunotherapy, Nature Reviews: Cancer, Vol. 12, April 2012, 253).

Chimeric antigen receptor T-cell therapy (CAR-T), attempts to use synthetic biology to redirect T-cells to specific cell surface tumor antigens. Genetic modification of T-cells is used to confer tumor antigen recognition by transgenic expression of a chimeric antigen receptor (CAR). CARs are engineered molecules that can be introduced into T cells to enable them to target tumor antigens (Frey, N. V., Porter, D. L., The Promise of Chimeric Antigen Receptor T-Cell Therapy, Oncology (2016); 30(1)) pii 219281). CAR T cells have been shown to have some efficacy against hematologic malignancies and to a lesser extent solid tumors. CAR T therapy, however, has been shown to cause several types of toxicities, including cytokine release syndrome, neurological toxicity, non-tumor recognition, and anaphylaxis (Bonifant C L, et al., Toxicity and management in CAR T-cell therapy, Molecular Therapy—Oncolytics (2016) 3, 16011).

Cellular vaccines have also been proposed as a cancer treatment. GVAX™ is a GM-CSF gene transduced tumor vaccine within either an autologous or allogeneic population of tumor cells. It was believed that GM-CSF secretion of genetically modified tumor cells would stimulate cytokine release at the vaccine site to activate antigen presenting cells to induce a tumor specific cellular immune response (Eager, R. & Nemunaitis, J., GM-CSF Gene-Transduced Tumor Vaccines, Molecular Therapy, Vol. 12, No. 1, 18 (July 2005)). However, GVAX™ yielded only limited clinical responses.

Tumor cell lines possess a broad array of antigens, many of which are common to a particular tumor type, as well as some that are shared across tumors. Many immunomodulatory components defined as a result of decades of research can be used to genetically engineer these tumor cell lines. An allogeneic approach to immunoactivation in the context of such allogeneic tumor cell lines modified to express at least 2/3/4 immunomodulators has been described.

The described invention provides a method for effective tumor cell killing through adoptive transfer of in vitro (or in vivo) activated mononuclear cells. The method described herein involves the in vitro immune activation of mononuclear cells following their co-incubation with allogeneic engineered leukocyte stimulator cells (ENLST™ cells) encoding at least three (3) immunomodulator peptides. Through cell contact, the mononuclear cells are stimulated to differentiation, proliferate and acquire an activated phenotype. The activated mononuclear cells, or subpopulations thereof comprised of serial killer cells are useful for passive adoptive transfer of the cell product to the patient. Since the cells are activated in a physiologic manner, the stimulated cells retain homeostatic control mechanisms of their cell type. Optionally, immortalizing the subpopulations comprising serial killer cells represents the possibility of creating an infinite supply.

BRIEF SUMMARY OF THE INVENTION

According to one aspect, the described invention provides a method for in vitro activation of cytotoxic T-cell populations followed by passive immunization of a cancer patient not currently under the influence of an immunosuppressive regimen with a composition comprising a cell product comprising an activated and expanded population of mononuclear cells comprising activated and expanded subpopulations of serial killer cells comprising, under sterile conditions: (a) Inducing an immune response in vitro by: (1) isolating a population of mononuclear cells (MNCs) from a biological sample; (2) preparing a population of engineered leukocyte stimulator cells comprising a population of tumor cells expressing one or more tumor specific antigens and genetically engineered to stably express a core group of three immunomodulatory molecules wherein the core group of immunomodulator molecules is OX40 Ligand (OX40L), CD27 Ligand (CD70) and CD28 Ligand (CD28L); (3) contacting the population of MNCs of step (a)(1) with the engineered leukocyte stimulator cells of step (a)(2) in vitro; wherein the contacting is effective to stimulate synergistic expansion of cytotoxic serial killer cells, to form an activated population of MNCs comprising activated subpopulations of cytotoxic serial killer cells; (b) expanding the activated population of MNCs comprising activated subpopulations of serial killer cells in vitro by culturing the activated MNCs to form a cell product containing an activated and expanded population of MNCs including expanded and activated subpopulations of serial killer cells; (c) preparing a unit dose package comprising an individual dose of the activated and expanded cell product, freezing the unit dose packages, and storing the frozen unit dose packages in cryostorage; (d) thawing a therapeutic amount of the frozen unit dose packages comprising the cell product under controlled conditions; (e) optionally combining the frozen and thawed cell product with a pharmaceutically acceptable carrier to form a pharmaceutical composition; and (f) administering the therapeutic amount of the cell product of (d) or the pharmaceutical composition of (e) comprising the activated and expanded cell product to the subject, wherein the therapeutic amount is effective to reduce tumor burden. According to one embodiment of the method, the amino acid sequence of a wild type OX40 Ligand codon optimized for human expression is SEQ ID NO: 108, the amino acid sequence of a wild type CD27 Ligand codon optimized for human expression is SEQ ID NO: 109, and the amino acid sequence of a wild type CD28 Ligand codon optimized for human expression is SEQ ID NO:110, SEQ ID NO: 111, or both. According to another embodiment, the engineered leukocyte stimulator cell population expressing one or more tumor specific antigens and genetically engineered to express a core group of three immunomodulatory molecules is additionally genetically engineered to express an additional number of immunomodulatory molecules comprising 3-25 immunomodulators ("R groups"). According to another embodiment, CD28 ligand comprises CD80, CD86 or both. According to another embodiment, the engineered leukocyte stimulator cell transduced or transformed to stably express the core immunomodulators OX40 Ligand, CD27 Ligand, and CD28 Ligand comprising CD80, CD86 or both is effective to synergistically induce a two-log expansion of activated CD8+ cells in peripheral blood mononuclear cells compared to an unmodified control cell line. According to another embodiment, in step (b)(i) subpopulations of the activated MNCs are identified and isolated by flow cytometry. According to another embodiment, the activated and expanded MNCs comprise activated and expanded supopulations of serial killer cells comprising one or more of an NK cell population, an NKT cell population, a CD8 CTL cell population, a CD4 cell population, and a TCRγδ cell population. According to another embodiment, the population of mononuclear cells is derived from peripheral blood or cord blood. According to another embodiment, the population of mononuclear cells is autologous to the subject. According to another embodiment, the population of mononuclear cells is allogeneic to the subject. According to another embodiment, cytotoxic serial killer activity of the activated and expanded serial killer cell populations is specific to cancer antigens of the genetically engineered leukocyte stimulator cells, without affecting normal cells. According to another embodiment, cytotoxic serial killer activity of the activated and expanded serial killer cell population(s) is effective to kill cancer cells regardless of cancer type, without affecting normal cells. According to another embodiment, the administering is in conjunction with a compatible inhibitor of immune checkpoints. According to another embodiment, the compatible immune checkpoints include one or more of PD-1, PD-L1, TIM-3, TIGIT, and LAG-3.

According to another aspect, the described invention provides a cell product comprising a population of expanded and activated mononuclear cells comprising activated subpopulations of cytotoxic serial killer cells prepared by a process comprising: (a) isolating a population of mononuclear cells (MNCs) from a biological sample; (b) preparing a population of engineered leukocyte stimulator cells comprising a population of tumor cells expressing one or more tumor specific antigens and genetically engineered to express a core group of three immunomodulator molecules wherein the core group of immunomodulator peptides is OX40 Ligand (OX40L), CD27 Ligand (CD70) and CD28 Ligand (CD28L); (c) contacting the population of MNCs of step (a) with the engineered leukocyte stimulator cells of step (b) in vitro to form an activated population of MNCs comprising activated subpopulations of cytotoxic serial killer cells; (d) expanding the activated population of MNCs comprising activated subpopulations of serial killer cells in vitro by culturing the activated MNCs to form the cell product comprising an activated and expanded population of MNCs comprising expanded and activated subpopulations of serial killer cells. According to one embodiment of the cell product prepared by the process, the activated and expanded MNCs comprising activated and expanded subpopulations of cytotoxic serial killer cells comprising one or more of an NK cell population, an NKT cell population, a CD8 CTL cell population, a CD4 cell population, and a TCRγδ cell population. According to another embodiment of the cell product prepared by the process, the cytotoxic serial killer cells are tumoricidal. According to another embodiment of the cell product prepared by the process, the amino acid sequence of a wild type OX40 Ligand codon optimized for human expression is SEQ ID NO: 108, the amino acid sequence of a wild type CD27 Ligand codon optimized for human expression is SEQ ID NO: 109, and the amino acid sequence of a wild type CD28 Ligand codon optimized for human expression is SEQ ID NO: 110, SEQ ID NO: 111, or both. According to another embodiment of the cell product prepared by the process the contacting in step (c) is effective to synergistically induce a two-log expansion of CD8+ cells. According to another embodiment of the cell product prepared by the process the biological sample is peripheral blood or cord blood.

These and other advantages of the invention will be apparent to those of ordinary skill in the art by reference to the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 54A and 54B show results of characterization of PBMC lymphocyte population induction by SK-MEL-2 derived engineered leukocyte stimulator cells (ENLST™ cells) compared to induction by unmodified SK-MEL-2 parental tumor cell line in vitro by phase contrast microscopy and flow cytometry. FIG. 54A shows day 9 PBMCs induced with unmodified parental 5K-MEL-2 cells, left, microscopy; right flow cytometry. FIG. 54B shows day 9 PBMC induced with 5K-MEL-2 derived 14-18-30 ENLST™ cells; left, microscopy, right flow cytometry. The oval outline in the flow cytometry in FIG. 54A corresponds to live unmodified SKMEL 2 parent tumor cells. The arrow in FIG. 54B shows that the ENLST™ cells are eliminated by the induced PBMCs.

FIG. 55A, FIG. 55C, and FIG. 55E show day 5, secondary mixed lymphocyte tumor response assay, FIG. 55A SK-MEL-2 derived ENLST™ cells coincubated with unmodified SK-MEL-2 cells; FIG. 55C unmodified SK-MEL-28 cells; FIG. 55E unmodified M14 cells. FIG. 55 B, FIG. 55D, and FIG. 55F show day 5, secondary mixed lymphocyte tumor response assay with SK-MEL-2 derived ENLST™ cell-activated MNCs coincubated with: FIG. 55B unmodified SK-MEL-2 cells; FIG. 55D, unmodified SK-MEL-28 cells; FIG. 55F unmodified M14 cells.

FIG. 56A shows a CyTOF mass cytometry single-cell phenotype analysis map of PBMC populations, FIGS. 56B, 56C, 56D, 56E, and 56F show visNE density contour plots of CyTOF staining following PBMC induction by parental (FIG. 56B) or immunomodulator expressing SK-MEL-2 derived ENLST™ cells (FIG. 56C, 56D 56D, 56E, 56F) after 9 days in primary mixed lymphocyte tumor response assay. FIG. 56B, shows a PBMC subpopulation shift following induction by parental SK MEL-2 cells; note that an NK cell population and a myeloid cell population are absent; FIG. 56C, shows a PBMC subpopulation shift following induction by ENLST™ cells transduced or transfected with vector 3, showing induction of B and myeloid cells. FIG. 56D, showing PBMC subpopulation shift following induction by ENLST™ cells transduced or transfected with vectors 3 and 4, showing induction of B cells; FIG. 56E, showing PBMC subpopulation shift following induction by ENLST™ cells transduced or transfected with vectors 3, 4 and 5, showing induction of B cells and Myeloid cells; FIG. 56F, showing PBMC subpopulation shift following induction by ENLST™ cells transduced or transfected with vectors 3, 4 and 6.

FIGS. 57A, 57B, 57C, 57D, and 57E show by flow cytometry (FIG. 57A) and phase contrast microscopy (FIG. 57B, FIG. 57C, FIG. 57D, and FIG. 57E) that PBMCs previously coincubated with 14-18-30 containing ENLST™ cells are able to lyse unmodified tumor cells. At least two distinct subpopulations of the PBMC's previously activated by coincubation with 14-18-30 ENLST™ cells are capable of cytolysis of unmodified tumor cells. FIG. 57A shows the sorting gates for CD56, CD3 and CD8 of PBMCs following a 9 day coincubation with 14-18-30 expressing ENLST™ cells in a primary mixed lymphocyte tumor cellassay; FIG. 57B shows CD56+CD3+ plus unmodified SKMEL2 at t=0 and (FIG. 57C) at t=8 hours; FIG. 57D shows CD56-CD3+ CD8+ plus unmodified SK-MEL-2 at t=0 and (FIG. 57E) at t=8 hours. The yellow arrows in FIG. 57B and FIG. 57D indicate that the smaller cells are lymphocytes and the larger cells allogeneic tumor cells. The yellow arrows in FIG. 57C and FIG. 57E indicate clusters of cytolytic cells surrounding allogeneic tumor cells and that the background is cleared of allogeneic tumor cells.

DETAILED DESCRIPTION

Definitions

Figure 1:
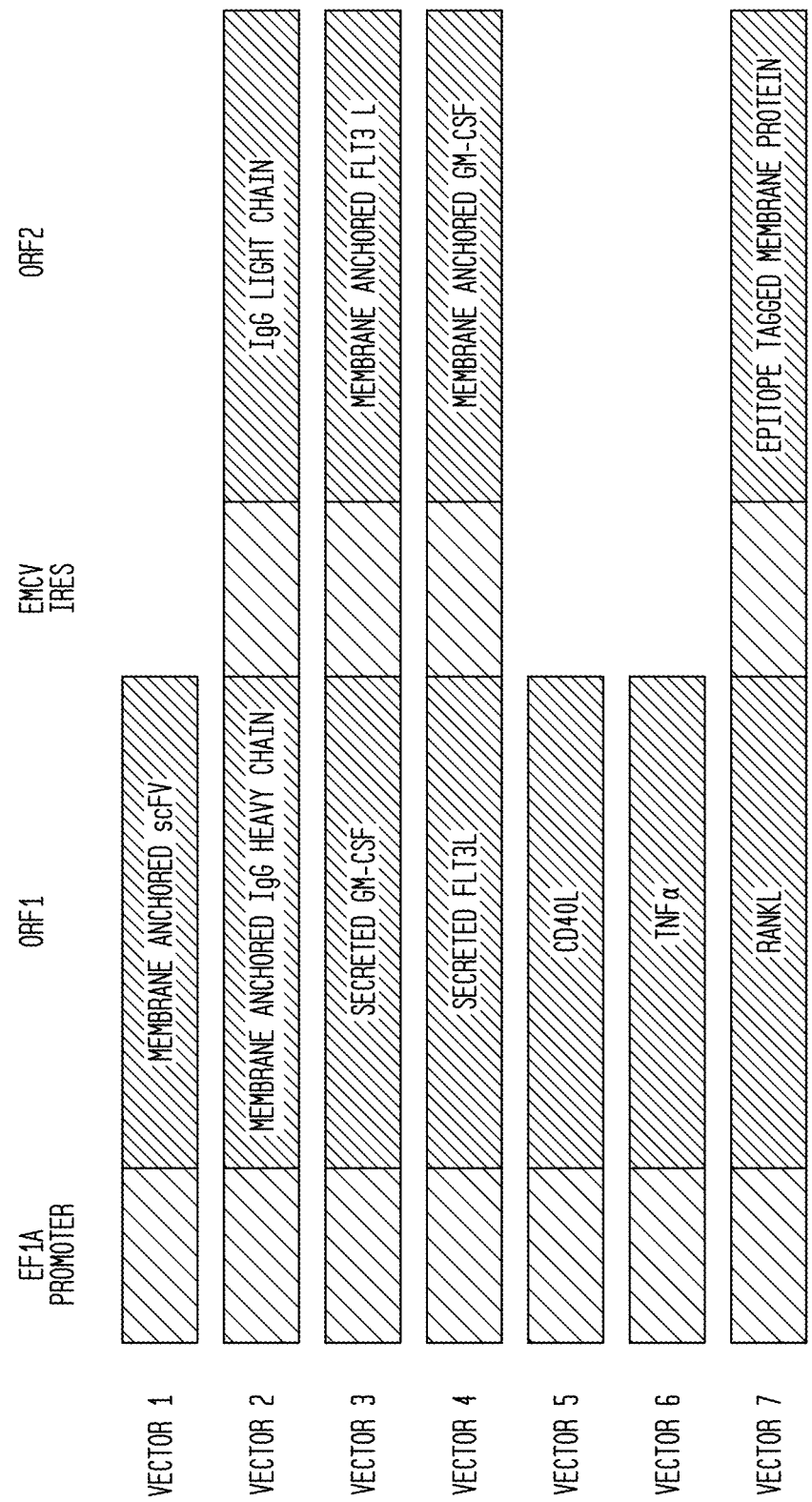
FIG. 1 shows a schematic of vectors 1 through 7.

As used herein and in the appended claims, the singular forms "a", "an", and "the" include plural reference unless the context clearly dictates otherwise. Thus, for example, reference to a "peptide" is a reference to one or more peptides and equivalents thereof known to those skilled in the art, and so forth.

As used herein, the term "about" means plus or minus 10% of the numerical value of the number with which it is being used. Therefore, about 50% means in the range of 40%-60%.

The term "activation" or "lymphocyte activation" refers to stimulation of lymphocytes by specific antigens, nonspecific mitogens, or allogeneic cells resulting in synthesis of RNA, protein and DNA and production of lymphokines; it is followed by proliferation and differentiation of various effector and memory cells. For example, a mature B cell can be activated by an encounter with an antigen that expresses epitopes that are recognized by its cell surface immunoglobulin Ig. The activation process may be a direct one, dependent on cross-linkage of membrane Ig molecules by the antigen (cross-linkage-dependent B cell activation) or an indirect one, occurring most efficiently in the context of an intimate interaction with a helper T cell ("cognate help process"). T-cell activation is dependent on the interaction of the TCR/CD3 complex with its cognate ligand, a peptide bound in the groove of a class I or class II MHC molecule. The molecular events set in motion by receptor engagement are complex. Among the earliest steps appears to be the activation of tyrosine kinases leading to the tyrosine phosphorylation of a set of substrates that control several signaling pathways. These include a set of adapter proteins that link the TCR to the ras pathway, phospholipase Cγ1, the tyrosine phosphorylation of which increases its catalytic activity and engages the inositol phospholipid metabolic pathway, leading to elevation of intracellular free calcium concentration and activation of protein kinase C, and a series of other enzymes that control cellular growth and differentiation. Full responsiveness of a T cell requires, in addition to receptor engagement, an accessory cell-delivered costimulatory activity, e.g., engagement of CD28 on the T cell by CD80 and/or CD86 on the APC. The soluble product of an activated B lymphocyte is immmunoglobulins (antibodies). The soluble product of an activated T lymphocyte is lymphokines.

The term "active immunization" as used herein refers to the production of active immunity, meaning immunity resulting from a naturally acquired infection or intentional vaccination (artificial active immunity). Active immunity can be induced by either natural or artificial mechanisms.

As used herein, the term "administration" and its various grammatical forms as it applies to a mammal, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. "Administration" also encompasses in vitro and ex vivo treatments, e.g., of a cell, by a reagent, diagnostic, binding composition, or by another cell.

The term "allogeneic" as used herein means that a donor and a recipient are of different genetic makeup, but of the same species. As used herein, an "allogeneic cell" refers to a cell that is not derived from the individual to which the cell is to be administered, that is, it has a genetic constitution different from the recipient individual. An allogeneic cell is generally obtained from the same species as the recipient individual to which the cell is to be administered. For example, the allogeneic cell can be a human cell, as disclosed herein, for administering to a human patient. As used herein, the term an "allogeneic serial killer cell population" refers to a serial killer cell population including its constituent cell types (such as NKs, NKTs, and CTLs) that is derived from a donor of genetic makeup different from the recipient individual to whom the allogeneic serial killer cell population is to be administered.

The term "allorecognition" as used herein refers to the recognition by T cells of MHC molecules (HLA in humans) other than self. The term "direct allorecognition" as used herein refers to the process by which CD4+ and CD8+ T cells recognize either intact allo-HLA molecules (HLA class II and I, respectively) on donor antigen-presenting cells (APCs). The term "indirect allorecognition" refers to the process by which APCs first engulf donor cells and then process donor antigen for redisplay to the recipient immune system; the recipient T cells then respond to processed donor HLA peptides in the context of recipient HLA molecules.

The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids. The amino acids may be L- or D-amino acids. An amino acid may be replaced by a synthetic amino acid, which is altered so as to increase the half-life of the peptide, increase the potency of the peptide, or increase the bioavailability of the peptide. The single letter designation for amino acids is used predominately herein. Such single letter designations are as follows: A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine. The following represents groups of amino acids that are conservative substitutions for one another: 1) Alanine (A), Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The term "antigen presenting cell" or "APC" as used herein refers to highly specialized cells that can process antigens and display their peptide fragments on the cell surface together with other co-stimulatory proteins required for activating naïve T cells. The main antigen presenting cells are dendritic cells (DCs), macrophages and B cells.

The term "autologous" as used herein means derived from the same individual.

The term "autocrine signaling" as used herein refers to a type of cell signaling in which a cell secretes signal molecules that act on itself or on other adjacent cells of the same type.

The term "binding" and its other grammatical forms means a lasting attraction between chemical substances.

The term "binding specificity" involves both binding to a specific partner and not binding to other molecules. Functionally important binding may occur at a range of affinities from low to high, and design elements may suppress undesired cross-interactions. Post-translational modifications also can alter the chemistry and structure of interactions. "Promiscuous binding" may involve degrees of structural plasticity, which may result in different subsets of residues being important for binding to different partners. "Relative binding specificity" is a characteristic whereby in a biochemical system, a molecule interacts with its targets or partners differentially, thereby impacting them distinctively depending on the identity of individual targets or partners.

CD3 (TCR complex) is a protein complex composed of four distinct chains. In mammals, the complex contains a CD3γ chain, a CD3δ chain, and two CD3ε chains, which associate with the T cell receptor (TCR) and the ζ-chain to generate an activation signal in T lymphocytes. Together, the TCR, the ζ-chain and CD3 molecules comprise the TCR complex. The intracellular tails of CD3 molecules contain a conserved motif known as the immunoreceptor tyrosine-based activation motif (ITAM), which is essential for the signaling capacity of the TCR. Upon phosphorylation of the ITAM, the CD3 chain can bind ZAP70 (zeta associated protein), a kinase involved in the signaling cascade of the T cell.

The term "cell line" as used herein, means a permanently established cell culture developed from a single cell and therefore consisting of a population of cells with a uniform genetic and functional makeup that will proliferate indefinitely.

The term "chemokine" as used herein refers to chemotactic cytokines, which constitute a family of low molecular mass (8-11 kDa) structurally-related proteins with diverse immune and neural functions (Mackay C. R. Nat Immunol., Vol. 2: 95-101, (2001); Youn B. et al. Immunol Rev. (2000) Vol. 177: 150-174) that can be categorized into four sub-families (C, CC, CXC and CX3C) based on the relative positions of conserved cysteine residues (Rossi D. et al. Annu Rev Immunol. (2000) 18: 217-242). Chemokines are essential molecules in directing leucocyte migration between blood, lymph nodes and tissues. They constitute a complex signaling network because they are not always restricted to one type of receptor (Loetscher P. et al. J. Biol. Chem. (2001). 276: 2986-2991). Chemokines affect cells by activating surface receptors that are seven-transmembrane-domain G-protein-coupled receptors. Leukocyte responses to particular chemokines are determined by their expression of chemokine receptors. The binding of the chemokine to the receptor activates various signaling cascades, similar to the action of cytokines that culminate in the activation of a biological response. Secretion of the ligands for the CCR5 receptor, regulated upon activation normal T cell expressed and secreted (RANTES), macrophage inflammatory protein (MIP)-1α/and MIP-1β (Schrum S. et al. J Immunol. (1996) 157: 3598-3604) and the ligand for CXC chemokine receptor 3 (CXCR3), induced protein (IP)-10 (Taub D. D. et al. J Exp Med. (1993) 177:1809-1814) have been associated with unwanted heightened TH1 responses. Additionally, elevated damaging pro-inflammatory cytokine levels of IL-2 and IFN-γ correlate with type 1 diabetes (T1D) (Rabinovitch A. et al. Cell Biochem Biophys. (2007) 48 (2-3): 159-63). Chemokines have been observed in TH1 pancreatic infiltrates and other inflammatory lesions characterized by T cell infiltration (Bradley L. M. et al. J Immunol. (1999). 162: 2511-2520).

The term "chemonaïve" as used herein means having or showing no experience with chemotherapy.

The term "chemotherapy" as used herein refers to a treatment that uses drugs to stop the growth of cancer cells.

The term "composition" as used herein refers to an aggregate material formed of two or more substances.

The term "contact" and its various grammatical forms as used herein refers to a state or condition of touching or of immediate or local proximity. Contacting a composition to a target destination may occur by any means of administration known to the skilled artisan.

The term "costimulatory molecule" as used herein refers to molecules that are displayed on the cell surface that have a role in enhancing the activation of a T cell that is already being stimulated through its TCR. For example, HLA proteins, which present foreign antigen to the T cell receptor, require costimulatory proteins which bind to complementary receptors on the T cell's surface to result in enhanced activation of the T cell. The term "co-stimulatory molecules" as used herein refers to highly active immunomodulatory proteins that play a critical role in the development and maintenance of an adaptive immune response (Kaufman and Wolchok eds., General Principles of Tumor Immunotherapy, Chpt 5, 67-121 (2007)). The two signal hypothesis of T cell response involves the interaction between an antigen bound to an HLA molecule and with its cognate T cell receptor (TCR), and an interaction of a co-stimulatory molecule and its ligand. Specialized APCs, which are carriers of a co-stimulatory second signal, are able to activate T cell responses following binding of the HLA molecule with TCR. By contrast, somatic tissues do not express the second signal and thereby induce T cell unresponsiveness (Id.). Many of the co-stimulatory molecules involved in the two-signal model can be blocked by co-inhibitory molecules that are expressed by normal tissue (Id.). In fact, many types of interacting immunomodulatory molecules expressed on a wide variety of tissues may exert both stimulatory and inhibitory functions depending on the immunologic context (Id.).

The term "cytokine" as used herein refers to small soluble protein substances secreted by cells, which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Cytokines can act both locally and distantly from a site of release. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of other cytokines. Nonlimiting examples of cytokines include e.g., IL-1α, IL-β, IL-2, IL-3, IL-4, IL-5, IL-6, IL-7, IL-8, IL-9, IL-10, IL-11, IL-12/IL-23 P40, IL13, IL-15, IL-17, IL-18, IL-21, IL-23, TGF-β, IFN-γ, GM-CSF, Gro-α, MCP-1 and TNF-α.

The term "derived from" as used herein encompasses any method for receiving, obtaining, or modifying something from a source of origin.

The term "derivative" or "variant" with respect to a peptide or DNA sequence (e.g. an immune modulator peptide sequence) as used herein refers to a non-identical peptide or DNA sequence that is modified from its original sequence. The terms "derivative" or "variant" with respect to cells as used herein refers to a tumor cell line that has been modified from its cell line of origin (e.g. modified to express recombinant DNA sequences).

The term "detectable marker" encompasses both selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like.

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

The term "dose" as used herein refers to the quantity of a therapeutic substance prescribed to be taken at one time.

The term "dye" (also referred to as "fluorochrome" or "fluorophore") as used herein refers to a component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1, ZsYellow1, DsRed2, DsRed monomer, AsRed2, mRFP1, HcRed1, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, X-rhodamine, Lissamine Rhodamine B, Texas Red, TruRed, and derivatives thereof.

The term "engineered leukocyte stimulator cells" (or "ENLST™ cells") as used herein refers to an allogeneic primary tumor cell line transfected or transduced with recombinant DNA sequences encoding at least 3 core immunomodulator peptides—OX40 Ligand, CD27 Ligand, and CD28 Ligand, comprising CD80, CD86 or both.

The term "enrich" as used herein refers to increasing the proportion of a desired substance, for example, to increase the relative frequency of a subtype of cell compared to its natural frequency in a cell population. Positive selection, negative selection, or both are generally considered necessary to any enrichment scheme. Selection methods include, without limitation, magnetic separation and fluorescence activated cell sorting (FACS). Regardless of the specific technology used for enrichment, the specific markers used in the selection process are critical, since developmental stages and activation-specific responses can change a cell's antigenic profile.

As used herein, the term "expression" encompasses the biosynthesis of mRNA, polypeptide biosynthesis, polypeptide activation, e.g., by post-translational modification, or an activation of expression by changing the subcellular location or by recruitment to chromatin.

The term "expression vector" refers to a DNA molecule comprising a gene that is expressed in a host cell. Typically, gene expression is placed under the control of certain regulatory elements including, but not limited to, promoters, tissue specific regulatory elements, and enhancers. Such a gene is said to be "operably linked to" the regulatory elements.

The term "flow cytometry" as used herein refers to a tool for interrogating the phenotype and characteristics of cells. It senses cells or particles as they move in a liquid stream through a laser (light amplification by stimulated emission of radiation)/light beam past a sensing area. The relative light-scattering and color-discriminated fluorescence of the microscopic particles is measured. Flow analysis and differentiation of the cells is based on size, granularity, and whether the cell is carrying fluorescent molecules in the form of either antibodies or dyes. As the cell passes through the laser beam, light is scattered in all directions, and the light scattered in the forward direction at low angles (0.5-10°) from the axis is proportional to the square of the radius of a sphere and so to the size of the cell or particle. Light may enter the cell; thus, the 90° light (right-angled, side) scatter may be labeled with fluorochrome-linked antibodies or stained with fluorescent membrane, cytoplasmic, or nuclear dyes. Thus, the differentiation of cell types, the presence of membrane receptors and antigens, membrane potential, pH, enzyme activity, and DNA content may be facilitated. Flow cytometers are multiparameter, recording several measurements on each cell; therefore, it is possible to identify a homogeneous subpopulation within a heterogeneous population (Marion G. Macey, Flow cytometry: principles and applications, Humana Press, 2007). Fluorescence-activated cell sorting (FACS), which allows isolation of distinct cell populations too similar in physical characteristics to be separated by size or density, uses fluorescent tags to detect surface proteins that are differentially expressed, allowing fine distinctions to be made among physically homogeneous populations of cells.

The term "functional equivalent" or "functionally equivalent" are used interchangeably herein to refer to substances, molecules, polynucleotides, proteins, peptides, or polypeptides having similar or identical effects or use.

The term "heteroclitic" is used herein to refer to variant peptides of higher biological potency than an original peptide. A "heteroclitic immunogen" is an immunogen that elicits an immune response, which cross-reacts with an original non-immunogenic or poorly immunogenic antigen.

The terms "immune response" and "immune-mediated" are used interchangeably herein to refer to any functional expression of a subject's immune system, against either foreign or self-antigens, whether the consequences of these reactions are beneficial or harmful to the subject.

The term "immunogen" and its various grammatical forms as used herein refers to a substance that elicits an immune response The terms "immunomodulatory", "immune modulator" and "immune modulatory" are used interchangeably herein to refer to a substance, agent, or cell that is capable of augmenting or diminishing immune responses directly or indirectly, e.g., by expressing chemokines, cytokines and other mediators of immune responses.

As used herein, the term "immunostimulatory amount" refers to an amount of an immunogenic composition that is effective to stimulate an immune response by a measurable amount, for example, as measured by ELISPOT assay (cellular immune response), ICS (intracellular cytokine staining assay) and major histocompatibility complex (MHC) tetramer assay to detect and quantify antigen-specific T cells, quantifying the blood population of antigen-specific CD4+ T cells, or quantifying the blood population of antigen specific CD8+ T cells, or where the increase is by at least 10%, at least 20%, at least 30%, at least 40%, at least 50%, at least 60%, at least 70%, at least 80%, at least 90%, at least 95%, at least 96%, at least 97%, at least 98%, at least 99%, at least 100%, when compared to a suitable control.

The term "induce" and its various grammatical forms as used herein with respect to immunity refers to a process or action of bringing about or giving rise to an immune response.

The term "inhibitor" as used herein refers to a second molecule that binds to, contacts or otherwise interferes with activity of a first molecule thereby decreasing the first molecule's activity.

The term "integrate into the genome" as used herein refers to a recombinant DNA sequence being concomitantly joined with and to the genomic DNA comprising a host cell's genome.

The term "isolated" is used herein to refer to material, such as, but not limited to, a nucleic acid, peptide, or cell, which is: (1) substantially or essentially free from components that normally accompany or interact with it as found in its naturally occurring environment. The terms "substantially free" or "essentially free" are used herein to refer to considerably or significantly free of other material, or more than about 95%, 96%, 97%, 98%, 99% or 100% free. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state.

The term "labeling" as used herein refers to a process of distinguishing a compound, structure, protein, peptide, antibody, cell or cell component by introducing a traceable constituent. Common traceable constituents include, but are not limited to, a fluorescent antibody, a fluorophore, a dye or a fluorescent dye, a stain or a fluorescent stain, a marker, a fluorescent marker, a chemical stain, a differential stain, a differential label, and a radioisotope.

The term "lymphocyte" refers to a small white blood cell (leukocyte) formed in lymphatic tissue throughout the body and in normal adults making up about 22-28% of the total number of leukocytes in the circulating blood, which plays a large role in defending the body against disease. Individual lymphocytes are specialized in that they are committed to respond to a limited set of structurally related antigens through recombination of their genetic material. This commitment, which exists before the first contact of the immune system with a given antigen, is expressed by the presence of receptors specific for determinants (epitopes) on the antigen on the lymphocyte's surface membrane. Each lymphocyte possesses a unique population of receptors, all of which have identical combining sites. One set, or clone, of lymphocytes differs from another clone in the structure of the combining region of its receptors and thus differs in the epitopes that it can recognize. Lymphocytes differ from each other not only in the specificity of their receptors, but also in their functions (Id.).

Two broad classes of lymphocytes are recognized: the B-lymphocytes (B-cells), which are precursors of antibody-secreting cells, and T-lymphocytes (T-cells).

B-Lymphocytes

B-lymphocytes are derived from hematopoietic cells of the bone marrow. A mature B-cell can be activated with an antigen that expresses epitopes recognized by its cell surface. The activation process may be direct, dependent on cross-linkage of membrane immunoglobulin (Ig) molecules by the antigen (cross-linkage-dependent B-cell activation), or indirect, via interaction with a helper T-cell, in a process referred to as cognate help. In many physiological situations, receptor cross-linkage stimuli and cognate help synergize to yield more vigorous B-cell responses (Paul, W. E., "Chapter 1: The immune system: an introduction," Fundamental Immunology, 4th Edition, Ed. Paul, W. E., Lippicott-Raven Publishers, Philadelphia, (1999)).

Cross-linkage dependent B-cell activation requires that the antigen express multiple copies of the epitope complementary to the binding site of the cell surface receptors, because each B-cell expresses Ig molecules with identical variable regions. Such a requirement is fulfilled by other antigens with repetitive epitopes, such as capsular polysaccharides of microorganisms or viral envelope proteins. Cross-linkage-dependent B-cell activation is a major protective immune response mounted against these microbes (Id.).

Cognate help allows B-cells to mount responses against antigens that cannot cross-link receptors and, at the same time, provides costimulatory signals that rescue B cells from inactivation when they are stimulated by weak cross-linkage events. Cognate help is dependent on the binding of antigen by the B-cell's membrane Ig, the endocytosis of the antigen, and its fragmentation into peptides within the endosomal/lysosomal compartment of the cell. Some of the resultant peptides are loaded into a groove in a specialized set of cell surface proteins known as class II major histocompatibility complex (MHC) molecules. The resultant class II/peptide complexes are expressed on the cell surface and act as ligands for the antigen-specific receptors of a set of T-cells designated as $CD4^+$ T-cells. The $CD4^+$ T-cells bear receptors on their surface specific for the B-cell's class II/peptide complex. B-cell activation depends not only on the binding of the T cell through its T cell receptor (TCR), but this interaction also allows an activation ligand on the T-cell (CD40 ligand) to bind to its receptor on the B-cell (CD40) signaling B-cell activation. In addition, T helper cells secrete several cytokines that regulate the growth and differentiation of the stimulated B-cell by binding to cytokine receptors on the B cell (Id.).

During cognate help for antibody production, the CD40 ligand (CD40L) is transiently expressed on activated $CD4^+$ T helper cells, and it binds to CD40 on the antigen-specific B cells, thereby transducing a second costimulatory signal. The latter signal is essential for B cell growth and differentiation and for the generation of memory B cells by preventing apoptosis of germinal center B cells that have encountered antigen. Hyperexpression of CD40L in both B and T cells is implicated in pathogenic autoantibody production in human SLE patients (Desai-Mehta, A. et al. J. Clin. Invest. Vol. 97(9), 2063-2073, (1996)).

T-Lymphocytes

T-lymphocytes, derived from precursors in hematopoietic tissue, undergo differentiation in the thymus, and are then seeded to peripheral lymphoid tissue and to the recirculating pool of lymphocytes. T-lymphocytes or T cells mediate a wide range of immunologic functions. These include the capacity to help B cells develop into antibody-producing cells, the capacity to increase the microbicidal action of monocytes/macrophages, the inhibition of certain types of immune responses, direct killing of target cells, and mobilization of the inflammatory response. These effects depend on T cell expression of specific cell surface molecules and the secretion of cytokines (Paul, W. E., "Chapter 1: The immune system: an introduction", Fundamental Immunology, 4th Edition, Ed. Paul, W. E., Lippicott-Raven Publishers, Philadelphia, (1999)).

T cells differ from B cells in their mechanism of antigen recognition. Immunoglobulin, the B cell's receptor, binds to individual epitopes on soluble molecules or on particulate surfaces. B-cell receptors therefore see epitopes expressed on the surface of native molecules. While antibodies and B-cell receptors evolved to bind to and to protect against microorganisms in extracellular fluids, T cells recognize antigens on the surface of other cells and mediate their functions by interacting with, and altering, the behavior of these antigen-presenting cells (APCs). There are three main types of APCs in peripheral lymphoid organs that can activate T cells: dendritic cells ("DCs), macrophages and B cells. The most potent of these are the DCs, whose only function is to present foreign antigens to T cells. Immature DCs are located in tissues throughout the body, including the skin, gut, and respiratory tract. When they encounter invading microbes at these sites, they endocytose the pathogens and their products, and carry them via the lymph to local lymph nodes or gut associated lymphoid organs. The encounter with a pathogen induces the DC to mature from an antigen-capturing cell to an APC that can activate T cells. APCs display three types of protein molecules on their surface that have a role in activating a T cell to become a T effector cell: (1) HLA proteins, which present foreign antigen to the T cell receptor; (2) costimulatory proteins which bind to complementary receptors on the T cell surface; and (3) cell-cell adhesion molecules, which enable a T cell to bind to the APC for long enough to become activated ("Chapter 24: The adaptive immune system," Molecular Biology of the Cell, Alberts, B. et al., Garland Science, NY, (2002)).

T-cells are subdivided into two distinct classes based on the cell surface receptors they express. The majority of T cells express T cell receptors (TCRs) consisting of $\alpha$ and $\beta$-chains. A small group of T cells express receptors made of $\gamma$ and $\delta$ chains. Among the $\alpha/\beta$ T cells are two sub-lineages: those that express the coreceptor molecule CD4 ($CD4^+$ T cells); and those that express CD8 ($CD8^+$ T cells). These cells differ in how they recognize antigen and in their effector and regulatory functions.

CD4+ T Cells.

$CD4^+$ T cells are the major regulatory cells of the immune system. Their regulatory function depends both on the expression of their cell-surface molecules, such as CD40L whose expression is induced when the T cells are activated, and the wide array of cytokines they secrete when activated. T cells also mediate important effector functions, some of which are determined by the patterns of cytokines they secrete. The cytokines can be directly toxic to target cells and can mobilize potent inflammatory mechanisms.

CD8+ T Cells.

In addition, T cells, particularly $CD8^+$ T cells, can develop into cytotoxic T-lymphocytes (CTLs) capable of efficiently lysing target cells that express antigens recognized by the CTLs (Paul, W. E., "Chapter 1: The immune system: an introduction," Fundamental Immunology, 4th Edition, Ed. Paul, W. E., Lippicott-Raven Publishers, Philadelphia, (1999)).

T cell receptors (TCRs) recognize a complex consisting of a peptide derived by proteolysis of the antigen bound to a specialized groove of a class II or class I HLA protein. $CD4^+$ T cells recognize only peptide/class II complexes while $CD8^+$ T cells recognize peptide/class I complexes (Id.).

The TCR's ligand (i.e., the peptide/HLA protein complex) is created within APCs. In general, class II MHC molecules bind peptides derived from proteins that have been taken up by the APC through an endocytic process. These peptide-loaded class II molecules are then expressed on the surface of the cell, where they are available to be bound by $CD4^+$ T cells with TCRs capable of recognizing the expressed cell surface complex. Thus, $CD4^+$ T cells are specialized to react with antigens derived from extracellular sources (Id.).

In contrast, class I HLA molecules are mainly loaded with peptides derived from internally synthesized proteins, such as viral proteins. These peptides are produced from cytosolic proteins by proteolysis by the proteosome and are translocated into the rough endoplasmic reticulum. Such peptides, generally composed of nine amino acids in length, are bound into the class I HLA molecules and brought to the cell surface, where they can be recognized by $CD8^+$ T cells expressing appropriate receptors. This gives the T cell system, particularly $CD8^+$ T cells, the ability to detect cells expressing proteins that are different from, or produced in much larger amounts than, those of cells of the remainder of the organism (e.g., viral antigens) or mutant antigens (such as active oncogene products), even if these proteins in their intact form are neither expressed on the cell surface nor secreted (Id.).

T cells can also be classified based on their function as helper T cells; T cells involved in inducing cellular immunity; suppressor T cells; and cytotoxic T cells.

Helper T Cells.

Helper T cells are T cells that stimulate B cells to make antibody responses to proteins and other T cell-dependent antigens. T cell-dependent antigens are immunogens in which individual epitopes appear only once or a limited number of times such that they are unable to cross-link the membrane Ig of B cells or do so inefficiently. B cells bind the antigen through their membrane Ig, and the complex undergoes endocytosis. Within the endosomal and lysosomal compartments, the antigen is fragmented into peptides by proteolytic enzymes, and one or more of the generated peptides are loaded into class II HLA molecules, which traffic through this vesicular compartment. The resulting peptide/class II HLA complex is then exported to the B-cell surface membrane. T cells with receptors specific for the peptide/class II molecular complex recognize this complex on the B-cell surface. (Id.).

B-cell activation depends both on the binding of the T cell through its TCR and on the interaction of the T-cell CD40L with CD40 on the B cell. T cells do not constitutively express CD40L. Rather, CD40L expression is induced as a result of an interaction with an APC that expresses both a cognate antigen recognized by the TCR of the T cell and CD80 or CD86. CD80/CD86 is generally expressed by activated, but not resting, B cells so that the helper interaction involving an activated B cell and a T cell can lead to efficient antibody production. In many cases, however, the initial induction of CD40L on T cells is dependent on their recognition of antigen on the surface of APCs that constitutively express CD80/86, such as DCs. Such activated helper T cells can then efficiently interact with and help B cells. Cross-linkage of membrane Ig on the B cell, even if inefficient, may synergize with the CD40L/CD40 interaction to yield vigorous B-cell activation. The subsequent events in the B-cell response, including proliferation, Ig secretion, and class switching of the Ig class being expressed, either depend or are enhanced by the actions of T cell-derived cytokines (Id.).

CD4$^+$ T cells tend to differentiate into cells that principally secrete the cytokines IL-4, IL-5, IL-6, and IL-10 ($T_H2$ cells) or into cells that mainly produce IL-2, IFN-$\gamma$, and lymphotoxin ($T_H1$ cells). The $T_H2$ cells are very effective in helping B-cells develop into antibody-producing cells, whereas the $T_H1$ cells are effective inducers of cellular immune responses, involving enhancement of microbicidal activity of monocytes and macrophages, and consequent increased efficiency in lysing microorganisms in intracellular vesicular compartments. Although CD4$^+$ T cells with the phenotype of $T_H2$ cells (i.e., IL-4, IL-5, IL-6 and IL-10) are efficient helper cells, $T_H1$ cells also have the capacity to be helpers (Id.).

T Cell Involvement in Cellular Immunity Induction.

T cells also may act to enhance the capacity of monocytes and macrophages to destroy intracellular microorganisms. In particular, interferon-gamma (IFN-$\gamma$) produced by helper T cells enhances several mechanisms through which mononuclear phagocytes destroy intracellular bacteria and parasitism including the generation of nitric oxide and induction of tumor necrosis factor (TNF) production. $T_{H1}$ cells are effective in enhancing the microbicidal action, because they produce IFN-$\gamma$. In contrast, two of the major cytokines produced by $T_{H2}$ cells, IL-4 and IL-10, block these activities (Id.).

Cytotoxic T Lymphocytes.

CD8$^+$ T cells that recognize peptides from proteins produced within the target cell have cytotoxic properties in that they lead to lysis of the target cells. The mechanism of CTL-induced lysis involves the production by the CTL of perforin, a molecule that can insert into the membrane of target cells and promote the lysis of that cell. Perforin-mediated lysis is enhanced by granzymes, a series of enzymes produced by activated CTLs. Many active CTLs also express large amounts of Fas ligand on their surface. The interaction of Fas ligand on the surface of CTL with Fas on the surface of the target cell initiates apoptosis in the target cell, leading to the death of these cells. CTL-mediated lysis appears to be a major mechanism for the destruction of virally infected cells.

Regulatory T (Treg) Cells.

Immune homeostasis is maintained by a controlled balance between initiation and downregulation of the immune response. The mechanisms of both apoptosis and T cell anergy (a tolerance mechanism in which the T cells are intrinsically functionally inactivated following an antigen encounter) contribute to the downregulation of the immune response (Scwartz, R. H. Annu. Rev. Immunol., 21: 305-334 (2003)). A third mechanism is provided by active suppression of activated T cells by suppressor or regulatory CD4$^+$ T (Treg) cells (Reviewed in Kronenberg, M. et al. Nature, 435: 598-604 (2005)). CD4$^+$ Tregs that constitutively express the IL-2 receptor alpha (IL-2Ra) chain (CD4$^+$CD25$^+$) are a naturally occurring T cell subset that are anergic and suppressive (Taams, L. S. et al. Eur. J. Immunol. 31: 1122-1131 (2001)). Depletion of CD4$^+$CD25$^+$ Tregs results in systemic autoimmune disease in mice. Furthermore, transfer of these Tregs prevents development of autoimmune disease. Human CD4$^+$CD25$^+$ Tregs, similar to their murine counterpart, are generated in the thymus and are characterized by the ability to suppress proliferation of responder T cells through a cell-cell contact-dependent mechanism, the inability to produce IL-2, and the anergic phenotype in vitro. Human CD4$^+$CD25$^+$ T cells can be split into suppressive (CD25$^{high}$) and nonsuppressive (CD25$^{low}$) cells, according to the level of CD25 expression. A member of the forkhead family of transcription factors, FOXP3, has been shown to be expressed in murine and human CD4$^+$CD25$^+$ Tregs and appears to be a master gene controlling CD4$^+$CD25$^+$ Treg development (Battaglia, M. et al. J. Immunol., 177: 8338-8347, (2006)).

T-Memory Cells.

Following the recognition and eradication of pathogens through adaptive immune responses, the vast majority (90-95%) of T cells undergo apoptosis with the remaining cells forming a pool of memory T cells, designated central memory T cells ($T_{CM}$), effector memory T cells ($T_{EM}$), and resident memory T cells ($T_{RM}$) (Clark, R. A. Sci. Transl. Med., 7, 269rv1, (2015)).

Compared to standard T cells, these memory T cells are long-lived with distinct phenotypes, such as expression of specific surface markers, rapid production of different cytokine profiles, capability of direct effector cell function, and unique homing distribution patterns. Memory T cells exhibit quick reactions upon re-exposure to their respective antigens in order to eliminate the reinfection by the offender and thereby restore balance of the immune system rapidly. Increasing evidence substantiates that autoimmune memory T cells hinder most attempts to treat or cure autoimmune diseases (Id.).

Dendritic Cells (DCs)

DCs reside in the tissues and play a key role in initiating and controlling the magnitude and quality of the adaptive immune response. Immature DCs act as sentinels for potentially dangerous signals from cancer cells or microbes and have strong phagocytic antigen capturing abilities. Upon receiving maturation stimuli, immature DCs lose adhesion molecule expression, undergo cytoskeleton reorganization, and migrate to the draining lymph node. Mature DCs are professional antigen presenting cells and have increased MHC class II and costimulatory molecule expression on their cell surface. The innate immune response detects molecules typical of pathogens using pattern recognition receptors that are germline encoded to recognize a limited number of patterns. These receptors include Toll-like receptors, cell surface C-type lectine receptors, and intracytoplasmic nucleotide oligomerization domain (NOD)-like receptors (See discussion infra; see also Alberts, D. S., and L. M. Hess, editors. Fundamentals of Cancer Prevention. Springer Nature, 2019).

Monocytes (MOs) and Macrophages (MΦs)

Monocytes (MOs), macrophages (MΦs), and tumor-associated macrophages (TAMs) are part of the myeloid family (a group of hematopoietic derived cells). Monocytes are direct precursors of hematopoietic stem cell-derived macrophages. After their recruitment into a tumor tissue, they can differentiate into tumor-associated macrophages (TAMs), a cell population with high phenotypic and pro-tumor function heterogeneous diversity. They have been found to support tumor initiation, local progression and distant metastis (Richards, David M, et al. "Monocytes and Macrophages in Cancer: Development and Functions." *Cancer Microenvironment: Official Journal of the International Cancer Microenvironment Society*, Springer Netherlands, August 2013, www.ncbi.nlm.nih.gov/pmc/articles/PMC3). However, other research has shown that TAMs have anti-tumor properties as well.

MO cells are largely found in bone marrow but are additionally found in the blood and spleen. Research shows that MO cells can also be generated by extra-medullary hematopoiesis in the spleen and increase under inflammatory conditions, such as the presence of cancer. MOs generated from hematopoietic stem cells (HSCs) undergo a sequential process of differentiation and commitment steps collectively called monopoiesis. Monopoiesis is tightly regulated by microenvironmental cues, modulating gene expression in developing cells and leading to the often irreversible, phenotypic and functional changes associated with hematopoietic differentiation. While it is known that cytokines such as M-CSF, GM-CSF, and IL-3 play a role in monopoiesis, other relatively unstudied factors, such as stromal cells, or extracellular matrix (ECM) components, may also have an impact on monopoiesis. (Id).

Different subsets of monocytes are generated from HSCs in the bone marrow via monopoiesis which proceeds via distinct proliferator progenitor stages, such as, common myeloid progenitors (CMP), granulocyte/macrophage progenitors (GMP), to the macrophage dendritic cell progenitor (MDP) that serves as a precursor for MOs, macrophages (MΦs) and DCs. Once differentiated into MOs, they can be organized into two groups: "classical" Ly6C$^{high}$ (non-patrolling) and "non-classical" Ly6C$^{low}$ (patrolling) MOs, however it should be noted that the phenotypic or behavioral importance is not completely understood between these two subsets. The monocyte subsets are mobilized from the bone marrow into the blood stream where they form a local reservoir in the spleen; in the spleen, they can be re-mobilized in response to injury or inflammation. In times of steady-state homeostasis, blood monocytes are recruited to different tissues where they give rise to MO-derived MΦs and DC's involved in tissue development and maintenance of homeostasis. (Id). On the contrary, in the presence of tumors, MOs may give rise to populations of immune-suppressive TAMs and monocytic MDSCs at the tumor microenvironment where they may promote tumor progression and immune evasion.

MΦs in tissue support homeostatic or trophic processes for tissue development/remodeling in developing or healing tissues. The mechanisms involved in this support include phagocytosis, growth factor production, angiogenesis and degradation of ECM components. In response to immunogenic signals, such as TLR signals or inflammatory cytokines, the functional properties of macrophages are polarized towards processes needed for immunity and pathogen defense. These include pathogen phagocytosis, release of cytotoxic reactive oxygen/reactive nitrogen species (RO/RNS), production of pro-inflammatory cytokines, and HLA class II-mediated antigen presentation. (See id).

MΦs can be organized on a linear scale according to polarization status, i.e., from pro-inflammatory M1-MΦs (classically activated) to anti-inflammatory M2-MΦs (alternatively activated). TAMs are produced when tumor derived factors attract and then differentiate into MΦs Similar to non-TAM MΦs, TAMs display phenotypic and functional heterogeneous diversity, which depends on the type of tissue and tumor, stage of tumor progression, and location within tumor tissue. For example, increased density of M2-like TAMs is a marker of poor prognosis in certain types of cancer (such as breast, cervical, and bladder cancer) whereas increased density of M1-like TAMs is a marker of better prognosis in other types of cancers (such as prostate, lung, and brain).

TAMs can influence nearly every stage of tumor development and progression. Research has shown that they have a wide variety of anti-tumor functions, including the production of cytotoxic factors, phagocytosis of tumor cells (such as metastatic cells), and participation in cancer immune-editing. (See Bingle L, Brown N J, Lewis C E. The role of tumor-associated macrophages in tumor progression: implications for new anticancer therapies. J Pathol. (2002) 196: 254-265; see also O'Sullivan T, Saddawi-Konefka R, Vermi W, Koebel C M, Arthur C, White J M, Uppaluri R, Andrews D M, Ngiow S F, Teng M W, Smyth M J, Schreiber R D, Bui J D. Cancer immunoediting by the innate immune system in the absence of adaptive immunity. J Exp Med. (2012) 209: 1869-1882).

Research has shown that TAMs may be polarized towards anti-tumor function. For example, activation of the CD40 pathway has been reported to program TAMs to upregulate expression of MHC class II and costimulatory molecule CD86 accumulation in tumor tissue and result in TAM-mediated lysis of tumor cells. IL-12 and TNF-α mediated treatment has also been reported to program TAMs to display their anti-tumor effector function. (See Watkins S K, Egilmez N K, Suttles J, Stout R D. IL-12 rapidly alters the functional profile of tumor-associated and tumor-infiltrating macrophages in vitro and in vivo. J Immunol. (2007) 178: 1357-1362). CD47 serves as an anti-phagocytic signal by binding to SIRPα, a protein expressed on MΦs and DCs. Blocking CD47 activity or blocking SIRPα access has been found to result in MΦ dependent phagocytosis of tumor cells. (See Chao M P, Weissman I L, Majeti R. The CD47-SIRPalpha pathway in cancer immune evasion and potential therapeutic implications. Curr Opin Immunol. (2012) 24: 225-232).

MOs, MΦs, DCs and related cells are currently identified by the phenotypic markers shown in Table 1.

TABLE 1

MOs, MΦs, and DC Phenotypes.

| Population | Subset | Phenotype |
|---|---|---|
| HSC | — | CD34−, CD38, CD48−, CD59, CD133, CD135−, CD150+, CD135(Flt3), CD338, Lin−, GATA-3, TdT |
| CMP | — | CD33, CD34−, CD45RA, CD123, CD131, CD135(Flt3), CD173, CD174, Lin−, IL-7, Rα−, FcγRlow, Ikaros, PU.1 |
| GMP | — | CD34−, IL-7, Rα−, FcγRlow |
| MDP | — | CD11b− CD115+ CD135+ CX3CR1+ Ly6C− Ly6G− |
| MO cells | Ly6C$^{high}$ Mo | CD14, CD33, CD172a (SIRPa), CD11b$^+$ CD115$^+$ CD135$^-$ CX3CR1$^{low}$ Ly6C$^{high}$ Ly6G$^-$ CCR2$^+$ F4/80$^{low}$ |
| MΦ cells | Monocyte-derived MΦ | CD11b$^{++}$ F4/80$^+$ |
| | M1 | CD16, CD16/CD32, CD32, CD64, CD68, Cd80, Cd86, Cd369 (Dectin-1), Mer (MerTK), MHCII, IRF5, STAT1 |
| | M2 | CD115, CD204, CD163, CD206 (MMR), CD209 (DC-SIGN), FceR1, VSIG4, IRF4, STAT6 |
| | TAMs | AXL, CD192 (CCR2), CD14, Cd68, CD115, Cd163, CD206, CD369 (Dectin-1), HLA-DR, CD273 (PD-L2), NOS2 |
| DC | SIGN-DC | CD11b$^+$ CD115$^-$ CD209a/DC-SIGN$^+$ |
| | Mo-DC | CD11c$^{high}$ Ly6C$^-$ Ly6G$^-$ F4/80$^{low}$ |
| | Plasmacytoid | CD85g (ILT7), CD123, CD283 (TLR3), CD303 (BCDA-2), CD304 (BDCA-4), CD370 (CLEC9A), CD287 (TLR7), CD289 (TLR9), E2-2, IRF8 |
| | CX3CR1+ lp Mo-DC | CD11b$^+$ CD14$^+$ CX3CR1$^{int/high}$ CD103$^-$ CD11c$^{high/int}$ |
| | Tip-DC | CD11b$^+$CD11c$^{int}$ Tnf-α$^+$ iNOS$^+$ CX3CR1$^+$ Ly6C$^+$ Ly6G$^-$ CCR2$^+$ |
| MDSC | MO-MDSC | CD11b+$^+$ CD115$^+$ Ly6C$^{high}$ Ly6G$^-$ CCR2$^+$ F4/80$^{low}$ |

The terms "Major Histocompatability Complex (MHC), MHC-like molecule" and "HLA" are used interchangeably herein to refer to cell-surface molecules that display a molecular fraction known as an epitope or an antigen and mediate interactions of leukocytes with other leukocyte or body cells. MHCs are encoded by a large gene group and can be organized into three subgroups—class I, class II, and class III. In humans, the MHC gene complex is called HLA ("Human leukocyte antigen"); in mice, it is called H-2 (for "histocompatibility"). Both species have three main MHC class I genes, which are called HLA-A, HLA-B, and HLA-C in humans, and H2-K, H2-D and H2-L in the mouse. These encode the α chain of the respective MHC class I proteins. The other subunit of an MHC class I molecule is β2-microglobulin. The class II region includes the genes for the α and β chains (designated A and B) of the MHC class II molecules HLA-DR, HLA-DP, and HLA-DQ in humans. Also in the MHC class II region are the genes for the TAP1:TAP2 peptide transporter, the PSMB (or LMP) genes that encode proteasome subunits, the genes encoding the DMα and BMβ chains (DMA and DMB), the genes encosing the α and β chains of the DO molecule (DOA and DOB, respectively), and the gene encoding tapasin (TAPBP). The class II genes encode various other proteins with functions in immunity. The DMA and DMB agenes conceding the subunits of the HLA-DM molecule that catalyzes peptide binding to MHC class II molecules are related to the MHC class II genes, as are the DOA and DOB genes that encode the subunits of the regulatory HLA-DO molecule. Janeways Immunobiology. 9th ed., GS, Garland Science, Taylor & Francis Group, 2017. pps. 232-233.

MHC-like molecules, while not encoded by the same gene group as true MHCs, have the same folding and overall structure of MHCs, and specifically MHC class I molecules, and thus possesses similar biological functions such as antigen presentation. The CD1 family of molecules is an example of a MHC-like molecule. It consists of two groups based on amino acid homology: group 1, which includes CD1a, b, and c; and group 2, which consists of CD1d. Group 1 CD1s can present antigens to a wide variety of T cells, whereas CD1d presents antigens mostly to NKT cells. (Brutkiewicz. "CD1d Ligands: The Good, the Bad, and the Ugly." The Journal of Immunology (2006) 177 (2) 769-775). While CD1d structurally resembles MHC Class I molecules, it traffics through the endosome of the exogenous antigen presentation pathway. The binding groove of the CD1d molecules tethers the lipid tail of a glycolipid antigen, while the carbohydrate head group of the antigen projects out of the groove for recognition by the TCR of the NKT cell. (Wah, MakTak, et al. "Chapter 11: NK, γδ T and NKT Cells." Primer to the Immune Response. Elsevier, 2014).

CD1d presents lipid antigens, and requires the presence of particular mechanisms to induce uptake of these molecules by APCs and subsequent loading onto CD1d molecules. Lipid transfer protein such as apolipoprotein E and fatty acid amide hydrolase (FAAH) have been shown to enhance the presentation of certain antigens by CD1d. Loading efficiency can be enhanced by specific proteins, such as saposins and microsomal triglyceride transfer protein, present in the endosomal and lysosomal compartments of cells by promoting lipid antigen exchange Similar to MHC antigens, lipid antigens can also be processed by lysosomal enzymes to yield active compounds, as demonstrated in the case of CD1d for synthetic antigens, microbial antigens, and self-antigens. Giradi and Zajonc (2012). "Molecular basis of lipid antigen presentation by CD1d and recognition by natural killer T cells." Immunol Rev. 250(1): 167-179.

MHC Class I-like molecules are nonclassical MHC type molecules, while including Cd1d also include CD1a, CD1b, CD1c, CD1e, and MR1 are also expressed on APCs and can activate various subsets of T cells. Kumar and Delovitch (2014) "Different subsets of natural killer T cells may vary in their roles in health and disease." Immunology 142: 321-336. Other non-classical histocompatibility molecules include MR1, which activate MAIT cells.

The terms "marker" or "cell surface marker" are used interchangeably herein to refer to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

The terms "mixed lymphocyte reaction" or "MLR" are used interchangeably herein to refer to an in vitro cellular immune assay that occurs between two allogeneic lymphocyte populations. In the classic mixed lymphocyte reaction (MLR), suspensions of responder T cells are cultured with allogeneic (donor) stimulator cells. The foreign MHC class I or class II molecules expressed on the allogeneic stimulator cells serve as the activating stimulus to the responding T lymphocytes. Proliferation of responding T lymphocytes then is measured. Stimulator cell populations that also contain T-cells will replicate in the presence of the responder cells (two-way mixed lymphocyte reaction). For a one-way mixed lymphocyte reaction, stimulator cells are prevented from replicating by, e.g., irradiation or treatment with mitomycin C, to prevent cell replication.

The terms "mixed lymphocyte tumor reaction" or "MLTR" are used interchangeably herein to refer to a reaction similar to a mixed lymphocyte reaction in which rather than using allogeneic lymphocytes to stimulate a response, allogeneic tumor cells are used. The MLTR method comprises contacting a mixed lymphocyte population with allogeneic tumor cells. One or more of cellular proliferation of the lymphocytes, cellular subset differentiation of the lymphocytes, cytokine release profile of the lymphocytes, and tumor cell death, is measured.

The term "modify" as used herein refers to a change of the form or qualities of.

The term "modulate" as used herein means to regulate, alter, adapt, or adjust to a certain measure or proportion. Such modulation may be any change, including an undetectable change. The terms "modified" or "modulated" as used herein in the context of serial killer cell types, such as NKCs, CTLs, and NKTs refers to changing the form or character of the cell type via one or more recombinant DNA techniques such that the immunostimulatory effect or immunosuppressive effect of the respective modified serial killer cell is reproducibly different from the respective parent serial killer cells.

The term "mononuclear cells" as used herein refers to cells having a single round nucleus such as, for example, lymphocytes (e.g., T cells, B cells, NK cells), monocytes and macrophages.

The term "myeloid suppressor cells" or "myeloid-derived suppressor cells", or "MDSCs" as used herein refers to a heterogeneous population of cells characterized by myeloid origin, immature state, and ability to potently suppress T cell responses. These cells regulate immune responses and tissue repair in healthy individuals and the population rapidly expands during inflammation.

The term "nucleic acid" is used herein to refer to a deoxyribonucleotide or ribonucleotide polymer in either single- or double-stranded form, and, unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" is used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The term "open reading frame" as used herein refers to a sequence of nucleotides in a DNA molecule that has the potential to encode a peptide or protein: it starts with a start triplet (ATG), is followed by a string of triplets each of which encodes an amino acid, and ends with a stop triplet (TAA, TAG or TGA).

The phrase "operably linked" refers (1) to a first sequence(s) or domain being positioned sufficiently proximal to a second sequence(s) or domain so that the first sequence(s) or domain can exert influence over the second sequence(s) or domain or a region under control of that second sequence or domain; and (2) to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, are in the same reading frame. According to some embodiments, the phrase "operatively linked" refers to a linkage in which two or more protein domains or polypeptides are ligated or combined via recombinant DNA technology or chemical reaction such that each protein domain or polypeptide of the resulting fusion protein retains its original function.

The term "overall survival" (OS) as used herein refers to the length of time from either the date of diagnosis or the start of treatment for a disease that patients diagnosed with the disease are still alive.

As used herein, the term "paracrine signaling" refers to short range cell-cell communication via secreted signal molecules that act on adjacent cells.

The term "parenteral" and its other grammatical forms as used herein refers to administration of a substance occurring in the body other than by the mouth or alimentary canal. For example, the term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), or infusion techniques.

The term "passive immunization" as used herein refers to the production of passive immunity, meaning immunity acquired from transfer of antibodies either naturally, as from mother to fetus, or by intentional inoculation (artificial passive immunity). Passive immunity can be induced by either natural or artificial mechanisms. Where antibodies are transferred, the passive immunity, with respect to the particular antibodies transferred, is specific. Passive cell-mediated immunity is produced by the transfer of living lymphoid cells from an immune cell source is sometimes referred to as adoptive or acquired immunity.

The terms "peripheral blood mononuclear cells" or "PBMCs" are used interchangeably herein to refer to mononuclear cells derived from peripheral blood.

The term "pharmaceutical composition" as used herein refers to a composition that is employed to prevent, reduce in intensity, cure or otherwise treat a target condition, syndrome, disorder or disease. The terms "formulation" and "composition" are used interchangeably herein to refer to a product of the described invention that comprises all active and inert ingredients.

The term "pharmaceutically acceptable carrier" as used herein refers to any substantially non-toxic carrier conventionally useable for administration of the active agent of the described invention in which the active agent will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine, and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation, and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well. According to some embodiments, the peptide is of any length or size.

The terms "protein domain" and "domain" are used interchangably to refer to a portion of a protein that has its own tertiary structure. Large proteins are generally composed of several domains connected to one another via flexible regions of polypeptide chain.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity." (a) The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence. (b) The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches. Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., Nucleic Acids Research 16:10881-90 (1988); Huang, et al., Computer Applications in the *Biosciences,* 8:155-65 (1992), and Pearson, et al., *Methods in Molecular Biology,* 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995). Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) *Proc. Natl. Acad. Sci. USA* 89:10915). In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar A number of low-complexity filter programs may be employed to reduce such low-complexity alignments. For example, the SEG (Wooten and Federhen, *Comput. Chem.,* 17:149-163 (1993)) and XNU (Claverie and States, *Comput. Chem.,* 17:191-201 (1993)) low-complexity filters may be employed alone or in combination. (c) The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4:11-17 (1988) e.g., as implemented in the program PC/GENE (Intelligenetics, Mountain View, Calif., USA). (d) The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. (e) The term "substantial identity" of polynucleotide sequences means that a polynucleotide comprises a sequence that has at least 60% sequence identity, at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid. Mutations may also be made to the nucleotide sequences of the present proteins by reference to the genetic code, including taking into account codon degeneracy.

The term "prime" (or "priming") as used herein refers to a process of increasing sensitivity to. When used in an immunological sense it refers to a process whereby T cells and B cell precursors encounter the antigen for which they are specific. The term "unprimed cells" (also referred to as virgin, naïve, or inexperienced cells) as used herein refers to T cells and B cells that have generated an antigen receptor (TCR for T cells, BCR for B cells) of a particular specificity, but have never encountered the antigen. For example, before helper T cells and B cells can interact to produce specific antibody, the antigen-specific T cell precursors must be primed. Priming involves several steps: antigen uptake, processing, and cell surface expression bound to class II MHC molecules by an antigen presenting cell, recirculation and antigen-specific trapping of helper T cell precursors in lymphoid tissue, and T cell proliferation and differentiation (Janeway, C A, Jr., Semin. Immunol. (1989) 1(1): 13-20). Helper T cells express CD4, but not all CD4 T cells are helper cells (Id.). The signals required for clonal expansion of helper T cells differ from those required by other CD4 T cells. The critical antigen-presenting cell for helper T cell priming appears to be a macrophage; and the critical second signal for helper T cell growth is the macrophage product interleukin 1 (IL-1) (Id.). If the primed T cells and/or B cells receive a second, co-stimulatory signal, they become activated T cells or B cells.

The term "progression free survival" or "PFS" as used herein refers to length of time during and after the treatment of a disease, such as an autoimmune disease, that a patient lives with the disease but it does not get worse. In a clinical trial, measuring the progression free survival is one way to determine how well a new treatment works.

The term "purification" and its various grammatical forms as used herein refers to the process of isolating or freeing from foreign, extraneous, or objectionable elements. The trm "purified substance" therefore refer to a substance freed from foreign, extraneous, or objectionable elements.

The term "reporter gene" ("reporter") or "assay marker" refers to a gene and/or peptide that can be detected, or easily identified and measured. The expression of the reporter may be measured at either the RNA level, or at the protein level. The gene product, which may be detected in an experimental assay protocol, includes, but is not limited to, marker enzymes, antigens, amino acid sequence markers, cellular phenotypic markers, nucleic acid sequence markers, and the like. Researchers may attach a reporter gene to another gene of interest in cell culture, bacteria, animals, or plants. For example, some reporters are selectable markers, or confer characteristics upon on organisms expressing them allowing the organism to be easily identified and assayed. To introduce a reporter gene into an organism, researchers may place the reporter gene and the gene of interest in the same DNA construct to be inserted into the cell or organism. For bacteria or eukaryotic cells in culture, this may be in the form of a plasmid. Commonly used reporter genes may include, but are not limited to, fluorescent proteins, luciferase, beta-galactosidase, and selectable markers, such as chloramphenicol and kanomycin.

The term "serial killer cell" as used herein refers to a population of cells that exhibit an ability to kill multiple tumor or pathogen-infected cells, while showing resistance to such killing action. There are multiple kinds of cells that display this effector function, e.g., NK cells, NKT cells, LAK cells, CIK cells, MAIT cells, CD8+ CTLs, CD4+ CTLs. The serial killer effector function may be direct, through cytolytic or cytotoxic activities, or indirect, through the immunoregulation of other cells and proteins that target pathogenic and cancerous cells.

Effector Serial Killer Cells

Serial killer cells of the immune system may provide rapid immunity against pathogens through their serial killing action. There are multiple kinds of cells that display this effector function. According to some embodiments, serial killer cells include Natural Killer (NK) cells, Natural Killer T (NKT) cells, CD8+ Cytolytic T lymphocytes (CTLs), and CD4+ CTLs. The serial killing function is defined as an ability to kill multiple tumor or pathogen infected cells, while showing resistance to such killing action. The serial killer effector function may be direct, through cytolytic or cytotoxic activities, or indirect, through the immunoregulation of other cells and proteins that target pathogenic and cancerous cells.

Although the activation pathway may differ, serial killer cells can kill target cells directly through a perforin/granzyme or granulysin mechanism. The first step of the cytotoxic process is target cell recognition that can be specific (in the case of CTLs) or nonspecific (in the case of NKs and NKTs). Then a lytic synapse is formed between the serial killer cell and the target cell. Adhesion molecules (such as the integrin LFA-1 with its ligands ICAM-1 or ICAM-2) on target cells result in the polarization of cytotoxic granules towards the immunological synapse. When Ig-superfamily receptor DNAM-1 (CD226), which is expressed by a number of immune cells such as NKs, T cells, and B cells, associates with adhesion molecules on the serial killer cell surface, it becomes phosphorylated and has the potential to transmit activating signals. Ligands for DNAM-1, such as PVR (CD155), a member of the nectin family of proteins, and nectin-2 (CD11), a member of the nectin-like family of protein, are frequently expressed by tumor cells. Once the serial killer cell is activated, cytotoxic granules that contain perforin and granzyme, specifically granzyme B, are released. (See Marcus, Assaf, et al. "Recognition of Tumors by the Innate Immune System and Natural Killer Cells." *Advances in Immunology*, U.S. National Library of Medicine, 2014, www.ncbi.nlm.nih.gov/pmc/articles/PMC4228931/).

Perforin is able to polymerize, bind to the target cell, and form a channel in the target cell membrane with the assistance of Ca2+ ions. Granzymes are serine proteases that enzymatically activate a caspase cascade leading to apoptosis. Perforin binds via membrane phospholipids, and the phosphatidycholine, which binds Ca2+, increases perforin's affinity to the target cell membrane. The pores formed by perforin disrupt the cell membrane and allow the free influx and efflux of ions and polypeptides and additionally allow for the delivery of granzyme molecules. The disruption of the cell and the delivery of cytotoxic granzymes ultimately induce activation of pro-apoptotic pathways and DNA degradation leading to cell death. This mechanism is not only dependent on expression of perforin/granzyme, but also on a multitude of other factors such as temperature, pH, calcium concentration, etc. (See Lopez, Jamie A., et al. "Perforin Forms Transient Pores on the Target Cell Plasma Membrane to Facilitate Rapid Access of Granzymes during Killer Cell Attack." Blood Journal, American Society of Hematology, 4 Apr. 2013, www.bloodjournal.org/content/121/14/2659; see also Murphy, Kenneth M., et al. "T-Cell Mediated Immunity." *Janeways Immunobiology.* 9th ed., GS, Garland Science, Taylor & Francis Group, 2017. pps. 387-395).

Serial killer cells also can induce apoptosis through a death receptor/ligand pathway. For example, some serial killer cells express the Fas ligand (FasL) on their cell membrane. When FasL contacts and binds with Fas present on the membranes of target cells, Fas becomes ligated which leads to the activation of caspases, inducing apoptosis in the target cell. (Paul, W. E., "Chapter 1: The immune system: an introduction," Fundamental Immunology, 4th Edition, Ed. Paul, W. E., Lippicott-Raven Publishers, Philadelphia, (1999)).

The tumor necrosis factor (TNF) related apoptosis inducing ligand (TRAIL) receptor/TRAIL mechanism is another death receptor/ligand pathway. TRAIL is a transmembrane protein expressed on many serial killer cell types that induces apoptotic death in a wide variety of tumor cells, but not in most normal cells. When the TRAIL ligand binds to either one of two apoptosis-inducing receptors TRAIL-R1 or TRAIL-R2, the receptors are trimerized, and the death-inducing signaling complex (DISC) is assembled on the target cell. (Falschlehner, Christina, et al. "Following TRAIL's Path in the Immune System." Immunology, Blackwell Science Inc., June 2009, www.ncbi.nlm.nih.gov/pmc/articles/PMC2691779/).

Both Fas/FasL and TRAIL-R/TRAIL proceed as following: the adaptor molecule, Fas-associated death domain (FADD) translocates to the DISC where it interacts with the intracellular death domain of the receptors. Via its second functional domain, the death effector domain (DED), FADD recruits procaspases 8 and 10 to the DISC where they are autocatalytically activated, thus initiating the caspase-dependent signaling cascade, leading ultimately to cell death. Id.

Many serial killer cells have immunoregulatory effects through the secretion of cytokines and chemokines that modulate the effector function of surrounding cells, such as Interferon-γ (IFN-γ), Granulocyte macrophage colony-stimulating factor (GM-CSF), Colony-stimulating factor 1 (CSF-1), Tumor necrosis factor α (TNFα), Transforming growth factor (TGFβ), Interleukin (IL-3 (IL-3), IL-5, IL-10, IL-13, chemokines (CCL1, 2, 3, 4) and (CXCL8). For example, several serial killer cells secrete pro-inflammatory cytokines. Target cells can be sensitized for TRAIL-mediated apoptosis by the presence of inflammatory cytokines, such as, TNF-α and IFN-γ. These cytokines can potentiate apoptosis by indirect means, but also through a direct, contact-independent cytotoxic mechanism where they induce the production of nitric oxide and other free radicals, or by activating death pathways within the tumor cells. IFN-γ has also been found to activate macrophages, and recruits them to the site of the attack for both effector cell function and as APCs. IFN-γ, synergistically with TNF-α or TNF-β, kills some target cells through their interaction with TNF Receptor I (TNFR-I). (Ito and Seishima (2010), "Regulation of the Induction and Function of Cytotoxic T Lymphocytes by Natural Killer T Cell." J Biomed Biotechnol, Art. ID. 641757).

There are several serial killer cell types, such as the various types of NKTs and NKs that cannot be easily categorized in one single arm of the immune system. These cell types include B-1 cells, marginal zone (MZ) B cells, and certain subsets of γδ T cells, CD8αα-expressing T cells in the gut, Cytokine-Induced Killer cells and MAIT cells. Each of these cell types expresses an antigen-specific receptor, either a B cell receptor or a T cell receptor (TCR), which is generated by VDJ recombination, a process by which T cells and B cells randomly assemble different gene segments, known as variable (V), diversity (D) and joining (J) genes, in order to generate unique antigen receptors that collectively can recognize many different types of molecules. Because the repertoire of specificities of these receptors is strongly limited, these cells react with a limited diversity of antigens.

The receptors expressed by the various types of NKTs and NKs bear similarities with pattern recognition receptors expressed by cells of the innate immune system. Cells of the T lymphocyte lineage further display unique characteristics, such as the inability to develop immunological memory, rapid elicitation of effector functions, and a tendency for autoreactivity. Despite sharing T-lymphocyte lineage with conventional T cells, these cells display characteristics that are distinctly NK-like and T-cell like, such as the ability to produce certain cytokines, the ability to activate other immune cells (such as conventional T cells, NKs, and/or DCs), and the ability to induce cell death through cytotoxic activity and/or expression and interaction with cell-death inducing effector molecules, such as the Fas ligand (FasL/Fas) and TNF-related apoptosis inducing ligand (TRAIL). (Ito and Seishima (2010), "Regulation of the Induction and Function of Cytotoxic T Lymphocytes by Natural Killer T Cell." J Biomed Biotechnol, Art. ID. 641757). Other cells that display similar effector function including CTLs, which share serial killing ability with NKTs and NKCs.

Natural Killer (NK) Cells

Natural Killer (NK) cells are cytolytic granular lymphocytes found in humans and other mammals. They are characterized by their innate capacity for lytic activity even in the absence of prior immunization to targets. (Seaman (2000) "Natural Killer Cells and Natural Killer T Cells." Arthritis & Rheumatism 43(6): 1204-1217).

NKs have the morphology of activated cytotoxic T cells, in that they are typically large with an expanded cytoplasm containing granules used in cytotoxicity. NKs currently can be identified by various surface receptors, such as those shown in Table 2.

TABLE 2

Natural Killer Cells

| Type | Receptor | Species | Ligand | Significance |
|---|---|---|---|---|
| Inhibitory Receptors | Killer immunoglobulin-like receptor (KIR) 2DL1 | Human | Human leukocyte antigen (HLA)-C2 | Inhibits activation |
| | KIR2DL2 | Human | HLA-C1 | |
| | KIR2DL3 | Human | HLA-C1 | |
| | KIR3DL1 | Human | DLA-Bw4 | |
| | KIR3DL2 | Human | HLA-A3, A-11 | |
| | Lymphocyte Antigen 49 (Ly49A) | Mouse | H-2D$^{b,\,d,\,k,\,p}$, H-2M3 | |
| | Ly49C | Mouse | H-2D$^{b,\,d,\,k}$ | |
| | Ly49I | Mouse | H-2D$^{b,\,s,\,q,\,v}$ | |
| | Ly49P | Mouse | H-2D$^{d,\,k}$ | |
| | CD158 | | | IG-like, inhibits activation |
| | Leukocyte inhibitory receptors (LIR1, LAIR-1) | | | |
| | NKR-P1A; also known as CD161 | Human | LLTI | |
| | NKR-P1B | Mouse | Clr-B | |
| | NKR-P1D | | | |
| | ILT2 (CD85j) | | HLA-A, -B, -C, HLA-G1, HCMV UL18 | |
| | CD244(2B4) | | CD48 | |
| | CD94 natural killer group (NKG) 2 member A (CD94-NKG2A) | Mouse Human | Qa1b HLA-E | A C-type lectin family that expresses as a heterodimer and contains immunoreceptor tyrosine-based inhibition motif (ITIM). Recognizes non-classical MHC molecules on target cells and protect host cell against inappropriate NK cell activation. There are several cyotkines present in the tissue environment that can modulate the expression of NKG2A and affect NKC function. |
| Activating receptor | KIR2DL4 | Human | HLA-G | Functionally equivalent homolog of Ly proteins discussed en infra, bind to the peptide binding region of HLA molecules that are present on the Class 1 MHC molecules. |
| | KIR2DS1 | Human | HLA-C2 | |
| | KIR2DS2 | Human | HLA-C1 | |
| | KIR2DS3 | Human | | |
| | KIR2DS4 | Human | HLA-A11 | |
| | KIR2DS5 | Human | | |
| | KIR3DS1 | Human | HLA-Bw4 | |
| | 2B4 | | | Activates cytotoxicity activity. 2B4 is a receptor that binds to CD48, a cell surface molecule widely expressed on hematopoietic cells, and activates lysis of the cell that presents CD48. |
| | NKp46 | | Heparin, vira HA and HN | Activates cytotoxicity. NKP46 is a receptor, blockade of which impairs target lysis. |
| | NKp44 | | Viral HA and HN, PCNA, proteoglycans | Activates cytotoxicity. Expression of NKp44 is induced on activated NKCs and may contribute to the expanded repertoire of targets killed by activated NK cells. |
| | NKp30 | | B7H6, BAT3, pp65 of HCMV, PfEMP1 of *Plasmodium faliciparum*, viral HA | NKp30 is a receptor, the blockade of which impairs target lysis. |
| | IL-2 Receptor | | | Once the IL-2 receptor is stimulated by IL-2, NKC is stimulated to proliferate, secrete cytokines, lyse atargets more effectively, and expand the range of tumors that they can lyse. |

TABLE 2-continued

Natural Killer Cells

| Type | Receptor | Species | Ligand | Significance |
|---|---|---|---|---|
| | IL-15 Receptor | | | The β and γ of the IL-2 receptor is shared with the IL-15 receptor and upon stimulation by IL-15, which further results in the same activity as IL-2 stimulation. IL-15 stimulation is also required for activation of killing activity for certain viruses. |
| | NKG2D | Mouse | Rae 1a-e, MULT-1, H60 | Natural Killer Group (NKG) receptors are C-type lectin like activating receptor that activates natural killing activity. |
| | | Human | MIC-A/-B, ULBP1-4 | |
| | CD94-NKG2C | | Qa1b, HLA-E | |
| | NKR-P1C | | | |
| | NKRP1F | | Clr-g, Clr-c | |
| | NKFP1G | | Clr-g, Clr-f | |
| | DNAM-1 | | CD112, CD155 | |
| | Cluster of differentiation molecule 16 (CD16) | | | Activates antibody-dependent cell-mediate cytotoxicity. CD16 is a receptor for Immuoglobulin G (IgG). NKC use CD16 to recognize and kill cells that are coated with antibody. |
| | Ly49D | Mouse | H-2D$^d$ | C-type lectin-like superfamily containing a C-terminal lectin domain known as the NK domain. The NK domain binds with MHC Class I molecules, this interaction is MHC-peptide independent. |
| | Ly49H | Mouse | M157 of MCMV | |
| Adhesion | CD56 | | CD56 | Allows binding to other molecules. CD56 is a form of neural cell adhesion molecule 1 (NCAM1). Molecules that express CD56 can bind to each other, known as homotypic adhesion. It is a characteristic marker of NKC. |

A particular NK cell will typically express two to four inhibitory receptors in addition to an array of activation receptors, and the varied combinations of inhibitory and activating receptors results in a sizeable heterogeneity within an NK population. It is for this reason that NKs are considered to have the ability to respond to a variety of stimuli and to participate in various immune responses under different pathological conditions. (Mandal and Viswanathan (2015). "Natural killer cells: In health and disease." Hematol. Oncol. Stem Cell The. 8(2): 47-55).

NK cells primarily develop in the bone-marrow, similar to B cells and myeloid origin cells. They have also been found to develop in lymph nodes and the liver. They can be generated from hematopoietic stem cells (HSCs) that show a commitment towards NK lineage, thus generating NK precursors (NKPs), which eventually mature into NKs under the influence of certain transcription factors. Transcription, soluble, and membrane factors involved in the development of NKs include, in the generation phase, Ets-1, Id2, Ikaros, and PU.1; in the maturation of immature NKs, Gata-3, and IRF-2; and in the functional differentiation of matured NKs, CEBP-γ, MEF, and MITF. The cytokine interleukin 15 (IL-15) has been shown to be essential for NK development homeostasis and survival. The cytokine interleukin-2 (IL-2), a peptide derived from T cells, has been implicated in the cytolytic functional maturation of NK cells. (Id.).

NKs are typically found circulating in peripheral blood until activated, when they infiltrate into most tissues that contain pathogen-infected or malignant cells. They represent 10% of all cells in the total peripheral blood mononuclear cells (PBMC) population of circulating human lymphocytes. NKs found in secondary lymphoid tissues, such as tonsils, lymph nodes, and the spleen, differ from NKs in peripheral blood in that lymphoid NKs are activated by DCs and secrete certain cytokines such as interferon, which stimulate a more efficient killing response by T cells. (Id.).

NK stimulation and effector function depends on the integration of signals derived from its various receptors. NKs can recognize and kill virally infected and neoplastic cells through their cytotoxic function.

NKs further play an immunoregulatory role where NKs stimulate the production of cytokines. In this manner, NKs have the capacity to regulate the activity of other cells, particularly the cells of the immune system. The pattern of cytokines released by NK induction varies with stimulus. Thus, NKs, like T cells, differentiate into discrete functional subsets with differing effectiveness on adaptive immunity.

The presence of IFN-γ and other functional immunostimulatory factors, such as IL-2, and IL-12, on NKs may lead to the activation and expansion of NKs into lymphokine-activated killer (LAK) cells, which may give rise to cytokine induced killer cells (CIKs), which are CD3-, CD56-positive, non-major histocompatibility complex (MHC)-restricted, natural killer (NK)-like T lymphocytes. LAK cells upregulate effectors or adhesion molecules, such as perforin, NKp44, granzymes, FasL and TRAIL, and secrete IFN-γ to adhere to and lyse tumor cells. (Nair and Dhodapkar (2017). "Natural Killer T Cells in Cancer Immunotherapy." Frontiers in Immunology 8:1178). CIKs may enhance the cytolytic activity on tumor targets).

NKG2D is an activating receptor expressed on the surface of NK cells, CD8+ T cells, and subsets of CD4+ T cells, type I NKT cells, and γδ T cells. (See Lanier, L L, Cancer Immunol. Res. (2015) 3(6): 575-82). In humans and mice, NK cells express a heterodimer of two different C type lectin like receptors, CD94 and NKG2, which interact with non-polymorphic MHC class I like molecules (HLA-E in humans and Qa1 in mice). HLA-E and Qa1 are unusual in that instead of binding peptides derived from pathogens, they bind fragments of the signal peptide derived from other MHC class I molecules during processing in the ER (See Murphy, Kenneth M., et al. *Janeways Immunobiology*. 9th ed., GS, Garland Science, Taylor & Francis Group, 2017. p. 129). This enables CD94:NKG2 to detect the presence of several different MHC class I variants, whose expression may be targeted by viruses, and to kill cells in which overall MHC molecule expression is diminished.

NKG2D has a specialized role in activating NK cells. Two NKG2D molecules form a homodimer that binds to several MHC class I like molecules that are induced by various types of cellular stress. These include the MIC molecules MIC-A and MIC-B, which are human inducible MHC class I-related molecules expressed by stressed and malignant cells, and the RAET1 family of of major histocompatibility complex (MHC) class I-related genes; RAET1 functions as a ligand for NKG2D receptor. Ligands for NKG2D are expressed in response to cellular or metabolic stress, and are upregulated on cells infected with intracellular bacteria and most viruses, as well as on incipient tumor cells that have become malignantly transformed. Thus recognition by NKG2D acts as a generalized "danger" signal to the immune system. (Murphy, Kenneth M., et al. *Janeways Immunobiology*. 9th ed., GS, Garland Science, Taylor & Francis Group, 2017. p. 130).

Natural Killer Like T Cells (NKTs)

NKTs are rapid responders of the immune system and mediate potent immunoregulatory and effector functions in a variety of disease settings. Upon activation, NKTs can immediately commence effector function, such as cytokine secretion or cytolytic activity, without first having to differentiate into effector cells. The rapidity of their response makes NKTs important players in the very first line of innate defense. In addition, many of the cytokines secreted by NKTs have powerful effects on αβ T cell differentiation and functions, thus linking NKTs to adaptive defense as well.

NKTs are cells that share morphological and functional characteristics with both conventional T cells and NKs. Despite NKTs having a T lineage and expressing T-cell antigen receptors (TCRs) characteristic of conventional T cells, they also express cell surface proteins characteristic of NKs. As such they are considered a bridge between innate and adaptive immunity.

NKTs can be found virtually everywhere T cells and NKs are found, such as in the spleen, liver, thymus, bone marrow, lymph nodes, umbilical cord blood, and peripheral blood. They typically comprise less than 1% of peripheral blood of humans and non-human primates. (Wah, MakTak, et al. "Chapter 11: NK, γδ T and NKT Cells." Primer to the Immune Response. Elsevier, 2014). Activation of the various types of NKTs results in varying immunomodulatory responses, such as the ability to produce certain cytokines, the ability to activate other immune cells such as conventional T cells, NKCs, and/or DCs, and the ability to induce cell death through cytotoxic activity and/or expression and interaction with cell-death inducing effector molecules, such as the Fas ligand (FasL/Fas) and TNF-related apoptosis inducing ligand (TRAIL).

As shown in Table 3 below (Adapted from Godfrey et al. (2004). "NKT cells: what's in a name?" Immunology, Nature Reviews 4:231-237), three NKT cell subtypes (type I, II, and NKT-like cells) express different TCRs and TCR activation, which promotes various intracellular events leading to specific functional activities. Each classification contains many further subtypes depending on its various phenotypes. Type 1 NKTs (also known as NKT-I, invariant NKTs, or iNKTs) have an invariant TCR α-chain with limited TCR β-chain repertoires. Type II NKTs (also known as diverse NKTs, dNKTs, variant NKTs, vNKTs, or NKT-II) are more diverse in that they express a broad range of different TCR chain combinations. Further, research suggests that there exist cells that are NKT-like, such as other CD1 restricted T-cells and MR1-restricted mucosal associated invariant Tcells (MAITs). Bennstein (2017), "Unraveling Natural Killer T-Cells Development" Front Immunol. 8:1950. However, much of what is known today is about type I NKTs.

TABLE 3

Classification of Natural Killer T Cells

| | Type I NKT Cells* | Type II NKT Cells | Type III NKT-Like Cells |
|---|---|---|---|
| APC Molecule | CD1d Dependent | CD1d Dependent | Non-MHC restricted |
| TCR α-chain | Vα14-Jα18 (m) Vα24-Jα18 (h) | Diverse but some Vα1 or Vα3 | Diverse/semi-invariant |
| TCR β-chain | Vβ8.2, Vβ7, Vβ2 (m) Vβ11 (h) | Diverse but some Vβ8.1 or Vβ3.1 | Diverse/semi-invariant |
| α-lipid reactive | + | − | |
| NK1.1(m) CD161(h) | | +/− | + |
| Coreceptor Expression | CD4$^+$CD8$^-$ CD4$^-$CD8$^+$ CD4$^-$CD8$^-$ | CD4+CD8− | CD4$^+$CD8$^-$ CD4$^-$CD8$^+$ CD4$^-$CD8$^-$ |

*(m)—mice; (h)—humans

Similar to T cells, NKTs express a diverse or semi-invariant αβ TCR, the TCR being noncovalently coupled to a conserved multisubunit signaling apparatus, the CD3 complex. However, unlike T-cells which express αβTCR that can be activated by peptide antigens bound to classic class I (CD8+) or class II (CD4+) MHC molecules, most NKTs responds to glycolipid antigens present on the non-classic class I MHC-like molecule, CD1d. (Seaman (2000) "Natural Killer Cells and Natural Killer T Cells." Arthirits & Rheumatism 43(6): 1204-1217). In other words, the TCRs of NKTs recognize glycolipid, glycosphingolipid or lipid structures presented on non-polymorphic CD1d molecules expressed by professional and nonprofessional APCs (antigen presenting cells), including DCs, macrophages (Mo), B cells, thymocytes, adipocytes, hepatocytes and endothelial cells. (Wah, MakTak, et al. "Chapter 11: NK, γδ T and NKT Cells." Primer to the Immune Response. Elsevier, 2014).

CD56 is present on some types of NKTs. This molecule, a form of neural cell adhesion molecule 1 (NCAM1), allows binding to other molecules. Therefore, molecules that express CD56 can bind to each other by homotypic adhesion (meaning adhesion mediated by undefined adhesion molecules between identical cell types). CD56 is the archetypal phenotypic marker of natural killer cells, but can actually be expressed by many more immune cells, including αβ T cells, γδ T cells, DCs, and monocytes. (Van Acker, H H, t al., "CD56 in the immune system: more than a marker for cytotoxicity?" Front. Immunol. (2017) 8: 892).

Generally, activation of NKTs may be regulated by a balance of activating and inhibitory signaling. However, NK receptor expression by NKTs varies with the developmental stage of an NKT, its activation status and the genetic background of the host. (Wah, MakTak, et al. "Chapter 11: NK, γδ T and NKT Cells." Primer to the Immune Response. Elsevier, 2014). Activation can occur directly through the engagement of NKT TCRs with suitable antigens on CD1d molecules, or indirectly through inducement via APCs.

Like NKs, NKT stimulation and effector function depends on the integration of signals derived from its various receptors. NKTs can recognize and kill virally infected and neoplastic cells through their cytotoxic function. NKTs can also activate APCs to initiate adaptive antitumor immunity. Additionally, NKTs may secrete pro-inflammatory cytokines that activate NK and CTL serial killing action.

NKTs can kill tumor cells through: the perforin/granzyme pathway; the Fas/FasL pathway; and the TRAIL pathway. Activated NKTs express perforin and Fas ligand on their surface, which can directly kill tumor cells. CD56+ NKTs seem to be more efficient killer cells than those that are CD56−. (Terabe, Masaki, and Jay A. Berzofsky. "Natural Killer T Cells Balancing the Regulation of Tumor Immunity." Springer New York, 2012, Ch. 5: The Regulation of CD1d+ and CD1d− Tumors by NKT Cells: The Roles of NKT Cells in Regulating CD1d+ and CD1d− Tumor Immunity" pp 71-93).

NKTs can also enhance ADCC mediated by NKs. (Terabe, Masaki, and Jay A. Berzofsky. "Natural Killer T Cells Balancing the Regulation of Tumor Immunity." Springer New York, 2012, Ch. 5: The Regulation of CD1d+ and CD1d− Tumors by NKT Cells: The Roles of NKT Cells in Regulating CD1d+ and CD1d− Tumor Immunity" pp 71-93).

NKTs further play an immunoregulatory role where NKTs stimulate the production of cytokines, including, without limitation, Interferon-γ (IFNγ), Granulocyte macrophase colony-stimulating factor (GM-CSF), Colony-stimulating factor 1 (CSF-1), Tumor necrosis factor α (TNFα), Transforming growth factor (TGFβ), Interleukin (IL) 3 (IL-3), IL-5, IL-10, IL-13, chemokines (CCL1, 2, 3, 4) and (CXCL8).

NKTs have been shown to regulate the immune response in many disease settings, including cancer, through direct cell lysis, immunomodulation of adaptive cellular function, and regulation of immunosuppressive cells. Once activated, NKTs in the spleen, liver, or bone marrow are stimulated to undergo rapid clonal expansion within 3 days of an antigen encounter. However, as discussed en supra, activated NKTs can immediately carry out effector function without the need for differentiation. Therefore, it has been said that NKTs exist in a "preactivated state," and supply timely and effective defense during the interval needed by conventional T cells for proliferation and differentiation into the effectors of the more finely tailored adaptive responses.

NKTs play a role in the regulation of immunity through the release of cytokines. NKTs carry preformed mRNAs for IL-4 and IFNγ so that massive amounts of these cytokines can be produced within 1-2 hours of activation. The secretion of IFNγ promotes a Th1 response, whereas the production of IL-4 promotes a Th2 response, specifically when the cells are contacted with an antibody to CD3. In addition, NKTs can synthesize IL-2, IL-10, IL-17, among other interleukins, as well as TGFβ, TNFα, and a large array of chemokines.

Like NKs, NKTs express inhibitory and activating NK receptors, including NKG2D and CD94/NKG2A in mice and humans, and certain KIRs in human. NKTs also express CD40L, ICOS, and PD-1. (Wah, MakTak, et al. "Chapter 11: NK, γδ T and NKT Cells." Primer to the Immune Response. Elsevier, 2014).

Type I NKTs

The type I NKT TCR is largely encoded by a germline Vα gene (Vα14/Jα18 in mice and Vα24/JαQ) in humans) and additionally by the more diverse, non-germline Vβ chain genes (Vβ8.2/7/2 in mice and Vβ11 in humans). They respond to both α- and β-linked glycolipids, and bind to CD1d in a parallel configuration that mainly involves the α-chain. (Kumar and Delovitch (2014) "Different subsets of natural killer T cells may vary in their roles in health and disease." Immunology 142: 321-336).

The TCRα chain is essentially invariant among the NKTs in a species, whereas the TCRβ chain can be diversified. For example, in humans all NKTs express a TCR in which the TCRα chain expresses Vα24 plus Jα18, and the TCRβ chain usually contains Vβ2, 7, or 8. Intracellular signalling is conveyed by the associated CD3 complex. (Wah, MakTak, et al. "Chapter 11: NK, γδ T and NKT Cells." Primer to the Immune Response. Elsevier, 2014).

While CD1d-dependent activation is characteristic of NKT type I cells, NKT type I cells can also be stimulated in a CD1d-independent manner by exposure to several cytokines, such as IL-12, IL-18, or IL-12 and Type I IFN. (Kumar and Delovitch (2014) "Different subsets of natural killer T cells may vary in their roles in health and disease." Immunology 142: 321-336.)

Researchers have been able to identify NKT type I cells in the laboratory by their ability to recognize the exogenous antigen α-galactosylceramide (α-GalCer). In vivo, experimental administration of the antigen to a mouse activates its NKT cells, which then help to promote tumor rejection or to protect the animal against infection with various pathogens. (Wah, MakTak, et al. "Chapter 11: NK, γδ T and NKT Cells." Primer to the Immune Response. Elsevier, 2014).

Because of their ability to produce an array of effector molecules, Type I NKTs have the potential to regulate the function of essentially every type of hematopoietic cell. It has been reported that type I NKTs regulate the functions of APCS, such as DCs, macrophages, and B cells, and other lymphocytes, including NKs and other T cell subsets. (Liao et al. (2014) "The Functions of Type I and Type II Natural Killer I (NKT) Cells in Inflammatory Bowel Diseases." Inflamm Bowel Dis. 19(6): 1330-1338).

Type II NKTs

Type II NKTs are more abundant in humans than are Type I NKTs. Unlike Type I NKTs, Type II NKTs are not reactive to a-GalCer or other a-linked glycolipids; instead, they likely recognize B-linked glycolipids such as sulfatide, lysosulfatide, lysophosphatidylcholine (Lyso-PC), and glucosylsphingosine (lyso-GL1). A major proportion of type II dNKTs recognize a naturally occurring self antigen known as sulphatide, which is enriched in several membranes, including myelin in the central nervous system, pancreas, kidney and liver. Generally, Type II NKTs mediate protection from autoimmune disease by down-regulation of inflammatory responses elicited by Type I NKTs. TCRs of Type II NKTs are encoded by Va- and VB-chain genes largely of the non-germline type. Type II NKTs typically contact ligands with their B chain rather than their a-chain, a mechanism shared by conventional T cells (convTCs), and to a lesser extent type I NKTs. (Kumar and Delovitch (2014) "Different subsets of natural killer T cells may vary in their roles in health and disease." Immunology 142: 321-336).

Research suggests that upon stimulation with sulfatide, type II NKTs have the ability to regulate the function of Type I NKTs.

NKT-Like Cells (e.g., Cytokine-Induced Killer (CIK) Cells)

NKTs that express a combination of CD3 (a T cell marker), and CD56 (a NK marker), are a major cytotxic subset of NKTs which may also be known as Cytokine-Induced Killer (CIK) cells. The phenotype of CIK cells varies between $CD3^+CD56^+$, $CD3^+CD56^-$, and $CD3^-CD56^+$, but may not express the Fc receptor CD16. Like other Serial Killer Cells, NKT-like cells have immunoregulatory effector function. (Gutegemann et al. (2007). "Cytokine-induced killer cells are type II natural killer T cells." GMS German Medical Science 5: 1-4).

CIK and NKT-like cell differentiation from Type I and Type II NKTs is not well understood.

Cytokine-Induced Killer Cells (CIKs)

CIK cells are a heterogenous population of CD8+ T cells that can be expanded ex vivo via incubation with an anti-CD3 antibody, IFN-y, and IL-2. They have cytotoxic activity mediated by FasL/Fas and perforin/granzyme action. CIKs are generally divided into two main subsets: CD3+CD56+ type and CD3+CD56− type. CD3+CD56+ T cells (NKT cells), are considered to be the major effector cells of CIK CIK cells can lyse cancer cells in a MHC-unrestricted manner through activating NK cell receptors, such as DNAX accessory molecule-1, NKp46, NKG2D, and NKp30. Several studies have indicated that after stimulation by tumor cells, the levels of pro-inflammatory cytokines, such as tumor necrosis factor (TNF)-α, IFN-γ, and IL-2 secreted by CIK cells, are significantly upregulated; these cytokines further enhance systemic antitumor activity and induce a Th1 immune response. (Gao, et al. "Cytokine-Induced Killer Cells As Pharmacological Tools for Cancer Immunotherapy." Frontiers, Frontiers, 19 Jun. 2017, www-.frontiersin.org/articles/10.3389/fimmu.2017.00774/full).

γδ T Cells (GDTs)

γδ T cells (GDTs) are another serial killer cell population that bridges the gap between innate and adaptive immunity. Despite being of a T cell lineage and expressing surface TCRs, γδ T cells also display NKG2D, an NK receptor, and display nonspecific recognition that activate their cytotoxic and immunomodulating effector function. (Wu Y L, Ding Y P, Tanaka Y, Shen L W, Wei C H, Minato N, Zhang W. γδ T Cells and Their Potential for Immunotherapy. Int J Biol Sci 2014; 10(2):119-135. doi:10.7150/ijbs.7823. Available from http://www.ijbs.com/v10p0119.htm).

GDTs can be organized into two major populations distinguished by their surface expression of αβ TCRs (discussed infra) and γδ TCRs. T cells that express the αβ TCR generally also express CD4 or CD8 lineage markers (discussed supra). However, GDTs generally do not express these markers, and further do not require conventional antigen presentation in the context of MHC presentation. GDTs can be further organized into populations based on δ chain expression, specifically, Vδ1, Vδ2, and Vδ3 chains. Like the combinatorial diversity of the αβ TCR repertoire, the diversity for GDTs is at least as large as that of the αβ TCR repertoire, due to extensive non-genetic mechanisms. Id.

Similar to other serial killer cells, GDTs have cytolytic/cytotoxic effector function through the perforin/granulysin-granzyme pathway as well as the death receptor/ligand pathway, such as Fas/FasL. Further, GDTs secrete Th1, Th2, and Th17 cytokines, each of which has an immunoregulatory impact on innate and adaptive immunity.

Cytolytic T Lymphocytes (CTLs)

Cytolytic T Lymphocytes (CTLs) constitute a distinct lymphocyte subpopulation. Unlike NKTs, they are induced by several diverse stimuli, including major histocompatibility antigens, protein antigens, viruses, and intracellular bacteria and peptides.

Like a number of other cells discussed herein, CTLs have cytolytic effector function. However, unlike NKs and NKTs, CTLs release the cytoxic proteins perforin and granzyme in an antigen-dependent manner.

CD8+ CTLs

Unlike some NKTs and NKs, CD8+ CTLs recognize peptides bound to class I MHCs. Activation and proliferation of the CTLs are induced by exposure to specific antigens. Like NKTs, activation of CD8+ CTLs results in the secretion of cytolytic mediators, such as perforin and granzyme that induce apoptosis in target cells, such as tumor cells. This action is cell specific: research suggests that CD8+ CTLs reorient their secretory apparatus toward each cell and attack at only one point of contact at any one time. (Murphy, Kenneth M., et al. *Janeways Immunobiology.* 9th ed., GS, Garland Science, Taylor & Francis Group, 2017. pps. 387-395).

In further similarity with NKTs, CTLs secrete various cytokines, such as IFNy and TNF-α, which enhance antigen presentation and mediate antipathogenic effects. IFN-y induces the increased expression of MHC Class I and other molecules involved in peptide loading of the newly synthesized MHC Class I proteins in infected cells. This increases the chance that target cells will be recognized for cytotoxic attack. TNF-α synergistically works with IFN-y to increase its effector function. It has been reported that various cytokines, such as IL-2 or IFNy producing CD4+ T cells, are required for the generation of effective CTL immunity. (Ito and Seishima (2010), "Regulation of the Induction and Function of Cytotoxic T Lymphocytes by Natural Killer T Cell." J Biomed Biotechnol, Art. ID. 641757).

The enhancement of CD8+ CTL induction and activation via type I NKT activation causes immunopotentiation against tumors or microbes. As discussed en supra, activation of type I NKTs, such as by IL-12 (CIKs), or a-GalCer (non-CIK NKT), can result in Th1 cytokine production (IFNy). However, research shows that Type I NKT activation by a-GalCer can result in NKTs secreting both Th1 cytokines (IFNy) and Th2 cytokines (IL-4). On the other hand, activated type II NKTs suppress CD8+ CTL activity via cytokine production, namely IL-4, IL-13, and TGF-B. (Ito and Seishima (2010), "Regulation of the Induction and Function of Cytotoxic T Lymphocytes by Natural Killer T Cell." J Biomed Biotechnol, Art. ID. 641757).

CD8+ CTLs are activated when naïve CD8+ T cells interact with APCs. This activation depends on the number of MHC complexes present on the APCs, the affinity of the CTL's TCR for the MHC complex, and the signals provided by the APCs in the form of costimulatory molecules. The B7/CD28 and CD40/CD40L costimulatory pathways are well known examples of costimulatory interaction pathways that contribute to T cell activation and production. NKT activation can upregulate costimulatory molecules (such as CD40, CD80, and CD86) in both CD8+ and CD8− DC subsets. Both B7/CD28 and CD40/CD40L costimulatory pathways are additionally linked to NKT activation. (Ito and Seishima (2010), "Regulation of the Induction and Function of Cytotoxic T Lymphocytes by Natural Killer T Cell." J Biomed Biotechnol, Art. ID. 641757).

Thus, various stimulatory substances of NKTs exhibit different types of cytokine production, which modulate levels of CTL activation.

CD4+ CTLs

Very little is known about the phenotype, function and transcriptional profile of cytolytic CD4+ T cells. Similar to NKTs, CD4+ CTLs display a multitude of markers and effector function that cross adaptive and innate immunity.

Despite being a Th1 lineage cell phenotypically, the cell marker profile of CD4+ T cells differ from other Th1 lineage cells. For example, CD4+ cells lose the ability to secrete IL-2, lack the expression of CD28 and CD27, and further upregulate the expression of integrin a chains CD11a and CD11b as well as CD57. Like NKs, cytolytic CD4+ cells express NKG2D, KIR2DS2 and KARAP/DAP12 receptors; NKG2D has been hypothesized to act as a receptor in cytolytic CD4+ T cells lacking CD28 CD28. In addition, CTLs express CD25, a cell marker that is characteristic of Tregs. (Soghoian, Damien Z, and Hendrik Streeck. "Cytolytic CD4( ) T Cells in Viral Immunity." Expert Review of Vaccines, U.S. National Library of Medicine, December 2010, www.ncbi.nlm.nih.gov/pmc/articles/PMC3033049/).

Cytolytic CD4+ cells additionally express FasL, and have been shown to kill targets that express Fas. CD4+ CTLs further express high levels of perforin and granzyme or granulysin, and have been shown to lyse target cells in an antigen dependent fashion. The degranulation of these cells upon antigenic stimulation directly may be enhanced by the availability of IL-2 potentially secreted by other serial killer cells. Additionally, research has shown that CD4+ CTLs that express TRAIL may induce bystander apoptosis in antigen-presenting cells as well as in TRAIL-sensitive tumor cell lines. Id.

CD4+ CTLs also play an immunoregulatory role, as they have been found to secrete TNF-α and INF-γ. As discussed en supra, target cells can be sensitized for TRAIL-mediated apoptosis by the presence of pro-inflammatory cytokines. These cytokines can potentiate apoptosis by indirect means, through a direct, contact-independent cytotoxic mechanism where they induce the production of NO and other free radicals thereby activating cytolytic activities, or by activating death pathways within the tumor cells. Id.

Mucosal-Associated Invariant T Cells (MAIT Cells)

MAIT cells are invariant Vα7.2 TCR expressing cells whose immune response to tumor cells is similar to NKTs. Unlike NKTs, MAIT cells are stimulated by MR1, a non-classical MHC class Ib molecule encoded by chromosome 1, similar to CD1d. Several lines of evidence suggest that MR1 presents ligands to MAIT cells, possibly glycolipids, similarly to NKT cell stimulation. Furthermore they are also activated in a co-receptor independent fashion. MAIT cells have both peripheral CD56+ and CD56− subsets, although the CD56− subset is thought to be linked to tumor infiltrating T cells. The CD56− subset of MAIT cells has been correlated with the expression of pro-inflammatory cytokines, although not IL-4, IL-5 and IL-10. (Peterfalvi, et al. "Invariant Vα7.2-Jα33 TCR Is Expressed in Human Kidney and Brain Tumors Indicating Infiltration by Mucosal-Associated Invariant T (MAIT) Cells." OUP Academic, Oxford University Press, 16 Oct. 2008, academic.oup.com/intimm/article/20/12/1517/684337).

Lymphokine Activated Killer Cells (LAKs)

Lymphokine-activated killer cells (LAKs) are cytotoxic effector cells with an exceptionally wide target cell spectrum including normal and malignant cells of different origins. They are killer cell lymphocytes activated in the presence of interleukin-2 (IL-2). LAK cells exhibit a profound heterogeneity with regard to phenotype surface marker expression; it remains to be determined if they represent a unique cell lineage Activation of Serial Killer Cell Populations Serial killer cells can directly or indirectly recognize histocompatibity molecules between genetically disparate individuals within the same species, otherwise known as "allorecognition." Some serial killer cells, through direct allorecognition, can recognize determinants on MHC, MHC-like complexes, and other molecules displayed on the surface of host cells (i.e., tumor infiltrated cells), without the requirement for antigen processing. Some serial killer cells can recognize processed peptides of antigens presented by MHC molecules via indirect allorecognition in a self-restricted manner. While innate serial killer cell populations can become activated by a single mechanism of allorecognition (e.g., direct allorecognition), some serial killer cells require multiple stimulatory signals in order to induce effector function (i.e., both indirect and direct allorecognition). There are also a number of inhibitory receptors present on serial kill cell surfaces that inhibit serial killer cell function. Therefore, the activation of serial killer cell effector function may further require prevention of inhibitory receptor ligand binding either on the surface of host cells or in the reaction environment, interference of inhibitory receptors on the surface of serial killer cells, or a blockade of the inhibitory signals induced in serial killer cells. (Benichou, G, and A W Thomson. "Direct versus Indirect Allorecognition Pathways: on the Right Track." *American Journal of Transplantation: Official Journal of the American Society of Transplantation and the American Society of Transplant Surgeons*, U.S. National Library of Medicine, April 2009, www.ncbi.nlm.nih.gov/pmc/articles/PMC3746751/).

The majority of T cells recognizes linear peptides presented by cell-surface MHC class I or class II molecules, and/or MHC-like molecules. However, most serial killing T cells must first be stimulated by a professional APC and further receive signals from costimulatory molecules and cytokines to become activated.

Natural cytotoxicity receptors (NCRs) exist on the surface of serial killer cells, such as NKs, NKTs, GDT, macrophages, CD4+ CTLs, and CD8+ CTLs. One example, NKG2D, is a C-type lectin-like type II transmembrane glycoprotein. Other natural cytotoxicity receptors include, without limitation, NKp46 (NCR1, CD335), NKp44 (NCR2, CD336), and NKp30 (NCR3, CD337). These natural cytotoxicity receptors act as activators of serial killer cells, or as co-stimulatory signals in heteroclitic cross-reactivity activation.

Exogenous microbial components termed pathogen-associated molecular patterns (PAMPs), or endogenous inflammatory factors released from necrotic cells known as damage associated molecular patterns (DAMPs), bind to the germline-encoded pattern recognition receptors (PRRs) including toll-like receptors (TLRs), nucleotide oligomerization domain (NOD)-like receptors (NLRs), and C-type lectin receptors (CLRs). Immature dendritic cells recognize a diverse array of PAMPs through TLRs present on their cell surface. After sensing the existence of a PAMP, immature DCs are transformed to the mature DC form, which results in increased surface levels of MHC proteins and co-stimulatory molecules. This maturation process effectivity primes naïve T cells, and helps to prime NKs as well. (Ebihara, et al. "Induction of NKG2D Ligands on Human Dendritic Cells by TLR Ligand Stimulation and RNA Virus Infection." *OUP Academic*, Oxford University Press, 18 Sep. 2007, academic.oup.com/intimm/article/19/10/1145/743680).

The triggering of PAMPs by TLRs on APCs results in the production of type I IFNs, IL-12, IL-18, and IL-15, which helps to prime some serial killer cells for activation.

The triggering of PRRs on APCs result in multiple immune system effects: 1) high level expression of stable "non-self" protein presenting MHC complexes on the cell surface, which triggers T cell responses; 2) expression of high levels of costimulatory molecules such as CD80 and CD86 that prime and activate antigen-specific T cells; and 3) the secretion of proinflammatory cytokines, such as IL-1, IL-6, IL-12, TNF-α, GM-CSF, and IFN-y. The secretion of proinflammatory cytokines then induces the activation of APCs, which directly activate non-specific serial killer cells and help to promote T-cell differentiation into antigen-specific helper T cells or cytotoxic T cells that mediate acquired immunity. (Mendelsohn, John, et al. The Molecular Basis of Cancer. Elsevier Health Sciences, 2015, pp. 695-739).

The same TLRs that identify PAMPs can also be activated by DAMPs. DAMPs are molecules that are not pathogen derived, but instead are molecules such as the intracellular contents of a cell that has undergone cell death. There is evidence that DAMP signaling through TLRs initiates and amplies pathogen-independent responses. In the context of normal tissue surveillance, NKG2D ligand expression indicates cellular stress and represents a self-identification mark for cyotoxic lymphocytes. NKG2D ligand expression has been found to be upregulated by the stimulation of immature DCs with PAMPs. Similarly, DAMPs also represent "danger" signals; a correlation has been shown between the activation of TLRs and the increased expression of NKG2D ligand in the context of cellular injury. It has been proposed that NKG2D activation occurs in response to cellular injury, which causes innate cells, such as NK cells, to be hyperresponsive to future activation. (Wortham, Brian W., et al. "TLR and NKG2D Signaling Pathways Mediate CS-Induced Pulmonary Pathologies." PLOS ONE, Public Library of Science, journals.plos.org/plosone/article?id=10.1371/journal.pone.0078735).

Ultimately, the binding of PAMPS to PRRs trigger the activation of MAPK cascades via adaptor proteins myeloid differentiation primary-response protein 88 (MyD88) and T1R domain-containing adaptor protein inducing IFNβ (TRIF (Qian, F. et al, (2016) "Pivotal role of mitogen-activated protein kinase-activated protein kinase 2 in inflammatory pulmonary diseases," Curr. Protein Pept. Sci. 17(4): 332-42; citing Qian, C. and Cao, X, (2013), "Regulation of Toll-like receptor signaling pathways in innate immune responses," Ann. NY Acad. Sci. 1283: 67-74).

In canonical signal transduction, p38 MAPK is selectively phosphorylated by MAPKKs (MKK3 and MKK6), which in turn are activated by MAPKKKs, including TGFβ-activated kinase 1 (TAK1), apoptosis signal-regulating kinase 1 (ASK1), mixed-lineage kinase 2 (MLK2) or MLK3. The p38 MAPK-mediated signals initiate the activation of several transcriptional factors including CREB, ATF2 and Myc, as well as other kinases including MK2, but also MK3, MNK1/2, and MSK1/2 (Id. citingId. citing Obata, T. et al, (2000) Crit. Care Med. 28 (4 Suppl.: N67-N77; Dong, C. et al, (2002) "MAP kinases in the immune response," Annu. Rev. Immunol. 20: 55-72)). Among these distal kinases, the role of MK2 has been determined to be essential for the regulation of innate immune responses, including modulating production of inflammatory cytokines and chemokines, reactive oxygen species (ROS) and nitric oxide (NO). Id.

The term "stable" as used herein refers to resisting molecular or chemical change. In the context of the ENLST™ cells of the described invention, it refers to a stably transfected ENLST™ cell population that yields a reproducible level of MNC immunostimulation in dose dependent fashion in an MLTR in vitro. It includes stably transfected live ENLST™ cells, membrane fragments of ENLST™ cells comprising an exogenous immunomodulatory protein, and dead necrotic ENLST™ cells comprising an immunomodulatory protein expressed on their surface, each of which is capable of MNC immunostimulation either directly or indirectly.

The term "stem cells" refers to undifferentiated cells having high proliferative potential with the ability to self-renew that can generate daughter cells that can undergo terminal differentiation into more than one distinct cell phenotype. The term "renewal" or "self renewal" as used herein, refers to the process by which a stem cell divides to generate one (asymmetric division) or two (symmetric division) daughter cells having development potential indistinguishable from the mother cell. Self renewal involves both proliferation and the maintenance of an undifferentiated state.

The term "stimulate" and any of its various grammatical forms as used herein refers to inducing activation or increasing activity.

As used herein, the terms "subject" or "individual" or "patient" are used interchangeably to refer to a member of an animal species of mammalian origin, including humans.

The term "subject in need thereof" as used herein refers to a patient that (i) will be administered a composition according to the described invention, (ii) is receiving an composition according to the described invention; or (iii) has received a composition according to the described invention, unless the context and usage of the phrase indicates otherwise. "Subject in need thereof" may also refer to a subject that has or is suspected of having an disorder susceptible to treatment with a composition of the described invention.

The term "substantially pure" with regard to a cell component of a composition as used herein refers to that cell component being substantially separated from substances with which it may be associated in living systems. It refers purity of at least 75%, at least 80%, at least 85%, at least 90%, at least 95% or at least 99% pure as determined by an analytical protocol. Such protocols may include, for example, but are not limited to, FACS.

The term "suppress" in any of its grammatical forms as used herein refers to inhibiting or decreasing activity.

The term "symptom" as used herein refers to a sign or an indication of disorder or disease, especially when experienced by an individual as a change from normal function, sensation, or appearance.

The term "therapeutic agent" as used herein refers to a drug, molecule, nucleic acid, protein, metabolite, cell, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably herein. The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The terms "therapeutic amount", an "amount effective", or "pharmaceutically effective amount" of an active agent is used interchangeably to refer to an amount that is sufficient to provide the intended benefit of treatment. However, dosage levels are based on a variety of factors, including the age, weight, sex, medical condition of the patient, the severity of the condition, the route of administration, and the particular active agent employed. Thus the dosage regimen may vary widely, but can be determined routinely by a physician using standard methods. Additionally, the terms "therapeutic amount", "and "pharmaceutically effective amounts" include prophylactic or preventative amounts of the compositions of the described invention. In prophylactic or preventative applications of the described invention, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition. It is generally preferred that a maximum dose be used, that is, the highest safe dose according to some medical judgment. The terms "dose" and "dosage" are used interchangeably herein.

The term "therapeutic effect" as used herein refers to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

For any therapeutic agent described herein the therapeutically effective amount may be initially determined from preliminary in vitro studies and/or animal models. A therapeutically effective dose may also be determined from human data. The applied dose may be adjusted based on the relative bioavailability and potency of the administered compound. Adjusting the dose to achieve maximal efficacy based on the methods described above and other well-known methods is within the capabilities of the ordinarily skilled artisan.

General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below.

Pharmacokinetic principles provide a basis for modifying a dosage regimen to obtain a desired degree of therapeutic efficacy with a minimum of unacceptable adverse effects. In situations where the drug's plasma concentration can be measured and related to the therapeutic window, additional guidance for dosage modification can be obtained.

Drug products are considered to be pharmaceutical equivalents if they contain the same active ingredients and are identical in strength or concentration, dosage form, and route of administration. Two pharmaceutically equivalent drug products are considered to be bioequivalent when the rates and extents of bioavailability of the active ingredient in the two products are not significantly different under suitable test conditions.

The term "therapeutic window" refers to a concentration range that provides therapeutic efficacy without unacceptable toxicity. Following administration of a dose of a drug, its effects usually show a characteristic temporal pattern. A lag period is present before the drug concentration exceeds the minimum effective concentration ("MEC") for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. Accordingly, the duration of a drug's action is determined by the time period over which concentrations exceed the MEC. The therapeutic goal is to obtain and maintain concentrations within the therapeutic window for the desired response with a minimum of toxicity. Drug response below the MEC for the desired effect will be subtherapeutic, whereas for an adverse effect, the probability of toxicity will increase above the MEC. Increasing or decreasing drug dosage shifts the response curve up or down the intensity scale and is used to modulate the drug's effect. Increasing the dose also prolongs a drug's duration of action but at the risk of increasing the likelihood of adverse effects. Accordingly, unless the drug is nontoxic, increasing the dose is not a useful strategy for extending a drug's duration of action.

Instead, another dose of drug should be given to maintain concentrations within the therapeutic window. In general, the lower limit of the therapeutic range of a drug appears to be approximately equal to the drug concentration that produces about half of the greatest possible therapeutic effect, and the upper limit of the therapeutic range is such that no more than about 5% to about 10% of patients will experience a toxic effect. These figures can be highly variable, and some patients may benefit greatly from drug concentrations that exceed the therapeutic range, while others may suffer significant toxicity at much lower values. The therapeutic goal is to maintain steady-state drug levels within the therapeutic window. For most drugs, the actual concentrations associated with this desired range are not and need not be known, and it is sufficient to understand that efficacy and toxicity are generally concentration-dependent, and how drug dosage and frequency of administration affect the drug level. For a small number of drugs where there is a small (two- to three-fold) difference between concentrations resulting in efficacy and toxicity, a plasma-concentration range associated with effective therapy has been defined.

In this case, a target level strategy is reasonable, wherein a desired target steady-state concentration of the drug (usually in plasma) associated with efficacy and minimal toxicity is chosen, and a dosage is computed that is expected to achieve this value. Drug concentrations subsequently are measured and dosage is adjusted if necessary to approximate the target more closely.

In most clinical situations, drugs are administered in a series of repetitive doses or as a continuous infusion to maintain a steady-state concentration of drug associated with the therapeutic window. To maintain the chosen steady-state or target concentration ("maintenance dose"), the rate of drug administration is adjusted such that the rate of input equals the rate of loss. If the clinician chooses the desired concentration of drug in plasma and knows the clearance and bioavailability for that drug in a particular patient, the appropriate dose and dosing interval can be calculated. However, living cellular therapies break this concept, since they divide and may even take up permanent residence in the body in the case of autologous cellular therapy. Hence what is initially administered can bear little correlation to what is present in the recipient over time.

As used herein the term "treating" includes abrogating, substantially inhibiting, slowing or reversing the progression of a condition, substantially ameliorating clinical symptoms of a condition, or substantially preventing the appearance of clinical symptoms of a condition. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s). Treatment also includes eliciting a clinically significant response, whether detectable or undetectable, without excessive levels of side effects.

The terms "tumor burden" and "tumor load" are used interchangeably to refer to the number of cancer cells, the size of a tumor, or the amount of cancer in the body.

As used herein, the terms "wild type," "naturally occurring," or grammatical equivalents thereof, are meant to refer to an amino acid sequence or a nucleotide sequence that is found in nature and includes allelic variations; that is, an amino acid sequence or a nucleotide sequence that usually has not been intentionally modified. Accordingly, the term "non-naturally occurring," "synthetic," "recombinant," or grammatical equivalents thereof, are used interchangeably to refer to an amino acid sequence or a nucleotide sequence that is not found in nature; that is, an amino acid sequence or a nucleotide sequence that usually has been intentionally modified. It is understood that once a recombinant nucleic acid is made and reintroduced into a host cell or organism, it will replicate non-recombinantly, i.e., using the in vivo cellular machinery of the host cell rather than in vitro manipulations, however, such nucleic acids, once produced recombinantly, although subsequently replicated non-recombinantly, are still considered recombinant for the purpose of the described invention.

Method for Preparing an Anti-Tumor Cellular Therapy for Passive Immunization of a Cancer Patient According to one aspect, the described invention provides a method for in vitro activation of cytotoxic T-cell populations followed by passive immunization of a cancer subject not currently under the influence of an immunosuppressive regimen with a composition comprising a cell product containing activated and expanded mononuclear cells including activated and expanded subpopulations of serial killer cells, the method comprising, under sterile conditions:

STEP 1: Inducing an immune response in vitro by:
(a) isolating a population of mononuclear cells (MNCs) from a biological sample;
(b) preparing a population of engineered leukocyte stimulator cells ("ENLST™ cells") comprising an allogeneic tumor cell line transfected or transduced with recombinant DNA sequences encoding at least three essential immunomodulators peptides, wherein the three essential immunomodulators peptides are OX40 Ligand (OX40L), CD27 Ligand (CD70), and CD28 Ligand (CD28L) comprising CD80, CD86 or both;
(c) contacting the population of MNCs of step (a) with the ENLST™ cells of step (b) in vitro to induce an immune response comprising an activated population of MNCs comprising activated serial killer cells effective to kill tumor cells;

STEP 2: expanding the activated population of MNCs comprising activated subpopulations of serial killer cells in vitro by culturing the activated MNC to form a cell product;

STEP 3: preparing a unit dose package comprising an individual dose of the cell product; freezing the unit packages containing the cell product at −86° C., and cryostoring the frozen unit dose packages in a vapor phase of a liquid nitrogen freezer (hereinafter "cryostorage");

STEP 4: thawing a therapeutic amount of the frozen unit dose packages comprising the cell product under controlled conditions; and optionally combining the frozen and thawed cell product of Step 4 with a pharmaceutically acceptable carrier component to form a pharmaceutical composition; and STEP 5: administering a therapeutic amount of the cell product or the pharmaceutical composition of Step 4 comprising the activated and expanded cell product to the subject.

According to some embodiments, the immune system of the cancer subject not currently under the influence of an immunosuppressive regimen is intact, meaning it is not depleted by the immunosuppressive regimen. According to some embodiments, the immunosuppressive regimen comprises chemotherapy. According to some embodiments, the subject is a melanoma patient. According to some embodiments, the subject is a prostate cancer patient. According to some embodiments, the subject is a breast cancer patient.

STEP 1: Inducing an Immune Response In Vitro (i) Isolating a Population of Mononuclear Cells (MNCs) from a Biological Sample According to some embodiments, the mononuclear cells are derived from a biological sample. According to some embodiments, the biological sample is autologous to the recipient subject. According to some embodiments, the biological sample is allogeneic to the recipient subject. According to some embodiments, the biological sample is derived from a subject not currently under the influence of an immunosuppressive regimen that is not the recipient. According to some embodiments, the biological sample is of mammalian origin. According to some embodiments, the biological sample is human. According to some embodiments, the source of the mononuclear cell population is a body fluid. According to some embodiments, the body fluid is umbilical cord blood, whole blood, peripheral blood, mobilized peripheral blood, or bone marrow. According to some embodiments, the source of the smononuclear cell population is whole blood. According to some embodiments, the biological sample is a bone marrow sample. According to some embodiments, the biological sample is umbilical cord blood.

According to some embodiments the biological sample is a peripheral blood sample. According to some embodiments, the sample is a mobilized peripheral blood sample. Treatment with hematopoietic growth factors has been shown to cause a marked rise in the number of hematopoietic progenitor cells in the peripheral blood as measured by the presence of CD34+ cells, or as measured in a colony formation assay as CFUs. Such mobilized-peripheral blood hematopoietic stem cells (HSCs) have been used for transplantation, immunotherapy, and cardiovascular regenerative medicine. Colony stimulating factors, for example, are agents used for hematopoietic stem cell mobilization. Examples of colony stimulating factors include, without limitation, G-CSF, GM-CSF, and pharmaceutically acceptable analogs and derivatives thereof. For example, filgrastim, a G-CSF analog produced by recombinant technology, is marketed under the brand names Neupogen® (Amgen); Religrast® (Reliance Life Sciences), Nugraf® (Zenotech Laboratories, Ltd., and Neukine® (Intas Biopharmaceuticals).

According to some embodiments, the mononuclear cells can be isolated from whole blood by density gradient centrifugation using a hydrophilic colloid (e.g., polymers formed by the copolymerization of sucrose and epichlorohydrin (Ficoll-Paque®) or polyvinylpyrrolidone-coated colloidal silica (Percoll®). In an exemplary protocol, a diluted mixture of PBS and peripheral blood is layered in a 50 ml centrifuge tube on top of Ficoll-Paque®, and centrifuged at 400×g for 30-40 minutes at 20° C. in a swinging-bucket rotor without brake. The upperlayer is aspirated, leaving the mononuclear cell layer (lymphocytes, monocytes and thrombocytes) undisturbed at the interface. The mononuclear cell layer is carefully transferred into a new 50 ml centrifuge tube. Cells are washed with PBS (pH 7.2) containing 2 mM EDTA, centrifuged at 300×g for 10 min at room temperature and the supernatant discarded. For removal of platelets, the cell pellet is resuspended in 50 mL buffer and centrifuged at 200×g for 10-15 minutes at room temperature. The supernatant containing the platelets is removed. This step is repeated. The cell pellet is resuspended in a suitable buffer solution or medium for downstream applications.

An alternative exemplary protocol for isolating PBMCs is via leukapheresis. For example, whole blood can be obtained from a patient with informed consent, and run through a device that automatically separates the target PBMC fraction from other components of the blood, such as plasma and red blood cells; the other components are then returned to the patient while the isolated PBMC is collected. The collected PBMC may undergo further processing, for example the removal of residual red blood cells through lysis.

According to some embodiments, mononuclear cells also can be isolated from an allogeneic source, e.g., umbilical cord blood. The mononuclear cell (MNC) fraction of umbilical cord blood is composed of lymphocytes (T cells, B cells, and NK cells), monocytes, dendritic cells and stem/progenitor cells. Anticoagulated cord blood citrate phosphate dextrose (Sigma-Aldrich, St. Louis, Mo.) is drawn directly into a 50 mL tube containing 5 mL buffer and stored at 4 C prior to separation. Anticoagulated cord blood is diluted with 3× volume of buffer. The diluted cell suspension is carefully layered over Ficoll-Paque® in a 50 ml conical tube and centrifuged at 400×g for 35 minutes at 20° C. in a swinging bucket rotor without brake. The upper layer is aspirated, leaving the mononuclear cell layer undisturbed at the interphase. The mononuclear layer is carefly transferred to a new 50 mL conical tube. The tube is filled with buffer, mixed and centrifuged at 300×g for 10 min at 20 C. The supernatant is carefully aspirated. For removal of platelets, the cell pellet is resuspended in 50 mL of buffer and centrifuged at 200×g for 10-15 minutes at 20 C. The supernatant is carefully removed completely. The cell pellet is resuspended in an appropriate amount of buffer for downstream applications.

According to some embodiments, mononuclear cells can be isolated from bone marrow: Bone marrow is collected from the upper iliac crest or the sternum using an aspiration needle. The aspirated human bone marrow is diluted at a ratio of 7:1 with a suitable buffer. The cells are passed through a 100 µm filter to remove bone fragments and cell clumps. The diluted cell suspension is layered over Ficoll-Paque® in a 50 ml conical tube, and centrifuged at 445×g for 35 minutes at 20° C. in a swinging bucket rotor without brake. The upper layer is aspirated, leaving the mononuclear cell layer undisturbed. The bone marrow MNCs at the interphase are carefully transferred to a new 50 ml conical tube. Cells are washed with buffer, mixed gently and centrifuged at 300×g for 10 min at 20° C. The supernatant is carefully removed. For removal of platelets, the cell pellet is resuspend in 50 ml buffer and centrifuged at 200×g for 10-15 minutes at 20° C. The supernatant is carefully removed. The cell pellet is resuspended in an appropriate buffer for downstream applications.

According to some embodiments the isolated population of MNCs comprises a mixed population of lymphocytes, a population of monocytes, and a population of dendritic cells. In humans, the frequencies of these populations in peripheral blood vary across individuals, but typically, lymphocytes are in the range of 70-90%, monocytes from 10 to 20%, while dendritic cells are rare, accounting for only 1-2%. (Kleiveland, C. R., "Peripheral Blood Monoclear Cells" in: Verhoeckx, K. et al. (eds). The Impact of Food Bioactives on Health (2015), Springer, Cham. Doi.org/10.1007/978-3-319-1610404_15) According to some embodiments, the mixed population of lymphocytes comprises a subpopulation of T cells, a subpopulation of B cells, and a subpopulation of NK cells. According to some embodiments, the T lymphocytes comprise a subpopulation of CD8 T lymphocytes and a subpopulation of CD4 T lymphocytes.

(ii) Preparing a Population of Engineered Leukocyte Stimulator Cells (ENLST™ Cells)

The term "ENLST™ cells" as used herein refers to engineered leukocyte stimulator cells. According to some embodiments, the ENLST™ cells comprise a primary tumor cell line transfected or transduced with recombinant DNA sequences. According to some embodiments, the recombinant DNA sequences encode a core of the following essential immunomodulatory peptides: OX40 Ligand (OX40L), CD27 Ligand (CD70) and CD28 Ligand (CD28L) comprising CD80, CD86, or both. According to some embodiments, the recombinant sequences can comprise one or more additional subsets of immunomodulators designated as R groups (by analogy to those in a core chemical structure), with each subset comprising 3-25 immunomodulators.

According to some embodiments, the method further comprises developing a clonal cell bank of the ENLST™ cell population(s) to minimize cell heterogeneity. According to some embodiments, the ENLST™s are clonal.

Tumor Cell Line(s)
Tumor Specific Antigens

According to some embodiments, the disclosure provides a population of ENLST™ cells expressing one or more tumor specific antigens. According to some embodiments, the tumor specific antigens may be encoded by a primary open reading frame of gene products that are differentially expressed by tumors, and not by normal tissues. According to some embodiments, the tumor specific antigens may be encoded by mutated genes, intronic sequences, or translated alternative open reading frames, pseudogenes, antisense strands, or may represent the products of gene translocation events. According to some embodiments, the tumor cell provides a broad array of tumor specific antigens, many of which are of unknown nature. According to some embodiments, the tumor antigen is a neoantigen.

Examples of tumor specific antigens include, without limitation: (a) nonmutated shared antigens (e.g., melanoma-associated antigen (MAGE), B-melanoma antigen (BAGE), renal tumor antigen (RAGE), and a cancer testis antigen (e.g. NY-ESO); (b) differentiation antigens (e.g., prostate-specific membrane antigen [PSMA] and prostate-specific antigen (PSA) in prostate carcinoma, Mart1/MelanA and tyrosinase present in many melanomas, and carcino embryonic antigen (CEA) present in a large percentage of colon cancers), which are tissue restricted and present in lineage-specific tumor cell; (c) mutated oncogenes and tumor suppressor genes (e.g., mutated ras, rearranged bcr/abl, mutated p53), which provide novel epitopes for immune recognition; (d) unique idiotypes (e.g., immunoglobulin antigensin myeloma and B-cell myeloma, T-cell receptor (TCR) expressed in CTCL), (e) oncovirus-derived epitopes (e.g., the human papillomavirus-encoded E6 and E7 proteins, Epstein-Barr virus-associated antigens present in primary brain lymphoma); and (f) nonmutated oncofetal proteins such as CEA, α-fetoprotein, and survivin. According to some embodiments, the tumor specific antigen is selected from an antigen listed in the publically available Cancer Antigenic Peptide Database (on the worldwide web at caped.icp.ucl.ac.be/Peptide/list, incorporated by reference in its entirety herein). According to some embodiments, the tumor specific antigen comprises an antigen set forth in Table 4, shown below.

TABLE 4

Tumor Specific Antigens.

| Gene/Protein | Tumor |
|---|---|
| PPP1R3B | melanoma |
| alpha-actinin-4 | lung carcinoma |
| ARTC1 | melanoma |
| CASP-8 | head and neck squamous cell carcinoma |
| beta-catenin | melanoma |
| Cdc27 | melanoma |
| CDK4 | melanoma |
| CDK12 | melanoma |
| CDKN2A | melanoma |
| CLPP | melanoma |
| CSNK1A1 | melanoma |
| EFTUD2 | melanoma |
| Elongation factor 2 | lung squamous CC |
| FN1 | melanoma |
| GAS7 | melanoma |
| GPNMB | melanoma |
| HAUS3 | melanoma |
| HSDL1 | ovarian cancer |
| LDLR-fucosyltransferaseAS fusion protein | melanoma |
| HLA-A2d | renal cell carcinoma |
| HLA-A11d | melanoma |
| hsp70-2 | renal cell carcinoma bladder tumor |
| MART2 | melanoma |
| MATN | melanoma |
| k-ras | non-small cell lung carcinoma |
| MUM-1f | melanoma |
| MUM-2 | melanoma |
| MUM-3 | melanoma |

TABLE 4-continued

Tumor Specific Antigens.

| Gene/Protein | Tumor |
|---|---|
| neo-PAP | melanoma |
| NFYC | lung squamous cell carcinoma |
| OS-9 | melanoma |
| PTPRK | melanoma |
| N-ras | melanoma |
| BRAF600 | melanoma |
| SIRT2 | melanoma |
| SNRPD1 | melanoma |
| Triosephosphate isomerase | melanoma |
| Myosin class I | melanoma |
| BCR-ABL fusion protein (b3a2) | chronic myeloid leukemia |
| B-RAF | melanoma |
| CASP-5 | colorectal, gastric, and endometrial carcinoma |
| dek-can fusion protein | myeloid leukemia |
| ETV6-AML1 fusion protein | acute lymphoblastic leukemia |
| FLT3-ITD | acute myelogenous leukemia |
| FNDC3B | chronic lymphocytic leukemia |
| OGT | colorectal carcinoma |
| p53 | head and neck squamous cell carcinoma |
| pml-RARalpha fusion protein | promyelocytic leukemia |
| PRDX5 | melanoma |
| K-ras | pancreatic adenocarcinoma |
| SYT-SSX1 or -SSX2 fusion protein | sarcoma |
| KIAAO205 | mutation |
| ME1 | mutation |
| EGFRvIII | Mutation |
| TGF-betaRII | colorectal carcinoma |
| gp100/Pmel17 | melanoma |
| mammaglobin-A | breast cancer |
| Melan-A/MART-1 | melanoma |
| NY-BR-1 | breast cancer |
| OA1 | melanoma |
| PAP | prostate cancer |
| PSA | prostate carcinoma |
| RAB38/NY-MEL-1 | melanoma |
| TRP-1/gp75 | melanoma |
| TRP-2 | melanoma |
| tyrosinase | melanoma |
| DKK1 | testis, prostate, |
| ENAH (hMena) | breast, prostate stroma and epithelium of colon-rectum, pancreas, endometrium |
| G250/MN/CAIX | stomach, liver, pancreas |
| Kallikrein 4 | prostate and ovarian cancer |
| D393-CD20n | B cell lymphomas and leukemias |
| Cyclin-A1 | AML, testicular, endometrial and epithelial ovarian cancer |
| GAGE-1,2,8 | |
| GAGE-3,4,5,6,7 | |
| GnTVf | |
| GPC3 | Hepatocellular carcinoma, melanoma, lung squamous cell carcinoma, hepatoblastoma, ovarian clear cell carcinoma, neuroblastoma, stoma ch |
| HERV-E | kidney |
| HERV-K-MEL | melanoma |
| KK-LC-1 | |
| KM-HN-1 | |
| LAGE-1 | Melanoma, non-small cell ung cardinoma, bladder, prostate and head and neck cancer |
| LY6K | Breast cancer |
| MAGE-A1 | melanoma |
| MAGE-A2 | Melanoma |
| MAGE-A3 | Melanoma |
| MAGE-A4 | Melanoma |
| MAGE-A5 | Melanoma |
| MAGE-A6 | Melanoma |
| MAGE-A7 | Melanoma |
| MAGE-A8 | Melanoma |
| MAGE-A9 | Melanoma |

TABLE 4-continued

Tumor Specific Antigens.

| Gene/Protein | Tumor |
|---|---|
| MAGE-A10 | Melanoma |
| MAGE-A11 | Melanoma |
| MAGE-A12m | Melanoma |
| MAGE-C1 | Melanoma |
| MAGE-C2 | Melanoma |
| MAGE-n | melanoma |
| mucink | |
| NA88-A | |
| NY-ESO-1/LAGE-2 | melanoma |
| Neutrophil granule proteases | |
| OFA-iLR | |
| PTH-rP | |
| S2 | |
| SAGE | |
| Sp17 | |
| SSX-2 | |
| SSX-4 | |
| TAG | |
| TAG-1 | |
| TAG-2 | |
| hTERT | Colorectal carcinoma |
| TPBG | |
| TRAG-3 | |
| TRP2-6b | |
| TRP2-INT2g | |
| TTK | |
| XAGE-1b/GAGED2a | |
| ART-4 | |
| CDCA1/NUF2 | |
| Cep55/c10orf3 | |
| CML28 (EXOSC5) | |
| DAM-6, -10 (MAGE-B1) | |
| IMP-3 | |
| OVA66 | |
| OY-TES-1 | |
| PASD1 | |
| RHAMM/CD168 | |
| SART-3 | |
| SART-1 | |

According to some embodiments, the population of tumor cells is derived from a cancer selected from the group consisting of melanoma, colorectal carcinoma, leukemia, chronic myeloid leukemia, prostate cancer, head and neck cancer, squamous cell carcinoma, tongue cancer, larynx cancer, tonsil cancer, hypopharynx cancer, nasalpharynx cancer, breast cancer, colon cancer, lung cancer, pancreatic cancer, hepatocellular carcinoma, glioblastoma and brain cancer.

According to some embodiments, the population of tumor cells is characterized by the expression of one or more of gp100, tyrosinase, Melan-A, tyrosinase-related protein (TRP-2-INT2), melanoma antigen-1 (MAGE-A1), NY-ESO-1, preferentially expressed antigen of melanoma (PRAME) CDK4 and multiple myeloma oncogene 1 (MUM-1).

According to some embodiments, the population of colorectal cancer tumor cells is characterized by the expression of one or more of carcinoembryonic antigen (CEA), MAGE, HPV, human telomerase reverse transcriptase (hTERT), EPCAM, PD-1, PD-L1, p53, cell surface-associated mucin 1 (MUC1).

Immunologic antigenic specificity may arise from one or more of the amino acid sequence of the antigen, from the degree of expression of that antigen by the tumor cell, from post-translational modification of the antigen, and the like.

Immunologic antigen specificity to a certain type of cancer cell may also arise from one or more of a particular fingerprint of a plurality of tumor antigens, from the fact that a particular antigen, while expressed by a wide variety of tumor cells, has particular use in immunotherapy against a smaller number of tumor types, from the fact that a particular collection of MHC class I presentable and MHC class II presentable epitopes exist on a particular polypeptide or polypeptide fragment, and by omitting one or more peptides that may provoke immunotolerance. The skilled artisan can locate the relevant nucleic acid and polypeptide sequences, e.g., on the U.S. Government's web site, at ncbi.nlm.nih.

According to some embodiments, the tumor cells are derived from a sample from a subject. According to some embodiments, the tumor cells are derived from a tumor cell line or tumor cell line variant.

According to some embodiments, tumor antigen specificity of the described invention may be determined by the parental tumor cell line or tumor cell line variant that is selected for modification with immunomodulators.

Parent Cell Lines

According to some embodiments, tumor cell line or tumor cell line variants may be derived from established cell lines from either public sources (e.g. NIH, DCTD Tumor Repository operated by Charles River Laboratories Inc.) or commercial sources (e.g. ATCC, Sigma Alrich, Thermo Fischer Scientific, Genescript, DSM2). According to some embodiments, new cell lines can be established de novo from tumor cells derived from the tumor of a cancer patient.

According to some embodiments, cancer tissues, cancer cells, cells infected with a cancer-causing agent, other pre-neoplastic cells, and cell lines of human origin can be used as a source. According to some embodiments, a cancer cell can be from an established tumor cell line or tumor cell line variant such as, without limitation, an established non-small cell lung carcinoma (NSCLC), a bladder cancer, a melanoma, an ovarian cancer, a renal cell carcinoma, a prostate carcinoma, a sarcoma, a breast carcinoma, a squamous cell carcinoma, a head and neck carcinoma, a hepatocellular carcinoma, a pancreatic carcinoma, or a colon carcinoma cell line.

According to some embodiments, the established cell lines comprise the LNCaP clone FGC (ATCC CRL-1740), which itself is derived from a metastatic prostate cancer that had migrated to a lymph node. According to some embodiments, the established cell lines comprise the PC-3 (ATCC CRL-1435) cell line, which itself is derived from metastatic prostate cancer that migrated to bone. According to some embodiments, the tumor cell line or tumor cell line variants are derived from one or more of the following ATCC cell lines: VCaP (ATCC CRL-2876); MDA PCa 2b (ATCC CRL-2422); or DU 145 (ATCC HTB-81).

According to some embodiments, the established cell lines comprise the SK-MEL-2 clone (ATCC HTB-68), which itself is derived from metastasis on skin of thigh.

According to some embodiments, the established cell lines comprise one or more of mammary carcinoma cell lines designated COO-G, DU4475, ELL-G, HIG-G, MCF/7, MDA-MB-436, MX-1, SW-613, and VAN-G. According to some embodiments, the established cell lines comprise one or more of alveolar soft part sarcoma cell lines designated ASPS, and ASPS-1. According to some embodiments, the established cell lines comprise one or more lung cell lines designated LX-1, COS-G, H-MESO-1, H-MESO-1A, NCI-H23, and NCI-H460. According to some embodiments, the established cell lines comprise one or more colon cancer cell lines designated CX-5, GOB-G, HCC-2998, HCT-15, KLO-G, KM20L2, MRI-H-194, LOVO I, LOVO II, and MRI-H-250. According to some embodiments, the established cell lines comprise one or more melanoma cell lines designated NIS-G, TRI-G, WIL-G, MRI-H-121B, MRI-H-187, MRI-H-221, and MRI-H-255. According to some embodiments, the established cell lines comprise one or more cervical cancer cell lines designated MRI-H-177, MRI-H-186, MRI-H-196, and MRI-H-215. According to some embodiments, the established cell lines comprise one or more kidney cancer cell lines designated MRI-H-121 and MRI-H-166. According to some embodiments, the established cell lines comprise one or more endometrium cancer cell lines designated MRI-H-147 and MRI-H-220. According to some embodiments, the established cell lines comprise one or more ovarian cancer cell lines designated MRI-H-258, MRI-H-273, MRI-H-1834, and SWA-G. According to some embodiments, the established cell lines comprise one or more sarcoma cell lines designated HS-1, OGL-G, and DEL-G. According to some embodiments, the established cell lines comprise the epidermoid cell line designated DEAC-1. According to some embodiments, the established cell line comprises the glioblastoma cell line designated SF 295. According to some embodiments, the established cell line comprises the prostate cancer cell line designated CWR-22. According to some embodiments, the established cell line comprises the Burkitt's lymphoma cell line designated DAU. According to some embodiments, the foregoing established cell lines described herein are commercially available, e.g. from American Type Culture Collection (ATCC), European Collection of Cell Cultures (ECACC), or any depository listed as an International Depositary Authority (IDA) under Article 7 of the Budapest Treaty.

According to some embodiments, exemplary established cell lines comprise one or more of the cell lines in the following table:

TABLE 5

Cell lines.

| Designation | Tissue of Origin | Histologic Type |
| --- | --- | --- |
| 786-0 | Kidney | Renal Cell Carcinoma |
| A2780 | Ovary | Adenocarcinoma |
| A498 | Kidney | Renal Cell Carcinoma |
| A549 | Lung | Non-small Cell |
| A704 | Kidney | Renal Cell Carcinoma |
| ACHN | Kidney | Renal Cell Carcinoma |
| ASPS-1 | Lymph Node | Alveolar Soft Part Sarcoma |
| BT-549 | Breast | Adenocarcinoma |
| CAKI-1 | Kidney | Renal Cell Carcinoma |
| CCRF-CEM | Lymph | Leukemia |
| CCRF-SB | Lymph | Leukemia |
| CHA-59 | Bone | Osteosarcoma |
| COLO 205 | Colon | Adenocarcinoma |
| DMS-114 | Lung | Small Cell |
| DU-145 | Prostate | Carcinoma |
| EKVX | Lung | Adenocarcinoma |
| HCC-2998 | Colon | Adenocarcinoma |
| HCT-15 | Colon | Carcinoma |
| HCT-116 | Colon | Adenocarcinoma |
| HOP-18 | Lung | Large Cell Carcinoma |
| HOP-62 | Lung | Adenocarcinoma |
| HL-60 | Ascites | Pro-myelocytic Leukemia |
| H-MESO-1 | | Mesothelioma |
| HS 578T | Breast | Adenocarcinoma |
| HS 913T | Lung | Mixed Cell |
| HT-29 | Colon | Adenocarcinoma |
| IGR-OV1 | Ovary | Adenocarcinoma |
| KM-12 | Colon | Adenocarcinoma |
| KM 20L2 | Colon | Adenocarcinoma |
| K-562 | Lymph | Leukemia |
| LOVO | Colon | Adenocarcinoma |
| LOX IMVI | Lymph Node Metastasis | Amelanotic Melanoma |
| LXFL 529 | Lung | Large Cell Carcinoma |
| NCI-H1299 | Lung | Adenocarcinoma |
| NCI-H2887 | Lung | Adenocarcinoma |

TABLE 5-continued

Cell lines.

| Designation | Tissue of Origin | Histologic Type |
| --- | --- | --- |
| NCI-H3122 | Lung | Adenocarcinoma |
| NCI-H322M | Lung | Adenocarcinoma |
| NCI-H3255 | Lung | Adenocarcinoma |
| NCI-H358M | Lung | Bronchioalveolar Carcinoma |
| NCI-H460 | Lung | Large Cell |
| NCI-H522 | Lung | Adenocarcinoma |
| NCI-H69 | Lung | Small Cell Carcinoma |
| NCI-H82 | Lung | Small Cell Carcinoma |
| NCI-H838 | Lung | Adenocarcinoma |
| NCI/ADR-RES | Ovary | Adenocarcinoma |
| OVCAR-3 | Ovary | Adenocarcinoma |
| OVCAR-4 | Ovary | Adenocarcinoma |
| OVCAR-5 | Ovary | Adenocarcinoma |
| OVCAR-8 | Ovary | Adenocarcinoma |
| PC-3 | Prostate | Carcinoma |
| PC-3/M | Prostate | Carcinoma |
| RPMI-7951 | Skin | Melanoma |
| RPMI-8226 | Lymph | Leukemia |
| RXF 393 | Kidney | Renal Cell Carcinoma |
| RXF 631 | Kidney | Renal Cell Carcinoma |
| TK-10 | Kidney | Renal Cell Carcinoma |
| UACC-62 | Skin | Melanoma |
| UACC-257 | Skin | Melanoma |
| UCSD 242L | Skin | Melanoma |
| UCSD 354K | Skin | Melanoma |
| UO-31 | Kidney | Renal Cell Carcinoma |
| U-251 | CNS | Glioblastoma |
| WIDR | Colon | Adenocarcinoma |
| XF 498 | CNS | Glioblastoma |

According to some embodiments, the choice of the parental cell line from which the tumor cell line or tumor cell line variant may be derived may affect the immune specificity of a given engineered leukocyte stimulator cell. For example, the use of a tumor cell line or tumor cell line variant derived from metastatic prostate cancer that migrated to the bone of a patient may result in ENLST™ cells that elicit an immune response specific for metastatic prostate cancer in the bone of a patient.

According to some embodiments, the tumor cell line or tumor cell line variants may be derived from a parental cell that comprises a universal cancer specific antigen. For example, the use of a parental tumor cell line or tumor cell line variant derived from metastatic prostate cancer that migrated to the bone of a patient may result in ENLST™ cells that elicits an immune response against all prostate cancer cells.

According to some embodiments, the tumor cell line or tumor cell line variants are derived from patient derived cells derived from various cancers. According to some embodiments, fresh tissue surgically removed from a tumor is enzymatically digested by type IV collagenase, followed by collection of disaggregated cells. According to some embodiments, disaggregated cells may then be grown in vitro in growth media with 10% fetal bovine serum on an extracellular matrix substrate, such as collagen or fibronectin, to promote attachment. According to some embodiments, adherent cells may then be passaged until the immortal cancer cells outgrow the non-cancerous fibroblast cells.

For example, according to some embodiments, the tumor cell line or tumor cell line variants may be derived from a solid tumor comprising tumor cells, including cancer stem cells, a metastatic cancer comprising metastatic tumor cells, comprising cancer stem cells, or a non-metastatic cancer. According to some embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. According to some embodiments, the cancer may be of a histological type, e.g., a cancer that begins in the skin or tissues that line or cover internal organs (carcinoma); a cancer that begins in bone or in the soft tissue of the body including cartilage, fat, muscle, blood vessels, and fibrous tissue (sarcoma); a cancer that starts in blood-forming tissue (leukemia); a cancer that begins in cells of the immune system (lymphoma); a cancer that arises in plasma cells (myeloma), or a brain/spinal cord cancer.

Examples of carcinomas include, without limitation, giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; an adenocarcinoma; a gastrinoma, a cholangiocarcinoma; a hepatocellular carcinoma; a combined hepatocellular carcinoma and cholangiocarcinoma; a trabecular adenocarcinoma; an adenoid cystic carcinoma; an adenocarcinoma in adenomatous polyp; an adenocarcinoma, familial polyposis coli; a solid carcinoma; a carcinoid tumor; a branchiolo-alveolar adenocarcinoma; a papillary adenocarcinoma; a chromophobe carcinoma; an acidophil carcinoma; an oxyphilic adenocarcinoma; a basophil carcinoma; a clear cell adenocarcinoma; a granular cell carcinoma; a follicular adenocarcinoma; a non-encapsulating sclerosing carcinoma; adrenal cortical carcinoma; an endometroid carcinoma; a skin appendage carcinoma; an apocrine adenocarcinoma; a sebaceous adenocarcinoma; a ceruminous adenocarcinoma; a mucoepidermoid carcinoma; a cystadenocarcinoma; a papillary cystadenocarcinoma; a papillary serous cystadenocarcinoma; a mucinous cystadenocarcinoma; a mucinous adenocarcinoma; a signet ring cell carcinoma; an infiltrating duct carcinoma; a medullary carcinoma; a lobular carcinoma; an inflammatory carcinoma; paget's disease, a mammary acinar cell carcinoma; an adenosquamous carcinoma; an adenocarcinoma w/squamous metaplasia; a sertoli cell carcinoma; embryonal carcinoma; choriocarcinoma.

Examples of sarcomas include, without limitation, glomangiosarcoma; sarcoma; fibrosarcoma; myxosarcoma; liposarcoma; leiomyosarcoma; rhabdomyosarcoma; embryonal rhabdomyosarcoma; alveolar rhabdomyosarcoma; stromal sarcoma; carcinosarcoma; synovial sarcoma; hemangiosarcoma; kaposi's sarcoma; lymphangiosarcoma; osteosarcoma; juxtacortical osteosarcoma; chondrosarcoma; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; myeloid sarcoma; mast cell sarcoma.

Examples of leukemias include, without limitation, leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; and hairy cell leukemia.

Examples of lymphomas and myelomas include, without limitation, malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant melanoma; amelanotic melanoma; superficial spreading melanoma; malignant melanoma in giant pigmented nevus; epithelioid cell melanoma; multiple myeloma.

Examples of brain/spinal cord cancers include, without limitation, pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibro sarcoma; neurilemmoma, malignant.

Examples of other cancers include, without limitation, a thymoma; an ovarian stromal tumor; a thecoma; a granulosa cell tumor; an androblastoma; a leydig cell tumor; a lipid cell tumor; a paraganglioma; an extra-mammary paraganglioma; a pheochromocytoma; blue nevus, malignant; fibrous histiocytoma, malignant; mixed tumor, malignant; mullerian mixed tumor; nephroblastoma; hepatoblastoma; mesenchymoma, malignant; brenner tumor, malignant; phyllodes tumor, malignant; mesothelioma, malignant; dysgerminoma; teratoma, malignant; struma ovarii, malignant; mesonephroma, malignant; hemangioendothelioma, malignant; hemangiopericytoma, malignant; chondroblastoma, malignant; granular cell tumor, malignant; malignant histiocytosis; immunoproliferative small intestinal disease.

For any given tumor type, several tumor cell line or tumor cell line variants may be commercially available. According to some embodiments, pooling of several of these cells lines, either as a mixture of whole cells or by making a membrane preparation out of the mixture of whole cells, may provide an array of cell surface tumor antigens for that tumor type.

According to some embodiments, the tumor cells or tumor cell line or tumor cell line variants may be rendered proliferation incompetent by irradiation.

Exogenous Immunomodulatory Molecules

According to some embodiments, an exogenous immunomodulatory molecule of the disclosed invention is a polypeptide that, alone or in combination with other exogenous immunomodulatory molecules, when incorporated into a population of ENLST™ cells, mediates stimulation of an immune cell.

According to some embodiments, an exogenous immunomodulatory molecule of the disclosed invention is a polypeptide that, alone or in combination with other exogenous immunomodulatory molecules, mediates stimulation of T-lymphocytes, natural killer (NK) cells, dendritic cells (DCs) or B lymphocytes. According to some embodiments, the NK cell is a memory-like NK cell. According to some embodiments, the T lymphocyte is a cytotoxic T-lymphocyte (CTL) (CD8+ T cell). According to some embodiments, the T lymphocyte is a memory T cell. According to some embodiments, the T lymphocyte is a regulatory T cell. According to some embodiments, the T lymphocyte is a helper T cell. According to some embodiments, the B lymphocyte is a memory B cell. It is a feature of the present invention that, according to some embodiments, the population of tumor cells comprising at least three core exogenous immunomodulatory molecules is effective to stimulate more than one type of immune cell, e.g. the allogeneic ENLST™ cells comprising a population of tumor cells of the present disclosure are effective to stimulate one or more of T-lymphocytes (e.g. CD8+ T cells), natural killer (NK) cells, dendritic cells (DCs) or B lymphocytes.

According to some embodiments, the expression "stimulating an immune cell" refers to activation of the immune cell. According to some embodiments, "stimulating an immune cell" refers to expansion of the immune cell. According to some embodiments, "stimulating an immune cell" refers to an increase in cytotoxicity of the immune cell. According to some embodiments, "stimulating an immune cell" refers to a combination of one or more of activation, expansion, and/or increased cytoxicity of the immune cell. According to some embodiments, the ENLST™ cells population of tumor cells comprising at least three core exogenous immunomodulatory molecules is effective to activate and/or expand immune cells (e.g. T-lymphocytes (e.g. CD8+ T cells), natural killer (NK) cells, dendritic cells (DCs) or B lymphocytes) ex vivo. According to some embodiments, the ENLST™ cells population of tumor cells comprising the at least three core exogenous immunomodulatory molecules is effective to activate and/or expand immune killer cells (e.g. T-lymphocytes (e.g. CD8+ T cells), natural killer (NK) cells, dendritic cells (DCs) or B lymphocytes) in vivo. Assays to detect if the ENLST™ cells population of tumor cells comprising the at least three core exogenous immunostimulatory molecules is effective to stimulate an immune killer cell population are described herein. According to one aspect, the disclosure thus provides an ENLST™ cell population comprising a population of tumor cells expressing one or more tumor specific antigens and genetically engineered to stably express a plurality of immunomodulatory molecules effective to stimulate one or more of T lymphocytes (e.g., CD8+ T cells), natural killer (NK) cells, dendritic cells (DCs) or B lymphocytes According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least three stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least four stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least five stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least six stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least seven stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least eight stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least nine stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of p tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least ten stably expressed exogenous immunomodulatory molecules effective to stimulate the T-lymphocytes, natural killer (NK) cells, dendritic cells (DCs) or B lymphocytes. According to some embodiments, the ENLST™ cell population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least eleven stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twelve stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least thirteen stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least fourteen stably expressed exogenous immunomodulatory molecules effective to stimulate the T-lymphocytes, natural killer (NK) cells, dendritic cells (DCs) or B lymphocytes. According to some embodiments, the ENLST™ cell population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least fifteen stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least sixteen stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least seventeen stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least eighteen stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least nineteen stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-one stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-two stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population oft tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-three stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-four stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-five stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-six stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-seven stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-eight stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-nine stably expressed exogenous immunomodulatory molecules effective to stimulate the T-lymphocytes, natural killer (NK) cells, dendritic cells (DCs) or B lymphocytes. According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least thirty stably expressed exogenous immunomodulatory molecules effective to stimulate the T-lymphocytes, natural killer (NK) cells, dendritic cells (DCs) or B lymphocytes.

According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population characterized by the expression of three essential stably expressed exogenous immunomodulatory molecules effective to stimulate the T-lymphocytes, natural killer (NK) cells, dendritic cells (DCs) or B lymphocytes, wherein the three essential stably expressed exogenous immunomoculatory molecules are GMCSF, OX40L and 4IBB-L.

According to some embodiments, the exogenous immunomodulatory molecules that constitute additional R subsets comprising from 3-25, inclusive immunomodulators may be particularly selected from a group for their ability to either initiate an anti-tumor immune response, and/or to sustain an anti-tumor immune response, and/or for their ability to abrogate pre-existing immunosuppression characteristically present in cancer patients, or a combination of all three. According to some embodiments, combinations of immunomodulatory molecules are evaluated and selected by a human mixed lymphocyte tumor cell reaction. According to some embodiments, exemplary classes of exogenous immunomodulatory molecule include a cytokine, a TNF-family member, a secreted receptor, a chaperone, an IgG superfamily member and a chemokine receptor or other immunomodulatory molecule.

According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a plurality of stably expressed exogenous immunomodulatory molecules effective to stimulate the T-lymphocytes, natural killer (NK) cells, dendritic cells (DCs) or B lymphocytes, wherein the exogenous immunomodulatory molecules comprise one or more cytokine family member proteins and one or more TNF family member proteins; wherein the exogenous immunomodulatory molecules comprise one or more cytokine family member proteins and one or more secreted receptor proteins; wherein the exogenous immunomodulatory molecules comprise one or more cytokine family member proteins and one or more chaperone proteins; wherein the exogenous immunomodulatory molecules comprise one or more cytokine family member proteins and one or more IgG superfamily member proteins; wherein the exogenous immunomodulatory molecules comprise one or more cytokine family member proteins and one or more chemokine receptor proteins.

According to some embodiments, the ENLST™ cells population comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a plurality of stably expressed exogenous immunomodulatory molecules effective to stimulate the T-lymphocytes, natural killer (NK) cells, dendritic cells (DCs) or B lymphocytes, wherein the exogenous immunomodulatory molecules comprise one or more TNF family member proteins and one or more secreted receptor proteins; wherein the exogenous immunomodulatory molecules comprise one or more TNF family member proteins and one or more chaperone proteins; wherein the exogenous immunomodulatory molecules comprise one or more TNF family member proteins and one or more IgG superfamily member proteins; wherein the exogenous immunomodulatory molecules comprise one or more TNF family member proteins and one or more chemokine receptor proteins.

According to some embodiments, the ENLST™ cells population comprises a population oft tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a plurality of stably expressed exogenous immunomodulatory molecules effective to stimulate the T-lymphocytes, natural killer (NK) cells, dendritic cells (DCs) or B lymphocytes, wherein the exogenous immunomodulatory molecules comprise one or more secreted receptor proteins and one or more chaperone proteins; wherein the exogenous immunomodulatory molecules comprise one or more secreted receptor proteins and one or more IgG superfamily member proteins; wherein the exogenous immunomodulatory molecules comprise one or more secreted receptor proteins and one or more chemokine receptor proteins.

According to some embodiments, the ENLST™ cells population comprises of the present disclosure comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a plurality of stably expressed exogenous immunomodulatory molecules effective to stimulate the T-lymphocytes, natural killer (NK) cells, dendritic cells (DCs) or B lymphocytes, wherein the exogenous immunomodulatory molecules comprise one or more chaperone proteins and one or more IgG superfamily member proteins; wherein the exogenous immunomodulatory molecules comprise one or more chaperone proteins and one or more chemokine receptor proteins.

According to some embodiments, the ENLST™ cells population comprises of the present disclosure comprises a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a plurality of stably expressed exogenous immunomodulatory molecules effective to stimulate the T-lymphocytes, natural killer (NK) cells, dendritic cells (DCs) or B lymphocytes, wherein the exogenous immunomodulatory molecules comprise one or more IgG superfamily member proteins and one or more chemokine receptor proteins.

Exemplary immunomodulators are shown in Table 6 below. According to some embodiments, the exogenous immunomodulatory molecule in the R subset is selected from one of more of a TNF-family member, a secreted receptor, a chaperone protein, an IgG superfamily member, a chemokine receptor. According to some embodiments, the TNF-family member is selected from a TNF-family member listed in Table 6. According to some embodiments, the secreted receptor is selected from a secreted receptor listed in Table 6. According to some embodiments, the chaperone protein is selected from a chaperone protein listed in Table 6. According to some embodiments, the IgG superfamily member is selected from an IgG superfamily member listed in Table 6. According to some embodiments, the chemokine receptor is selected from a chemokine receptor listed in Table 6. According to some embodiments, the exogenous immunomodulatory molecule is derived from a mouse. According to some embodiments, the exogenous immunomodulatory molecule is derived from a human.

TABLE 6

Exogenous Immunomodulatory Molecules

| Category | Examples |
| --- | --- |
| Cytokines | Granulocyte-macrophage colony-stimulating factor (GM-CSF), Granulocyte colony-stimulating factor (G-CSF), Fms-related tyrosine kinase 3 ligand (Flt3L), Flt3, interleukin-1 (IL-1), IL-1a, IL-1b, Il-1rα, IL-2, IL-3, IL-4, IL-5, IL-6, IL-7, IL-8, IL-9, IL-10, IL-10rα, IL-11, IL-12, IL-12p40, IL-12p70, IL-12/IL-23 P40, IL13, IL-15, IL-15/IL15-RA, IL-17, IL-17A, IL-18, IL-21, IL-23, TGF-β, MCP-1, TNF-α and interferon alpha (IFNα), IFNγ, MIP1b, Rantes, Tweak, TREM-1, mIFNα, mINγ |
| TNF-family members | Tumor necrosis factor alpha (TNF-α), TNF, 4-1BBL, APRIL, BAFF, LIGHT, RANK ligand (RANKL), CD40 ligand (CD40L), OX40 Ligand (OX40L), FAS ligand (FASL), CD27 ligand (CD70), CD30 ligand (CD30L), CD137 ligand (CD137L), TNFSF8, TNFSF9, TNFSF10, TNFSF11, TNFS12, TNFSF13, TNFSF13B, TNFSF14, TNFSF15, TNFSF18, TNFβ, TNFSF1B, TNFγ, Ectodysplasin A (EDA) |
| Receptors | TGFbeta Receptor III |
| Chaperone Proteins | GRP78/BiP, GRP94, GRP170, Calnexin, calreticulin, Hsp47, ERp29, Protein disulfide isomerase (PDI), Peptidyl prolyl cis-trans-isomerase (PPI), Erp57, Hsp60, Hsp70, Hsp90, Hsp100 |
| IgG Superfamily Members | CD80, CD86, ICOS ligand, PVR/CD155, CD48, Nectin2, NK-T-B antigen, PD-L2 |
| Chemokine Receptors | CXCR1, CXCR2, CXCR3, CXCR5, CXCR6, CXCR8, CCR8, CCR1, CCR2, CCR3, CCR5, CCR4, CCR6, CCR7, CCR9, CCR10, XCR1, CXCR3 |
| Others | Transforming Growth Factor Beta (TGFb) receptor, PSGL1, HSP70, HSP-90B1 (GRP94/96), TL1A |

According to some embodiments, the exogenous immunomodulatory molecule of Table 6 is in a membrane bound form (i.e. comprises a membrane anchor). According to other embodiments, the exogenous immunomodulatory molecule of Table 6 is in a secreted form. According to some embodiments, the membrane bound form of the exogenous immunomodulator is one or more selected from the group consisting of 4-1BB ligand, BAFF, April, CD40 ligand, CD80, CD86, Flt3 Ligand, GM-CSF, HSP90, ICOS ligand, IL-12, IL-15, IL-18, IL-2, IL-21, IL-23, IL7, LIGHT, OX40 ligand, RANK ligand and TNF. According to some embodiments, the secreted form of the immunomodulator is one or more selected from the group consisting of Flt3 ligand, GM-CSF, IL10R, IL7 and TGFbeta Receptor.

According to some embodiments, the exogenous immunomodulatory molecule is a molecule with a wild-type amino acid sequence. According to some embodiments, the exogenous immunomodulatory molecule is a molecule with a variant amino acid sequence.

According to some embodiments, the exogenous immunomodulatory molecule is one or more selected from the group consisting of 4-1BB Ligand, APRIL, BAFF, CD27 Ligand, CD30L, CD40 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, OX-40 Ligand, RANK Ligand, TGF-b Receptor, and TNF.

According to some embodiments, the one or more exogenous immunomodulatory molecules comprise at least three essential immunomodulatory molecules, wherein the three essential immunomodulatory molecules are OX40 Ligand (OX40L), CD27 Ligand (CD70), and CD28 Ligand (CD28L) comprising CD80, CD86 or both. According to some embodiments, additional immunomodulatory components identified as R may also be present.

According to some embodiments, an ENLST™ cell population comprises a population of tumor cells expressing one or more tumor specific antigens and three stably expressed essential exogenous immunomodulatory molecules, OX40L, CD70, and CD28L, effective to stimulate the MNC population. According to some embodiments, the ENLST™ cells population comprising a population of tumor cells expressing one or more tumor specific antigens and the three stably expressed essential exogenous immunomodulatory molecules OX40L, CD70, and CD28L comprising CD80, CD86 or both is effective to stimulate synergistic expansion of CTLs. According to some embodiments, the ENLST™ cell population further comprises one or more subsets of R immunomodulators comprising 3, 4, 5, 6, 7, 8, 9, 10, 11, 12, 13, 14, 15, 16, 17, 18, 19, 20, 21, 22, 23, 24, or 25 immunomodulators. According to some embodiments, the ENLST™ cells population comprises a population of tumor cells expressing one or more tumor specific antigens, wherein the tumor cells are genetically engineered to stably express at least the four stably expressed exogenous immunomodulatory molecules OX40L, CD70, and CD28L comprising CD80, CD86 or both, plus one R subset comprising 3-25, inclusive immunomodulators. According to some embodiments, the ENLST™ cells population comprises a population of tumor cells expressing one or more tumor specific antigens, wherein the tumor cells are genetically engineered to stably express at least the four stably expressed exogenous immunomoculatory molecules OX40L, CD70, and CD28L comprising CD80, CD86 or both, plus two R subsets comprising 3-25, inclusive immunomodulators. According to some embodiments, the ENLST™ cells population comprises a population of tumor cells expressing one or more tumor specific antigens, wherein the tumor cells are genetically engineered to stably express at least the four stably expressed exogenous immunomoculatory molecules OX40L, CD70, and CD28L comprising CD80, CD86 or both, plus three R subsets comprising 3-25, inclusive immunomodulators. According to some embodiments, the ENLST™ cells population comprises a population of tumor cells expressing one or more tumor specific antigens, wherein the tumor cells are genetically engineered to stably express at least the three essential stably expressed exogenous immunomodulatory molecules OX40L, CD70, and CD28L comprising CD80, CD86 or both, plus four R subsets comprising 3-25, inclusive immunomodulators. According to some embodiments, the ENLST™ cells population comprises a population of tumor cells expressing one or more tumor specific antigens, wherein the tumor cells are genetically engineered to stably express at least the three essential stably expressed exogenous immunomoculatory molecules OX40L, CD70, and CD28L comprising CD80, CD86 or both, plus five R subsets comprising 3-25, inclusive immunomodulators. According to some embodiments, the ENLST™ cells population comprises a population of tumor cells expressing one or more tumor specific antigens, wherein the tumor cells are genetically engineered to stably express at least the three essential stably expressed exogenous immunomoculatory molecules OX40L, CD70, and CD28L comprising CD80, CD86 or both, plus six R subsets comprising 3-25, inclusive immunomodulators. According to some embodiments, the ENLST™ cells population comprises a population of tumor cells expressing one or more tumor specific antigens, wherein the tumor cells are genetically engineered to stably express at least the three essential stably expressed exogenous immunomoculatory molecules OX40L, CD70, and CD28L comprising CD80, CD86 or both, plus seven R subsets comprising 3-25, inclusive immunomodulators. According to some embodiments, the ENLST™ cells population comprises a population of tumor cells expressing one or more tumor specific antigens, wherein the tumor cells are genetically engineered to stably express at least the three essential stably expressed exogenous immunomoculatory molecules OX40L, CD70, and CD28L comprising CD80, CD86 or both, plus eight R subsets comprising 3-25, inclusive immunomodulators. According to some embodiments, the ENLST™ cells population comprises a population of tumor cells expressing one or more tumor specific antigens, wherein the tumor cells are genetically engineered to stably express at least the three essential stably expressed exogenous immunomoculatory molecules OX40L, CD70, and CD28L comprising CD80, CD86 or both, plus nine R subsets comprising 3-25, inclusive immunomodulators. According to some embodiments, the ENLST™ cells population comprises a population of tumor cells expressing one or more tumor specific antigens, wherein the tumor cells are genetically engineered to stably express at least the three essential stably expressed exogenous immunomoculatory molecules OX40L, CD70, and CD28L comprising CD80, CD86 or both, plus ten R subsets comprising 3-25, inclusive immunomodulators.

According to some embodiments, the exogenous immunomodulatory molecule $R^1$ is APRIL. According to some embodiments, the exogenous immunomodulatory molecule $R^2$ is BAFF. According to some embodiments, the exogenous immunomodulatory molecule $R^3$ is 4-IBB Ligand. According to some embodiments, the exogenous immunomodulatory molecule $R^4$ is CD30 Ligand. According to some embodiments, the exogenous immunomodulatory molecule $R^5$ is CD40 Ligand. According to some embodiments, the exogenous immunomodulatory molecule $R^6$ is CD80. According to some embodiments, the exogenous immunomodulatory molecule $R^7$ is CD86. According to some embodiments, the exogenous immunomodulatory molecule $R^8$ is FLT-3 Ligand. According to some embodiments, the exogenous immunomodulatory molecule $R^9$ is HSP-70. According to some embodiments, the exogenous immunomodulatory molecule $R^{10}$ is HSP-90. According to some embodiments, the exogenous immunomodulatory molecule $R^{11}$ is ICOS Ligand. According to some embodiments, the exogenous immunomodulatory molecule $R^{12}$ is IL-10R. According to some embodiments, the exogenous immunomodulatory molecule $R^{13}$ is IL-12. According to some embodiments, the exogenous immunomodulatory molecule $R^{14}$ is IL-15. According to some embodiments, the exogenous immunomodulatory molecule $R^{15}$ is IL-18. According to some embodiments, the exogenous immunomodulatory molecule $R^{16}$ is IL-2. According to some embodiments, the exogenous immunomodulatory molecule $R^{17}$ is IL-21. According to some embodiments, the exogenous immunomodulatory molecule $R^{18}$ is IL-23. According to some embodiments, the exogenous immunomodulatory molecule $R^{19}$ is IL-7. According to some embodiments, the exogenous immunomodulatory molecule $R^{20}$ is LIGHT. According to some embodiments, the exogenous immunomodulatory molecule $R^{21}$ is RANK Ligand. According to some embodiments, the exogenous immunomodulatory molecule $R^{22}$ is TGF-b Receptor. According to some embodiments, the exogenous immunomodulatory molecule $R^{23}$ is TNF, According to some embodiments, the exogenous immunomodulatory molecule $R^{24}$ is GM-CSF.

According to some embodiments, the exogenous immunomodulatory molecule R comprises between 1 and 30 immunomodulators, inclusive, i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 exogenous immunomodulatory molecules selected from the group consisting of APRIL, BAFF, 4-IBB Ligand, CD30 Ligand, CD80, CD86, FLT-3 Ligand, FLT-3 ligand engineered to remove transmembrane region, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor and GM-CSF.

According to some embodiments, the exogenous immunomodulatory molecule comprises between 1 and 30, inclusive, i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 exogenous immunomodulatory molecules, wherein at least three immunomodulatory molecules are OX40 Ligand (OX40L), CD27 Ligand, and CD28 Ligand comprising CD80, CD86 or both, and wherein additional immunomodulatory components identified as $R^1$-$R^{24}$ are selected from the group consisting of APRIL, BAFF, 4-IBB Ligand (4-IBBL), CD30L, CD40 Ligand, CD80, CD86, FLT-3 Ligand, FLT-3 ligand engineered to remove transmembrane region, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor, and TNF.

According to some embodiments, the exogenous immunomodulatory molecule comprises between 1 and 20, inclusive, i.e., 1, 2, 3, 4, 5, 6, 7, 8, 9, 10, 11, 12, 13, 14, 15, 16, 17, 18, 19 or 20 exogenous immunomodulatory molecules selected from the group consisting of 4-1BB Ligand, APRIL, BAFF, CD27 Ligand, CD28 Ligand, CD30 Ligand, CD40 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, OX-40 Ligand, RANK Ligand, TGF-b Receptor, and TNF. According to some embodiments, the exogenous immunomodulatory molecule comprises between 1 and 20, inclusive, i.e., 1, 2, 3, 4, 5, 6, 7, 8, 9, 10, 11, 12, 13, 14, 15, 16, 17, 18, 19 or 20 exogenous immunomodulatory molecules, wherein at least three immunomodulatory molecules are OX40 Ligand (OX40L), CD27 Ligand, and CD28 Ligand, and wherein additional immunomodulatory components identified as $R^1$-$R^{24}$ are selected from the group consisting of APRIL, BAFF, 4-IBB Ligand, CD30L, CD40 Ligand, CD80, CD86, FLT-3 Ligand, FLT-3 ligand engineered to remove transmembrane region, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor, and TNF.

According to some embodiments, the exogenous immunomodulatory molecule comprises between 1 and 10, inclusive, i.e., 1, 2, 3, 4, 5, 6, 7, 8, 9 or 10 exogenous immunomodulatory molecules selected from the group consisting of 4-1BB Ligand, APRIL, BAFF, CD27 Ligand, CD28 Ligand, CD30 Ligand, CD40 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, OX-40 Ligand, RANK Ligand, TGF-b Receptor, and TNF. According to some embodiments, the exogenous immunomodulatory molecule comprises between 1 and 10, inclusive, i.e., 1, 2, 3, 4, 5, 6, 7, 8, 9 or 10 exogenous immunomodulatory molecules, wherein at least three immunomodulatory molecules are OX40 Ligand (OX40L), CD27 Ligand, and CD28Ligand, and wherein additional immunomodulatory components identified as $R^1$-$R^{24}$ are selected from the group consisting of APRIL, BAFF, 4-IBB Ligand, CD30 Ligand, CD40 Ligand, CD80, CD86, FLT-3 Ligand, FLT-3 ligand engineered to remove transmembrane region, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor, and TNF.

According to some embodiments, the exogenous immunomodulatory molecule comprises between 5 and 20, inclusive, i.e., 5, 6, 7, 8, 9, 10, 11, 12, 13, 14, 15, 16, 17, 18, 19, or 20 exogenous immunomodulatory molecules R selected from the group consisting of, APRIL, BAFF, 4-IBB Ligand, CD30 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor., and TNF. According to some embodiments, the exogenous immunomodulatory molecule comprises between 5 and 20, inclusive, i.e., 5, 6, 7, 8, 9, 10, 11, 12, 13, 14, 15, 16, 17, 18, 19, or 20 exogenous immunomodulatory molecules, wherein at least three immunomodulatory molecules are OX40 Ligand (OX40L), CD27 Ligand (CD70), and CD28 Ligand (CD28L) comprising CD80, CD86 or both, and wherein additional immunomodulatory components identified as $R^1$-$R^{24}$ are selected from the group consisting of APRIL, BAFF, 4-IBB Ligand, CD30 Ligand, CD40 Ligand, CD80, CD86, FLT-3 Ligand, FLT-3 ligand engineered to remove transmembrane region, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor, and TNF.

According to some embodiments, the exogenous immunomodulatory molecule R comprises between 10 and 15, inclusive, i.e., 10, 11, 12, 13, 14 or 15 exogenous immunomodulatory molecules selected from the group consisting of APRIL, BAFF, 4-IBB Ligand, CD30 Ligand, CD80, CD86, FLT-3 Ligand, FLT-3 ligand engineered to remove transmembrane region, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor, and TNF. According to some embodiments, the exogenous immunomodulatory molecule comprises between 10 and 15, inclusive, i.e., 10, 11, 12, 13, 14 or 15 exogenous immunomodulatory molecules, wherein at least three immunomodulatory molecules are OX40 Ligand (OX40L), CD27 Ligand (CD70), and CD28 Ligand (CD28L) comprising CD80, CD86 or both, and wherein additional immunomodulatory components identified as $R^1$-$R^{24}$ are selected from the group consisting of APRIL, BAFF, 4-IBB Ligand, CD30 Ligand, CD40 Ligand, CD80, CD86, FLT-3 Ligand, FLT-3 ligand engineered to remove transmembrane region, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor, and TNF.

According to some embodiments, the exogenous immunomodulatory molecule comprises 14 exogenous immunomodulatory molecules selected from the group consisting of APRIL, BAFF, 4-IBB Ligand, CD30L, CD80, CD86, FLT-3 Ligand, FLT-3 ligand engineered to remove transmembrane region, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor, and TNF. According to some embodiments, the exogenous immunomodulatory molecule comprises 14 exogenous immunomodulatory molecules, wherein at least three immunomodulatory molecules are OX40 Ligand (OX40L), CD27 Ligand (CD70), and CD28 Ligand comprising CD80, CD86 or both, and wherein additional immunomodulatory components identified as $R^1$-$R^{24}$ are selected from the group consisting of APRIL, BAFF, 4-IBB Ligand, CD30 Ligand, CD40 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, OX-40 Ligand, RANK Ligand, TGF-b Receptor, and TNF.

According to some embodiments, each of the exogenous immunomodulatory molecules 4-1BB Ligand, APRIL, BAFF, CD27 Ligand, CD28 Ligand, CD30L, CD40 Ligand, CD80, CD86, FLT-3 Ligand, GM-CSF, HSP-70, HSP-90, ICOS Ligand, IL-10R, IL-12, IL-15, IL-18, IL-2, IL-21, IL-23, IL-7, LIGHT, OX-40 Ligand, RANK Ligand, TGF-b Receptor, and TNF is a wild type molecule. According to some embodiments, each of the exogenous immunomodulatory molecules 4-1BB Ligand, APRIL, BAFF, CD27 Ligand, CD28 Ligand, CD30L, CD40 Ligand, CD80, CD86, FLT-3 Ligand, GM-CSF, HSP-70, HSP-90, ICOS Ligand, IL-10R, IL-12, IL-15, IL-18, IL-2, IL-21, IL-23, IL-7, LIGHT, OX-40 Ligand, RANK Ligand, TGF-b Receptor, and TNF is a mutant or variant sequence.

According to some embodiments, the exogenous immunomodulatory molecule $R^1$ is APRIL. According to some embodiments, the exogenous immunomodulatory molecule $R^2$ is BAFF. According to some embodiments, the exogenous immunomodulatory molecule $R^3$ is 4-IBB Ligand. According to some embodiments, the exogenous immunomodulatory molecule $R^4$ is CD30L. According to some embodiments, the exogenous immunomodulatory molecule $R^5$ is CD40 Ligand. According to some embodiments, the exogenous immunomodulatory molecule $R^6$ is CD80. According to some embodiments, the exogenous immunomodulatory molecule $R^7$ is CD86. According to some embodiments, the exogenous immunomodulatory molecule $R^8$ is FLT-3 Ligand. According to some embodiments, the exogenous immunomodulatory molecule $R^9$ is HSP-70.

According to some embodiments, the exogenous immunomodulatory molecule $R^{10}$ is HSP-90. According to some embodiments, the exogenous immunomodulatory molecule $R^{11}$ is ICOS Ligand. According to some embodiments, the exogenous immunomodulatory molecule $R^{12}$ is IL-10R. According to some embodiments, the exogenous immunomodulatory molecule $R^{13}$ is IL-12. According to some embodiments, the exogenous immunomodulatory molecule $R^{14}$ is IL-15. According to some embodiments, the exogenous immunomodulatory molecule $R^{15}$ is IL-18. According to some embodiments, the exogenous immunomodulatory molecule $R^{16}$ is IL-2. According to some embodiments, the exogenous immunomodulatory molecule $R^{17}$ is IL-21. According to some embodiments, the exogenous immunomodulatory molecule $R^{18}$ is IL-23. According to some embodiments, the exogenous immunomodulatory molecule $R^{19}$ is IL-7. According to some embodiments, the exogenous immunomodulatory molecule $R^{20}$ is LIGHT. According to some embodiments, the exogenous immunomodulatory molecule $R^{21}$ is RANK Ligand. According to some embodiments, the exogenous immunomodulatory molecule $R^{22}$ is TGF-b Receptor. According to some embodiments, the exogenous immunomodulatory molecule $R^{23}$ is TNF. According to some embodiments, the exogenous immunomodulatory molecule $R^{24}$ is a CD86 variant that has been engineered with an IRES compatible signal sequence. According to some embodiments, the exogenous immunomodulatory molecule $R^{25}$ is a FLT3L variant that has been engineered to remove the transmembrane region. According to some embodiments, the exogenous immunomodulatory molecule $R^{26}$ is a GM-CSF variant that has been engineered with a CD8 membrane anchor and IRES compatible Signal Sequence. According to some embodiments, the exogenous immunomodulatory molecule $R^{27}$ is an HSP70 variant that has been engineered with a CD8 membrane anchor. According to some embodiments, the exogenous immunomodulatory molecule $R^{28}$ is an HSP-90B1 (GRP94/96) variant that has been engineered with a CD8 membrane anchor. According to some embodiments, the exogenous immunomodulatory molecule $R^{29}$ is an HSP90 variant that has been engineered with a CD8 membrane anchor. According to some embodiments, the exogenous immunomodulatory molecule $R^{30}$ is an ICOSL variant that has been engineered with an IRES compatible signal sequence. According to some embodiments, the exogenous immunomodulatory molecule $R^{31}$ is an IL10R variant that has been engineered to remove the transmembrane region. According to some embodiments, the exogenous immunomodulatory molecule $R^{32}$ is an IL-Rα variant that has been engineered to remove transmembrane region (VSV-GM-CSF tag). According to some embodiments, the exogenous immunomodulatory molecule $R^{33}$ is an IL12 variant that has been engineered to be a single chain with a CD8 membrane anchor. According to some embodiments, the exogenous immunomodulatory molecule $R^{34}$ is an IL15 variant that has been engineered with CD8 membrane anchor. According to some embodiments, the exogenous immunomodulatory molecule $R^{35}$ is an IL18 variant that has been engineered with a CD8 membrane anchor. According to some embodiments, the exogenous immunomodulatory molecule $R^{36}$ is an IL2 variant that has been engineered with a CD8 membrane anchor and IRES compatible sequence. According to some embodiments, the exogenous immunomodulatory molecule $R^{37}$ is an IL21 variant that has been engineered with a CD8 membrane anchor. According to some embodiments, the exogenous immunomodulatory molecule $R^{38}$ is an IL23 variant that has been engineered to be a single chain with a CD8 membrane anchor. According to some embodiments, the exogenous immunomodulatory molecule $R^{39}$ is an IL7 variant that has been engineered with a CD8 membrane anchor. According to some embodiments, the exogenous immunomodulatory molecule $R^{40}$ is a TGFb-R variant that has been engineered to remove the transmembrane region. According to some embodiments, the exogenous immunomodulatory molecule $R^{41}$ is a TGFb Receptor III variant engineered to remove transmembrane region. According to some embodiments, the exogenous immunomodulatory molecule $R^{42}$ is an mIFNα variant modified to be membrane bound. According to some embodiments, the exogenous immunomodulatory molecule $R^{43}$ is an mIFNαγ variant which is modified to be membrane bound. According to some embodiments, the exogenous immunomodulatory molecule $R^{44}$ is a CD40 Ligand (CD40L) variant which is cleavage resistant. Table 7 below sets forth R groups $R^1$-$R^{44}$.

TABLE 7

| $R^x$ | Description |
|---|---|
| $R^1$ | APRIL |
| $R^2$ | BAFF |
| $R^3$ | 4-IBB Ligand |
| $R^4$ | CD30 Ligand |
| $R^5$ | CD40 Ligand |
| $R^6$ | CD80 |
| $R^7$ | CD86 |
| $R^8$ | FLT-3 Ligand |
| $R^9$ | HSP-70 |
| $R^{10}$ | HSP-90 |
| $R^{11}$ | ICOS Ligand |
| $R^{12}$ | IL-10R |
| $R^{13}$ | IL-12 |
| $R^{14}$ | IL-15 |
| $R^{15}$ | IL-18 |
| $R^{16}$ | IL-2 |
| $R^{17}$ | IL-21 |
| $R^{18}$ | IL-23 |
| $R^{19}$ | IL-7 |
| $R^{20}$ | LIGHT |
| $R^{21}$ | RANK ligand |
| $R^{22}$ | TGF-b Receptor |
| $R^{23}$ | TNF |
| $R^{24}$ | CD86 variant engineered with an IRES compatible signal sequence |
| $R^{25}$ | FLT3L variant engineered to remove the transmembrane region |
| $R^{26}$ | GMCSF variant with a CD8 membrane anchor and IRES compatible Signal Sequence |
| $R^{27}$ | HSP70 variant with a CD8 membrane anchor |
| $R^{28}$ | HSP-90B1 (GRP94/96) variant engineered with a CD8 membrane anchor |
| $R^{29}$ | HSP90 variant engineered with a CD8 membrane anchor |
| $R^{30}$ | ICOSL variant engineered with an IRES compatible signal sequence |
| $R^{31}$ | IL10R variant engineered to remove the transmembrane region |
| $R^{32}$ | IL-Rα variant engineered to remove transmembrane region (VSV-GM-CSF tag) |
| $R^{33}$ | IL12 variant engineered to be a single chain with a CD8 membrane anchor |
| $R^{34}$ | IL15 variant engineered with CD8 membrane anchor |
| $R^{35}$ | IL18 variant engineered with a CD8 membrane anchor |

TABLE 7-continued

| R$^x$ | Description |
| --- | --- |
| R$^{36}$ | IL2 variant engineered with a CD8 membrane anchor and IRES compatible sequence |
| R$^{37}$ | IL21 variant engineered with a CD8 membrane anchor |
| R$^{38}$ | IL23 variant engineered to be a single chain with a CD8 membrane anchor |
| R$^{39}$ | IL7 variant engineered with a CD8 membrane anchor |
| R$^{40}$ | TGFb-R variant engineered to remove transmembrane region |
| R$^{41}$ | TGFb Receptor III variant engineered to remove transmembrane region |
| R$^{42}$ | mIFNα variant modified to be membrane bound |
| R$^{43}$ | mIFNαγ variant which is modified to be membrane bound |
| R$^{44}$ | CD40L variant which is cleavage resistant |

According to some embodiments, at least 12 vectors comprise 14 immunomodulators, wherein three essential immunomodulatory molecules are OX40 Ligand (OX40L), CD27 Ligand (CD70), and CD28 Ligand (CD28L) comprising CD80, CD86 or both, and wherein the remaining 11 immunomodulators are selected from R$^1$-R$^{44}$ in Table 7. According to some embodiments, at least 11 vectors comprise 14 immunomodulators, wherein three essential immunomodulatory molecules are OX40 Ligand (OX40L), CD27 Ligand (CD70), and CD28 Ligand (CD28L) comprising CD80, CD86 or both, and wherein the remaining 11 immunomodulators are selected from R$^1$-R$^{44}$ in Table 7. According to some embodiments, at least 10 vectors comprise 14 immunomodulators, wherein three essential immunomodulatory molecules are OX40 Ligand (OX40L) CD27 Ligand (CD70), and CD28 Ligand (CD28L) comprising CD80, CD86 or both, and wherein the remaining 11 immunomodulators are selected from R$^1$-R$^{44}$ in Table 7. According to some embodiments, 14 immunomodulators are selected from Table 6, wherein at least three immunomodulatory molecules are, OX40 Ligand (OX40L), CD27 Ligand (CD70), and CD28 Ligand (CD28L) comprising CD80, CD86 or both, wherein the remaining 11 immunomodulators are selected from R$^1$-R$^{44}$ in Table 7 and wherein the 14 immunomodulators are in 12 vectors. According to some embodiments, 14 immunomodulators are selected from Table 6, wherein the three essential immunomodulatory molecules are OX40 Ligand (OX40L), CD27 Ligand (CD70), and CD28 Ligand (CD28L) comprising CD80, CD86 or both, wherein the remaining 11 immunomodulators are selected from R$^1$-R$^{44}$ in Table 7, and wherein the 14 immunomodulators are in 11 vectors. According to some embodiments, 14 immunomodulators are selected from Table 6, wherein the three essential immunomodulatory molecules are OX40 Ligand (OX40L), CD27 Ligand (CD70), and CD28 Ligand (CD28L) comprising CD80, CD86 or both, wherein the remaining 11 immunomodulators are selected from R$^1$-R$^{44}$ in Table 7, and wherein the 14 immunomodulators are in 10 vectors. The vectors may further comprise tags.

According to some embodiments, the immunomodulators are codon optimized. "Codon optimization" means a modification of a codon of a polynucleotide encoding a protein with a codon that is used first before others in a specific organism such that the coded protein can be more efficiently expressed therein. Because most amino acids are described by several codons that are referred to as "synonym" or "synonymous codon", genetic codes have degeneracy. However, codon usage by a specific organism is not random, and it is rather biased to specific codon triplets. Such codon usage bias may be even higher in relation with a certain gene, a gene with common function or ancestor origin, protein expressed at high level vs. proteins with low copy number, or a group protein coding region of a genome of an organism.

Cytokines

According to some embodiments, the disclosure encompasses an ENLST™ cell population comprising a population of tumor cells expressing one or more tumor specific antigens and genetically engineered to express a core group of three immunomodulatory molecules plus optionally one or more R groups of immunomodulatory molecules comprising one or more cytokines, wherein the ENLST™ cells population is effective to stimulate one or more populations of serial killer cells, including T lymphocytes, natural killer (NK) cells, dendritic cells (DCs) or B lymphocytes. Thus, the disclosure encompasses a cytokine, including a full-length, fragment, homologue, variant or mutant of the cytokine. A cytokine includes a protein that is capable of affecting the biological function of another cell. A biological function affected by a cytokine can include, but is not limited to, cell growth, cell differentiation or cell death. According to some embodiments, a cytokine of the present disclosure is capable of binding to a specific receptor on the surface of a cell, thereby stimulating an immune cell (e.g. T lymphocytes (e.g., CD8+ T cell), natural killer (NK) cells, dendritic cells (DCs) or B lymphocytes).

According to some embodiments, the cytokine is selected from Granulocyte-macrophage colony-stimulating factor (GM-CSF), Granulocyte colony-stimulating factor (G-CSF), Fms-related tyrosine kinase 3 ligand (FLT3LG), interleukin-1 (IL-1), IL-1a, IL-1b, Il-1ra, IL-2, IL-3, IL-4, IL-5, IL-6, IL-7, IL-8, IL-9, IL-10, IL-11, IL-12p40, IL-12p70, IL-12/IL-23 P40, IL13, IL-15, IL-15/IL15-RA, IL-17, IL-17A, IL-18, IL-21, IL-23, TGF-β, MCP-1, TNF-α and interferon alpha (IFNα), IFNγ, MIP1b, Rantes, Tweak, and TREM-1. According to some embodiments, the cytokine is granulocyte-macrophage colony-stimulating factor (GM-CSF). According to some embodiments, the cytokine is Fms-related tyrosine kinase 3 ligand (FLT3LG).

According to some embodiments, the cytokine is secreted. According to some embodiments, the cytokine is membrane bound.

Granulocyte-Macrophage Colony Stimulating Factor (GM-CSF)

Granulocyte-macrophage colony-stimulating factor (GM-CSF; colony stimulating factor 2; CSF2) is found in monocytes/macrophages and activated T cells, and can act as a growth factor to stimulate and recruit dendritic cells. GM-CSF is a monomeric glycoprotein secreted by cells of the immune system, as well as endothelial cells and fibroblasts. Human GM-CSF is a 144 amino acid protein comprising a 17 amino acid signal peptide that can be cleaved to produce a mature 127 amino acid protein. Biological activity of GM-CSF occurs via binding to heteromeric cell surface receptors that are expressed on monocytes, macrophages, granulocytes, lymphocytes, endothelial cells and alveolar epithelial cells. The GM-CSF receptor (GM-CSFR) typically has a low expression (e.g. 20-200/cell), but has a high affinity (Shi Y et al., Granulocyte-macrophage colony-stimulating factor (GM-CSF) and T-cell responses: what we do and don't know, Cell Research (2006) 16: 126-133).

Melanoma patients treated with soluble GM-CSF as an adjuvant therapy displayed an increase in disease free survival compared to controls. GM-CSF has been used as an immune adjuvant in various ways, including, without limitation, systemic and topical application of soluble GM-CSF, GM-CSF fusion proteins, transfection of tumor cells with GM-CSF and injection of GM-CSF DNA. Recombinant GM-CSF has been used an adjuvant for various peptide, protein, and viral vaccines, and has been shown to be an effective adjuvant in patients with melanoma, breast, and ovarian cancer. A fusion protein comprising GM-CSF has also been shown to enhance immunogenicity of an antigen. GM-CSF has been tested for use in a gene therapy approach where allogeneic or autologous GM-CSF expressing cells are used as a vaccine (Kaufman and Wolchok eds., General Principles of Tumor Immunotherapy, Chpt 5, 67-121 (2007)). Such treatments have had varying degrees of effectiveness among several different cancer types.

According to some embodiments, a tumor cell line or tumor cell line variant may express the GM-CSF peptide of SEQ ID NO: 13. According to some embodiments, a tumor cell line or tumor cell line variant may comprise one or more proteins with a sequence identity of at least 60% to the protein of SEQ ID NO: 13. According to some embodiments, a tumor cell line or tumor cell line variant may comprise one or more proteins with a sequence identity of at least 70% to the protein of SEQ ID NO: 13. According to some embodiments, a tumor cell line or tumor cell line variant may comprise one or more proteins with a sequence identity of at least 80% to the protein of SEQ ID NO: 13. According to some embodiments, a tumor cell line or tumor cell line variant may comprise one or more proteins with a sequence identity of at least 90% to the protein of SEQ ID NO: 13. According to some embodiments, a tumor cell line or tumor cell line variant may comprise one or more proteins with a sequence identity of at least 95% to the protein of SEQ ID NO: 13. According to some embodiments, a tumor cell line or tumor cell line variant may comprise one or more proteins with a sequence identity of at least 96% to the protein of SEQ ID NO: 13. According to some embodiments, a tumor cell line or tumor cell line variant may comprise one or more proteins with a sequence identity of at least 97% to the protein of SEQ ID NO: 13. According to some embodiments, a tumor cell line or tumor cell line variant may comprise one or more proteins with a sequence identity of at least 98% to the protein of SEQ ID NO: 13. According to some embodiments, a tumor cell line or tumor cell line variant may comprise one or more proteins with a sequence identity of at least 99% to the protein of SEQ ID NO: 13.

According to some embodiments, a tumor cell line or tumor cell line variant may comprise one or more proteins comprising a fusion between GM-CSF and HLA-I to enable membrane expression. According to some embodiments, a tumor cell line or tumor cell line variant may comprise one or more proteins with a sequence identity of at least 60% to the protein of SEQ ID NO: 42 or SEQ ID NO: 5. According to some embodiments, a tumor cell line or tumor cell line variant may comprise one or more proteins with a sequence identity of at least 70% to the protein of SEQ ID NO: 42 or SEQ ID NO: 5. According to some embodiments, a tumor cell line or tumor cell line variant may comprise one or more proteins with a sequence identity of at least 80% to the protein of SEQ ID NO: 42 or SEQ ID NO: 5. According to some embodiments, a tumor cell line or tumor cell line variant may comprise one or more proteins with a sequence identity of at least 90% to the protein of SEQ ID NO: 42 or SEQ ID NO: 5. According to some embodiments, a tumor cell line or tumor cell line variant may comprise one or more proteins with a sequence identity of at least 95% to the protein of SEQ ID NO: 42 or SEQ ID NO: 5. According to some embodiments, a tumor cell line or tumor cell line variant may comprise one or more proteins with a sequence identity of at least 96% to the protein of SEQ ID NO: 42 or SEQ ID NO: 5. According to some embodiments, a tumor cell line or tumor cell line variant may comprise one or more proteins with a sequence identity of at least 97% to the protein of SEQ ID NO: 42 or SEQ ID NO: 5. According to some embodiments, a tumor cell line or tumor cell line variant may comprise one or more proteins with a sequence identity of at least 98% to the protein of SEQ ID NO: 42 or SEQ ID NO: 5. According to some embodiments, a tumor cell line or tumor cell line variant may comprise one or more proteins with a sequence identity of at least 99% to the protein of SEQ ID NO: 42 or SEQ ID NO: 5.

Fms-Like Tyrosine Kinase-3 Ligand (Flt-3L)

According to some embodiments, the human Flt3L protein is a membrane bound hematopoietic four helical bundle cytokine encoded by the FLT3LG gene. Flt3L acts as a growth factor that stimulates proliferation and differentiation of various blood cell progenitors, and is crucial for production and development of dendritic cells. Mice that lack Flt3L have low levels of dendritic cells, while Flt3L administered to mice or humans results in very high levels of dendritic cells (Shortman et al., Steady-state and inflammatory dendritic-cell development, Nature Reviews Immunology, Vol. 7. 19-30 (2007)).

According to some embodiments, a subset of R immunomodulators may comprise the membrane bound form of Flt-3L. According to some embodiments, the ENLST™ cells expresses the Flt3L peptide of SEQ ID NO: 14. According to some embodiments, the ENLST™ cells may be genetically engineered to comprise one or more proteins with a sequence identity of at least 60% to the protein of SEQ ID NO: 14. According to some embodiments, the ENLST™ cells may be genetically engineered to comprise one or more proteins with a sequence identity of at least 70% to the protein of SEQ ID NO: 14. According to some embodiments, the ENLST™ cells may be genetically engineered to comprise one or more proteins with a sequence identity of at least 80% to the protein of SEQ ID NO: 14. According to some embodiments, the ENLST™ cells may be genetically engineered to comprise one or more proteins with a sequence identity of at least 90% to the protein of SEQ ID NO: 14. According to some embodiments, the ENLST™ cells may be genetically engineered to comprise one or more proteins with a sequence identity of at least 95% to the protein of SEQ ID NO: 14. According to some embodiments, the ENLST™ cells may be genetically engineered to comprise one or more proteins with a sequence identity of at least 96% to the protein of SEQ ID NO: 14. According to some embodiments, the ENLST™ cells may be genetically engineered to comprise one or more proteins with a sequence identity of at least 97% to the protein of SEQ ID NO: 14. According to some embodiments, the ENLST™ cells may be genetically engineered to comprise one or more proteins with a sequence identity of at least 98% to the protein of SEQ ID NO: 14. According to some embodiments, the ENLST™ cells may be genetically engineered to comprise one or more proteins with a sequence identity of at least 99% to the protein of SEQ ID NO: 14.

According to some embodiments, an R subset of immunomodulators may comprise a soluble form of Flt3L. According to some embodiments, the ENLST™ cells may be genetically engineered to comprise one or more proteins with a sequence identity of at least 60% to the protein of SEQ ID NO: 44. According to some embodiments, the ENLST™ cells may be genetically engineered to comprise one or more proteins with a sequence identity of at least 70% to the protein of SEQ ID NO: 44. According to some embodiments, the ENLST™ cells may be genetically engineered to comprise one or more proteins with a sequence identity of at least 80% to the protein of SEQ ID NO: 44. According to some embodiments, the ENLST™ cells may be genetically engineered to comprise one or more proteins with a sequence identity of at least 90% to the protein of SEQ ID NO: 44. According to some embodiments, the ENLST™ cells may be genetically engineered to comprise one or more proteins with a sequence identity of at least 95% to the protein of SEQ ID NO: 44. According to some embodiments, a ENLST™ tumor cell line or tumor cell line variant may be genetically engineered to comprise one or more proteins with a sequence identity of at least 96% to the protein of SEQ ID NO: 44. According to some embodiments, the ENLST™ cells may be genetically engineered to comprise one or more proteins with a sequence identity of at least 97% to the protein of SEQ ID NO: 44. According to some embodiments, the ENLST™ cells may be genetically engineered to comprise one or more proteins with a sequence identity of at least 98% to the protein of SEQ ID NO: 44. According to some embodiments, the ENLST™ cells may be genetically engineered to comprise one or more proteins with a sequence identity of at least 99% to the protein of SEQ ID NO: 44.

One skilled in the art, once armed with the teachings provided herein, would appreciate that the invention encompasses any cytokine, whether well-known in the art now, or discovered in the future.

According to some embodiments, a population of allogeneic ENLST™ cells comprising a population of tumor cells expressing one or more tumor specific antigens, and genetically engineered to express a core group of three immunomodulators comprises one or more (e.g., 2, 3, 4, 5, or more) cytokines, or variants or fragments thereof.

TNF-Family Members

According to some embodiments, the disclosure encompasses a ENLST™ cell population comprising a population of tumor cells expressing one or more tumor specific antigens and genetically engineered to express a core group of three immunomodulatory molecules plus optionally one or more R group of immunomodulatory molecules comprising one or more TNF-family members, wherein the ENLST™ cell population is effective to activate serial killer cells effective to kill tumor cells comprising one or more of T lymphocytes, natural killer (NK) cells, NKT cells, dendritic cells (DCs) or B lymphocytes. Thus, the disclosure encompasses one or more TNF-family member proteins, including a full-length, fragment, homologue, variant or mutant of the TNF-family protein. According to some embodiments, the TNF superfamily member is selected from one or more of tumor necrosis factor alpha (TNFα), CD40 ligand (CD40L), OX40 Ligand (OX40L), FAS ligand (FASL), CD27 ligand (CD70), CD30 ligand (CD30L), CD137 ligand (CD137L), TNFSF8, TNFSF9, TNFSF10, TNFSF11, TNFS12, TNFSF13, TNFSF13B, TNFSF14, TNFSF15, TNFSF18, TNFβ, TNFSF1B, TNFγ, Ectodysplasin A (EDA), 4-IBB, and its ligand 4-IBB Ligand (4-IBBL). According to some embodiments, the TNF superfamily member is TNFα. According to some embodiments, the TNF superfamily member is CD40L. According to some embodiments, the TNF superfamily member is OX40 Ligand. According to some embodiments, the TNF superfamily member is CD27 Ligand. According to some embodiments, the TNF superfamily member is 4-IBBL.

According to some embodiments, the TNF family member is membrane bound.

The tumor necrosis factor (TNF) superfamily is a protein superfamily of type II transmembrane proteins containing TNF homology domain and forming trimers. Members of this superfamily can be released from the cell membrane by extracellular proteolytic cleavage and function as a cytokine. These proteins are expressed predominantly by immune cells and regulate diverse cell functions, including regulation of immune response and inflammation, but also proliferation, differentiation, apoptosis and embryogenesis. The superfamily contains 19 members that bind to 29 members of the TNF receptor superfamily.

Several TNF-family molecules deliver co-stimulatory signals. These seem to function by activating NFκB through a TRAF-dependent pathway. For example, the binding of CD70 on dendritic cells to its constituitively expressed CD20 receptor on naïve T cells delivers a potent co-stimulatory signal to T cells early in the activation process. The receptor CD40 on dendritic cells binds to CD40 ligand expressed on T cells, initiating two-way signaling that transmits activating signals to the T cell, and also induces the dendritic cell to express increased B7, thus stimulating further-cell proliferation. The T-cell molecule 4-IBB (CD137) and its ligant 4-IBBL, which is expressed on activated dendritic cells, macrophages and B cells, make up a pair of TNF-family co-stimulators. The effects of this interaction are bidirectional, with both the T cell and the antigen-presenting cell receiving activating signals. Another costimulatory receptor and its ligand, OX40 and OX40L, are expressed on activated T cells and dendritic cells, respectively. Murphy, Kenneth. *Janeway's Immunobiology:* 8th ed. Chapter 15: Garland Science. (2012), at 370.

TNFR family members OX40 (CD134) and 4-IBB (CD137) have been found to play major roles as costimulatory receptors for both CD4 and CD8 T cells. Both OX40 and 4-IBB signal through TRAF adaptor molecules that are shared; distinct; inflammatory cascades also can be triggered through these receptors. OX40 and CD28 signaling activates multiple signaling pathways, such as those involving PI3K/Akt, AP-1, and NF-κB pathways. In addition, OX40 and 4-IBB are strong controllers of immunosuppressive or immunomodulatory cells, including Tregs. So, T et al, Cytokine Growth Factor Rev. (2008) 19 (3-4): 253-62).

OX40L (TNFSF4, bTNF Superfamily Member 4)

The OX40 Ligand (OX40L) (CD252, TNFSF4), which was originally termed glycoprotein 34 kDa (GP34), belongs to the TNF superfamily; it is mainly expressed on the surface of antigen-presenting cells (APC), including activated dendritic cells (DCs), B cells, macrophages, T cells as well as endothelial cells [Huang, L. et al., J. Trans. Med. (2018) 16: 74; doi: 10.1186/s12967-018-1436-4, citing DeSmedt, T et al, J. Immunol (2002) 168: 661-670. doi: 10.4049/jimmunol. 168.2.661; Ohshima, Y. et al., Blood (1998) 92: 3338-3345].

OX40 (ACT35, CD134, TNFRSF4) is constitutively expressed on the cell surface of activated CD4+ T cells [Id., citing Ogawa R, et al., Cytokine Growth Factor Rev. (2008) 19:253-262. doi: 10.1016/j.cytogfr.2008.04.003, Paterson D J, et al. Mol Immunol. (1987) 24:1281-1290. doi: 10.1016/0161-5890(87)90122-2]. It can specially bind to OX40L and initiate a series of reactions which contribute to facilitate the proliferation and survival of CD4+ T cells and cytokine secretion [Id., citing Kaur D, Brightling C. Chest. (2012) 141:494-499. doi: 10.1378/chest.11-1730].The OX-40 receptor (OX-40R) is a transmembrane protein found on the surface of activated CD4(+) T cells. Weinberg, A D, et al., "OX-40: life beyond the effector T cell stage," Semin. Immunol. (1998) 10(6): 471-80). When engaged by an agonist such as anti-OX-40 antibody or the OX-40 ligand (OX-40L) during antigen presentation to T cell lines, the OX-40R generates a costimulatory signal that is as potent as CD28 costimulation. Id. Engagement of OX-40R enhances effector and memory-effector T cell function by up-regulating IL-2 production and increasing the life-span of effector T cells. Id.

CD25-Foxp3-naïve CD4 T cells can aquire Foxp3 driven by TGF-βR and IL-2R signals leading to differentiation into an inducible Treg (iTreg). So, T et al, Cytokine Growth Factor Rev. (2008) 19 (3-4): 253-62. Costimulatory signals from OX40 have been found to be antagonistic for Foxp3 induction in antigen-responding naïve CD4 T cells and suppress the development of high numbers of CD25+ Foxp3+iTregs (Id, citing Vu M D, et al. Blood. (2007) 110:2501-10; So T, Croft M. J Immunol. (2007) 179:1427-30).

According to some embodiments of the disclosed invention, the ENLST™ cells may be engineered to express a membrane bound form of OX40L on the membrane of the ENLST™ cells. According to some embodiments of the disclosed invention, the ENLST™ cells may be engineered to express a soluble form of OX40L.

According to some embodiments of the disclosed invention, ENLST™ cells may be engineered to express a membrane bound form of OX40L on the membrane of the ENLST™ cells of SEQ ID NO: 108. According to some embodiments, the ENLST™ tumor cell line or tumor cell line variant may comprise one or more proteins with a sequence identity of at least 60% to the protein of SEQ ID NO: 108. According to some embodiments, the ENLST™ cells may comprise one or more proteins with a sequence identity of at least 70% to the protein of SEQ ID NO: 108. According to some embodiments, the ENLST™ cells may comprise one or more proteins with a sequence identity of at least 80% to the protein of SEQ ID NO: 108. According to some embodiments, the ENLST™ cells variant may comprise one or more proteins with a sequence identity of at least 90% to the protein of SEQ ID NO: 108. According to some embodiments, the ENLST™ cells may comprise one or more proteins with a sequence identity of at least 95% to the protein of SEQ ID NO:108. According to some embodiments, the ENLST™ cells may comprise one or more proteins with a sequence identity of at least 96% to the protein of SEQ ID NO: 108. According to some embodiments, the ENLST™ cells may comprise one or more proteins with a sequence identity of at least 97% to the protein of SEQ ID NO: 108. According to some embodiments, the ENLST™ cells may comprise one or more proteins with a sequence identity of at least 98% to the protein of SEQ ID NO:108. According to some embodiments, the ENLST™ cells may comprise one or more proteins with a sequence identity of at least 99% to the protein of SEQ ID NO: 108.

CD27 Ligand (CD70)

CD27 ligand (CD70), a type II transmembrane protein, is a member of the TNF superfamily. It is expressed on activated T and B lymphocytes, as well as NK cells. CD27 Ligand and its receptor CD27 regulate the immune response by promoting T cell expansion and differentiation, as well as NK enhancement. CD27 signals, during the later phase of the primary CD8+ T cell response, prevent apoptosis of antigen-specific CD8+ T cells. Lack of CD27 signals decreases the quality of memory CD8+ T cell responses. Memory CD8+ T cells, which express surface CD27 similar to naïve cells, however, do not require CD27 costimulation during a secondary response. Thus, in vivo, CD27 acts indirectly to regulate primary antigen-specific CD8+ T cell responses by preventing apoptosis of CD8+ T cells during the later phase of the primary response, and is required for optimal quality of memory cells, but is not required during normally primed secondary CD8+ T cell responses. Dolfi, D V, et a., J. Immunol. (2008) 180(5): 2912-2921). Full length CD27 Ligand (CD70) is a 193 amino acid protein, consisting of a 17 amino acid cytoplasmic domain, a 21 amino acid transmembrane domain, and a 155 amino acid extracellular domain. Human soluble CD70 corresponds to the 155 amino acid extracellular domain of the full length CD70 protein.

According to some embodiments of the disclosed invention, an ENLST™ cells tumor cell line or tumor cell line variant may be engineered to express a membrane bound form of CD70 on the membrane of the ENLST™ cells.

According to some embodiments of the disclosed invention, an ENLST™ cell tumor cell line or tumor cell line variant may be engineered to express a soluble form of CD70.

According to some embodiments of the disclosed invention, the ENLST™ cells may be engineered to express a membrane bound form of CD70 on the membrane of the ENLST™ cells of SEQ ID NO: 109. According to some embodiments, the ENLST™ cells may comprise one or more proteins with a sequence identity of at least 60% to the protein of SEQ ID NO: 109. According to some embodiments, the ENLST™ cells may comprise one or more proteins with a sequence identity of at least 70% to the protein of SEQ ID NO: 109. According to some embodiments, the ENLST™ cells may comprise one or more proteins with a sequence identity of at least 80% to the protein of SEQ ID NO: 109. According to some embodiments, the ENLST™ cells may comprise one or more proteins with a sequence identity of at least 90% to the protein of SEQ ID NO: 109. According to some embodiments, the ENLST™ cells may comprise one or more proteins with a sequence identity of at least 95% to the protein of SEQ ID NO: 109. According to some embodiments, the ENLST™ cells may comprise one or more proteins with a sequence identity of at least 96% to the protein of SEQ ID NO: 109. According to some embodiments, the ENLST™ cells may comprise one or more proteins with a sequence identity of at least 97% to the protein of SEQ ID NO: 109. According to some embodiments, the ENLST™ cells may comprise one or more proteins with a sequence identity of at least 98% to the protein of SEQ ID NO: 109. According to some embodiments, the ENLST™ cells may comprise one or more proteins with a sequence identity of at least 99% to the protein of SEQ ID NO: 109.

4-1BBL

Naïve CD8 T cells require more co-stimulatory activity to drive them to become activated effector cells than do naïve CD4 T cells. This requirement can be met in two ways. The simplest is priming by activated DCs, which have high intrinsic co-stimulatory activity. In some viral infections, dendritic cells become sufficiently activated to directly induce CD8 T cells to produce the IL-2 required for their differentiation into cytotoxic effector cells, without help from CD4 T cells. This property of DCs has been exploited to generate cytotoxic T cell responses against tumors. In the majority of viral infections, however, CD8 T-cell activation requires additional help, which is provided by CD4 effector T cells. CD4 T cells that recognize related antigens presented by the APC can amplify the activation of naïve CD T cells by further activating the APC. B7 expressed by the DC first activates the CD4 T cells to express IL-2 and CD40L. CD40L binds CD40 on the DC, delivering an additional signal that increases the expression of B7 and 4-IBBL by the dendritic cell, which in turn provides additional co-stimulation to the naïve CD8 T cell. The IL-2 produced by activated CD4 T cells also acts to promote effector CD8 T-cell differentiation. Murphy, Kenneth. *Janeway's Immunobiology:* 8th ed. Chapter 15: Garland Science. (2012), at 372.

4-IBB has a pattern of expression that follows the primary activation of T cells and is restricted to activated CD4+ and CD8+ T cells. Guinn, B, et al., J. Immuno. (1999) 162: 5003-5010. Engagement of the 4-IBB receptor has been shown to relay strong costimulatory signals within activated T cells, which lead to their enhanced proliferation and cytokine secretion. Id. Such signaling prevents activation-induced cell death following TCR cross-linking in the absence of other accessory signals. Id. 4-IBBL, a high affinity ligand for 4-IBB, expressed on the surface of activated APCs, is a type II membrane protein that shows homology to members of the TNF receptor family. T cells purified from CD28−/− mice have been shown to secrete cytokines and proliferate in response to lymphomas expressing 4-IBBL; this response can be inhibited by the soluble 4-IBB receptor fusion protein. Id. In the absence of a CD28 signal, the 4-IBBL:4-IBB interaction has been shown to play a role in the production of a Th2 response in mixed lymphocyte reactions. Id.

According to some embodiments of the disclosed invention, the ENLST™ cells may be engineered to express a membrane bound form of 4-IBBL. According to some embodiments of the disclosed invention, an ENLST™ tumor cell line or tumor cell line variant may be engineered to express a soluble form of 4-IBBL.

CD40 Ligand (CD40L)

The ligand of CD40, known as CD154 or CD40L, is a type II transmembrane protein, with a variable molecular weight between 32 and 39 kDa because of post-translation modifications (Elgueta R et al., Molecular mechanism and function of CD40/CD40L engagement in the immune system. Immunological reviews. 2009; 229(1):10.1111/j.1600-065X.2009.00782.x. doi:10.1111/j.1600-065X.2009.00782.x, citing van Kooten C et al., J. Leukoc Biol. 2000 January; 67(1):2-17). A soluble form of CD40L has been reported that has activities similar to the transmembrane form (Id. citing Graf D et al., Eur J Immunol. 1995 June; 25(6):1749-54; Mazzei G J et al., J Biol Chem. 1995 Mar. 31; 270(13):7025-8).

In nature, CD40L is a member of the TNF superfamily and is characterized by a sandwich extracellular structure that is composed of a β-sheet, α-helix loop, and a β-sheet, which allows for the trimerization of CD40L (Id. citing Karpusas M et al., Structure. 1995 Oct. 15; 3(10):1031-9). CD40L is expressed primarily by activated T cells, as well as activated B cells and platelets; under inflammatory conditions it is also induced on monocytic cells, natural killer cells, mast cells, and basophils (Id. citing Carbone E et al., J Exp Med. 1997 Jun. 16; 185(12):2053-60). The widespread expression of the costimulatory pair of CD40L and CD40 indicates the pivotal roles they play in different cellular immune processes.

CD40L has three binding partners: CD40, α5β1 integrin and αIIbβ3 integrin. CD40L acts as a costimulatory molecule and is particularly important on a subset of T cells called T follicular helper cells (TFH cells), where it promotes B cell maturation and function by engaging CD40 on the B cell surface facilitating cell-cell communication. A defect in the CD40L gene results in an inability to undergo immunoglobulin class switching and is associated with hyper-IgM syndrome. Absence of CD40L also stops the formation of germinal centers thereby prohibiting antibody affinity maturation, an important process in the adaptive immune system.

CD40 has been found to be expressed on APCs, while its ligand, CD40L, has been found on activated T cells. CD40 has been found to play a critical role in the humoral immune response, and has been identified as enabling APCs to activate T cells. Several pathologies have been associated with the CD40/CD40L pathway including lupus and atherosclerosis, but anti-CD40L antibodies have been limited to clinical applications of thrombic complications from CD40 expression on activated platelets (Kaufman and Wolchok eds., General Principles of Tumor Immunotherapy, Chpt 5, 67-121 (2007)).

CD40 has also been found on several types of cancer, including solid tumors and hematologic malignancies. Signaling through CD40 in hematological cancer may mediate growth or regression, while CD40 signaling in solid tumors is only tumoricidal. These characteristics are found even in SCID mouse models, and therefore are likely due to TNF death domain signaling. There is also evidence of immune modulation, for example blockade of the CD40/CD40L pathway mitigates the protective effect of GM-CSF secreting melanoma vaccines (Kaufman and Wolchok eds., General Principles of Tumor Immunotherapy, Chpt 5, 67-121 (2007)).

Tumor cell vaccines expressing CD40L have proved useful in cancer models. For example, ligation of CD40 with CD40L or anti-CD40 antibodies has shown synergy with GM-CSF, IFN-gamma, IL-2, and CTLA-4 blockade. Furthermore, anti-CD40 antibodies have been reported to have anti-tumor activity in a pre-clinical mouse model (Kaufman and Wolchok eds., General Principles of Tumor Immunotherapy, Chpt 5, 67-121 (2007)).

According to some embodiments, an R subset of immunomodulators may comprise CD40 Ligand (CD40L). According to some embodiments of the disclosed invention, the ENLST™ tumor cell line or tumor cell line variant may be engineered to express a noncleavable CD40L peptide of SEQ ID NO: 6. According to some embodiments, the ENLST™ cells may be genetically engineered to comprise one or more proteins with a sequence identity of at least 60% to the protein of SEQ ID NO: 6. According to some embodiments, the ENLST™ cells may be genetically engineered to comprise one or more proteins with a sequence identity of at least 70% to the protein of SEQ ID NO: 6. According to some embodiments, the ENLST™ cells may be genetically engineered to comprise one or more proteins with a sequence identity of at least 80% to the protein of SEQ ID NO: 6. According to some embodiments, the ENLST™ cells may be genetically engineered to comprise one or more proteins with a sequence identity of at least 90% to the protein of SEQ ID NO: 6. According to some embodiments, the ENLST™ cells may be genetically engineered to comprise one or more proteins with a sequence identity of at least 95% to the protein of SEQ ID NO: 6. According to some embodiments, the ENLST™ cells may be genetically engineered to comprise one or more proteins with a sequence identity of at least 96% to the protein of SEQ ID NO: 6. According to some embodiments, the ENLST™ cells may be genetically engineered to comprise one or more proteins with a sequence identity of at least 97% to the protein of SEQ ID NO: 6. According to some embodiments, the ENLST™ cells may be genetically engineered to comprise one or more proteins with a sequence identity of at least 98% to the protein of SEQ ID NO: 6. According to some embodiments, the ENLST™ cells may be genetically engineered to comprise one or more proteins with a sequence identity of at least 99% to the protein of SEQ ID NO: 6.

According to some embodiments, the ENLST™ cells may be engineered to express the non-cleavable membrane bound CD40L peptide of SEQ ID NO: 7 on the membrane surface of the tumor cell. According to some embodiments, the ENLST™ cells may be genetically engineered to comprise one or more proteins with a sequence identity of at least 60% to the protein of SEQ ID NO: 7. According to some embodiments, the ENLST™ cells may be genetically engineered to comprise one or more proteins with a sequence identity of at least 70% to the protein of SEQ ID NO: 7. According to some embodiments, the ENLST™ cells may be genetically engineered to comprise one or more proteins with a sequence identity of at least 80% to the protein of SEQ ID NO: 7. According to some embodiments, the ENLST™ cells may be genetically engineered to comprise one or more proteins with a sequence identity of at least 90% to the protein of SEQ ID NO: 7. According to some embodiments, the ENLST™ cells may be genetically engineered to comprise one or more proteins with a sequence identity of at least 95% to the protein of SEQ ID NO: 7. According to some embodiments, the ENLST™ cells may be genetically engineered to comprise one or more proteins with a sequence identity of at least 96% to the protein of SEQ ID NO: 7. According to some embodiments, the ENLST™ cells may be genetically engineered to comprise one or more proteins with a sequence identity of at least 97% to the protein of SEQ ID NO: 7. According to some embodiments, the ENLST™ cells may be genetically engineered to comprise one or more proteins with a sequence identity of at least 98% to the protein of SEQ ID NO: 7. According to some embodiments, the ENLST™ cells may be genetically engineered to comprise one or more proteins with a sequence identity of at least 99% to the protein of SEQ ID NO: 7.

Tumor Necrosis Factor Alpha (TNFα)

Tumor necrosis factor (TNF; tumor necrosis factor alpha (TNFα); cachexin, cachectin) is a cytokine, primarily produced by activated macrophages and lymphocytes, which is involved in systemic inflammation. It is also one of the cytokines involved in the acute phase of an immunogenic response. TNF may be produced by other cell types such as, for example, CD4+ lymphocytes, NK cells, neutrophils, mast cells, eosinophils, and neurons.

In its primary role as a regulator of immune cells, TNF is capable of inducing fever, apoptotic cell death, cachexia, inflammation, and inhibition of tumorigenesis; of inhibiting viral replication; and of initiating a response to sepsis vial IL-1 and IL-6 producing cells. Dysregulated TNF production has been associated with a wide array of human diseases, including Alzheimer's disease, major depression, psoriasis, and inflammatory bowel disease (IBD). TNF can be produced ectopically in the setting of malignancy and parallels parathyroid hormone both in causing secondary hypercalcemia and in the cancers with which excessive production is associated.

TNF comprises a 26 kDa membrane bound form and 17 kDa soluble cytokine form. The soluble form of TNF is derived from proteolytic cleavage of the membrane bound form by TNF-alpha converting enzyme (TACE) (Grell M. et al., The Transmembrane Form of Tumor Necrosis Factor Is the Prime Activating Ligand of the 80 kDa Tumor Necrosis Factor Receptor, Cell, Vol. 83, 793-802). TACE is a matrix metalloprotease that recognizes a cleavage site in the extracellular domain of full-length TNF (Rieger, R., Chimeric form of tumor necrosis factor-alpha has enhanced surface expression and antitumor activity, Cancer Gene Therapy, 2009, 16, 53-64). Deletion of the cleavage site on TNF results in enhanced membrane stability of TNF (Id.).

TNF has antiproliferative and cytotoxic effects on cells, is known to reduce tumor blood flow and tumor vascular damage, and is able to modulate immune response by stimulating macrophage and NK cell activity. However, the use of TNF as a therapeutic itself has been limited by dose-dependent hypotension and capillary leak that can cause a sepsis-like syndrome. For that reason, it must be delivered in a manner that limits systemic effects. TNF has been added to standard chemotherapy agents to improve response rates. Other approaches to administering TNF include injection of adenovirus altered to express TNF in gastrointestinal malignancies. A tumor vascular-targeted TNF compound has also been developed (Kaufman and Wolchok eds., General Principles of Tumor Immunotherapy, Chpt 5, 67-121 (2007)). Recombinant TNF has been used as an immunostimulant under the name tasonermin, while HUMIRA® is an antibody to TNF, useful for the treatment of inflammatory diseases (e.g. psoriasis and rheumatoid arthritis). In recognition of this role, molecules such as antibodies have been designed to interfere with TNF activity. However, such therapies pose the risk of initiating a cytokine storm caused by the inappropriate systemic release of cytokines, resulting in a positive feedback loop of white blood cell activation/cytokine release that potentially can be fatal.

According to some embodiments, a subset of R immunomodulators may comprise TNF. According to some embodiments, the ENLST™ cellsmay be genetically engineered to express the membrane bound form of TNF on the membrane of the tumor cell. For example, according to some embodiments, the cell line variants comprise the peptide of SEQ ID NO: 8. According to some embodiments, the ENLST™ cells may be genetically engineered to comprise one or more proteins with a sequence identity of at least 60% to the protein of SEQ ID NO: 8. According to some embodiments, the ENLST™ cells may be genetically engineered to comprise one or more proteins with a sequence identity of at least 70% to the protein of SEQ ID NO: 8. According to some embodiments, the ENLST™ cells may be genetically engineered to comprise one or more proteins with a sequence identity of at least 80% to the protein of SEQ ID NO: 8. According to some embodiments, the ENLST™ cells may be genetically engineered to comprise one or more proteins with a sequence identity of at least 90% to the protein of SEQ ID NO: 8. According to some embodiments, the ENLST™ cells may be genetically engineered to comprise one or more proteins with a sequence identity of at least 95% to the protein of SEQ ID NO: 8. According to some embodiments, the ENLST™ cells may be genetically engineered to comprise one or more proteins with a sequence identity of at least 96% to the protein of SEQ ID NO: 8. According to some embodiments, the ENLST™ cells may be genetically engineered to comprise one or more proteins with a sequence identity of at least 97% to the protein of SEQ ID NO: 8. According to some embodiments, the ENLST™ cells may be genetically engineered to comprise one or more proteins with a sequence identity of at least 98% to the protein of SEQ ID NO: 8. According to some embodiments, the ENLST™ cells may be genetically engineered to comprise one or more proteins with a sequence identity of at least 99% to the protein of SEQ ID NO: 8.

According to some embodiments, the ENLST™ cells may be genetically engineered to express a non-cleavable membrane bound form of TNF. For example, according to some embodiments, the ENLST™ tumor cell line or tumor cell line variant may be genetically engineered to comprise the TNF protein of SEQ ID NO: 8 with one or more of amino acids VRSSSRTPSDKP (SEQ ID NO 104) deleted (see e.g. SEQ ID NO: 26).

According to some embodiments, the ENLST™ cells may be genetically engineered to express a soluble form of TNF. For example, according to some embodiments, the ENLST™ tumor cell line or tumor cell line variant may be genetically engineered to express the TNF protein of SEQ ID NO: 8 with part or the entire transmembrane region removed. For example, according to some embodiments, the ENLST™ tumor cell line or tumor cell line variant may be genetically engineered to comprise a derivative TNF protein of SEQ ID NO: 8 with one or more of amino acids F, S, F, L, I, V, A, G, A, T, T, L, F, C, L, L, H, F, G, V, I deleted (see e.g. SEQ ID NO: 27).

According to some embodiments, the ENLST™ cells may be genetically engineered to express a non-cleavable membrane bound chimeric form of CD40L and TNF. For example, according to some embodiments, the ligand binding portion of a TNF molecule may be fused with the transmembrane and proximal extracellular domains of CD40L, such that the TNF lacks a defined TNF alpha cleaving enzyme (TACE) site. According to some embodiments, the intracellular, transmembrane, and partial extracellular portions CD40L may be fused with the extracellular region of TNF distal to the TACE cleavage site. According to some embodiments, the chimeric form of CD40L/TNF may comprise the CD40L sequence of SEQ ID NO: 9 and the TNF sequence of SEQ ID NO: 10. According to some embodiments, the CD40L/TNF sequences are operably linked via a linking peptide between 1 and 30 amino acids in length. According to some embodiments, the ENLST™ cells may be genetically engineered to comprise a fusion protein with a sequence identity of at least 60% to the proteins of SEQ ID NO: 9 and SEQ ID NO: 10. According to some embodiments, the ENLST™ cells may be genetically engineered to comprise a fusion protein with a sequence identity of at least 70% to the proteins of SEQ ID NO: 9 and SEQ ID NO: 10. According to some embodiments, the ENLST™ cells may be genetically engineered to comprise a fusion protein with a sequence identity of at least 80% to the proteins of SEQ ID NO: 9 and SEQ ID NO: 10. According to some embodiments, the ENLST™ cells may be genetically engineered to comprise a fusion protein with a sequence identity of at least 90% to the proteins of SEQ ID NO: 9 and SEQ ID NO: 10. According to some embodiments, the ENLST™ cells may be genetically engineered to comprise a fusion protein with a sequence identity of at least 95% to the proteins of SEQ ID NO: 9 and SEQ ID NO: 10. According to some embodiments, the ENLST™ cells may be genetically engineered to comprise a fusion protein with a sequence identity of at least 96% to the proteins of SEQ ID NO: 9 and SEQ ID NO: 10. According to some embodiments, the ENLST™ cells may be genetically engineered to comprise a fusion protein with a sequence identity of at least 97% to the proteins of SEQ ID NO: 9 and SEQ ID NO: 10. According to some embodiments, the ENLST™ cells may be genetically engineered to comprise a fusion protein with a sequence identity of at least 98% to the proteins of SEQ ID NO: 9 and SEQ ID NO: 10. According to some embodiments, the ENLST™ cells may be genetically engineered to comprise a fusion protein with a sequence identity of at least 99% to the proteins of SEQ ID NO: 9 and SEQ ID NO: 10.

According to some embodiments, the ENLST™ cells may be genetically engineered to express a non-cleavable membrane bound form of TNF with a sequence identity of at least 60% to the protein of SEQ ID NO: 11. According to some embodiments, the ENLST™ cells may be genetically engineered to express a non-cleavable membrane bound form of TNF with a sequence identity of at least 70% to the protein of SEQ ID NO: 11. According to some embodiments, the ENLST™ cells may be genetically engineered to express a non-cleavable membrane bound form of TNF with a sequence identity of at least 80% to the protein of SEQ ID NO: 11. According to some embodiments, the ENLST™ cells may be genetically engineered to express a non-cleavable membrane bound form of TNF with a sequence identity of at least 90% to the protein of SEQ ID NO: 11. According to some embodiments, the ENLST™ cells may be genetically engineered to express a non-cleavable membrane bound form of TNF with a sequence identity of at least 95% to the protein of SEQ ID NO: 11. According to some embodiments, the ENLST™ cells may be genetically engineered to express a non-cleavable membrane bound form of TNF with a sequence identity of at least 96% to the protein of SEQ ID NO: 11. According to some embodiments, the ENLST™ cells may be genetically engineered to express a non-cleavable membrane bound form of TNF with a sequence identity of at least 97% to the protein of SEQ ID NO: 11. According to some embodiments, the ENLST™ cells may be genetically engineered to express a non-cleavable membrane bound form of TNF with a sequence identity of at least 98% to the protein of SEQ ID NO: 11. According to some embodiments, the ENLST™ cells may be genetically engineered to express a non-cleavable membrane bound form of TNF with a sequence identity of at least 99% to the protein of SEQ ID NO: 11.

According to some embodiments, the ENLST™ cells may be genetically engineered to express a non-cleavable membrane bound chimeric form of CD40L and TNF. For example, according to some embodiments, the ligand portion of a TNF molecule may be fused with extracellular portions of CD40L, wherein CD40L comprises an extracellular portion that is non-cleavable and the TNF lacks a defined TACE site (e.g. cleavage site between amino acids 76 and 77). According to some embodiments, some or all of a CD40L peptide sequence is fused with the extracellular region of a TNF peptide sequence distal to the TACE cleavage site. According to some embodiments, the chimeric form of CD40L/TNF may comprise the sequence of SEQ ID NO: 31. According to some embodiments, the ENLST™ cells may be genetically engineered to comprise a fusion protein with a sequence identity of at least 60% to the protein of SEQ ID NO: 31. According to some embodiments, the ENLST™ cells may be genetically engineered to comprise a fusion protein with a sequence identity of at least 70% to the protein of SEQ ID NO: 31. According to some embodiments, the ENLST™ cells may be genetically engineered to comprise a fusion protein with a sequence identity of at least 80% to the protein of SEQ ID NO: 31. According to some embodiments, the ENLST™ cells may be genetically engineered to comprise a fusion protein with a sequence identity of at least 90% to the protein of SEQ ID NO: 31. According to some embodiments, the ENLST™ cells may be genetically engineered to comprise a fusion protein with a sequence identity of at least 95% to the protein of SEQ ID NO: 31. According to some embodiments, the ENLST™ cells may be genetically engineered to comprise a fusion protein with a sequence identity of at least 96% to the protein of SEQ ID NO: 31. According to some embodiments, the ENLST™ cells may be genetically engineered to comprise a fusion protein with a sequence identity of at least 97% to the protein of SEQ ID NO: 31. According to some embodiments, the ENLST™ cells may be genetically engineered to comprise a fusion protein with a sequence identity of at least 98% to the protein of SEQ ID NO: 31. According to some embodiments, the ENLST™ cells may be genetically engineered to comprise a fusion protein with a sequence identity of at least 99% to the protein of SEQ ID NO: 31.

Secreted Receptors

According to some embodiments, the disclosure encompasses an ENLST™ cell population comprising a population of tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a subset of R immunomodulators comprising one or more secreted receptors. According to some embodiments, R immunomodulators may comprise one or more (e.g., 2, 3, 4, 5, or more) secreted receptor proteins, or variants or fragments thereof. According to some embodiments, the secreted receptor is IL10R, TGFβR3, or both.

Interleukin-10 (IL-10) is a key immunosuppressive cytokine that is produced by a wide range of leukocytes, as well as nonhematopoietic cells. Shouval, D S., et al., Immunity (2014) 40: 706-719. IL-10 mediates its anti-inflammatory effects through IL-10 receptor (IL-10R)-dependent signals emanating from the cell surface. The IL-10R is a heterotetramer that consists of two subunits of IL-10Rα and two subunits of IL-10Rβ. Id., citing Moore, K W, et al., Annu. Rev. Immunol. (2001) 19: 683-765). Whereas the IL-10Rα subunit is unique to IL-10 signaling, the IL-10Rβ subunit is shared by other cytokine receptors, including IL-22, IL-26, and interferon λ, Id. IL-10 downstream signaling through the IL-10R inhibits the induction of proinflammatory cytokines by blocking NF-κB-dependent signals. (Id., citing Saraiva, M., and O'Garra, A. Nat. Rev. Immunol. (2010) 10: 180-181).

Transforming growth factor-beta receptor 3 (TbetaRIII or TbetaR3) is an 853 amino acid transmembrane proteoglycan, which contains a short 41 amino acid cytoplasmic domain. It is ubiquitously expressed on nearly all cell types. The level of TbetaRIII expression is cell type specific. It is a member of the TGF-beta superfamily signaling pathways, which have essential roles in mediating cell proliferation, apoptosis, differentiation, and migration in most human tissues. TbetaRIII is the most abundantly expressed TGF-beta superfamily receptor and functions as a TGF-beta superfamily co-receptor, by binding the TGF-beta superfamily members, TGF-beta1, TGF-beta2, or TGF-beta3, inhibin, BMP-2, BMP-4, BMP-7, and GDF-5 and presents these ligand to their respective signaling receptors to activate or repress (in the case of inhibin) TGF-beta1, BMP, or activin signaling to the Smad transcription factors. For example, in the case of TGF-beta1, 2, or 3, TbetaRIII presents ligand to the TGF-beta type II receptor (TbetaRII). Once bound to ligand, TbetaRII then recruits and transphosphorylates the TGF-beta type I receptor (TbetaRI), activating its kinase function and leading to the phosphorylation of Smad2/3. Phosphorylation of Smad2 and Smad3 leads to formation of a complex with Smad4, and accumulation of this complex in the nucleus, where along with co-activators and co-repressors they regulate the transcription of genes involved in proliferation, angiogenesis, apoptosis, and differentiation. In addition to regulating receptor mediated Smad signaling, TbetaRIII also mediates ligand dependent and independent p38 pathway signaling. TbetaRIII can also undergo ectodomain shedding to generate soluble TbetaRIII (sTbetaRIII), which binds and sequesters TGF-beta superfamily members to inhibit their signaling. Although sTbetaRIII expression has been demonstrated to correlate with the cell surface expression of TbetaRIII, little is known about the regulation of sTbetaRIII production. TbetaRIII shedding may be mediated in part by the membrane type matrix metalloproteases (MT-MMP) MT1-MMP and/or MT3-MMP, and plasmin, a serine proteinase which has been shown to cleave the extracellular domain of TbetaRIII. In addition, TbetaRIII shedding is modulated by pervanadate, a tyrosine phosphatase inhibitor. Supporting this, TAPI-2, a MT-MMP and ADAM protease inhibitor, has been shown to inhibit TbetaRIII shedding. The regulation of TbetaRIII expression is sufficient to alter TGF-beta signaling. The cytoplasmic domain of TbetaRIII interacts with GAIP interacting protein, C terminus (GIPC), a PDZ-domain containing protein, which stabilizes TbetaRIII cell surface expression and increases TGF-beta signaling. The interaction between TbetaRIII and GIPC also plays an important role in TbetaRIII mediated inhibition of TGF-beta signaling, cell migration, and invasion during breast cancer progression. The cytoplasmic domain of TbetaRIII is phosphorylated by TbetaRII, which results in TbetaRIII binding to the scaffolding protein beta-arrestin2. The TbetaRIII/beta-arrestin2 interaction results in the co-internalization of beta-arrestin2/TbetaRIII/TbetaRII and the down-regulation of TGF-beta signaling. The interaction between TbetaRIII and beta-arrestin2 regulates BMP signaling as well as TGF-beta signaling. TbetaRIII complexes with ALK6, a BMP type I receptor, in a beta-arrestin2 dependent manner to mediate the internalization of ALK6 and stimulation of ALK6 specific BMP signaling events. Through its interaction with beta-arrestin2, TbetaRIII negatively regulates NFκ-B signaling in the context of breast cancer, regulates epithelial cellular adhesion to fibronectin, fibrillogenesis, and focal adhesion formation via regulation of alpha5beta1 internalization and trafficking to nascent focal adhesions, activates Cdc42, to alter the actin cytoskeleton and suppresses migration in normal and cancerous ovarian epithelial cells. During development, TbetaRIII has an important role in the formation of the atrioventricular cushion in the heart. Consistent with an important role for TbetaRIII during development, TGF-betaR3 null mice are embryonic lethal due to heart and liver defects. TGFbetaR3 has been recently identified as a tumor suppressor in multiple types of human cancers, including breast, lung, ovarian, pancreatic and prostate cancer. The loss of TGFbetaR3 in these cancer types correlates with disease progression, and results in increased motility and invasion in vitro and increased invasion and metastasis in vivo. (http://atlasgeneticsoncology.org/Genes/TGFBR3ID42541ch1p33.html, visited Aug. 26, 2019).

Chaperones

According to some embodiments, the disclosure encompasses an ENLST™ cell population comprising a population of tumor cells expressing one or more tumor specific antigens, wherein the tumor cells are genetically engineered to stimulate one or more of T lymphocytes, natural killer (NK) cells, dendritic cells (DCs) or B lymphocytes, the population a subset of R immunomodulators comprising one or more chaperone proteins. According to some embodiments, the disclosure encompasses a chaperone protein, including a full-length, fragment, homologue, variant or mutant of the chaperone protein.

Chaperones are a functionally related group of proteins that assist protein folding in the cell under physiological and stress conditions. According to some embodiments, the chaperone protein is selected from one or more of GRP78/BiP, GRP94, GRP170, Calnexin, calreticulin, HSP47, ERp29, Protein disulfide isomerase (PDI), Peptidyl prolyl cis-trans-isomerase (PPI), Erp57, Hsp60, Hsp70, Hsp90, Hsp100.

According to some embodiments, the chaperone protein is membrane bound.

According to some embodiments, a population of ENLST™ cells expressing one or more tumor specific antigens may be genetically engineered to comprise one or more (e.g., 2, 3, 4, 5, or more) chaperone proteins, or variants or fragments thereof.

Immunoglobulin Superfamily (IgSF)

According to some embodiments, a subset of R immunomodulators may comprise one or more IgSF proteins. Thus, the disclosure encompasses a member of the IgSF superfamily, including a full-length, fragment, homologue, variant or mutant of the IgSF superfamily member.

The immunoglobulin superfamily (IgSF) is a class of proteins that are associated with the adhesion, binding and recognition processes of cells. Molecules are categorized as members of this superfamily based on shared structural features with immunoglobulins; they all possess a domain known as an immunoglobulin domain or fold. Members of the IgSF include cell surface antigen receptors, co-receptors and co-stimulatory molecules of the immune system, molecules involved in antigen presentation to lymphocytes, cell adhesion molecules, certain cytokine receptors and intracellular muscle proteins. Members of the IgSF can be classified as follows: antigen receptors (e.g. antibodies or immunoglobulins: IgA, IgD, IgE, IgG, IgM); antigen presenting molecules (e.g. MHC class I, MHC class II); co-receptors (e.g. CD4, CD8); co-stimulatory or inhibitory molecules (e.g. CD28, Cd80, CD86); receptors on Natural Killer cells (e.g. killer-cell immunoglobulin-like receptors (KIR)); receptors on leukocytes (e.g., leukocyte immunoglobulin-like receptors (LILR)); IGSF CAMs (e.g., NCAMs, ICAM-1); cytokine receptors; growth factor receptors; receptor tyrosine kinases/phosphatases; IgG binding receptors.

According to some embodiments, the IgSF member is membrane bound.

Poliovirus Receptor (PVR/CD155) is a transmembrane glycoprotein belonging to the immunoglobulin superfamily. PVR/CD155 mediates NK cell adhesion and triggers NK cell effector functions. PVR/CD155 binds two different NK cell receptors: CD96 and CD226. These interactions accumulate at the cell-cell contact site, leading to the formation of a mature immunological synapse between NK cell and target cell. This may trigger adhesion and secretion of lytic granules and IFN-gamma (IFNγ) and activate cytoxicity of activated NK cells, and may also promote NK cell-target cell modular exchange, and PVR transfer to the NK cell.

Poliovirus receptor-related 2 (PVRL2), also known as Nectin-2, is a single-pass type I membrane glycoprotein with two Ig-like C2-type domains and an Ig-like V-type domain. This protein is one of the plasma membrane components of adherens junctions.

CD48 antigen (Cluster of Differentiation 48), also known as B-lymphocyte activation marker (BLAST-1) or signaling lymphocytic activation molecule 2 (SLAMF2), is a protein that in humans is encoded by the CD48 gene. CD48 is a member of the CD2 subfamily of the IgSF, which includes SLAM (signaling lymphocyte activation molecules) proteins, such as CD84, CD150, CD229 and CD244. CD48 is found on the surface of lymphocytes and other immune cells, dendritic cells and endothelial cells, and participates in activation and differentiation pathways in these cells.

NK-T-B antigen (NTBA) is a surface molecule expressed on NK, T, and B cells. In human NK cells, NTBA has been shown to act primarily as a coreceptor since it could trigger cytolytic activity only in cells expressing high surface densities of natural cytotoxicity receptors (NCR). Molecular cloning revealed that NTBA is a member of the Ig superfamily characterized by structural features that allowed its assignment to the CD2 family.

According to some embodiments, the IgSF protein is IgG. According to some embodiments, the IgSF protein is PVR/CD155. According to some embodiments, the IgSF protein is CD48. According to some embodiments, the IgSF protein is Nectin2. According to some embodiments, the IgSF protein is NK-T-B antigen.

Immunoglobulins (Ig) are glycoproteins produced by immune cells. Antibodies are serum proteins, the molecules of which possess small areas of their surface that are complementary to small chemical groupings on their targets. These complementary regions (referred to as complementary determining regions (CDRs), or antibody combining sites, or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice. Immunoglobulins play a critical role in an immune response by binding to particular antigens, such as those exhibited by bacteria or viruses. According to some embodiments, the binding of immunoglobulins to antigens may target them for destruction by the subject's immune cells.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

In mammals, there are five classes of antibodies, IgA, IgD, IgE, IgG, and IgM, each with its own class of heavy chain-α (for IgA), δ (for IgD), ε (for IgE), γ (for IgG) and μ (for IgM). In addition, there are four subclasses of IgG immunoglobulins (IgG1, IgG2, IgG3, IgG4) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

Diverse libraries of immunoglobulin heavy (VH) and light (Vκ and Vλ) chain variable genes from peripheral blood lymphocytes also can be amplified by polymerase chain reaction (PCR) amplification. Genes encoding single polypeptide chains in which the heavy and light chain variable domains are linked by a polypeptide spacer can be made by randomly combining heavy and light chain V-genes using PCR.

According to some embodiments, the ENLST™ cells may be engineered to express an IgG1 heavy chain constant region. In nature, the Ig gamma-1 (IgG-1) chain C region is a protein encoded by the IGHG1 gene in humans. According to some embodiments, the ENLST™ cells may express a membrane bound form IgG-1 chain C protein of SEQ ID NO: 1. According to some embodiments, the ENLST™ cells may be genetically engineered to express a secreted form of IgG-1 chain C of SEQ ID NO: 2. According to some embodiments, the ENLST™ cells may be genetically engineered to express a secreted form of IgG-1 chain C of SEQ ID NO: 3. According to some embodiments, the ENLST™ cells may be genetically engineered to comprise one or more proteins with a sequence identity of at least 60% to one or more of proteins with an amino acid sequence SEQ ID NO: 1, SEQ ID NO: 2, and SEQ ID NO: 3. According to some embodiments, the ENLST™ cells may be genetically engineered to comprise one or more proteins with a sequence identity of at least 70% to one or more of proteins with an amino acid sequence SEQ ID NO: 1, SEQ ID NO: 2, and SEQ ID NO: 3. According to some embodiments, the ENLST™ cells may be genetically engineered to comprise one or more proteins with a sequence identity of at least 80% to one or more of proteins with an amino acid sequence SEQ ID NO: 1, SEQ ID NO: 2, and SEQ ID NO: 3. According to some embodiments, the ENLST™ cells may be genetically engineered to comprise one or more proteins with a sequence identity of at least 90% to one or more of proteins with an amino acid sequence SEQ ID NO: 1, SEQ ID NO: 2, and SEQ ID NO: 3. According to some embodiments, the ENLST™ cells may be genetically engineered to comprise one or more proteins with a sequence identity of at least 95% to one or more of proteins with an amino acid sequence SEQ ID NO: 1, SEQ ID NO: 2, and SEQ ID NO: 3. According to some embodiments, the ENLST™ cells may be genetically engineered to comprise one or more proteins with a sequence identity of at least 96% to one or more of proteins with an amino acid sequence SEQ ID NO: 1, SEQ ID NO: 2, and SEQ ID NO: 3. According to some embodiments, the ENLST™ cells may be genetically engineered to comprise one or more proteins with a sequence identity of at least 97% to one or more of proteins with an amino acid sequence SEQ ID NO: 1, SEQ ID NO: 2, and SEQ ID NO: 3. According to some embodiments, the ENLST™ cells may be genetically engineered to comprise one or more proteins with a sequence identity of at least 98% to one or more of proteins with an amino acid sequence SEQ ID NO: 1, SEQ ID NO: 2, and SEQ ID NO: 3. According to some embodiments, the ENLST™ cells may be genetically engineered to comprise one or more proteins with a sequence identity of at least 99% to one or more of proteins with an amino acid sequence SEQ ID NO: 1, SEQ ID NO: 2, and SEQ ID NO: 3.

According to some embodiments, the ENLST™ cells may be genetically engineered to comprise one or more proteins with a sequence identity of at least 60% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, the ENLST™ cells may be genetically engineered to comprise one or more proteins with a sequence identity of at least 70% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, the ENLST™ cells may be genetically engineered to comprise one or more proteins with a sequence identity of at least 80% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, the ENLST™ cells may be genetically engineered to comprise one or more proteins with a sequence identity of at least 90% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, the ENLST™ cells may be genetically engineered to comprise one or more proteins with a sequence identity of at least 95% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, the ENLST™ cells may be genetically engineered to comprise one or more proteins with a sequence identity of at least 96% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, the ENLST™ cells may be genetically engineered to comprise one or more proteins with a sequence identity of at least 97% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, the ENLST™ cells may be genetically engineered to comprise one or more proteins with a sequence identity of at least 98% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, the ENLST™ cells may be genetically engineered to comprise one or more proteins with a sequence identity of at least 99% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46.

According to some embodiments, the ENLST™ cells may be engineered to express an IgG protein that is capable of binding to tumor cell specific antigens. For example, the ENLST™ cells may be engineered to express an IgG protein capable of binding to a prostate cancer specific antigen; e.g., the extracellular region of prostate-specific membrane antigen (PSMA) (See Chang, S., Overview of Prostate-Specific Membrane Antigen, Reviews in Urology, Vol. 6 Suppl. 10, S13 (2004)). According to some embodiments, the ENLST™ cells may be engineered to express an IgG protein that is capable of binding to immune cell specific antigens. For example, the ENLST™ cells may be engineered to express an IgG protein capable of binding to T cell markers, e.g., CD3, CD4, or CD8. According to another example, the ENLST™ cells may be engineered to express an IgG protein capable of binding to dendritic cell markers, e.g. CD11c or CD123.

According to some embodiments, the ENLST™ cells may be engineered to express an IgG3 heavy chain constant region. In nature, the IgG3 heavy chain constant region comprises CH1-hinge-CH2-CH3 domains, and is encoded by the IGHG3 gene in humans; the IGHG3 gene comprises structural polymorphisms comprising different hinge lengths. According to some embodiments, the ENLST™ cells may be genetically engineered to express an IgG-3 heavy chain constant region of SEQ ID NO: 4. According to some embodiments, the ENLST™ cells may be genetically engineered to express a derivative of SEQ ID NO: 4 with amino acids 1-76 missing. According to some embodiments, the ENLST™ cells may be genetically engineered to express the derivative of SEQ ID NO: 4 with amino acids 1-76 missing. According to some embodiments, the ENLST™ cells may be genetically engineered to express the derivative of SEQ ID NO: 4 with amino acids 77-98 replaced with amino acids QMQGVNCTVSS (SEQ ID NO: 101). According to some embodiments, the ENLST™ cells may be genetically engineered to express the derivative of SEQ ID NO: 4 comprising an E213Q variant (SEQ ID NO: 16). According to some embodiments, the ENLST™ cells may be genetically engineered to express the derivative of SEQ ID NO: 4 comprising a P221L variant (SEQ ID NO: 17). According to some embodiments, the ENLST™ cells may be genetically engineered to express the derivative of SEQ ID NO: 4 comprising an E224Q variant (SEQ ID NO: 18). According to some embodiments, the ENLST™ cells may be genetically engineered to express the derivative of SEQ ID NO: 4 comprising a Y226F variant (SEQ ID NO: 19). According to some embodiments, the ENLST™ cells may be genetically engineered to express the derivative of SEQ ID NO: 4 comprising a D242N variant (SEQ ID NO: 20). According to some embodiments, the ENLST™ cells may be genetically engineered to express the derivative of SEQ ID NO: 4 comprising a N245D variant (SEQ ID NO: 21). According to some embodiments, the ENLST™ cells may express the derivative of SEQ ID NO: 4 comprising a T269A variant (SEQ ID NO: 22). According to some embodiments, the ENLST™ cells may be genetically engineered to express the derivative of SEQ ID NO: 4 comprising a S314N variant (SEQ ID NO: 23). According to some embodiments, the ENLST™ cells may be genetically engineered to express the derivative of SEQ ID NO: 4 comprising a deleted S314 (SEQ ID NO: 24). According to some embodiments, the ENLST™ cells may be genetically engineered to express the derivative of SEQ ID NO: 4 comprising F366Y variant (SEQ ID NO: 25).

According to some embodiments, the ENLST™ cells may be genetically engineered to comprise one or more proteins with a sequence identity of at least 60% to the protein of SEQ ID NO: 4. According to some embodiments, the ENLST™ cells may be genetically engineered to comprise one or more proteins with a sequence identity of at least 70% to the protein of SEQ ID NO: 4. According to some embodiments, the ENLST™ cells may be genetically engineered to comprise one or more proteins with a sequence identity of at least 80% to the protein of SEQ ID NO: 4. According to some embodiments, the ENLST™ cells may be genetically engineered to comprise one or more proteins with a sequence identity of at least 90% to the protein of SEQ ID NO: 4. According to some embodiments, the ENLST™ cells may be genetically engineered to comprise one or more proteins with a sequence identity of at least 95% to the protein of SEQ ID NO: 4. According to some embodiments, the ENLST™ cells may be genetically engineered to comprise one or more proteins with a sequence identity of at least 96% to the protein of SEQ ID NO: 4. According to some embodiments, the ENLST™ cells may be genetically engineered to comprise one or more proteins with a sequence identity of at least 97% to the protein of SEQ ID NO: 4. According to some embodiments, the ENLST™ cells may be genetically engineered to comprise one or more proteins with a sequence identity of at least 98% to the protein of SEQ ID NO: 4. According to some embodiments, the ENLST™ cells may be genetically engineered to comprise one or more proteins with a sequence identity of at least 99% to the protein of SEQ ID NO: 4.

According to some embodiments, the ENLST™ cells may be engineered to express one or more IgG heavy chain variable regions. According to some embodiments, the ENLST™ cells may be engineered to express a lambda/kappa light chain constant and/or light chain variable region. According to some embodiments, the hinge region of IgG binds to the FcyR receptors on immune cells. According to some embodiments, the IgG is effective to activate the FcyR and enhance presentation of antigens (e.g. PSA associated with prostate cancer cells).

According to some embodiments, the ENLST™ cells may be engineered to express an intact monoclonal or polyclonal antibody on the cell surface of the tumor cell. According to some embodiments, the intact monoclonal or polyclonal antibody may be designed to deliver a molecule that elicits an immunogenic response. For example, according to some embodiments, the intact monoclonal antibody may be designed to bind to DNA to deliver CpG motifs to immune cells.

According to some embodiments, the immunostimulatory activity of bacterial DNA may be mimicked by engineering an immunomodulator to deliver unmethylated CpG motifs to immune cells. For example, according to some embodiments, the IgG may be engineered to bind to biotin, which is then capable of delivering biotinylated CpG to cells of the immune system. According to some embodiments, CpG motifs may be bound directly or indirectly to the surface of the tumor cells of the ENLST™ cells. According to some embodiments, CpG motifs may be conjugated to one or more antigens presented on the surface of tumor cells from the tumor cell line or tumor cell line variant. According to some embodiments, the CpG is a class A CpG. According to some embodiments, the CpG is a class B CpG. According to some embodiments, the CpG is a class C CpG. According to some embodiments, the CpG is a CpG 30-mer of the sequence 5' EEAACCGTATCGGCGATATCGGT-TEEEEEG 3' (SEQ ID NO: 102). As used herein with respect to CpG motifs, "E" is a G-phosphorothioate and this linkage refers to the 3' end of the nucleotide (i.e. the phosphorothioate bond substitutes a sulfur atom for a non-bridging oxygen in the nucleotide backbone). According to some embodiments, the CpG is a biotinylated 30-mer of the sequence 5'-biotin-EEAACCGTATCGGCGATATCGGT-TEEEEG-3' (SEQ ID NO: 102). According to some embodiments, the CpG is a CpG 30-mer of the sequence 5' EEAACCGTATGCGGCATATCGGTTEEEEEG 3' (SEQ ID NO: 103). According to some embodiments, the CpG is a biotinylated CpG 30-mer of the sequence 5'-biotin-EE-AACCGTATGCGGCATATCGGTTEEEEEG-3'(SEQ ID NO: 103).

According to some embodiments, the IgG may be engineered as a hybrid of one or more IgG subclasses. For example, according to some embodiments, the IgG comprises sequences from IgG1 and IgG3. According to some embodiments, the IgG may be engineered to have an affinity for biotin. According to some embodiments, the ENLST™ cells may be genetically engineered to comprise one or more proteins with a sequence identity of at least 60% to the protein of SEQ ID NO: 45. According to some embodiments, the ENLST™ cells may be genetically engineered to comprise one or more proteins with a sequence identity of at least 70% to the protein of SEQ ID NO: 45. According to some embodiments, the ENLST™ cells may be genetically engineered to comprise one or more proteins with a sequence identity of at least 80% to the protein of SEQ ID NO: 45. According to some embodiments, the ENLST™ cells may be genetically engineered to comprise one or more proteins with a sequence identity of at least 90% to the protein of SEQ ID NO: 45. According to some embodiments, the ENLST™ cells may be genetically engineered to comprise one or more proteins with a sequence identity of at least 95% to the protein of SEQ ID NO: 45. According to some embodiments, the ENLST™ cells may be genetically engineered to comprise one or more proteins with a sequence identity of at least 96% to the protein of SEQ ID NO: 45. According to some embodiments, the ENLST™ cells may be genetically engineered to comprise one or more proteins with a sequence identity of at least 97% to the protein of SEQ ID NO: 45. According to some embodiments, the ENLST™ cells may be genetically engineered to comprise one or more proteins with a sequence identity of at least 98% to the protein of SEQ ID NO: 45. According to some embodiments, the ENLST™ cells may be genetically engineered to comprise one or more proteins with a sequence identity of at least 99% to the protein of SEQ ID NO: 45.

According to some embodiments, the IgG comprises one or more mutations relative to wild type IgG that enhance affinity for Fc receptors for IgG (FcγR). According to some embodiments, an ENLST™ tumor cell line or tumor cell line variant may be genetically engineered to comprise one or more proteins of SEQ ID NO: 45 with one or more of mutations T323A and E325A. According to some embodiments, the ENLST™ cells may be genetically engineered to comprise one or more proteins with a sequence identity of at least 60% to the proteins of one or more of SEQ ID NO: 41, SEQ ID NO: 30, and SEQ ID NO: 43. According to some embodiments, the ENLST™ cells may be genetically engineered to comprise one or more proteins with a sequence identity of at least 70% to the proteins of one or more of SEQ ID NO: 41, SEQ ID NO: 30, and SEQ ID NO: 43. According to some embodiments, the ENLST™ cells may be genetically engineered to comprise one or more proteins with a sequence identity of at least 80% to the proteins of one or more of SEQ ID NO: 41, SEQ ID NO: 30, and SEQ ID NO: 43. According to some embodiments, the ENLST™ cells may be genetically engineered to comprise one or more proteins with a sequence identity of at least 90% to the proteins of one or more of SEQ ID NO: 41, SEQ ID NO: 30, and SEQ ID NO: 43. According to some embodiments, the ENLST™ cells may be genetically engineered to comprise one or more proteins with a sequence identity of at least 95% to the proteins of one or more of SEQ ID NO: 41, SEQ ID NO: 30, and SEQ ID NO: 43. According to some embodiments, the ENLST™ cells may be genetically engineered to comprise one or more proteins with a sequence identity of at least 96% to the proteins of one or more of SEQ ID NO: 41, SEQ ID NO: 30, and SEQ ID NO: 43. According to some embodiments, the ENLST™ cells may be genetically engineered to comprise one or more proteins with a sequence identity of at least 97% to the proteins of one or more of SEQ ID NO: 41, SEQ ID NO: 30, and SEQ ID NO: 43. According to some embodiments, the ENLST™ cells may be genetically engineered to comprise one or more proteins with a sequence identity of at least 98% to the proteins of one or more of SEQ ID NO: 41, SEQ ID NO: 30, and SEQ ID NO: 43. According to some embodiments, the ENLST™ cells may be genetically engineered to comprise one or more proteins with a sequence identity of at least 99% to the proteins of one or more of SEQ ID NO: 41, SEQ ID NO: 30, and SEQ ID NO: 43.

Chemokine Receptors

According to some embodiments, a subset of R immunomodulators may comprise one or more chemokine receptors. Chemokine receptors are defined as mediators that activate cellular responses upon binding of chemokines. Twenty-three subtypes of human chemokine receptors have been identified, all of which are members of the seven-transmembrane (7TM) domain superfamily of receptors. They can be divided into two main groups: the G protein-coupled chemotactic chemokine receptors (n=19) and the atypical chemokine receptors (n=4). Chemokine binding, membrane anchoring, and signaling domains for receptors from both groups come from a single polypeptide chain. Structural and biochemical evidence exists that these receptors form homo- and heterodimers.

According to some embodiments, the disclosure encompasses a chemokine receptor, including a full-length, fragment, homologue, variant or mutant of the chemokine receptor. A cytokine includes a protein that is effective to affect the biological function of another cell. A biological function affected by a cytokine can include, but is not limited to, cell growth, cell differentiation or cell death. For example, a chemokine receptor of the present disclosure is capable of stimulating an immune cell (e.g. T lymphocytes (e.g., CD8+ T cell), natural killer (NK) cells, dendritic cells (DCs) or B lymphocytes).

According to some embodiments, the chemokine receptor is selected from CXCR1, CXCR2, CXCR3, CXCR5, CXCR6, CXCR8, CCR8, CCR1, CCR2, CCR3, CCR5, CCR4, CCR6, CCR7, CCR9, CCR10, CXCR1, and CXCR3. According to some embodiments, the chemokine receptor is membrane bound.

According to some embodiments, the three or more discrete biologics are expressed by the ENLST™ tumor cell line or tumor cell line variant in either soluble or membrane bound form. According to some embodiments, expression and activity of the soluble and membrane bound forms can be confirmed, in vitro, by flow cytometry and mixed lymphocyte tumor assays, respectively. According to some embodiments, expression and activity of the soluble and membrane bound forms are confirmed, in vitro, by flow cytometry and by mixed lymphocyte tumor assays.

According to some aspects, the genetic material for transfecting or transducing the ENLST™ cell tumor cell line or tumor cell line variant is effective to stably introduce one or more immunomodulatory molecules into a tumor cell line or tumor cell line variant. According to some embodiments, the genetic material can be introduced by viral transduction techniques and isolated by positive selection for the genetically introduced immune modulator. For example, according to some embodiments, the positive selection of the genetically introduced immune modulator molecule comprises selection using antibodies.

CD28 Ligand (CD28L)

Ligation of the CD28 receptor on T cells provides a critical second signal alongside T cell receptor (TCR) ligation for naive T cell activation. Esenstein, J H et al, Immunity (2016) 44(5): 973-988). CD28 drives critical intracellular biochemical events including unique phosphorylation and transcriptional signaling, metabolism, and the production of key cytokines, chemokines, and survival signals that are essential for long-term expansion and differentiation of T cells (Id., citing Bluestone, J A et al., Immunity. (2006)24: 233-238; Bour-Jordan, H. et al., Immunol Rev. (2011) 241:180-205; Martin, P J et al., J Immunol. (1986) 136: 3282-3287; Weiss, A. et al., J Immunol. (1986) 137:819-825).

CD28 is the founding member of a subfamily of costimulatory molecules characterized by an extracellular variable immunoglobulin-like domain. Other members of the subfamily include ICOS, CTLA4, PD1, PD1H, and BTLA (Id., citing Chen, L. and Flies, D. B., Nat Rev Immunol. 2013; 13:227-242). CD28 is expressed constitutively on mouse T cells, whereas the expression of other family members ICOS and CTLA4 is induced by T cell receptor stimulation and in response to cytokines such as interleukin 2 (IL-2). CD28 is expressed on roughly 80% of human CD4+ T cells and 50% CD8+ T cells. The proportion of CD28 positive T cells in humans declines with age. Although CD28 expression has been identified on other cell lineages, including bone marrow stromal cells, plasma cells, neutrophils, and eosinophils, the functional importance of CD28 on these cells is not completely understood (Id., citing Gray Parkin, K., et al., J Immunol. (2002) 169:2292-2302; Rozanski, C H et al., J Exp Med. (2011) 208:1435-1446; Venuprasad, K., et al., Eur J Immunol. (2001) 31:1536-1543; Woerly, G. et al., Clin Exp Allergy. (2004) 34:1379-1387).

The CD28 ligands CD80 and CD86 diverge in their expression patterns, multimeric states, and functionality, adding another layer of complexity to the regulation of CD28 signaling. CD80 is present in predominantly dimeric form on the cell surface whereas CD86 is monomeric (Id., citing Bhatia, S. et al., Proc Natl Acad Sci USA. (2005) 102:15569-155742005). CD86 is expressed constitutively on antigen presenting cells (APCs) and is rapidly upregulated by innate stimuli of APCs (Id., citing Lenschow, D J et al., J Immunol. (1994) 153:1990-1997), whereas the other CD28 ligand, CD80, is upregulated at later time points (Id., citing Sharpe, A J and Freeman, G J, Nat Rev Immunol. (2002) 2:116-126). CD86 may therefore be more important in the initiation of immune responses. CD80 and CD86 are induced by different stimuli in different cell types and they are not interchangeable in function.

CD28 and CTLA4 have opposing effects on T cell stimulation. CD28 provides an activating signal and CTLA4 provides an inhibitory signal, which is now considered a prototypical immune checkpoint (Id., citing Krummel, M F and Allison, J P, J Exp Med. 1995; 182:459-465; Walunas, T L et al., Immunity. (1994) 1:405-413). ICOS, which also contributes to activation, binds to its ligand B7H2 (ICOSL), which also serves as a ligand for human CD28 and CTLA4 (Id., citing Chen, L. and Flies, D B, Nat Rev Immunol. (2013) 13:227-242; Yao, S. et al., Immunity (2011) 34:729-740). Thus, this family of receptors and ligands has considerable complexity in both binding pattern and biological effect. Overall, the opposing roles of CD28 and ICOS compared with CTLA4 allow this family of receptors and ligands to serve as a rheostat for the immune response through competing pro- and anti-inflammatory effects. Id.

It has been suggested that CD80 and CD86 may also act as signal transducing receptors themselves, since ligation with CTLA4Ig has been shown to regulate tryptophan metabolism in APCs (Id., citing Grohmann, U et al., Nat Immunol. (2002) 3:1097-1101). In addition to T cells, plasma cells also express CD28. CD28 signals may regulate antibody production by plasma cells or plasma cell survival although the precise role that CD28 plays in plasma cell biology is still unclear (Id., citing Njau, N M and Jacob, J., Adv Exp Med Biol. (2013) 785:67-75).

The CD28 gene is composed of four exons encoding a protein of 220 amino acids that is expressed on the cell surface as a glycosylated, disulfide-linked homodimer of 44 kDa. Members of the CD28 family share a number of common features. These receptors consist of paired V-set immunoglobulin superfamily (IgSF) domains attached to single transmembrane domains and cytoplasmic domains that contain critical signaling motifs (Id., citing Carreno, B M and Collins, M, Annu Rev Immunol. (2002) 20: 29-53). The CD28 and CTLA4 ligands, CD80 and CD86, consist of single V-set and Cl-set IgSF domains. The interaction of these costimulatory receptors with ligand is mediated through the MYPPPY motif (SEQ ID NO: 105) within the receptor V-set domains (Id., citing Evans, E J et al., Nat Immunol. (2005) 6:271-279; Metzler, W J et al., Nat Struct Biol. (1997) 4: 527-531).

CD28 engagement by its ligand initiates signal transduction events that are dependent on specific associations of proteins with the cytoplasmic tail of CD28. Despite having no intrinsic enzymatic activity, the 41 amino acid cytoplasmic tail of human CD28 contains highly conserved tyrosine-based signaling motifs that are phosphorylated in response to TCR or CD28 stimulation, and bind targets with SH2 domains in a phosphotyrosine-dependent manner. Proline rich sequences within the cytoplasmic tail also bind SH3-domain containing proteins. In particular, the membrane proximal YMNM motif (SEQ ID NO: 106), and the distal PYAP motif (SEQ ID NO: 107) have been shown to complex with several kinases and adaptor proteins, with some proteins being able to bind to either or both motifs via SH2 and/or SH3 domain interactions (Id., citing Boomer, J S and Green, J M, Cold Spring Harb Perspect Biol. (2010) 2: a002436). These motifs are important for IL-2 gene expression, which is mediated by the CD28-dependent activation of NFAT, AP-1, and NF-κB family transcription factors (Id., citing Fraser, J D et al., Science. (1991) 251:313-316; June, C H et al., Mol Cell Biol. (1987) 7: 4472-4481; Thompson, C B et al., Proc Natl Acad Sci USA. (1989) 86:1333-1337).

The membrane-proximal YXXM motif is shared between CD28, CTLA4, and ICOS, and is a consensus site for the p85 subunit of the lipid kinase phosphatidylinositol 3-kinase (PI3K) (Id., citing August, A. and Dupont, B. Int Immunol. (1994) 6:769-774; Pages, F., et al., Nature. (1994) 369: 327-329; Prasad, K V et al., Proc Natl Acad Sci USA. (1994) 91: 2834-2838; Rudd, C E and Schneider, H., Nat Rev Immunol. (2003) 3: 544-556). In addition to the +3 methionine of the CD28 sequence, YMNM (SEQ ID NO: 106), which confers PI3K specificity, the +2 asparagine confers specificity for the adaptor proteins GRB2 and GADS on CD28 (Id., citing Cai, Y C et al., Immunity. (1995) 3: 417-426; Kim, H H et al., J Biol Chem. (1998) 273: 296-301; Okkenhaug, K. and Rottapel, R., 1998; Okkenhaug et al., J Biol Chem. (1998) 273: 21194-21202; Raab, M et al., Proc Natl Acad Sci USA. (1995) 92: 8891-8895; Stein, P H et al., Mol Cell Biol. (1994) 14: 3392-3402). Both ICOS and CTLA4 can bind to PI3K but lack the ability to bind GRB2, which may account for some of the functional and signaling differences between these costimulatory receptors (Id., citing Rudd, C E and Schneider, H Nat Rev Immunol. (2003) 3: 544-556). The importance of the YMNM motif (SEQ ID NO: 106) in mediating proliferation and IL-2 secretion has been controversial, Signaling events downstream of the C-terminal PYAP motif (SEQ ID NO: 107) are thought to include the phosphorylation and activation of the kinases PDK1 and PKCθ, and the subsequent inactivation of GSK3β, ultimately leading to enhanced transcription of NFAT-dependent genes, including IL-2. SH3-mediated binding and activation of the Src kinase Lck (Id., citing Holdorf, A D et al., J Exp Med. (1999) 190: 375-384; King, P D et al., J Immunol. (1997) 158: 580-590) is proposed as a potential regulator of this pathway. The adaptor proteins, GRB2 and GADS can bind to CD28 either through their SH3 domains at the distal PYAP motif (SEQ ID NO: 107) or via their SH2 domains to the membrane proximal YMNM motif (SEQ ID NO: 106). However, it is the C-terminal PYAP motif (SEQ ID NO: 107) that is thought to play the greater role in NF-κB activation, suggesting that other signaling molecules important for NF-κB activation bind to the C-terminal PYAP motif (SEQ ID NO: 107), such as Lck, as discussed above ((Id., citing Holdorf, A D et al., J Exp Med. (1999) 190: 375-384; Watanabe, R. et al., J Immunol. (2006) 177:1085-1091).

Although CD28 ligation is critical in promoting proliferation and effector function of conventional T cells, it also promotes the anti-inflammatory function of regulatory T (Treg) cells. Thus, CD28 serves both pro- and anti-inflammatory roles depending on the cell type and context in which it is expressed. CD28 signals are critical for allowing effector T cells to overcome Treg cell-mediated suppression to immunization (Id., citing Lyddane, C et al., J Immunol. (2006) 176: 3306-3310), but CD28 in another context prevents spontaneous autoimmunity by promoting Treg function (Id., citing Salomon B. et al., Immunity. 2000; 12:431-440).

CD28 supports T cell homeostasis and function in a variety of ways. CD28 signals support the expression of miR17-92 family members, which are critical for maximal IL-10 production by Treg cells (de Kouchkovsky, D et al., J Immunol. (2013) 191: 1594-1605). Thymocytes require simultaneous TCR and CD28 signals to upregulate Foxp3 and differentiate into Treg cells. CD28 is also necessary for the production of peripheral induced Treg cells. CD4+ CD25- T cells required CD28 ligation to differentiate into functional Foxp3+ Treg cells when activated with TGF-β.

According to some embodiments of the disclosed invention, the ENLST™ cells may be engineered to express a membrane bound form of CD80 on the membrane of the ENLST™ of SEQ ID NO: 110. According to some embodiments, the ENLST™ tumor cell line or tumor cell line variant may comprise one or more proteins with a sequence identity of at least 60% to the protein of SEQ ID NO: 110. According to some embodiments, the ENLST™ tumor cell line or tumor cell line variant may comprise one or more proteins with a sequence identity of at least 70% to the protein of SEQ ID NO: 110. According to some embodiments, the ENLST™ tumor cell line or tumor cell line variant may comprise one or more proteins with a sequence identity of at least 80% to the protein of SEQ ID NO: 110. According to some embodiments, the ENLST™ tumor cell line or tumor cell line variant may comprise one or more proteins with a sequence identity of at least 90% to the protein of SEQ ID NO: 110. According to some embodiments, the ENLST™ tumor cell line or tumor cell line variant may comprise one or more proteins with a sequence identity of at least 95% to the protein of SEQ ID NO: 110. According to some embodiments, the ENLST™ tumor cell line or tumor cell line variant may comprise one or more proteins with a sequence identity of at least 96% to the protein of SEQ ID NO: 110. According to some embodiments, the ENLST™ tumor cell line or tumor cell line variant may comprise one or more proteins with a sequence identity of at least 97% to the protein of SEQ ID NO: 110. According to some embodiments, the ENLST™ tumor cell line or tumor cell line variant may comprise one or more proteins with a sequence identity of at least 98% to the protein of SEQ ID NO:110. According to some embodiments, the ENLST™ tumor cell line or tumor cell line variant may comprise one or more proteins with a sequence identity of at least 99% to the protein of SEQ ID NO: 110.

According to some embodiments of the disclosed invention, the ENLST™ cells may be engineered to express a membrane bound form of CD86 on the membrane of the ENLST™ of SEQ ID NO: 111. According to some embodiments, the ENLST™ tumor cell line or tumor cell line variant may comprise one or more proteins with a sequence identity of at least 60% to the protein of SEQ ID NO: 111. According to some embodiments, the ENLST™ tumor cell line or tumor cell line variant may comprise one or more proteins with a sequence identity of at least 70% to the protein of SEQ ID NO: 111. According to some embodiments, the ENLST™ tumor cell line or tumor cell line variant may comprise one or more proteins with a sequence identity of at least 80% to the protein of SEQ ID NO: 111. According to some embodiments, the ENLST™ tumor cell line or tumor cell line variant may comprise one or more proteins with a sequence identity of at least 90% to the protein of SEQ ID NO: 111. According to some embodiments, the ENLST™ tumor cell line or tumor cell line variant may comprise one or more proteins with a sequence identity of at least 95% to the protein of SEQ ID NO: 111. According to some embodiments, the ENLST™ tumor cell line or tumor cell line variant may comprise one or more proteins with a sequence identity of at least 96% to the protein of SEQ ID NO: 111. According to some embodiments, the ENLST™ tumor cell line or tumor cell line variant may comprise one or more proteins with a sequence identity of at least 97% to the protein of SEQ ID NO: 111. According to some embodiments, the ENLST™ tumor cell line or tumor cell line variant may comprise one or more proteins with a sequence identity of at least 98% to the protein of SEQ ID NO:111. According to some embodiments, the ENLST™ tumor cell line or tumor cell line variant may comprise one or more proteins with a sequence identity of at least 99% to the protein of SEQ ID NO: 111.

(c) contacting the population of MNCs of step 1(i) with the ENLST™ cells of step 1(ii) in vitro to induce an immune response comprising an activated population of MNCs (in vitro immune activation);

According to some embodiments, the contacting of the ENLST™ cells population and the MNC population is effective to induce an immune response comprising an activated population of MNCs comprising one or more serial killer cell subpopulations. According to some embodiments, the one or more serial killer cell subpopulations include, without limitation, one or more of an NK cell subpopulation, an NKT subpopulation, a CIK subpopulation, a GDT subpopulation, a MAIT cell subpopulation, a CD8+ CTL cell population, or a CD4+ CTL cell subpopulation. According to some embodiments, the activated serial killer cell population comprises an activated NK cell population. According to some embodiments, the activated serial killer cell population comprises an activated NKT population. According to some embodiments, the activated serial killer cell population comprises an activated NK cell population. According to some embodiments, the activated serial killer cell population comprises an activated CIK population. According to some embodiments, the activated serial killer cell population comprises an activated GDT population. According to some embodiments, the activated serial killer cell population comprises an activated MAIT cell population. According to some embodiments, the activated serial killer cell population comprises an activated, CD8+ CTL population. According to some embodiments, the activated serial killer cell population comprises an activated, CD4+ CTL population.

According to some embodiments, the NK cell subpopulation comprises cytotoxic effector-like NK cells. According to some embodiments, the NKT cell subpopulation comprises cytotoxic effector $T_{eff}$ cells. According to some embodiments, the CIK cell population comprises cytotoxic $T_{eff}$ cells. According to some embodiments, the GDT cell population comprises cytotoxic effector $T_{eff}$ cells. According to some embodiments, the MAIT cell population comprises cytotoxic $T_{eff}$ cells. According to some embodiments, the CD8+ CTL cell subpopulation comprises cytotoxic $T_{eff}$ cells. According to some embodiments, the CD4+ CTL cell subpopulation comprises cytotoxic $T_{eff}$ cells.

According to some embodiments, the term "stimulate" with reference to the MNC population" refers to one or more of expansion of the activated MNC population," activation of one or more subpopulations of the activated MNC population, or an increase in cytoxic activity of one or more subpopulations of the active MNC population. According to some embodiments, "stimulating the serial killer cell" refers to a combination of expansion, activation and/or increased cytoxic activity of one or more subpopulations of the activated MNC population. According to some embodiments, the activated MNCs comprise one or more activated serial killer cell population(s). According to some embodiments, the activated serial killer cell population(s) may comprise one or more of an activated NK cell population, an activated NKT population, an activated CIK population; an activated GDT population; an activated MAIT cell population; an activated, CD8+ CTL population; and an activated CD4+ CTL population.

Serial Killer Cell Population(s)
Inducement and Activation of Serial Killer Cell Population(s)

According to some embodiments, the population of ENLST™ cells is effective to activate subpopulations of the population of MNCs in a mixed lymphocyte tumor cell reaction (MLTR). The exemplary method for activating the MNC population comprises incubating the MNC population comprising contacting the population of MNCs with the ENLST™ cells population in vitro for several days to allow the ENLST™ cells to elicit an immune response from the mixed lymphocytes. According to some embodiments, the immune response against the allogeneic ENLST™ cells comprises a heteroclitic cross reaction between a peptide native to the ENLST™ tumor cell line or tumor cell line variant and a peptide native to the tumor cells of a patient. According to some embodiments, the heteroclitic cross-reaction enhances immunogenicity via enhanced binding of a T cell receptor with a tumor cell peptide-MHC complex that normally provides a non-immunogenic surface.

Mixed Lymphocyte Tumor Cell Reactivity

According to some embodiments, the genetically engineered immunomodulators may be assessed for their immunogenic potential by a mixed lymphocyte tumor cell reaction (MLTR). The MLTR assay comprises incubating mixed lymphocytes with tumor cell line or tumor cell line variants (or controls) for several days to allow the tumor cells of the ENLST™ cells population ENLST™ cells population(s) to elicit an immune response from the mixed lymphocytes in vitro. This method is a rapid in vitro method to assess mixed lymphocyte responses (such as cellular proliferation of lymphocytes, cellular subset differentiation of lymphocytes, cytokine release profile of lymphocytes, and tumor cell death) to tumor cells or lysates. This approach can enable comprehensive monitoring of cellular, humoral, or both, immunity responses to phenotypically modified transfected tumor cells using human peripheral blood mononuclear cells. The MLTR also can provide an alternative to murine tumor survival studies, and can result in selection of optimal tumor cell line or tumor cell line variants for anti-tumor response. A similar assay has been described by Hunter T B et al., (2007) Scandanavian J. Immunology 65, 479-486, which is incorporated herein by reference in its entirety.

According to some embodiments, the ENLST™ cells population of tumor cell line or tumor cell line variants may be tested for immunogenic potential by contacting transfected tumor cells with mixed lymphocytes from MNCs, for example, peripheral blood mononuclear cells, followed by measuring cellular proliferation, cellular subset differentiation, cytokine release profile, and tumor cell lysate.

According to some embodiments, the MNCs containing mixed lymphocyte populations can be co-cultured with the genetically engineered ENLST™ cells for up to 28 days.

An exemplary protocol for co-culture of the MNC population and the genetically engineered ENLST™ cell population comprises combining the MNCs with ENLST™ cells in Lonza's X-Vivo medium+antibiotics+glutaMax (Thermo Fisher Scientific) in a Thermo Fisher Scientific T flask of defined geometry (volume, surface area, and cell number) until cell concentration reaches 100-300 million cells/liter. According to some embodiments, nicotinamide 5 mM may be added to the culture medium. According to some embodiments, 2.5% by volume human plasma autologous to the mononuclear cells may be added to the culture medium. The culture is rocked at a 6° angle at 6 tilts per minute for up to 28 days at 37° C. and 5% $CO_2$.

According to some embodiments, the co-culturing of the MNC populations with the genetically engineered ENLST™ cells is effective to activate one or more serial killer cell populations. According to some embodiments, the serial killer cell populations comprise one or more of an NK cell population, an NKT cell population, a CIK cell population, a GDT cell population, a MAIT cell population, a CD8+ CTL cell population, or a CD4+ CTL cell population. According to some embodiments, the co-culturing of the MNC population with the genetically engineered ENLST™ cells is effective to activate one or more populations of antigen presenting cells. According to some embodiments, the antigen presenting cell population comprises a macrophage cell population, a dendritic cell population, or both. According to some embodiments, the serial killer activity of the activated serial killer cell populations is specific to cancer cancer antigens of the genetically engineered ENLST™ cells, without affecting normal cells. According to some embodiments, the serial killer activity of the serial killer cell population(s) is cancer-generalized, i.e., the serial killer cell population may kill cancer cells regardless of the cancer type, and yet not affect normal cells.

According to some embodiments, subpopulations of the activated MNCs effective to kill tumor cells may be identified, isolated/sorted, e.g., by flow cytometry, and then each subpopulation expanded to form an expanded, enriched isolated subpopulations of serial killer cells.

Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus.

Flow cytometry utilizes a beam of light (usually laser light) of a single wavelength that is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals found in the particle or attached to the particle may be excited into emitting light at a lower frequency than the light source. This combination of scattered and fluorescent light is picked up by the detectors, and by analyzing fluctuations in brightness at each detector (usually one for each fluorescent emission peak) it then is possible to derive various types of information about the physical and chemical structure of each individual particle. FSC correlates with the cell volume and SSC depends on the inner complexity of the particle (i.e. shape of the nucleus, the amount and type of cytoplasmic granules or the membrane roughness).

The use of fluorescent molecules, such as fluorophore-labeled antibodies, in flow cytometry is a common way to study cellular characteristics. Within these types of experiments, a labeled antibody is added to the cell sample. The antibody then binds to a specific molecule on the cell surface or inside the cell. Finally, when the laser light of the appropriate wavelength strikes the fluorophore, a fluorescent signal is emitted and detected by the flow cytometer.

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. It provides fast, objective and quantitative recording of fluorescent signals from individual cells as well as physical separation of cells of particular interest.

Utilizing FACS, a cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell being in a droplet. Before the stream breaks into droplets the flow passes through a fluorescence measuring station where the fluorescent character of interest of each cell is measured. An electrical charging ring or plane is placed just at the point where the stream breaks into droplets. A charge is placed on the ring based on the prior light scatter and fluorescence intensity measurements, and the opposite charge is trapped on the droplet as it breaks from the stream. The charged droplets then fall through an electrostatic deflection system that diverts droplets into containers based upon their charge. In some systems the charge is applied directly to the stream while a nearby plane or ring is held at ground potential and the droplet breaking off retains charge of the same sign as the stream. The stream is then is returned to neutral after the droplet breaks off.

Mass cytometry, or CyTOF (Fluidigm), is a variation of flow cytometry in which antibodies are labeled with heavy metal ion tags rather than fluorochromes. Readout is by time-of-flight mass spectrometry. viSNE plots individual cells in a visual similar to a scatter plot, while using all pairwise distances in high dimension to determine each cell's location in the plot According to some embodiments, activated NK and non-NK cells can be sorted and isolated based on expression of the markers CD56, CD3, CD8, and CD4. According to some embodiments, exemplary phenotypes of the activated MNC cell populations can include: CD4+, CD8+, CD56+CD3+, CD56+CD3−, TCRγδ+, and TCRVα7.2+.

According to some embodiments, the activated serial killer cells in the activated mixed mononuclear cell population can be identified by one or more of cellular proliferation of the activated lymphocytes, cellular subset differentiation of the activated lymphocytes, cytokine release profile of the lymphocytes, and tumor cell death.

Cytotoxicity Markers

According to some embodiments, the MNC population and ENLST population are cocultured for up to 28 days. At one or more times during the culturing, parameters indicative of cellular proliferation of the activated lymphocytes, cellular subset differentiation of the activated lymphocytes, cytokine release profile of the lymphocytes, and tumor cell death can be measured.

The defining functional feature of NK cells remains their intrinsic ability to conduct "natural killing" of cellular targets without prior sensitization. According to some embodiments, the ENLST™ cells population ENLST™ cells population(s) described herein are effective to activate and expand NK cells, such that the NK cells that are activated and expanded exhibit higher degranulation activity compared to control NK cells. According to some embodiments, cytotoxic degranulation activity can be estimated by determining expression of a cell marker that correlates with degranulation activity. For example, surface expression of CD107a correlates closely with degranulation and release of cytotoxic granules. CD107a expression can be measured, for example, by flow cytometry. (See, e.g., BD FastImmune™ CD107a (H4A3, Becton Dickinson & Co.; Alter G, Malenfant J M, Altfeld M. CD107a as a functional marker for the identification of natural killer cell activity. J Immunol Methods. (2004) 294: 15-22, the entire contents of which are incorporated herein by reference).

According to some embodiments, the expanded and activated NK cells, obtained by contact with the ENLST™ cells population ENLST™ cells population(s) of the described invention, comprise at least about 50%, about 60%, about 70%, about 80% or about 90% increased cytotoxicity, e.g. as measured by degranulation activity, compared to non expanded NK cells. According to some embodiments, the expanded and activated NK cells comprise at least about 100% increased cytotoxicity compared to non expanded NK cells. According to some embodiments, the expanded and activated NK cells comprise at least about 200% increased cytotoxicity compared to non expanded NK cells. According to some embodiments, the expanded and activated NK cells comprise at least about 300% increased cytotoxicity compared to non-ex vivo expanded NK cells. According to some embodiments, the expanded and activated NK cells comprise at least about 400% increased cytotoxicity compared to non-ex vivo expanded NK cells.

According to some embodiments the expanded and activated NK cells, following contact with the ENLST™ cells population ENLST™ cells population(s) of the described invention, comprise at least about 50%, about 60%, about 70%, about 80% or about 90% increased degranulation activity compared to non expanded NK cells. According to some embodiments the expanded and activated NK cells comprise at least about 100% increased degranulation activity compared to non expanded NK cells. According to some embodiments, the expanded and activated NK cells comprise at least about 200% increased degranulation activity compared to non expanded NK cells. According to some embodiments, the expanded and activated NK cells comprise at least about 300% increased degranulation activity compared to non-ex vivo expanded NK cells. According to some embodiments, the expanded and activated NK cells comprise at least about 400% increased degranulation activity compared to non-ex vivo expanded NK cells.

Tumor Cell Toxicity

According to some embodiments, tumor cell toxicity can be used to measure immune activation of MNCs comprising mixed lymphocytes comprising activated serial killer cells. For example, according to some embodiments, a lactic dehydrogenase (LDH)-cytotoxicity colorimetric assay kit (BioVision Cat. # K311-400) can be used to measure tumor cell cytotoxicity. LDH, a soluble cytosolic enzyme present in most eukaryotic cells, is released into culture medium upon cell death due to damage of the plasma membrane. The increase of LDH activity in the culture supernatant is proportional to the number of lysed cells. Briefly, 100 µl of media from each of the control group (comprising untransfected MSCs), the experimental group (comprising immune modulator transfected MSCs), and media alone is pipetted into the wells of a 96 well plate. 100 µl of the LDH reaction mixture, comprising dye solution and catalyst solution, can then be added to the wells of the 96 well plate and incubated for 30 minutes at room temperature. Then light absorbance at 490-500 nm can be measured using a microtiter plate reader.

Phenotyptic Markers

According to some embodiments, serial killer cell types can be identified by their phenotypic markers. Exemplary phenotypic markers of NKs, LAKs, CIKs, NKTs, GDTs, MAIT cells, CD8+ CTLs, and CD4+ CDLs are shown in Table 8.

TABLE 8

Phenotypic Markers

| Cell Type | Marker | Secreted |
|---|---|---|
| NK cells | Table 2, CD3, CD11b+/−, CD16, CD16 (FCγRIIIA), CD27+/−, CD56+/−, CD62L, CD69, CD94+/−, CD57+/−, CD94, CD96, CD96 (Tactile), CD100, CD100 (SEMA4D), CD122, CD158 (family), CD160, CD160(BY55), CD161, CD226, CD244, CD244 (2B4, SLAMF4), CD266, CD314 (NKG2D), CD319, CD335 (NKp46), CD336 (NKp44), CD337 (NKp30), CLEC5C, CRACC, CS1, CRTAM, CEACAM1, DNAM1 (CD226), DAP12, DAP12 (TYROβP), E4BP4, Eomes, DAP10(HCST), FCRγ, GATA-3, HCST, Id2, IL-21R, IL-18R, IL-12R, IL-15R, INFAR, ITAM, ITSM, KLRG1, KLRF1, KIR2DS1, KIR2DS2, KIR2DS3, KIR2DS4, KIR2DS5, KIR3DS1, NKTB-A (SLAMF6), NCR1, NCR3, NCR2, NKG2, NKG2D, NKG2C/E, NKp64, NKp30, NKp44, NKp80, NKp80 (KLRFI, CLEC5C), NK1.1+/−, PSGL1, Runx1, SEMA4D, SLAMF4, SLAMF6, SLAMF7, SLAMF7 (CRACC, CS1, CD139), Tactile, TIGIT, T-bet, TOX, YxxM, 2B4 | Granulysin, Granzyme A, Granzyme B, Granzyme K, Granzyme M, IL-2, IL-10, IL-12, IL-15α, IL-15β, IL-18, IL-21, IL-22, Type I IFNs, IFN-γ, TNF, Perforin, |
| LAKs | Table 2, Table 3 NKTs, CD3, CD8, CD45, CD45R, CD57, CD244, | IL-2, IL-4, IL-7, IL-10, IL-12, IL-13, IL-15, IL-17/IL-17A, IL-17E/IL-25, IL-21, IL-22, TGFβ, TNFα, IFNγ, CXCL16, GM-CSF, |
| CIKs | Table 2, Table 3 NKTs, CD3+, CD8+/−, CD16, CD25, CD27+/−, CD28+/−, CD56+/−, CD62L, CD40L, KLRD1, PD-1, FASLG, TNSFSF10, CTLA4, NKG2D, DNAM-1, NKG2D, NKp30, | IL-2, IL-4, IL-7, IL-10, IL-12, IL-13, IL-15, IL-17/IL-17A, IL-17E/IL-25, IL-21, IL-22, TGFβ, TNFα, IFNγ, CXCL16, GM-CSF, |
| NKTs | Table 2, Table 3 NKTs, CD3, CD4$^{+/-}$, CD8$^{+/-}$, CD 16, CD19, CD24, CD28, CD44, CD48/SLAMF2, CD56, CD57, CD69, CD84/SLAMF5, CD94, CD160, CD161, CD161/NK1.1, Common Γ Chain/IL-2R Γ, FasL/TNFSF6, CD335$^{+/-}$, TCR Vα24, TCR Vβ11, NKG2D, CD94/NKG2A, CD40L, ICOS, PD-1, PLZF, Id2, Fc γ RIIIA (CD16a), Fc γ RIIIb (CD16B), Fc γ RIII (CD16), Granulysin, Granzyme B, IL-1R, IL-2R beta, IL-15R alpha, IL-17RB, IL-21, IL21R, IL-23R, IL7R alpha/CD127, Integrin alpha 2/CD49b, Integrin alpha E/CD103, KIR2DL1/CD158a, KIR2DL1/KIR2DS5, KIR2DL3/CD158b2, KIR2DL4/CD158d, KIR2DS1/CD158i, KIR2DS5/CD158g, KIR3DL1, KIR3DL2/CD158k, KIR3DL3/CD158a, | IL-2, IL-4, IL-7, IL-10, IL-12, IL-13, IL-15, IL-17/IL-17A, IL-17E/IL-25, IL-21, IL-22, TGFβ, TNFα, IFNγ, CXCL16, GM-CSF, |

TABLE 8-continued

Phenotypic Markers

| Cell Type | Marker | Secreted |
|---|---|---|
| | KIR3DS1/CD158e2, Klre-1, NCAM-1/CD57, NKG2A/NKG2B isoform 2, NKG2C/CD159c, NKG2D/CD314, NKG2H, NKG2E, NKp30/NCR3, NKp44/NCR2, NKp46(NCR1), NKp80/KLRF-1, NTB-A/SLAMF6, PD-1, Peroxiredoxi 1, S1P1/EDG-1, L-Selectin/CD62L, SLAM/CD150, TRAIL/TNFSF10, VDR/NR1I1 | |
| GDTs | CD3+, CD4+/−, CD5, CD8+/−, CD16, CD27, CD27/TNFRSF7, CD27 Ligand/TNFSF7, CD28, CD40/TNFRF5, CD40 Ligand/TNFRSF5, CD45RA, CD56, CD57, CD62L, CD69, CD70, CD83, CD107a, CD161, CD161/NK1.1CD314 (NKG2D), TCRγ/δ+, TCRVδ1, TCRVδ2, TCRVδ3, CXCR4, Dectin-1/CLEC7A, Fas/TNFRSF6, CD95, Fas Ligand/TNFsF6, FC γ RIII (CD16), FC γ RIIIA/CD16a, Fc γ RIIIB/CD16b, ICOS, IL-18 R alpha/IL-1 R5, IL-23R, NKG2D/CD314, NKG2E, Occludin, TCR γ/delta, TLR2, TRAIL/TNFSF10 | GM-CSF, Granulysin, Granzyme A, Granzyme B, IFNγ, IL-2, IL-4, IL-5, IL-6, IL-6/IL-6R alpha complex, IL-10, IL-12, IL-12/IL-23 p40, IL-13, IL-17/Il-17A, IL-22, Perforin, TNFα, LAP (TGF-beta 1), TFG-beta, TNF-alpha, CCL2/JE/MCP-1, CXCL13, BLC/BCA-1, beta-Defensin 2, beta-Defensin 3, alpha-Defensin 1, EGF, KGF-FGF-7, FGF-10, IGF-I/IGF-1 |
| MAIT cells | CD4, +/−, CD8+/−, CD25, CD27CD45RO, CD56+/−, CD62L+/−, CD69, CD95, CD103, CD161, CCR2, CCR5, CCR6, CXCR6, CCR9, a4B7, Vα7.2 TCR, Vβ2/13 TCR, DN, IL-7Ra, IL-12R, IL-18Ra, IL-23R, NKR-P1A, | IFNγ, IL-2, TNFα, |
| CD8+ CTL | CD2, CD3+, CD5, CD7, CD8+, CD25+ (IL2RA) CD27+/−, CD 28+/−, CD30, CD44+, CD45RA+/−, CD45RO+/−, CD57+, CD62L+/− (L-Selectin), CD69+, CD95+ (FasR), CD107a+ (LAMP-1), CD122, CD127+/− (IL7Rα), CD134+ (OX40), CD137+ (4-1BB), CD178+(FasL), CD197+/− (CCR7), CD223 (LAG-3), CD272 (BTLA), CD278 (ICOS), CD279(PD-1), CD366 (TIM3), Granzyme B+, Perforin+, Ki-67+, KLRG1+, KRG1, NKG2D, | Granzyme A, Granzyme B, Granzyme K, Perforin, IFNγ, IL-2, TNFα, CCL3 (MIP-1α), CCL4 (MIP-1β), CCL5 (RANTES) |
| CD4+ CTL cells | CD2, CD3+, CD4+, CD5, CD7, CD25+ (IL2RA), CD27, CD28, CD44+, CD45RA+/−, CD45RO+/− CD62L, CD69+, CD94+, CD95+ (FasR), CD119 (IFNγR1), CD127, CD134+ (OX40), CD137+ (4-1BB), CD152 (CTLA-4), CD154(CD40L), CD183+ (CXCR3), CD186(CXCR6), CD191 (CCR1), CD195 (CCR5), CD212 (IL-12Rβ1), CD218a (IL-18Rα), CD254 (RANKL), CD272 (BTLA), CD279(PD-1), CD366 (TIM3), Ki-67+, KLRG1+, NKG2D, | IL-2, IFNγ, TNFα, TNFβ (LTα), Perforin, |
| DCs | Table 1, CD1b, CD1c (BCDA-1), CD11b, CD11c, CD13, CD14, CD33, CD 40, CD49d, CD80, CD83, CD85g (ILT7), CD86, CD123, CD141 (BCDA-3), CD172a (SIRPa), CD197 (CCR7), CD205 (DEC-205), CD207 (Langerin), CD206, CD273, CD282 (TLR2), CD283 (TLR3), CD284 (TLR4), CD303 (BCDA-2), CD304 (BCDA-4), CD369 (Dectin-1), CD370 (CLEC9A), MHCII | IDO, IL-1β, IL-6, IL-8, IL-12, IL-15, IL-23, INFα, INFβ |
| MΦ | Table 1, CD11b, CD14, CD15, CD16, CD16/CD32, CD32, CD33, CD40, CD63, CD64, CD68, CD80, CD85, CD86, CD105, CD115, CD163, CD169, CD172a (SIRPα), CD192 (CCR2), CD195 (CCR5), CD206 (MMR), CD209 (DC-SIGN), CD273 (PD-L2), CD282 (TLR2), CD284 (TLR4), CD354 (Trem-1), CD369 (Dectin-1), CXCL9, CXCL10, CXCL11, GPNMB, MIP-2α (CXCL2), FcεR1, VSIG4, Mer (MerTK), MHCII, Axl, HLA-DR, NOS2 | IDO, IL-10, TGFβ, IFNγ, TNFα, IL-1α, IL-1β, IL6, IL-12, IL-23, |

For example, human NK cells are phenotypically characterized by the expression of CD56 and the absence of CD3 and can be further subdivided into a CD56$^{bright}$ population and a CD56$^{dim}$ population. The CD56$^{bright}$ population produces immunoregulatory cytokines, including interferon-γ (IFNγ), tumor necrosis factor-beta (TNF-B), tumor necrosis factor-α (TNF-α), granulocyte macrophage-colony stimulating factor (GMCSF), IL-10, and IL-13 (4). The CD56$^{dim}$ subset is the terminally differentiated successor of the CD56$^{bright}$ population and is primarily responsible for exerting cytolytic functions. However, CD56$^{dim}$ NK cells can produce cytokines, specifically IFNγ, after cell triggering via NKp46 of NKp30 activating receptors or after stimulation with combinations of IL-2, IL-12, and IL-15.

According to some embodiments, various markers of NK cell maturation and/or activation can be detected using, e.g. flow cytometric methods. For example, a classical marker of NK cells is the activating receptor FcγRIII, also called CD16.

The activation of NK cells leads to the release of cytotoxic granules containing perforin and various granzymes and to cytokine production, most prominently interferon-γ (IFNγ). In addition, the expression at the cell surface of death-inducing ligands belonging to the tumor necrosis factor (TNF) family, such as Fas ligand (FasL) and TNF-related apoptosis-inducing ligand (TRAIL), also drives the activation of the caspase enzymatic cascade through the binding to the death receptors (DRs), namely, Fas, DR4 (TRAIL-RI), and DR5 (TRAIL-RII), on target cells.

According to some embodiments, the induction of an immune response by the allogeneic ENLST™ cells as described herein upregulates at least one NK cell activating receptor (e.g., an activating receptor listed in Table 3) by at least about 20%, about 30%, about 40%, about 50%, about 60%, about 70%, about 80%, about 90%, about 100%, about 150%, about 200%, about 300% or more. According to some embodiments, the induction of an immune response by the allogeneic ENLST™ cells described herein upregulates at least one NK cell activating receptor by at least about 75%, i.e., at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 100%, at least about 110%, at least about 120%, at least about 130%, at least about 140%, at least about 150%, at least about 160%, at least about 170%, at least about 180%, at least about 190%, at least about 200%. According to some embodiments, the induction of an immune response by the allogeneic ENLST™ cells described herein upregulate at least one NK cell activating receptor by at least about 100%. According to some embodiments, the induction of an immune response by the allogeneic ENLST™ cells described herein upregulate at least one NK cell activating receptor by at least about 200%.

According to another embodiment, the induction of an immune response by the allogeneic ENLST™ cells as described herein downregulates expression of at least one NK cell receptor, such as an inhibitory receptor or a chemokine receptor (e.g. CCR7). For example, certain NK cell inhibitory receptors are called KIRs (Killing Inhibitory Receptors or CD158). Non-limiting examples of inhibitory receptors are inhibitory killer immunoglobulin-like receptors (KIRs), GL183, KIR2DL 1, Lir-1, NKB1, and NKG2A.

According to some embodiments, the induction of an immune response by the allogeneic ENLST™ cells as described herein downregulates at least one NK cell inhibitory receptor (e.g., an inhibitory receptor listed in Table 4) by at least about 20%, at least about 30%, at least about 40%, at least about 50%, at least about 60%, at least about 70%, at least about 80%, at least about 90%, at least about 100%, at least about 110%, 120%, at least about 130%, about 140%, at least about 150%, at least about 160%, at least about 170%, at least about 180%, at least about 190%, at least about 200%, at least about 220%, at least about 230%, at least about 240%, at least about 250%, at least about 260%, at least about 270%, at least about 280%, at least about 290%, at least about 300% or more. According to some embodiments, the induction of an immune response by the allogeneic ENLST™ cells described herein downregulates at least one NK cell inhibitory receptor by at least about 75%. According to some embodiments, the induction of an immune response by the allogeneic ENLST™ cells described herein downregulates at least one NK cell inhibitory receptor by at least about 100%. According to some embodiments, the induction of an immune response by the allogeneic ENLST™ cells described herein downregulates at least one NK cell inhibitory receptor by at least about 200%.

The change in receptor expression can be calculated by mean fluorescence intensity (MFI) ratios:

$$MFI_{dayX}/MFI_{day0}$$

where x is the number of days of expansion of the NK cell.

When the MFI for day X samples is higher than for day 0, the MFI ratio will be higher than 1, which indicates the relative extent of upregulation in that receptor. Thus, an MFI ratio of e.g. 1.5 would mean a 50% upregulation of a specific receptor. The calculation of MFI ratios is well known to persons skilled in the art.

Exemplary NK cell activating or inhibitory receptors are shown below in Table 9.

TABLE 9

| Receptor Family | Species | Activating/Inhibitory |
|---|---|---|
| CD16 | H | Act |
| KIR | H | Act/Inhib |
| KIR2DL1 | | Inhib |
| KIR2DL2/3 | | Inhib |
| KIR2DL4 | | Act |
| KIR2DL5 | | Inhib |
| KIR3DL1 | | Inhib |
| KIR3DL2 | | Inhib |
| KIR2DS1 | | Act |
| KIR2DS2 | | Act |
| KIR2DS3 | | Act |
| KIR2DS4 | | Act |
| KIR2DS5 | | Act |
| KIR3DS1 | | Act |
| CD94-NKG2 | H/M | Act/Inhib |
| NKG2A | | Inhib |
| NKG2C | | Act |
| NKG2E | | Act |
| NKG2D | H/M | Act |
| NCRs | H/M | Act |
| NKp30 | | Act |
| NKp44 | | Act |
| NKp46 | | Act |
| NKp80 | | Act |
| LILR | H/M | Inhib |
| 2B4 | H/M | Act/Inhib |
| KLRG1 | H/M | Inhib |
| DNAM-1 | H/M | Act |

Abbreviations in Table 4: ACT, activation; BAT-3, HLA-B-associated transcript 3; H, human; HA, hemagglutinin; HLA, human leukocyte antigen; INHIB, inhibitory; KIR, killer immunoglobulin-like receptor; KLRG1, killer cell lectin-like receptor G1; LILR, leukocyte immunoglobulin-like receptor; M, mouse; MHC, major histocompatibility complex; MULT-1, mouse UL16-binding-like transcript-1; NCR, natural cytotoxicity receptor; NK, natural killer; PVR, polio virus receptor; RAE-1, retinoic acid early transcript-1. BOLD indicates family.

The human killer cell immunoglobulin-like receptors (KIR; also known as CD158) are a family of transmembrane glycoproteins expressed on NK cells and a subset of T cells. (Campbell, K. S. and Purdy, A. K., "Structure/function of human killer cell immunoglobulin-like receptors: lessons from polymorphisms, evolution, crystal structures and mutations," Immunol. (2011) 132(3): 315-325). The KIR are key regulators of the development, tolerance and activation of NK cells. Id. The major ligands for KIR are MHC class I (HLA-A, -B or -C) molecules, which are expressed on the surface of nearly every normal nucleated cell in the body, are encoded by the most polymorphic genes in humans, and define immune 'self'. Id. Tolerance of NK cells toward normal cells is achieved through their expression of MHC-I-binding inhibitory receptors, which include KIR, NKG2A/CD94 and CD85j (ILT2, LIR1). Id. For example, binding of LIR-1 (a class I MHC receptor related to KIRs) or KIRs to class I molecules results in inhibitory signals. See Chapman, T L, et al, "The inhibitory receptor LIR-1 uses a common binding interaction to recognize class I MHC molecules and the viral homolog UL18," Immunity (1999) 11 (5): 603-13) The KIR family is encoded by 14 highly polymorphic genes (2DL1 to 2DL5, 3DL1 to 3DL3, 2DS1 to 2DS5, and 3DS1], and distinct family members can transduce either activating or inhibitory signals (Campbell, K. S. and Purdy, A. K., "Structure/function of human killer cell immunoglobulin-like receptors: lessons from polymorphism, s evolution, crystal structures and mutations," Immunol. (2011) 132(3): 315-325). Nomenclature of KIR is based upon the number of C2-type immunoglobulin-like domains in the extracellular region (2D for two domains, 3D for three domains) and by the length of the cytoplasmic domain (L for long-tailed receptors and S for short ones) (Id. All inhibitory KIR have long cytoplasmic domains possessing immunoreceptor tyrosine-based inhibitory motifs (ITIMs; I/VxYxxL/V), which recruit protein tyrosine phosphatases that are critical for mediating inhibitory function. Id. In contrast, KIR with short cytoplasmic domains associate with a transmembrane signalling adaptor protein, DAP12 (also called KARAP). Id. Consistent with antigen receptor signalling, DAP12-dependent activation occurs through the recruitment of Syk/ZAP-70 tyrosine kinases by immunoreceptor tyrosine-based activation motifs [ITAM; Yxx(L/I/V)x6-8Yxx(L/I/V)]. Id. The only exception to this short/long-tailed rule is KIR2DL4, which is a unique long-tailed activating KIR. Compared with other KIR family members, 2DL4 is only expressed on CD56high NK cells, functions as a more potent activator of cytokine production rather than cytotoxicity, and associates with ITAM-containing FcεRI-γ adaptor instead of DAP12 Id. KIR are expressed by 5-40% of CD8+ TILs, and contribute to the altered cytotoxic activity of tumor-reactive CTLs (See Gati, A. et al., CD158 Receptor Controls T-Lymphocyte Susceptibility to Tumor-mediated Activation-induced Cell Death by Interfering with Fas signaling," Cancer Res. (2003) 63 (21): 7475-82). KIR3DL1, originally named NKB1, is specific for HLABw4. GL183 is a surface molecule capable of mediating cell activation selectively expressed by a subset of human CD3-CD16+ NK cells. Moretta, A. et al., "A Novel surface antigen expressed by a subset of human CD3-CD16+ natural killer cells. Role in cell activation and regulation of cytolytic function." J. Exptl. Med. (1990) 3: 695).

CD8+ T Cell Activation and Expansion

According to some embodiments, the induction of an immune response by the allogeneic ENLST™ cells as described herein is effective to activate CD8+ T-cells. According to some embodiments, the induction of an immune response by the allogeneic ENLST™ cells is effective to expand CD8+ T-cells. According to some embodiments, the induction of an immune response by the allogeneic ENLST™ cells is effective to lead to activation and expansion of the population of CD8+ T cells, compared to a parental cell control.

T cell activation and expansion can be measured by various assays as described herein. For example, T cell activities that may be measured include the induction of proliferation of T cells, the induction of signaling in T cells, the induction of expression of activation markers in T cells, the induction of cytokine secretion by T cells, and the cytotoxic activity of T cells. For example, in certain embodiments, CD8+ T cell activation is measured by a proliferation assay.

Cytokine Secretion

The induction of an immune response comprising activation of CD8+ T-cells by the allogeneic ENLST™ cells of the invention may be assessed or measured by determining secretion of cytokines, such as gamma interferon (IFNγ), tumor necrosis factor alpha (TNFa), interleukin-12 (IL-12) or interleukin 2 (IL-2). according to some embodiments, ELISA is used to determine cytokine secretion, for example secretion of gamma interferon (IFNγ), tumor necrosis factor alpha (TNFa), interleukin-12 (IL-12) or interleukin 2 (IL-2). The ELISPOT (enzyme-linked immunospot) technique may be used to detect T cells that secrete a given cytokine (e.g., gamma interferon (IFNγ)) in response to stimulation with the engineered ENLST™ cells described herein. T cells are cultured with engineered ENLST™ cells in wells which have been coated with anti-IFNγ antibodies. The secreted IFNγ is captured by the coated antibody and then revealed with a second antibody coupled to a chromogenic substrate. Thus, locally secreted cytokine molecules form spots, with each spot corresponding to one IFNγ-secreting cell. The number of spots allows one to determine the frequency of IFNγ-secreting cells in the analyzed sample. The ELISPOT assay has also been described for the detection of tumor necrosis factor alpha, interleukin-4 (IL-4), IL-5, IL-6, IL-10, IL-12, granulocyte-macrophage colony-stimulating factor, and granzyme B-secreting lymphocytes (Klinman D, Nutman T. Current protocols in immunology. New York, N.Y.: John Wiley & Sons, Inc.; 1994. pp. 6.19.1-6.19.8, incorporated by reference in its entirety herein).

Flow cytometric analyses of intracellular cytokines may be used to measure the cytokine content in culture supernatants, but provides no information on the number of T cells that actually secrete the cytokine. When T cells are treated with inhibitors of secretion such as monensin or brefeldin A, they accumulate cytokines within their cytoplasm upon activation (e.g. with engineered ENLST™ cells of the present invention). After fixation and permeabilization of the lymphocytes, intracellular cytokines can be quantified by cytometry. This technique allows the determination of the cytokines produced, the type of cells that produce these cytokines, and the quantity of cytokine produced per cell.

Cytotoxicity

The activation of CD8+ T-cells by contact with ENLST™ cells of the described invention may be assessed by assaying the cytotoxic activity of the CD8+ T-cells.

The cytotoxic activity of T cells may be assessed by any suitable technique known to those of skill in the art. For example, a sample comprising T cells that have been exposed to the ENLST™ cells can be assayed for cytotoxic activity after an appropriate period of time, in a standard cytotoxicity assay, for example, $Cr^{51}$ release, or Almar Blue™ fluorescence (See for example, Wolint, Petra, et al.

"Immediate Cytotoxicity but Not Degranulation Distinguishes Effector and Memory Subsets of CD8 T Cells." J. Experimental Medicine, The Rockefeller University Press, (5 Apr. 2004), www.ncbi.nlm.nih.gov/pmc/articles/PMC2211884/).

For the chromium$^{51}$ release assay, target cells (ENLST™ cells) are labeled with $^{51}$Cr ENLST™ cells; MNCs are added in an appropriate medium. The label is released from the target cells by cytolysis, and can be isolated by centrifuging the samples and collecting the supernatants. Supernatants from centrifugation can either be counted directly in a gamma counter, or mixed with scintillation cocktail in a microplate (or dried on a LumaPlate™) and counted in a liquid scintillation counter.

For the alamarBlue™ fluorescence viability assay (Thermofisher), MNCs and ENLST™ cells are added in appropriate medium to microplate wells. Either alarmaBlue HS or alarmaBlue reagent is added to the wells and incubated at 37° C. for 1 to 4 hours. Fluorescence (560/590 nm) or absorbance (570) is read (the signal is stable for 7 hours). Upon entering living cells, resazurin is reduced to resorufin, a compound that is red in color and highly fluorescent. After viability determination, the diluted alamarBlue HS or alamarBlue reagent can be replaced with complete media and returned to the incubator. The cells will continue to proliferate normally.

Proliferation/Expansion

The ability of the ENLST™ cells to stimulate expansion of T cell populations can be evaluated by using CFSE staining. To compare the initial rate of cell expansion, the cells are subject to CFSE staining to determine how well the ENLST™ cells induced the proliferation of T cells. CFSE staining provides a much more quantitative endpoint and allows simultaneous phenotyping of the expanded cells. Every day after stimulation, an aliquot of cells is removed from each culture and analyzed by flow cytometry. CFSE staining makes cells highly fluorescent. Upon cell division, the fluorescence is halved and thus the more times a cell divides the less fluorescent it becomes. The ability of the ENLST™ cells to induce T cell proliferation is quantitated by measuring the number of cells that divided once, twice, three times and so on. The ENLSTcells™ population(s) that induce the greatest number of cell divisions at a particular time point is/are deemed the most potent expander.

To determine how well the ENLSTcells™ populations promote long-term growth of T cells, cell growth curves can be generated. These experiments are set up as the foregoing CFSE experiments, but no CFSE is used. Every 2-3 days of culture, T cells are removed from the respective cultures and counted using a Coulter counter which measures how many cells are present and the mean volume of the cells. The mean cell volume is the best predictor of when to restimulate the cells. In general, when T cells are properly stimulated they triple their cell volume. When this volume is reduced to more than about half of the initial blast, it may be necessary to restimulate the T cells to maintain a log linear expansion (Levine et al., 1996, Science 272:1939-1943; Levine et al., 1997, J. Immunol. 159:5921-5930). The time it takes T cell populations to induce 20 population doublings is calculated. The relative differences of each ENLST™ cell population to induce this level of T cell expansion is one criterion for assessing potency of the ENLST™ cell population.

In addition, the phenotypes of the cells expanded by each ENLST™ cell population can be characterized to determine whether a particular subset is preferentially expanded. Prior to each restimulation, a phenotype analysis of the expanding T cell populations is performed to define the differentiation state of the expanded T cells using the CD27 and CD28 definitions proposed by Appay et al. (2002, Nature Med. 8, 379-385, incorporated by reference in its entirety herein) and CCR7 definitions proposed by Sallusto et al. (1999, Nature 401:708-712, incorporated by reference in its entirety herein). Perforin and Granzyme B intracellular staining can be used to perform a gross measure to estimate cytolytic potential.

Apoptosis Markers

According to certain embodiments of the present invention, stimulation, activation, and expansion of T cells following contact with the ENLST™ cell population(s) as described herein enhances expression of certain key molecules in T cells that protect against apoptosis or otherwise prolong survival in vivo or in vitro. Apoptosis usually results from induction of a specific signal in the T cell. Thus, the ENLST™ cells of the invention may provide for protecting a T cell from cell death resulting from stimulation of the T cell. Therefore, also included in the present invention is enhanced T cell growth by protection from premature death or from absence or depletion of recognized T cell growth markers, such as Bcl-xL, growth factors, cytokines, or lymphokines normally necessary for T cell survival, as well as from Fas or Tumor Necrosis Factor Receptor (TNFR) cross-linking or by exposure to certain hormones or stress.

Immunosuppressive Populations

T regulatory cells (Tregs) are characterized by constitutive expression of high levels of the interleukin (IL)-2 receptor α chain (CD25). DeMatteis, S. et al., "Immunosuppressive Treg cells acquire the phenotype of effector T cells in chronic lymphocytic leukemia patients," J. Translational Medicine (2018) 16: article 172). The majority of CD4+ CD25$^{high}$ Tregs also express a forkhead family transcription factor (FoxP3) which is required for both their differentiation and their immunosuppressive function. Id. Without being limited by theory, the suppressive function of Tregs may be related to different factors, such as modulation of target cell signaling via cell-cell contact and/or secretion of immunosuppressive cytokines such as IL-10, IL-35 and transforming growth factor β (TGF-β). Id.

According to some embodiments, FoxP3+ cells constitute less than 1% of the activated MNC population.

STEP 2: Expanding the Activated Population of MNCs Comprising Subpopulations of Activated Serial Killer Cells In Vitro to Form a Cell Product Comprising the Activated Population of MNCs Comprising Subpopulations of Activated Serial Killer Cells Proliferation/Expansion According to some embodiments, the activated MNC population comprising activated subpopulations of serial killer cells can be expanded in vitro in Lonza's X-Vivo basal medium plus antibiotics plus GlutaMax (Thermo Fisher Scientific) in a Thermo-Fisher T flask of defined geometry (volume, surface area, and cell number). According to some embodiments, nicotinamide 5 mM may be added to the medium. According to some embodiments, 2.5% by volume human plasma autologous to the mononuclear cells may be added to the medium. According to some embodiments, one or more cytokines (RND Systems, 5-10 ng/ml) may be added to the medium. According to some embodiments, the cytokine is one or more selected from IL2, IL7, and IL15. According to some embodiments, the conditions of expansion are effective to boost cell number at least two-fold. The expansion results in formation of a cell product comprising either the activated MNC population comprising the activated subpopulations of serial killer cells, or a cell product comprising one or more of the isolated, expanded and enriched populations of serial killer cells.

Expansion of the activated MNC population comprising activated subpopulations of serial killer cells can be evaluated by cytofluorimetric techniques, for example by the use of 5- (and 6-) carboxy fluorescein diacetatesuccinimidyl ester (CFSE) staining. According to some embodiments, to compare the initial rate of cell expansion, the cells are subject to CFSE staining. CFSE staining provides a quantitative endpoint and allows simultaneous phenotyping of the expanded cells because CFSE staining makes cells highly fluorescent. Every day after stimulation, an aliquot of cells is removed from each culture and analyzed by flow cytometry. Upon cell division, the fluorescence is halved and thus the more times a cell divides the less fluorescent it becomes.

The ability of the ENLST™ cells to induce MNC proliferation is quantified by measuring the number of cells that divided once, twice, three times and so on.

According to some embodiments, cell growth curves can be generated. These experiments are set up like the foregoing CFSE experiments, but no CFSE is used. Every 2-3 days of culture, MNCs comprising serial killer cells are removed from the respective cultures and counted using a Coulter counter which measures how many cells are present and the mean volume of the cells. The mean cell volume is the best predicator of when to restimulate the cells. In general, when serial killer cells are properly stimulated they triple their cell volume. When this volume is reduced to more than about half of the initial blast, it may be necessary to restimulate the MNCs comprising the serial killer cells to maintain a log linear expansion (Levine et al., 1996, Science 272:1939-1943; Levine et al., 1997, J. Immunol. 159:5921-5930). The time it takes each engineered cell to induce 20 population doublings is calculated. The relative differences of each allogeneic primary tumor cell line transfected or transduced with recombinant DNA sequences encoding at least 4 immunomodulator peptides to induce this level of each MNC comprising serial killer cells expansion is one criteria on which a particular allogeneic primary tumor cell line transfected or transduced with recombinant DNA sequences encoding at least 4 immunomodulator peptides is assessed.

According to some embodiments, proliferation can be detected by $^3$H-thymidine incorporation. Cells can then be harvested onto filter mats, and $^3$H-thymidine incorporation can be measured using a scintillation counter. For example, proliferation of MNCs comprising one or more serial killer cell population(s) with tumor cell line variants compared to non-transfected tumor cell controls can be measured. An increase, a decrease, or no change in proliferation relative to controls, are possible outcomes.

According to some embodiments, the proliferation of the expanded activated MNC population comprising activated subpopulations of serial killer cells, can be characterized by flow cytometry analysis.

STEP 3: Preparing a Unit Dose Package Comprising an Individual Dose of the Cell Product; Freezing the Unit Packages Containing the Cell Product at −86° C., and Cryostoring the Frozen Unit Dose Packages in Cryostorage, e.g., a Vapor Phase of a Liquid Nitrogen Freezer;

According to some embodiments, the cell product comprising the expanded activated MNC population comprising subpopulations of activated serial killer cells is centrifuged through Ficoll-Paque®, and resuspended in a pharmaceutical composition comprising X-Vivo basal media plus a cryoprotectant fluid. According to some embodiments, recombinant human albumin may be added. The cell product is aliquoted into individually labeled unit dose packages, frozen at −86° C.; and cryostored in the vapor phase of a liquid nitrogen freezer.

Cryoprotectants are chemicals that protect the cells during freezing and therefore minimize the detrimental effects of increased solute concentration and ice crystal formation. The most commonly used cryoprotective agents are dimethylsulfoxide (DMSO) and glycerol, which generally are used in concentrations ranging from 5-10% (v/v). Other cryoprotectants that have been used include polyethylene glycol, propylene glycol, glycerin, polyvinylpyrrolidone, sorbital, dextran and trehalose.

Cryoprotective agents serve several functions during the freezing process. Freezing point depression is observed when DMSO is used which serves to encourage greater dehydration of the cells prior to intracellular freezing. Cryoprotective agents also seem to be most effective when they can penetrate the cell, delay intracellular freezing, and minimize the solution effects.

The choice of a cryoprotective agent is dependent upon the type of cell to be preserved. When preparing mammalian cells for cryopreservation, for example, cell populations need to be adjusted to levels that ensure adequate recovery. For most mammalian cells, a starting population between $10^6$ to $10^7$ cells/mL is optimum.

The cell suspension initially can be prepared at a concentration twice that desired for preservation so that an equal volume of cryoprotectant (2×cryoprotective agent+medium) can be added. Alternatively, the cell pellet can be resuspended in the cryoprotectant (1×cryoprotective agent+medium) to the desired cell concentration.

Once the cells and the cryoprotectant have been combined and dispensed into containers for freezing, the next step is to cool the suspension. The rate of cooling affects the rate of formation and size of ice crystals, as well as the solution effects that occur during freezing. Different types of cells may require different cooling rates, however a uniform cooling rate of 1° C. per minute from ambient temperature is effective for a wide variety of cells and organisms. A programmable-rate cell freezing apparatus may be used to achieve uniform, controlled cooling rates.

According to some embodiments, the activated and expanded MNC population comprising activated and expanded serial killer cells can be frozen and thawed multiple times without loss of effector function due to prolonged stimulation (T cell exhaustion). According to some embodiments, at least some of the activated and expanded serial killer cell subpopulations, once rested, may be reactivated.

According to some embodiments, the pharmaceutical compositions according to the described invention may further include one or more compatible active ingredients, which are aimed at proving the composition with another pharmaceutical effect in addition to that provided by the cell product. "Compatible" as used herein means that the active ingredients of such a composition are capable of being combined with each other in such a manner so that there is no interaction that would substantially reduce the efficacy of each active ingredient or the composition under ordinary use conditions.

STEP 4: Thawing a Therapeutic Amount of the Frozen Unit Dose Packages Comprising the Cell Product Under Controlled Conditions; and Optionally Combining the Frozen and Thawed Cell Product of Step 4 with a Pharmaceutically Acceptable Carrier Component to Form a Pharmaceutical Composition; and When the frozen unit dose packages are removed from the liquid nitrogen freezer, they are thawed under controlled conditions, i.e., the temperature is changed slowly to preserve the health of the cells. As soon as the contents of the unit dose packaging have been thawed, the external surface of the unit dose package is disinfected prior to opening. According to some embodiments, the cell product contents of the unit dose package may be immediately transferred to fresh X-Vivo medium following thawing to minimize exposure to the cryoprotective agent. According to some embodiments, the cell product may be centrifuged at 100×g for 10 minutes after initial dilution, the supernatant removed, and the cells resuspended into fresh X-Vivo growth media. According to some embodiments, cell recovery is determined by estimating the number of viable cells.

STEP 5: Administering to a Subject in Need Thereof a Therapeutic Amount of the Cell Product or the Pharmaceutical Composition of Step 4

Patients eligible for treatment in accordance with the described invention are patients that are not currently under the influence of an immunosuppressive regimen, for example, patients diagnosed with myeloma, prostate; and early breast cancer.

According to some embodiments, an exemplary regimen for treating the patent with cancer not currently under the influence of an immunosuppressive regimen comprises administering parenterally on one or more dates during the lifetime of the subject a therapeutic amount of the cell product comprising the expanded ENLST™ cell activated MNC population comprising activated and expanded subpopulations of serial killer cells. According to some embodiments, "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), or infusion techniques.

According to some embodiments, the composition is administered multiple times, or as needed in the judgment of the treating physician. According to one such embodiment, the composition is administered at the first infusion date, and optionally at a second infusion date, a third infusion date, a fourth infusion date, a fifth infusion date, a sixth infusion date, a seventh infusion date, an eighth infusion date, a ninth infusion date, a tenth infusion date, and so on.

According to some embodiments, the first infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after diagnosis. According to some embodiments, the second infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after the first infusion date. According to some embodiments, the third infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after the second infusion. Further infusions are envisioned over time as needed in order to decrease tumor burden or tumor recurrence (meaning cancer that has recurred (come back), usually after a period of time during which the cancer could not be detected either to the same place as the original (primary) tumor or to another place in the body).

If infused through a catheter, the viability and potential efficacy of the cell product of the described invention depends on the expanded activated MNC population comprising activated subpopulations of serial killer cells maintaining their potency as they pass through a catheter. According to some embodiments, the catheter used in the methods of the described invention has an internal diameter of at least 0.3175 cm Any type of catheter having an internal diameter of at least 0.3175 cm may be effective in delivering the pharmaceutical compositions of the described invention.

For example, a flow control catheter, which slows drainage of blood through the vasculature, allows the activated cells time to transit through the blood vessel wall and into tissue. According to some embodiments, the catheter is a balloon catheter.

According to some embodiments, a catheter is used to directly inject the pharmaceutical composition into contact with a tumor.

According to some embodiments, the cell product compositions of the described invention may be administered in conjunction with a compatible inhibitor of immune checkpoints. Exemplary compatible immune checkpoints include PD-1, PD-L1, TIM-3, TIGIT, and LAG-3. According to some embodiments, inhibitors of these immune checkpoints may be effective to control immune excape tumor cells.

According to some embodiments, the administering of the therapeutic amount of the cell product, or pharmaceutical composition is effective to reduce tumor burden.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

The Examples make use of, but are not limited to, the methods described hereinbelow.
Western Blotting
Briefly, cells are lysed with cold lysis buffer and centrifuged to pellet cellular debris. Protein concentration of the supernatant is determined by a protein quantification assay (e.g., Bradford Protein Assay, Bio-Rad Laboratories). The lysate supernatant is then combined with an equal volume of 2×SDS sample buffer and boiled at 100° C. for 5 minutes. Equal amounts of protein in sample buffer are loaded into the wells of an SDS-PAGE gel along with molecular weight marker and electrophoresed for 1-2 hours at 100 V. Proteins are then transferred to a nitrocellulose or PVDF membrane. The membrane is then blocked for 1 hour at room temperature using 5% non-fat dry milk in TBST blocking buffer. The membrane is then incubated with a 1:500 dilution of primary antibody in 5% non-fat dry milk in TBST blocking buffer, followed by three washes in 20 Mn Tris, Ph 7.5; 150 mM NaCl, 0.1% Tween 20 (TBST) for 5 minutes. The membrane is then incubated with conjugated secondary antibody at a 1:2000 dilution in 5% non-fat dry milk in TBST blocking buffer for 1 hour at room temperature, followed by three washes in TBST for 5 minutes each. Images of the blot are obtained using dark room development techniques for chemiluminesence detection, or using image scanning techniques for colorimetric or fluorescent detection.
Real Time PCR
Real-time PCR techniques may be performed as described to analyze expression level of mRNAs (Zhao Y. et al., Biochemical and Biophysical Research Communications 360 (2007) 205-211). Briefly, total RNA is extracted from cells using the Quiagen kit (Valencia Calif.), followed by first strand cDNA synthesis using random hexamer primers (Fermentas, Hanover Md.). Real-time PCR is performed on each sample using the Mx3000p Quantitative PCR system (Stratagene, La Jolla, Calif.), for 40 cycles using validated gene specific RT-PCR primer sets for each gene of interest. Relative expression level of each transcript is corrected for that of the house keeping gene beta-actin as an internal control.
Immunofluorescence
Briefly, adherent tumor cell line variant cells are fixed with 4% formaldehyde diluted in warm PBS for 15 minutes at room temperature. The fixative is aspirated and the cells washed three times with PBS for 5 minutes each. Cells are blocked in a 5% BSA blocking buffer for 60 minutes at room temperature. Blocking buffer is then aspirated and a solution of primary antibody (e.g. 1:100 dilution) is incubated with the cells overnight at 4° C. Cells are then rinsed three times with PBS for 5 minutes each, and subsequently incubated with a solution of fluorochrome conjugated secondary antibody (e.g. 1:1000 dilution) for 1-2 hours at room temperature. Cells are then washed three times with PBS for 5 minutes each and visualized by fluorescence microscopy.
Flow Cytometry
Flow Cytometry analysis may be performed as described (Zhao Y. et al., Exp. Cell Res., 312, 2454 (2006)). Briefly, tumor cell line variant cells that are either treated with trypsin/EDTA or left untreated are collected by centrifugation and re-suspended in PBS. The cells are fixed in 4% formaldehyde for 10 minutes at 37° C. For extracellular staining with antibodies, cells are not permeabilized. For intracellular staining, cells are permeabilized by adding ice-cold 100% methanol to pre-chilled cells to a final concentration of 90% methanol and incubated on ice for 30 minutes. Cells are immunostained by first resuspending cells in incubation buffer and adding dilutions of primary antibody. Cells are incubated with primary antibody for 1 hour at room temperature, followed by three washes with incubation buffer. Cells are then resuspended in incubation buffer with dilutions of conjugated secondary antibody for 30 minutes at room temperature, followed by three washes in incubation buffer. Stained cells are then analyzed by flow cytometry.
Enzyme-Linked Immunosorbent Assay (ELISA)
Briefly, a capture antibody, specific for a protein of interest, is coated onto the wells of a microplate. Samples, including a standard containing protein of interest, control specimens, and unknowns, are pipetted into wells of the microplate, where the protein antigen binds to the capture antibody. After washing 4 times, a detection antibody is added to the wells for one hour, binding to the immobilized protein captured during the first incubation. After removal of excess detection antibody and washing 4 times, a horse radish peroxidase (HRP) conjugate (secondary antibody or streptavidin) is added for 30 minutes to bind to the detection antibody. After washing 4 more times to remove the excess HRP conjugate, a substrate solution is added for 30 minutes in the dark to be converted by the enzyme to a detectable form (color signal). A stop solution is added to each well of the microplate and evaluated within 30 minutes of stopping the reaction. Intensity of the colored product may be directly proportional to the concentration of antigen present in the original specimen.

Human Mixed Lymphocyte Tumor Reaction (MLTR) Testing

A mixed lymphocyte tumor reaction (MLTR) is an all human, in vitro assay, designed to optimize lead candidates. In the MLTR, optimization is achieved through the qualitative and quantitative assessment of human peripheral blood mononuclear cell (PBMC) responses to engineered allogeneic tumor cells. The MLTR measures proliferation and differentiation by flow cytometry and mass cytometry (CyTOF), by cytotoxicity, measured by lactate dehydrogenase (LDH) release assay, and by cytokine profile. According to some embodiments, allogeneic cell pools expressing a single immunomodulatory protein are used in the MLTR. According to some embodiments, allogenic cell pools expressing one or more, two or more, three or more, four or more or five or more immunomodulatory proteins are used in the MLTR.

The basic MLTR one day procedure is carried out as follows:

A vial of PBMC (20 MN cells) is thawed. Cells are then washed in dPBS. PMBC cells are resuspended at $2.5 \times 10^6$ cell per ml in X-VIVO (~8 ml). The cells are characterized by flow cytometry to document the nature of the cell population.

Use in the MLTR is carried out as follows:
$2.5 \times 10^5$ cell PBMC (100 µl of stock)
$0.5 \times 10^5$ allogeneic cells (100 µl of stock), when used
$0.5 \times 10^5$ allogeneic cell (100 µl of stock). These cells will be inactivated with Mitomycin C.
Positive control 50 µl of a 6× stock (anti-CD28/CD3)
Total volume 300 µl in a 96-well flat bottom—total volume of a 96-well is 360 µl.
Incubate for 4 days
100 µl is removed for cytokine analysis with Luminex
CyTOF is conducted on the remaining 200 µl.
Supernatants for Cytokine Profiling are removed after 1 day.

CyTOF has been previously described, for example in Bendall et al. (Science, Vol. 332, 6 May 2011) and Bendall and Nolan (Nature Biotechnology, Vol. 30 No. 7, July 2012), both of which are incorporated by reference in their entireties herein. Human markers employed in CyTOF staining are shown below in Table 10.

TABLE 10

Human Markers for CyTOF Staining

| | Marker | Clone | Metal |
|---|---|---|---|
| | HLA-DR | L243 | 89Y |
| | CD3 | UCHT1 | 115In |
| | CD27 | O323 | 141Pr |
| | CD19 | HIB19 | 142Nd |
| | CD134/OX40 | Ber-ACT35 | 143Nd |
| * | Granzyme B | GB11 | 144Nd |
| | CD258/LIGHT | 115520 | 145Nd |
| | CD8A | RPA t8 | 146Nd |
| | CD45RO | UCHL1 | 147Sm |
| | CD226/DNAM-1 | 11A8 | 149Sm |
| | CD194/CCR4 | L291H4 | 150Nd |
| | PD1 (CD279) | EH12.2H7 | 151Eu |
| | CD170 | 1A5 | 152Sm |
| | CD69 | FN50 | 153Eu |
| | CD70 | 113-16 | 154Sm |
| | CD4 | RPA T4 | 155Gd |
| | CD8b | SIDI8BEE | 156Gd |
| | IL-17R | W15177A | 158Gd |
| * | CTLA-4 CD152 | L3D10 | 159Tb |
| | CD278/ICOS | C398.4A | 160Gd |
| * | AHR | FF3399 | 161Dy |
| | CD56 | NCAM16.2 | 162Dy |

TABLE 10-continued

Human Markers for CyTOF Staining

| | Marker | Clone | Metal |
|---|---|---|---|
| | CD195/CCR5 | J418F1 | 163Dy |
| * | Ki67 | 8D5 | 164Dy |
| * | FoxP3 | Use Ebio | 165Ho |
| | CD40 | 5C3 | 166Er |
| * | Helios | 22F6 | 168Er |
| * | PU.1 | puph13 | 169Tm |
| * | RORgt | 1181A | 170Er |
| | CD127/IL-7R | 40131 | 171Yb |
| | CD38 | HIT2 | 172Yb |
| | CD25 | M-A251 | 173Yb |
| | CD86 | IT2.2 | 174Yb |
| * | T-bet | 4B10 | 175Lu |
| * | Perforin | dG9 | 176Yb |

* denotes intracellular target while all other are cell surface targets

Luminex Multiplex Assay

The Luminex xMAP technology (formerly LabMAP, FlowMetrix) uses digital signal processing capable of classifying polystyrene beads (microspheres) dyed with distinct proportions of red and near-infrared fluorophores. These proportions define 'spectral addresses' for each bead population. As a result, up to one hundred different detection reactions can be carried out simultaneously on the various bead populations in very small sample volumes (Earley et al. Report from a Workshop on Multianalyte Microsphere Arrays. Cytometry 2002; 50:239-242; Oliver et al. Clin Chem 1998; 44(9):2057-2060; Eishal and McCoy, Methods 38(4): 317-323, April 2006, all of which are incorporated by reference in their entireties herein).

The Luminex Multiplex Assay is commercially available and is described on the world wide web at thermofisher.com/us/en/home/life-science/protein-biology/protein-assays-analysis/luminex-multiplex-assays.html, incorporated by reference in its entirety herein.

Mitomycin C Preparation of Cells

Mitomycin C is prepared from dry powder (2 mg per vial) using 400 µl of DMSO (500× stock=5 mg/ml), dissolved completely and aliquoted into 25 ul volumes, and stored at −80 C. 20 µl of 1 aliquot is used in 10 ml warmed C5 to yield 10 µg/ml final working solution. The solution is filter sterilized.

The solution can be used on resuspended cells or adherent cells in flasks.

Cells are incubated at 37 C for 30 minutes in the dark, then washed in warm C5 3 times. Cells are resuspended in 1 ml X-VIVO. 40 ul are counted into 200 ul on plate. The cells are resuspended at a final concentration of $1 \times 10^6$/ml in X-VIVO (serum free media, Lonza).

Example 2

A tumor cell line can be selected for modification, and lentiviral transfection of recombinant immune modulator sequences may be used to stably integrate immunomodulators into the cell genome. Example 3 below describes 7 lentiviral vectors (vector 1, vector 2, vector 3, vector 4, vector 5, vector 6 and vector 7) that may be used to stably integrate immunomodulators into the cell genome.

According to some embodiments, two recombinant immunomodulator proteins may be transfected simultaneously, followed by transfections of two more recombinant immunomodulator proteins simultaneously, followed by transfection of a single recombinant immunomodulator protein to achieve the total of five recombinant peptides.

According to some embodiments, two recombinant peptides may be transfected simultaneously, followed by transfection of a single recombinant peptide, followed by transfection of a single recombinant peptide, followed by transfection of a single recombinant peptide to achieve the total of five recombinant peptides. According to some embodiments, a single recombinant peptide is transfected, followed by transfection of two recombinant peptides simultaneously, followed by transfection of two recombinant peptides simultaneously to achieve a total of five recombinant peptide.

Example 3 below describes the lentiviral vectors that may be used to stably integrate immunomodulators into the ENLST™ cell genome.

Lentiviral Vectors

The described invention provides nucleic acid constructs that encode two or more immunomodulators that can be expressed in prokaryotic and eukaryotic cells. For example, the described invention provides expression vectors (e.g., DNA- or RNA-based vectors) containing nucleotide sequences that encode two or more immunomodulators. In addition, the described invention provides methods for making the vectors described herein, as well as methods for introducing the vectors into appropriate host cells for expression of the encoded polypeptides. In general, the methods provided herein include constructing nucleic acid sequences encoding two or more immunomodulators, and cloning the sequences into an expression vector. The expression vector can be introduced into host cells or incorporated into virus particles, either of which can be administered to a subject to, for example, treat cancer.

cDNA or DNA sequences encoding two or more immunomodulators can be obtained (and, if desired, modified) using conventional DNA cloning and mutagenesis methods, DNA amplification methods, and/or synthetic methods. In general, a sequence encoding two or more immunomodulators can be inserted into a cloning vector for genetic modification and replication purposes prior to expression. Each coding sequence can be operably linked to a regulatory element, such as a promoter, for purposes of expressing the encoded protein in suitable host cells in vitro and in vivo.

Expression vectors can be introduced into host cells for producing secreted immunomodulators. There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; and natural polymer-based delivery vehicles, such as chitosan and gelatin; viral vectors are also suitable for in vivo transduction. In some situations it is desirable to provide a targeting agent, such as an antibody or ligand specific for a cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), FIp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003).

Cells may be cultured in vitro or genetically engineered, for example. Host cells can be obtained from normal or affected subjects, including healthy humans, cancer patients, private laboratory deposits, public culture collections such as the American Type Culture Collection, or from commercial suppliers.

Cells that can be used for production and secretion of two or more immunomodulators in vivo include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, or granulocytes, various stem or progenitor cells, such as hematopoietic stem or progenitor cells (e.g., as obtained from bone marrow), umbilical cord blood, peripheral blood, fetal liver, etc., and tumor cells (e.g., human tumor cells). The choice of cell type depends on the type of tumor or infectious disease being treated or prevented, and can be determined by one of skill in the art.

Different host cells have characteristic and specific mechanisms for post-translational processing and modification of proteins. A host cell may be chosen which modifies and processes the expressed gene products in a specific fashion similar to the way the recipient processes its heat shock proteins (hsps).

According to some embodiments, an expression construct as provided herein can be introduced into an antigenic cell. As used herein, antigenic cells can include preneoplastic cells that are infected with a cancer-causing infectious agent, such as a virus, but that are not yet neoplastic, or antigenic cells that have been exposed to a mutagen or cancer-causing agent, such as a DNA-damaging agent or radiation, for example. Other cells that can be used are preneoplastic cells that are in transition from a normal to a neoplastic form as characterized by morphology or physiological or biochemical function. According to some embodiments, an expression construct as provided herein can be introduced into a non-antigenic cell, for example a serial killer cells, such as NK cells, NKTs, CIKs, GDTs, DCs, MAIT cells, and CD8+ and/or CD4+ CTL cells.

Typically, the cancer cells and preneoplastic cells used in the methods provided herein are of mammalian origin. According to some embodiments, cancer cells (e.g., human tumor cells) can be used in the methods described herein. Cell lines derived from a preneoplastic lesion, cancer tissue, or cancer cells also can be used. Cancer tissues, cancer cells, cells infected with a cancer-causing agent, other preneoplastic cells, and cell lines of human origin can be used. According to some embodiments, a cancer cell can be from an established tumor cell line or tumor cell line variant such as, without limitation, an established non-small cell lung carcinoma (NSCLC), bladder cancer, melanoma, ovarian cancer, renal cell carcinoma, prostate carcinoma, sarcoma, breast carcinoma, squamous cell carcinoma, head and neck carcinoma, hepatocellular carcinoma, pancreatic carcinoma, or colon carcinoma cell line.

Parent cell lines are described supra.

Further, according to some embodiments, the activated serial killer cell compositions provide for an adjuvant effect that further allows the immune system of a patient, when used in the various methods described herein, to be activated against a disease of interest.

Both prokaryotic and eukaryotic vectors can be used for expression of the two or more immunomodulators in the methods provided herein. Prokaryotic vectors include constructs based on E. coli sequences (see, e.g., Makrides, Microbiol Rev 1996, 60:512-538). Non-limiting examples of regulatory regions that can be used for expression in E. coli include lac, trp, 1pp, phoA, recA, tac, T3, T7 and lamda PL. Non-limiting examples of prokaryotic expression vectors may include the Agt vector series such as .lamda.gt11 (Huynh et al., in "DNA Cloning Techniques, Vol. I: A Practical Approach," 1984, (D. Glover, ed.), pp. 49-78, IRL Press, Oxford), and the pET vector series (Studier et al., Methods Enzymol 1990, 185:60-89).

A variety of regulatory regions can be used for expression of the exogenous immunomodulators in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the n-interferon gene, and the hsp70 gene (see, Williams et al., Cancer Res 1989, 49:2735-42; and Taylor et al., Mol Cell Biol 1990, 10:165-75). Heat shock promoters or stress promoters also may be advantageous for driving expression of the fusion proteins in recombinant host cells.

Animal regulatory regions that exhibit tissue specificity and have been utilized in transgenic animals also can be used in tumor cells of a particular tissue type: the elastase I gene control region that is active in pancreatic acinar cells (Swift et al., Cell 1984, 38:639-646; Ornitz et al., Cold Spring Harbor Symp Quant Biol 1986, 50:399-409; and MacDonald, Hepatology 1987, 7:425-515); the insulin gene control region that is active in pancreatic beta cells (Hanahan, Nature 1985, 315:115-122), the immunoglobulin gene control region that is active in lymphoid cells (Grosschedl et al., Cell 1984, 38:647-658; Adames et al., Nature 1985, 318: 533-538; and Alexander et al., Mol Cell Biol 1987, 7:1436-1444), the mouse mammary tumor virus control region that is active in testicular, breast, lymphoid and mast cells (Leder et al., Cell 1986, 45:485-495), the albumin gene control region that is active in liver (Pinkert et al., Genes Devel, 1987, 1:268-276), the alpha-fetoprotein gene control region that is active in liver (Krumlauf et al., Mol Cell Biol 1985, 5:1639-1648; and Hammer et al., Science 1987, 235:53-58); the alpha 1-antitrypsin gene control region that is active in liver (Kelsey et al., Genes Devel 1987, 1:161-171), the beta-globin gene control region that is active in myeloid cells (Mogram et al., Nature 1985, 315:338-340; and Kollias et al., Cell 1986, 46:89-94); the myelin basic protein gene control region that is active in oligodendrocyte cells in the brain (Readhead et al., Cell 1987, 48:703-712); the myosin light chain-2 gene control region that is active in skeletal muscle (Sani, Nature 1985, 314:283-286), and the gonadotropic releasing hormone gene control region that is active in the hypothalamus (Mason et al., Science 1986, 234:1372-1378).

An expression vector also can include transcription enhancer elements, such as those found in SV40 virus, Hepatitis B virus, cytomegalovirus, immunoglobulin genes, metallothionein, and .beta.-actin (see, Bittner et al., Meth Enzymol 1987, 153:516-544; and Gorman, Curr Op Biotechnol 1990, 1:36-47). In addition, an expression vector can contain sequences that permit maintenance and replication of the vector in more than one type of host cell, or integration of the vector into the host chromosome. Such sequences include, without limitation, to replication origins, autonomously replicating sequences (ARS), centromere DNA, and telomere DNA.

In addition, an expression vector can contain one or more selectable or screenable marker genes for initially isolating, identifying, or tracking host cells that contain DNA encoding the immunogenic proteins as described herein. For long term, high yield production of gp96-Ig and T cell costimulatory fusion proteins, stable expression in mammalian cells can be useful. A number of selection systems can be used for mammalian cells. For example, the Herpes simplex virus thymidine kinase (Wigler et al., Cell 1977, 11:223), hypoxanthine-guanine phosphoribosyltransferase (Szybalski and Szybalski, Proc Natl Acad Sci USA 1962, 48:2026), and adenine phosphoribosyltransferase (Lowy et al., Cell 1980, 22:817) genes can be employed in tk–, hgprf–, or aprf– cells, respectively. In addition, antimetabolite resistance can be used as the basis of selection for dihydrofolate reductase (dhfr), which confers resistance to methotrexate (Wigler et al., Proc Natl Acad Sci USA 1980, 77:3567; O'Hare et al., Proc Natl Acad Sci USA 1981, 78:1527); gpt, which confers resistance to mycophenolic acid (Mulligan and Berg, Proc Natl Acad Sci USA 1981, 78:2072); neomycin phosphotransferase (neo), which confers resistance to the aminoglycoside G-418 (Colberre-Garapin et al., J Mol Biol 1981, 150:1); and hygromycin phosphotransferase (hyg), which confers resistance to hygromycin (Santerre et al., Gene 1984, 30:147). Other selectable markers such as histidinol and Zeocin™ also can be used.

A number of viral-based expression systems also can be used with mammalian cells to produce the allogeneic ENLST™ cells. Vectors using DNA virus backbones have been derived from simian virus 40 (SV40) (Hamer et al., Cell 1979, 17:725), adenovirus (Van Doren et al., Mol Cell Biol 1984, 4:1653), adeno-associated virus (McLaughlin et al., J Virol 1988, 62:1963), and bovine papillomas virus (Zinn et al., Proc Natl Acad Sci USA 1982, 79:4897). When an adenovirus is used as an expression vector, the donor DNA sequence may be ligated to an adenovirus transcription/translation control complex, e.g., the late promoter and tripartite leader sequence. This fusion gene may then be inserted in the adenovirus genome by in vitro or in vivo recombination. Insertion in a non-essential region of the viral genome (e.g., region E1 or E3) can result in a recombinant virus that is viable and capable of expressing heterologous products in infected hosts. (See, e.g., Logan and Shenk, Proc Natl Acad Sci USA 1984, 81:3655-3659).

Bovine papillomavirus (BPV) can infect many higher vertebrates, including man, and its DNA replicates as an episome. A number of shuttle vectors have been developed for recombinant gene expression, which exist as stable, multicopy (20-300 copies/cell) extrachromosomal elements in mammalian cells. Typically, these vectors contain a segment of BPV DNA (the entire genome or a 69% transforming fragment), a promoter with a broad host range, a polyadenylation signal, splice signals, a selectable marker, and "poisonless" plasmid sequences that allow the vector to be propagated in E. coli. Following construction and amplification in bacteria, the expression gene constructs are transfected into cultured mammalian cells by, for example, calcium phosphate coprecipitation. For those host cells that do not manifest a transformed phenotype, selection of transformants is achieved by use of a dominant selectable marker, such as histidinol and G418 resistance.

Alternatively, the vaccinia 7.5K promoter can be used. (See, e.g., Mackett et al., Proc Natl Acad Sci USA 1982, 79:7415-7419; Mackett et al., J Virol 1984, 49:857-864; and Panicali et al., Proc Natl Acad Sci USA 1982, 79:4927-4931.) In cases where a human host cell is used, vectors based on the Epstein-Barr virus (EBV) origin (OriP) and EBV nuclear antigen 1 (EBNA-1; a trans-acting replication factor) can be used. Such vectors can be used with a broad range of human host cells, e.g., EBO-pCD (Spickofsky et al., DNA Prot Eng Tech 1990, 2:14-18); pDR2 and .lamda.DR2 (available from Clontech Laboratories).

ENLST™ cell populations also can be made with retrovirus-based expression systems. Retroviruses, such as Moloney murine leukemia virus, can be used since most of the viral gene sequence can be removed and replaced with exogenous coding sequence while the missing viral functions can be supplied in trans. In contrast to transfection, retroviruses can efficiently infect and transfer genes to a wide range of cell types including, for example, primary hematopoietic cells. Moreover, the host range for infection by a retroviral vector can be manipulated by the choice of envelope used for vector packaging.

For example, a retroviral vector can comprise a 5' long terminal repeat (LTR), a 3' LTR, a packaging signal, a bacterial origin of replication, and a selectable marker. The gp96-Ig fusion protein coding sequence, for example, can be inserted into a position between the 5' LTR and 3' LTR, such that transcription from the 5' LTR promoter transcribes the cloned DNA. The 5' LTR contains a promoter (e.g., an LTR promoter), an R region, a U5 region, and a primer binding site, in that order. Nucleotide sequences of these LTR elements are well known in the art. A heterologous promoter as well as multiple drug selection markers also can be included in the expression vector to facilitate selection of infected cells. See, McLauchlin et al., Prog Nucleic Acid Res Mol Biol 1990, 38:91-135; Morgenstern et al., Nucleic Acid Res 1990, 18:3587-3596; Choulika et al., J Virol 1996, 70:1792-1798; Boesen et al., Biotherapy 1994, 6:291-302; Salmons and Gunzberg, Human Gene Ther 1993, 4:129-141; and Grossman and Wilson, Curr Opin Genet Devel 1993, 3:110-114.

Any of the cloning and expression vectors described herein may be synthesized and assembled from known DNA sequences using techniques that are known in the art. The regulatory regions and enhancer elements can be of a variety of origins, both natural and synthetic. Some vectors and host cells may be obtained commercially. Non-limiting examples of useful vectors are described in Appendix 5 of Current Protocols in Molecular Biology, 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

Recombinant Immunomodulators

According to some embodiments, two or more immunomodulators may be cloned into two or more plasmid constructs for transfection (via, e.g., lipids, calcium phosphate, cationic polymers, DEAE-dextran, activated dendrimers, magnetic beads, electroporation, biolistic technology, microinjection, laserfection/optoinjection) or transduction (via, e.g., retrovirus, lentivirus, adenovirus, adeno-associated virus) into cells of tumor cell line or tumor cell line variants. According to some embodiments, recombinant DNA encoding each immune modulator protein may be cloned into a lentiviral vector plasmid for integration into the genome of cells of tumor cell line or tumor cell line variants. According to some embodiments, recombinant DNA encoding the immune modulator protein may be cloned into a plasmid DNA construct encoding a selectable trait, such as an antibiotic resistance gene. According to some embodiments, recombinant DNA encoding the immune modulator protein may be cloned into a plasmid construct that is adapted to stably express each recombinant protein in the cells of the tumor cell line or tumor cell line variant. According to some embodiments, the transfected or transduced tumor cells may be clonally expanded to achieve a cell line variant with a homogenous site of integration of the recombinant DNA encoding each immune modulator protein into the genome of the cells of the tumor cell line or tumor cell line variant.

Lentiviral Constructs

According to some embodiments, the DNA sequences coding for exogenous immunomodulatory molecules may be cloned into a lentiviral vector for transduction into mammalian cells. According to some embodiments, the lentiviral system may comprise a lentiviral transfer plasmid encoding the two or more immune modulator sequences, packaging plasmids encoding the GAG, POL, TAT, and REV sequences, and an envelope plasmid encoding the ENV sequences. According to some embodiments, the lentiviral transfer plasmid uses a viral LTR promoter for gene expression. According to some embodiments, the lentiviral transfer plasmid uses a hybrid promoter, or other specialized promoter. According to some embodiments, the promoter of the lentiviral transfer plasmid is selected to express the two or more immune modulator sequences at a desired level relative to other immunomodulatory sequences. According to some embodiments, the relative level is measured on the level of transcription as mRNA transcripts. According to some embodiments, the relative level is measured on the level of translation as protein expression.

Multicistronic Plasmid Constructs

According to some embodiments, one or more immune modulator sequence may be cloned in a multicistronic vector for co-expression of one immune modulator with a second immune modulator or other recombinant sequence. According to some embodiments, an immune modulator sequence may be cloned into a plasmid comprising an IRES element to promote translation of two or more proteins from a single transcript. According to some embodiments, one or more immune modulator sequences is cloned into a multicistronic vector comprising sequences for a self cleaving 2A peptide to produce two or more exogenous immunomodulatory molecules from a single transcript.

Genetic Introduction of Exogenous Immunomodulatory Molecules

According to some embodiments, plasmid constructs comprising the recombinant immune modulator sequences may be transfected or transduced into tumor cell line or tumor cell line variants.

According to some embodiments, up to 25 immunomodulators (i.e., 1, 2, 3, 4, 5, 6, 7, 8, 9, 10, 11, 12, 13, 14, 15, 16, 17, 18, 19, 20, 21, 22, 23, 24, or 25) may be cloned into 10 separate vectors for transduction into mammalian cells. According to some embodiments, up to 25 immunomodulators (i.e., 1, 2, 3, 4, 5, 6, 7, 8, 9, 10, 11, 12, 13, 14, 15, 16, 17, 18, 19, 20, 21, 22, 23, 24, or 25) may be cloned into 11 separate vectors for transduction into mammalian cells. According to some embodiments, up to 25 immunomodulators (i.e., 1, 2, 3, 4, 5, 6, 7, 8, 9, 10, 11, 12, 13, 14, 15, 16, 17, 18, 19, 20, 21, 22, 23, 24, or 25) may be cloned into 12 separate vectors for transduction into mammalian cells. According to some embodiments, 14 or more immunomodulators (i.e., 1, 2, 3, 4, 5, 6, 7, 8, 9, 10, 11, 12, 13, 14 or more) may be cloned into 10 separate vectors for transduction into mammalian cells. According to some embodiments, 14 or more immunomodulators (i.e., 1, 2, 3, 4, 5, 6, 7, 8, 9, 10, 11, 12, 13, 14 or more) may be cloned into 11 separate vectors for transduction into mammalian cells. According to some embodiments, 14 or more immunomodulators (i.e., 1, 2, 3, 4, 5, 6, 7, 8, 9, 10, 11, 12, 13, 14 or more) may be cloned into 12 separate vectors for transduction into mammalian cells. According to some embodiments, 14 or more immunomodulators (i.e., 1, 2, 3, 4, 5, 6, 7, 8, 9, 10, 11, 12, 13, 14 or more) may be cloned into 13 separate vectors for transduction into mammalian cells. According to some embodiments, 14 or more immunomodulators (i.e., 1, 2, 3, 4, 5, 6, 7, 8, 9, 10, 11, 12, 13, 14 or more) may be cloned into 14 separate vectors for transduction into mammalian cells.

According to some embodiments, the vector constructs further comprise one or more tags, as described herein.

Lentiviral System

According to some embodiments, the lentiviral system may be employed where the transfer vector with immune modulator sequences, an envelope vector, and a packaging vector are each transfected into host cells for virus production. According to some embodiments, the lentiviral vectors may be transfected into 293T cells by any of calcium phosphate precipitation transfection, lipid based transfection, or electroporation, and incubated overnight. For embodiments where the immune modulator sequence may be accompanied by a fluorescence reporter, inspection of the 293T cells for florescence may be checked after overnight incubation. The culture medium of the 293T cells comprising virus particles may be harvested 2 or 3 times every 8-12 hours and centrifuged to sediment detached cells and debris. The culture medium may then be used directly, frozen or concentrated as needed.

The ENLST™ cell tumor cell line or tumor cell line variants may be grown to a confluency of about 70% under standard tissue culture conditions. The cells may then be treated with hexadimethrine bromide (to enhance transduction of cells) and lentiviral particles comprising recombinant constructs in fresh media, and incubated for 18-20 hours followed by a media change.

Lipid Based Transfection

According to some embodiments, ENLST™ cells of tumor cell lines or tumor cell line variants may be transfected with immune modulator sequences using a lipid based transfection method. According to some embodiments, established lipid based transfection reagents, such as LIPOFECTAMINE, may be used. Tumor cell line or tumor cell line variants may be grown to about 70-90% confluence in a tissue culture vessel. Appropriate amounts of Lipofectamine® and plasmid construct comprising the immune modulator sequences may be separately diluted in tissue culture media and briefly incubated at room temperature. The diluted Lipofectamine® and plasmid constructs in media may be mixed together and incubated briefly at room temperature. The plasmid LIPOFECTAMINE mixture may then be added to the cells of the tumor cell line or tumor cell line variants in the tissue culture vessel and incubated for 1-3 days under standard tissue culture conditions.

Selection of Expressing Clones

According to some embodiments, ENLST™ cell populations of tumor cells of the tumor cell line or tumor cell line variant that have been transfected with immune modulator sequences may be selected for various levels of expression.

According to some embodiments, the immunomodulator sequences may be accompanied by antibiotic resistance genes, which may be used to select for clones with stable integration of the recombinant DNA encoding the immunomodulator sequences. According to some embodiments, the immunomodulator sequences may be cloned into a plasmid construct comprising antibiotic resistance, such as the Neomycin/Kanamycin resistance gene. Transfected cells are treated with antibiotics according to the manufacturer's protocol for 1-2 weeks or more with daily media changes. At some point during antibiotic treatment, there is massive tumor cell death of all cells that have not stably integrated the antibiotic resistance gene, leaving behind small colonies of stably expressing clones. Each of the stably expressing clones may be picked, cultured in a separate tissue culture container, and tested for levels of immunomodulator expression by any established method, such as western blot, flow cytometry, and fluorescence microscopy.

According to some embodiments, transfected ENLST™ cells may be selected for high expression of the immunomodulators by fluorescence activated cell sorting (FACS). According to some embodiments, immune modulator sequences may be accompanied by one or more fluorescent proteins (e.g. GFP), which can be used to quantify expression of immune modulator. For example, a bicistronic plasmid comprising an immune modulator sequence connected to a GFP sequence via IRES sequence would result in both an immune modulator and GFP protein translated from the same transcript. Thus, the GFP expression level would act as a proxy for the expression level of immune modulator. Single cell suspensions of immune modulator/GFP transfected tumor cells could be selected for the desired level of expression by FACS based on the fluorescence intensity. Any fluorescent protein may be used in this regard. For example, any of the following recombinant fluorescent proteins (rXFP) may be used: EBFP, ECFP, EGFP, YFP, mHoneydew, mBanana, mOrange, tdTomato, mTangerine, mStrawberry, mCherry, mGrape, mRasberry, mGrape2, mPlum.

Alternatively, the expression of the recombinant immunomodulator may be directly observed by fluorescent antibodies specific to each immunomodulator or specific to a tag engineered onto each immunomodulator. For example, according to some embodiments the extracellular region of an immunomodulator sequence may be fused with a FLAG tag or HA tag. Anti-FLAG or anti-HA antibodies may be used, along with a fluorophore attached to the primary antibody or a secondary antibody) to detect the expression of the immunomodulator on the surface of the transfected tumor cells. Tumor cells expressing the desired level of immunomodulator may be selected by FACS sorting and cultured separately.

Sequentially Add New Plasmid Constructs to the Clones

According to some embodiments, a tumor cell line or tumor cell line variants that expresses one or more immunomodulator sequence(s) is transfected with additional immunomodulators for stable expression in a sequential manner. By sequentially adding recombinant immunomodulators in successive fashion, cells of a tumor cell line or tumor cell line variant may be created that express several immunomodulators simultaneously. According to some embodiments, a tumor cell line or tumor cell line variant may be created that expresses two immunomodulators simultaneously. According to some embodiments, a tumor cell line or tumor cell line variant may be created that expresses three immunomodulators simultaneously. According to some embodiments, a tumor cell line or tumor cell line variant may be created that expresses four immunomodulators simultaneously. According to some embodiments, a tumor cell line or tumor cell line variant may be created that expresses five immunomodulators simultaneously. According to some embodiments, a tumor cell line or tumor cell line variant may be created that expresses six immunomodulators simultaneously. According to some embodiments, a tumor cell line or tumor cell line variant may be created that expresses seven immunomodulators simultaneously. According to some embodiments, a tumor cell line or tumor cell line variant may be created that expresses eight immunomodulators simultaneously. According to some embodiments, a tumor cell line or tumor cell line variant may be created that expresses nine immunomodulators simultaneously. According to some embodiments, a tumor cell line or tumor cell line variant may be created that expresses ten immunomodulators simultaneously. According to some embodiments, a tumor cell line or tumor cell line variant may be created that expresses eleven immunomodulators simultaneously. According to some embodiments, a tumor cell line or tumor cell line variant may be created that expresses twelve immunomodulators simultaneously. According to some embodiments, a tumor cell line or tumor cell line variant may be created that expresses thirteen immunomodulators simultaneously. According to some embodiments, a tumor cell line or tumor cell line variant may be created that expresses fourteen immunomodulators simultaneously. According to some embodiments, a tumor cell line or tumor cell line variant may be created that expresses fifteen immunomodulators simultaneously. According to some embodiments, a tumor cell line or tumor cell line variant may be created that expresses sixteen immunomodulators simultaneously. According to some embodiments, a tumor cell line or tumor cell line variant may be created that expresses seventeen immunomodulators simultaneously. According to some embodiments, a tumor cell line or tumor cell line variant may be created that expresses eighteen immunomodulators simultaneously. According to some embodiments, a tumor cell line or tumor cell line variant may be created that expresses nineteen immunomodulators simultaneously. According to some embodiments, a tumor cell line or tumor cell line variant may be created that expresses twenty immunomodulators simultaneously. According to some embodiments, a tumor cell line or tumor cell line variant may be created that expresses twenty-one immunomodulators simultaneously. According to some embodiments, a tumor cell line or tumor cell line variant may be created that expresses twenty-two immunomodulators simultaneously. According to some embodiments, a tumor cell line or tumor cell line variant may be created that expresses twenty-three immunomodulators simultaneously. According to some embodiments, a tumor cell line or tumor cell line variant may be created that expresses twenty-four immunomodulators simultaneously. According to some embodiments, a tumor cell line or tumor cell line variant may be created that expresses twenty-five immunomodulators simultaneously. According to some embodiments, a tumor cell line or tumor cell line variant may be created that expresses twenty-six immunomodulators simultaneously. According to some embodiments, a tumor cell line or tumor cell line variant may be created that expresses twenty-seven immunomodulators simultaneously. According to some embodiments, a tumor cell line or tumor cell line variant may be created that expresses twenty-eight immunomodulators simultaneously. According to some embodiments, a tumor cell line or tumor cell line variant may be created that expresses twenty-nine immunomodulators simultaneously. According to some embodiments, a tumor cell line or tumor cell line variant may be created that expresses thirty immunomodulators simultaneously.

Variably Expressing Clones

According to one aspect of the disclosed invention, multiple recombinant immunomodulator peptides may be expressed in a single clonally derived tumor cell line or tumor cell line variant. According to some embodiments, the amount (or level) of each individual immunomodulator expressed in each cell is the same as the level of expression of all other immunomodulator peptides. According to some embodiments, however, the level of each individual immunomodulator expressed in each cell is different from the level of expression of the other immunomodulators expressed in the cell. According to some embodiments, clonally derived tumor cell line or tumor cell line variants that express the same complement of immunomodulators stably express those immunomodulators in varying amounts relative to each other.

The relative amount of recombinant immune modulator expressed within each clonally derived tumor cell line or tumor cell line variant, and between tumor cell line or tumor cell line variants, can be measured on the level of transcription or translation. For example, the relative amount of recombinant immunomodulator can be quantified by western blot, RT-PCR, flow cytometry, immunofluorescence, and northern blot, among others.

According to some embodiments, the differences in the amount of expressed immunomodulators relative to one another may be a result of random integration into more or less transcriptionally active regions of the genome of the tumor cell line or tumor cell line variant. According to some embodiments, the relative differences in the amount of expressed immunomodulator may be achieved by elements engineered into the transfected or transduced DNA used to create the tumor cell line or tumor cell line variant.

For example, according to some embodiments, the level of expression of the exogenous immunomodulatory molecules may be achieved on the transcriptional level by engineering stronger or weaker gene promoter sequences to control expression of the immune modulator gene. According to some embodiments, one or more of the following promoters may be used to control expression of immunomodulators: simian virus 40 early promoter (SV40), cytomegalovirus immediate-early promoter (CMV), human Ubiquitin C promoter (UBC), human elongation factor 1α promoter (EF1A), mouse phosphoglycerate kinase 1 promoter (PGK), and chicken β-Actin promoter coupled with CMV early enhancer (CAGG).

According to some embodiments, the level of expression of the exogenous immunomodulatory molecules may be achieved on the translational level by engineering stronger or weaker Kozak consensus sequences around the start codon of the immunomodulator transcript. According to some embodiments, the following nucleotide sequences may be provided to control immune modulator translation: GCCGCC(A/G)CCAUGG (SEQ ID NO: 15). According to some embodiments, a sequence that is at least 60% identical to SEQ ID NO: 15 may be provided to control immunomodulator translation. According to some embodiments, a sequence that is at least 70% identical to SEQ ID NO: 15 may be provided to control immunomodulator translation. According to some embodiments, a sequence that is at least 80% identical to SEQ ID NO: 15 may be provided to control immunomodulator translation. According to some embodiments, a sequence that is at least 90% identical to SEQ ID NO: 15 may be provided to control immunomodulator translation. According to some embodiments, a sequence that is at least 95% identical to SEQ ID NO: 15 may be provided to control immunomodulator translation. According to some embodiments, a sequence that is at least 96% identical to SEQ ID NO: 15 may be provided to control immunomodulator translation. According to some embodiments, a sequence that is at least 97% identical to SEQ ID NO: 15 may be provided to control immunomodulator translation. According to some embodiments, a sequence that is at least 98% identical to SEQ ID NO: 15 may be provided to control immunomodulator translation. According to some embodiments, a sequence that is at least 99% identical to SEQ ID NO: 15 may be provided to control immunomodulator translation.

Non-viral approaches can also be employed for the introduction of a vector encoding one or more immunomodulatory molecules to a cell derived from a patient having a tumor or a tumor cell line or variant. For example, a nucleic acid molecule encoding an immunomodulatory molecule can be introduced into a cell by administering the nucleic acid molecule in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by microinjection under surgical conditions (Wolff et al., Science 247:1465, 1990). Preferably the nucleic acids are administered in combination with a liposome and protamine.

Methods for accomplishing transfection in vitro include the use of calcium phosphate, DEAE dextran, electroporation, and protoplast fusion. Liposomes can also be potentially beneficial for delivery of DNA into a cell.

According to some embodiments, immunomodulators whose functionality has been modified by genetic engineering are intended to be included within the scope of the claimed invention. For example, an immunomodulator may be modified by genetic engineering to change a signal sequence, to make the immunomodulator product a secreted product, to increase stability of the immunomodulator in the membrane; to alter key amino acids, or to codon optimize sequences for humans. All such modification are included within the scope of the claimed invention.

Example 3 below describes 47 lentiviral vectors (vector 44, vector 97, vector 84, vector 29, vector 107, vector 116, vector 86, vector 18, vector 17, vector 98, vector 5, vector 30, vector 109, vector 3, vector 4, vector 106, vector 16, vector 83, vector 31, vector 12, vector 99, vector 121, vector 105, vector 32, vector 37, vector 22, vector 19, vector 20, vector 89, vector 21, vector 23, vector 108, vector 15, vector 124, vector 65, vector 64, vector 88, vector 96, vector 14, vector 119, vector 120, vector 45, vector 60, vector 59, vector 8, vector 128, vector 35, and vector 6) that may be used to stably integrate immunomodulators into the cell genome.

According to some embodiments, vector 44 comprises one or more TNF family member immunomodulators. According to some embodiments, vector 29 comprises one or more TNF family member immunomodulators. According to some embodiments, vector 18 comprises one or more TNF family member immunomodulators. According to some embodiments, vector 17 comprises one or more TNF family member immunomodulators. According to some embodiments, vector 5 comprises one or more TNF family member immunomodulators. According to some embodiments, vector 16 comprises one or more TNF family member immunomodulators. According to some embodiments, vector 99 comprises one or more TNF family member immunomodulators. According to some embodiments, vector 15 comprises one or more TNF family member immunomodulators. According to some embodiments, vector 14 comprises one or more TNF family member immunomodulators. According to some embodiments, vector 45 comprises one or more TNF family member immunomodulators. According to some embodiments, vector 6 comprises one or more TNF family member immunomodulators. According to some embodiments, the one or more TNF family immunomodulators are selected from those listed in Table 6 or Table 7.

According to some embodiments, vector 44 comprises between 3-25, inclusive TNF family member immunomodulators. According to some embodiments, vector 29 comprises between 3-25, inclusive TNF family member immunomodulators. According to some embodiments, vector 18 comprises between 3-25, inclusive TNF family member immunomodulators. According to some embodiments, vector 17 comprises between 3-25, inclusive TNF family member immunomodulators. According to some embodiments, vector 5 comprises between 3-25, inclusive TNF family member immunomodulators. According to some embodiments, vector 16 comprises between 3-25, inclusive TNF family member immunomodulators. According to some embodiments, vector 99 comprises between 3-25, inclusive TNF family member immunomodulators. According to some embodiments, vector 15 comprises between 3-25, inclusive TNF family member immunomodulators. According to some embodiments, vector 14 comprises between 3-25, inclusive TNF family member immunomodulators. According to some embodiments, vector 45 comprises between 3-25, inclusive TNF family member immunomodulators. According to some embodiments, vector 6 comprises between 3-25, inclusive TNF family member immunomodulators. According to some embodiments, the between 3-25, inclusive TNF family immunomodulators are selected from those listed in Table 6 or Table 7.

According to some embodiments, vector 97 comprises one or more Ig family member immunomodulators. According to some embodiments, vector 84 comprises one or more Ig family member immunomodulators. According to some embodiments, vector 107 comprises one or more Ig family member immunomodulators. According to some embodiments, vector 98 comprises one or more Ig family member immunomodulators. According to some embodiments, vector 30 comprises one or more Ig family member immunomodulators. According to some embodiments, vector 83 comprises one or more Ig family member immunomodulators. According to some embodiments, vector 121 comprises one or more Ig family member immunomodulators. According to some embodiments, vector 119 comprises one or more Ig family member immunomodulators. According to some embodiments, the one or more Ig family member immunomodulators are selected from those listed in Table 6 or Table 7.

According to some embodiments, vector 97 comprises between 3-25, inclusive Ig family member immunomodulators. According to some embodiments, vector 84 comprises between 3-25, inclusive Ig family member immunomodulators. According to some embodiments, vector 107 comprises between 3-25, inclusive Ig family member immunomodulators. According to some embodiments, vector 98 comprises between 3-25, inclusive Ig family member immunomodulators. According to some embodiments, vector 30 comprises between 3-25, inclusive Ig family member immunomodulators. According to some embodiments, vector 83 comprises between 3-25, inclusive Ig family member immunomodulators. According to some embodiments, vector 121 comprises between 3-25, inclusive Ig family member immunomodulators. According to some embodiments, vector 119 comprises between 3-25, inclusive Ig family member immunomodulators. According to some embodiments, the between 3-25, inclusive Ig family member immunomodulators are selected from those listed in Table 6 or Table 7.

According to some embodiments, vector 116 comprises one or more chemokine immunomodulators. According to some embodiments, the one or more chemokine immunomodulators are selected from those listed in Table 6 or Table 7.

According to some embodiments, vector 116 comprises between 3-25, inclusive chemokine immunomodulators. According to some embodiments, the between 3-25, inclusive chemokine immunomodulators are selected from those listed in Table 6 or Table 7.

According to some embodiments, vector 109 comprises one or more growth factor immunomodulators.

According to some embodiments, vector 109 comprises between 3-25, inclusive growth factor immunomodulators.

According to some embodiments, vector 3 comprises one or more cytokine immunomodulators. According to some embodiments, vector 4 comprises one or more cytokine immunomodulators. According to some embodiments, vector 32 comprises one or more cytokine immunomodulators. According to some embodiments, vector 22 comprises one or more cytokine immunomodulators. According to some embodiments, vector 19 comprises one or more cytokine immunomodulators. According to some embodiments, vector 20 comprises one or more cytokine immunomodulators. According to some embodiments, vector 89 comprises one or more cytokine immunomodulators. According to some embodiments, vector 21 comprises one or more cytokine immunomodulators. According to some embodiments, vector 23 comprises one or more cytokine immunomodulators. According to some embodiments, vector 121 comprises one or more cytokine immunomodulators. According to some embodiments, vector 65 comprises one or more cytokine immunomodulators. According to some embodiments, vector 64 comprises one or more cytokine immunomodulators. According to some embodiments, vector 88 comprises one or more cytokine immunomodulators. According to some embodiments, vector 96 comprises one or more cytokine immunomodulators. According to some embodiments, vector 60 comprises one or more cytokine immunomodulators. According to some embodiments, vector 59 comprises one or more cytokine immunomodulators. According to some embodiments, vector 128 comprises one or more cytokine immunomodulators. According to some embodiments, the one or more cytokine immunomodulators are selected from those listed in Table 6 or Table 7.

According to some embodiments, vector 3 comprises between 3-25, inclusive cytokine immunomodulators. According to some embodiments, vector 4 comprises between 3-25, inclusive cytokine immunomodulators. According to some embodiments, vector 32 comprises between 3-25, inclusive cytokine immunomodulators. According to some embodiments, vector 22 comprises between 3-25, inclusive cytokine immunomodulators. According to some embodiments, vector 19 comprises between 3-25, inclusive cytokine immunomodulators. According to some embodiments, vector 20 comprises between 3-25, inclusive cytokine immunomodulators. According to some embodiments, vector 89 comprises between 3-25, inclusive cytokine immunomodulators. According to some embodiments, vector 21 comprises between 3-25, inclusive cytokine immunomodulators. According to some embodiments, vector 23 comprises between 3-25, inclusive cytokine immunomodulators. According to some embodiments, vector 121 comprises between 3-25, inclusive cytokine immunomodulators. According to some embodiments, vector 65 comprises between 3-25, inclusive cytokine immunomodulators. According to some embodiments, vector 64 comprises between 3-25, inclusive cytokine immunomodulators. According to some embodiments, vector 88 comprises between 3-25, inclusive cytokine immunomodulators. According to some embodiments, vector 96 comprises between 3-25, inclusive cytokine immunomodulators. According to some embodiments, vector 60 comprises between 3-25, inclusive cytokine immunomodulators. According to some embodiments, vector 59 comprises between 3-25, inclusive cytokine immunomodulators. According to some embodiments, vector 128 comprises between 3-25, inclusive cytokine immunomodulators. According to some embodiments, the between 3-25, inclusive cytokine immunomodulators are selected from those listed in Table 6 or Table 7.

According to some embodiments, vector 37 comprises one or more receptor immunomodulators. According to some embodiments, vector 124 comprises one or more receptor immunomodulators. According to some embodiments, vector 88 comprises one or more receptor immunomodulators. According to some embodiments, vector 8 comprises one or more receptor immunomodulators. According to some embodiments, the one or more receptor immunomodulators are selected from those listed in Table 6 or Table 7.

According to some embodiments, vector 37 comprises between 3-25, inclusive receptor immunomodulators. According to some embodiments, vector 124 comprises between 3-25, inclusive receptor immunomodulators. According to some embodiments, vector 88 comprises between 3-25, inclusive receptor immunomodulators. According to some embodiments, vector 8 comprises between 3-25, inclusive receptor immunomodulators. According to some embodiments, the between 3-25, inclusive receptor immunomodulators are selected from those listed in Table 6 or Table 7.

According to some embodiments, vector 86 comprises one or more other immunomodulators. According to some embodiments, vector 106 comprises one or more other immunomodulators. According to some embodiments, vector 107 comprises one or more other immunomodulators. According to some embodiments, vector 31 comprises one or more other immunomodulators. According to some embodiments, vector 12 comprises one or more other immunomodulators. According to some embodiments, vector 105 comprises one or more other immunomodulators. According to some embodiments, vector 108 comprises one or more other immunomodulators. According to some embodiments, vector 120 comprises one or more other immunomodulators. According to some embodiments, vector 35 comprises one or more other immunomodulators. According to some embodiments, the one or more other immunomodulators are selected from those listed in Table 6 or Table 7.

According to some embodiments, vector 86 comprises between 3-25, inclusive other immunomodulators. According to some embodiments, vector 106 comprises between 3-25, inclusive other immunomodulators. According to some embodiments, vector 107 comprises between 3-25, inclusive other immunomodulators. According to some embodiments, vector 31 comprises between 3-25, inclusive other immunomodulators. According to some embodiments, vector 12 comprises between 3-25, inclusive other immunomodulators. According to some embodiments, vector 105 comprises between 3-25, inclusive other immunomodulators. According to some embodiments, vector 108 comprises between 3-25, inclusive other immunomodulators. According to some embodiments, vector 120 comprises between 3-25, inclusive other immunomodulators. According to some embodiments, vector 35 comprises between 3-25, inclusive other immunomodulators. According to some embodiments, the between 3-25, inclusive other immunomodulators are selected from those listed in Table 6 or Table 7.

According to one embodiment of the disclosed invention, combinations of allogeneic cell pools, each expressing a single immunomodulatory protein, are used to model what a single cell expressing multiple immunomodulatory proteins might do (e.g. additivity, synergy, interference)

Example 3

A schematic of the core lentiviral vectors employed is shown in FIG. 1. The promoter is human elongation factor 1 alpha (EF1α) promoter and the internal ribosomal entry sequence (IRES) is derived from encephalomyocarditis virus (EMCV). The core vectors are described in detail hereinbelow:

Vector 1. Immunomodulator: scFv-anti-biotin-G3hinge-mIgG1 (to Generate Surface IgG).

Figure 2:
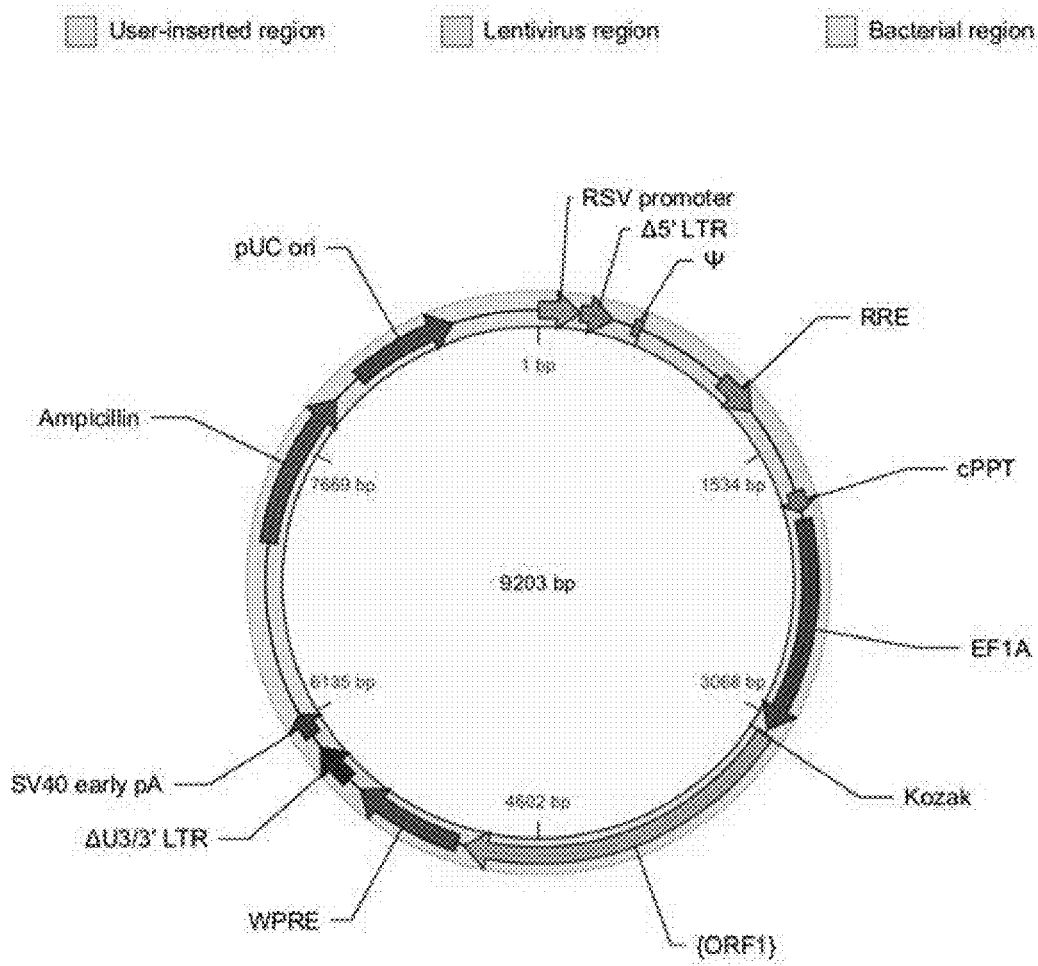
FIG. 2 shows a schematic of the organization of the scFv-anti-biotin-G3hinge-mIgG1 vector 1.
Figure 3:
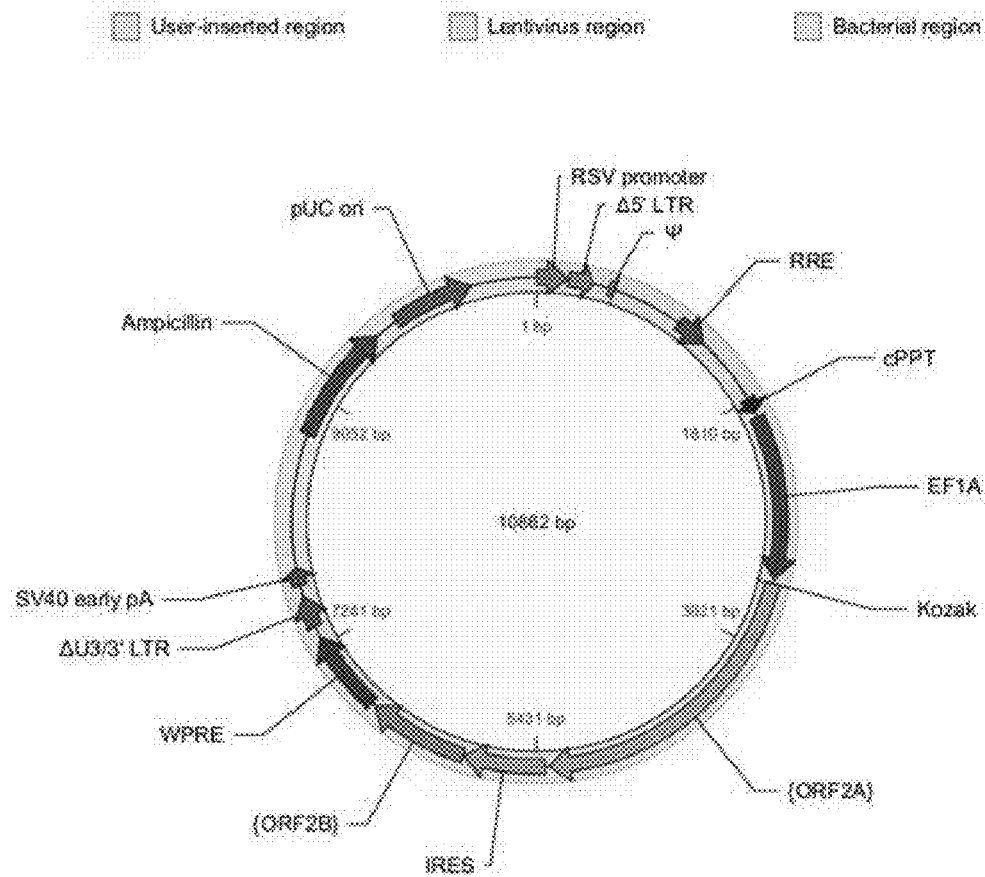
FIG. 3 shows a schematic of the organization of the full anti-biotin-G3hinge-mIgG1 vector 2.
Figure 4:
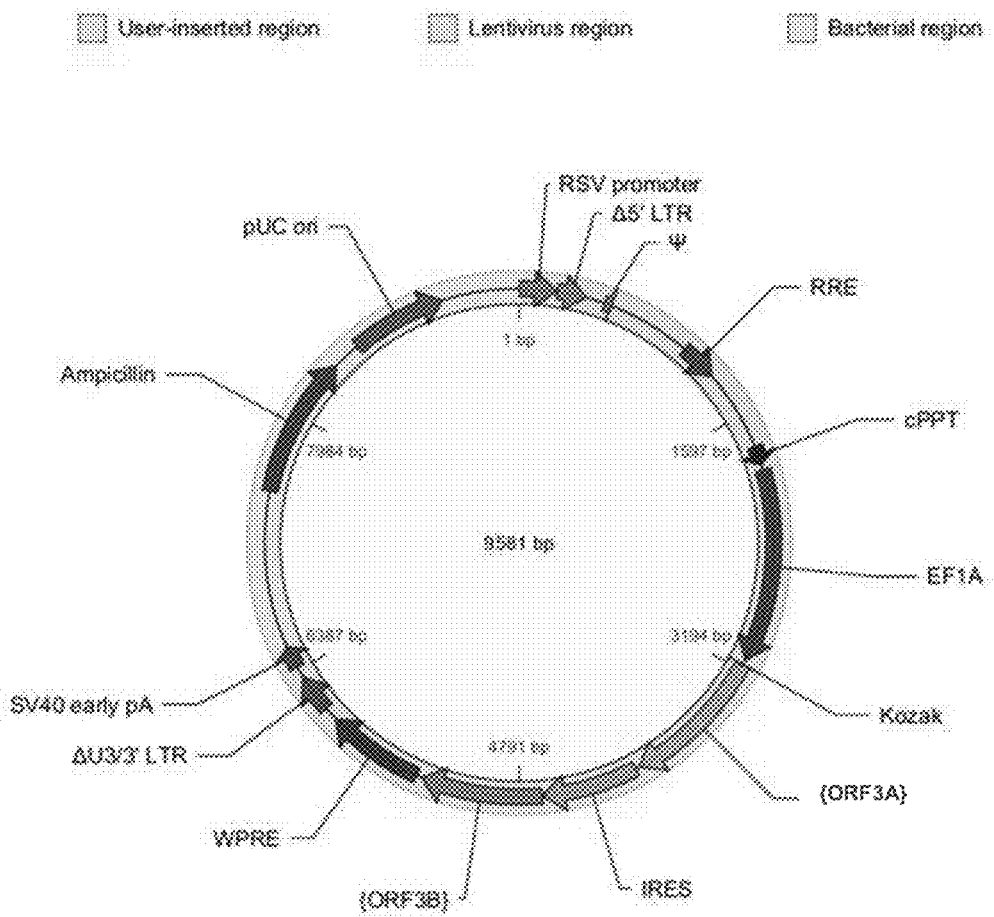
FIG. 4 shows a schematic of the organization of the sGM-CSF/ires/mFLT3L vector 3.
Figure 5:
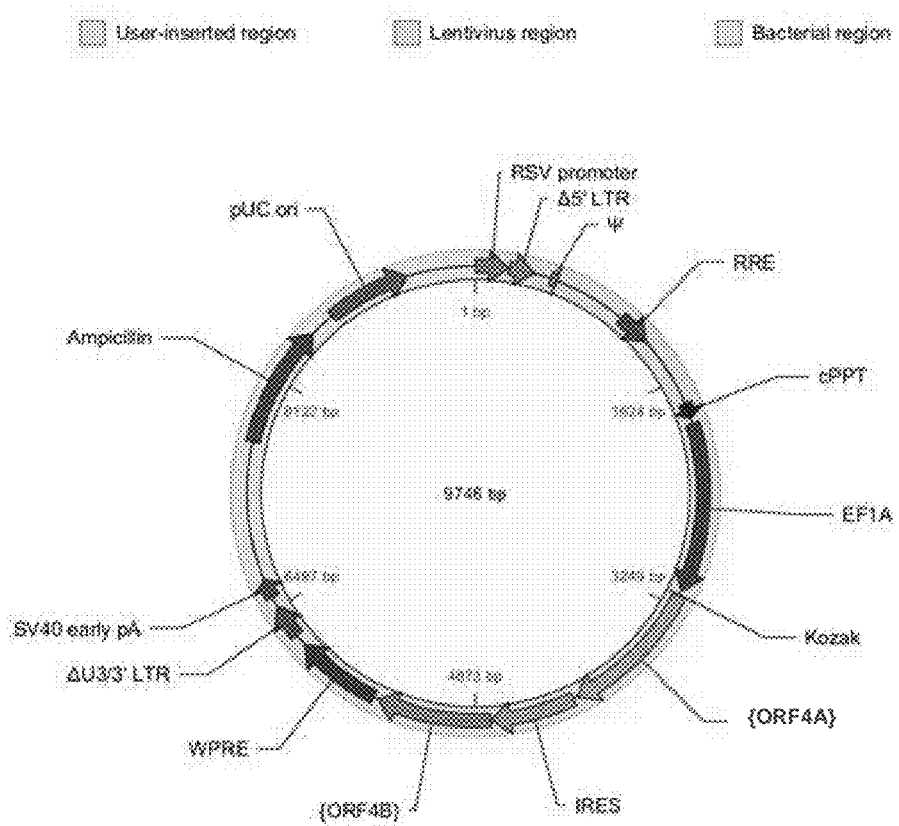
FIG. 5 shows a schematic of the organization of the sFLT3L/ires/(FLT3 signal-GM-CSF-Tm) vector 4.
Figure 6:
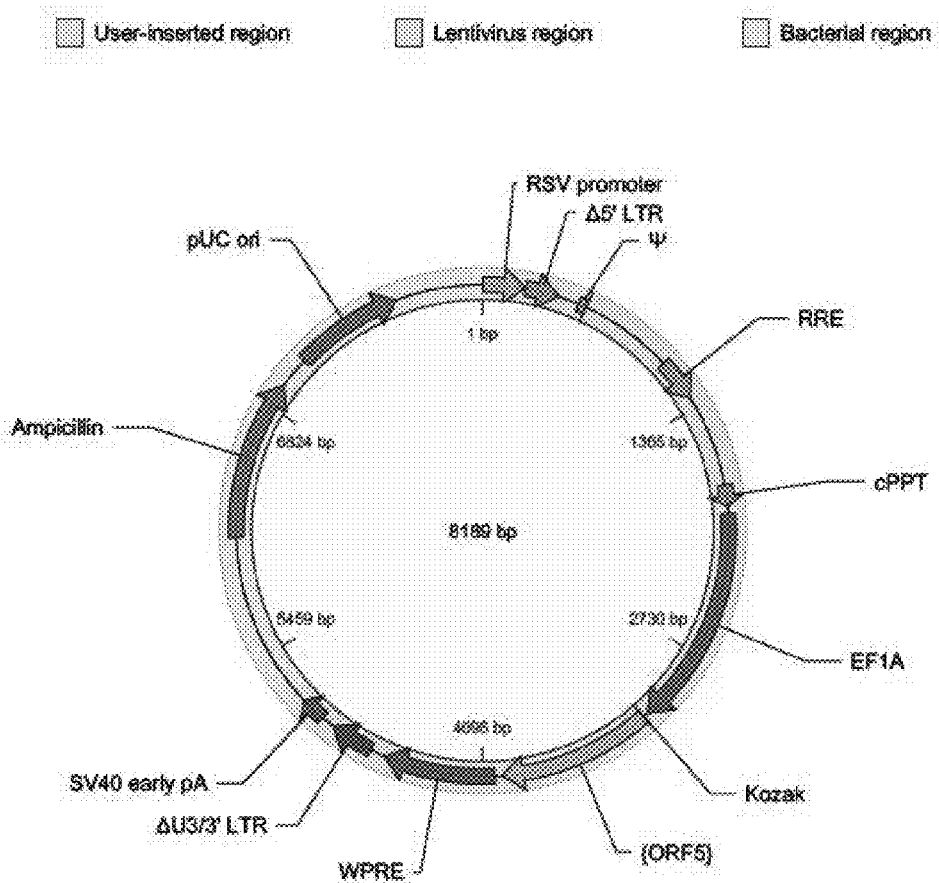
FIG. 6 shows a schematic of the organization of the mCD40L vector 5.

A schematic of the organization of vector 1, used for the immunomodulator scFv-anti-biotin-G3hinge-mIgG1 is shown in FIG. 2. Table 11, below, shows the vector component name, the corresponding nucleotide position, the full name of the component and a description.

TABLE 11

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRET | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1959-3137 | EF1A | Component entered by user |
| Kozak | 3162-3167 | Kozak | Component entered by user |
| {ORF1} | 3168-5005 | {ORF1} | Component entered by user |
| WPRE | 5044-5641 | Woodchuck hepatitis virus posttranscriptional regulatory element | Facilitates effective transcription termination at the 3'TLTR.T |
| ΔU3/3' LTR | 5723-5957 | HIV-1 truncated 3' LTR | Allows viral packaging but self-inactivates the 5'LTR for biosafety purposes. The element also contains apolyadenylation signal for transcription termination and polyadenylation of mRNA in transduced cells. |

TABLE 11-continued

| Component Name | Nucleotide Position | Full Name | Description |
|---|---|---|---|
| SV40 early pA | 6030-6164 | SV40 early polyadenation signal | Allows transcription termination and polyadenylation of mRNA. |
| Ampicillin | 7118-7978 | Ampicillin resistance gene | Allows selection of the plasmid in E. coli. |
| pUC ori | 8149-8737 | pUC origin of replication | Permits high-copy replication and maintenance in E. coli. |

When vector 1 is employed, anti-IgG is used for flow detection. A biotin+fluorescent labelled oligodeoxynucleotides (ODN) is used as a secondary detection method. The following is a description of the immunomodulator scFv-anti-biotin-G3hinge-IgG1-Tm.
Type: Immunoglobulin Annotation:

H7 heavy chain leader

Anti-biotin Variable Heavy chain (VH) allows for loading biotin labeled CpG

Inter-domain disulfide linkage VH44 (G→C) and VL100 (G→C)

IgG3 hinge to enhance FcγR interaction

Linkage is standard

IgG1 (CH2-CH3-Tm-Cyt) used for interaction with FcγR/FcRn and membrane anchoring T233A mutation to enhance FcRn and FcγR interaction Vector 2. Immunomodulator: Full Anti-Biotin-G3hinge-mIgG1 (Using Heavy Chain/Ices/Light Chain)

A schematic of the organization of vector 2, used for the immunomodulator full anti-biotin-G3hinge-mIgG1 is shown in FIG. 3. Vector 2 is bicistronic.

Table 12, below, shows the vector component name, the corresponding nucleotide position in SEQ ID NO. 48, the full name of the component and a description.

TABLE 12

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-56g | HIV-1 psi packaging signal | Allows viral packaging. |
| RRET | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1950-3128 | EF1A | Component entered by user |
| Kozak | 3153-3158 | Kozak | Component entered by user |
| {ORF1} | 3159-5342 | {ORF1} | Component entered by user |
| WPRE | 6703-7300 | Woodchuck hepatitis virus posttranscriptional regulatory element | Facilitates effective transcription termination at the 3'TLTR.T |
| ΔU3/3' LTR | 7382-7616 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 7689-7823 | SV40 early polyadenation signal | Allows transcription termination and polyadenylation of mRNA. |
| Ampicillin | 8777-9637 | Ampicillin resistance gene | Allows selection of the plasmid in *E. coli*. |
| pUC ori | 9808-10396 | pUC origin of replication | Permits high-copy replication and maintenance in *E. coli*. |

When vector 2 is employed, anti-IgG is used for flow detection. Biotin+fluorescent labelled ODN is used as a secondary detection method.

The following is a description of the immunomodulator full anti-biotin-G3hinge-mIgG1 (using heavy chain/ires/light chain).
Type: Membrane anchored Immunoglobulin
  Annotation:
  H7 heavy chain leader
  IgG3 hinge to enhance FcyR interaction
  T233A mutation to enhance FcRn and FcyR interaction
  Anti-biotin Variable H allows for loading biotin labeled CpG CH1 (generic)

LC Variable (human lambda variable)

LC Constant Region 1 from Lambda (http://www.uniprot.org/uniprot/POCG04)

Interdomain disulfide linkage VH44 (G→C) and VL100 (G→C) (ref)

Linkage is standard

IgG1 (CH2-CH3-Tm-Cyt) for interaction with FcyR/FcRn and membrane anchoring

Vector 3. Immunomodulator: sGM-CSF/ires/mFLT3L

A schematic of the organization of vector 3, used for the immunomodulator sGM-CSF/ires/mFLT3L is shown inFIG. 4. Vector 3 is bicistronic. Table 13, below, shows the vector component name, the corresponding nucleotide position in SEQ ID NO. 49, the full name of the component and a description.

TABLE 13

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRET | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1950-3128 | EF1A | Component entered by user |
| Kozak | 3153-3158 | Kozak | Component entered by user |
| {ORF3A_wSPACER} | 3159-4040 | {ORF3A_wSPACER} | Component entered by user |
| IRES | 4065-4652 | IRES | Component entered by user |
| {ORF3B} | 4653-5392 | {ORF3B} | Component entered by user |
| WPRE | 5422-6019 | Woodchuck hepatitis virus posttranscriptional regulatory element | Facilitates effective transcription termination at the 3' LTR. |
| AU3/3' LTR | 6101-6335 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 6408-6542 | SV40 early polyadenation signal | Allows transcription termination and polyadenylation of mRNA. |
| Ampicillin | 7496-8356 | Ampicillin resistance gene | Allows selection of the plasmid in *E. coli.* |
| pUC ori | 8527-9115 | pUC origin of replication | Permits high-copy replication and maintenance in *E. coli.* |

When vector 3 is employed, anti-FLT3L is used for flow detection. The highest surface FLT3L expressor will have the highest secreted GM-CSF expression.

The following is a description of the immunomodulator sGM-CSF/ires/mFLT3L.

Type: cytokine, growth and differentiation factor

Annotation: wild-type sequence

Vector 4. Immunomodulator: sFLT3L/ires/(FLT3 Signal-GM-CSF-Tm)

A schematic of the organization of vector 4, used for the immunomodulator sFLT3L/ires/(FLT3 signal-GM-CSF-Tm) is shown in FIG. 5. Vector 4 is bicistronic. Table 14, below, shows the vector component name, the corresponding nucleotide position in SEQ ID NO. 50, the full name of the component and a description.

TABLE 14

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRET | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1950-3128 | EF1A | Component entered by user |
| Kozak | 3153-3158 | Kozak | Component entered by user |
| {ORF4A_wSPACER} | 3159-4157 | {ORF4A_wSPACER} | Component entered by user |
| IRES | 4182-4769 | IRES | Component entered by user |
| {ORF4B} | 4770-5557 | {ORF4B} | Component entered by user |
| WPRE | 5587-6184 | Woodchuck hepatitis virus posttranscriptional regulatory element | Facilitates effective transcription termination at the 3' LTR. |
| ΔU3/3' LTR | 6266-6500 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 6573-6707 | SV40 early polyadenation signal | Allows transcription termination and polyadenylation of mRNA. |
| Ampicillin | 7661-8521 | Ampicillin resistance gene | Allows selection of the plasmid in E. coli. |
| pUC ori | 8692-9280 | pUC origin of replication | Permits high-copy replication and maintenance in E. coli. |

When vector 4 is employed, anti-GM-CSF is used for flow detection. The highest surface GMCSF expressor will have highest secreted FLT3L expression.

The following is a description of the immunomodulator sFLT3L/ires/(FLT3 signal-GM-CSF-Tm)
Type: cytokine, growth and differentiation factor
Annotation: wild-type sequence Vector 5. Immunomodulator: mCD40L A schematic of the organization of vector 5, used for the immunomodulator mCD40L is shown in FIG. 6. Vector 5 is monocistronic. Table 15, below, shows the vector component name, the corresponding nucleotide position, the full name of the component and a description.

TABLE 15

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRET | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1959-3137 | EF1A | Component entered by user |
| Kozak | 3162-3167 | Kozak | Component entered by user |
| {ORF5} | 3168-3991 | {ORF5} | Component entered by user |
| WPRE | 4030-4627 | Woodchuck hepatitis virus posttranscriptional regulatory element | Facilitates effective transcription termination at the 3' LTR. |
| AU3/3' LTR | 4709-4943 | HIV-1 truncated 3' LTR | Allows viral packaging but self-inactivates the 5'LTR for biosafety purposes. The element also contains apolyadenylation signal for transcription termination and polyadenylation of mRNA in transduced cells. |

TABLE 15-continued

| Component Name | Nucleotide Position | Full Name | Description |
|---|---|---|---|
| SV40 early pA | 5016-5150 | SV40 early polyadenation signal | Allows transcription termination and polyadenylation of mRNA. |
| Ampicillin | 6104-6964 | Ampicillin resistance gene | Allows selection of the plasmid in E. coli. |
| pUC ori | 7135-7723 | pUC origin of replication | Permits high-copy replication and maintenance in E. coli. |

When Vector 5 is employed, anti-CD40L is used for flow detection.

The following is a description of the immunomodulator mCD40L.

Type: TNF type II transmembrane protein

Annotation: Mutations introduced to make a non-cleavable version.

Vector 6. Immunomodulator: mTNFalpha (TNFα)

Figure 7:
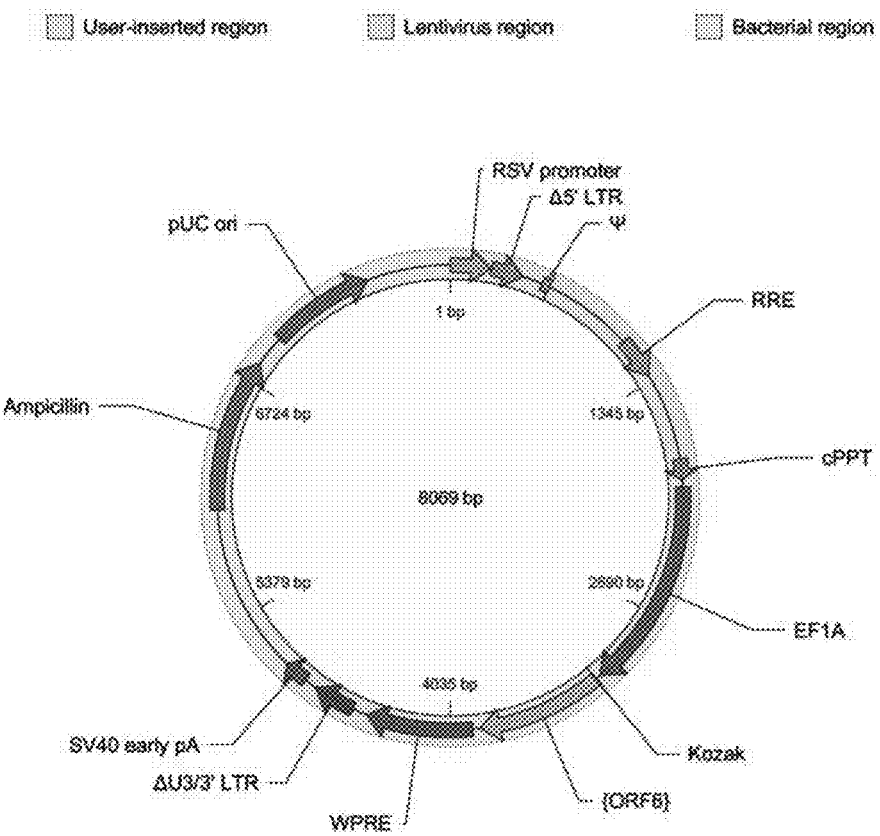
FIG. 7 shows a schematic of the organization of the mTNFa vector 6.

A schematic of the organization of vector 6, used for the immunomodulator mTNFα is shown in FIG. 7. Vector 6 is monocistronic. Table 16, below, shows the vector component name, the corresponding nucleotide position in SEQ ID NO. 52, the full name of the component and a description.

TABLE 16

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRET | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1959-3137 | EF1A | Component entered by user |
| Kozak | 3162-3167 | Kozak | Component entered by user |
| {ORF6} | 3168-3871 | {ORF6} | Component entered by user |
| WPRE | 3910-4507 | Woodchuck hepatitis virus posttranscriptional regulatory element | Facilitates effective transcription termination at the 3' LTR. |
| ΔU3/3' LTR | 4859-4823 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 4896-5030 | SV40 early polyadenation signal | Allows transcription termination and polyadenylation of mRNA. |
| Ampicillin | 5984-6844 | Ampicillin resistance gene | Allows selection of the plasmid in E. coli. |
| pUC ori | 7015-7603 | pUC origin of replication | Permits high-copy replication and maintenance in E. coli. |

When vector 6 is employed, anti-TNFα is used for flow detection.

The following is a description of the immunomodulator mTNFα.

Type: TNF type II transmembrane protein

Annotation: Mutations were introduced to make a non-cleavable version.

Vector 7. Immunomodulator: mRANKL/ires/FLT3 Signal-V5-scFV Anti-Biotin-Tm

Figure 8:
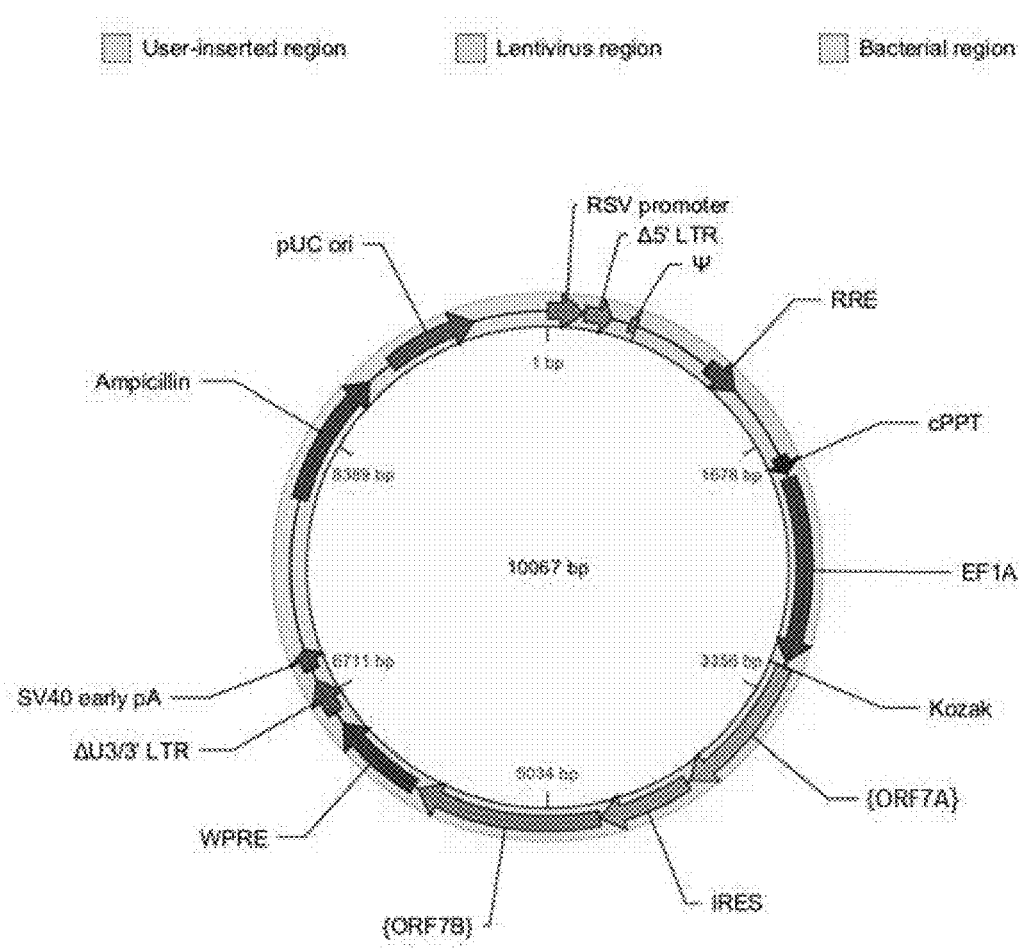
FIG. 8 shows a schematic of the organization of the mRANKL/ires/FLT3 signal-V5-scFV anti-biotin-Tm vector 7.

A schematic of the organization of vector 7, used for the immunomodulator mRANKL/ires/FLT3 signal-V5-scFV anti-biotin-Tm is shown in FIG. 8. Table 17, below, shows the vector component name, the corresponding nucleotide position, the full name of the component and a description.

TABLE 17

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRET | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1950-3128 | EF1A | Component entered by user |
| Kozak | 3153-3158 | Kozak | Component entered by user |
| {ORF7_wSPACER} | 3159-4091 | {ORF7_wSPACER} | Component entered by user |
| IRES | 4116-4703 | IRES | Component entered by user |
| {ORF7B} | 4704-5878 | {ORF7B} | Component entered by user |
| WPRE | 5908-6505 | Woodchuck hepatitis virus posttranscriptional regulatory element | Facilitates effective transcription termination at the 3' LTR. |
| ΔU3/3' LTR | 6587-3821 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 6894-7028 | SV40 early polyadenation signal | Allows transcription termination and polyadenylation of mRNA. |
| Ampicillin | 7982-8842 | Ampicillin resistance gene | Allows selection of the plasmid in E. coli. |
| pUC ori | 9013-9601 | pUC origin of replication | Permits high-copy replication and maintenance in E. coli. |

When vector 7 is employed, anti-RANKL is used for flow detection. Anti-V5 mAb is used as a secondary detection method.

Figure 9:
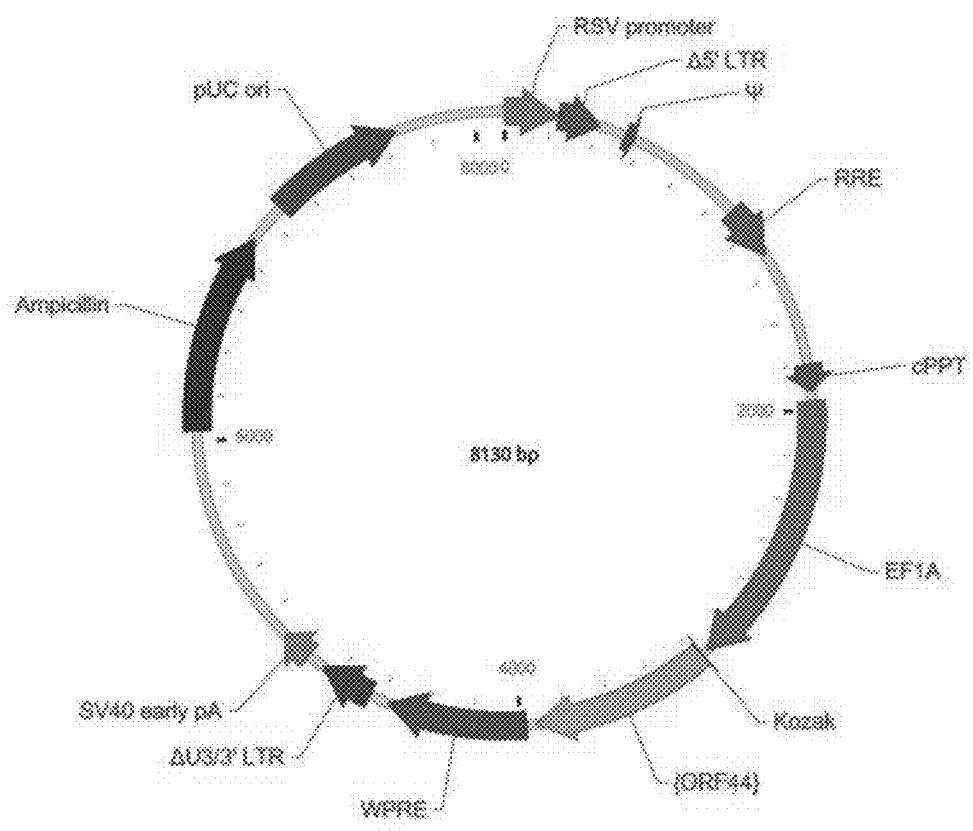
FIG. 9 shows a schematic of vector 44.

The following is a description of the immunomodulator mRANKL/ires/FLT3 signal-V5-scFV anti-biotin-Tm.
Type: TNF type II transmembrane protein
Annotation: wild-type sequence
Vector 44
FIG. 9 shows a schematic of vector 44.

Table 18 below, shows the vector component name, the corresponding nucleotide position, the full name of the component and a description.

TABLE 18

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF44A} | 3168-3932 | 765 | None |
| WPRE | 3971-4568 | 598 | Woodchuck hepatitis virus posttranscriptional regulatory element |
| ΔU3/3' LTR | 4650-4884 | 235 | Truncated HIV-1 3' long terminal repeat |
| SV40 early pA | 4957-5091 | 135 | Simian virus 40 early polyadenylation signal |
| Ampicillin | 6045-6905 | 861 | Ampicillin resistance gene |
| pUC ori | 7076-7664 | 589 | pUC origin of replication |

Vector 97

Figure 10:
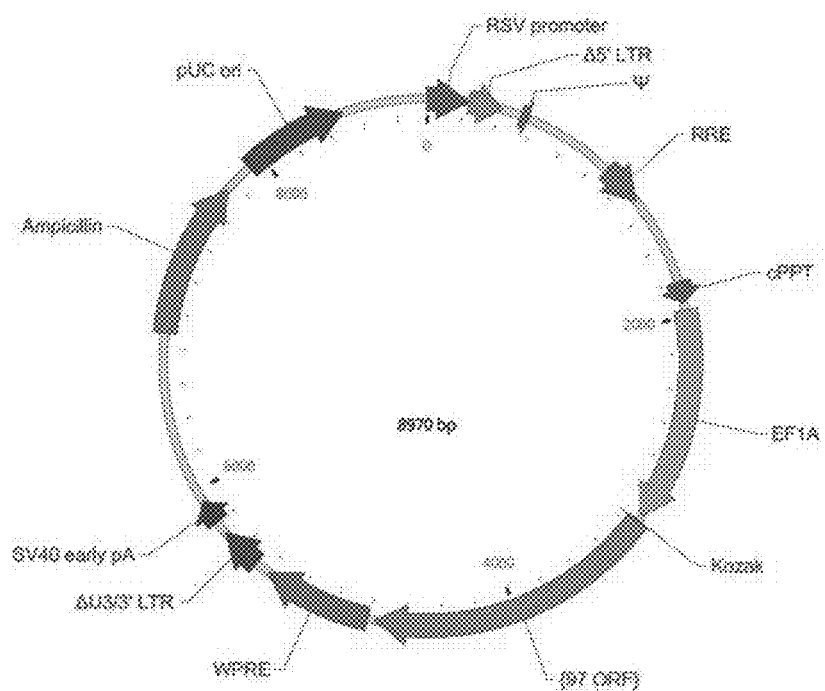
FIG. 10 shows a schematic of vector 97.

FIG. 10 shows a schematic of vector 97.

Table 19 below, shows the vector component name, the corresponding nucleotide position, the full name of the component and a description.

TABLE 19

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF97} | 3168-4772 | 1605 | None |
| WPRE | 4811-5408 | 598 | Woodchuck hepatitis virus posttranscriptional regulatory element |
| ΔU3/3' LTR | 5490-5724 | 235 | Truncated HIV-1 3' long terminal repeat |
| SV40 early pA | 5797-5931 | 135 | Simian virus 40 early polyadenylation signal |
| Ampicillin | 6885-7745 | 861 | Ampicillin resistance gene |
| pUC ori | 7916-8504 | 589 | pUC origin of replication |

Vector 84.

Figure 11:
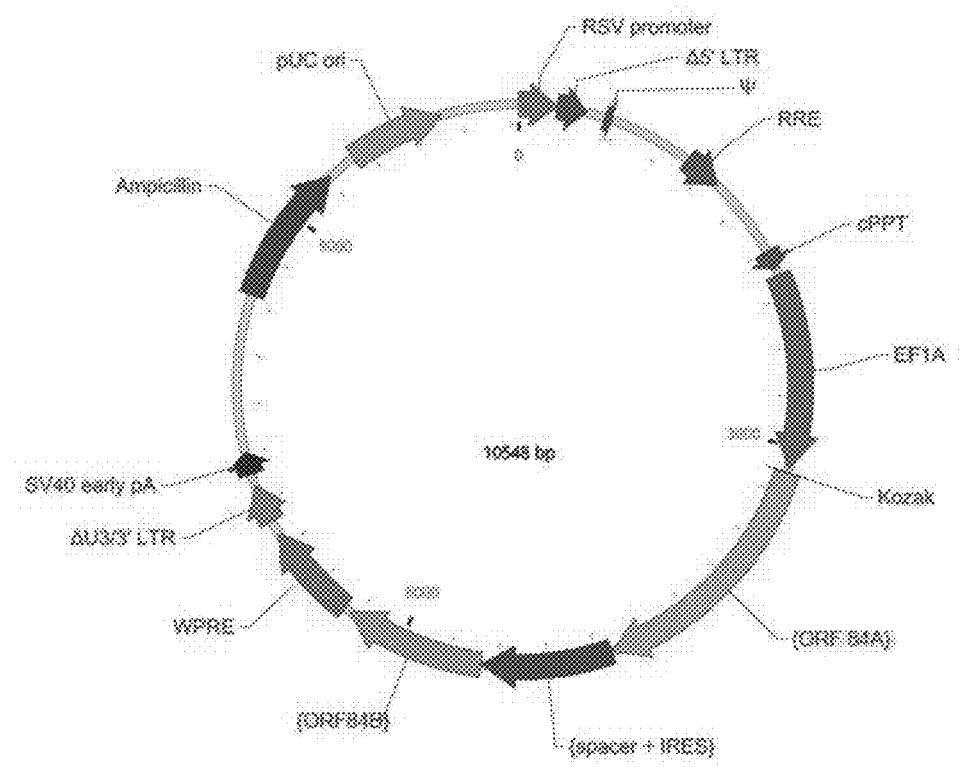
FIG. 11 shows a schematic of vector 84.

FIG. 11 shows a schematic of vector 84.

Table 20 below, shows the vector component name, the corresponding nucleotide position, the full name of the component and a description.

TABLE 20

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF84A} | 3168-4709 | 1542 | None |
| IRES+ spacer | 4710-5501 | 792 | Linker |
| {ORF84B} | 5502-6350 | 849 | None |
| WPRE | 6389-6986 | 598 | Woodchuck hepatitis virus posttranscriptional regulatory element |
| ΔU3/3' LTR | 7068-7302 | 235 | Truncated HIV-1 3' long terminal repeat |
| SV40 early pA | 7375-7509 | 135 | Simian virus 40 early polyadenylation signal |
| Ampicillin | 8463-9323 | 861 | Ampicillin resistance gene |
| pUC ori | 9494-10082 | 589 | pUC origin of replication |

Vector 29.

Figure 12:
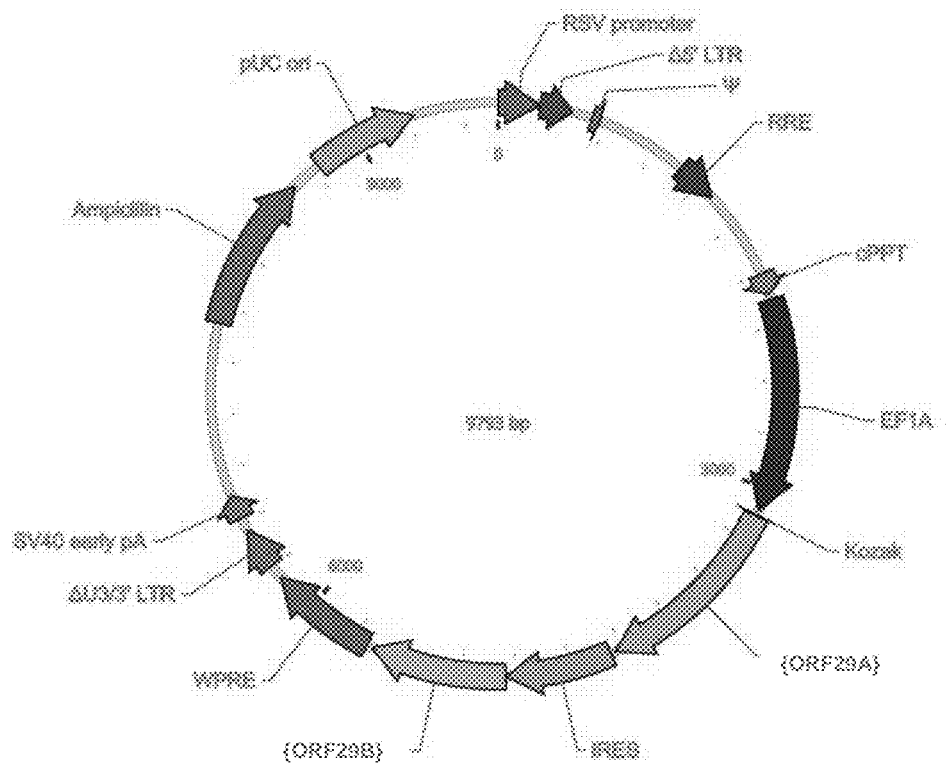
FIG. 12 shows a schematic of vector 29.

FIG. 12 shows a schematic of vector 29.

Table 21 below, shows the vector component name, the corresponding nucleotide position, the full name of the component and a description.

TABLE 21

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |

TABLE 21-continued

| Component Name | Nucleotide Position | Size (bp) | Description |
| --- | --- | --- | --- |
| Kozak | 3153-3158 | 6 | Kozak translation initiation sequence |
| {ORF29a(285aa) + SPACER} | 3159-4242 | 1084 | None |
| IRES | 4267-4854 | 588 | Encephalomyocarditis virus internal ribosome entry site |
| {ORF29b(250aa)vi | 4855-5604 | 750 | None |
| WPRE | 5634-6231 | 598 | Woodchuck hepatitis virus posttranscriptional regulatory element |
| ΔU3/3' LTR | 6313-6547 | 235 | Truncated HIV-1 3' long terminal repeat |
| SV40 early pA | 6620-6754 | 135 | Simian virus 40 early polyadenylation signal |
| Ampicillin | 7708-8568 | 861 | Ampicillin resistance gene |
| pUC ori | 8739-9327 | 589 | pUC origin of replication |

Vector 107

Figure 13:
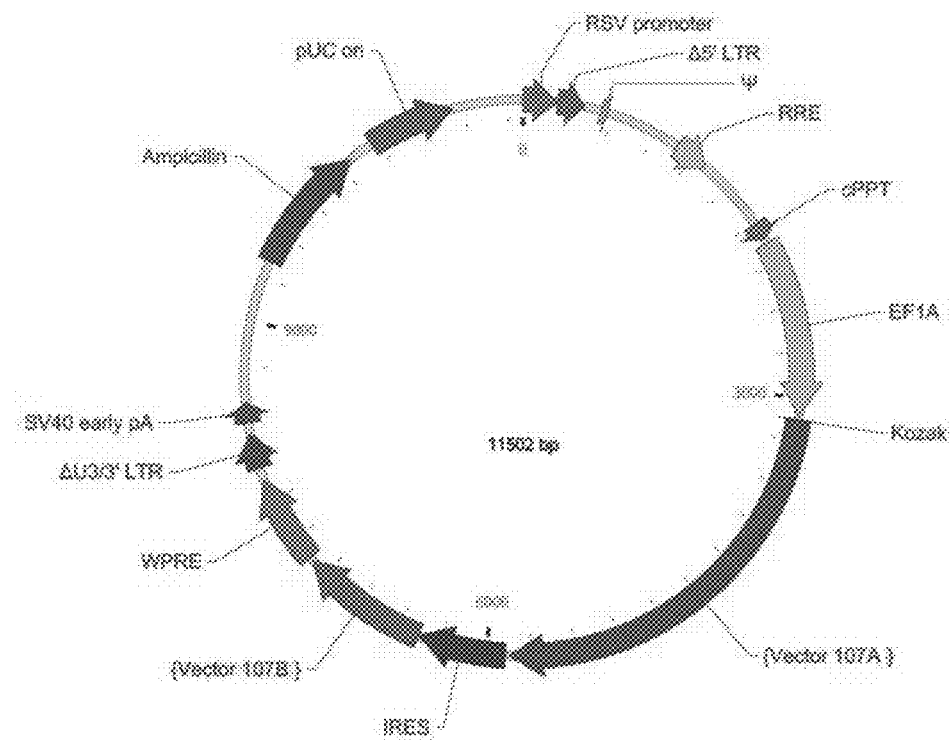
FIG. 13 shows a schematic of vector 107.

FIG. 13 shows a schematic of vector 107.

Table 22 below, shows the vector component name, the corresponding nucleotide position, the full name of the component and a description.

TABLE 22

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF3107A} | 3159-5843 | 2685 | None |
| IRES | 5868-6455 | 588 | Linker |
| {ORF107B} | 6456-7313 | 858 | None |
| WPRE | 7343-7940 | 598 | Woodchuck hepatitis virus posttranscriptional regulatory element |
| ΔU3/3' LTR | 8022-8256 | 235 | Truncated HIV-1 3' long terminal repeat |
| SV40 early pA | 8329-8463 | 135 | Simian virus 40 early polyadenylation signal |
| Ampicillin | 9417-10277 | 861 | Ampicillin resistance gene |
| pUC ori | 10448-11036 | 589 | pUC origin of replication |

Vector 116

Figure 14:
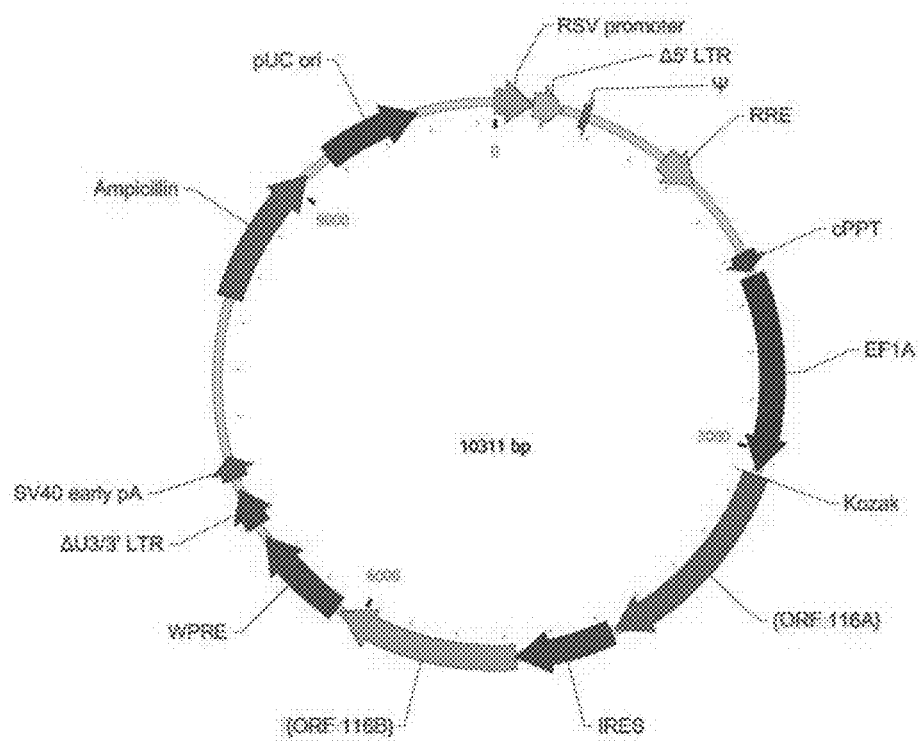
FIG. 14 shows a schematic of vector 116.

FIG. 14 shows a schematic of vector 116.

Table 23 below, shows the vector component name, the corresponding nucleotide position, the full name of the component and a description.

TABLE 23

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF116A} | 3159-4421 | 1263 | None |
| IRES | 446-5033 | 588 | Linker |
| {ORF116B} | 5034-6122 | 1089 | None |
| WPRE | 6152-6749 | 598 | Woodchuck hepatitis virus posttranscriptional regulatory element |
| ΔU3/3' LTR | 6831-7065 | 235 | Truncated HIV-1 3' long terminal repeat |
| SV40 early pA | 7138-7272 | 135 | Simian virus 40 early polyadenylation signal |

TABLE 23-continued

| Component Name | Nucleotide Position | Size (bp) | Description |
|---|---|---|---|
| Ampicillin | 8226-9086 | 861 | Ampicillin resistance gene |
| pUC ori | 9257-9845 | 589 | pUC origin of replication |

Vector 86

Figure 15:
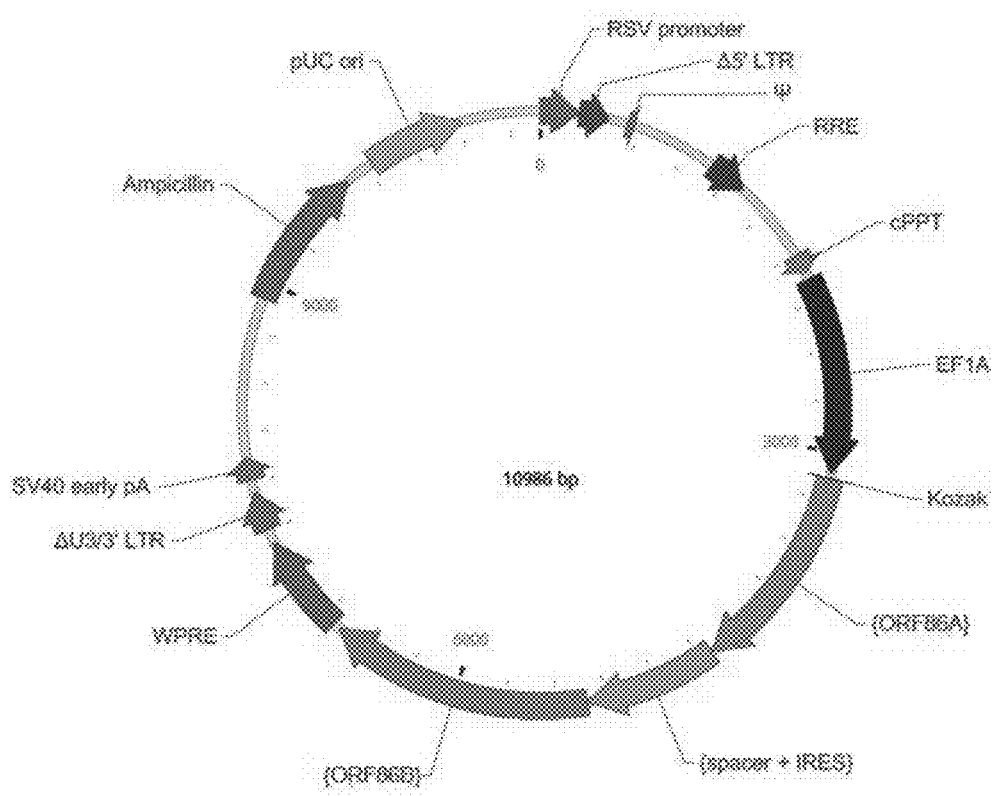
FIG. 15 shows a schematic of vector 86.

FIG. 15 shows a schematic of vector 86.

Table 24 below, shows the vector component name, the corresponding nucleotide position, the full name of the component and a description.

TABLE 24

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF86A} | 3168-4421 | 1254 | None |
| IRES+ spacer | 4422-5213 | 792 | Linker |
| {ORF86B} | 5214-6788 | 1575 | None |
| WPRE | 6827-7424 | 598 | Woodchuck hepatitis virus posttranscriptional regulatory element |
| ΔU3/3' LTR | 7506-7740 | 235 | Truncated HIV-1 3' long terminal repeat |
| SV40 early pA | 7813-7947 | 135 | Simian virus 40 early polyadenylation signal |
| Ampicillin | 8901-9761 | 861 | Ampicillin resistance gene |
| pUC ori | 9932-10520 | 589 | pUC origin of replication |

Vector 18

Figure 16:
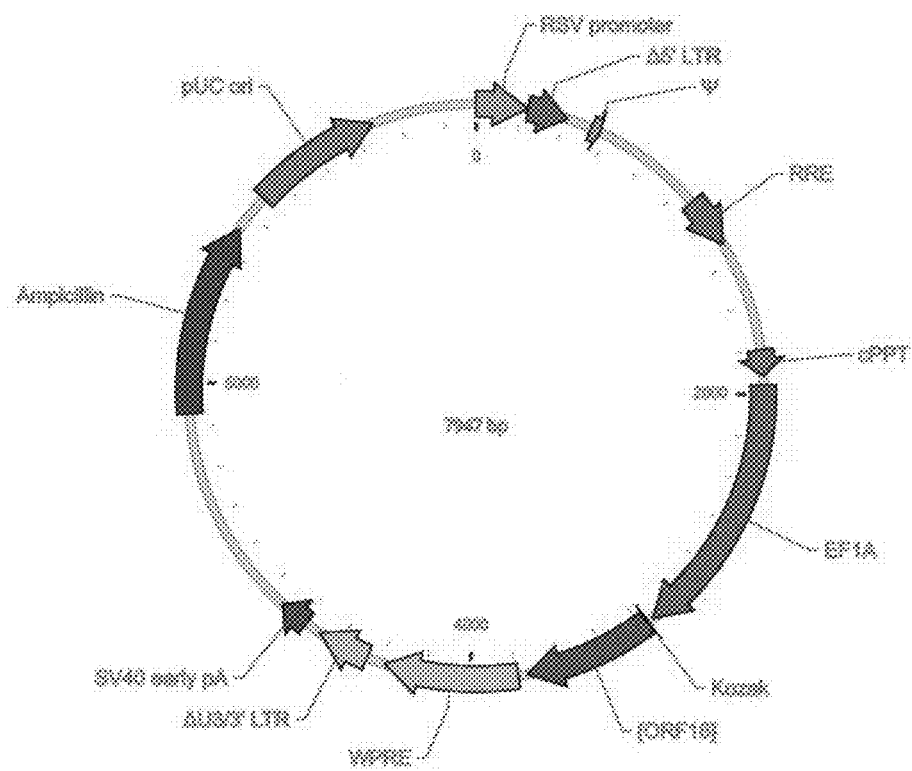
FIG. 16 shows a schematic of vector 18.

FIG. 16 shows a schematic of vector 18.

Table 25, below, shows the vector component name, the corresponding nucleotide position, the full name of the component and a description.

TABLE 25

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF18(193)} | 3168-3749 | 582 | None |
| WPRE | 3788-4385 | 598 | Woodchuck hepatitis virus posttranscriptional regulatory element |
| ΔU3/3' LTR | 4467-4701 | 235 | Truncated HIV-1 3' long terminal repeat |
| SV40 early pA | 4774-4908 | 135 | Simian virus 40 early polyadenylation signal |
| Ampicillin | 5862-6722 | 861 | Ampicillin resistance gene |
| pUC ori | 6893-7481 | 589 | pUC origin of replication |

Vector 17

Figure 17:
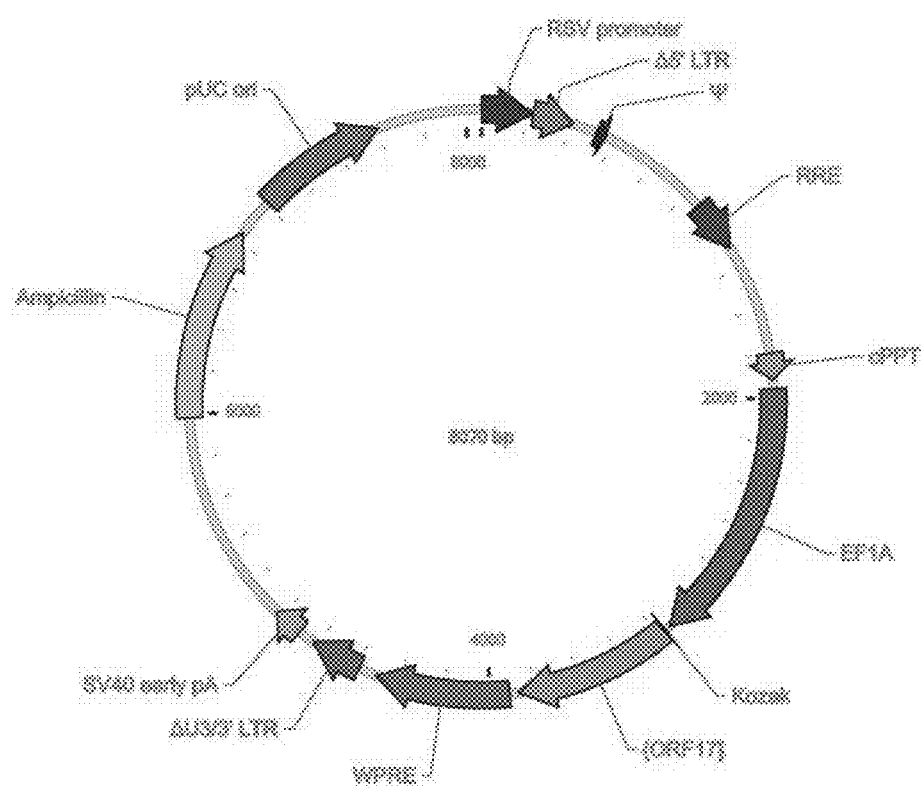
FIG. 17 shows a schematic of vector 17.

FIG. 17 shows a schematic of vector 17.

Table 26 below, shows the vector component name, the corresponding nucleotide position, the full name of the component and a description.

TABLE 26

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF17} | 3168-3872 | 705 | None |
| WPRE | 3911-4508 | 598 | Woodchuck hepatitis virus posttranscriptional regulatory element |
| ΔU3/3' LTR | 4590-4824 | 235 | Truncated HIV-1 3' long terminal repeat |
| SV40 early pA | 4897-5031 | 135 | Simian virus 40 early polyadenylation signal |
| Ampicillin | 5985-6845 | 861 | Ampicillin resistance gene |
| pUC ori | 7016-7604 | 589 | pUC origin of replication |

Vector 98

Figure 18:
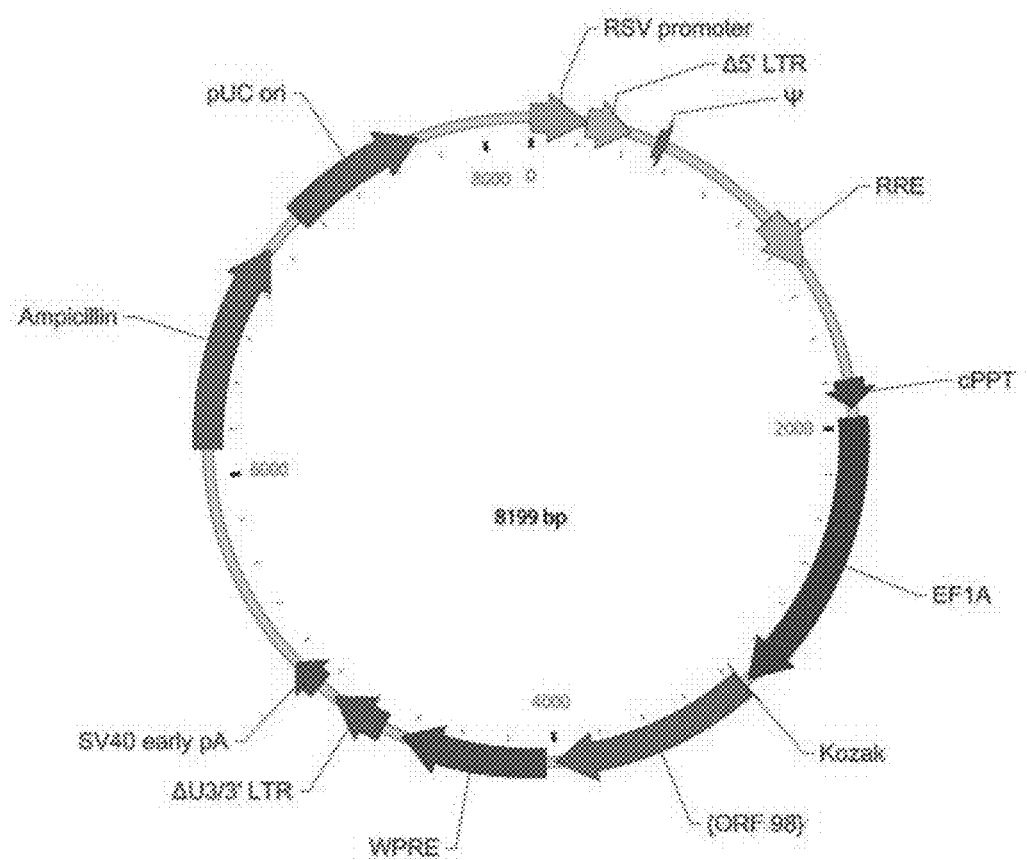
FIG. 18 shows a schematic of vector 98.

FIG. 18 shows a schematic of vector 98.

Table 27 below, shows the vector component name, the corresponding nucleotide position, the full name of the component and a description.

TABLE 27

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF98} | 3168-4001 | 834 | None |
| WPRE | 4040-4637 | 598 | Woodchuck hepatitis virus posttranscriptional regulatory element |
| ΔU3/3' LTR | 4719-4953 | 235 | Truncated HIV-1 3' long terminal repeat |
| SV40 early pA | 5026-5160 | 135 | Simian virus 40 early polyadenylation signal |
| Ampicillin | 6114-6974 | 861 | Ampicillin resistance gene |
| pUC ori | 7145-7733 | 589 | pUC origin of replication |

Vector 30

Figure 19:
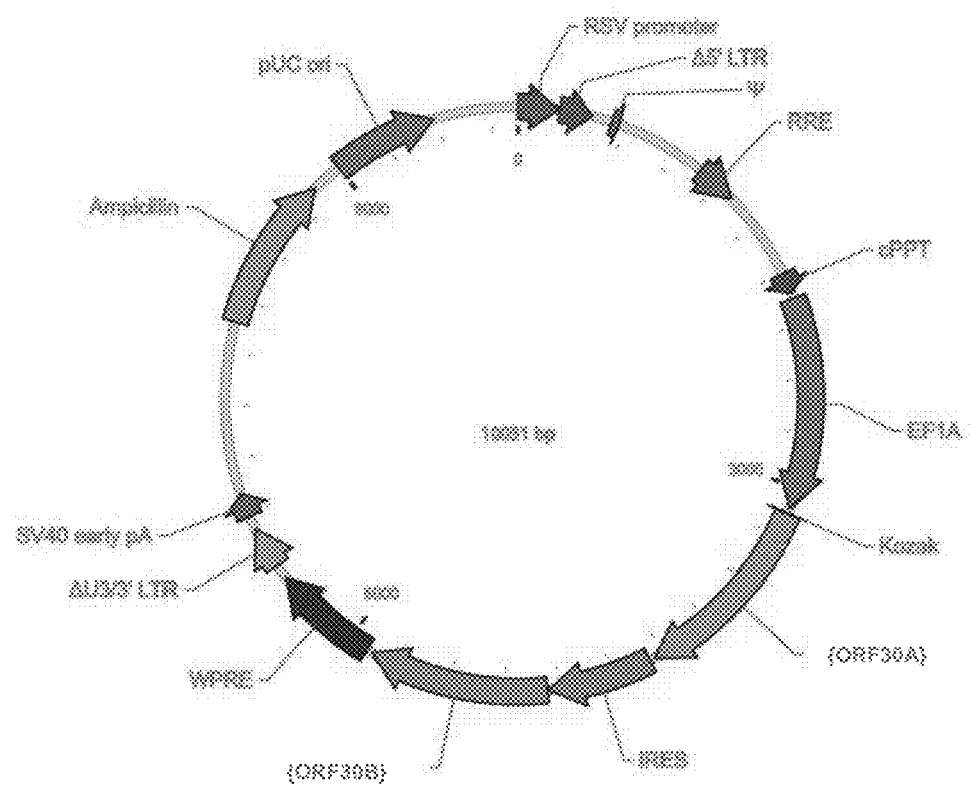
FIG. 19 shows a schematic of vector 30.

FIG. 19 shows a schematic of vector 30.

Table 28 below, shows the vector component name, the corresponding nucleotide position, the full name of the component and a description.

TABLE 28

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF30a(288aa) + SPACER} | 3159-4251 | 1093 | None |
| IRES | 4276-4863 | 588 | Linker |
| {ORF30B(332aa)} | 4864-5862 | 999 | None |
| WPRE | 5892-6489 | 598 | Woodchuck hepatitis virus posttranscriptional regulatory element |
| ΔU3/3' LTR | 6571-6805 | 235 | Truncated HIV-1 3' long terminal repeat |
| SV40 early pA | 6878-7012 | 135 | Simian virus 40 early polyadenylation signal |
| Ampicillin | 7966-8826 | 861 | Ampicillin resistance gene |
| pUC ori | 8997-9585 | 589 | pUC origin of replication |

Vector 109

Figure 20:
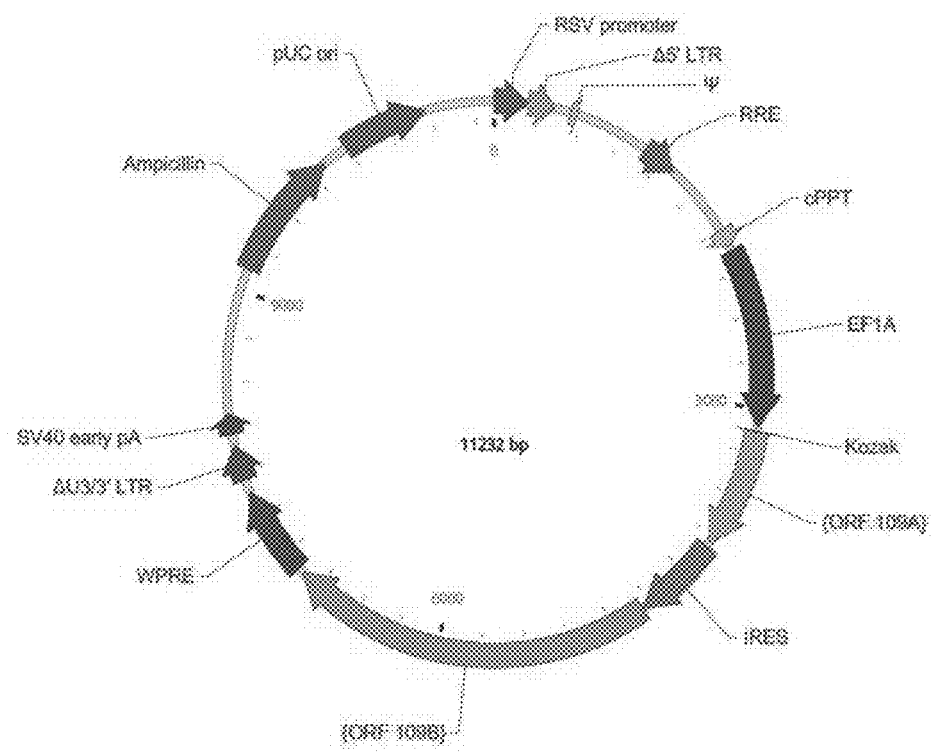
FIG. 20 shows a schematic of vector 109.

FIG. 20 shows a schematic of vector 109.

Table 29 below, shows the vector component name, the corresponding nucleotide position, the full name of the component and a description.

TABLE 29

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF109A} | 3159-3947 | 789 | None |
| IRES | 3972-4559 | 588 | Linker |
| {ORF109B} | 4560-7043 | 2484 | None |
| WPRE | 7073-7670 | 598 | Woodchuck hepatitis virus posttranscriptional regulatory element |
| ΔU3/3' ETR | 7752-7986 | 235 | Truncated HIV-1 3' long terminal repeat |
| SV40 early pA | 8059-8193 | 135 | Simian virus 40 early polyadenylation signal |
| Ampicillin | 9147-10007 | 861 | Ampicillin resistance gene |
| pUC ori | 10178-10766 | 589 | pUC origin of replication |

Vector 106

Figure 21:
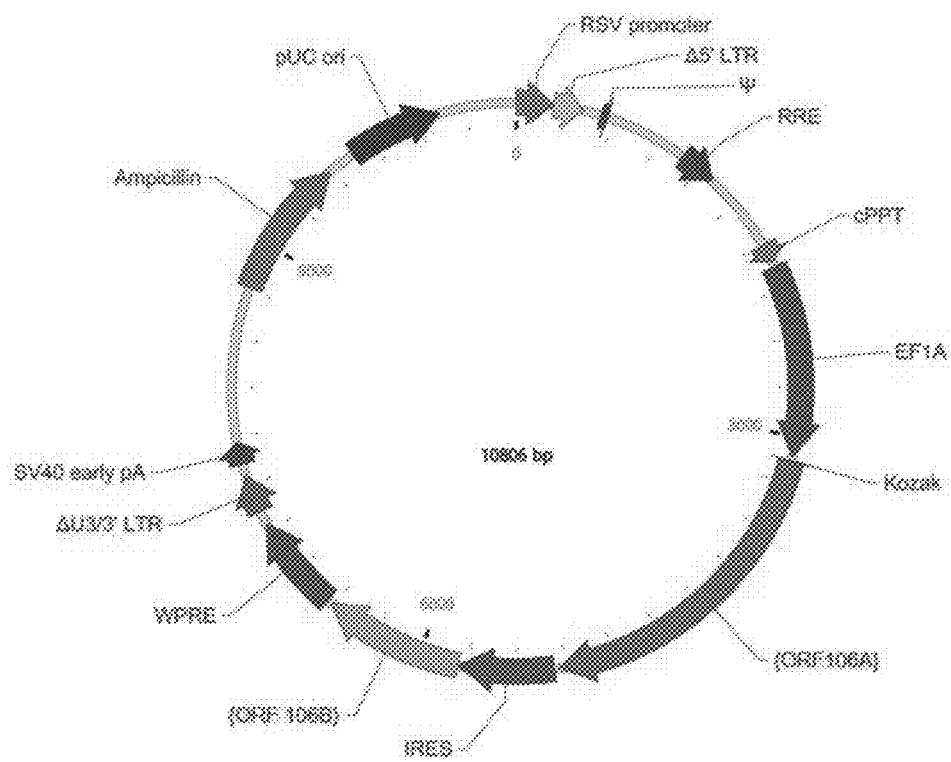
FIG. 21 shows a schematic of vector 106.

FIG. 21 shows a schematic of vector 106.

Table 30 below, shows the vector component name, the corresponding nucleotide position, the full name of the component and a description.

TABLE 30

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF106A} | 3159-5147 | 1989 | None |
| IRES | 5172-5759 | 588 | Linker |
| {ORF106B} | 5760-6617 | 858 | None |
| WPRE | 6477-7244 | 598 | Woodchuck hepatitis virus posttranscriptional regulatory element |
| ΔU3/3' LTR | 7326-7560 | 235 | Truncated HIV-1 3' long terminal repeat |
| SV40 early pA | 7633-7767 | 135 | Simian virus 40 early polyadenylation signal |
| Ampicillin | 8721-9581 | 861 | Ampicillin resistance gene |
| pUC ori | 9752-10340 | 589 | pUC origin of replication |

Vector 16

Figure 22:
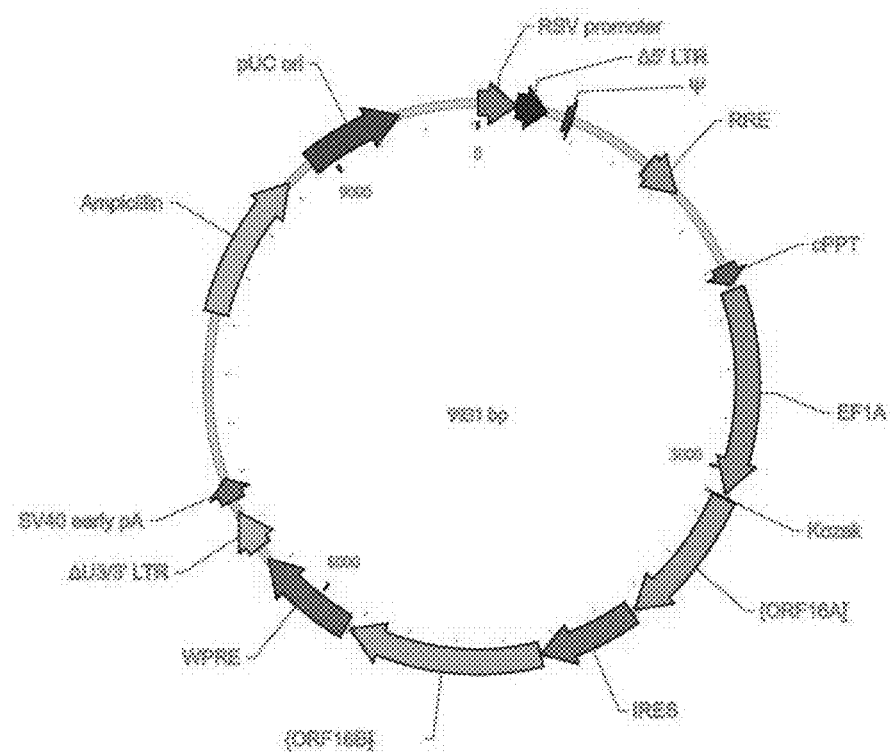
FIG. 22 shows a schematic of vector 16.

FIG. 22 shows a schematic of vector 16.

Table 31 below, shows the vector component name, the corresponding nucleotide position, the full name of the component and a description.

TABLE 31

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF16A}_w/SPACER | 3159-3984 | 826 | None |
| IRES | 4009-4596 | 588 | Linker |
| {ORF16B} | 4597-5742 | 1146 | None |
| WPRE | 5772-6369 | 598 | Woodchuck hepatitis virus posttranscriptional regulatory element |
| ΔU3/3' LTR | 6451-6685 | 235 | Truncated HIV-1 3' long terminal repeat |
| SV40 early pA | 6758-6892 | 135 | Simian virus 40 early polyadenylation signal |
| Ampicillin | 7846-8706 | 861 | Ampicillin resistance gene |
| pUC ori | 8877-945 | 589 | pUC origin of replication |

Vector 83

Figure 23:
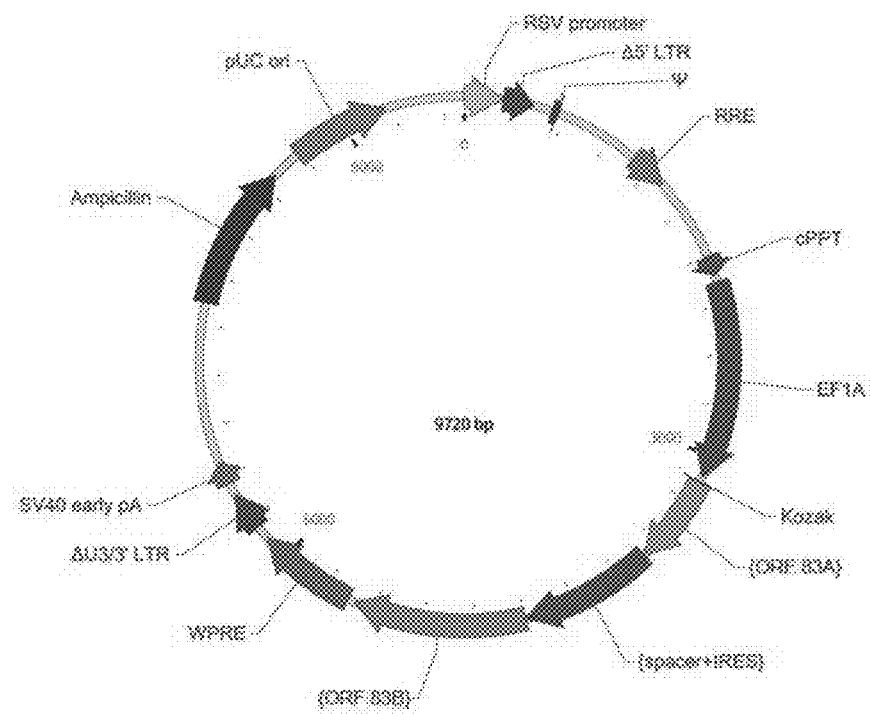
FIG. 23 shows a schematic of vector 83.

FIG. 23 shows a schematic of vector 83.

Table 32 below, shows the vector component name, the corresponding nucleotide position, the full name of the component and a description.

TABLE 32

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF83A} | 3168-3704 | 537 | None |
| IRES + spacer | 3705-4496 | 792 | Linker |
| {ORF83B} | 4497-5522 | 1026 | None |
| WPRE | 5561-6158 | 598 | Woodchuck hepatitis virus posttranscriptional regulatory element |
| ΔU3/3' LTR | 6240-6474 | 235 | Truncated HIV-1 3' long terminal repeat |
| SV40 early pA | 6547-6681 | 135 | Simian virus 40 early polyadenylation signal |
| Ampicillin | 7635-8495 | 861 | Ampicillin resistance gene |
| pUC ori | 8666-9254 | 589 | pUC origin of replication |

Vector 31

Figure 24:
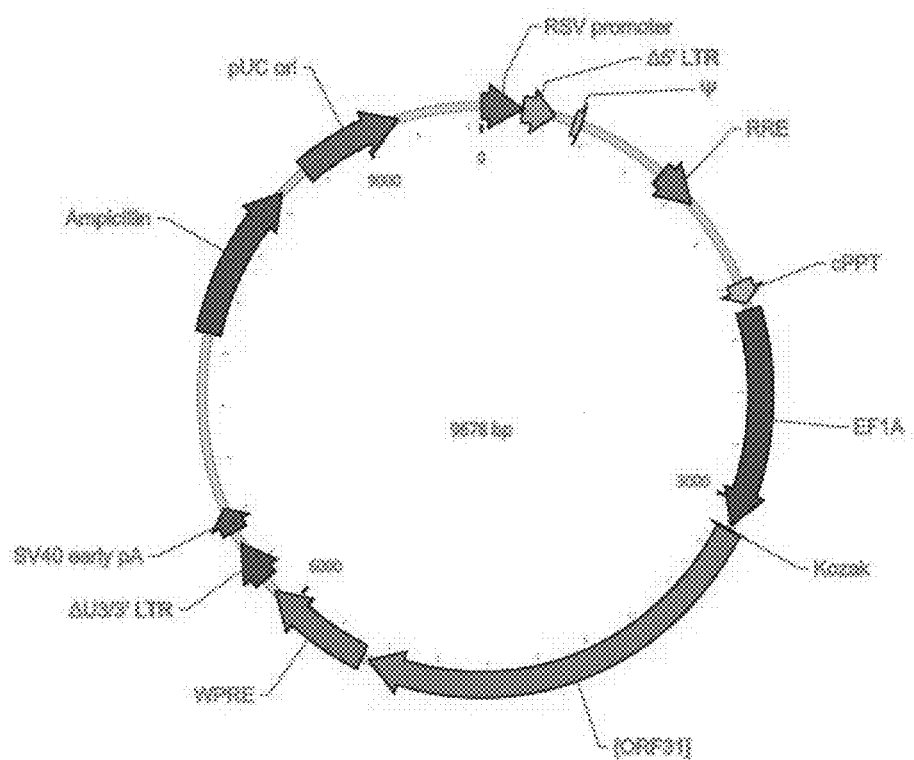
FIG. 24 shows a schematic of vector 31.

FIG. 24 shows a schematic of vector 31.

Table 33 below, shows the vector component name, the corresponding nucleotide position, the full name of the component and a description.

TABLE 33

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF31} | 3168-5480 | 2313 | None |
| WPRE | 5519-6116 | 598 | Woodchuck hepatitis virus posttranscriptional regulatory element |
| ΔU3/3' LTR | 6198-6432 | 235 | Truncated HIV-1 3' long terminal repeat |
| SV40 early pA | 6505-6639 | 135 | Simian virus 40 early polyadenylation signal |
| Ampicillin | 7593-8453 | 861 | Ampicillin resistance gene |
| pUC ori | 8624-9212 | 589 | pUC origin of replication |

Vector 12

Figure 25:
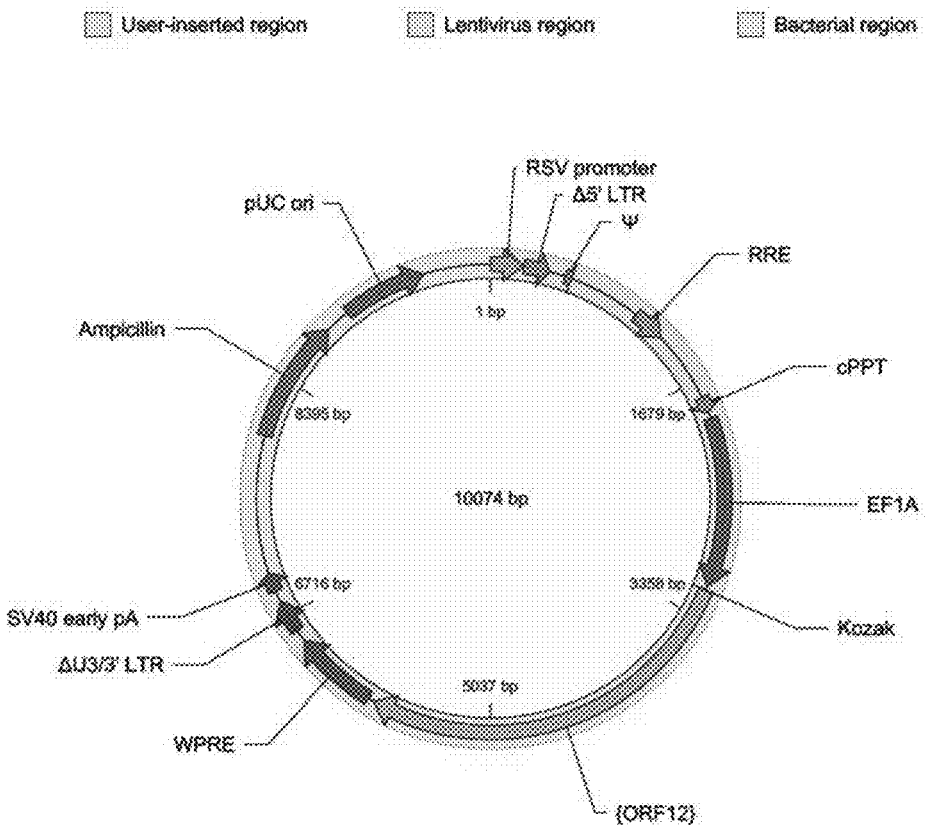
FIG. 25 shows a schematic of vector 12.

FIG. 25 shows a schematic of vector 12.

Table 34 below, shows the vector component name, the corresponding nucleotide position, the full name of the component and a description.

TABLE 34

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF12} | 3168-5876 | | None |
| WPRE | 5915-6512 | 598 | Woodchuck hepatitis virus posttranscriptional regulatory element |
| ΔU3/3' LTR | 6594-6828 | 235 | Truncated HIV-1 3' long terminal repeat |
| SV40 early pA | 6901-7035 | 135 | Simian virus 40 early polyadenylation signal |
| Ampicillin | 7989-8849 | 861 | Ampicillin resistance gene |
| pUC ori | 9020-9608 | 589 | pUC origin of replication |

Vector 99

Figure 26:
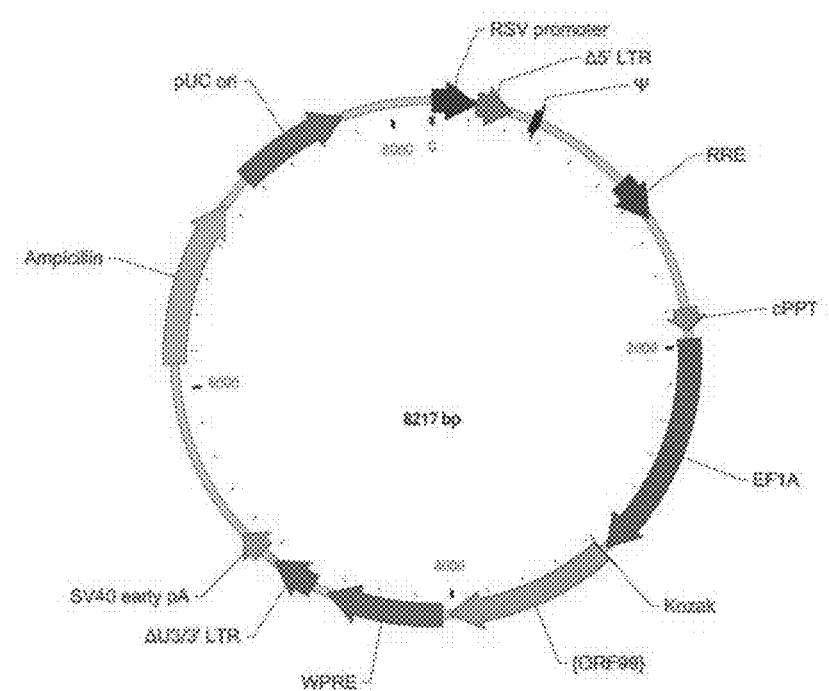
FIG. 26 shows a schematic of vector 99.

FIG. 26 shows a schematic of vector 99.

Table 35 below, shows the vector component name, the corresponding nucleotide position, the full name of the component and a description.

TABLE 35

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |

TABLE 35-continued

| Component Name | Nucleotide Position | Size (bp) | Description |
| --- | --- | --- | --- |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF99} | 3168-4019 | 852 | None |
| WPRE | 4058-4655 | 598 | Woodchuck hepatitis virus posttranscriptional regulatory element |
| ΔU3/3' LTR | 4737-4971 | 235 | Truncated HIV-1 3' long terminal repeat |
| SV40 early pA | 5044-5178 | 135 | Simian virus 40 early polyadenylation signal |
| Ampicillin | 6132-6992 | 861 | Ampicillin resistance gene |
| pUC ori | 7163-7751 | 589 | pUC origin of replication |

Vector 121

Figure 27:
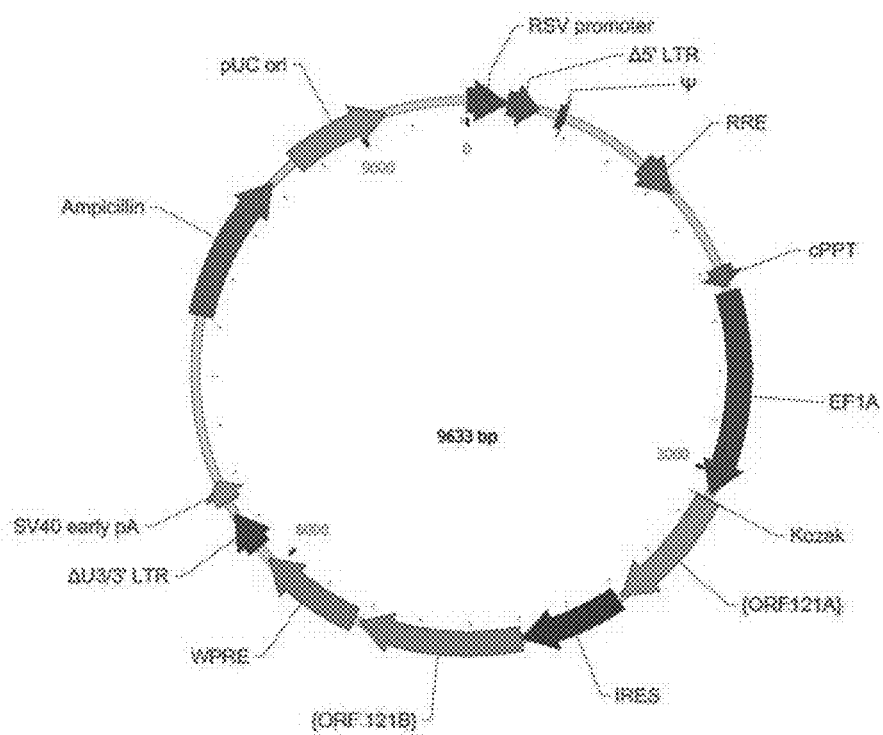
FIG. 27 shows a schematic of vector 121.

FIG. 27 shows a schematic of vector 121.

Table 36 below, shows the vector component name, the corresponding nucleotide position, the full name of the component and a description.

TABLE 36

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF121A} | 3159-3896 | 738 | None |
| IRES | 3921-4508 | 588 | Linker |
| {ORF121B} | 4509-5444 | 936 | None |
| WPRE | 5474-6071 | 598 | Woodchuck hepatitis virus posttranscriptional regulatory element |
| ΔU3/3' LTR | 6153-6387 | 235 | Truncated HIV-1 3' long terminal repeat |
| SV40 early pA | 6460-6594 | 135 | Simian virus 40 early polyadenylation signal |
| Ampicillin | 7548-8408 | 861 | Ampicillin resistance gene |
| pUC ori | 8579-9167 | 589 | pUC origin of replication |

Vector 105

Figure 28:
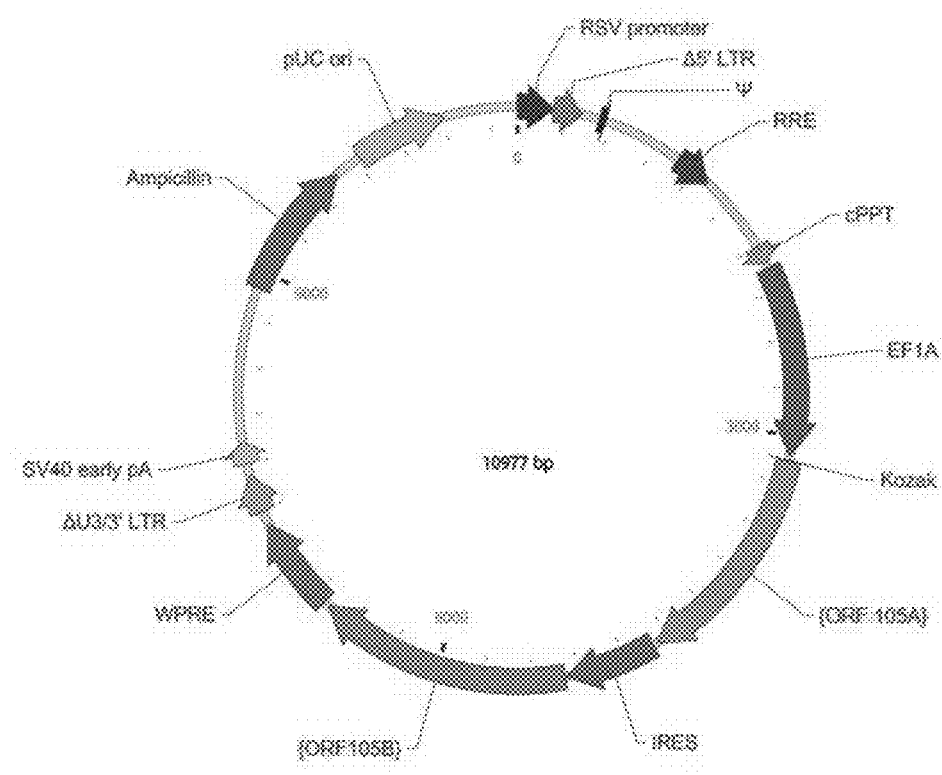
FIG. 28 shows a schematic of vector 105.

FIG. 28 shows a schematic of vector 105.

Table 37 below, shows the vector component name, the corresponding nucleotide position, the full name of the component and a description.

TABLE 37

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |

TABLE 37-continued

| Component Name | Nucleotide Position | Size (bp) | Description |
| --- | --- | --- | --- |
| Kozak | 3153-3158 | 6 | Kozak translation initiation sequence |
| {ORF105A} | 3159-4574 | 1416 | None |
| IRES | 4599-5186 | 588 | Linker |
| {ORF105B} | 5187-6788 | 1602 | None |
| WPRE | 6818-7415 | 598 | Woodchuck hepatitis virus posttranscriptional regulatory element |
| ΔU3/3' LTR | 7497-7731 | 235 | Truncated HIV-1 3' long terminal repeat |
| SV40 early pA | 7804-7938 | 135 | Simian virus 40 early polyadenylation signal |
| Ampicillin | 8892-9752 | 861 | Ampicillin resistance gene |
| pUC ori | 9923-10511 | 589 | pUC origin of replication |

Vector 32

Figure 29:
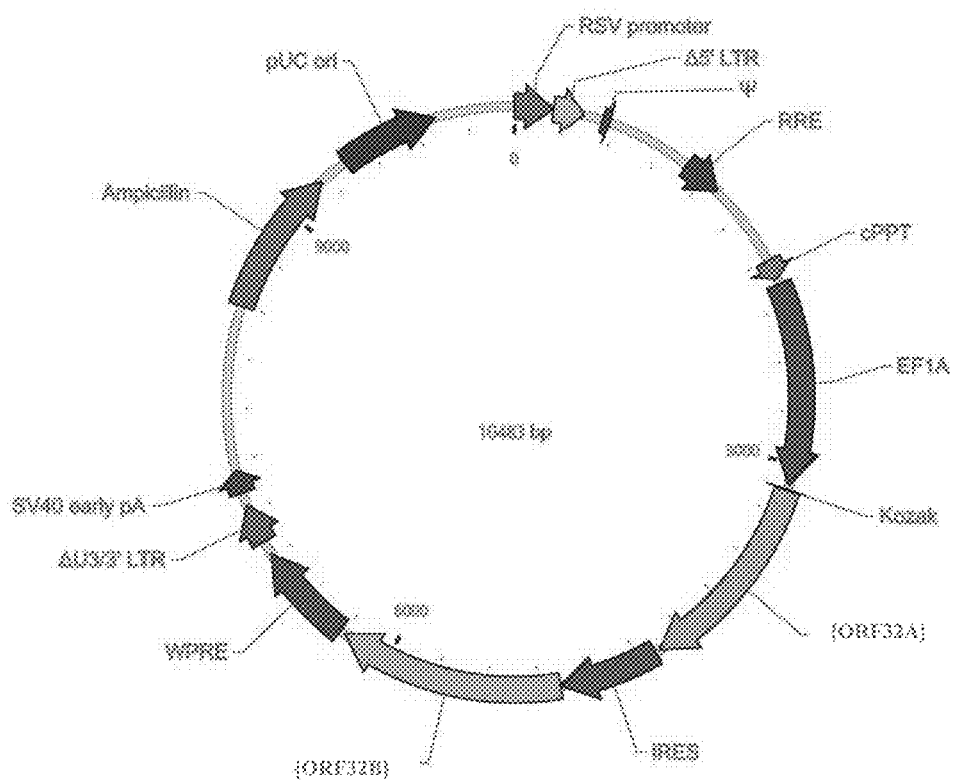
FIG. 29 shows a schematic of vector 32.

FIG. 29 shows a schematic of vector 32.

Table 38 below, shows the vector component name, the corresponding nucleotide position, the full name of the component and a description.

TABLE 38

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF32A} + SPACER | 3159-4359 | 1201 | None |
| IRES | 4384-4971 | 588 | Linker |
| {ORF32B} | 4972-6294 | 1323 | None |
| WPRE | 6324-6921 | 598 | Woodchuck hepatitis virus posttranscriptional regulatory element |
| ΔU3/3' LTR | 7003-7237 | 235 | Truncated HIV-1 3' long terminal repeat |
| SV40 early pA | 7310-7444 | 135 | Simian virus 40 early polyadenylation signal |
| Ampicillin | 8398-9258 | 861 | Ampicillin resistance gene |
| pUC ori | 9429-10017 | 589 | pUC origin of replication |

Vector 37

Figure 30:
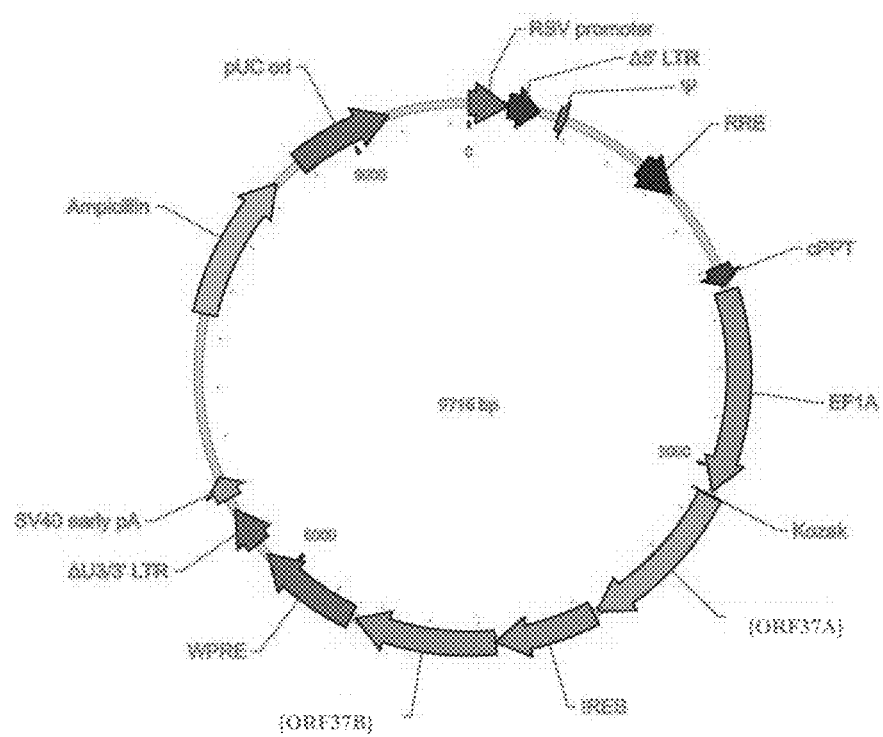
FIG. 30 shows a schematic of vector 37.

FIG. 30 shows a schematic of vector 37.

Table 39 below, shows the vector component name, the corresponding nucleotide position, the full name of the component and a description.

TABLE 39

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |

TABLE 39-continued

| Component Name | Nucleotide Position | Size (bp) | Description |
|---|---|---|---|
| EF1A | 1950-3128 | 1179 | Human eukaryotic translation elongation factor 1 α1 promoter |
| Kozak | 3153-3158 | 6 | Kozak translation initiation sequence |
| {ORF37A} + SPACER | 3159-4093 | 935 | None |
| IRES | 4118-4705 | 588 | Linker |
| {ORF37B} | 4706-5527 | 822 | None |
| WPRE | 5557-6154 | 598 | Woodchuck hepatitis virus posttranscriptional regulatory element |
| ΔU3/3' LTR | 6236-6470 | 235 | Truncated HIV-1 3' long terminal repeat |
| SV40 early pA | 6543-6677 | 135 | Simian virus 40 early polyadenylation signal |
| Ampicillin | 7631-8491 | 861 | Ampicillin resistance gene |
| pUC ori | 8662-9250 | 589 | pUC origin of replication |

Vector 22

Figure 31:
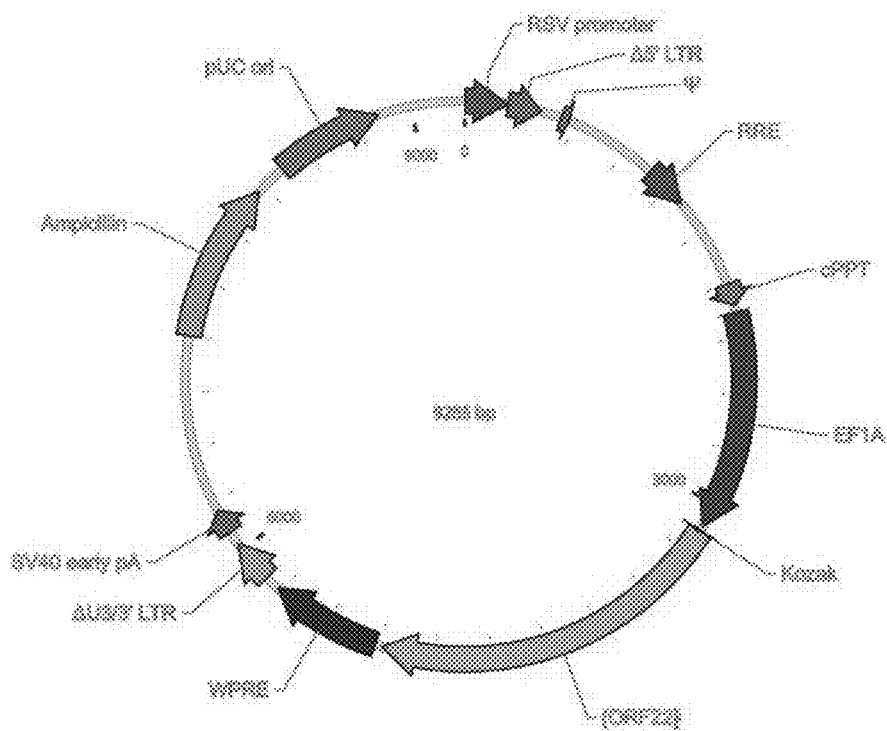
FIG. 31 shows a schematic of vector 22.

FIG. 31 shows a schematic of vector 22.

Table 40 below, shows the vector component name, the corresponding nucleotide position, the full name of the component and a description.

TABLE 40

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF22} | 3168-5087 | 1920 | None |
| WPRE | 5126-5723 | 598 | Woodchuck hepatitis virus posttranscriptional regulatory element |
| ΔU3/3' LTR | 5805-6039 | 235 | Truncated HIV-1 3' long terminal repeat |
| SV40 early pA | 6112-6246 | 135 | Simian virus 40 early polyadenylation signal |
| Ampicillin | 7200-8060 | 861 | Ampicillin resistance gene |
| pUC ori | 8231-8819 | 589 | pUC origin of replication |

Vector 19

Figure 32:
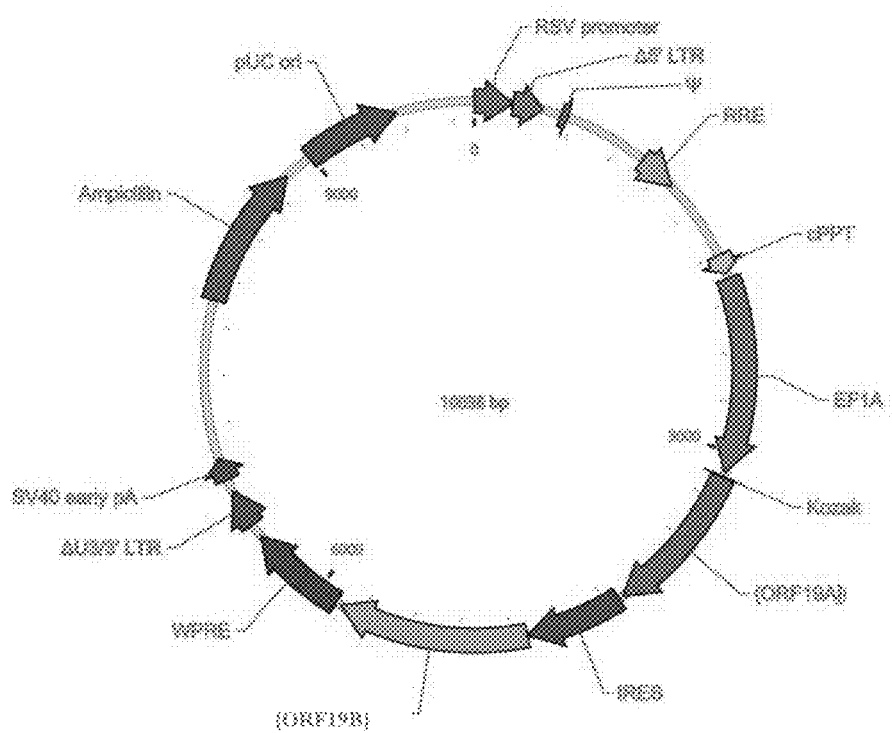
FIG. 32 shows a schematic of vector 19.

FIG. 32 shows a schematic of vector 19.

Table 41 below, shows the vector component name, the corresponding nucleotide position, the full name of the component and a description.

TABLE 41

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |

TABLE 41-continued

| Component Name | Nucleotide Position | Size (bp) | Description |
|---|---|---|---|
| EF1A | 1950-3128 | 1179 | Human eukaryotic translation elongation factor 1 α1 promoter |
| Kozak | 3153-3158 | 6 | Kozak translation initiation sequence |
| {ORF19A} w_SPACER | 3159-40892 | 931 | None |
| IRES | 4114-4701 | 588 | Linker |
| {ORF19B} | 4702-5847 | 1146 | None |
| WPRE | 5877-6474 | 598 | Woodchuck hepatitis virus posttranscriptional regulatory element |
| ΔU3/3' LTR | 6556-6790 | 235 | Truncated HIV-1 3' long terminal repeat |
| SV40 early pA | 6863-6997 | 135 | Simian virus 40 early polyadenylation signal |
| Ampicillin | 7951-8811 | 861 | Ampicillin resistance gene |
| pUC ori | 8982-9570 | 589 | pUC origin of replication |

Vector 20

Figure 33:
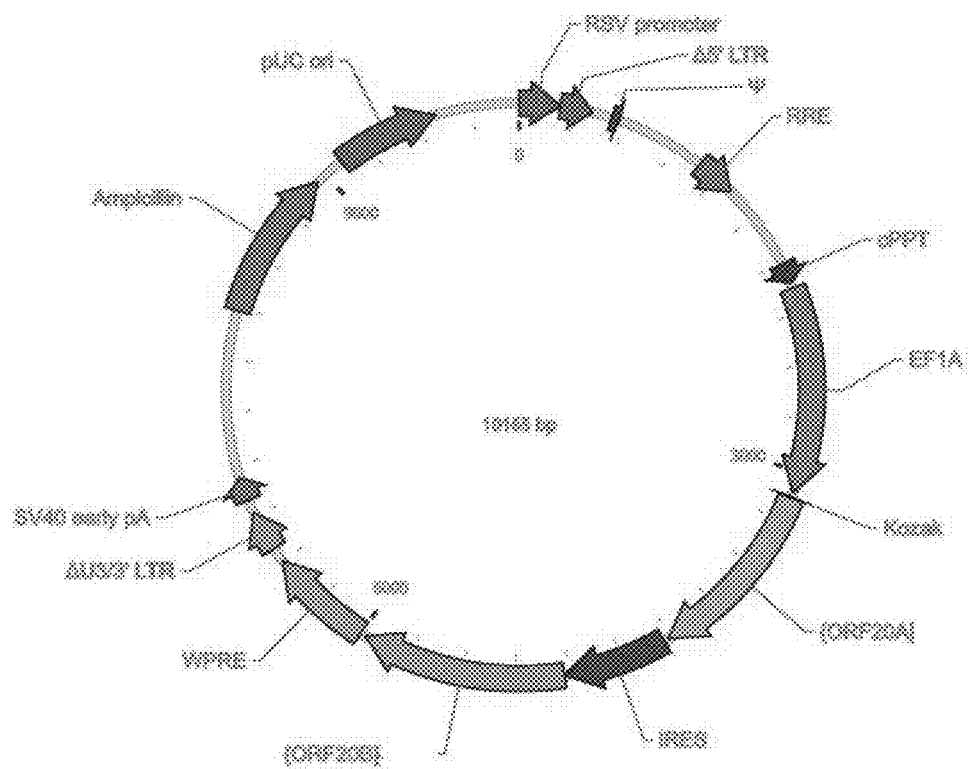
FIG. 33 shows a schematic of vector 20.

FIG. 33 shows a schematic of vector 20.

Table 42 below, shows the vector component name, the corresponding nucleotide position, the full name of the component and a description.

TABLE 42

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A- | 1950-3128 | 1179 | Human eukaryotic translation elongation factor 1 α1 promoter |
| Kozak | 3153-3158 | 6 | Kozak translation initiation sequence |
| {ORF20}w_spacer | 3159-4218 | 1060 | None |
| IRES | 4243-4830 | 588 | Linker |
| {ORF20B} | 4831-5976 | 1146 | None |
| WPRE | 6066-6603 | 598 | Woodchuck hepatitis virus posttranscriptional regulatory element |
| ΔU3/3' LTR | 6685-6919 | 235 | Truncated HIV-1 3' long terminal repeat |
| SV40 early pA | 6992-7126 | 135 | Simian virus 40 early polyadenylation signal |
| Ampicillin | 8080-8940 | 861 | Ampicillin resistance gene |
| pUC ori | 9111-9699 | 589 | pUC origin of replication |

Vector 89

Figure 34:
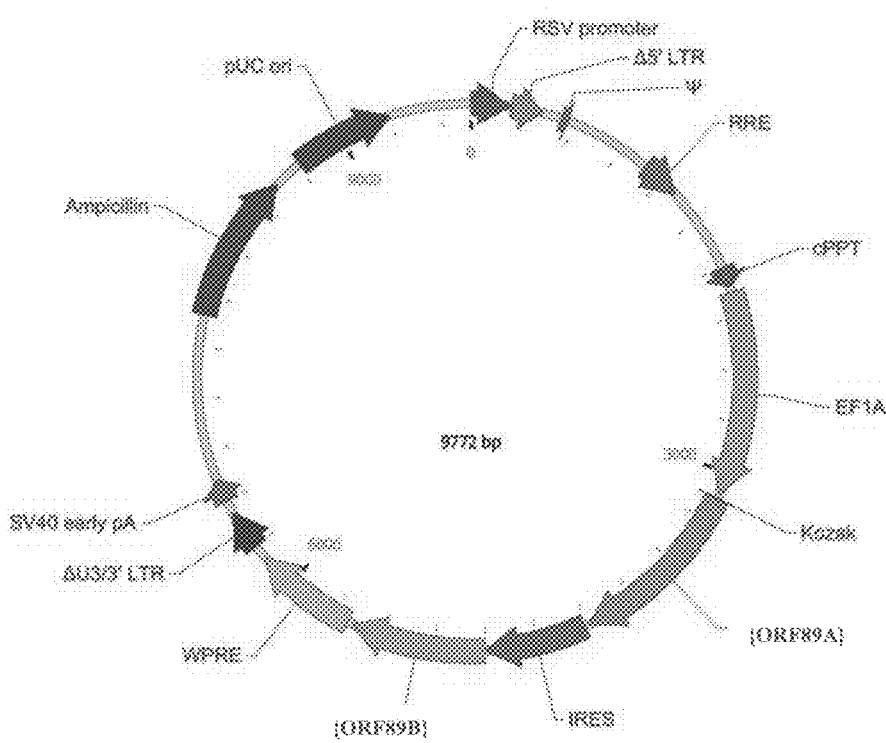
FIG. 34 shows a schematic of vector 89.

FIG. 34 shows a schematic of vector 89.

Table 43 below, shows the vector component name, the corresponding nucleotide position, the full name of the component and a description.

TABLE 43

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |

TABLE 43-continued

| Component Name | Nucleotide Position | Size (bp) | Description |
|---|---|---|---|
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF89A} + Spacer | 3159-4194 | 1036 | None |
| IRES | 4219-4806 | 588 | Linker |
| {ORF89B} | 4807-5583 | 777 | None |
| WPRE | 5613-6210 | 598 | Woodchuck hepatitis virus posttranscriptional regulatory element |
| ΔU3/3' LTR | 6292-6526 | 235 | Truncated HIV-1 3' long terminal repeat |
| SV40 early pA | 6599-6733 | 135 | Simian virus 40 early polyadenylation signal |
| Ampicillin | 7687-8547 | 861 | Ampicillin resistance gene |
| pUC ori | 8718-9306 | 589 | pUC origin of replication |

Vector 21

Figure 35:
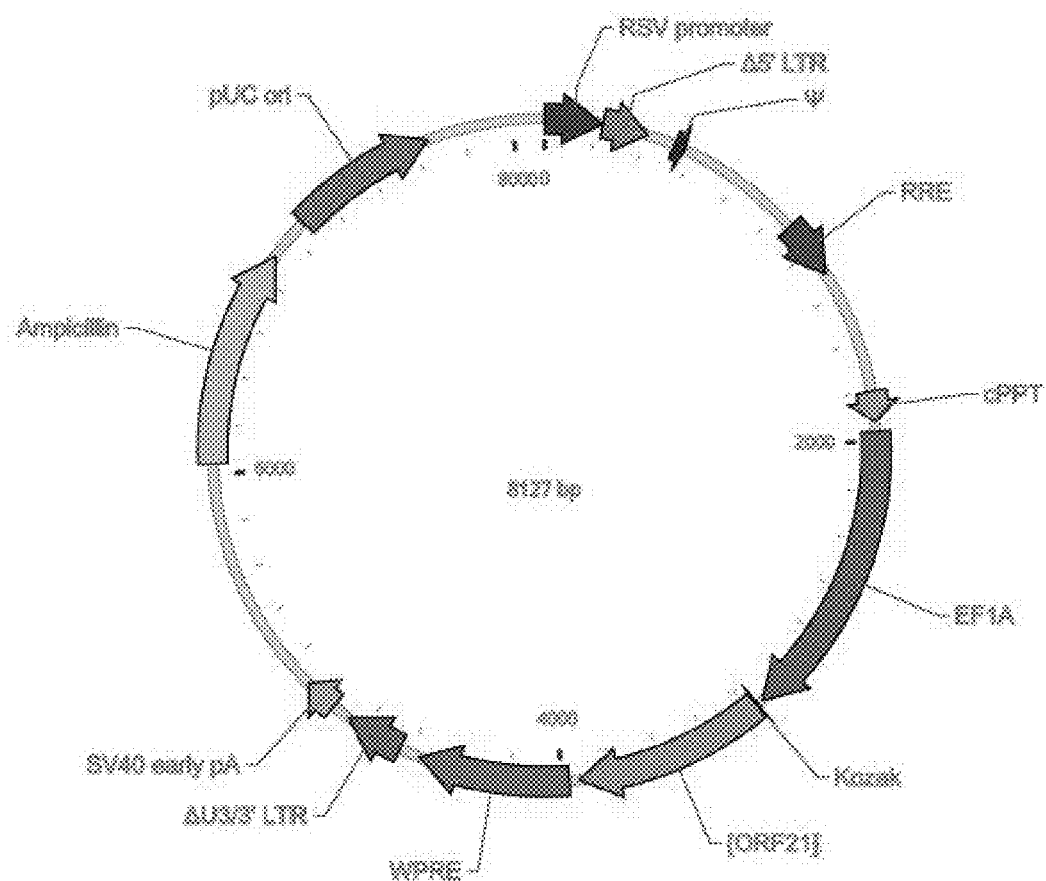
FIG. 35 shows a schematic of vector 21.

FIG. 35 shows a schematic of vector 21.

Table 44 below, shows the vector component name, the corresponding nucleotide position, the full name of the component and a description.

TABLE 44

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF21} | 3168-3929 | 762 | None |
| WPRE | 3968-4565 | 598 | Woodchuck hepatitis virus posttranscriptional regulatory element |
| ΔU3/3' LTR | 4647-4881 | 235 | Truncated HIV-1 3' long terminal repeat |
| SV40 early pA | 4954-5088 | 135 | Simian virus 40 early polyadenylation signal |
| Ampicillin | 6042-6902 | 861 | Ampicillin resistance gene |
| pUC ori | 7073-7661 | 589 | pUC origin of replication |

Vector 23

Figure 36:
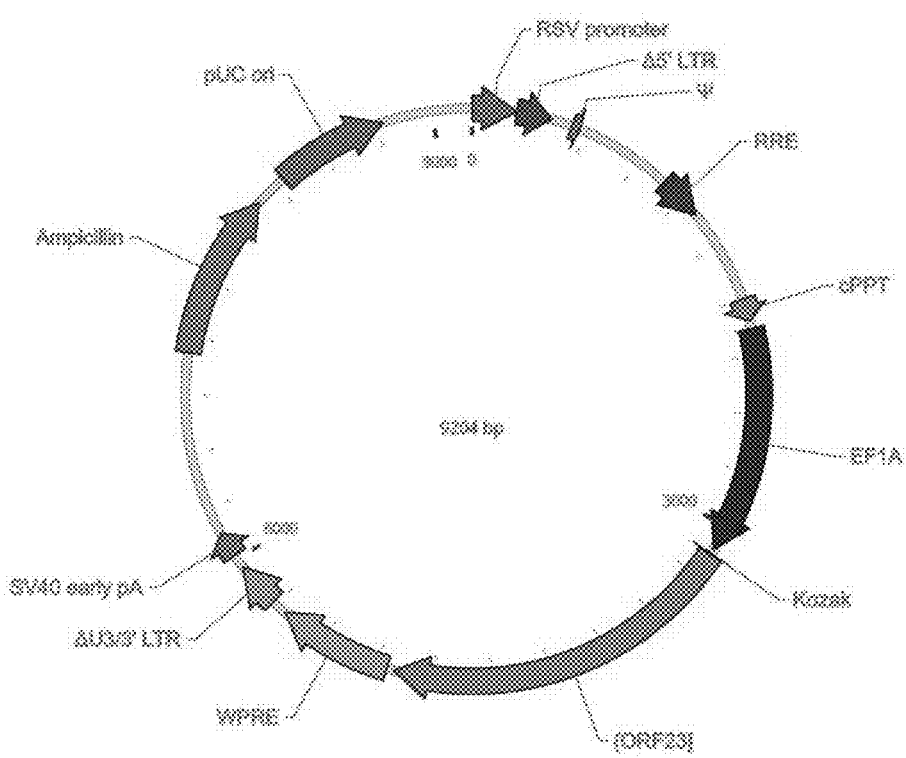
FIG. 36 shows a schematic of vector 23.

FIG. 36 shows a schematic of vector 23.

Table 45 below, shows the vector component name, the corresponding nucleotide position, the full name of the component and a description.

TABLE 45

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |

TABLE 45-continued

| Component Name | Nucleotide Position | Size (bp) | Description |
|---|---|---|---|
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 11959-3137 | 1179 | Human eukaryotic translation elongation factor 1 α1 promoter |
| Kozak | 3162-3167 | 6 | Kozak translation initiation sequence |
| {ORF23} | 3168-5006 | 1839 | None |
| WPRE | 5045-5642 | 598 | Woodchuck hepatitis virus posttranscriptional regulatory element |
| ΔU3/3' LTR | 5724-958 | 235 | Truncated HIV-1 3' long terminal repeat |
| SV40 early pA | 6031-6165 | 135 | Simian virus 40 early polyadenylation signal |
| Ampicillin | 7119-7979 | 861 | Ampicillin resistance gene |
| pUC ori | 8150-8738 | 589 | pUC origin of replication |

Vector 108

Figure 37:
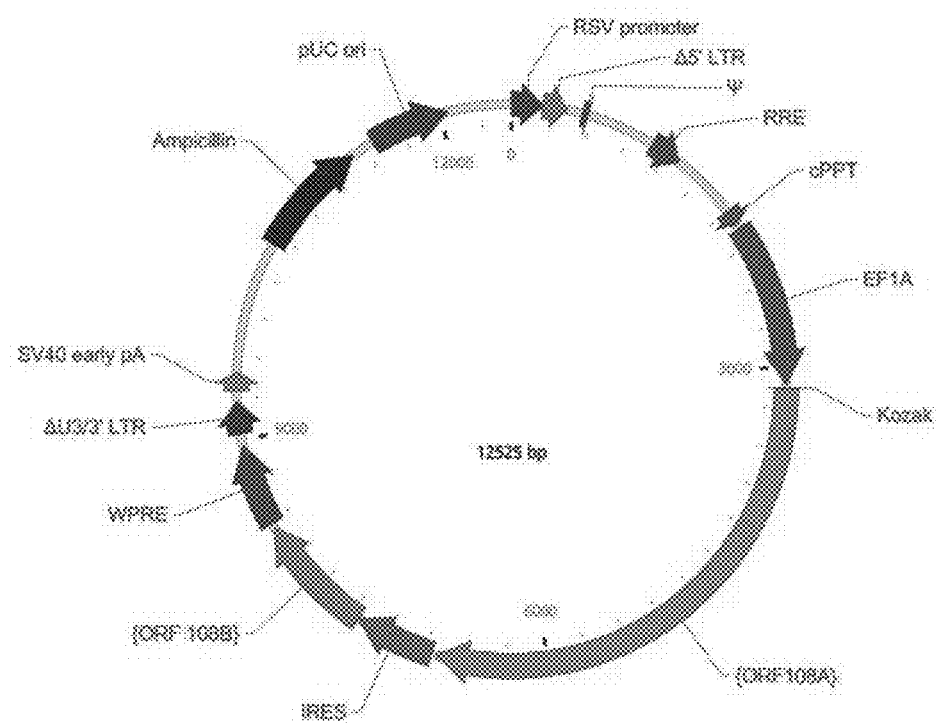
FIG. 37 shows a schematic of vector 108.

FIG. 37 shows a schematic of vector 108.

Table 46 below, shows the vector component name, the corresponding nucleotide position, the full name of the component and a description.

TABLE 46

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF108A} | 3159-6824 | 3666 | None |
| IRES | 6849-7436 | 588 | Linker |
| {ORF108B} | 7437-8336 | 900 | None |
| WPRE | 8366-8963 | 598 | Woodchuck hepatitis virus posttranscriptional regulatory element |
| ΔU3/3' LTR | 9045-9279 | 235 | Truncated HIV-1 3' long terminal repeat |
| SV40 early pA | 9352-9486 | 135 | Simian virus 40 early polyadenylation signal |
| Ampicillin | 10440-11300 | 861 | Ampicillin resistance gene |
| pUC ori | 11471-12059 | 589 | pUC origin of replication |

Vector 15

Figure 38:
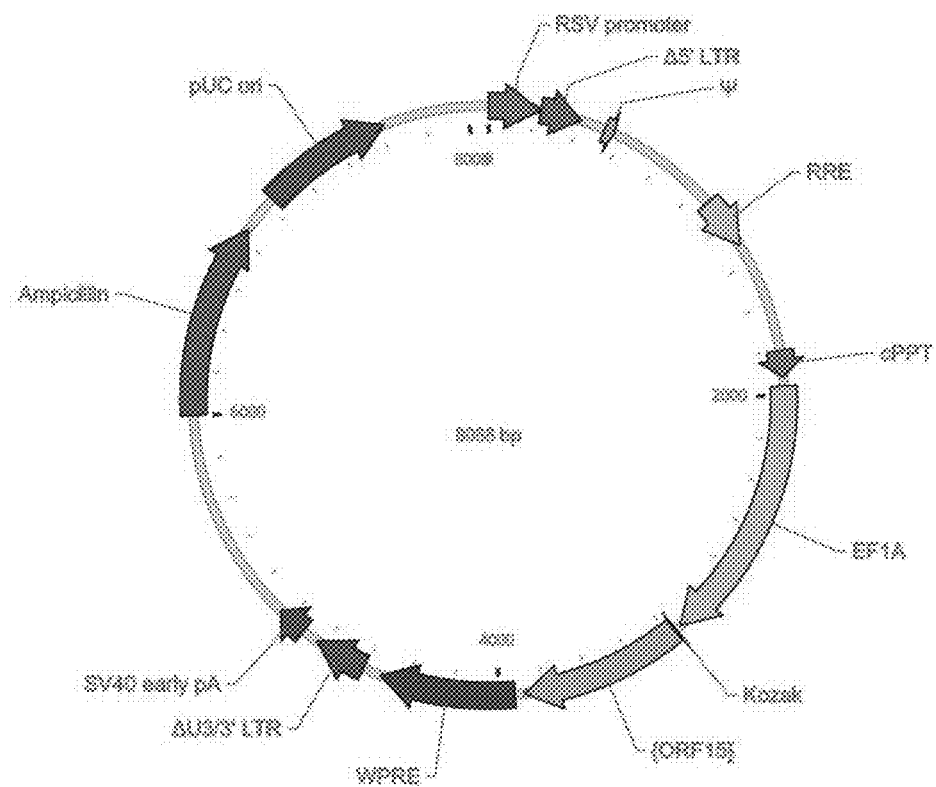
FIG. 38 shows a schematic of vector 15.

FIG. 38 shows a schematic of vector 15.

Table 47 below, shows the vector component name, the corresponding nucleotide position, the full name of the component and a description.

TABLE 47

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3153-3158 | 6 | Kozak translation initiation sequence |
| {ORF15} | 3168-3890 | 723 | None |
| WPRE | 3929-4526 | 598 | Woodchuck hepatitis virus posttranscriptional regulatory element |
| ΔU3/3' LTR | 4608-4842 | 235 | Truncated HIV-1 3' long terminal repeat |
| SV40 early pA | 4915-5049 | 135 | Simian virus 40 early polyadenylation signal |
| Ampicillin | 6003-6863 | 861 | Ampicillin resistance gene |
| pUC ori | 7034-7622 | 589 | pUC origin of replication |

Vector 124

Figure 39:
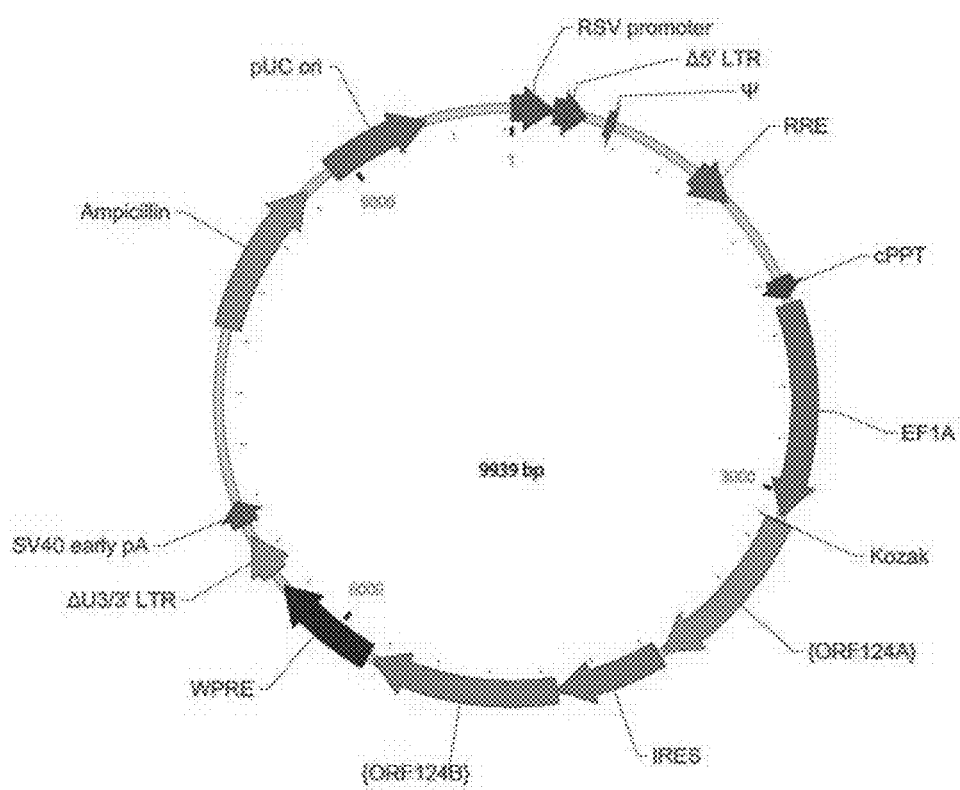
FIG. 39 shows a schematic of vector 124.

FIG. 39 shows a schematic of vector 124.

Table 48 below, shows the vector component name, the corresponding nucleotide position, the full name of the component and a description.

TABLE 48

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF124A} | 3159-4112 | 954 | None |
| IRES | 4137-4724 | 588 | Linker |
| {ORF124B} | 4725-5750 | 1026 | None |
| WPRE | 5780-6377 | 598 | Woodchuck hepatitis virus posttranscriptional regulatory element |
| ΔU3/3' LTR | 6459-6693 | 235 | Truncated HIV-1 3' long terminal repeat |
| SV40 early pA | 6766-6900 | 135 | Simian virus 40 early polyadenylation signal |
| Ampicillin | 7854-8714 | 861 | Ampicillin resistance gene |
| pUC ori | 8885-9473 | 589 | pUC origin of replication |

Vector 65

Figure 40:
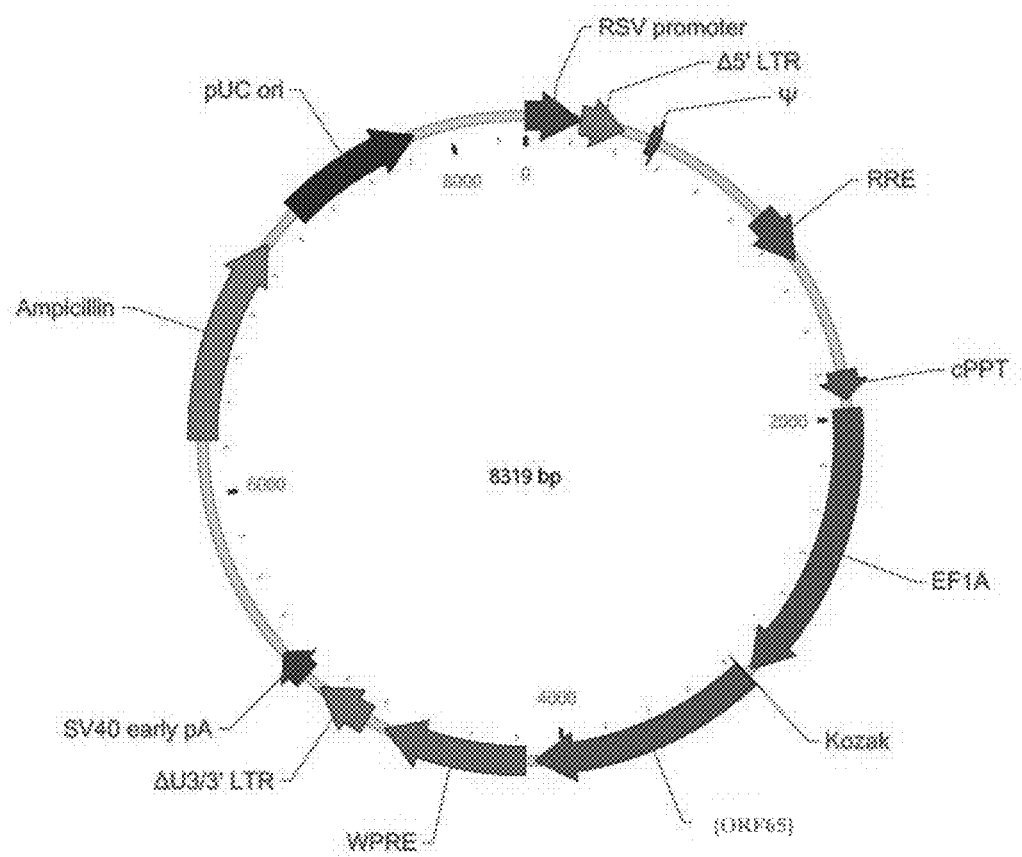
FIG. 40 shows a schematic of vector 65.

FIG. 40 shows a schematic of vector 65.

Table 49 below, shows the vector component name, the corresponding nucleotide position, the full name of the component and a description.

TABLE 49

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF65} | 3168-4121 | 954 | None |
| WPRE | 4160-4757 | 598 | Woodchuck hepatitis virus posttranscriptional regulatory element |
| ΔU3/3' LTR | 4839-5073 | 235 | Truncated HIV-1 3' long terminal repeat |
| SV40 early pA | 5146-5280 | 135 | Simian virus 40 early polyadenylation signal |
| Ampicillin | 6234-7094 | 861 | Ampicillin resistance gene |
| pUC ori | 7265-7853 | 589 | pUC origin of replication |

Vector 64

Figure 41:
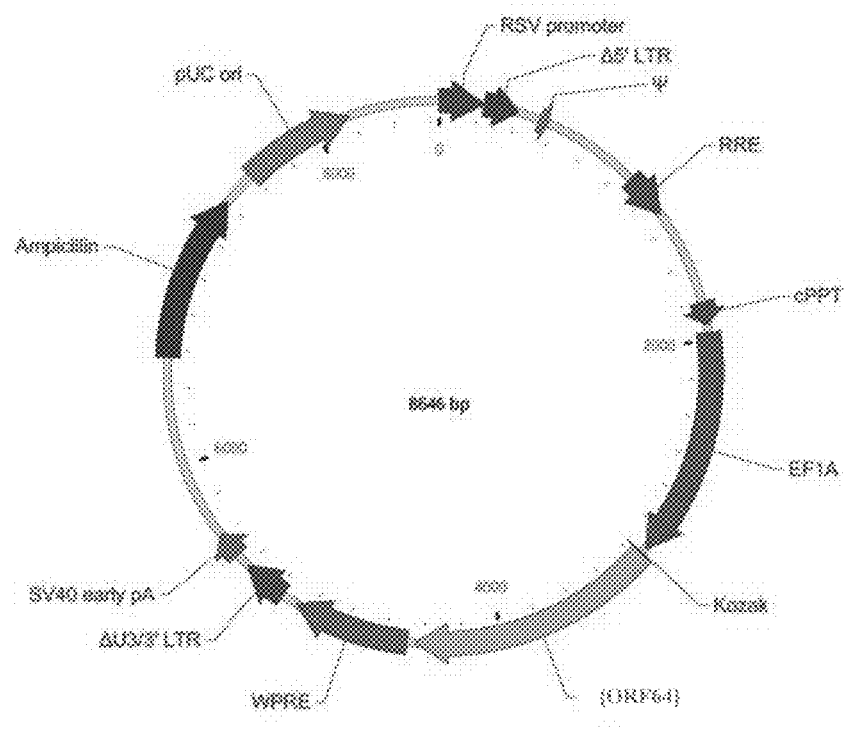
FIG. 41 shows a schematic of vector 64.

FIG. 41 shows a schematic of vector 64.

Table 50 below, shows the vector component name, the corresponding nucleotide position, the full name of the component and a description.

TABLE 50

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF64} | 3168-4448 | 1281 | None |
| WPRE | 4487-5084 | 598 | Woodchuck hepatitis virus posttranscriptional regulatory element |
| ΔU3/3' LTR | 5166-5400 | 235 | Truncated HIV-1 3' long terminal repeat |
| SV40 early pA | 5473-5607 | 135 | Simian virus 40 early polyadenylation signal |
| Ampicillin | 6561-7421 | 861 | Ampicillin resistance gene |
| pUC ori | 7592-8180 | 589 | pUC origin of replication |

Vector 88

Figure 42:
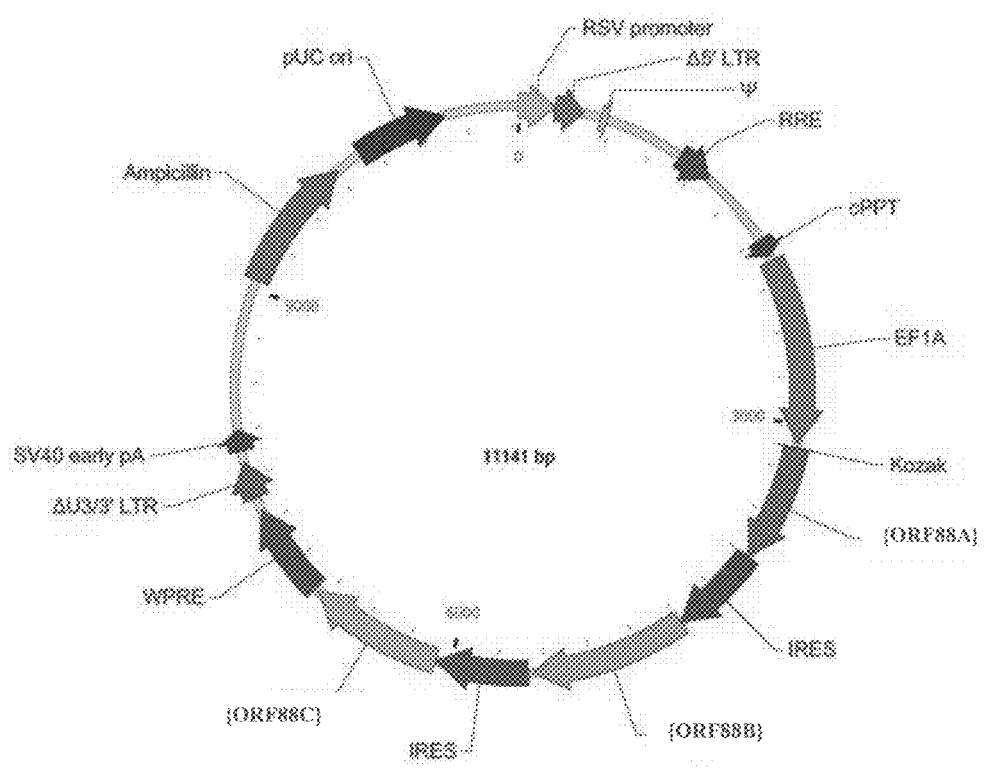
FIG. 42 shows a schematic of vector 88.

FIG. 42 shows a schematic of vector 88.

Table 51 below, shows the vector component name, the corresponding nucleotide position, the full name of the component and a description.

TABLE 51

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |

TABLE 51-continued

| Component Name | Nucleotide Position | Size (bp) | Description |
|---|---|---|---|
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF88A} + spacer | 3159-3900 | 742 | None |
| IRES | 3901-4488 | 588 | Linker |
| {ORF88B} + spacer | 4489-5485 | 997 | None |
| IRES | 5510-6097 | 588 | Linker |
| {ORF99C} | 6098-6952 | 855 | None |
| WPRE | 6982-7579 | 598 | Woodchuck hepatitis virus posttranscriptional regulatory element |
| ΔU3/3' LTR | 7661-7895 | 235 | Truncated HIV-1 3' long terminal repeat |
| SV40 early pA | 7968-8102 | 135 | Simian virus 40 early polyadenylation signal |
| Ampicillin | 9056-9916 | 861 | Ampicillin resistance gene |
| pUC ori | 10087-10675 | 589 | pUC origin of replication |

Vector 96

Figure 43:
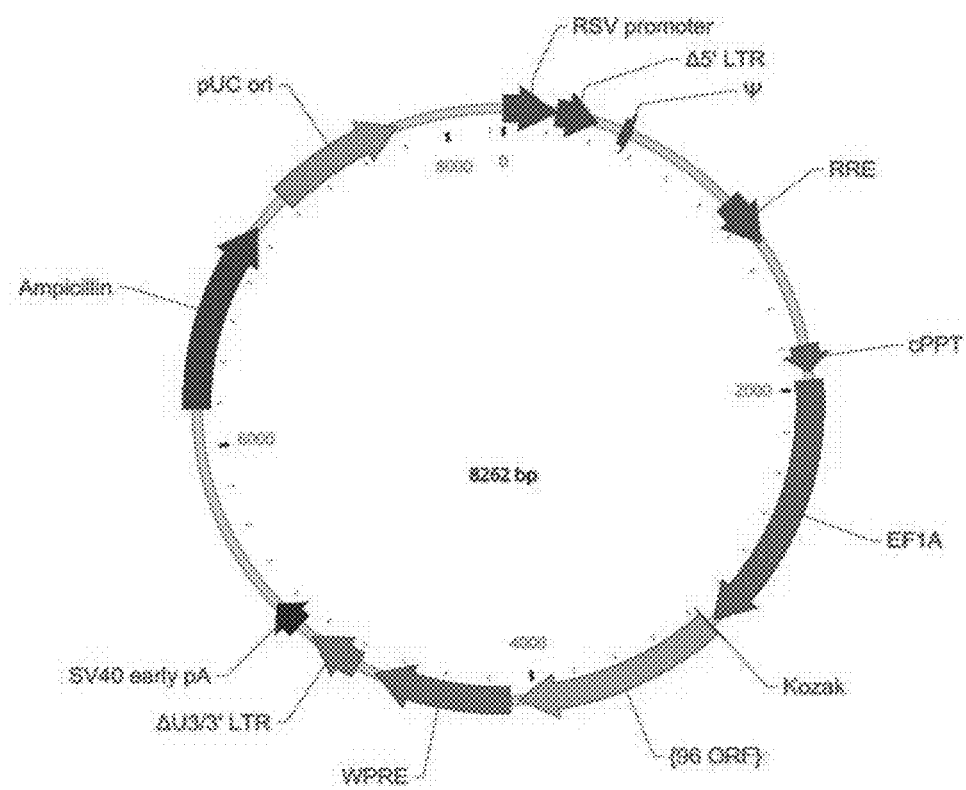
FIG. 43 shows a schematic of vector 96.

FIG. 43 shows a schematic of vector 96.

Table 52 below, shows the vector component name, the corresponding nucleotide position, the full name of the component and a description.

TABLE 52

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongationfactor 1 α1 promoter |
| Kozak | 3162-3167 | 6 | Kozak translation initiation sequence |
| {ORF96} | 3168-4064 | 897 | None |
| WPRE | 4103-4700 | 598 | Woodchuck hepatitis virus posttranscriptional regulatory element |
| ΔU3/3' LTR | 4782-5016 | 235 | Truncated HIV-1 3' long terminal repeat |
| SV40 early pA | 5089-5223 | 135 | Simian virus 40 early polyadenylation signal |
| Ampicillin | 6177-7037 | 861 | Ampicillin resistance gene |
| pUC ori | 7208-7796 | 589 | pUC origin of replication |

Vector 14

Figure 44:
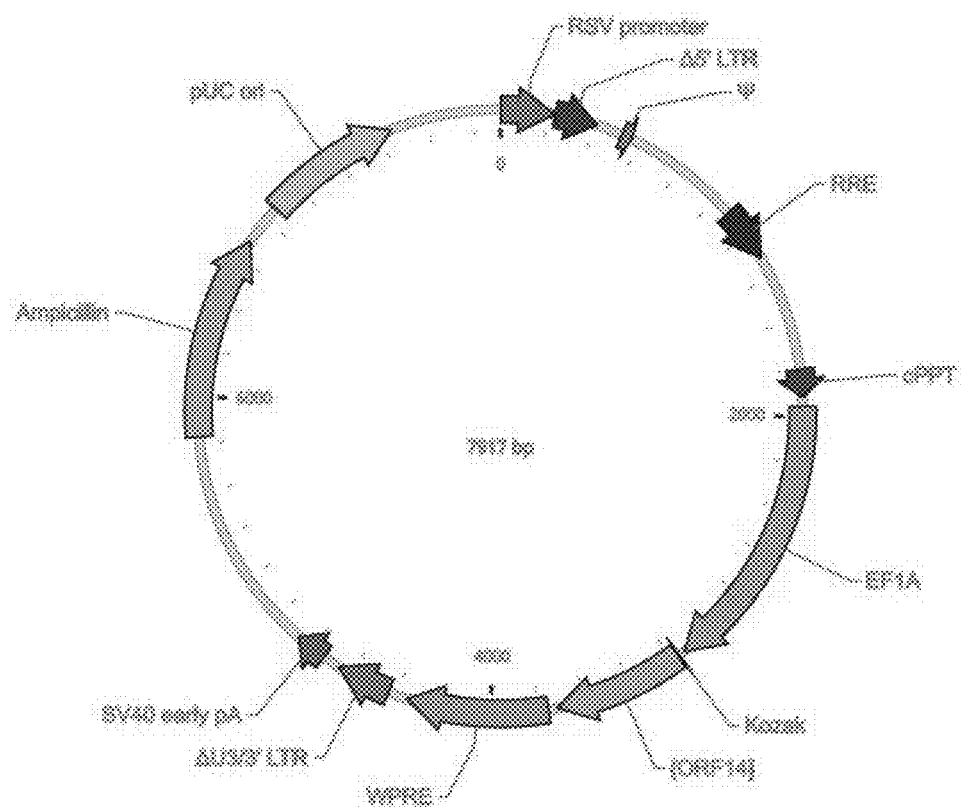
FIG. 44 shows a schematic of vector 14.

FIG. 44 shows a schematic of vector 14.

Table 53 below, shows the vector component name, the corresponding nucleotide position, the full name of the component and a description.

TABLE 53

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |

TABLE 53-continued

| Component Name | Nucleotide Position | Size (bp) | Description |
|---|---|---|---|
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF14(183)} | 3168-3719 | 552 | None |
| WPRE | 3758-4355 | 598 | Woodchuck hepatitis virus posttranscriptional regulatory element |
| ΔU3/3' LTR | 4647-4671 | 235 | Truncated HIV-1 3' long terminal repeat |
| SV40 early pA | 4744-4878 | 135 | Simian virus 40 early polyadenylation signal |
| Ampicillin | 5832-6692 | 861 | Ampicillin resistance gene |
| pUC ori | 6863-7451 | 589 | pUC origin of replication |

Vector 119

Figure 45:
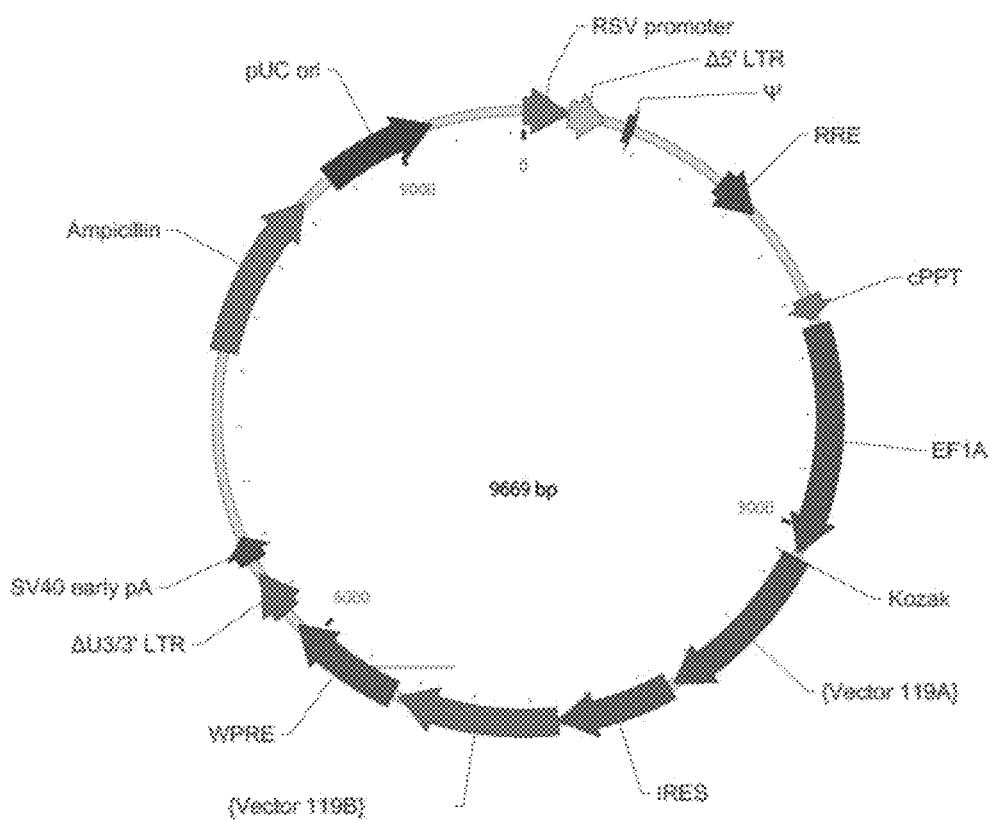
FIG. 45 shows a schematic of vector 119.

FIG. 45 shows a schematic of vector 119.

Table 54 below, shows the vector component name, the corresponding nucleotide position, the full name of the component and a description.

TABLE 54

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF119A} | 3159-4049 | 891 | None |
| IRES | 4074-4661 | 588 | Linker |
| {0RF119B} | 4662-5480 | 819 | None |
| WPRE | 5510-6107 | 598 | Woodchuck hepatitis virus posttranscriptional regulatory element |
| ΔU3/3' LTR | 6189-6423 | 235 | Truncated HIV-1 3' long terminal repeat |
| SV40 early pA | 6496-6630 | 135 | Simian virus 40 early polyadenylation signal |
| Ampicillin | 7584-8444 | 861 | Ampicillin resistance gene |
| pUC ori | 8615-9203 | 589 | pUC origin of replication |

Vector 120

Figure 46:
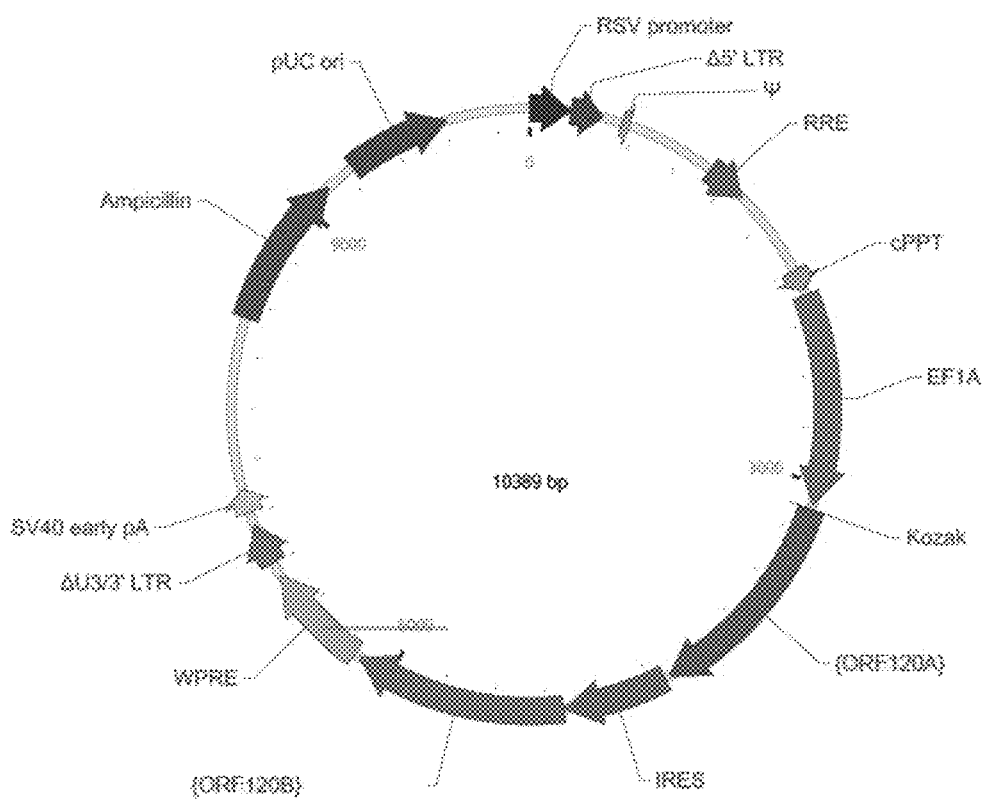
FIG. 46 shows a schematic of vector 120.

FIG. 46 shows a schematic of vector 120.

Table 55 below, shows the vector component name, the corresponding nucleotide position, the full name of the component and a description.

TABLE 55

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |

TABLE 55-continued

| Component Name | Nucleotide Position | Size (bp) | Description |
|---|---|---|---|
| EF1A | 1950-3128 | 1179 | Human eukaryotic translation elongation factor 1 α1 promoter |
| Kozak | 3153-3158 | 6 | Kozak translation initiation sequence |
| {ORF120A} | 3159-4391 | 1233 | None |
| IRES | 4416-5003 | 588 | Linker |
| {ORF120B} | 5004-6200 | 1197 | None |
| WPRE | 6230-6827 | 598 | Woodchuck hepatitis virus posttranscriptional regulatory element |
| ΔU3/3' LTR | 6909-7143 | 235 | Truncated HIV-1 3' long terminal repeat |
| SV40 early pA | 7216-7350 | 135 | Simian virus 40 early polyadenylation signal |
| Ampicillin | 8304-9164 | 861 | Ampicillin resistance gene |
| pUC ori | 9335-9923 | 589 | pUC origin of replication |

Vector 45

Figure 47:
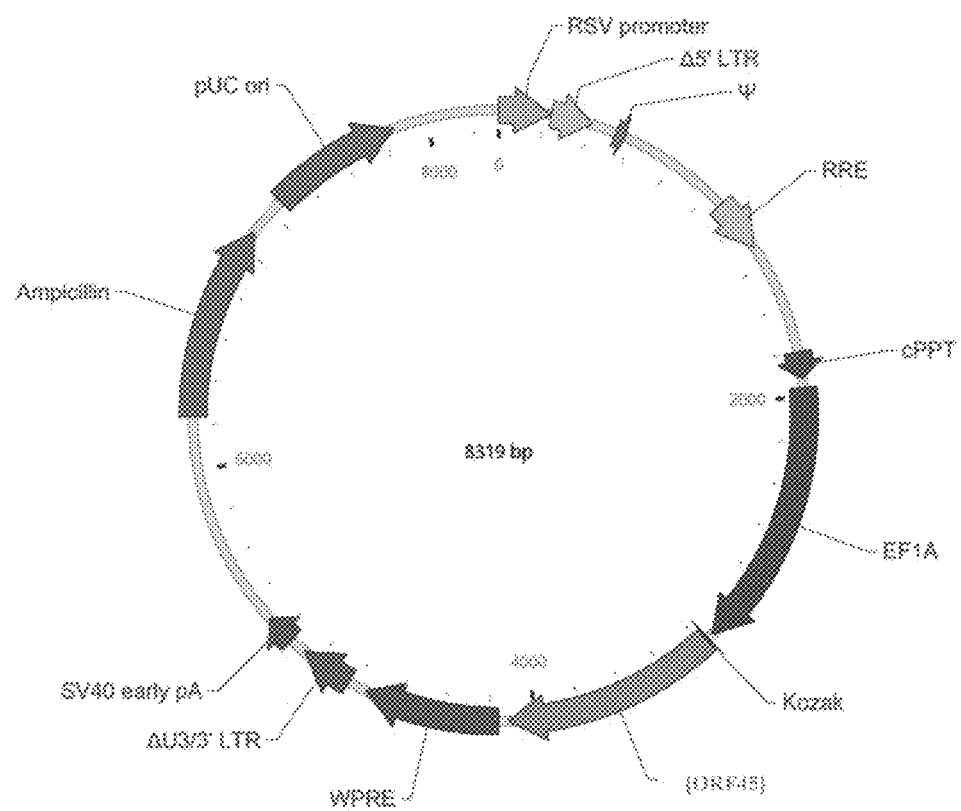
FIG. 47 shows a schematic of vector 45.

FIG. 47 shows a schematic of vector 45.

Table 56 below, shows the vector component name, the corresponding nucleotide position, the full name of the component and a description.

TABLE 56

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF45} | 3168-4121 | 954 | None |
| WPRE | 4160-4757 | 598 | Woodchuck hepatitis virus posttranscriptional regulatory element |
| ΔU3/3' LTR | 4839-5073 | 235 | Truncated HIV-1 3' long terminal repeat |
| SV40 early pA | 5146-5280 | 135 | Simian virus 40 early polyadenylation signal |
| Ampicillin | 6234-7094 | 861 | Ampicillin resistance gene |
| pUC ori | 7265-7853 | 589 | pUC origin of replication |

Vector 60

Figure 48:
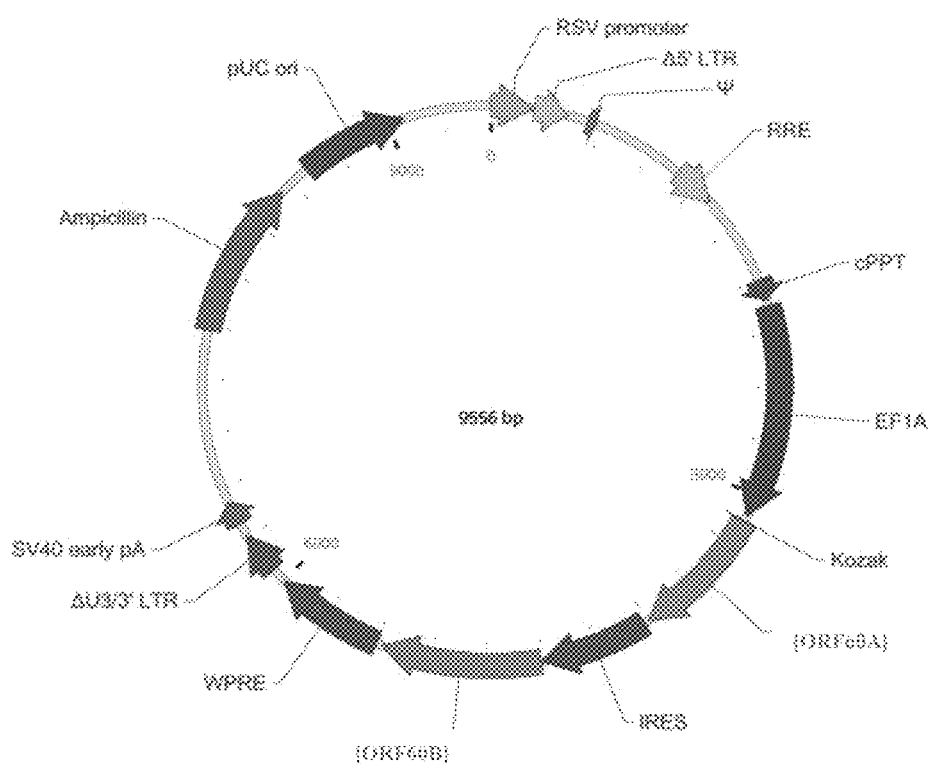
FIG. 48 shows a schematic of vector 60.

FIG. 48 shows a schematic of vector 60.

Table 57 below, shows the vector component name, the corresponding nucleotide position, the full name of the component and a description.

TABLE 57

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |

TABLE 57-continued

| Component Name | Nucleotide Position | Size (bp) | Description |
|---|---|---|---|
| {ORF60A} + Spacer | 3159-3900 | 742 | None |
| IRES | 3925-4512 | 588 | Linker |
| {ORF60B} | 4513-5367 | 855 | None |
| WPRE | 5397-5994 | 598 | Woodchuck hepatitis virus posttranscriptional regulatory element |
| ΔU3/3' LTR | 6076-6310 | 235 | Truncated HIV-1 3' long terminal repeat |
| SV40 early pA | 6383-6517 | 135 | Simian virus 40 early polyadenylation signal |
| Ampicillin | 7471-8331 | 861 | Ampicillin resistance gene |
| pUC ori | 8502-9090 | 589 | pUC origin of replication |

Vector 59

Figure 49:
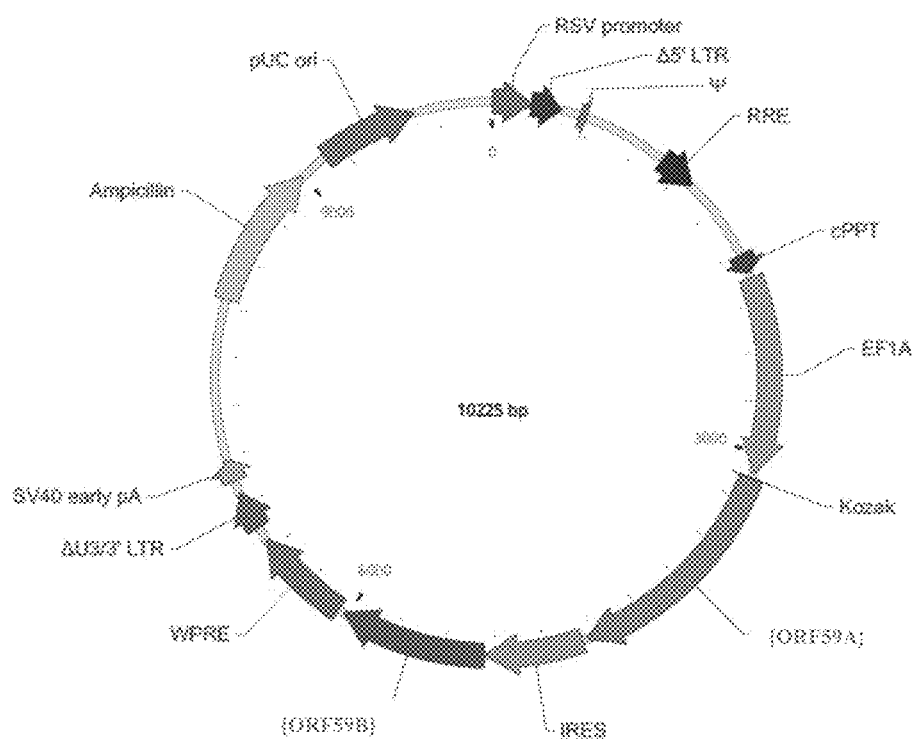
FIG. 49 shows a schematic of vector 59.

FIG. 49 shows a schematic of vector 59.

Table 58 below, shows the vector component name, the corresponding nucleotide position, the full name of the component and a description.

TABLE 58

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF59A} + spacer | 3159-4548 | 1390 | None |
| IRES | 4573-5160 | 588 | Linker |
| {ORF59B} | 5161-6036 | 876 | None |
| WPRE | 6066-6663 | 598 | Woodchuck hepatitis virus posttranscriptional regulatory element |
| ΔU3/3' LTR | 6745-6979 | 235 | Truncated HIV-1 3' long terminal repeat |
| SV40 early pA | 7052-7186 | 135 | Simian virus 40 early polyadenylation signal |
| Ampicillin | 8140-9000 | 861 | Ampicillin resistance gene |
| pUC ori | 9171-9759 | 589 | pUC origin of replication |

Vector 8

Figure 50:
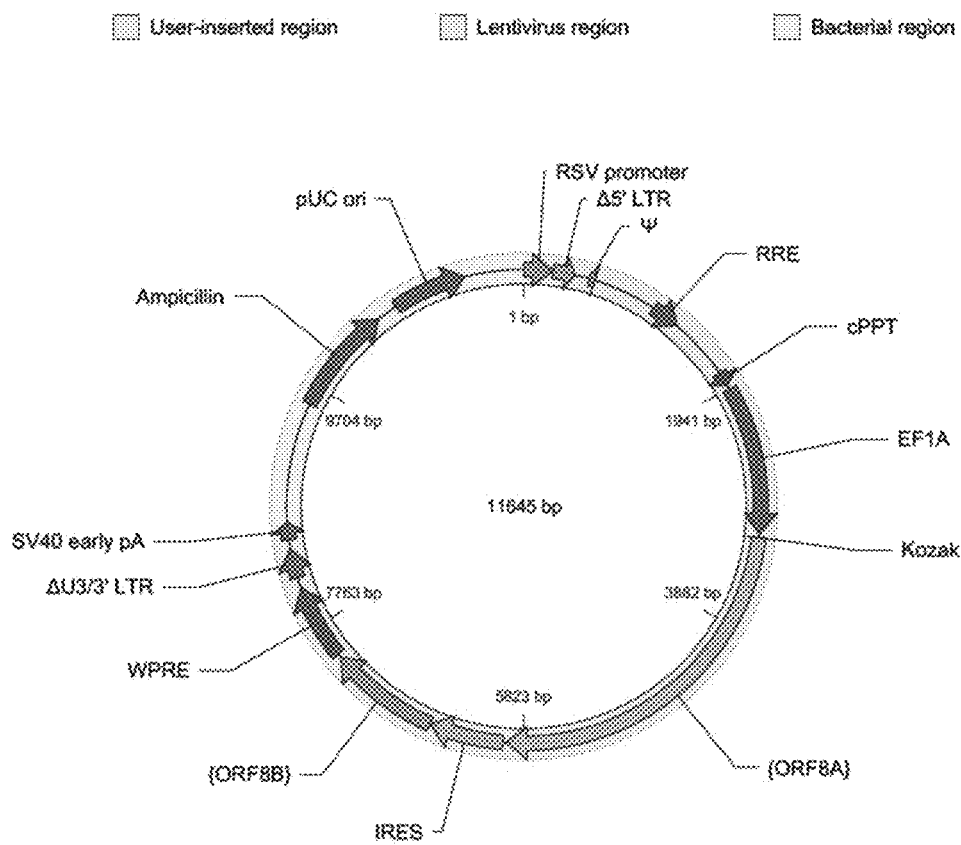
FIG. 50 shows a schematic of vector 8.

FIG. 50 shows a schematic of vector 8.

Table 59 below, shows the vector component name, the corresponding nucleotide position, the full name of the component and a description.

TABLE 59

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |

TABLE 59-continued

| Component Name | Nucleotide Position | Size (bp) | Description |
|---|---|---|---|
| {ORF8A} | 3159-5960 | | None |
| IRES | 5985-6572 | 588 | Linker |
| {ORF8B} | 6573-7456 | | None |
| WPRE | 7486-8083 | 598 | Woodchuck hepatitis virus posttranscriptional regulatory element |
| ΔU3/3' LTR | 8165-8399 | 235 | Truncated HIV-1 3' long terminal repeat |
| SV40 early pA | 8472-8606 | 135 | Simian virus 40 early polyadenylation signal |
| Ampicillin | 9560-10420 | 861 | Ampicillin resistance gene |
| pUC ori | 10591-11179 | 589 | pUC origin of replication |

Vector 128

Figure 51:
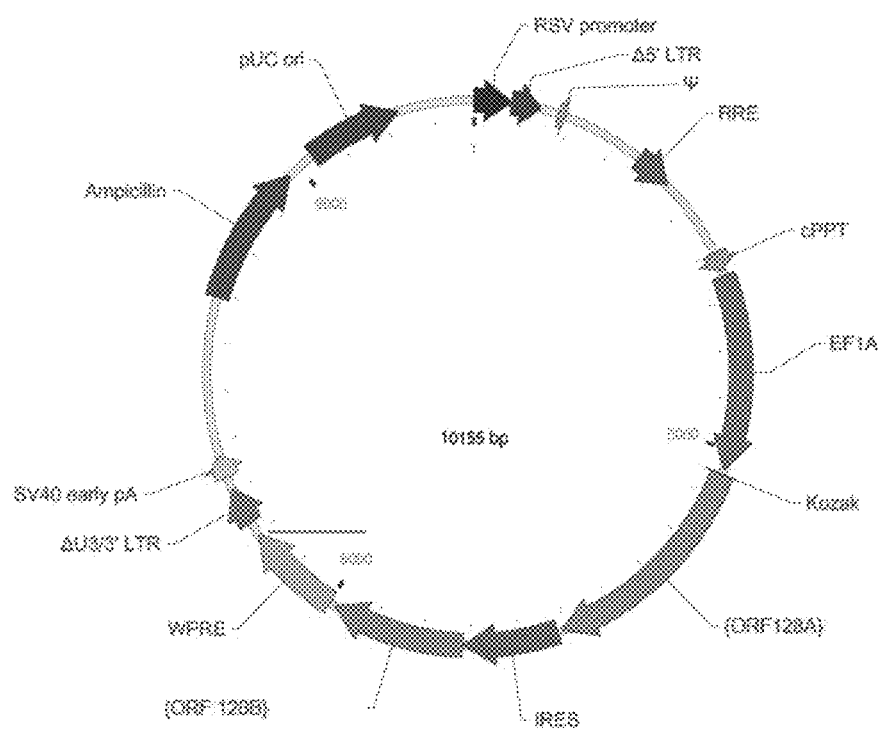
FIG. 51 shows a schematic of vector 128.

FIG. 51 shows a schematic of vector 128.

Table 60 below, shows the vector component name, the corresponding nucleotide position, the full name of the component and a description.

TABLE 60

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF128A} | 3159-4535 | 1377 | None |
| IRES | 4560-5147 | 588 | Linker |
| {ORF128B} | 5148-5966 | 819 | None |
| WPRE | 5996-6593 | 598 | Woodchuck hepatitis virus posttranscriptional regulatory element |
| ΔU3/3' LTR | 6675-6909 | 235 | Truncated HIV-1 3' long terminal repeat |
| SV40 early pA | 6982-7116 | 135 | Simian virus 40 early polyadenylation signal |
| Ampicillin | 8070-8930 | 861 | Ampicillin resistance gene |
| pUC ori | 9101-9689 | 589 | pUC origin of replication |

Vector 35

Figure 52:
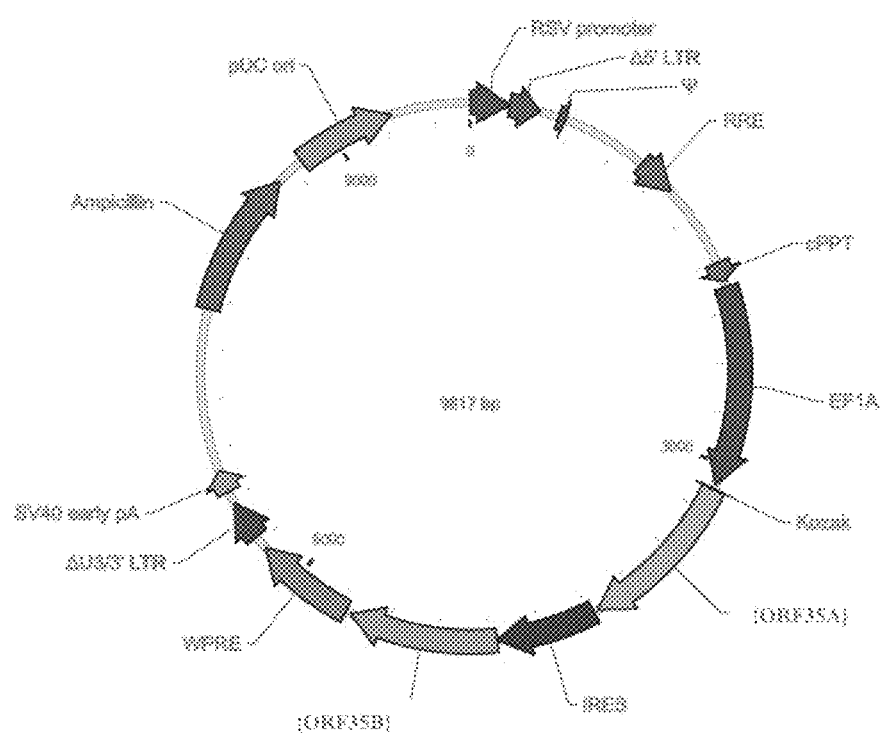
FIG. 52 shows a schematic of vector 35.

FIG. 52 shows a schematic of vector 35

Table 61 below, shows the vector component name, the corresponding nucleotide position, the full name of the component and a description.

TABLE 61

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF35A} + SPACER | 3159-4140 | 982 | None |

TABLE 61-continued

| Component Name | Nucleotide Position | Size (bp) | Description |
|---|---|---|---|
| IRES | 4165-4752 | 588 | Linker |
| (ORF35B) | 4753-5628 | 876 | None |
| WPRE | 5658-6255 | 598 | Woodchuck hepatitis virus posttranscriptional regulatory element |
| ΔU3/3' LTR | 6337-6571 | 235 | Truncated HIV-1 3' long terminal repeat |
| SV40 early pA | 6644-6778 | 135 | Simian virus 40 early polyadenylation signal |
| Ampicillin | 7732-8592 | 861 | Ampicillin resistance gene |
| pUC ori | 8763-9351 | 589 | pUC origin of replication |

Example 4. Primary Human Mixed Lymphocyte Tumor Reaction (MLTR) Testing for In Vitro Activation ENLST™ cells derived from an allogeneic human melanoma cell line (SK-MEL2) are genetically engineered to express the core three essential human immunomodulators OX40 Ligand (OX40L), CD27 Ligand (CD70), and CD28 Ligand (CD28L) by the following process.

Vector 14 comprising an exogenous nucleic acid encoding a stably expressed immunomodulatory molecule, wherein the immunomodulatory molecule is OX40L is introduced into a population of live SK-MEL2 tumor cells; Vector 18 comprising an exogenous nucleic acid encoding a stably expressed immunomodulatory molecule, wherein the immunomodulatory molecule is CD27 Ligand (CD70) is introduced into a second population of live SK-MEL2 tumor cells; and Vector 30 comprising an exogenous nucleic acid encoding a stably expressed immunomodulatory molecule, wherein the immunomodulatory molecule is CD28 Ligand (CD28L) is introduced into a third population of live SK-MEL2 tumor cells. A fourth population of live SK-MEL2 tumor cells is transduced or transfected with Vector 14 comprising an exogenous nucleic acid encoding stably expressed OX40L, Vector 18 comprising an exogenous nucleic acid encoding stably expressed CD70, and Vector 30 comprising an exogenous nucleic acid encoding stably expressed CD28L The resulting live SK-MEL2 tumor cell stably expresses OX40L, CD70 and CD28L (hereinafter "14-18-30").

The same process may be used to introduce one or more additional subsets of immunomodulators designated as R, with each subset comprising 3-25, inclusive immunomodulators.

Tumor cell line variants are generated by selecting for tumor cell clones that stably express an immunogenic amount of the exogenous subset of the immunomodulatory molecules. Clonally derived cell line variants are selecting in a mixed lymphocyte tumor cell reaction (MLTR) by one or more parameters selected from: cellular proliferation, cellular subset differentiation, cytokine release profile, and tumor cell lysis; wherein the selected clonally derived cell line variant is effective to stimulate activation of one or more of T-lymphocytes, natural killer (NK) cells, dendritic cells (DCs) or B lymphocytes.

The allogeneic genetically engineered SK-MEL2 tumor cell lines are tested for their immunomodulatory potential by primary and secondary MLTR assay.

Stable expression of OX40 Ligand (OX40-L), CD27 Ligand (CD70), or CD28 Ligand (CD28L) by the SK-MEL2 ENLST™ cells and by SK-MEL2 ENLST™ cells genetically engineered to simultaneously express immunomodulators OX40 Ligand, CD27 Ligand and CD28 Ligand is effective to induce one or more subpopulations of PBMCs to proliferate in response to the expressed immunomodulatory molecules and to then enter an effector phase for killing of tumor cells.

Primary MLTR Assay.

Peripheral blood mononuclear cells (PBMCs) are obtained from the peripheral blood of healthy individuals and from cancer patients, and the blood cells separated using a Ficoll-Paque gradient. Anticoagulant-treated blood is diluted in the range of 1:2 to 1:4 with PBS/EDTA to reduce aggregation of erythrocytes. The diluted blood is then layered above a Ficoll-Paque solution in a centrifuge tube, without mixing. The layered blood/Ficoll-Paque is centrifuged for 40 minutes at 400×g between 18° and 20° C., without the use of the centrifuge brake, resulting in the formation of blood fractions comprising, from top to bottom, a first fraction comprising blood plasma; a second fraction comprising mononuclear cells; a third fraction comprising Ficoll-Paque media; and a fourth fraction comprising granulocytes and erythrocytes. The fraction comprising mononuclear cells is selected for further processing.

Each of the cells from the transfected ENLST™ cells and from parental tumor cell line SK-MEL2 (control) is co-cultured with PBMCs for up to 28 days under standard tissue culture conditions, followed by evaluation for immune cell proliferation, immune cell differentiation, measured by flow cytometry and CyTOF, cytokine release profile, and cytoxicity, measured by LDH release assay.

Experiments were carried out to determine the effect of contacting PBMCs with SKMEL-2 derived ENLST™ cells transfected or transduced with recombinant DNA sequences encoding one or more of immunomodulators OX40 Ligand, CD27 Ligand, and CD28 Ligand on CD8+ T cell activation and expansion. Parental cell line SKMEL2 was modified with Vector 14 encoding OX40L ("14"), with Vector 18 encoding CD27 Ligand only ("18"), with Vector 30 encoding CD28 Ligand comprising CD80 and CD86 only ("30"), and with Vectors 14, 18 and 30 ("14-18-30"). Functional characterization of the immunostimulatory effects of the ENLST™ cells was performed using a primary MLTR assay, as described in Example 1. CD8+ T-cell proliferation was measured by flow cytometry. Tumor cell killing was observed on day 9.

Figure 53A:
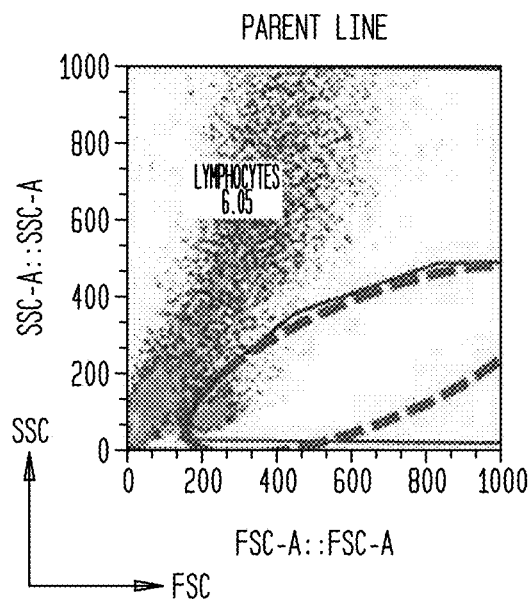
FIGS. 53A and 53B show flow cytometry forward (FSC) and side scatter (SSC) plots for size and granularity after incubating parent line SKMEL2 (53A) and SKMEL-2 containing immunomodulators 14, 18 and 30 (FIG. 53B) with PBMCs in a mixed lymphocyte tumor response assay. The dotted oval in FIGS. 53A and 53B indicates the lymphocyte gate.
Figure 53B:
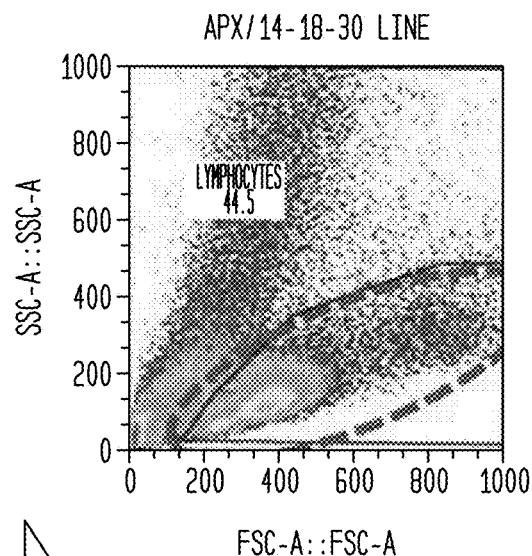
Figure 53C:
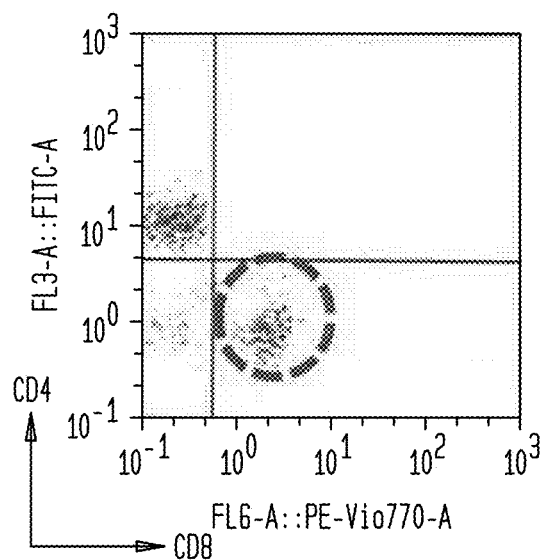
FIG. 53C and FIG. 53D show the CD8 population after incubation of the PBMCs in the mixed lymphocyte tumor response assay with the parent cell line (FIG. 53C) and SKMEL2 transfected or transduced with recombinant DNA sequences encoding immunomodulators OX40 Ligand (Vector 14), CD27 Ligand (Vector 18), and CD28 Ligand (Vector 30 comprising CD80, CD86, or both) (FIG. 53D). The dotted circle in the bottom panel of graphs shows the CD8 gate. In PBMCs following coincubation with the parental cell line (SKMEL-2), there is an approximately equal number of CD4+ and CD8+ T cells, whereas in the PBMCs following coincubation with the Engineered Leukocyte Stimulator cells ("ENLST™ cells") engineered to express the immunomodulators OX40 Ligand (Vector 14), CD27 Ligand (Vector 18), and CD28 Ligand (Vector 30 comprising CD80, CD86 or both) there is a large approximate 2 log number of CD8+ T cells. This large increase in CD8+ T cells is only evident when all three signals are delivered simultaneously and is not present when each signal is delivered individually, hence providing an example of synergistic signaling previously unrecognized.
Figure 53D:
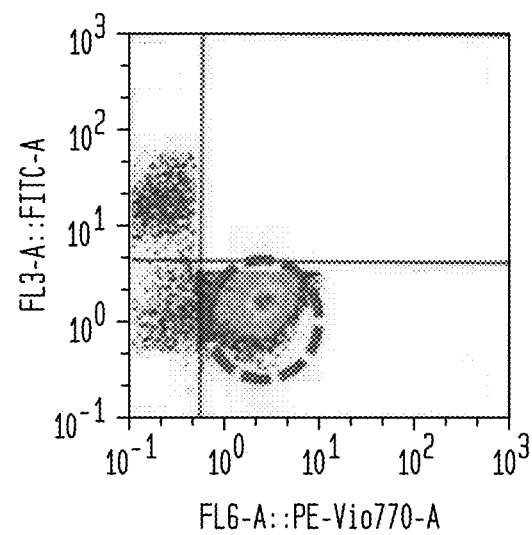

FIGS. 53A and 53B show flow cytometry forward (FSC) and side scatter (SSC) plots for size and granularity after incubating parent line SKMEL2 (FIG. 53A) and SKMEL-2 containing immunomodulators 14, 18 and 30 (FIG. 53B) with PBMCs in a mixed lymphocyte tumor response assay. The dotted oval in FIGS. 53A and 53B indicates the lymphocyte gate. FIG. 53C and FIG. 53D show the CD8 population after incubation of the PBMCs in the mixed lymphocyte tumor response assay with the parent cell line (FIG. 53C) and SKMEL2 transfected or transduced with recombinant DNA sequences encoding immunomodulators OX40 Ligand (Vector 14), CD27 Ligand (Vector 18), and CD28 Ligand (Vector 30 comprising CD80, CD86, or both) (FIG. 53D). The dotted circle in the bottom panel of graphs shows the CD8 gate. In PBMCs following coincubation with the parental cell line (SKMEL-2), there is an approximately equal number of CD4+ and CD8+ T cells. No induction was observed by flow cytometry and no tumor cell killing was observed. In the PBMCs following coincubation with the ENLST™ cells engineered to express the immunomodulators OX40 Ligand (Vector 14), CD27 Ligand (Vector 18), and CD28 Ligand (Vector 30 comprising CD80, CD86 or both) there is a large increase in the number of CD8+ T cells. As measured by flow cytometry, PBMCs following coincubation with ENLSTs comprising simultaneous expression of 14-18-30 expressed a two-log greater number of activated CD8+ cells compared to PBMC following coincubation with the unmodified parent cell line. This large increase in CD8+ T cells is only evident when all three signals are delivered simultaneously and is not present when each signal (i.e., OX40 Ligand alone, CD27 Ligand alone, or CD28 Ligand alone) is delivered individually, hence providing an example of synergistic signaling previously unrecognized.

Example 5. Characterization of PBMC Lymphocyte Population Induction by SK-MEL-2 Derived ENLST™ Cells Naïve PBMCs were co-incubated with unmodified SD-MEL-2 cells) ("SK") (control) or activated with SK-MEL-2 ENLST™ cells genetically engineered to express 14-18-30, and the composition of the cell populations assessed on day 9.

Primary MLTR-PBMC Stimulation (Induction Phase).

Results are shown in FIGS. 54A and 54B. On day 9, PBMCs were induced with unmodified 5K-MEL2 (SK) cells (control) (FIG. 54A) or with the genetically engineered 14-18-30 5K-MEL2 ENLST™ cells ("activation cells") (FIG. 54B). FIG. 54A shows day 9 PBMCs induced with unmodified parental 5K-MEL-2 cells, left, microscopy; right flow cytometry. As shown in FIG. 54A, the lymphocyte population neither expands in reaction to unmodified tumor cells, nor does it lyse them. FIG. 54B shows day 9 PBMC induced with 5K-MEL-2 derived ENLST™ cells; left, microscopy, right flow cytometry. The oval outline in the flow cytometry in FIG. 54A corresponds to live unmodified SKMEL 2 parent tumor cells. The arrow in FIG. 54B shows that the ENLST™ cells are eliminated by the induced PBMCs.

Example 6. Characterization of Tumoricidal Properties of the MNCs Following In Vitro Activation Since the ENLST™ cells genetically engineered to express 14-18-30 were derived from SK melanoma cells, the cytolytic activity of PBMCs activated by the ENLST™ cells against other melanoma cell lines, unmodified melanoma cell lines, and against non-melanoma cell lines was assessed.

Secondary MLTR Assay.

A secondary effector assay was used to assess by flow cytometry the tumoricidal properties of the MNCs following in vitro activation. PBMCs were tested against parental cell line SK-MEL-2 and two unrelated melanoma cell lines (SK-MEL-28 cell line, and M14 cell line) which are distinct from 5K-MEL-2. Unmodified SK-MEL-28 and unmodified M14 represent third party cell lines to which the SK-MEL-2-derived activated PBMCs are naïve.

Figure 55A:
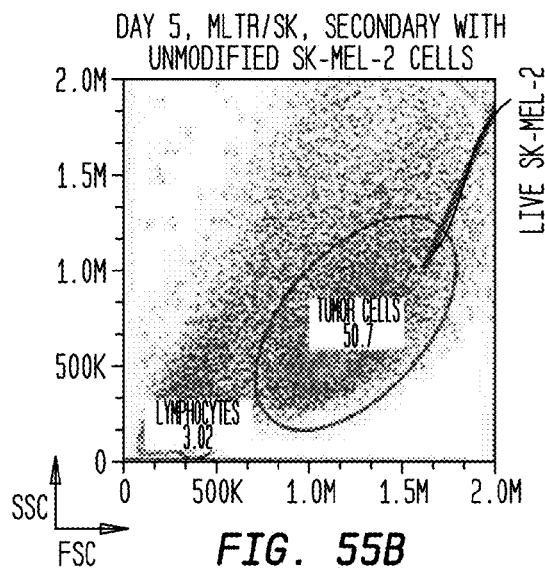
FIGS. 55A, 55B, 55C, 55D, 55E, and 55F shows results of characterization of the tumoricidal properties of PBMCs following their in vitro activation by 14-18-30 expressing SK-MEL-2-derived ENLST™ cells with SK-MEL-2 cells, SK-MEL-28 cells, and M14 cells by flow cytometry forward (FSC) and side scatter (SSC) plots for size and granularity.
Figure 55B:
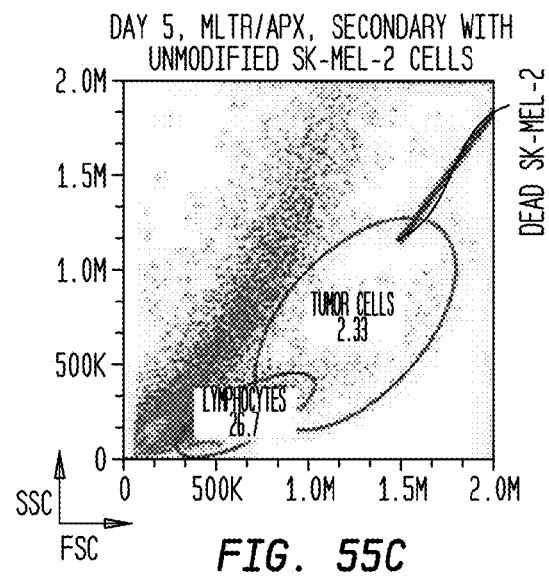
Figure 55C:
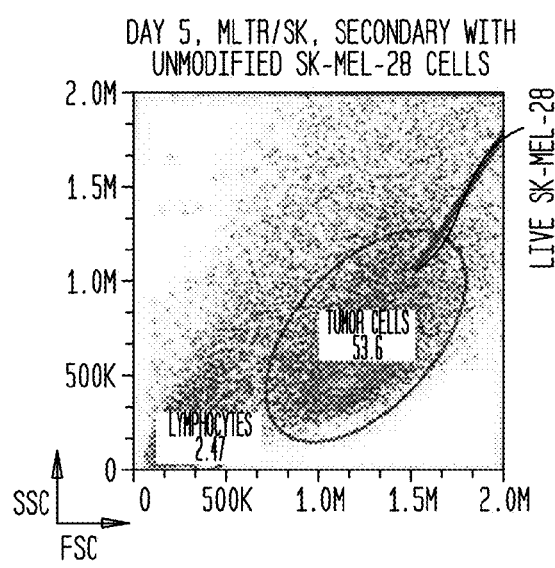
Figure 55D:
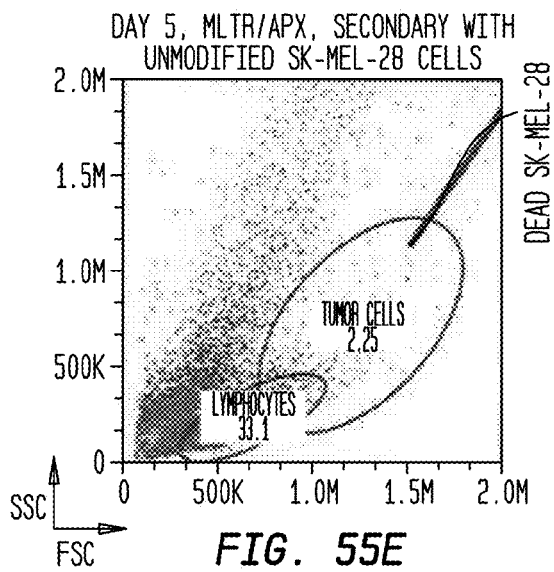
Figure 55E:
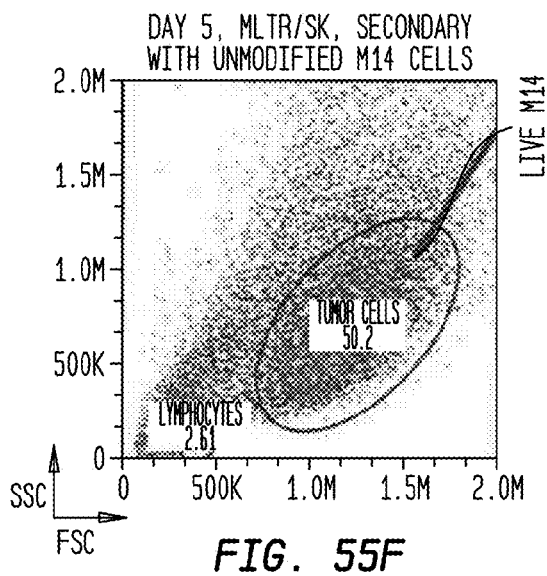
Figure 55F:
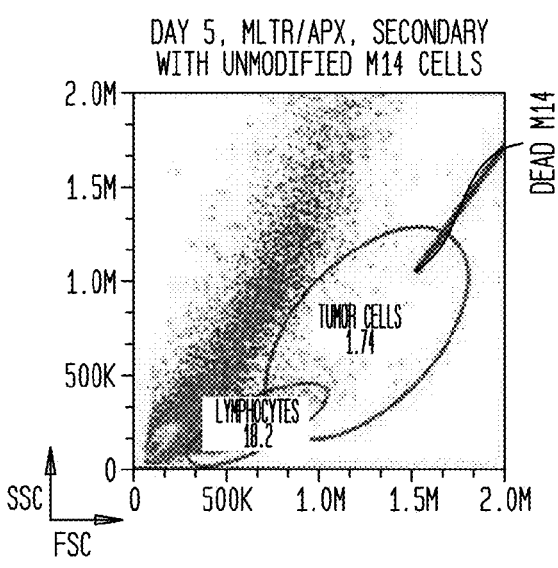

Results by flow cytometry forward (FSC) and side scatter (SSC) plots for size and granularity are shown in FIGS. 55A, 55B, 55C, 55D, 55E, and 55F. FIG. 55A, FIG. 55C, and FIG. 55E show day 5 secondary mixed lymphocyte tumor response assays assessing cytolysis of PBMC against unmodified tumor targets; FIG. 55A shows that PBMCs previously incubated with unmodified SK-MEL-2 cells do not lyse unmodified SK-MEL-2 cells; FIG. 55C shows that PBMCs previously incubated with unmodified SK-MEL-2 cells do not lyse unmodified SK-MEL-28 cells; FIG. 55E shows that PBMCs previously incubated with unmodified SK-MEL-2 cells do not lyse unmodified M14 cells. FIG. 55B, FIG. 55D, and FIG. 55F show day 5, secondary mixed lymphocyte tumor response assay with SK-MEL-2 derived 14-18-30 ENLST™ cell-activated MNCs coincubated with: FIG. 55B PBMCs previously coincubated with ENLST™ cells lyse unmodified SK-MEL-2 cells; FIG. 55D, PBMCs previously coincubated with ENLST™ cells lyse unmodified SK-MEL-28 cells; FIG. 55F PBMCs previously coincubated with ENLST™ cells lyse unmodified M14 cells. Therefore, cytolytic activity was dependent on prior treatment with the genetically engineered ENLST™ tumor cell lines.

Unmodified SK-MEL-2 cells, SK-MEL-28 cells, or ML14 cells therefore are unable to induce PBMC activation; however, each of these cell lines is lysed by PBMCs activated by SK-MEL-2-derived ENLST™ cells once the activated PBMCs are formed. Therefore, cytolytic activity was dependent on prior treatment with the genetically engineered ENLST™ cells.

The following non-melanoma tumor lines were also lysed in the secondary assay by PBMCs activated by the genetically engineered 14-18-30 SKMEL-2 ENLST™ cells:

TABLE 62

| Tumor cell line | Origin |
| --- | --- |
| K562 | Leukemia |
| COLO205 | Colorectal |
| HOP62, | Lung |
| IGR-OV1 | Ovarian |
| SKOV | Ovarian |
| PC3, | Prostate |
| SN12C | renal |

The PBMCs activated by 14-18-30 ENLST™ cells however do not kill normal MNCs whether autologous or allogeneic (data not shown).

The induced cytotoxic activity therefore is broad and extends beyond melanoma.

Example 7. Characterization of PBMC Populations Following PBMC Induction by SK-MEL-2 Derived ENLST™ Cells after 9 Days in Primary Mixed Lymphocyte Tumor Response Assay FIG. 56A shows a CyTOF mass cytometry single-cell phenotype analysis map of PBMC populations, FIG. 56B, 56C, 56D, 56E, 56F show visNE density contour plots of CyTOF staining following PBMC induction by parental (FIG. 56B) or immunomodulator expressing SK-MEL-2 derived ENLST™ cells (FIGS. 56C, 56D 56D, 56E, 56F) after 9 days in primary mixed lymphocyte tumor response assay. FIG. 56B, shows a PBMC subpopulation shift following induction by parental SK MEL-2 cells; note that an NK cell population and a myeloid cell population are absent; FIG. 56C, shows a PBMC subpopulation shift following induction by ENLST™ cells transduced or transfected with vector 3, showing induction of B and myeloid cells. FIG. 56D, showing PBMC subpopulation shift following induction by ENLST™ cells transduced or transfected with vectors 3 and 4, showing induction of B cells; FIG. 56E, showing PBMC subpopulation shift following induction by ENLST™ cells transduced or transfected with vectors 3, 4 and 5, showing induction of B cells and Myeloid cells; FIG. 56F, showing PBMC subpopulation shift following induction by ENLST™ cells transduced or transfected with vectors 3, 4 and 6.

FIGS. 57A, 57B, 57C, 57D, and 57E show by flow cytometry (FIG. 57A) and phase contrast microscopy (FIG. 57B, FIG. 57C, FIG. 57D, and FIG. 57E) that PBMCs previously coincubated with 14-18-30 containing ENLST™ cells are able to lyse unmodified tumor cells. At least two distinct subpopulations of the PBMC's previously activated by coincubation with 14-18-30 ENLST™ cells are capable of cytolysis of unmodified tumor cells. FIG. 57A shows the sorting gates for CD56, CD3 and CD8 of PBMCs following a 9 day coincubation with 14-18-30 expressing ENLST™ cells in a primary mixed lymphocyte tumor cell assay; FIG. 57B shows CD56+CD3+ plus unmodified SKMEL2 at t=0 and (FIG. 57C) at t=8 hours; FIG. 57D shows CD56−CD3+ CD8+ plus unmodified SK-MEL-2 at t=0 and (FIG. 57E) at t=8 hours.

Example 8. In Vivo Xenograft Mouse Experiments

Six week old female in-bred SCID mice are obtained from Charles River Laboratories (Hartford, Conn., USA). Animals are handled according to a protocol approved by the Institutional Animal Care and Use Committee of the facility. Mice are allowed to acclimate to animal housing.

A human tumor xenograft was established in NSG (NOD scid gamma mice (Jackson Laboratory). Human tumors were implanted on the flank of the NSG mice Human tumor cells were implanted on the flank of NGS (NOD scid gamma) mice and allowed to grow to 150 mm$^3$. Mice were randomly divided into two groups, a control and a treated group, with 6 mice per group. The treated group was treated with expanded activated PBMCs comprising expanded activated serial killer cells activated by 14-18-30 expressing ENLST™ cells. On day 30 (t=0) mice in the control group were inoculated with vehicle only, and mice in the treated group were inoculated with $3\times10^6$ expanded activated PBMCs comprising expanded activated serial killer cells. Tumor size was measured by caliper over time after inoculation in both groups.

Figure 58:
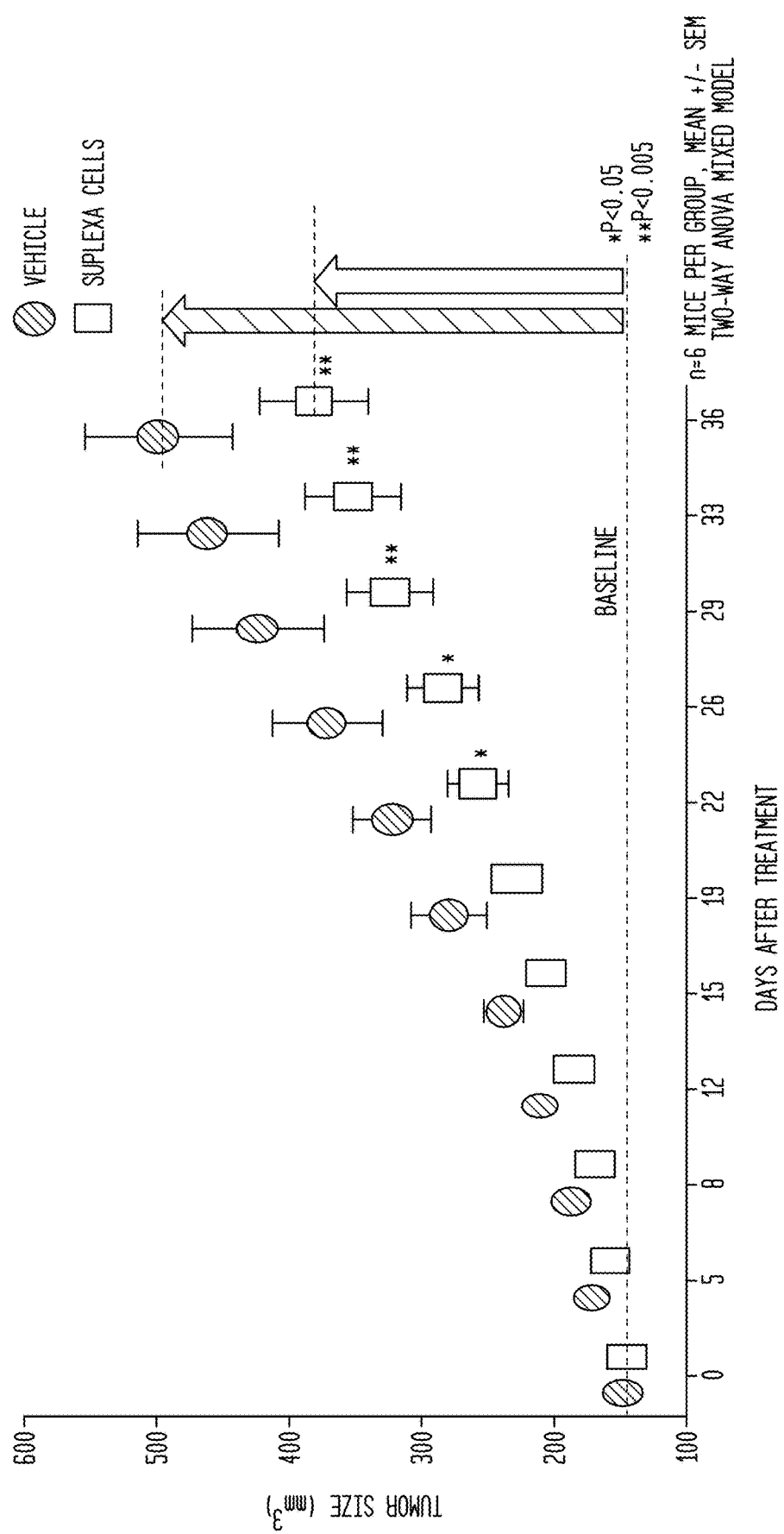
FIG. 58 is a box and whisker plot of shows results of a xenograft treatment study using NGS mice. The ends of each box are the upper and lower quartiles; the median is marked by a vertical line inside the box, and the whiskers are the two lines outside the box that extend to the highest and lowest observations. Human tumor cells were implanted on the flank of NGS (NOD scid gamma) mice. The tumors were allowed to grow to 150 mm³. Mice were divided into two groups, a control and a treated group, with 6 mice per group. On day 30 (t=0) mices in the control group were inoculated with vehicle only, and mice in the treated group were inoculated with 3×10⁶ PBMCs activated by 14-18-30 expressing ENLST™ cells ("SUPLEXA™ cells"). Tumor size was measured at intervals through 36 days after inoculation. Divergence between the two groups appeared within 5 days. After day 22, the divergence became statistically significant (*P<0.05; **P<005).

FIG. 58 is a box and whisker plot of shows results of a xenograft treatment study using NGS mice. The ends of each box are the upper and lower quartiles; the median is marked by a vertical line inside the box, and the whiskers are the two lines outside the box that extend to the highest and lowest observations. Human tumor cells were implanted on the flank of NGS (NOD scid gamma) mice. The tumors were allowed to grow to 150 mm$^3$. Mice were randomly divided into two groups, a control and a treated group, with 6 mice per group. On day 30 (t=0) mices in the control group were inoculated with vehicle only, and mice in the treated group were inoculated with $3\times10^6$ PBMCs activated by 14-18-30 expressing ENLST™ cells ("SUPLEXA cells"). Tumor size was measured at intervals through 36 days after inoculation. Divergence between the two groups appeared within 5 days. After day 22, the divergence became statistically significant (*$P<0.05$; **$P<005$).

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method of treating a patient with melanoma, wherein the patient is not currently under the influence of an immunosuppressive regimen, the method comprising: preparing a composition comprising a cell product comprising an activated and expanded population of mononuclear cells (MNCs), the MNCs comprising activated and expanded subpopulations of cytotoxic serial killer cells by:

(a) inducing an immune response in vitro by:

(1) isolating a population of MNCs derived from peripheral blood or cord blood;

(2) preparing a population of engineered leukocyte stimulator (ENLST™) cells comprising a population of tumor cells derived from a primary SKMEL-2 melanoma tumor cell line that is genetically engineered by transfecting or transducing recombinant DNA sequences coding for at least three core immunomodulator peptides comprising OX40 Ligand (OX40L), CD27 Ligand (CD70) and CD28 Ligand (CD28L) and selecting for ENLST™ cell clones that stably express the three core immunomodulator peptides, wherein the amino acid sequence of a wild type OX40 Ligand comprises SEQ ID NO: 108, the amino acid sequence of a wild type CD27 ligand comprises SEQ ID NO: 109, and the amino acid sequence of a wild type CD28 ligand comprises SEQ ID NO: 110, SEQ ID NO: 111, or both;

(3) contacting the population of MNCs of step (a)(1) with the ENLST™ cells of step (a)(2) in vitro in a mixed lymphocyte tumor cell reaction (MLTR) assay; wherein the contacting is effective to stimulate synergistic expansion of cytotoxic serial killer cells, to form an activated population of MNCs comprising activated subpopulations of cytotoxic serial killer cells;

(b) culturing the activated MNCs to form a cell product containing an activated and expanded population of MNCs including expanded and activated subpopulations of cytotoxic serial killer cells;

(c) preparing a unit dose package comprising an individual dose of the activated and expanded cell product, freezing the unit dose packages, and storing the frozen unit dose packages in cryostorage;

(d) thawing a therapeutic amount of the frozen unit dose packages comprising the cell product under controlled conditions;

(e) optionally combining the frozen and thawed cell product with a pharmaceutically acceptable carrier to form a pharmaceutical composition; and (f) administering the therapeutic amount of the cell product of (d) or the pharmaceutical composition of (e) comprising the activated and expanded cell product to the patient with melanoma, wherein the therapeutic amount is effective to reduce melanoma burden.

2. The method according to claim 1, wherein the population of ENLST™ cells is further genetically engineered to express an additional number of immunomodulatory molecules comprising 3-25 immunomodulators ("R groups").

3. The method according to claim 1, wherein CD28 ligand comprises CD80, CD86 or both.

4. The method according to claim 1, wherein the engineered leukocyte stimulator (ENLST™) cell transduced or transformed to stably express the core immunomodulators OX40 Ligand, CD27 Ligand, and CD28 Ligand comprising CD80, CD86 or both is effective to synergistically induce a two-log expansion of activated CD8+ cells in peripheral blood mononuclear cells compared to an unmodified control cell line.

5. The method according to claim 1, wherein in step (b)(i) subpopulations of the activated MNCs are identified and isolated by flow cytometry.

6. The method according to claim 1, wherein the activated and expanded MNCs comprise activated and expanded subpopulations of serial killer cells comprising one or more of an NK cell population, an NKT cell population, a CD8 CTL cell population, a CD4 cell population, and a TCRγδ cell population.

7. The method according to claim 1, wherein the population of mononuclear cells is autologous to the subject.

8. The method according to claim 1, wherein the population of mononuclear cells is allogeneic to the subject.

9. The method according to claim 1, wherein cytotoxic serial killer activity of the activated and expanded serial killer cell populations is specific to cancer antigens of the genetically engineered leukocyte stimulator cells, without affecting normal cells.

10. The method according to claim 1, wherein cytotoxic serial killer activity of the activated and expanded serial killer cell population(s) is effective to kill cancer cells regardless of cancer type, without affecting normal cells.

11. The method according to claim 1, further comprising administering an immune checkpoint inhibitor.

12. The method according to claim 11, wherein the immune checkpoint inhibitor is selected from one or more of a PD-1 inhibitor, a PD-L1 inhibitor, a TIM-3 inhibitor, a TIGIT inhibitor, and a LAG-3 inhibitor.

13. A cell product comprising a population of expanded and activated mononuclear cells comprising activated subpopulations of cytotoxic serial killer cells prepared by a process comprising:

(a) isolating a population of MNCs derived from peripheral blood or cord blood;

(b) preparing a population of engineered leukocyte stimulator (ENLST™) cells comprising a population of tumor cells derived from a primary SKMEL-2 melanoma tumor cell line that is genetically engineered by transfecting or transducing recombinant DNA sequences coding for at least three core immunomodulator peptides comprising OX40 Ligand (OX40L), CD27 Ligand (CD70) and CD28 Ligand (CD28L) and selecting for ENLST™ cell clones that stably express the three core immunomodulator peptides, wherein the amino acid sequence of a wild type OX40 Ligand comprises SEQ ID NO: 108, the amino acid sequence of a wild type CD27 ligand comprises SEQ ID NO: 109, and the amino acid sequence of a wild type CD28 ligand comprises SEQ ID NO: 110, SEQ ID NO: 111, or both;

(c) contacting the population of MNCs of step (a) with the ENLST™ cells of step cells of step (b) in vitro in a mixed lymphocyte tumor cell reaction (MLTR) assay to form an activated population of MNCs comprising activated subpopulations of cytotoxic serial killer cells;

(d) expanding the activated population of MNCs comprising activated subpopulations of serial killer cells in vitro by culturing the activated MNCs to form the cell product comprising an activated and expanded population of MNCs comprising expanded and activated subpopulations of cytotoxic serial killer cells.

14. The cell product prepared by the process according to claim 13, wherein the activated and expanded MNCs comprising activated and expanded subpopulations of cytotoxic serial killer cells comprising one or more of an NK cell population, an NKT cell population, a CD8 CTL cell population, a CD4 cell population, and a TCRγδ cell population.

15. The cell product prepared by the process according to claim 13, wherein the cytotoxic serial killer cells are tumoricidal.

16. The cell product prepared by the process according to claim 14, wherein an amino acid sequence of a wild type OX40 Ligand codon optimized for human expression is SEQ ID NO: 108, an amino acid sequence of a wild type CD27 Ligand codon optimized for human expression is SEQ ID NO: 109, and an amino acid sequence of a wild type CD28 Ligand codon optimized for human expression is SEQ ID NO: 110, SEQ ID NO: 111, or both.

17. The cell product prepared by the process according to claim 13, wherein the contacting in step (c) is effective to synergistically induce a two-log expansion of CD8+ cells.

18. The cell product prepared by the process according to claim 13, wherein the biological sample is peripheral blood or cord blood.

* * * * *

UNITED STATES PATENT AND TRADEMARK OFFICE
CERTIFICATE OF CORRECTION

| | |
|---|---|
| PATENT NO. | : 10,731,128 B2 |
| APPLICATION NO. | : 16/660442 |
| DATED | : August 4, 2020 |
| INVENTOR(S) | : Frank Borriello |

It is certified that error appears in the above-identified patent and that said Letters Patent is hereby corrected as shown below:

In the Specification
Column 9, Line 13, "FM receptor" should be -- Flt1 receptor --
Column 130, Line 12, "trehalo se" should be --trehalose --
Column 151-152, Table 11, under Component Name heading, first column, "RRET" should be -- RRE --
Column 154, Line 20, "Ices" should be -- Ires --
Column 153-154, Table 12, under Component Name heading, first column, "RRET" should be -- RRE --
Column 153-154, Table 12, under Full Name heading, third column, "ORF1" should be -- ORF2A --
Column 155-156, Table 13, under Component Name heading, first column, "RRET" should be -- RRE --
Column 157-158, Table 14, under Component Name heading, first column, "RRET" should be -- RRE --
Column 157-158, Table 15, under Component Name heading, first column, "RRET" should be -- RRE --
Column 159-160, Table 16, under Component Name heading, first column, "RRET" should be -- RRE --
Column 161-162, Table 17, under Component Name heading, first column, "RRET" should be -- RRE --

In the Claims
Claim 11: at Column 396, Line 4, delete "inhibitor"

Signed and Sealed this
Twentieth Day of December, 2022

Katherine Kelly Vidal
*Director of the United States Patent and Trademark Office*

SEQUENCE LISTING

<160> NUMBER OF SEQ ID NOS: 114

<210> SEQ ID NO 1
<211> LENGTH: 399
<212> TYPE: PRT
<213> ORGANISM: Artificial Sequence
<220> FEATURE:
<223> OTHER INFORMATION: Description of Artificial Sequence: Synthetic
      membrane IgG-1 heavy chain

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Glu Leu Gln Leu Glu Glu Ser Cys
                325                 330                 335

Ala Glu Ala Gln Asp Gly Glu Leu Asp Gly Leu Trp Thr Thr Ile Thr
            340                 345                 350

```
Ile Phe Ile Thr Leu Phe Leu Leu Ser Val Cys Tyr Ser Ala Thr Val
            355                 360                 365

Thr Phe Phe Lys Val Lys Trp Ile Phe Ser Ser Val Val Asp Leu Lys
370                 375                 380

Gln Thr Ile Ile Pro Asp Tyr Arg Asn Met Ile Gly Gln Gly Ala
385                 390                 395

<210> SEQ ID NO 2
<211> LENGTH: 330
<212> TYPE: PRT
<213> ORGANISM: Artificial Sequence
<220> FEATURE:
<223> OTHER INFORMATION: Description of Artificial Sequence: Synthetic
      secreted IgG-1 heavy chain

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly Lys
                325                 330

<210> SEQ ID NO 3
<211> LENGTH: 295
<212> TYPE: PRT
<213> ORGANISM: Artificial Sequence
<220> FEATURE:
<223> OTHER INFORMATION: Description of Artificial Sequence: Synthetic
      fragment secreted IgG-1 heavy chain

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
            180                 185                 190

Glu Pro Gln Val Tyr Thr Leu Pro Pro Ser Arg Asp Glu Leu Thr Lys
        195                 200                 205

Asn Gln Val Ser Leu Thr Cys Leu Val Lys Gly Phe Tyr Pro Ser Asp
    210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
            260                 265                 270

Cys Ser Val Met His Glu Ala Leu His Asn His Tyr Thr Gln Lys Ser
        275                 280                 285

Leu Ser Leu Ser Pro Gly Lys
    290                 295

<210> SEQ ID NO 4
<211> LENGTH: 377
<212> TYPE: PRT
<213> ORGANISM: Artificial Sequence
<220> FEATURE:
<223> OTHER INFORMATION: Description of Artificial Sequence: Synthetic
```

IgG-3 heavy chain constant region

<400> SEQUENCE: 4

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375
```

<210> SEQ ID NO 5
<211> LENGTH: 184

```
<212> TYPE: PRT
<213> ORGANISM: Artificial Sequence
<220> FEATURE:
<223> OTHER INFORMATION: Description of Artificial Sequence: Synthetic
      mGM-CSF HLA derived TM and SHORTENED cytoplasmic domain

<400> SEQUENCE: 5

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
130                 135                 140

Glu Leu Ser Ser Gln Pro Thr Ile Pro Ile Val Gly Ile Ile Ala Gly
145                 150                 155                 160

Leu Val Leu Leu Gly Ala Val Ile Thr Gly Ala Val Val Ala Ala Val
                165                 170                 175

Met Trp Arg Arg Lys Ser Ser Asp
            180

<210> SEQ ID NO 6
<211> LENGTH: 261
<212> TYPE: PRT
<213> ORGANISM: Artificial Sequence
<220> FEATURE:
<223> OTHER INFORMATION: Description of Artificial Sequence: Synthetic
      CD40L sequence

<400> SEQUENCE: 6

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125
```

```
Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 7
<211> LENGTH: 261
<212> TYPE: PRT
<213> ORGANISM: Artificial Sequence
<220> FEATURE:
<223> OTHER INFORMATION: Description of Artificial Sequence: Synthetic
      non-cleavable CD40L sequence

<400> SEQUENCE: 7

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
                100                 105                 110

Met Pro Arg Gly Glu Glu Asp Ser Gln Ile Ala Ala His Val Ile Ser
            115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
    210                 215                 220
```

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 8
<211> LENGTH: 233
<212> TYPE: PRT
<213> ORGANISM: Artificial Sequence
<220> FEATURE:
<223> OTHER INFORMATION: Description of Artificial Sequence: Synthetic
      TNF sequence

<400> SEQUENCE: 8

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      CD40L piece

<400> SEQUENCE: 9

Met Ile Glu Thr Tyr Asn Gln Thr Ser Pro Arg Ser Ala Ala Thr Gly
1               5                   10                  15

```
Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
                35                  40                  45

Arg Leu Asp Lys Ile Glu Asp Glu Arg Asn Leu His Glu Asp Phe Val
50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Gly Phe Val Lys
                85                  90                  95

Asp Ile Met Leu Asn Lys Glu Glu Thr Lys Lys Glu
            100                 105
```

<210> SEQ ID NO 10
<211> LENGTH: 141
<212> TYPE: PRT
<213> ORGANISM: Artificial Sequence
<220> FEATURE:
<223> OTHER INFORMATION: Description of Artificial Sequence: Synthetic
    TNF piece

<400> SEQUENCE: 10

```
Val Ala Asn Pro Gln Ala Glu Gly Gln Leu Gln Trp Leu Asn Arg Arg
1               5                   10                  15

Ala Asn Ala Leu Leu Ala Asn Gly Val Glu Leu Arg Asp Asn Gln Leu
            20                  25                  30

Val Val Pro Ser Glu Gly Leu Tyr Leu Ile Tyr Ser Gln Val Leu Phe
        35                  40                  45

Lys Gly Gln Gly Cys Pro Ser Thr His Val Leu Leu Thr His Thr Ile
50                  55                  60

Ser Arg Ile Ala Val Ser Tyr Gln Thr Lys Val Asn Leu Leu Ser Ala
65                  70                  75                  80

Ile Lys Ser Pro Cys Gln Arg Glu Thr Pro Glu Gly Ala Glu Ala Lys
                85                  90                  95

Pro Trp Tyr Glu Pro Ile Tyr Leu Gly Gly Val Phe Gln Leu Glu Lys
            100                 105                 110

Gly Asp Arg Leu Ser Ala Glu Ile Asn Arg Pro Asp Tyr Leu Asp Phe
        115                 120                 125

Ala Glu Ser Gly Gln Val Tyr Phe Gly Ile Ile Ala Leu
    130                 135                 140
```

<210> SEQ ID NO 11
<211> LENGTH: 233
<212> TYPE: PRT
<213> ORGANISM: Artificial Sequence
<220> FEATURE:
<223> OTHER INFORMATION: Description of Artificial Sequence: Synthetic
    mTNF-a

<400> SEQUENCE: 11

```
Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
50                  55                  60
```

```
Arg Asp Leu Ser Leu Ile Ser Pro Leu Ala Gln Ala Ser Gly Ser Gly
 65                  70                  75                  80

Ser Gly Ser Gly Ser Gly Glu Pro Val Ala His Val Val Ala Asn Pro
                 85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
            210                 215                 220

Gln Val Tyr Phe Gly Ile Ile Ala Leu
225                 230

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic
      HC Constant Region 3 from IgG1

<400> SEQUENCE: 12

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Glu Leu Gln Leu Glu Glu Ser
            100                 105                 110

Cys

<210> SEQ ID NO 13
<211> LENGTH: 144
<212> TYPE: PRT
<213> ORGANISM: Artificial Sequence
<220> FEATURE:
<223> OTHER INFORMATION: Description of Artificial Sequence: Synthetic
      native GM-CSF

<400> SEQUENCE: 13
```

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
                35                  40                  45

Thr Ala Glu Met Asn Glu Thr Val Glu Val Ile Ser Glu Met Phe
50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
130                 135                 140

<210> SEQ ID NO 14
<211> LENGTH: 235
<212> TYPE: PRT
<213> ORGANISM: Artificial Sequence
<220> FEATURE:
<223> OTHER INFORMATION: Description of Artificial Sequence: Synthetic
      Flt3L

<400> SEQUENCE: 14

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
                100                 105                 110

Phe Gln Pro Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
            165                 170                 175

Thr Ala Pro Thr Ala Pro Gln Pro Pro Leu Leu Leu Leu Leu Leu Leu
            180                 185                 190

Pro Val Gly Leu Leu Leu Leu Ala Ala Ala Trp Cys Leu His Trp Gln
            195                 200                 205

Arg Thr Arg Arg Arg Thr Pro Arg Pro Gly Glu Gln Val Pro Pro Val
210                 215                 220

```
Pro Ser Pro Gln Asp Leu Leu Leu Val Glu His
225                 230                 235
```

<210> SEQ ID NO 15
<211> LENGTH: 13
<212> TYPE: RNA
<213> ORGANISM: Artificial Sequence
<220> FEATURE:
<223> OTHER INFORMATION: Description of Artificial Sequence: Synthetic
      Kozak sequence

<400> SEQUENCE: 15
gccgccrcca ugg                                                         13

<210> SEQ ID NO 16
<211> LENGTH: 377
<212> TYPE: PRT
<213> ORGANISM: Artificial Sequence
<220> FEATURE:
<223> OTHER INFORMATION: Description of Artificial Sequence: Synthetic
      IgG-3 heavy chain constant region E213Q

<400> SEQUENCE: 16

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Gln Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270
```

```
Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 17
<211> LENGTH: 377
<212> TYPE: PRT
<213> ORGANISM: Artificial Sequence
<220> FEATURE:
<223> OTHER INFORMATION: Description of Artificial Sequence: Synthetic
      IgG-3 heavy chain constant region P221L

<400> SEQUENCE: 17

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Leu Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255
```

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 18
<211> LENGTH: 377
<212> TYPE: PRT
<213> ORGANISM: Artificial Sequence
<220> FEATURE:
<223> OTHER INFORMATION: Description of Artificial Sequence: Synthetic
      IgG-3 heavy chain constant region E224Q

<400> SEQUENCE: 18

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Gln
    210                 215                 220

Gln Tyr Asn Ser Thr Phe Arg Val Val Ser Val Leu Thr Val Leu His

```
                 225                 230                 235                 240

Gln Asp Trp Leu Asn Gly Lys Glu Tyr Lys Cys Lys Val Ser Asn Lys
                        245                 250                 255

Ala Leu Pro Ala Pro Ile Glu Lys Thr Ile Ser Lys Thr Lys Gly Gln
                        260                 265                 270

Pro Arg Glu Pro Gln Val Tyr Thr Leu Pro Pro Ser Arg Glu Glu Met
                        275                 280                 285

Thr Lys Asn Gln Val Ser Leu Thr Cys Leu Val Lys Gly Phe Tyr Pro
                        290                 295                 300

Ser Asp Ile Ala Val Glu Trp Glu Ser Ser Gly Gln Pro Glu Asn Asn
        305                 310                 315                 320

Tyr Asn Thr Thr Pro Pro Met Leu Asp Ser Asp Gly Ser Phe Phe Leu
                        325                 330                 335

Tyr Ser Lys Leu Thr Val Asp Lys Ser Arg Trp Gln Gln Gly Asn Ile
                        340                 345                 350

Phe Ser Cys Ser Val Met His Glu Ala Leu His Asn Arg Phe Thr Gln
                        355                 360                 365

Lys Ser Leu Ser Leu Ser Pro Gly Lys
                        370                 375

<210> SEQ ID NO 19
<211> LENGTH: 377
<212> TYPE: PRT
<213> ORGANISM: Artificial Sequence
<220> FEATURE:
<223> OTHER INFORMATION: Description of Artificial Sequence: Synthetic
      IgG-3 heavy chain constant region Y226F

<400> SEQUENCE: 19

Ala Ser Thr Lys Gly Pro Ser Val Phe Pro Leu Ala Pro Cys Ser Arg
        1               5                   10                  15

Ser Thr Ser Gly Gly Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                        50                  55                  60

Leu Ser Ser Val Val Thr Val Pro Ser Ser Ser Leu Gly Thr Gln Thr
        65                  70                  75                  80

Tyr Thr Cys Asn Val Asn His Lys Pro Ser Asn Thr Lys Val Asp Lys
                        85                  90                  95

Arg Val Glu Leu Lys Thr Pro Leu Gly Asp Thr Thr His Thr Cys Pro
                        100                 105                 110

Arg Cys Pro Glu Pro Lys Ser Cys Asp Thr Pro Pro Pro Cys Pro Arg
                        115                 120                 125

Cys Pro Glu Pro Lys Ser Cys Asp Thr Pro Pro Pro Cys Pro Arg Cys
                        130                 135                 140

Pro Glu Pro Lys Ser Cys Asp Thr Pro Pro Pro Cys Pro Arg Cys Pro
        145                 150                 155                 160

Ala Pro Glu Leu Leu Gly Gly Pro Ser Val Phe Leu Phe Pro Pro Lys
                        165                 170                 175

Pro Lys Asp Thr Leu Met Ile Ser Arg Thr Pro Glu Val Thr Cys Val
                        180                 185                 190

Val Val Asp Val Ser His Glu Asp Pro Glu Val Gln Phe Lys Trp Tyr
                        195                 200                 205
```

```
Val Asp Gly Val Glu Val His Asn Ala Lys Thr Lys Pro Arg Glu Glu
    210                 215                 220

Gln Phe Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
                275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
                355                 360                 365

Lys Ser Leu Ser Leu Ser Pro Gly Lys
370                 375

<210> SEQ ID NO 20
<211> LENGTH: 377
<212> TYPE: PRT
<213> ORGANISM: Artificial Sequence
<220> FEATURE:
<223> OTHER INFORMATION: Description of Artificial Sequence: Synthetic
      IgG-3 heavy chain constant region D242N

<400> SEQUENCE: 20

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190
```

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asn Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 21
<211> LENGTH: 377
<212> TYPE: PRT
<213> ORGANISM: Artificial Sequence
<220> FEATURE:
<223> OTHER INFORMATION: Description of Artificial Sequence: Synthetic
      IgG-3 heavy chain constant region N245D

<400> SEQUENCE: 21

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
            85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
            130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys

```
                    165                 170                 175
Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
            210                 215                 220

Gln Tyr Asn Ser Thr Phe Arg Val Val Ser Val Leu Thr Val Leu His
225                 230                 235                 240

Gln Asp Trp Leu Asp Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
                275                 280                 285

Thr Lys Asn Gln Val Ser Leu Thr Cys Leu Val Lys Gly Phe Tyr Pro
                290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro Gly Lys
                370                 375

<210> SEQ ID NO 22
<211> LENGTH: 377
<212> TYPE: PRT
<213> ORGANISM: Artificial Sequence
<220> FEATURE:
<223> OTHER INFORMATION: Description of Artificial Sequence: Synthetic
      IgG-3 heavy chain constant region T269A

<400> SEQUENCE: 22

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140
```

```
Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 23
<211> LENGTH: 377
<212> TYPE: PRT
<213> ORGANISM: Artificial Sequence
<220> FEATURE:
<223> OTHER INFORMATION: Description of Artificial Sequence: Synthetic
      IgG-3 heavy chain constant region S314N

<400> SEQUENCE: 23

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
            85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125
```

```
Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
            355                 360                 365

Lys Ser Leu Ser Leu Ser Pro Gly Lys
    370                 375

<210> SEQ ID NO 24
<211> LENGTH: 376
<212> TYPE: PRT
<213> ORGANISM: Artificial Sequence
<220> FEATURE:
<223> OTHER INFORMATION: Description of Artificial Sequence: Synthetic
      IgG-3 heavy chain constant region S314 del

<400> SEQUENCE: 24

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
```

```
                    100                 105                 110
Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
            130                 135             140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Gly Gln Pro Glu Asn Asn Tyr
305                 310                 315                 320

Asn Thr Thr Pro Pro Met Leu Asp Ser Asp Gly Ser Phe Phe Leu Tyr
            325                 330                 335

Ser Lys Leu Thr Val Asp Lys Ser Arg Trp Gln Gln Gly Asn Ile Phe
            340                 345                 350

Ser Cys Ser Val Met His Glu Ala Leu His Asn Arg Phe Thr Gln Lys
            355                 360                 365

Ser Leu Ser Leu Ser Pro Gly Lys
            370                 375

<210> SEQ ID NO 25
<211> LENGTH: 377
<212> TYPE: PRT
<213> ORGANISM: Artificial Sequence
<220> FEATURE:
<223> OTHER INFORMATION: Description of Artificial Sequence: Synthetic
      IgG-3 heavy chain constant region F366Y

<400> SEQUENCE: 25

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80
```

Tyr Thr Cys Asn Val Asn His Lys Pro Ser Asn Thr Lys Val Asp Lys
            85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
            130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
            210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Tyr Thr Gln
            355                 360                 365

Lys Ser Leu Ser Leu Ser Pro Gly Lys
            370                 375

<210> SEQ ID NO 26
<211> LENGTH: 221
<212> TYPE: PRT
<213> ORGANISM: Artificial Sequence
<220> FEATURE:
<223> OTHER INFORMATION: Description of Artificial Sequence: Synthetic
      TNF - VRSSSRTPSDKP del

<400> SEQUENCE: 26

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
            50                  55                  60

```
Arg Asp Leu Ser Leu Ile Ser Pro Leu Ala Gln Ala Val Ala His Val
65                  70                  75                  80

Val Ala Asn Pro Gln Ala Glu Gly Gln Leu Gln Trp Leu Asn Arg Arg
                85                  90                  95

Ala Asn Ala Leu Leu Ala Asn Gly Val Glu Leu Arg Asp Asn Gln Leu
            100                 105                 110

Val Val Pro Ser Glu Gly Leu Tyr Leu Ile Tyr Ser Gln Val Leu Phe
            115                 120                 125

Lys Gly Gln Gly Cys Pro Ser Thr His Val Leu Leu Thr His Thr Ile
130                 135                 140

Ser Arg Ile Ala Val Ser Tyr Gln Thr Lys Val Asn Leu Leu Ser Ala
145                 150                 155                 160

Ile Lys Ser Pro Cys Gln Arg Glu Thr Pro Glu Gly Ala Glu Ala Lys
                165                 170                 175

Pro Trp Tyr Glu Pro Ile Tyr Leu Gly Gly Val Phe Gln Leu Glu Lys
            180                 185                 190

Gly Asp Arg Leu Ser Ala Glu Ile Asn Arg Pro Asp Tyr Leu Asp Phe
            195                 200                 205

Ala Glu Ser Gly Gln Val Tyr Phe Gly Ile Ile Ala Leu
            210                 215                 220

<210> SEQ ID NO 27
<211> LENGTH: 212
<212> TYPE: PRT
<213> ORGANISM: Artificial Sequence
<220> FEATURE:
<223> OTHER INFORMATION: Description of Artificial Sequence: Synthetic
      TNF - FSFLIVAGATTLFCLLHFGVI del

<400> SEQUENCE: 27

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Gly Pro Gln Arg Glu Glu Phe Pro Arg Asp Leu Ser Leu
        35                  40                  45

Ile Ser Pro Leu Ala Gln Ala Val Arg Ser Ser Ser Arg Thr Pro Ser
50                  55                  60

Asp Lys Pro Val Ala His Val Val Ala Asn Pro Gln Ala Glu Gly Gln
65                  70                  75                  80

Leu Gln Trp Leu Asn Arg Arg Ala Asn Ala Leu Leu Ala Asn Gly Val
                85                  90                  95

Glu Leu Arg Asp Asn Gln Leu Val Val Pro Ser Glu Gly Leu Tyr Leu
            100                 105                 110

Ile Tyr Ser Gln Val Leu Phe Lys Gly Gln Gly Cys Pro Ser Thr His
        115                 120                 125

Val Leu Leu Thr His Thr Ile Ser Arg Ile Ala Val Ser Tyr Gln Thr
130                 135                 140

Lys Val Asn Leu Leu Ser Ala Ile Lys Ser Pro Cys Gln Arg Glu Thr
145                 150                 155                 160

Pro Glu Gly Ala Glu Ala Lys Pro Trp Tyr Glu Pro Ile Tyr Leu Gly
                165                 170                 175

Gly Val Phe Gln Leu Glu Lys Gly Asp Arg Leu Ser Ala Glu Ile Asn
            180                 185                 190

Arg Pro Asp Tyr Leu Asp Phe Ala Glu Ser Gly Gln Val Tyr Phe Gly
```

Ile Ile Ala Leu
    210

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      HA tag seq

<400> SEQUENCE: 28

Tyr Pro Tyr Asp Val Pro Asp Tyr Ala
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      FLAG TAG

<400> SEQUENCE: 29

Asp Tyr Lys Asp Asp Asp Asp Lys
1               5

<210> SEQ ID NO 30
<211> LENGTH: 583
<212> TYPE: PRT
<213> ORGANISM: Artificial Sequence
<220> FEATURE:
<223> OTHER INFORMATION: Description of Artificial Sequence: Synthetic
      mIgG Heavy Chain IgG 1/3 hybrid anti-biotin heavy chain
      - E325A mutant sequence

<400> SEQUENCE: 30

Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asp Trp Val Arg Gln Pro Pro Gly Lys Gly Leu
    50                  55                  60

Glu Trp Leu Gly Val Ile Trp Gly Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
            100                 105                 110

Tyr Cys Val Lys His Thr Asn Trp Asp Gly Gly Phe Ala Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala

```
                180                 185                 190
Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
        210                 215                 220

Lys Pro Ser Asn Thr Lys Val Asp Lys Val Glu Leu Lys Thr Pro
225                 230                 235                 240

Leu Gly Asp Thr Thr His Thr Cys Pro Arg Cys Pro Glu Pro Lys Ser
                245                 250                 255

Cys Asp Thr Pro Pro Cys Pro Arg Cys Pro Glu Pro Lys Ser Cys
            260                 265                 270

Asp Thr Pro Pro Cys Pro Arg Cys Pro Glu Pro Lys Ser Cys Asp
        275                 280                 285

Thr Pro Pro Cys Pro Arg Cys Pro Ala Pro Glu Leu Leu Gly Gly
    290                 295                 300

Pro Ser Val Phe Leu Phe Pro Pro Lys Pro Lys Asp Thr Leu Met Ile
305                 310                 315                 320

Ser Arg Thr Pro Ala Val Thr Cys Val Val Val Asp Val Ser His Glu
                325                 330                 335

Asp Pro Glu Val Lys Phe Asn Trp Tyr Val Asp Gly Val Glu Val His
            340                 345                 350

Asn Ala Lys Thr Lys Pro Arg Glu Glu Gln Tyr Asn Ser Thr Tyr Arg
        355                 360                 365

Val Val Ser Val Leu Thr Val Leu His Gln Asp Trp Leu Asn Gly Lys
    370                 375                 380

Glu Tyr Lys Cys Lys Val Ser Asn Lys Ala Leu Pro Ala Pro Ile Glu
385                 390                 395                 400

Lys Thr Ile Ser Lys Ala Lys Gly Gln Pro Arg Glu Pro Gln Val Tyr
                405                 410                 415

Thr Leu Pro Pro Ser Arg Asp Glu Leu Thr Lys Asn Gln Val Ser Leu
            420                 425                 430

Thr Cys Leu Val Lys Gly Phe Tyr Pro Ser Asp Ile Ala Val Glu Trp
        435                 440                 445

Glu Ser Asn Gly Gln Pro Glu Asn Asn Tyr Lys Thr Thr Pro Pro Val
    450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
                485                 490                 495

Glu Ala Leu His Asn His Tyr Thr Gln Lys Ser Leu Ser Leu Ser Pro
            500                 505                 510

Glu Leu Gln Leu Glu Glu Ser Cys Ala Glu Ala Gln Asp Gly Glu Leu
        515                 520                 525

Asp Gly Leu Trp Thr Thr Ile Thr Ile Phe Ile Thr Leu Phe Leu Leu
    530                 535                 540

Ser Val Cys Tyr Ser Ala Thr Val Thr Phe Phe Lys Val Lys Trp Ile
545                 550                 555                 560

Phe Ser Ser Val Val Asp Leu Lys Gln Thr Ile Ile Pro Asp Tyr Arg
                565                 570                 575

Asn Met Ile Gly Gln Gly Ala
            580

<210> SEQ ID NO 31
```

```
<211> LENGTH: 223
<212> TYPE: PRT
<213> ORGANISM: Artificial Sequence
<220> FEATURE:
<223> OTHER INFORMATION: Description of Artificial Sequence: Synthetic
      CD40L-TNFa fusion protein

<400> SEQUENCE: 31

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Pro Val Ala
65                  70                  75                  80

His Val Val Ala Asn Pro Gln Ala Glu Gly Gln Leu Gln Trp Leu Asn
                85                  90                  95

Arg Arg Ala Asn Ala Leu Leu Ala Asn Gly Val Glu Leu Arg Asp Asn
            100                 105                 110

Gln Leu Val Val Pro Ser Glu Gly Leu Tyr Leu Ile Tyr Ser Gln Val
        115                 120                 125

Leu Phe Lys Gly Gln Gly Cys Pro Ser Thr His Val Leu Leu Thr His
130                 135                 140

Thr Ile Ser Arg Ile Ala Val Ser Tyr Gln Thr Lys Val Asn Leu Leu
145                 150                 155                 160

Ser Ala Ile Lys Ser Pro Cys Gln Arg Glu Thr Pro Glu Gly Ala Glu
                165                 170                 175

Ala Lys Pro Trp Tyr Glu Pro Ile Tyr Leu Gly Gly Val Phe Gln Leu
            180                 185                 190

Glu Lys Gly Asp Arg Leu Ser Ala Glu Ile Asn Arg Pro Asp Tyr Leu
        195                 200                 205

Asp Phe Ala Glu Ser Gly Gln Val Tyr Phe Gly Ile Ile Ala Leu
    210                 215                 220

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      HC Signal

<400> SEQUENCE: 32

Met Glu Phe Gly Leu Ser Trp Val Phe Leu Val Ala Leu Phe Arg Gly
1               5                   10                  15

Val Gln Cys

<210> SEQ ID NO 33
<211> LENGTH: 118
<212> TYPE: PRT
<213> ORGANISM: Artificial Sequence
<220> FEATURE:
<223> OTHER INFORMATION: Description of Artificial Sequence: Synthetic
      HC Variable anti-biotin sequence

<400> SEQUENCE: 33

Gln Val Lys Leu Gln Glu Ser Gly Pro Gly Leu Val Ala Pro Ser Gln
```

```
                1               5                   10                  15
Ser Leu Ser Ile Thr Cys Thr Val Ser Gly Phe Ser Leu Thr Ala Tyr
            20                  25                  30

Gly Val Asp Trp Val Arg Gln Pro Gly Lys Gly Leu Glu Trp Leu
            35                  40                  45

Gly Val Ile Trp Gly Gly Gly Arg Thr Asn Tyr Asn Ser Gly Leu Met
    50                  55                  60

Ser Arg Leu Ser Ile Arg Lys Asp Asn Ser Lys Ser Gln Val Phe Leu
65                  70                  75                  80

Thr Met Asn Ser Leu Gln Thr Asp Asp Thr Ala Lys Tyr Tyr Cys Val
                85                  90                  95

Lys His Thr Asn Trp Asp Gly Gly Phe Ala Tyr Trp Gly Gln Gly Thr
                100                 105                 110

Thr Val Thr Val Ser Ser
            115
```

```
<210> SEQ ID NO 34
<211> LENGTH: 99
<212> TYPE: PRT
<213> ORGANISM: Artificial Sequence
<220> FEATURE:
<223> OTHER INFORMATION: Description of Artificial Sequence: Synthetic
      HC Constant Region 1 from IgG1 sequence

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu
```

```
<210> SEQ ID NO 35
<211> LENGTH: 61
<212> TYPE: PRT
<213> ORGANISM: Artificial Sequence
<220> FEATURE:
<223> OTHER INFORMATION: Description of Artificial Sequence: Synthetic
      HC Hinge Region from IgG3 sequence

<400> SEQUENCE: 35

Leu Lys Thr Pro Leu Gly Asp Thr Thr His Thr Cys Pro Arg Cys Pro
1               5                   10                  15

Glu Pro Lys Ser Cys Asp Thr Pro Pro Pro Cys Pro Arg Cys Pro Glu
            20                  25                  30

Pro Lys Ser Cys Asp Thr Pro Pro Pro Cys Pro Arg Cys Pro Glu Pro
            35                  40                  45

Lys Ser Cys Asp Thr Pro Pro Pro Cys Pro Arg Cys Pro
    50                  55                  60

<210> SEQ ID NO 36
```

```
<211> LENGTH: 110
<212> TYPE: PRT
<213> ORGANISM: Artificial Sequence
<220> FEATURE:
<223> OTHER INFORMATION: Description of Artificial Sequence: Synthetic
      HC Constant Region 2 from IgG1 sequence

<400> SEQUENCE: 36

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 37
<211> LENGTH: 63
<212> TYPE: PRT
<213> ORGANISM: Artificial Sequence
<220> FEATURE:
<223> OTHER INFORMATION: Description of Artificial Sequence: Synthetic
      HC Transmembrane and Cytoplasmic region from IgG1 sequence

<400> SEQUENCE: 37

Ala Glu Ala Gln Asp Gly Glu Leu Asp Gly Leu Trp Thr Thr Ile Thr
1               5                   10                  15

Ile Phe Ile Thr Leu Phe Leu Leu Ser Val Cys Tyr Ser Ala Thr Val
            20                  25                  30

Thr Phe Phe Lys Val Lys Trp Ile Phe Ser Ser Val Val Asp Leu Lys
        35                  40                  45

Gln Thr Ile Ile Pro Asp Tyr Arg Asn Met Ile Gly Gln Gly Ala
    50                  55                  60

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Synthetic
      LC Signal sequence

<400> SEQUENCE: 38

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 39
<211> LENGTH: 99
<212> TYPE: PRT
<213> ORGANISM: Artificial Sequence
<220> FEATURE:
<223> OTHER INFORMATION: Description of Artificial Sequence: Synthetic
      LC Variable sequence
```

<400> SEQUENCE: 39

Gly Ser Pro Gly Gln Ser Val Ser Ile Ser Cys Ser Gly Ser Ser
1               5                   10                  15

Asn Ile Gly Asn Asn Tyr Val Tyr Trp Tyr Gln His Leu Pro Gly Thr
            20                  25                  30

Ala Pro Lys Leu Leu Ile Tyr Ser Asp Thr Lys Arg Pro Ser Gly Val
        35                  40                  45

Pro Asp Arg Ile Ser Gly Ser Lys Ser Gly Thr Ser Ala Ser Leu Ala
50                  55                  60

Ile Ser Gly Leu Gln Ser Glu Asp Glu Ala Asp Tyr Tyr Cys Ala Ser
65                  70                  75                  80

Trp Asp Asp Ser Leu Asp Gly Pro Val Phe Gly Gly Gly Thr Lys Leu
                85                  90                  95

Thr Val Leu

<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      LC Constant Region 1 sequence

<400> SEQUENCE: 40

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 41
<211> LENGTH: 583
<212> TYPE: PRT
<213> ORGANISM: Artificial Sequence
<220> FEATURE:
<223> OTHER INFORMATION: Description of Artificial Sequence: Synthetic
      mIgG Heavy Chain IgG 1/3 hybrid anti-biotin heavy chain
      sequence - T323A mutant

<400> SEQUENCE: 41

Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asp Trp Val Arg Gln Pro Pro Gly Lys Gly Leu
50                  55                  60

Glu Trp Leu Gly Val Ile Trp Gly Gly Gly Arg Thr Asn Tyr Asn Ser

```
                65                  70                  75                  80
Gly Leu Met Ser Arg Leu Ser Ile Arg Lys Asp Asn Ser Lys Ser Gln
                    85                  90                  95
Val Phe Leu Thr Met Asn Ser Leu Gln Thr Asp Asp Thr Ala Lys Tyr
                    100                 105                 110
Tyr Cys Val Lys His Thr Asn Trp Asp Gly Gly Phe Ala Tyr Trp Gly
                    115                 120                 125
Gln Gly Thr Thr Val Thr Val Ser Ser Ala Ser Thr Lys Gly Pro Ser
130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                    165                 170                 175
Ser Trp Asn Ser Gly Ala Leu Thr Ser Gly Val His Thr Phe Pro Ala
                    180                 185                 190
Val Leu Gln Ser Ser Gly Leu Tyr Ser Leu Ser Ser Val Val Thr Val
                    195                 200                 205
Pro Ser Ser Ser Leu Gly Thr Gln Thr Tyr Ile Cys Asn Val Asn His
                    210                 215                 220
Lys Pro Ser Asn Thr Lys Val Asp Lys Lys Val Glu Leu Lys Thr Pro
225                 230                 235                 240
Leu Gly Asp Thr Thr His Thr Cys Pro Arg Cys Pro Glu Pro Lys Ser
                    245                 250                 255
Cys Asp Thr Pro Pro Pro Cys Pro Arg Cys Pro Glu Pro Lys Ser Cys
                    260                 265                 270
Asp Thr Pro Pro Pro Cys Pro Arg Cys Pro Glu Pro Lys Ser Cys Asp
                    275                 280                 285
Thr Pro Pro Pro Cys Pro Arg Cys Pro Ala Pro Glu Leu Leu Gly Gly
                    290                 295                 300
Pro Ser Val Phe Leu Phe Pro Pro Lys Pro Lys Asp Thr Leu Met Ile
305                 310                 315                 320
Ser Arg Ala Pro Glu Val Thr Cys Val Val Val Asp Val Ser His Glu
                    325                 330                 335
Asp Pro Glu Val Lys Phe Asn Trp Tyr Val Asp Gly Val Glu Val His
                    340                 345                 350
Asn Ala Lys Thr Lys Pro Arg Glu Glu Gln Tyr Asn Ser Thr Tyr Arg
                    355                 360                 365
Val Val Ser Val Leu Thr Val Leu His Gln Asp Trp Leu Asn Gly Lys
                    370                 375                 380
Glu Tyr Lys Cys Lys Val Ser Asn Lys Ala Leu Pro Ala Pro Ile Glu
385                 390                 395                 400
Lys Thr Ile Ser Lys Ala Lys Gly Gln Pro Arg Glu Pro Gln Val Tyr
                    405                 410                 415
Thr Leu Pro Pro Ser Arg Asp Glu Leu Thr Lys Asn Gln Val Ser Leu
                    420                 425                 430
Thr Cys Leu Val Lys Gly Phe Tyr Pro Ser Asp Ile Ala Val Glu Trp
                    435                 440                 445
Glu Ser Asn Gly Gln Pro Glu Asn Asn Tyr Lys Thr Thr Pro Pro Val
                    450                 455                 460
Leu Asp Ser Asp Gly Ser Phe Phe Leu Tyr Ser Lys Leu Thr Val Asp
465                 470                 475                 480
Lys Ser Arg Trp Gln Gln Gly Asn Val Phe Ser Cys Ser Val Met His
                    485                 490                 495
```

```
Glu Ala Leu His Asn His Tyr Thr Gln Lys Ser Leu Ser Leu Ser Pro
            500                 505                 510

Glu Leu Gln Leu Glu Glu Ser Cys Ala Glu Ala Gln Asp Gly Glu Leu
        515                 520                 525

Asp Gly Leu Trp Thr Thr Ile Thr Ile Phe Ile Thr Leu Phe Leu Leu
    530                 535                 540

Ser Val Cys Tyr Ser Ala Thr Val Thr Phe Phe Lys Val Lys Trp Ile
545                 550                 555                 560

Phe Ser Ser Val Val Asp Leu Lys Gln Thr Ile Ile Pro Asp Tyr Arg
                565                 570                 575

Asn Met Ile Gly Gln Gly Ala
            580

<210> SEQ ID NO 42
<211> LENGTH: 211
<212> TYPE: PRT
<213> ORGANISM: Artificial Sequence
<220> FEATURE:
<223> OTHER INFORMATION: Description of Artificial Sequence: Synthetic
      GM-CSF - HLA-I fusion peptide

<400> SEQUENCE: 42

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

Glu Leu Ser Ser Gln Pro Thr Ile Pro Ile Val Gly Ile Ile Ala Gly
145                 150                 155                 160

Leu Val Leu Leu Gly Ala Val Ile Thr Gly Ala Val Val Ala Ala Val
                165                 170                 175

Met Trp Arg Arg Lys Ser Ser Asp Arg Lys Gly Gly Ser Tyr Thr Gln
            180                 185                 190

Ala Ala Ser Ser Asp Ser Ala Gln Gly Ser Asp Val Ser Leu Thr Ala
        195                 200                 205

Cys Lys Val
    210

<210> SEQ ID NO 43
<211> LENGTH: 583
<212> TYPE: PRT
<213> ORGANISM: Artificial Sequence
<220> FEATURE:
<223> OTHER INFORMATION: Description of Artificial Sequence: Synthetic
``` mIgG Heavy Chain IgG 1/3 hybrid anti-biotin heavy chain
- E325A, T323A mutant

<400> SEQUENCE: 43

Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asp Trp Val Arg Gln Pro Pro Gly Lys Gly Leu
    50                  55                  60

Glu Trp Leu Gly Val Ile Trp Gly Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
            100                 105                 110

Tyr Cys Val Lys His Thr Asn Trp Asp Gly Phe Ala Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Leu Lys Thr Pro
225                 230                 235                 240

Leu Gly Asp Thr Thr His Thr Cys Pro Arg Cys Pro Glu Pro Lys Ser
                245                 250                 255

Cys Asp Thr Pro Pro Pro Cys Pro Arg Cys Pro Glu Pro Lys Ser Cys
            260                 265                 270

Asp Thr Pro Pro Pro Cys Pro Arg Cys Pro Glu Pro Lys Ser Cys Asp
        275                 280                 285

Thr Pro Pro Pro Cys Pro Arg Cys Pro Ala Pro Glu Leu Leu Gly Gly
    290                 295                 300

Pro Ser Val Phe Leu Phe Pro Pro Lys Pro Lys Asp Thr Leu Met Ile
305                 310                 315                 320

Ser Arg Ala Pro Ala Val Thr Cys Val Val Val Asp Val Ser His Glu
                325                 330                 335

Asp Pro Glu Val Lys Phe Asn Trp Tyr Val Asp Gly Val Glu Val His
            340                 345                 350

Asn Ala Lys Thr Lys Pro Arg Glu Glu Gln Tyr Asn Ser Thr Tyr Arg
        355                 360                 365

Val Val Ser Val Leu Thr Val Leu His Gln Asp Trp Leu Asn Gly Lys
    370                 375                 380

Glu Tyr Lys Cys Lys Val Ser Asn Lys Ala Leu Pro Ala Pro Ile Glu
385                 390                 395                 400

```
Lys Thr Ile Ser Lys Ala Lys Gly Gln Pro Arg Glu Pro Gln Val Tyr
            405                 410                 415

Thr Leu Pro Pro Ser Arg Asp Glu Leu Thr Lys Asn Gln Val Ser Leu
            420                 425                 430

Thr Cys Leu Val Lys Gly Phe Tyr Pro Ser Asp Ile Ala Val Glu Trp
            435                 440                 445

Glu Ser Asn Gly Gln Pro Glu Asn Asn Tyr Lys Thr Thr Pro Pro Val
            450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
            485                 490                 495

Glu Ala Leu His Asn His Tyr Thr Gln Lys Ser Leu Ser Leu Ser Pro
            500                 505                 510

Glu Leu Gln Leu Glu Glu Ser Cys Ala Glu Ala Gln Asp Gly Glu Leu
            515                 520                 525

Asp Gly Leu Trp Thr Thr Ile Thr Ile Phe Ile Thr Leu Phe Leu Leu
            530                 535                 540

Ser Val Cys Tyr Ser Ala Thr Val Thr Phe Phe Lys Val Lys Trp Ile
545                 550                 555                 560

Phe Ser Ser Val Val Asp Leu Lys Gln Thr Ile Ile Pro Asp Tyr Arg
            565                 570                 575

Asn Met Ile Gly Gln Gly Ala
            580

<210> SEQ ID NO 44
<211> LENGTH: 183
<212> TYPE: PRT
<213> ORGANISM: Artificial Sequence
<220> FEATURE:
<223> OTHER INFORMATION: Description of Artificial Sequence: Synthetic
      Soluble Flt3-L sequence

<400> SEQUENCE: 44

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
            85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
            130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
```

-continued

```
                    165                 170                 175
Thr Ala Pro Thr Ala Pro Gln
                180

<210> SEQ ID NO 45
<211> LENGTH: 583
<212> TYPE: PRT
<213> ORGANISM: Artificial Sequence
<220> FEATURE:
<223> OTHER INFORMATION: Description of Artificial Sequence: Synthetic
      mIgG Heavy Chain IgG 1/3 hybrid anti-biotin heavy chain
      sequence

<400> SEQUENCE: 45

Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
                20                  25                  30

Pro Ser Gln Ser Leu Ser Ile Thr Cys Thr Val Ser Gly Phe Ser Leu
            35                  40                  45

Thr Ala Tyr Gly Val Asp Trp Val Arg Gln Pro Pro Gly Lys Gly Leu
        50                  55                  60

Glu Trp Leu Gly Val Ile Trp Gly Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
            100                 105                 110

Tyr Cys Val Lys His Thr Asn Trp Asp Gly Phe Ala Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Leu Lys Thr Pro
225                 230                 235                 240

Leu Gly Asp Thr Thr His Thr Cys Pro Arg Cys Pro Glu Pro Lys Ser
                245                 250                 255

Cys Asp Thr Pro Pro Pro Cys Pro Arg Cys Pro Glu Pro Lys Ser Cys
            260                 265                 270

Asp Thr Pro Pro Pro Cys Pro Arg Cys Pro Glu Pro Lys Ser Cys Asp
        275                 280                 285

Thr Pro Pro Pro Cys Pro Arg Cys Pro Ala Pro Glu Leu Leu Gly Gly
    290                 295                 300

Pro Ser Val Phe Leu Phe Pro Pro Lys Pro Lys Asp Thr Leu Met Ile
305                 310                 315                 320

Ser Arg Thr Pro Glu Val Thr Cys Val Val Val Asp Val Ser His Glu
                325                 330                 335
```

```
Asp Pro Glu Val Lys Phe Asn Trp Tyr Val Asp Gly Val Glu Val His
            340                 345                 350

Asn Ala Lys Thr Lys Pro Arg Glu Glu Gln Tyr Asn Ser Thr Tyr Arg
        355                 360                 365

Val Val Ser Val Leu Thr Val Leu His Gln Asp Trp Leu Asn Gly Lys
    370                 375                 380

Glu Tyr Lys Cys Lys Val Ser Asn Lys Ala Leu Pro Ala Pro Ile Glu
385                 390                 395                 400

Lys Thr Ile Ser Lys Ala Lys Gly Gln Pro Arg Glu Pro Gln Val Tyr
                405                 410                 415

Thr Leu Pro Pro Ser Arg Asp Glu Leu Thr Lys Asn Gln Val Ser Leu
            420                 425                 430

Thr Cys Leu Val Lys Gly Phe Tyr Pro Ser Asp Ile Ala Val Glu Trp
        435                 440                 445

Glu Ser Asn Gly Gln Pro Glu Asn Asn Tyr Lys Thr Thr Pro Pro Val
    450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
                485                 490                 495

Glu Ala Leu His Asn His Tyr Thr Gln Lys Ser Leu Ser Leu Ser Pro
            500                 505                 510

Glu Leu Gln Leu Glu Glu Ser Cys Ala Glu Ala Gln Asp Gly Glu Leu
        515                 520                 525

Asp Gly Leu Trp Thr Thr Thr Ile Thr Ile Phe Ile Thr Leu Phe Leu
    530                 535                 540

Ser Val Cys Tyr Ser Ala Thr Val Thr Phe Phe Lys Val Lys Trp Ile
545                 550                 555                 560

Phe Ser Ser Val Val Asp Leu Lys Gln Thr Ile Ile Pro Asp Tyr Arg
                565                 570                 575

Asn Met Ile Gly Gln Gly Ala
            580

<210> SEQ ID NO 46
<211> LENGTH: 227
<212> TYPE: PRT
<213> ORGANISM: Artificial Sequence
<220> FEATURE:
<223> OTHER INFORMATION: Description of Artificial Sequence: Synthetic
      IgG Light Chain sequence

<400> SEQUENCE: 46

Met Lys Tyr Leu Leu Pro Thr Ala Ala Ala Gly Leu Leu Leu Leu Ala
1               5                   10                  15

Ala Gln Pro Ala Met Ala Gly Ser Pro Gly Gln Ser Val Ser Ile Ser
            20                  25                  30

Cys Ser Gly Ser Ser Ser Asn Ile Gly Asn Asn Tyr Val Tyr Trp Tyr
        35                  40                  45

Gln His Leu Pro Gly Thr Ala Pro Lys Leu Leu Ile Tyr Ser Asp Thr
    50                  55                  60

Lys Arg Pro Ser Gly Val Pro Asp Arg Ile Ser Gly Ser Lys Ser Gly
65                  70                  75                  80

Thr Ser Ala Ser Leu Ala Ile Ser Gly Leu Gln Ser Glu Asp Glu Ala
                85                  90                  95

Asp Tyr Tyr Cys Ala Ser Trp Asp Asp Ser Leu Asp Gly Pro Val Phe
```

```
                   100                 105                 110
Gly Gly Gly Thr Lys Leu Thr Val Leu Gly Gln Pro Lys Ala Asn Pro
            115                 120                 125

Thr Val Thr Leu Phe Pro Pro Ser Ser Glu Glu Leu Gln Ala Asn Lys
        130                 135                 140

Ala Thr Leu Val Cys Leu Ile Ser Asp Phe Tyr Pro Gly Ala Val Thr
145                 150                 155                 160

Val Ala Trp Lys Ala Asp Gly Ser Pro Val Lys Ala Gly Val Glu Thr
                165                 170                 175

Thr Lys Pro Ser Lys Gln Ser Asn Asn Lys Tyr Ala Ala Ser Ser Tyr
            180                 185                 190

Leu Ser Leu Thr Pro Glu Gln Trp Lys Ser His Arg Ser Tyr Ser Cys
        195                 200                 205

Gln Val Thr His Glu Gly Ser Thr Val Glu Lys Thr Val Ala Pro Thr
    210                 215                 220

Glu Cys Ser
225

<210> SEQ ID NO 47
<211> LENGTH: 9203
<212> TYPE: DNA
<213> ORGANISM: Artificial Sequence
<220> FEATURE:
<223> OTHER INFORMATION: Description of Artificial Sequence: Synthetic
      Vector 1 sequence

<400> SEQUENCE: 47
```

| | | | | | |
|---|---|---|---|---|---|
| aatgtagtct | tatgcaatac | tcttgtagtc | ttgcaacatg | gtaacgatga | gttagcaaca | 60 |
| tgccttacaa | ggagagaaaa | agcaccgtgc | atgccgattg | gtggaagtaa | ggtggtacga | 120 |
| tcgtgcctta | ttaggaaggc | aacagacggg | tctgacatgg | attggacgaa | ccactgaatt | 180 |
| gccgcattgc | agagatattg | tatttaagtg | cctagctcga | tacataaacg | ggtctctctg | 240 |
| gttagaccag | atctgagcct | gggagctctc | tggctaacta | gggaacccac | tgcttaagcc | 300 |
| tcaataaagc | ttgccttgag | tgcttcaagt | agtgtgtgcc | cgtctgttgt | gtgactctgg | 360 |
| taactagaga | tccctcagac | ccttttagtc | agtgtggaaa | atctctagca | gtggcgcccg | 420 |
| aacaggggact | tgaaagcgaa | agggaaacca | gaggagctct | ctcgacgcag | gactcggctt | 480 |
| gctgaagcgc | gcacggcaag | aggcgagggg | cggcgactgg | tgagtacgcc | aaaaattttg | 540 |
| actagcggag | gctagaagga | gagagatggg | tgcgagagcg | tcagtattaa | gcggggggaga | 600 |
| attagatcgc | gatgggaaaa | aattcggtta | aggccagggg | gaaagaaaaa | atataaatta | 660 |
| aaacatatag | tatgggcaag | cagggagcta | gaacgattcg | cagttaatcc | tggcctgtta | 720 |
| gaaacatcag | aaggctgtag | acaaatactg | ggacagctac | aaccatccct | tcagacagga | 780 |
| tcagaagaac | ttagatcatt | atataataca | gtagcaaccc | tctattgtgt | gcatcaaagg | 840 |
| atagagataa | aagacaccaa | ggaagcttta | gacaagatag | aggaagagca | aaacaaaagt | 900 |
| aagaccaccg | cacagcaagc | ggccgctgat | cttcagacct | ggaggaggag | atatgaggga | 960 |
| caattggaga | agtgaattat | ataaatataa | agtagtaaaa | attgaaccat | taggagtagc | 1020 |
| acccaccaag | gcaaagagaa | gagtggtgca | gagagaaaaa | agagcagtgg | aataggagc | 1080 |
| tttgttcctt | gggttcttgg | gagcagcagg | aagcactatg | ggcgcagcgt | caatgacgct | 1140 |
| gacggtacag | gccagacaat | tattgtctgg | tatagtgcag | cagcagaaca | atttgctgag | 1200 |
| ggctattgag | gcgcaacagc | atctgttgca | actcacagtc | tggggcatca | agcagctcca | 1260 |

```
ggcaagaatc ctggctgtgg aaagatacct aaaggatcaa cagctcctgg ggatttgggg      1320
ttgctctgga aaactcattt gcaccactgc tgtgccttgg aatgctagtt ggagtaataa      1380
atctctggaa cagatttgga atcacacgac ctggatggag tgggacagag aaattaacaa      1440
ttacacaagc ttaatacact ccttaattga agaatcgcaa aaccagcaag aaaagaatga      1500
acaagaatta ttggaattag ataaatgggc aagtttgtgg aattggttta acataacaaa      1560
ttggctgtgg tatataaaat tattcataat gatagtagga ggcttggtag gtttaagaat      1620 agttttgct gtactttcta tagtgaatag agttaggcag ggatattcac cattatcgtt       1680
tcagacccac ctcccaaccc cgaggggacc cgacaggccc gaaggaatag aagaagaagg      1740
tggagagaga gacagagaca gatccattcg attagtgaac ggatctcgac ggtatcgcta      1800
gcttttaaaa gaaaggggg gattgggggg tacagtgcag gggaagaat agtagacata       1860 atagcaacag acatacaaac taagaatta caaaaacaaa ttacaaaaat tcaaaatttt       1920
actagtgatt atcggatcaa ctttgtatag aaaagttggg ctccggtgcc cgtcagtggg      1980 cagacgcac atcgcccaca gtccccgaga agttggggg aggggtcggc aattgaaccg        2040
gtgcctagag aagtggcgc ggggtaaact gggaaagtga tgtcgtgtac tggctccgcc       2100
tttttcccga gggtgggga aaccgtata taagtgcagt agtcgccgtg aacgttcttt        2160
ttcgcaacgg gtttgccgcc agaacacagg taagtgccgt gtgtggttcc cgcgggcctg      2220
gcctctttac gggttatggc ccttgcgtgc cttgaattac ttccacctgg ctgcagtacg      2280
tgattcttga tcccgagctt cgggttggaa gtgggtggga gagttcgagg ccttgcgctt      2340
aaggagcccc ttcgcctcgt gcttgagttg aggcctggcc tgggcgctgg ggccgccgcg      2400
tgcgaatctg gtggcacctt cgcgcctgtc tcgctgcttt cgataagtct ctagccattt      2460
aaaatttttg atgacctgct gcgacgcttt ttttctggca agatagtctt gtaaatgcgg      2520
gccaagatct gcacactggt atttcggttt ttggggccgc gggcggcgac ggggcccgtg      2580
cgtcccagcg cacatgttcg gcgaggcggg gcctgcgagc gcggccaccg agaatcggac      2640
gggggtagtc tcaagctggc cggcctgctc tggtgcctgg tctcgcgccg ccgtgtatcg      2700
ccccgccctg ggcggcaagg ctggcccggt cggcaccagt tgcgtgagcg aaagatggc       2760 cgcttcccgg ccctgctgca gggagctcaa aatggaggac gcggcgctcg ggagagcggg      2820
cgggtgagtc acccacacaa aggaaaaggg cctttccgtc ctcagccgtc gcttcatgtg      2880
actccacgga gtaccgggcg ccgtccaggc acctcgatta gttctcgagc ttttggagta      2940
cgtcgtcttt aggttggggg gaggggtttt atgcgatgga gtttccccac actgagtggg      3000
tggagactga agttaggcca gcttggcact tgatgtaatt ctccttggaa tttgcccttt      3060
ttgagtttgg atcttggttc attctcaagc ctcagacagt ggttcaaagt ttttttcttc      3120
catttcaggt gtcgtgacaa gtttgtacaa aaaagcaggc tgccaccatg gagttcggcc      3180
tgagctgggt gttcctggtg gccctgttca gaggcgtgca gtgccaggtg aagctgcagg      3240
agagcggccc cggcctggtg gcccccagcc agagcctgag catcacctgc accgtgagcg      3300
gcttcagcct gaccgcctac ggcgtggact gggtgagaca gccccccggc aagtgcctgg      3360
agtggctggg cgtgatctgg ggcggcggca gaaccaacta caacagcggc ctgatgagca      3420
gactgagcat cagaaaggac aacagcaaga gccaggtgtt cctgaccatg aacagcctgc      3480
agaccgacga caccgccaag tactactgcg tgaagcacac caactgggac ggcggcttcg      3540
cctactgggg ccagggcacc accgtgaccg tgagcagcgg cggcggcggc agcggcggcg      3600
gcggcagcgg cggcggcggc agcggcagcc ccggccagag cgtgagcatc agctgcagcg      3660
```

```
gcagcagcag caacatcggc aacaactacg tgtactggta ccagcacctg cccggcaccg    3720
cccccaagct gctgatctac agcgacacca agagacccag cggcgtgccc gacagaatca    3780
gcggcagcaa gagcggcacc agcgccagcc tggccatcag cggcctgcag agcgaggacg    3840
aggccgacta ctactgcgcc agctgggacg acagcctgga cggccccgtg ttcggctgcg    3900
gcaccaagct gaccgtgctg ctgaagaccc ccctgggcga caccacccac acctgcccca    3960
gatgccccga gcccaagagc tgcgacaccc ccccccctg cccagatgc cccgagccca      4020 agagctgcga cacccccccc ccctgcccca gatgccccga gcccaagagc tgcgacaccc    4080 ccccccctg cccagatgc cccgccccg agctgctggg cggccccagc gtgttcctgt      4140
tcccccccaa gcccaaggac accctgatga tcagcagagc cccgaggtg acctgcgtgg    4200 tggtggacgt gagccacgag gaccccgagg tgaagttcaa ctggtacgtg gacggcgtgg    4260
aggtgcacaa cgccaagacc aagcccagag aggagcagta caacagcacc tacagagtgg    4320
tgagcgtgct gaccgtgctg caccaggact ggctgaacgg caaggagtac aagtgcaagg    4380
tgagcaacaa ggccctgccc gcccccatcg agaagaccat cagcaaggcc aagggccagc    4440
ccagagagcc ccaggtgtac accctgcccc cagcagaga cgagctgacc aagaaccagg    4500
tgagcctgac ctgcctggtg aagggcttct accccagcga catcgccgtg gagtgggaga    4560
gcaacggcca gcccgagaac aactacaaga ccaccccccc cgtgctggac agcgacggca    4620
gcttcttcct gtacagcaag ctgaccgtgg acaagagcag atggcagcag ggcaacgtgt    4680
tcagctgcag cgtgatgcac gaggccctgc acaaccacta cacccagaag agcctgagcc    4740
tgagccccga gctgcagctg aggagagct cgccgaggc ccaggacggc gagctggacg    4800
gcctgtggac caccatcacc atcttcatca ccctgttcct gctgagcgtg tgctacagcg    4860
ccaccgtgac cttcttcaag gtgaagtgga tcttcagcag cgtggtggac ctgaagcaga    4920
ccatcatccc cgactacaga aacatgatcg gccaggcgc ctaaacccag ctttcttgta    4980
caaagtggtg ataatcgaat ctaaacccca gctttcttgt acaaagtggt gataatcgaa    5040
ttccgataat caacctctgg attacaaaat ttgtgaaaga ttgactggta ttcttaacta    5100
tgttgctcct tttacgctat gtggatacgc tgctttaatg cctttgtatc atgctattgc    5160
ttcccgtatg gctttcattt tctcctcctt gtataaatcc tggttgctgt ctctttatga    5220
ggagttgtgg cccgttgtca ggcaacgtgg cgtggtgtgc actgtgtttg ctgacgcaac    5280
ccccactggt tggggcattg ccaccacctg tcagctcctt tccgggactt tcgctttccc    5340
cctccctatt gccacggcgg aactcatcgc cgcctgcctt gcccgctgct ggacaggggc    5400
tcggctgttg ggcactgaca attccgtggt gttgtcgggg aagctgacgt cctttccatg    5460
gctgctcgcc tgtgttgcca cctggattct gcgcgggacg tccttctgct acgtcccttc    5520
ggccctcaat ccagcggacc ttccttcccg cggcctgctg ccggctctgc ggcctcttcc    5580
gcgtcttcgc cttcgccctc agacgagtcg atctccctt gggccgcct cccgcatcg     5640 ggaattcccg cggttcgctt taagaccaat gacttacaag gcagctgtag atcttagcca    5700
ctttttaaaa gaaagggggg actggaagg gctaattcac tcccaacgaa gacaagatct    5760
gctttttgct tgtactgggt ctctctggtt agaccagatc tgagcctggg agctctctgg    5820
ctaactaggg aacccactgc ttaagcctca ataaagcttg ccttgagtgc ttcaagtagt    5880
gtgtgcccgt ctgttgtgtg actctggtaa ctagagatcc ctcagaccct tttagtcagt    5940
gtggaaaatc tctagcagta gtagttcatg tcatcttatt attcagtatt tataacttgc    6000
```

```
aaagaaatga atatcagaga gtgagaggaa cttgtttatt gcagcttata atggttacaa    6060
ataaagcaat agcatcacaa atttcacaaa taaagcattt ttttcactgc attctagttg    6120
tggtttgtcc aaactcatca atgtatctta tcatgtctgg ctctagctat cccgcccta    6180 actccgccca tcccgcccct aactccgccc agttccgccc attctccgcc ccatggctga    6240
ctaatttttt ttatttatgc agaggccgag gccgcctcgg cctctgagct attccagaag    6300
tagtgaggag gctttttggg aggcctaggg acgtacccaa ttcgccctat agtgagtcgt    6360
attacgcgcg ctcactggcc gtcgttttac aacgtcgtga ctgggaaaac cctggcgtta    6420
cccaacttaa tcgccttgca gcacatcccc ctttcgccag ctggcgtaat agcgaagagg    6480
cccgcaccga tcgcccttcc caacagttgc gcagcctgaa tggcgaatgg gacgcgccct    6540
gtagcggcgc attaagcgcg gcgggtgtgg tggttacgcg cagcgtgacc gctacacttg    6600
ccagcgccct agcgcccgct cctttcgctt tcttcccttc ctttctcgcc acgttcgccg    6660
gctttccccg tcaagctcta aatcggggc tcccctttagg gttccgattt agtgctttac    6720
ggcacctcga ccccaaaaaa cttgattagg gtgatggttc acgtagtggg ccatcgccct    6780
gatagacggt ttttcgccct ttgacgttgg agtccacgtt ctttaatagt ggactcttgt    6840
tccaaactgg aacaacactc aaccctatct cggtctattc ttttgattta agggattt    6900 tgccgatttc ggcctattgg ttaaaaaatg agctgattta caaaaatttt aacgcgaatt    6960
ttaacaaaat attaacgctt acaatttagg tggcactttt cggggaaatg tgcgcggaac    7020
ccctatttgt ttatttttct aaatacattc aaatatgtat ccgctcatga caataaacc    7080 ctgataaatg cttcaataat attgaaaaag gaagagtatg agtattcaac atttccgtgt    7140
cgcccttatt cccttttttg cggcattttg ccttcctgtt tttgctcacc cagaaacgct    7200
ggtgaaagta aaagatgctg aagatcagtt gggtgcacga gtgggttaca tcgaactgga    7260
tctcaacagc ggtaagatcc ttgagagttt tcgccccgaa gaacgttttc caatgatgag    7320
cacttttaaa gttctgctat gtggcgcggt attatcccgt attgacgccg ggcaagagca    7380
actcggtcgc cgcatacact attctcagaa tgacttggtt gagtactcac cagtcacaga    7440
aaagcatctt acggatggca tgacagtaag agaattatgc agtgctgcca taaccatgag    7500
tgataacact gcggccaact tacttctgac aacgatcgga ggaccgaagg agctaaccgc    7560
ttttttgcac aacatggggg atcatgtaac tcgccttgat cgttgggaac cggagctgaa    7620
tgaagccata ccaaacgacg agcgtgacac cacgatgcct gtagcaatgg caacaacgtt    7680
gcgcaaacta ttaactggcg aactacttac tctagcttcc cggcaacaat taatagactg    7740
gatggaggcg gataaagttg caggaccact tctgcgctcg gcccttccgg ctggctggtt    7800
tattgctgat aaatctggag ccggtgagcg tgggtctcgc ggtatcattg cagcactggg    7860
gccagatggt aagccctccc gtatcgtagt tatctacacg acggggagtc aggcaactat    7920
ggatgaacga aatagacaga tcgctgagat aggtgcctca ctgattaagc attggtaact    7980
gtcagaccaa gtttactcat atatacttta gattgattta aaacttcatt tttaatttaa    8040
aaggatctag gtgaagatcc ttttgataa tctcatgacc aaaatccctt aacgtgagtt    8100
ttcgttccac tgagcgtcag accccgtaga aaagatcaaa ggatcttctt gagatccttt    8160
ttttctgcgc gtaatctgct gcttgcaaac aaaaaaacca ccgctaccag cggtggtttg    8220
tttgccggat caagagctac caactctttt tccgaaggta actggcttca gcagagcgca    8280
gataccaaat actgttcttc tagtgtagcc gtagttaggc caccacttca agaactctgt    8340
agcaccgcct acatacctcg ctctgctaat cctgttacca gtggctgctg ccagtggcga    8400
```

```
taagtcgtgt cttaccgggt tggactcaag acgatagtta ccggataagg cgcagcggtc    8460
gggctgaacg gggggttcgt gcacacagcc cagcttggag cgaacgacct acaccgaact    8520
gagataccta cagcgtgagc tatgagaaag cgccacgctt cccgaagaga gaaaggcgga    8580
caggtatccg gtaagcggca gggtcggaac aggagagcgc acgagggagc ttccaggggg    8640
aaacgcctgg tatctttata gtcctgtcgg gtttcgccac ctctgacttg agcgtcgatt    8700
tttgtgatgc tcgtcagggg gcggagcct atggaaaaac gccagcaacg cggcttttt    8760 acggttcctg gccttttgct ggccttttgc tcacatgttc tttcctgcgt tatcccctga    8820
ttctgtggat aaccgtatta ccgcctttga gtgagctgat accgctcgcc gcagccgaac    8880
gaccgagcgc agcgagtcag tgagcgagga gcggaagag cgcccaatac gcaaaccgcc    8940
tctccccgcg cgttggccga ttcattaatg cagctggcac gacaggtttc ccgactggaa    9000
agcgggcagt gagcgcaacg caattaatgt gagttagctc actcattagg caccccaggc    9060
tttcactttt atgcttccgg ctcgtatgtt gtgtggaatt gtgagcggat aacaatttca    9120
cacaggaaac agctatgacc atgattacgc caagcgcgca attaaccctc actaaaggga    9180
acaaaagctg agctgcaag ctt                                              9203
```

<210> SEQ ID NO 48
<211> LENGTH: 10862
<212> TYPE: DNA
<213> ORGANISM: Artificial Sequence
<220> FEATURE:
<223> OTHER INFORMATION: Description of Artificial Sequence: Synthetic
      Vector 2 sequence

<400> SEQUENCE: 48

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac cctttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcgggggaga     600
attagatcgc gatgggaaaa aattcggtta aggccagggg gaagaaaaa atataaatta     660 aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggcgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
```

```
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggga tgggacagag aaattaacaa   1440
ttacacaagc ttaatacact ccttaattga agaatcgcaa aaccagcaag aaagaatga    1500
acaagaatta ttggaattag ataaatgggc aagtttgtgg aattggttta acataacaaa   1560
ttggctgtgg tatataaaat tattcataat gatagtagga ggcttggtag gtttaagaat   1620
agttttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattgggggg tacagtgcag gggaagaat agtagacata    1860
atagcaacag acatacaaac taagaatta caaaaacaaa ttacaaaaat tcaaaattt     1920
actagtatca actttgtata gaaaagttgg gctccggtgc ccgtcagtgg gcagagcgca   1980
catcgcccac agtccccgag aagttggggg gaggggtcgg caattgaacc ggtgcctaga   2040
gaaggtggcg cggggtaaac tgggaaagtg atgtcgtgta ctggctccgc cttttttcccg  2100
agggtggggg agaaccgtat ataagtgcag tagtcgccgt gaacgttctt tttcgcaacg   2160
ggtttgccgc cagaacacag gtaagtgccg tgtgtggttc ccgcgggcct ggcctcttta   2220
cgggttatgg cccttgcgtg ccttgaatta cttccacctg gctgcagtac gtgattcttg   2280
atcccgagct tcgggttgga agtgggtggg agagttcgag gccttgcgct taaggagccc   2340
cttcgcctcg tgcttgagtt gaggcctggc ctgggcgctg gggccgccgc gtgcgaatct   2400
ggtggcacct tcgcgcctgt ctcgctgctt tcgataagtc tctagccatt taaaattttt   2460
gatgacctgc tgcgacgctt tttttctggc aagatagtct tgtaaatgcg gccaagatc    2520
tgcacactgg tatttcggtt tttggggccg cgggcggcga cggggcccgt gcgtcccagc   2580
gcacatgttc ggcgaggcgg ggcctgcgag cgcggccacc gagaatcgga cgggggtagt   2640
ctcaagctgg ccggcctgct ctggtgcctg gtctcgcgcc gccgtgtatc gccccgccct   2700
gggcggcaag gctggcccgg tcggcaccag ttgcgtgagc ggaaagatgg ccgcttcccg   2760
gccctgctgc agggagctca aaatggagga cgcggcgctc gggagagcgg gcgggtgagt   2820
cacccacaca aaggaaaagg gcctttccgt cctcagccgt cgcttcatgt gactccacgg   2880
agtaccgggc gccgtccagg cacctcgatt agttctcgag cttttggagt acgtcgtctt   2940
taggttgggg ggagggtt tatgcgatgg agtttcccca cactgagtgg gtggagactg    3000
aagttaggcc agcttggcac ttgatgtaat tctccttgga atttgccctt tttgagtttg   3060
gatcttggtt cattctcaag cctcagacag tggttcaaag tttttttcttt ccatttcagg  3120
tgtcgtgaca agtttgtaca aaaaagcagg ctgccaccat ggagttcggc ctgagctggg   3180
tgttcctggt ggccctgttc agaggcgtgc agtgccaggt gaagctgcag gagagcggcc   3240
ccggcctggt ggcccccagc cagagcctga gcatcacctg caccgtgagc ggcttcagcc   3300
tgaccgccta cggcgtggac tgggtgagac agccccccgg caagggcctg gagtggctgg   3360
gcgtgatctg gggcggcggc agaaccaact acaacagcgg cctgatgagc agactgagca   3420
tcagaaagga caacagcaag agccaggtgt tcctgaccat gaacagcctg cagaccgacg   3480
acaccgccaa gtactactgc gtgaagcaca ccaactggga cggcggcttc gcctactggg   3540
```

```
gccagggcac caccgtgacc gtgagcagcc ccagcgtgtt cccccctggcc cccagcagca    3600
agagcaccag cggcggcacc gccgcccctgg gctgcctggt gaaggactac ttcccccgagc   3660
ccgtgaccgt gagctggaac agcggcgccc tgaccagcgg cgtgcacacc ttccccgccg    3720
tgctgcagag cagcggcctg tacagcctga gcagcgtggt gaccgtgccc agcagcagcc    3780
tgggcaccca gacctacatc tgcaacgtga accacaagcc cagcaacacc aaggtggaca    3840
agaaggtgga gctgaagacc ccctgggcg acaccaccca cacctgcccc agatgccccg     3900
agcccaagag ctgcgacacc ccccccccct gccccagatg cccgagccc aagagctgcg     3960
acacccccc cccctgcccc agatgccccg agcccaagag ctgcgacacc ccccccccct     4020
gccccagatg cccgcccccc gagctgctgg gcggcccag cgtgttcctg ttccccccca     4080
agcccaagga caccctgatg atcagcagag ccccgaggt gacctgcgtg gtggtggacg     4140
tgagccacga ggaccccgag gtgaagttca actggtacgt ggacggcgtg gaggtgcaca    4200
acgccaagac caagcccaga gaggagcagt acaacagcac ctacagagtg gtgagcgtgc    4260
tgaccgtgct gcaccaggac tggctgaacg gcaaggagta caagtgcaag gtgagcaaca    4320
aggccctgcc cgcccccatc gagaagacca tcagcaaggc caagggccag cccagagagc    4380
cccaggtgta caccctgccc cccagcagag acgagctgac caagaaccag gtgagcctga    4440
cctgcctggt gaagggcttc taccccagcg acatcgccgt ggagtgggag agcaacggcc    4500
agcccgagaa caactacaag accaccccccc cgtgctggaa cagcgacggc agcttcttcc    4560
tgtacagcaa gctgaccgtg gacaagagca gatggcagca gggcaacgtg ttcagctgca    4620
gcgtgatgca cgaggccctg cacaaccact acacccagaa gagcctgagc ctgagccccg    4680
agctgcagct ggaggagagc tgcgccgagg cccaggacgg cgagctggac ggcctgtgga    4740
ccaccatcac catcttcatc accctgttcc tgctgagcgt gtgctacagc gccaccgtga    4800
ccttcttcaa ggtgaagtgg atcttcagca gcgtggtgga cctgaagcag accatcatcc    4860
ccgactacag aaacatgatc ggccagggcg cctaaaacaa caacaattgc attcatttta    4920
tgtttcaggt tcaggggggag gtgtgggagg ttttttaaag caagtaaaac ctctacaaat    4980
gtggtacgcg ttaacaacaa caattgcatt cattttatgt ttcaggttca gggggaggtg   5040
tgggaggttt tttaaagcaa gtaaaaccctc tacaaatgtg gtacgcgtta cccagctttc    5100
ttgtacaaag tggtaaatag atagaacaac aacaattgca ttcattttttg atttcaggtt    5160
caggggaggg tgtgggaggt ttttaaagc aagtaaaaccc tctacactga cggtacgcgt    5220
taacaacaac aattgcattc atttgtagtt tcaggttcag ggggaggtgt gggaggtttt    5280
ttaaagcaag ttaaacctct aaaatagtgg tacgcgttac ccagctttct tgtacaaagt    5340
ggacccagct ttcttgtaca agtgggccc ctctccctcc ccccccccta acgttactgg     5400
ccgaagccgc ttggaataag gccggtgtgc gtttgtctat atgttatttt ccaccatatt    5460
gccgtcttt ggcaatgtga gggcccggaa acctggccct gtcttcttga cgagcattcc     5520
tagggtctt tcccctctcg ccaaaggaat gcaaggtctg ttgaatgtcg tgaaggaagc    5580
agttcctctg gaagcttctt gaagacaaac aacgtctgta gcgaccctttt gcaggcagcg   5640
gaacccccca cctggcgaca ggtgcctctg cggccaaaag ccacgtgtat aagatacacc    5700
tgcaaaggcg gcacaacccc agtgccacgt tgtgagttgg atagttgtgg aaagagtcaa    5760
atggctctcc tcaagcgtat tcaacaaggg gctgaaggat gcccagaagg taccccattg    5820
tatgggatct gatctggggc ctcggtgcac atgctttaca tgtgtttagt cgaggttaaa    5880
aaaacgtcta ggccccccga accacgggga cgtggttttc ctttgaaaaa cacgatgata    5940
```

```
atatggccac aaccatggcc accgacatga gagtgcccgc ccagctgctg ggcctgctgc   6000
tgctgtggct gagcggcgcc agatgcggca gccccggcca gagcgtgagc atcagctgca   6060
gcggcagcag cagcaacatc ggcaacaact acgtgtactg gtaccagcac ctgcccggca   6120
ccgcccccaa gctgctgatc tacagcgaca ccaagagacc cagcggcgtg cccgacagaa   6180
tcagcggcag caagagcggc accagcgcca gcctggccat cagcggcctg cagagcgagg   6240
acgaggccga ctactactgc gccagctggg acgacagcct ggacgcccc gtgttcggcg   6300 gcggcaccaa gctgaccgtg ctgggccagc ccaaggccaa ccccaccgtg accctgttcc   6360
cccccagcag cgaggagctg caggccaaca aggccaccct ggtgtgcctg atcagcgact   6420
tctaccccgg cgccgtgacc gtggcctgga aggccgacgg cagccccgtg aaggccggcg   6480
tggagaccac caagcccagc aagcagagca acaacaagta cgccgccagc agctacctga   6540
gcctgacccc cgagcagtgg aagagccaca aagctacag ctgccaggtg acccacgagg   6600
gcagcaccgt ggagaagacc gtggccccca ccgagtgcag ctaacaactt tattatacat   6660
agttgatcaa ttccaacttt attatacata gttgatcaat tccgataatc aacctctgga   6720
ttacaaaatt tgtgaaagat tgactggtat tcttaactat gttgctcctt ttacgctatg   6780
tggatacgct gctttaatgc ctttgtatca tgctattgct tcccgtatgg ctttcatttt   6840
ctcctccttg tataaatcct ggttgctgtc tctttatgag gagttgtggc ccgttgtcag   6900
gcaacgtggc gtggtgtgca ctgtgtttgc tgacgcaacc cccactggtt ggggcattgc   6960
caccacctgt cagctccttt ccgggacttt cgctttcccc ctccctattg ccacggcgga   7020
actcatcgcc gcctgccttg cccgctgctg gacagggctc ggctgttgg gcactgacaa   7080 ttccgtggtg ttgtcgggga agctgacgtc ctttccatgg ctgctcgcct gtgttgccac   7140
ctggattctg cgcgggacgt ccttctgcta cgtcccttcg gccctcaatc cagcggacct   7200
tccttcccgc ggcctgctgc cggctctgcg gcctcttccg cgtcttcgcc ttcgccctca   7260
gacgagtcgg atctcccttt gggccgcctc cccgcatcgg gaattcccgc ggttcgcttt   7320
aagaccaatg acttacaagg cagctgtaga tcttagccac ttttttaaaag aaaaggggggg   7380 actggaaggg ctaattcact cccaacgaag acaagatctg cttttttgctt gtactgggtc   7440 tctctggtta gaccagatct gagcctggga gctctctggc taactaggga acccactgct   7500
taagcctcaa taaagcttgc cttgagtgct tcaagtagtg tgtgcccgtc tgttgtgtga   7560
ctctggtaac tagagatccc tcagaccctt ttagtcagtg tggaaaatct ctagcagtag   7620
tagttcatgt catcttatta ttcagtattt ataacttgca aagaaatgaa tatcagagag   7680
tgagaggaac ttgtttattg cagcttataa tggttacaaa taaagcaata gcatcacaaa   7740
tttcacaaat aaagcatttt tttcactgca ttctagttgt ggtttgtcca aactcatcaa   7800
tgtatcttat catgtctggc tctagctatc ccgcccctaa ctccgcccat cccgccccta   7860
actccgccca gttccgccca ttctccgccc catggctgac taattttttt tatttatgca   7920
gaggccgagg ccgcctcggc ctctgagcta ttccagaagt agtgaggagg ctttttggga   7980
ggcctaggga cgtacccaat tcgccctata gtgagtcgta ttacgcgcgc tcactggccg   8040
tcgttttaca acgtcgtgac tgggaaaacc ctggcgttac ccaacttaat cgccttgcag   8100
cacatccccc tttcgccagc tggcgtaata gcgaagaggc ccgcaccgat cgcccttccc   8160
aacagttgcg cagcctgaat ggcgaatggg acgcgccctg tagcggcgca ttaagcgcgg   8220
cgggtgtggt ggttacgcgc agcgtgaccg ctacacttgc cagcgcccta gcgcccgctc   8280
```

```
ctttcgcttt cttcccttcc tttctcgcca cgttcgccgg ctttccccgt caagctctaa    8340
atcgggggct cccttaggg ttccgattta gtgctttacg gcacctcgac cccaaaaaac    8400
ttgattaggg tgatggttca cgtagtgggc catcgccctg atagacggtt tttcgccctt    8460
tgacgttgga gtccacgttc tttaatagtg gactcttgtt ccaaactgga caacactca    8520
accctatctc ggtctattct tttgatttat aagggatttt gccgatttcg gcctattggt    8580
taaaaaatga gctgatttaa caaaaattta acgcgaattt taacaaaata ttaacgctta    8640
caatttaggt ggcacttttc ggggaaatgt gcgcggaacc cctatttgtt tatttttcta    8700
aatacattca aatatgtatc cgctcatgag acaataaccc tgataaatgc ttcaataata    8760
ttgaaaaagg aagagtatga gtattcaaca tttccgtgtc gcccttattc ccttttttgc    8820
ggcattttgc cttcctgttt ttgctcaccc agaaacgctg gtgaaagtaa aagatgctga    8880
agatcagttg ggtgcacgag tgggttacat cgaactggat ctcaacagcg gtaagatcct    8940
tgagagtttt cgccccgaag aacgttttcc aatgatgagc acttttaaag ttctgctatg    9000
tggcgcggta ttatcccgta ttgacgccgg gcaagagcaa ctcggtcgcc gcatacacta    9060
ttctcagaat gacttggttg agtactcacc agtcacagaa aagcatctta cggatggcat    9120
gacagtaaga gaattatgca gtgctgccat aaccatgagt gataacactg cggccaactt    9180
acttctgaca acgatcggag gaccgaagga gctaaccgct tttttgcaca acatggggga    9240
tcatgtaact cgccttgatc gttgggaacc ggagctgaat gaagccatac caaacgacga    9300
gcgtgacacc acgatgcctg tagcaatggc aacaacgttg cgcaaactat taactggcga    9360
actacttact ctagcttccc ggcaacaatt aatagactgg atggaggcgg ataaagttgc    9420
aggaccactt ctgcgctcgg cccttccggc tggctggttt attgctgata atctggagc    9480
cggtgagcgt gggtctcgcg gtatcattgc agcactgggg ccagatggta gccctcccg    9540
tatcgtagtt atctacacga cggggagtca ggcaactatg gatgaacgaa atagacagat    9600
cgctgagata ggtgcctcac tgattaagca ttggtaactg tcagaccaag tttactcata    9660
tatactttag attgatttaa aacttcattt ttaatttaaa aggatctagg tgaagatcct    9720
ttttgataat ctcatgacca aaatccctta acgtgagttt tcgttccact gagcgtcaga    9780
ccccgtagaa aagatcaaag gatcttcttg agatcctttt tttctgcgcg taatctgctg    9840
cttgcaaaca aaaaaaccac cgctaccagc ggtggtttgt ttgccggatc aagagctacc    9900
aactcttttt ccgaaggtaa ctggcttcag cagagcgcag ataccaaata ctgttcttct    9960
agtgtagccg tagttaggcc accacttcaa gaactctgta gcaccgccta catacctcgc   10020
tctgctaatc ctgttaccag tggctgctgc cagtggcgat aagtcgtgtc ttaccgggtt   10080
ggactcaaga cgatagttac cggataaggc gcagcggtcg ggctgaacgg ggggttcgtg   10140
cacacagccc agcttggagc gaacgaccta caccgaactg agatacctac agcgtgagct   10200
atgagaaagc gccacgcttc ccgaagagag aaaggcggac aggtatccgg taagcggcag   10260
ggtcggaaca ggagagcgca cgagggagct tccaggggga aacgcctggt atctttatag   10320
tcctgtcggg tttcgccacc tctgacttga gcgtcgattt ttgtgatgct cgtcaggggg   10380
gcggagccta tggaaaaacg ccagcaacgc ggcctttttta cggttcctgg ccttttgctg   10440
gccttttgct cacatgttct ttcctgcgtt atcccctgat tctgtggata accgtattac   10500
cgcctttgag tgagctgata ccgctcgccg cagccgaacg accgagcgca gcgagtcagt   10560
gagcgaggaa gcggaagagc gcccaatacg caaaccgcct ctccccgcgc gttggccgat   10620
tcattaatgc agctggcacg acaggtttcc cgactggaaa gcgggcagtg agcgcaacgc   10680
```

```
aattaatgtg agttagctca ctcattaggc acccagggct ttacacttta tgcttccggc    10740
tcgtatgttg tgtggaattg tgagcggata acaatttcac acaggaaaca gctatgacca    10800
tgattacgcc aagcgcgcaa ttaaccctca ctaaagggaa caaaagctgg agctgcaagc    10860
tt                                                                  10862

<210> SEQ ID NO 49
<211> LENGTH: 9581
<212> TYPE: DNA
<213> ORGANISM: Artificial Sequence
<220> FEATURE:
<223> OTHER INFORMATION: Description of Artificial Sequence: Synthetic
      Vector 3 sequence

<400> SEQUENCE: 49
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca ggagagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggggaga    600 attagatcgc gatgggaaaa aattcggtta aggccagggg gaagaaaaa atataaatta     660 aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620 agttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
```

```
gcttttaaaa gaaaaggggg gattgggggg tacagtgcag gggaaagaat agtagacata    1860
atagcaacag acatacaaac taaagaatta caaaaacaaa ttacaaaaat tcaaaatttt    1920
actagtatca actttgtata gaaaagttgg gctccggtgc ccgtcagtgg gcagagcgca    1980
catcgcccac agtccccgag aagttggggg aggggtcgg caattgaacc ggtgcctaga     2040
gaaggtggcg cggggtaaac tgggaaagtg atgtcgtgta ctggctccgc cttttttccg    2100
agggtggggg agaaccgtat ataagtgcag tagtcgccgt gaacgttctt tttcgcaacg    2160
ggtttgccgc cagaacacag gtaagtgccg tgtgtggttc ccgcgggcct ggcctcttta    2220
cgggttatgg cccttgcgtg ccttgaatta cttccacctg gctgcagtac gtgattcttg    2280
atcccgagct tcgggttgga agtgggtggg agagttcgag gccttgcgct taaggagccc    2340
cttcgcctcg tgcttgagtt gaggcctggc ctgggcgctg gggccgccgc gtgcgaatct    2400
ggtggcacct tcgcgcctgt ctcgctgctt tcgataagtc tctagccatt taaaattttt    2460
gatgacctgc tgcgacgctt ttttctggc aagatagtct tgtaaatgcg ggccaagatc     2520
tgcacactgg tatttcggtt tttggggccg cgggcggcga cggggcccgt gcgtcccagc    2580
gcacatgttc ggcgaggcgg ggcctgcgag cgcggccacc gagaatcgga cggggggtagt   2640
ctcaagctgg ccggcctgct ctggtgcctg gtctcgcgcc gccgtgtatc gccccgccct    2700
gggcggcaag gctggcccgg tcggcaccag ttgcgtgagc ggaaagatgg ccgcttcccg    2760
gccctgctgc agggagctca aaatggagga cgcggcgctc gggagagcgg gcgggtgagt    2820
cacccacaca aaggaaaagg gccttttccgt cctcagccgt cgcttcatgt gactccacgg   2880
agtaccgggc gccgtccagg cacctcgatt agttctcgag cttttggagt acgtcgtctt    2940
taggttgggg ggaggggttt tatgcgatgg agtttcccca cactgagtgg gtggagactg    3000
aagttaggcc agcttggcac ttgatgtaat tctccttgga atttgccctt tttgagtttg    3060
gatcttggtt cattctcaag cctcagacag tggttcaaag ttttttttctt ccatttcagg   3120
tgtcgtgaca agtttgtaca aaaaagcagg ctgccaccat gtggctgcag agcctgctgc    3180
tgctgggcac cgtggcctgc agcatcagcc ccccgccag aagccccagc cccagcaccc    3240
agcccctggga gcacgtgaac gccatccagg aggccagaag actgctgaac ctgagcagag    3300
acaccgccgc cgagatgaac gagaccgtgg aggtgatcag cgagatgttc gacctgcagg    3360
agcccacctg cctgcagacc agactggagc tgtacaagca gggcctgaga ggcagcctga    3420
ccaagctgaa gggcccccctg accatgatgg ccagccacta caagcagcac tgcccccccca   3480
cccccgagac cagctgcgcc acccagatca tcaccttcga gagcttcaag agaacctga    3540
aggacttcct gctggtgatc cccttcgact gctgggagcc cgtgcaggag taaaacaaca    3600
acaattgcat tcatttatg tttcaggttc agggggaggt gtgggaggtt ttttaaagca     3660
agtaaaacct ctacaaatgt ggtacgcgtt aacaacaaca attgcattca ttttatgttt    3720
caggttcagg gggaggtgtg ggaggttttt taaagcaagt aaaacctcta caaatgtggt    3780
acgcgttacc cagctttctt gtacaaagtg gtaaatagat agaacaacaa caattgcatt    3840
cattttttgat tcaggttca gggggaggtg tgggaggttt tttaaagcaa gtaaaacctc    3900
tacactgacg gtacgcgtta acaacaacaa ttgcattcat ttgtagtttc aggttcaggg    3960
ggaggtgtgg gaggtttttt aaagcaagtt aaacctctaa aatagtggta cgcgttaccc    4020
agctttcttg tacaaagtgg acccagcttt cttgtacaaa gtgggcccct ctccctcccc    4080
cccccctaac gttactggcc gaagccgctt ggaataaggc cggtgtgcgt ttgtctatat    4140
```

```
gttatttttcc accatattgc cgtcttttgg caatgtgagg gcccggaaac ctggccctgt    4200
cttcttgacg agcattccta ggggtctttc ccctctcgcc aaaggaatgc aaggtctgtt    4260
gaatgtcgtg aaggaagcag ttcctctgga agcttcttga agacaaacaa cgtctgtagc    4320
gaccctttgc aggcagcgga accccccacc tggcgacagg tgcctctgcg gccaaaagcc    4380
acgtgtataa gatacacctg caaaggcggc acaaccccag tgccacgttg tgagttggat    4440
agttgtggaa agagtcaaat ggctctcctc aagcgtattc aacaaggggc tgaaggatgc    4500
ccagaaggta ccccattgta tgggatctga tctggggcct cggtgcacat gctttacatg    4560
tgtttagtcg aggttaaaaa aacgtctagg ccccccgaac cacggggacg tggttttcct    4620
ttgaaaaaca cgatgataat atggccacaa ccatggccac cgtgctggcc cccgcctgga    4680
gccccaccac ctacctgctg ctgctgctgc tgctgagcag cggcctgagc ggcacccagg    4740
actgcagctt ccagcacagc cccatcagca gcgacttcgc cgtgaagatc agagagctga    4800
gcgactacct gctgcaggac taccccgtga ccgtggccag caacctgcag gacgaggagc    4860
tgtgcggcgg cctgtggaga ctggtgctgg cccagagatg gatggagaga ctgaagaccg    4920
tggccggcag caagatgcag ggcctgctgg agagagtgaa caccgagatc cacttcgtga    4980
ccaagtgcgc cttccagccc cccccagct gcctgagatt cgtgcagacc aacatcagca    5040
gactgctgca ggagaccagc gagcagctgg tggccctgaa gccctggatc accagacaga    5100
acttcagcag atgcctggag ctgcagtgcc agcccgacag cagcacctg cccccccct    5160 ggagccccag acccctggag gccaccgccc ccaccgcccc ccagccccc ctgctgctgc    5220 tgctgctgct gcccgtgggc ctgctgctgc tggccgccgc ctggtgcctg cactggcaga    5280
gaaccagaag aagaaccccc agacccggcg agcaggtgcc cccgtgccc agcccccagg    5340 acctgctgct ggtggagcac taacaacttt attatacata gttgatcaat tccaacttta    5400
ttatacatag ttgatcaatt ccgataatca acctctggat tacaaaattt gtgaaagatt    5460
gactggtatt cttaactatg ttgctccttt tacgctatgt ggatacgctg ctttaatgcc    5520
tttgtatcat gctattgctt cccgtatggc tttcattttc tcctccttgt ataaatcctg    5580
gttgctgtct ctttatgagg agttgtggcc cgttgtcagg caacgtggcg tggtgtgcac    5640
tgtgtttgct gacgcaaccc ccactggttg gggcattgcc accacctgtc agctcctttc    5700
cgggactttc gctttccccc tccctattgc cacggcggaa ctcatcgccg cctgccttgc    5760
ccgctgctgg acaggggctc ggctgttggg cactgacaat tccgtggtgt tgtcggggaa    5820
gctgacgtcc tttccatggc tgctcgcctg tgttgccacc tggattctgc gcggacgtc    5880 cttctgctac gtcccttcgg ccctcaatcc agcggacctt ccttcccgcg gcctgctgcc    5940
ggctctgcgg cctcttccgc gtcttcgcct tcgccctcag acgagtcgga tctccctttg    6000
ggccgcctcc ccgcatcggg aattcccgcg gttcgcttta agaccaatga cttacaaggc    6060
agctgtagat cttagccact ttttaaaaga aaaggggga ctggaagggc taattcactc    6120
ccaacgaaga caagatctgc ttttttgcttg tactgggtct ctctggttag accagatctg    6180
agcctgggag ctctctggct aactagggaa cccactgctt aagcctcaat aaagcttgcc    6240
ttgagtgctt caagtagtgt gtgcccgtct gttgtgtgac tctggtaact agagatccct    6300
cagacccttt tagtcagtgt ggaaaatctc tagcagtagt agttcatgtc atcttattat    6360 tcagtatttta taacttgcaa agaaatgaat atcagagagt gagaggaact tgtttattgc    6420
agcttataat ggttacaaat aaagcaatag catcacaaat ttcacaaata aagcatttt    6480 ttcactgcat tctagttgtg gtttgtccaa actcatcaat gtatcttatc atgtctggct    6540
```

```
ctagctatcc cgccctaac tccgcccatc ccgcccctaa ctccgcccag ttccgcccat   6600
tctccgcccc atggctgact aattttttt atttatgcag aggccgaggc cgcctcggcc    6660
tctgagctat tccagaagta gtgaggaggc ttttttggag gcctagggac gtacccaatt   6720
cgccctatag tgagtcgtat tacgcgcgct cactggccgt cgttttacaa cgtcgtgact   6780
gggaaaaccc tggcgttacc caacttaatc gccttgcagc acatccccct ttcgccagct   6840
ggcgtaatag cgaagaggcc cgcaccgatc gcccttccca acagttgcgc agcctgaatg   6900
gcgaatggga cgcgccctgt agcggcgcat taagcgcggc gggtgtggtg gttacgcgca   6960
gcgtgaccgc tacacttgcc agcgccctag cgcccgctcc tttcgctttc ttcccttcct   7020
ttctcgccac gttcgccggc tttccccgtc aagctctaaa tcggggggctc cctttagggt   7080
tccgatttag tgctttacgg cacctcgacc ccaaaaaact tgattagggt gatggttcac   7140
gtagtgggcc atcgccctga tagacggttt ttcgcccttt gacgttggag tccacgttct   7200
ttaatagtgg actcttgttc caaactggaa caacactcaa ccctatctcg gtctattctt   7260
ttgatttata agggattttg ccgatttcgg cctattggtt aaaaaatgag ctgatttaac   7320
aaaaatttaa cgcgaatttt aacaaaatat taacgcttac aatttaggtg cacttttcg    7380
gggaaatgtg cgcggaaccc ctatttgttt attttctaa atacattcaa atatgtatcc    7440
gctcatgaga caataaccct gataaatgct tcaataatat tgaaaaagga agagtatgag   7500
tattcaacat ttccgtgtcg cccttattcc cttttttgcg gcattttgcc ttcctgtttt   7560
tgctcaccca gaaacgctgg tgaaagtaaa agatgctgaa gatcagttgg gtgcacgagt   7620
gggttacatc gaactggatc tcaacagcgg taagatcctt gagagttttc gccccgaaga   7680
acgttttcca atgatgagca cttttaaagt tctgctatgt ggcgcggtat tatcccgtat   7740
tgacgccggg caagagcaac tcggtcgccg catacactat tctcagaatg acttggttga   7800
gtactcacca gtcacagaaa agcatcttac ggatggcatg acagtaagag aattatgcag   7860
tgctgccata accatgagtg ataacactgc ggccaactta cttctgacaa cgatcggagg   7920
accgaaggag ctaaccgctt ttttgcacaa catgggggat catgtaactc gccttgatcg   7980
ttgggaaccg gagctgaatg aagccatacc aaacgacgag cgtgacacca cgatgcctgt   8040
agcaatggca acaacgttgc gcaaactatt aactggcgaa ctacttactc tagcttcccg   8100
gcaacaatta atagactgga tggaggcgga taaagttgca ggaccacttc tgcgctcggc   8160
ccttccggct ggctggttta ttgctgataa atctggagcc ggtgagcgtg gtctcgcgg    8220
tatcattgca gcactggggc cagatggtaa gccctcccgt atcgtagtta tctacacgac   8280
ggggagtcag gcaactatgg atgaacgaaa tagacagatc gctgagatag gtgcctcact   8340
gattaagcat tggtaactgt cagaccaagt ttactcatat atactttaga ttgatttaaa   8400
acttcatttt taatttaaaa ggatctaggt gaagatcctt tttgataatc tcatgaccaa   8460
aatcccttaa cgtgagtttt cgttccactg agcgtcagac cccgtagaaa agatcaaagg   8520
atcttcttga gatccttttt tctgcgcgt aatctgctgc ttgcaaacaa aaaaaccacc    8580
gctaccagcg gtggtttgtt tgccggatca gagctacca actctttttc cgaaggtaac   8640
tggcttcagc agagcgcaga taccaaatac tgttcttcta gtgtagccgt agttaggcca   8700
ccacttcaag aactctgtag caccgcctac atacctcgct ctgctaatcc tgttaccagt   8760
ggctgctgcc agtggcgata agtcgtgtct taccggggttg gactcaagac gatagttacc   8820
ggataaggcg cagcggtcgg gctgaacggg gggttcgtgc acacagccca gcttggagcg   8880
```

| | |
|---|---:|
| aacgacctac accgaactga gatacctaca gcgtgagcta tgagaaagcg ccacgcttcc | 8940 |
| cgaagagaga aaggcggaca ggtatccggt aagcggcagg gtcggaacag gagagcgcac | 9000 |
| gagggagctt ccagggggaa acgcctggta tctttatagt cctgtcgggt ttcgccacct | 9060 |
| ctgacttgag cgtcgatttt tgtgatgctc gtcaggggg cggagcctat ggaaaaacgc | 9120 |
| cagcaacgcg gcctttttac ggttcctggc cttttgctgg ccttttgctc acatgttctt | 9180 |
| tcctgcgtta tcccctgatt ctgtggataa ccgtattacc gcctttgagt gagctgatac | 9240 |
| cgctcgccgc agccgaacga ccgagcgcag cgagtcagtg agcgaggaag cggaagagcg | 9300 |
| cccaatacgc aaaccgcctc tccccgcgcg ttggccgatt cattaatgca gctggcacga | 9360 |
| caggtttccc gactggaaag cgggcagtga gcgcaacgca attaatgtga gttagctcac | 9420 |
| tcattaggca ccccaggctt tacactttat gcttccggct cgtatgttgt gtggaattgt | 9480 |
| gagcggataa caatttcaca caggaaacag ctatgaccat gattacgcca agcgcgcaat | 9540 |
| taaccctcac taaagggaac aaaagctgga gctgcaagct t | 9581 |

<210> SEQ ID NO 50
<211> LENGTH: 9746
<212> TYPE: DNA
<213> ORGANISM: Artificial Sequence
<220> FEATURE:
<223> OTHER INFORMATION: Description of Artificial Sequence: Synthetic Vector 4 sequence

<400> SEQUENCE: 50

| | |
|---|---:|
| aatgtagtct tatgcaatac tcttgtagtc ttgcaacatg gtaacgatga gttagcaaca | 60 |
| tgccttacaa ggagagaaaa agcaccgtgc atgccgattg gtggaagtaa ggtggtacga | 120 |
| tcgtgcctta ttaggaaggc aacagacggg tctgacatgg attggacgaa ccactgaatt | 180 |
| gccgcattgc agagatattg tatttaagtg cctagctcga tacataaacg ggtctctctg | 240 |
| gttagaccag atctgagcct gggagctctc tggctaacta gggaacccac tgcttaagcc | 300 |
| tcaataaagc ttgccttgag tgcttcaagt agtgtgtgcc cgtctgttgt gtgactctgg | 360 |
| taactagaga tccctcagac ccttttagtc agtgtggaaa atctctagca gtggcgcccg | 420 |
| aacagggact tgaaagcgaa agggaaacca gaggagctct ctcgacgcag gactcggctt | 480 |
| gctgaagcgc gcacggcaag aggcgagggg cggcgactgg tgagtacgcc aaaaattttg | 540 |
| actagcggag gctagaagga gagagatggg tgcgagagcg tcagtattaa gcggggagaa | 600 |
| attagatcgc gatgggaaaa aattcggtta aggccagggg gaagaaaaa atataaatta | 660 |
| aaacatatag tatgggcaag cagggagcta gaacgattcg cagttaatcc tggcctgtta | 720 |
| gaaacatcag aaggctgtag acaaatactg ggacagctac aaccatccct tcagacagga | 780 |
| tcagaagaac ttagatcatt atataataca gtagcaaccc tctattgtgt gcatcaaagg | 840 |
| atagagataa aagacaccaa ggaagcttta gacaagatag aggaagagca aaacaaaagt | 900 |
| aagaccaccg cacagcaagc ggccgctgat cttcagacct ggaggaggag atatgaggga | 960 |
| caattggaga agtgaattat ataaatataa agtagtaaaa attgaaccat taggagtagc | 1020 |
| acccaccaag gcaaagagaa gagtggtgca gagagaaaaa agagcagtgg gaataggagc | 1080 |
| tttgttcctt gggttcttgg gagcagcagg aagcactatg ggcgcagcgt caatgacgct | 1140 |
| gacggtacag gccagacaat tattgtctgg tatagtgcag cagcagaaca atttgctgag | 1200 |
| ggctattgag gcgcaacagc atctgttgca actcacagtc tggggcatca agcagctcca | 1260 |
| ggcaagaatc ctggctgtgg aaagatacct aaaggatcaa cagctcctgg ggatttgggg | 1320 |

```
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620
agttttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
gcttttaaaa gaaaaggggg gattgggggg tacagtgcag gggaaagaat agtagacata    1860
atagcaacag acatacaaac taagaatta caaaaacaaa ttacaaaaat tcaaaatttt    1920
actagtatca actttgtata gaaaagttgg ctccggtgc ccgtcagtgg gcagagcgca    1980
catcgcccac agtccccgag aagttggggg gaggggtcgg caattgaacc ggtgcctaga    2040
gaaggtggcg cggggtaaac tgggaaagtg atgtcgtgta ctggctccgc cttttccccg    2100
agggtgggg agaaccgtat ataagtgcag tagtcgccgt gaacgttctt tttcgcaacg    2160
ggtttgccgc cagaacacag gtaagtgccg tgtgtggttc ccgcgggcct ggcctcttta    2220
cgggttatgg cccttgcgtg ccttgaatta cttccacctg gctgcagtac gtgattcttg    2280
atcccgagct tcgggttgga agtgggtggg agagttcgag gccttgcgct taaggagccc    2340
cttcgcctcg tgcttgagtt gaggcctggc ctgggcgctg gggccgccgc gtgcgaatct    2400
ggtggcacct tcgcgcctgt ctcgctgctt tcgataagtc tctagccatt taaaatttt    2460
gatgacctgc tgcgacgctt ttttctggc aagatagtct tgtaaatgcg ggccaagatc    2520
tgcacactgg tatttcggtt tttggggccg cgggcggcga cggggcccgt gcgtcccagc    2580
gcacatgttc ggcgaggcgg ggcctgcgag cgcggccacc gagaatcgga cggggtagt    2640
ctcaagctgg ccggcctgct ctggtgcctg gtctcgcgcc ccgtgtatc gccccgccct    2700
gggcggcaag gctggcccgg tcggcaccag ttgcgtgagc ggaaagatgg ccgcttcccg    2760
gccctgctgc agggagctca aaatggagga cgcggcgctc gggagagcgg gcgggtgagt    2820
cacccacaca aaggaaaagg gccctttccgt cctcagccgt cgcttcatgt gactccacgg    2880
agtaccgggc gccgtccagg cacctcgatt agttctcgag cttttggagt acgtcgtctt    2940
taggttgggg ggagggggttt tatgcgatgg agtttcccca cactgagtgg gtggagactg    3000
aagttaggcc agcttggcac ttgatgtaat tctccttgga atttgccctt tttgagtttg    3060
gatcttggtt cattctcaag cctcagacag tggttcaaag ttttttttctt ccatttcagg    3120
tgtcgtgaca agtttgtaca aaaaagcagg ctgccaccat gaccgtgctg gccccgcct    3180
ggagccccac cacctacctg ctgctgctgc tgctgctgag cagcggcctg agcggcaccc    3240
aggactgcag cttccagcac agccccatca gcagcgactt cgccgtgaag atcagagagc    3300
tgagcgacta cctgctgcag gactacccg tgaccgtggc cagcaacctg caggacgagg    3360
agctgtgcgg cggcctgtgg agactggtgc tggcccagag atggatggag agactgaaga    3420
ccgtggccgg cagcaagatg cagggcctgc tggagagagt gaacaccgag atccacttcg    3480
tgaccaagtg cgccttccag cccccccccca gctgcctgag attcgtgcag accaacatca    3540
gcagactgct gcaggagacc agcgagcagc tggtggccct gaagccctgg atcaccagac    3600
agaacttcag cagatgcctg gagctgcagt gccagcccga cagcagcacc ctgccccccc    3660
cctggagccc cagacccctg gaggccaccg ccccccaccgc ccccccagtaa aacaacaaca    3720
```

| | |
|---|---|
| attgcattca tttatgttt caggttcagg gggaggtgtg ggaggttttt taaagcaagt | 3780 |
| aaaacctcta caaatgtggt acgcgttaac aacaacaatt gcattcattt tatgtttcag | 3840 |
| gttcagggg aggtgtggga ggtttttaa agcaagtaaa acctctacaa atgtggtacg | 3900 |
| cgttacccag ctttcttgta caaagtggta aatagataga caacaacaa ttgcattcat | 3960 |
| ttttgatttc aggttcaggg ggaggtgtgg gaggtttttt aaagcaagta aaacctctac | 4020 |
| actgacggta cgcgttaaca acaacaattg cattcatttg tagtttcagg ttcaggggga | 4080 |
| ggtgtgggag gtttttaaa gcaagttaaa cctctaaaat agtggtacgc gttacccagc | 4140 |
| tttcttgtac aaagtggacc cagctttctt gtacaaagtg ggcccctctc cctcccccc | 4200 |
| ccctaacgtt actggccgaa gccgcttgga ataaggccgg tgtgcgtttg tctatatgtt | 4260 |
| attttccacc atattgccgt cttttggcaa tgtgagggcc cggaaacctg gccctgtctt | 4320 |
| cttgacgagc attcctaggg gtctttcccc tctcgccaaa ggaatgcaag gtctgttgaa | 4380 |
| tgtcgtgaag gaagcagttc ctctggaagc ttcttgaaga caacaacgt ctgtagcgac | 4440 |
| cctttgcagg cagcggaacc ccccacctgg cgacaggtgc ctctgcggcc aaaagccacg | 4500 |
| tgtataagat acacctgcaa aggcggcaca accccagtgc cacgttgtga gttggatagt | 4560 |
| tgtggaaaga gtcaaatggc tctcctcaag cgtattcaac aaggggctga aggatgccca | 4620 |
| gaaggtaccc cattgtatgg gatctgatct ggggcctcgg tgcacatgct ttacatgtgt | 4680 |
| ttagtcgagg ttaaaaaaac gtctaggccc cccgaaccac ggggacgtgg ttttcctttg | 4740 |
| aaaaacacga tgataatatg gccacaacca tggccaccgt gctggcccc gcctggagcc | 4800 |
| ccaccaccta cctgctgctg ctgctgctgc tgagcagcgg cctgagcgcc cccgccagaa | 4860 |
| gccccagccc cagcacccag ccctgggagc acgtgaacgc catccaggag gccagaagac | 4920 |
| tgctgaacct gagcagagac accgccgccg agatgaacga gaccgtggag gtgatcagcg | 4980 |
| agatgttcga cctgcaggag cccacctgcc tgcagaccag actggagctg tacaagcagg | 5040 |
| gcctgagagg cagcctgacc aagctgaagg gccccctgac catgatggcc agccactaca | 5100 |
| agcagcactg ccccccccacc cccgagacca gctgcgccac ccagatcatc accttcgaga | 5160 |
| gcttcaagga gaacctgaag gacttcctgc tggtgatccc cttcgactgc tgggagcccg | 5220 |
| tgcaggagcc caccaccacc cccgcccca gacccccac cccgccccc accatcgcca | 5280 |
| gccagcccct gagcctgaga cccgaggcct gcagacccgc cgccggcggc gccgtgcaca | 5340 |
| ccagaggcct ggacttcgcc tgcgacatct acatctgggc cccctggcc ggcacctgcg | 5400 |
| gcgtgctgct gctgagcctg gtgatcaccc tgtactgcaa ccacagaaac agaagaagag | 5460 |
| tgtgcaagtg ccccagaccc gtggtgaaga gcggcgacaa gcccagcctg agcgccagat | 5520 |
| acgtgtaaca actttattat acatagttga tcaattccaa ctttattata catagttgat | 5580 |
| caattccgat aatcaacctc tggattacaa aatttgtgaa agattgactg gtattcttaa | 5640 |
| ctatgttgct ccttttacgc tatgtggata cgctgcttta atgcctttgt atcatgctat | 5700 |
| tgcttcccgt atggctttca ttttctcctc cttgtataaa tcctggttgc tgtctcttta | 5760 |
| tgaggagttg tggcccgttg tcaggcaacg tggcgtggtg tgcactgtgt ttgctgacgc | 5820 |
| aacccccact ggttggggca ttgccaccac ctgtcagctc ctttccggga ctttcgcttt | 5880 |
| ccccctccct attgccacgg cggaactcat cgccgcctgc cttgcccgct gctggacagg | 5940 |
| ggctcggctg ttgggcactg acaattccgt ggtgttgtcg gggaagctga cgtccttttcc | 6000 |
| atggctgctc gcctgtgttg ccacctggat tctgcgcggg acgtccttct gctacgtccc | 6060 |

```
ttcggccctc aatccagcgg accttccttc ccgcggcctg ctgccggctc tgcggcctct    6120
tccgcgtctt cgccttcgcc ctcagacgag tcggatctcc ctttgggccg cctcccgca     6180 tcgggaattc ccgcggttcg ctttaagacc aatgacttac aaggcagctg tagatcttag    6240
ccacttttta aaagaaaagg ggggactgga agggctaatt cactcccaac gaagacaaga    6300
tctgcttttt gcttgtactg ggtctctctg gttagaccag atctgagcct gggagctctc    6360
tggctaacta gggaacccac tgcttaagcc tcaataaagc ttgccttgag tgcttcaagt    6420
agtgtgtgcc cgtctgttgt gtgactctgg taactagaga tccctcagac ccttttagtc    6480
agtgtggaaa atctctagca gtagtagttc atgtcatctt attattcagt atttataact    6540
tgcaaagaaa tgaatatcag agagtgagag gaacttgttt attgcagctt ataatggtta    6600
caaataaagc aatagcatca caaatttcac aaataaagca ttttttttcac tgcattctag    6660 ttgtggtttg tccaaactca tcaatgtatc ttatcatgtc tggctctagc tatcccgccc    6720
ctaactccgc ccatcccgcc cctaactccg cccagttccg cccattctcc gccccatggc    6780
tgactaattt tttttattta tgcagaggcc gaggccgcct cggcctctga gctattccag    6840
aagtagtgag gaggcttttt tggaggccta gggacgtacc caattcgccc tatagtgagt    6900
cgtattacgc gcgctcactg gccgtcgttt tacaacgtcg tgactgggaa aaccctggcg    6960
ttacccaact taatcgcctt gcagcacatc cccctttcgc cagctggcgt aatagcgaag    7020
aggcccgcac cgatcgccct tcccaacagt tgcgcagcct gaatggcgaa tgggacgcgc    7080
cctgtagcgg cgcattaagc gcggcgggtg tggtggttac gcgcagcgtg accgctacac    7140
ttgccagcgc cctagcgccc gctcctttcg ctttcttccc ttcctttctc gccacgttcg    7200
ccggctttcc ccgtcaagct ctaaatcggg ggctcccttt agggttccga tttagtgctt    7260
tacggcacct cgaccccaaa aaacttgatt agggtgatgg ttcacgtagt gggccatcgc    7320
cctgatagac ggttttcgc cctttgacgt tggagtccac gttctttaat agtggactct    7380
tgttccaaac tggaacaaca ctcaacccta tctcggtcta ttcttttgat ttataaggga    7440
ttttgccgat ttcggcctat tggttaaaaa atgagctgat ttaacaaaaa tttaacgcga    7500
attttaacaa aatattaacg cttacaattt aggtggcact tttcggggaa atgtgcgcgg    7560 aaccccctatt tgtttatttt tctaaataca ttcaaatatg tatccgctca tgagacaata    7620
accctgataa atgcttcaat aatattgaaa aaggaagagt atgagtattc aacatttccg    7680
tgtcgccctt attcccttttt tgcggcatt ttgccttcct gttttgctc acccagaaac    7740 gctggtgaaa gtaaaagatg ctgaagatca gttgggtgca cgagtgggtt acatcgaact    7800
ggatctcaac agcggtaaga tccttgagag ttttcgcccc gaagaacgtt ttccaatgat    7860
gagcactttt aaagttctgc tatgtggcgc ggtattatcc cgtattgacg ccgggcaaga    7920
gcaactcggt cgccgcatac actattctca gaatgacttg gttgagtact caccagtcac    7980
agaaaagcat cttacggatg gcatgacagt aagagaatta tgcagtgctg ccataaccat    8040
gagtgataac actgcggcca acttacttct gacaacgatc ggaggaccga aggagctaac    8100
cgcttttttg cacaacatgg gggatcatgt aactcgcctt gatcgttggg aaccggagct    8160
gaatgaagcc ataccaaacg acgagcgtga ccacgatg cctgtagcaa tggcaacaac    8220
gttgcgcaaa ctattaactg gcgaactact tactctagct tcccggcaac aattaataga    8280
ctggatggag gcggataaag ttgcaggacc acttctgcgc tcggcccttc cggctggctg    8340
gtttattgct gataaatctg gagccggtga gcgtgggtct cgcggtatca ttgcagcact    8400
ggggccagat ggtaagccct cccgtatcgt agttatctac acgacgggga gtcaggcaac    8460
```

```
tatggatgaa cgaaatagac agatcgctga gataggtgcc tcactgatta agcattggta      8520
actgtcagac caagtttact catatatact ttagattgat ttaaaacttc atttttaatt      8580
taaaaggatc taggtgaaga tccttttttga taatctcatg accaaaatcc cttaacgtga     8640
gttttcgttc cactgagcgt cagacccccgt agaaaagatc aaaggatctt cttgagatcc    8700
tttttttctg cgcgtaatct gctgcttgca acaaaaaaaa ccaccgctac cagcggtggt     8760
ttgtttgccg gatcaagagc taccaactct ttttccgaag gtaactggct tcagcagagc     8820
gcagatacca aatactgttc ttctagtgta gccgtagtta ggccaccact tcaagaactc     8880
tgtagcaccg cctacatacc tcgctctgct aatcctgtta ccagtggctg ctgccagtgg     8940
cgataagtcg tgtcttaccg ggttggactc aagacgatag ttaccggata aggcgcagcg     9000
gtcgggctga acggggggtt cgtgcacaca gcccagcttg gagcgaacga cctacaccga     9060
actgagatac ctacagcgtg agctatgaga aagcgccacg cttcccgaag agagaaaggc     9120
ggacaggtat ccggtaagcg gcagggtcgg aacaggagag cgcacgaggg agcttccagg     9180
gggaaacgcc tggtatcttt atagtcctgt cgggtttcgc cacctctgac ttgagcgtcg     9240 attttttgtga tgctcgtcag gggggcggag cctatggaaa aacgccagca acgcggcctt    9300
tttacggttc ctggcctttt gctggccttt tgctcacatg ttctttcctg cgttatcccc     9360
tgattctgtg gataaccgta ttaccgcctt tgagtgagct gataccgctc gccgcagccg     9420
aacgaccgag cgcagcgagt cagtgagcga ggaagcggaa gagcgcccaa tacgcaaacc     9480
gcctctcccc gcgcgttggc cgattcatta atgcagctgg cacgacaggt ttcccgactg     9540
gaaagcgggc agtgagcgca acgcaattaa tgtgagttag ctcactcatt aggcacccca    9600
ggctttacac tttatgcttc cggctcgtat gttgtgtgga attgtgagcg gataacaatt    9660
tcacacagga aacagctatg accatgatta cgccaagcgc gcaattaacc ctcactaaag    9720
ggaacaaaag ctggagctgc aagctt                                          9746
```

<210> SEQ ID NO 51
<211> LENGTH: 8189
<212> TYPE: DNA
<213> ORGANISM: Artificial Sequence
<220> FEATURE:
<223> OTHER INFORMATION: Description of Artificial Sequence: Synthetic Vector 5 sequence

<400> SEQUENCE: 51

```
aatgtagtct tatgcaatac tcttgtagtc ttgcaacatg gtaacgatga gttagcaaca       60
tgccttacaa ggagagaaaa agcaccgtgc atgccgattg gtggaagtaa ggtggtacga      120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca ggagctct ctcgacgcag gactcggctt       480
gctgaagcgc gcacggcaag aggcgagggg cggcgactgg tgagtacgcc aaaaattttg    540
actagcggag gctagaagga gagagatggg tgcgagagcg tcagtattaa gcgggggaga     600
attagatcgc gatgggaaaa aattcggtta aggccagggg gaagaaaaa atataaatta     660 aaacatatag tatgggcaag cagggagcta gaacgattcg cagttaatcc tggcctgtta    720
```

```
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620 agttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattggggggg tacagtgcag gggaaagaat agtagacata   1860
atagcaacag acatcaaaac taagaaatta caaaaacaaa ttacaaaaat tcaaaatttt   1920
actagtgatt atcggatcaa cttttgtatag aaaagttggg ctccggtgcc cgtcagtggg   1980
cagagcgcac atcgcccaca gtccccgaga agttgggggg aggggtcggc aattgaaccg   2040
gtgcctagag aaggtggcgc ggggtaaact gggaaagtga tgtcgtgtac tggctccgcc   2100
tttttcccga gggtggggga gaaccgtata taagtgcagt agtcgccgtg aacgttcttt   2160
ttcgcaacgg gtttgccgcc agaacacagg taagtgccgt gtgtggttcc cgcgggcctg   2220
gcctctttac gggttatggc ccttgcgtgc cttgaattac ttccacctgg ctgcagtacg   2280
tgattcttga tcccgagctt cgggttggaa gtgggtggga gagttcgagg ccttgcgctt   2340
aaggagcccc ttcgcctcgt gcttgagttg aggcctggcc tgggcgctgg ggccgccgcg   2400
tgcgaatctg gtggcacctt cgcgcctgtc tcgctgcttt cgataagtct ctagccattt   2460 aaaattttg atgacctgct gcgacgcttt ttttctggca agatagtctt gtaaatgcgg   2520
gccaagatct gcacactggt atttcggttt ttggggccgc gggcggcgac ggggcccgtg   2580
cgtcccagcg cacatgttcg gcgaggcggg gcctgcgagc gcggccaccg agaatcggac   2640
gggggtagtc tcaagctggc cggcctgctc tggtgcctgg tctcgcgccg ccgtgtatcg   2700
ccccgccctg gcggcaagg ctggcccggt cggcaccagt gcgtgagcg aaagatggc    2760 cgcttcccgg ccctgctgca gggagctcaa aatggaggac gcggcgctcg ggagagcggg   2820
cgggtgagtc acccacacaa aggaaaaggg cctttccgtc ctcagccgtc gcttcatgtg   2880
actccacgga gtaccgggcg ccgtccaggc acctcgatta gttctcgagc ttttggagta   2940
cgtcgtcttt aggttggggg gagggggtttt atgcgatgga gtttccccac actgagtggg   3000
tggagactga agttaggcca gcttggcact tgatgtaatt ctccttggaa tttgcccttt   3060
```

```
ttgagtttgg atcttggttc attctcaagc ctcagacagt ggttcaaagt tttttttcttc     3120 catttcaggt gtcgtgacaa gtttgtacaa aaaagcaggc tgccaccatg atcgagacct     3180
acaaccagac cagccccaga agcgccgcca ccggcctgcc catcagcatg aagatcttca     3240
tgtacctgct gaccgtgttc ctgatcaccc agatgatcgg cagcgccctg ttcgccgtgt     3300
acctgcacag aagactggac aagatcgagg acgagagaaa cctgcacgag gacttcgtgt     3360
tcatgaagac catccagaga tgcaacaccg gcgagagaag cctgagcctg ctgaactgcg     3420
aggagatcaa gagccagttc gagggcttcg tgaaggacat catgctgaac aaggaggaga     3480
ccaagaagga gaacagcttc gagatgccca gaggcgagga ggacagccag atcgccgccc     3540
acgtgatcag cgaggccagc agcaagacca ccagcgtgct gcagtgggcc gagaagggct     3600
actacaccat gagcaacaac ctggtgaccc tggagaacgg caagcagctg accgtgaaga     3660
gacagggcct gtactacatc tacgcccagg tgaccttctg cagcaacaga gaggccagca     3720
gccaggcccc cttcatcgcc agcctgtgcc tgaagagccc cggcagattc gagagaatcc     3780
tgctgagagc cgccaacacc cacagcagcg ccaagccctg cggccagcag agcatccacc     3840
tgggcggcgt gttcgagctg cagcccggcg ccagcgtgtt cgtgaacgtg accgaccccc     3900
gccaggtgag ccacggcacc ggcttcacca gcttcggcct gctgaagctg taaacccagc     3960
tttcttgtac aaagtggtga taatcgaatt cacccagctt tcttgtacaa agtggtgata     4020
atcgaattcc gataatcaac ctctggatta caaaatttgt gaaagattga ctggtattct     4080
taactatgtt gctccttta cgctatgtgg atacgctgct ttaatgcctt tgtatcatgc     4140
tattgcttcc cgtatggctt tcattttctc ctccttgtat aaatcctggt tgctgtctct     4200
ttatgaggag ttgtggcccg ttgtcaggca acgtggcgtg gtgtgcactg tgtttgctga     4260
cgcaaccccc actggttggg gcattgccac cacctgtcag ctcctttccg gactttcgc      4320 tttccccctc cctattgcca cggcggaact catcgccgcc tgccttgccc gctgctggac     4380
aggggctcgg ctgttgggca ctgacaattc cgtggtgttg tcggggaagc tgacgtcctt     4440
tccatggctg ctcgcctgtg ttgccacctg gattctgcgc gggacgtcct tctgctacgt     4500
cccttcggcc ctcaatccag cggaccttcc ttcccgcggc ctgctgccgg ctctgcggcc     4560
tcttccgcgt cttcgccttc gccctcagac gagtcggatc tccctttggg ccgcctcccc     4620
gcatcgggaa ttcccgcggt tcgctttaag accaatgact acaaggcag ctgtagatct      4680 tagccacttt ttaaaagaaa agggggact ggaagggcta attcactccc aacgaagaca      4740
agatctgctt tttgcttgta ctgggtctct ctggttagac cagatctgag cctgggagct     4800
ctctggctaa ctagggaacc cactgcttaa gcctcaataa agcttgcctt gagtgcttca     4860
agtagtgtgt gcccgtctgt tgtgtgactc tggtaactag agatccctca gaccctttta     4920
gtcagtgtgg aaaatctcta gcagtagtag ttcatgtcat cttattattc agtatttata     4980
acttgcaaag aaatgaatat cagagagtga aggaacttg tttattgcag cttataatgg      5040
ttacaaataa agcaatagca tcacaaattt cacaataaa gcattttttt cactgcattc       5100
tagttgtggt ttgtccaaac tcatcaatgt atcttatcat gtctggctct agctatcccg     5160
cccctaactc cgcccatccc gcccctaact ccgcccagtt ccgcccattc tccgccccat     5220
ggctgactaa ttttttttat ttatgcagag gccgaggccg cctcggcctc tgagctattc     5280
cagaagtagt gaggaggctt ttttggaggc ctaggacgt acccaattcg ccctatagtg      5340
agtcgtatta cgcgcgctca ctggccgtcg ttttacaacg tcgtgactgg gaaaaccctg     5400
gcgttaccca acttaatcgc cttgcagcac atccccctt cgccagctgg cgtaatagcg       5460
```

```
aagaggcccg caccgatcgc ccttcccaac agttgcgcag cctgaatggc gaatgggacg    5520
cgccctgtag cggcgcatta agcgcggcgg gtgtggtggt tacgcgcagc gtgaccgcta    5580
cacttgccag cgccctagcg cccgctcctt tcgctttctt cccttccttt ctcgccacgt    5640
tcgccggctt tccccgtcaa gctctaaatc gggggctccc tttagggttc cgatttagtg    5700
ctttacggca cctcgacccc aaaaaacttg attagggtga tggttcacgt agtgggccat    5760
cgccctgata gacggttttt cgcccttga cgttggagtc cacgttcttt aatagtggac    5820
tcttgttcca aactggaaca acactcaacc ctatctcggt ctattctttt gatttataag    5880
ggattttgcc gatttcggcc tattggttaa aaaatgagct gatttaacaa aaatttaacg    5940
cgaattttaa caaatatta acgcttacaa tttaggtggc acttttcggg gaaatgtgcg    6000
cggaacccct atttgtttat ttttctaaat acattcaaat atgtatccgc tcatgagaca    6060
ataaccctga taaatgcttc aataatattg aaaaaggaag agtatgagta ttcaacattt    6120
ccgtgtcgcc cttattccct tttttgcggc attttgcctt cctgttttg ctcacccaga    6180 aacgctggtg aaagtaaaag atgctgaaga tcagttgggt gcacgagtgg gttacatcga    6240
actggatctc aacagcggta agatccttga gagttttcgc cccgaagaac gttttccaat    6300
gatgagcact tttaaagttc tgctatgtgg cgcggtatta cccgtattg acgccgggca    6360 agagcaactc ggtcgccgca tacactattc tcagaatgac ttggttgagt actcaccagt    6420
cacagaaaag catcttacgg atggcatgac agtaagagaa ttatgcagtg ctgccataac    6480
catgagtgat aacactgcgg ccaacttact tctgacaacg atcggaggac cgaaggagct    6540
aaccgctttt ttgcacaaca tgggggatca tgtaactcgc cttgatcgtt gggaaccgga    6600
gctgaatgaa gccataccaa acgacgagcg tgacaccacg atgcctgtag caatggcaac    6660
aacgttgcgc aaactattaa ctggcgaact acttactcta gcttcccggc aacaattaat    6720
agactggatg gaggcggata agttgcagg accacttctg cgctcggccc ttccggctgg    6780
ctggtttatt gctgataaat ctggagccgg tgagcgtggg tctcgcggta tcattgcagc    6840
actggggcca gatggtaagc cctcccgtat cgtagttatc tacacgacgg ggagtcaggc    6900
aactatggat gaacgaaata gacagatcgc tgagataggt gcctcactga ttaagcattg    6960
gtaactgtca gaccaagttt actcatatat actttagatt gatttaaaac ttcatttta    7020 atttaaaagg atctaggtga agatccttt tgataatctc atgaccaaaa tcccttaacg    7080
tgagttttcg ttccactgag cgtcagaccc cgtagaaaag atcaaaggat cttcttgaga    7140 tcctttttt ctgcgcgtaa tctgctgctt gcaaacaaaa aaaccaccgc taccagcggt    7200
ggtttgtttg ccggatcaag agctaccaac tcttttccg aaggtaactg gcttcagcag    7260
agcgcagata ccaaatactg ttcttctagt gtagccgtag ttaggccacc acttcaagaa    7320
ctctgtagca ccgcctacat acctcgctct gctaatcctg ttaccagtgg ctgctgccag    7380
tggcgataag tcgtgtctta ccgggttgga ctcaagacga tagttaccgg ataaggcgca    7440
gcggtcgggc tgaacggggg gttcgtgcac acagcccagc ttggagcgaa cgacctacac    7500
cgaactgaga tacctacagc gtgagctatg agaaagcgcc acgcttcccg aagagagaaa    7560
ggcggacagg tatccggtaa gcggcagggt cggaacagga gagcgcacga gggagcttcc    7620
agggggaaac gcctggtatc tttatagtcc tgtcgggttt cgccacctct gacttgagcg    7680
tcgatttttg tgatgctcgt cagggggcg gagcctatgg aaaaacgcca gcaacgcggc    7740 cttttacgg ttcctggcct tttgctggcc ttttgctcac atgttctttc ctgcgttatc    7800
```

```
ccctgattct gtggataacc gtattaccgc ctttgagtga gctgataccg ctcgccgcag   7860
ccgaacgacc gagcgcagcg agtcagtgag cgaggaagcg gaagagcgcc caatacgcaa   7920
accgcctctc cccgcgcgtt ggccgattca ttaatgcagc tggcacgaca ggtttcccga   7980
ctggaaagcg ggcagtgagc gcaacgcaat taatgtgagt tagctcactc attaggcacc   8040
ccaggcttta cactttatgc ttccggctcg tatgttgtgt ggaattgtga gcggataaca   8100
atttcacaca ggaaacagct atgaccatga ttacgccaag cgcgcaatta accctcacta   8160
aagggaacaa aagctgggagc tgcaagctt                                     8189

<210> SEQ ID NO 52
<211> LENGTH: 8069
<212> TYPE: DNA
<213> ORGANISM: Artificial Sequence
<220> FEATURE:
<223> OTHER INFORMATION: Description of Artificial Sequence: Synthetic
      Vector 6 sequence

<400> SEQUENCE: 52
aatgtagtct tatgcaatac tcttgtagtc ttgcaacatg gtaacgatga gttagcaaca     60
tgccttacaa ggagagaaaa agcaccgtgc atgccgattg gtggaagtaa ggtggtacga    120
tcgtgcctta ttaggaaggc aacagacggg tctgacatgg attggacgaa ccactgaatt    180
gccgcattgc agagatattg tatttaagtg cctagctcga tacataaacg ggtctctctg    240
gttagaccag atctgagcct gggagctctc tggctaacta gggaacccac tgcttaagcc    300
tcaataaagc ttgccttgag tgcttcaagt agtgtgtgcc cgtctgttgt gtgactctgg    360
taactagaga tccctcagac ccttttagtc agtgtggaaa atctctagca gtggcgcccg    420
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcggggggaga    600 attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
```

| | | | | | |
|---|---|---|---|---|---|
| agtttttgct | gtactttcta | tagtgaatag | agttaggcag | ggatattcac | cattatcgtt | 1680 |
| tcagacccac | ctcccaaccc | cgaggggacc | cgacaggccc | gaaggaatag | aagaagaagg | 1740 |
| tggagagaga | gacagagaca | gatccattcg | attagtgaac | ggatctcgac | ggtatcgcta | 1800 |
| gcttttaaaa | gaaaaggggg | gattgggggg | tacagtgcag | gggaaagaat | agtagacata | 1860 |
| atagcaacag | acatacaaac | taaagaatta | caaaaacaaa | ttacaaaaat | tcaaaatttt | 1920 |
| actagtgatt | atcggatcaa | ctttgtatag | aaaagttggg | ctccggtgcc | cgtcagtggg | 1980 |
| cagagcgcac | atcgcccaca | gtccccgaga | agttgggggg | aggggtcggc | aattgaaccg | 2040 |
| gtgcctagag | aaggtggcgc | ggggtaaact | gggaaagtga | tgtcgtgtac | tggctccgcc | 2100 |
| ttttccccga | gggtggggga | gaaccgtata | aagtgcagt | agtcgccgtg | aacgttcttt | 2160 |
| ttcgcaacgg | gtttgccgcc | agaacacagg | taagtgccgt | gtgtggttcc | cgcgggcctg | 2220 |
| gcctctttac | gggttatggc | ccttgcgtgc | cttgaattac | ttccacctgg | ctgcagtacg | 2280 |
| tgattcttga | tcccgagctt | cgggttggaa | gtgggtggga | gagttcgagg | ccttgcgctt | 2340 |
| aaggagcccc | ttcgcctcgt | gcttgagttg | aggcctggcc | tgggcgctgg | ggccgccgcg | 2400 |
| tgcgaatctg | gtggcacctt | cgcgcctgtc | tcgctgcttt | cgataagtct | ctagccattt | 2460 |
| aaaatttttg | atgacctgct | gcgacgcttt | ttttctggca | agatagtctt | gtaaatgcgg | 2520 |
| gccaagatct | gcacactggt | atttcggttt | ttggggccgc | gggcggcgac | ggggcccgtg | 2580 |
| cgtcccagcg | cacatgttcg | gcgaggcggg | gcctgcgagc | gcggccaccg | agaatcggac | 2640 |
| gggggtagtc | tcaagctggc | cggcctgctc | tggtgcctgg | tctcgcgccg | ccgtgtatcg | 2700 |
| ccccgccctg | ggcggcaagg | ctggcccggt | cggcaccagt | tgcgtgagcg | gaaagatggc | 2760 |
| cgcttcccgg | ccctgctgca | gggagctcaa | aatggaggac | gcggcgctcg | ggagagcggg | 2820 |
| cgggtgagtc | acccacacaa | aggaaaaggg | cctttccgtc | ctcagccgtc | gcttcatgtg | 2880 |
| actccacgga | gtaccgggcg | ccgtccaggc | acctcgatta | gttctcgagc | ttttggagta | 2940 |
| cgtcgtcttt | aggttggggg | gaggggtttt | atgcgatgga | gtttccccac | actgagtggg | 3000 |
| tggagactga | agttaggcca | gcttggcact | tgatgtaatt | ctccttggaa | tttgcccttt | 3060 |
| ttgagtttgg | atcttggttc | attctcaagc | ctcagacagt | ggttcaaagt | ttttttcttc | 3120 |
| catttcaggt | gtcgtgacaa | gtttgtacaa | aaaagcaggc | tgccaccatg | agcaccgaga | 3180 |
| gcatgatcag | agacgtggag | ctggccgagg | aggccctgcc | caagaagacc | ggcggccccc | 3240 |
| agggcagcag | aagatgcctg | ttcctgagcc | tgttcagctt | cctgatcgtg | gccggcgcca | 3300 |
| ccaccctgtt | ctgcctgctg | cacttccgcg | tgatcggccc | cagagagag | gagttcccca | 3360 |
| gagacctgag | cctgatcagc | ccctggccc | aggccgtggc | ccacgtggtg | gccaaccccc | 3420 |
| aggccgaggg | ccagctgcag | tggctgaaca | agagagccaa | cgccctgctg | gccaacggcg | 3480 |
| tggagctgag | agacaaccag | ctggtggtgc | ccagcgaggg | cctgtacctg | atctacagcc | 3540 |
| aggtgctgtt | caagggccag | ggctgcccca | gcacccacgt | gctgctgacc | cacaccatca | 3600 |
| gcagaatcgc | cgtgagctac | cagaccaagg | tgaacctgct | gagcgccatc | aagagcccct | 3660 |
| gccagagaga | gaccccccgag | ggcgccgagg | ccaagccctg | gtacgagccc | atctacctgg | 3720 |
| gcggcgtgtt | ccagctggag | aagggcgaca | gactgagcgc | cgagatcaac | agacccgact | 3780 |
| acctggactt | cgccgagagc | ggccaggtgt | acttcggcat | catcgccctg | taaacccagc | 3840 |
| tttcttgtac | aaagtggtga | taatcgaatt | cacccagctt | tcttgtacaa | agtggtgata | 3900 |
| atcgaattcc | gataatcaac | ctctggatta | caaaatttgt | gaaagattga | ctggtattct | 3960 |
| taactatgtt | gctcctttta | cgctatgtgg | atacgctgct | ttaatgcctt | tgtatcatgc | 4020 |

```
tattgcttcc cgtatggctt tcattttctc ctccttgtat aaatcctggt tgctgtctct    4080
ttatgaggag ttgtggcccg ttgtcaggca acgtggcgtg gtgtgcactg tgtttgctga    4140
cgcaaccccc actggttggg gcattgccac cacctgtcag ctcctttccg ggactttcgc    4200 tttcccctc cctattgcca cggcggaact catcgccgcc tgccttgccc gctgctggac    4260
aggggctcgg ctgttgggca ctgacaattc cgtggtgttg tcggggaagc tgacgtcctt    4320
tccatggctg ctcgcctgtg ttgccacctg gattctgcgc gggacgtcct tctgctacgt    4380
cccttcggcc ctcaatccag cggaccttcc ttcccgcggc ctgctgccgg ctctgcggcc    4440
tcttccgcgt cttcgccttc gccctcagac gagtcggatc tccctttggg ccgcctcccc    4500
gcatcgggaa ttcccgcggt tcgctttaag accaatgact tacaaggcag ctgtagatct    4560
tagccacttt ttaaaagaaa agggggggact ggaagggcta attcactccc aacgaagaca    4620
agatctgctt tttgcttgta ctgggtctct ctggttagac cagatctgag cctgggagct    4680
ctctggctaa ctagggaacc cactgcttaa gcctcaataa agcttgcctt gagtgcttca    4740
agtagtgtgt gcccgtctgt tgtgtgactc tggtaactag agatccctca gacccttta    4800 gtcagtgtgg aaaatctcta gcagtagtag ttcatgtcat cttattattc agtatttata    4860
acttgcaaag aaatgaatat cagagagtga gaggaacttg tttattgcag cttataatgg    4920
ttacaaataa agcaatagca tcacaaattt cacaaataaa gcattttttt cactgcattc    4980
tagttgtggt ttgtccaaac tcatcaatgt atcttatcat gtctggctct agctatcccg    5040
cccctaactc cgcccatccc gcccctaact ccgcccagtt ccgcccattc tccgccccat    5100
ggctgactaa tttttttat ttatgcagag gccgaggccg cctcggcctc tgagctattc    5160
cagaagtagt gaggaggctt ttttggaggc ctagggacgt acccaattcg ccctatagtg    5220
agtcgtatta cgcgcgctca ctggccgtcg ttttacaacg tcgtgactgg gaaaaccctg    5280
gcgttaccca acttaatcgc cttgcagcac atccccctt cgccagctgg cgtaatagcg    5340
aagaggcccg caccgatcgc ccttcccaac agttgcgcag cctgaatggc gaatgggacg    5400
cgccctgtag cggcgcatta agcgcggcgg gtgtggtggt tacgcgcagc gtgaccgcta    5460
cacttgccag cgccctagcg cccgctcctt tcgctttctt cccttccttt ctcgccacgt    5520
tcgccggctt tccccgtcaa gctctaaatc ggggctccc tttagggttc cgatttagtg    5580
ctttacggca cctcgacccc aaaaaacttg attagggtga tggttcacgt agtgggccat    5640
cgccctgata cggttttt cgcccttga cgttggagtc cacgttcttt aatagtggac    5700
tcttgttcca aactggaaca cactcaacc ctatctcggt ctattctttt gatttataag    5760
ggattttgcc gatttcggcc tattggttaa aaaatgagct gatttaacaa aaatttaacg    5820
cgaattttaa caaatatta acgcttacaa ttaggtggc acttttcggg gaaatgtgcg    5880
cggaacccct atttgtttat ttttctaaat acattcaaat atgtatccgc tcatgagaca    5940 ataacctga taaatgcttc aataatattg aaaaaggaag agtatgagta ttcaacattt    6000
ccgtgtcgcc cttattccct tttttgcggc attttgcctt cctgtttttg ctcacccaga    6060
aacgctggtg aaagtaaaag atgctgaaga tcagttgggt gcacgagtgg gttacatcga    6120
actggatctc aacagcggta agatccttga gagtttttcgc cccgaagaac gttttccaat    6180
gatgagcact tttaaagttc tgctatgtgg cgcggtatta tcccgtattg acgccgggca    6240
agagcaactc ggtcgccgca tacactattc tcagaatgac ttggttgagt actcaccagt    6300
cacagaaaag catcttacgg atggcatgac agtaagagaa ttatgcagtg ctgccataac    6360
```

```
catgagtgat aacactgcgg ccaacttact tctgacaacg atcggaggac cgaaggagct    6420
aaccgctttt ttgcacaaca tgggggatca tgtaactcgc cttgatcgtt gggaaccgga    6480
gctgaatgaa gccataccaa acgacgagcg tgacaccacg atgcctgtag caatggcaac    6540
aacgttgcgc aaactattaa ctggcgaact acttactcta gcttcccggc aacaattaat    6600
agactggatg gaggcggata agttgcagg accacttctg cgctcggccc ttccggctgg    6660
ctggtttatt gctgataaat ctggagccgg tgagcgtggg tctcgcggta tcattgcagc    6720
actggggcca gatggtaagc cctcccgtat cgtagttatc tacacgacgg ggagtcaggc    6780
aactatggat gaacgaaata gacagatcgc tgagataggt gcctcactga ttaagcattg    6840
gtaactgtca gaccaagttt actcatatat actttagatt gatttaaaac ttcattttta    6900
atttaaaagg atctaggtga agatcctttt tgataatctc atgaccaaaa tcccttaacg    6960
tgagttttcg ttccactgag cgtcagaccc cgtagaaaag atcaaaggat cttcttgaga    7020
tccttttttt ctgcgcgtaa tctgctgctt gcaaacaaaa aaaccaccgc taccagcggt    7080
ggtttgtttg ccggatcaag agctaccaac tcttttccg aaggtaactg gcttcagcag    7140
agcgcagata ccaaatactg ttcttctagt gtagccgtag ttaggccacc acttcaagaa    7200
ctctgtagca ccgcctacat acctcgctct gctaatcctg ttaccagtgg ctgctgccag    7260
tggcgataag tcgtgtctta ccgggttgga ctcaagacga tagttaccgg ataaggcgca    7320
gcggtcgggc tgaacgggggg gttcgtgcac acagcccagc ttggagcgaa cgacctacac    7380
cgaactgaga tacctacagc gtgagctatg agaaagcgcc acgcttcccg aagagagaaa    7440
ggcggacagg tatccggtaa gcggcagggt cggaacagga gagcgcacga gggagcttcc    7500
agggggaaac gcctggtatc tttatagtcc tgtcgggttt cgccacctct gacttgagcg    7560
tcgatttttg tgatgctcgt caggggggcg gagcctatgg aaaaacgcca gcaacgcggc    7620 cttttacgg ttcctggcct tttgctggcc ttttgctcac atgttctttc ctgcgttatc    7680
ccctgattct gtggataacc gtattaccgc ctttgagtga gctgataccg ctcgccgcag    7740
ccgaacgacc gagcgcagcg agtcagtgag cgaggaagcg gaagagcgcc caatacgcaa    7800
accgcctctc cccgcgcgtt ggccgattca ttaatgcagc tggcacgaca ggtttcccga    7860
ctggaaagcg ggcagtgagc gcaacgcaat taatgtgagt tagctcactc attaggcacc    7920
ccaggcttta cactttatgc ttccggctcg tatgttgtgt ggaattgtga gcggataaca    7980
atttcacaca ggaaacagct atgaccatga ttacgccaag cgcgcaatta accctcacta    8040
aagggaacaa aagctggagc tgcaagctt                                      8069
```

<210> SEQ ID NO 53
<211> LENGTH: 10067
<212> TYPE: DNA
<213> ORGANISM: Artificial Sequence
<220> FEATURE:
<223> OTHER INFORMATION: Description of Artificial Sequence: Synthetic Vector 7 sequence

<400> SEQUENCE: 53

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
```

```
tcaataaagc ttgccttgag tgcttcaagt agtgtgtgcc cgtctgttgt gtgactctgg      360
taactagaga tccctcagac ccttttagtc agtgtggaaa atctctagca gtggcgcccg      420
aacagggact tgaaagcgaa agggaaacca gaggagctct ctcgacgcag gactcggctt      480
gctgaagcgc gcacggcaag aggcgagggg cggcgactgg tgagtacgcc aaaaattttg      540
actagcggag gctagaagga gagagatggg tgcgagagcg tcagtattaa gcggggga      600
attagatcgc gatgggaaaa aattcggtta aggccagggg gaaagaaaaa atataaatta      660
aaacatatag tatgggcaag cagggagcta gaacgattcg cagttaatcc tggcctgtta      720
gaaacatcag aaggctgtag acaaatactg ggacagctac aaccatccct tcagacagga      780
tcagaagaac ttagatcatt atataataca gtagcaaccc tctattgtgt gcatcaaagg      840
atagagataa aagacaccaa ggaagcttta gacaagatag aggaagagca aaacaaaagt      900
aagaccaccg cacagcaagc ggccgctgat cttcagacct ggaggaggag atatgaggga      960
caattggaga agtgaattat ataaatataa agtagtaaaa attgaaccat taggagtagc     1020
acccaccaag gcaaagagaa gagtggtgca gagagaaaaa agagcagtgg gaataggagc     1080
tttgttcctt gggttcttgg gagcagcagg aagcactatg ggcgcagcgt caatgacgct     1140
gacggtacag gccagacaat tattgtctgg tatagtgcag cagcagaaca atttgctgag     1200
ggctattgag gcgcaacagc atctgttgca actcacagtc tggggcatca agcagctcca     1260
ggcaagaatc ctggctgtgg aaagatacct aaaggatcaa cagctcctgg ggatttgggg     1320
ttgctctgga aaactcattt gcaccactgc tgtgccttgg aatgctagtt ggagtaataa     1380
atctctggaa cagatttgga atcacacgac ctggatggag tgggacagag aaattaacaa     1440
ttacacaagc ttaatacact ccttaattga agaatcgcaa aaccagcaag aaaagaatga     1500
acaagaatta ttggaattag ataaatgggc aagtttgtgg aattggttta cataacaaa     1560
ttggctgtgg tatataaaat tattcataat gatagtagga ggcttggtag gtttaagaat     1620
agttttgct gtactttcta tagtgaatag agttaggcag ggatattcac cattatcgtt     1680
tcagacccac ctcccaaccc cgaggggacc cgacaggccc gaaggaatag aagaagaagg     1740
tggagagaga gacagagaca gatccattcg attagtgaac ggatctcgac ggtatcgcta     1800
gcttttaaaa gaaaagggggg gattgggggg tacagtgcag gggaaagaat agtagacata     1860
atagcaacag acatacaaac taagaattac aaaaacaaa ttacaaaaat tcaaaatttt     1920
actagtatca acttttgtata gaaaagttgg gctccggtgc ccgtcagtgg gcagagcgca     1980
catcgcccac agtccccgag aagttggggg gaggggtcgg caattgaacc ggtgcctaga     2040
gaaggtggcg cggggtaaac tgggaaagtg atgtcgtgta ctggctccgc cttttttccg     2100
agggtggggg agaaccgtat ataagtgcag tagtcgccgt gaacgttctt tttcgcaacg     2160
ggtttgccgc cagaacacag gtaagtgccg tgtgtggttc ccgcgggcct ggcctcttta     2220
cgggttatgg cccttgcgtg ccttgaatta cttccacctg gctgcagtac gtgattcttg     2280
atcccgagct tcgggttgga agtgggtggg agagttcgag gccttgcgct taaggagccc     2340
cttcgcctcg tgcttgagtt gaggcctggc ctgggcgctg gggccgccgc gtgcgaatct     2400
ggtggcacct tcgcgcctgt ctcgctgctt tcgataagtc tctagccatt taaaattttt     2460
gatgacctgc tgcgacgctt ttttttctggc aagatagtct tgtaaatgcg ggccaagatc     2520
tgcacactgg tatttcggtt tttggggccg cgggcggcga cggggcccgt gcgtcccagc     2580
gcacatgttc ggcgaggcgg ggcctgcgag cgcggccacc gagaatcgga cgggggtagt     2640
ctcaagctgg ccggcctgct ctggtgcctg gtctcgcgcc gccgtgtatc gccccgccct     2700
```

```
gggcggcaag gctggcccgg tcggcaccag ttgcgtgagc ggaaagatgg ccgcttcccg   2760
gccctgctgc agggagctca aaatggagga cgcggcgctc gggagagcgg gcgggtgagt   2820
cacccacaca aaggaaaagg gcctttccgt cctcagccgt cgcttcatgt gactccacgg   2880
agtaccgggc gccgtccagg cacctcgatt agttctcgag cttttggagt acgtcgtctt   2940
taggttgggg ggaggggttt tatgcgatgg agtttcccca cactgagtgg gtggagactg   3000
aagttaggcc agcttggcac ttgatgtaat tctccttgga atttgccctt tttgagtttg   3060
gatcttggtt cattctcaag cctcagacag tggttcaaag ttttttttctt ccatttcagg   3120 tgtcgtgaca agtttgtaca aaaaagcagg ctgccaccat gagcaccgag agcatgatca   3180
gagacgtgga gctggccgag gaggccctgc ccaagaagac cggcggcccc cagggcagca   3240
gaagatgcct gttcctgagc ctgttcagct tcctgatcgt ggccggcgcc accaccctgt   3300
tctgcctgct gcacttcggc gtgatcggcc cccagagaga ggagttcccc agagacctga   3360
gcctgatcag cccccctggcc caggccgtgg cccacgtggt ggccaacccc caggccgagg   3420
gccagctgca gtggctgaac agaagagcca acgccctgct ggccaacggc gtggagctga   3480
gagacaacca gctggtggtg cccagcgagg gcctgtacct gatctacagc caggtgctgt   3540
tcaagggcca gggctgcccc agcacccacg tgctgctgac ccacaccatc agcagaatcg   3600
ccgtgagcta ccagaccaag gtgaacctgc tgagcgccat caagagcccc tgccagagag   3660 agaccccga gggcgccgag gccaagccct ggtacgagcc catctacctg gcggcgtgt   3720 tccagctgga aagggcgac agactgagcg ccgagatcaa cagacccgac tacctggact   3780
tcgccgagag cggccaggtg tacttcggca tcatcgccct gtaaacccag ctttcttgta   3840
caaagtggtg ataatcgaat ctaaataga tagaacaaca acaattgcat tcatttttga   3900
tttcaggttc agggggaggt gtgggaggtt ttttaaagca agtaaaacct ctacactgac   3960
ggtacgcgtt aacaacaaca attgcattca tttgtagttt caggttcagg gggaggtgtg   4020
ggaggttttt taaagcaagt taaacctcta aaatagtggt acgcgttacc cagctttctt   4080
gtacaaagtg gacccagctt tcttgtacaa agtgggcccc tctccctccc ccccccctaa   4140
cgttactggc cgaagccgct tggaataagg ccggtgtgcg tttgtctata tgttattttc   4200
caccatattg ccgtcttttg gcaatgtgag ggcccggaaa cctggccctg tcttcttgac   4260
gagcattcct aggggtcttt cccctctcgc caaaggaatg caaggtctgt tgaatgtcgt   4320
gaaggaagca gttcctctgg aagcttcttg aagacaaaca acgtctgtag cgaccctttg   4380
caggcagcgg aacccccac ctggcgacag gtgcctctgc ggccaaaagc cacgtgtata   4440
agatacacct gcaaaggcgg cacaaccca gtgccacgtt gtgagttgga tagttgtgga   4500
aagagtcaaa tggctctcct caagcgtatt caacaagggg ctgaaggatg cccagaaggt   4560
accccattgt atgggatctg atctggggcc tcggtgcaca tgctttacat gtgtttagtc   4620
gaggttaaaa aaacgtctag gcccccgaa ccacggggac gtggttttcc tttgaaaaac   4680
acgatgataa tatggccaca accatggcca ccgtgctggc cccgcctgg agccccacca   4740 cctacctgct gctgctgctg ctgctgagca gcggcctgag cggcggcggc ggcagcggca   4800
agcccatccc caacccctg ctgggcctgg acagcaccgg cggcggcggc agccaggtga   4860
agctgcagga gagcggccc ggctcggtgg cccccagcca gagcctgagc atcacctgca   4920
ccgtgagcgg cttcagcctg accgcctacg gcgtggactg ggtgagacag ccccccggca   4980
agtgcctgga gtggctgggc gtgatctggg gcggcggcag aaccaactac aacagcggcc   5040
```

```
tgatgagcag actgagcatc agaaaggaca acagcaagag ccaggtgttc ctgaccatga      5100
acagcctgca gaccgacgac accgccaagt actactgcgt gaagcacacc aactgggacg      5160
gcggcttcgc ctactggggc cagggcacca ccgtgaccgt gagcagcggc ggcggcggca      5220
gcggcggcgg cggcagcggc ggcggcggca gcggcagccc cggccagagc gtgagcatca      5280
gctgcagcgg cagcagcagc aacatcggca caactacgt gtactggtac cagcacctgc      5340
ccggcaccgc ccccaagctg ctgatctaca gcgacaccaa gagacccagc ggcgtgcccg      5400
acagaatcag cggcagcaag agcggcacca cgccagcct ggccatcagc ggcctgcaga      5460
gcgaggacga ggccgactac tactgcgcca gctgggacga cagcctggac ggccccgtgt      5520
tcggctgcgg caccaagctg accgtgctgc ccaccaccac ccccgccccc agacccccca      5580
cccccgcccc caccatcgcc agccagcccc tgagcctgag acccgaggcc tgcagacccg      5640
ccgccggcgg cgccgtgcac accagaggcc tggacttcgc ctgcgacatc tacatctggg      5700
cccccctggc cggcacctgc ggcgtgctgc tgctgagcct ggtgatcacc ctgtactgca      5760
accacagaaa cagaagaaga gtgtgcaagt gccccagacc cgtggtgaag agcggcgaca      5820
agcccagcct gagcgccaga tacgtgtaac aactttatta tacatagttg atcaattcca      5880
actttattat acatagttga tcaattccga taatcaacct ctggattaca aaatttgtga      5940
aagattgact ggtattctta actatgttgc tccttttacg ctatgtggat acgctgcttt      6000
aatgcctttg tatcatgcta ttgcttccg tatggctttc attttctcct ccttgtataa      6060
atcctggttg ctgtctcttt atgaggagtt gtggcccgtt gtcaggcaac gtggcgtggt      6120
gtgcactgtg tttgctgacg caaccccccac tggttgggc attgccacca cctgtcagct      6180
cctttccggg actttcgctt tccccctccc tattgccacg gcggaactca tcgccgcctg      6240 ccttgccgc tgctggacag gggctcggct gttgggcact gacaattccg tggtgttgtc      6300
ggggaagctg acgtcctttc catggctgct cgcctgtgtt gccacctgga ttctgcgcgg      6360
gacgtccttc tgctacgtcc cttcggcccct caatccagcg accttccctt cccgcggcct      6420
gctgccggct ctgcggcctc ttccgcgtct tcgccttcgc cctcagacga tcggatctc      6480 cctttgggcc gcctccccgc atcgggaatt cccgcggttc gctttaagac caatgactta      6540
caaggcagct gtagatctta gccactttt aaaagaaaag ggggggactgg aagggctaat      6600 tcactcccaa cgaagacaag atctgctttt tgcttgtact gggtctctct ggttagacca      6660
gatctgagcc tgggagctct ctggctaact agggaaccca ctgcttaagc ctcaataaag      6720
cttgccttga gtgcttcaag tagtgtgtgc ccgtctgttg tgtgactctg gtaactagag      6780
atccctcaga cccttttagt cagtgtggaa atctctagc agtagtagtt catgtcatct      6840
tattattcag tatttataac ttgcaaagaa atgaatatca gagagtgaga ggaacttgtt      6900
tattgcagct tataatggtt acaaataaag caatagcatc acaaatttca caaataaagc      6960 attttttca ctgcattcta gttgtggttt gtccaaactc atcaatgtat cttatcatgt      7020
ctggctctag ctatcccgcc cctaactccg cccatcccgc cctaactccg cccagttcc      7080 gcccattctc cgccccatgg ctgactaatt ttttttattt atgcagaggc cgaggccgcc      7140
tcggcctctg agctattcca gaagtagtga ggaggctttt ttggaggcct agggacgtac      7200
ccaattcgcc ctatagtgag tcgtattacg cgcgctcact ggccgtcgtt ttacaacgtc      7260
gtgactggga aaaccctggc gttacccaac ttaatcgcct tgcagcacat ccccctttcg      7320
ccagctggcg taatagcgaa gaggcccgca ccgatcgccc ttcccaacag ttgcgcagcc      7380
tgaatggcga atgggacgcg ccctgtagcg gcgcattaag cgcggcgggt gtggtggtta      7440
```

```
cgcgcagcgt gaccgctaca cttgccagcg ccctagcgcc cgctcctttc gctttcttcc   7500
cttcctttct cgccacgttc gccggctttc cccgtcaagc tctaaatcgg gggctccctt   7560
tagggttccg atttagtgct ttacggcacc tcgaccccaa aaaacttgat tagggtgatg   7620
gttcacgtag tgggccatcg ccctgataga cggttttttcg cccttttgacg ttggagtcca   7680 cgttctttaa tagtggactc ttgttccaaa ctggaacaac actcaaccct atctcggtct   7740
attcttttga tttataaggg attttgccga tttcggccta ttggttaaaa aatgagctga   7800
tttaacaaaa atttaacgcg aattttaaca aaatattaac gcttacaatt taggtggcac   7860
ttttcgggga aatgtgcgcg gaacccctat ttgtttattt ttctaaatac attcaaatat   7920
gtatccgctc atgagacaat aaccctgata aatgcttcaa taatattgaa aaaggaagag   7980
tatgagtatt caacatttcc gtgtcgccct tattccctttt tttgcggcat tttgccttcc   8040 tgttttttgct cacccagaaa cgctggtgaa agtaaaagat gctgaagatc agttgggtgc   8100
acgagtgggt tacatcgaac tggatctcaa cagcggtaag atccttgaga gttttcgccc   8160
cgaagaacgt tttccaatga tgagcacttt taaagttctg ctatgtggcg cggtattatc   8220
ccgtattgac gccgggcaag agcaactcgg tcgccgcata cactattctc agaatgactt   8280
ggttgagtac tcaccagtca cagaaaagca tcttacggat ggcatgacag taagagaatt   8340
atgcagtgct gccataacca tgagtgataa cactgcggcc aacttacttc tgacaacgat   8400
cggaggaccg aaggagctaa ccgcttttttt gcacaacatg ggggatcatg taactcgcct   8460
tgatcgttgg gaaccggagc tgaatgaagc cataccaaac gacgagcgtg acaccacgat   8520
gcctgtagca atggcaacaa cgttgcgcaa actattaact ggcgaactac ttactctagc   8580
ttcccggcaa caattaatag actggatgga ggcggataaa gttgcaggac cacttctgcg   8640
ctcggccctt ccggctggct ggtttattgc tgataaatct ggagccggtg agcgtgggtc   8700
tcgcggtatc attgcagcac tggggccaga tggtaagccc tcccgtatcg tagttatcta   8760
cacgacgggg agtcaggcaa ctatggatga acgaaataga cagatcgctg agataggtgc   8820
ctcactgatt aagcattggt aactgtcaga ccaagtttac tcatatatac tttagattga   8880 tttaaaacttt cattttttaat ttaaaaggat ctaggtgaag atccttttttg ataatctcat   8940 gaccaaaatc ccttaacgtg agttttcgtt ccactgagcg tcagaccccg tagaaaagat   9000
caaaggatct tcttgagatc cttttttttct gcgcgtaatc tgctgcttgc aaacaaaaaa   9060
accaccgcta ccagcggtgg tttgtttgcc ggatcaagag ctaccaactc tttttccgaa   9120
ggtaactggc ttcagcagag cgcagatacc aaatactgtt cttctagtgt agccgtagtt   9180
aggccaccac ttcaagaact ctgtagcacc gcctacatac ctcgctctgc taatcctgtt   9240
accagtggct gctgccagtg gcgataagtc gtgtcttacc gggttggact caagacgata   9300
gttaccggat aaggcgcagc ggtcgggctg aacggggggt tcgtgcacac agcccagctt   9360
ggagcgaacg acctacaccg aactgagata cctacagcgt gagctatgag aaagcgccac   9420
gcttcccgaa gagagaaagg cggacaggta tccggtaagc ggcagggtcg gaacaggaga   9480
gcgcacgagg gagcttccag ggggaaacgc ctggtatctt tatagtcctg tcgggtttcg   9540
ccacctctga cttgagcgtc gatttttgtg atgctcgtca gggggggcgga gcctatggaa   9600 aaacgccagc aacgcggcct ttttacggtt cctggccttt tgctggcctt tgctcacat    9660 gttctttcct gcgttatccc ctgattctgt ggataaccgt attaccgcct ttgagtgagc   9720
tgataccgct cgccgcagcc gaacgaccga gcgcagcgag tcagtgagcg aggaagcgga   9780
```

```
agagcgccca atacgcaaac cgcctctccc cgcgcgttgg ccgattcatt aatgcagctg   9840
gcacgacagg tttcccgact ggaaagcggg cagtgagcgc aacgcaatta atgtgagtta   9900
gctcactcat taggcacccc aggctttaca ctttatgctt ccggctcgta tgttgtgtgg   9960
aattgtgagc ggataacaat ttcacacagg aaacagctat gaccatgatt acgccaagcg  10020
cgcaattaac cctcactaaa gggaacaaaa gctggagctg caagctt              10067
```

<210> SEQ ID NO 54
<211> LENGTH: 24
<212> TYPE: PRT
<213> ORGANISM: Artificial Sequence
<220> FEATURE:
<223> OTHER INFORMATION: Description of Artificial Sequence: Synthetic
      L1 light chain leader sequence

<400> SEQUENCE: 54

Met Ala Thr Asp Met Arg Val Pro Ala Gln Leu Leu Gly Leu Leu Leu
1               5                   10                  15

Leu Trp Leu Ser Gly Ala Arg Cys
            20

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      anti-biotin murine sequence vH with inserted Cys for
      inter-domain linkage

<400> SEQUENCE: 55

Gln Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30

Gly Val Asp Trp Val Arg Gln Pro Pro Gly Lys Cys Leu Glu Trp Leu
        35                  40                  45

Gly Val Ile Trp Gly Gly Gly Arg Thr Asn Tyr Asn Ser Gly Leu Met
    50                  55                  60

Ser Arg Leu Ser Ile Arg Lys Asp Asn Ser Lys Ser Gln Val Phe Leu
65                  70                  75                  80

Thr Met Asn Ser Leu Gln Thr Asp Asp Thr Ala Lys Tyr Tyr Cys Val
                85                  90                  95

Lys His Thr Asn Trp Asp Gly Phe Ala Tyr Trp Gly Gln Gly Thr
            100                 105                 110

Thr Val Thr Val Ser Ser
        115

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 56

Gly Gly Gly Gly Ser Gly Gly Gly Ser Gly Gly Gly Gly Ser
1               5                   10                  15

<210> SEQ ID NO 57

```
<211> LENGTH: 99
<212> TYPE: PRT
<213> ORGANISM: Artificial Sequence
<220> FEATURE:
<223> OTHER INFORMATION: Description of Artificial Sequence: Synthetic
      Light Chain Variable (human lambda variable) sequence

<400> SEQUENCE: 57

Gly Ser Pro Gly Gln Ser Val Ser Ile Ser Cys Ser Gly Ser Ser Ser
1               5                   10                  15

Asn Ile Gly Asn Asn Tyr Val Tyr Trp Tyr Gln His Leu Pro Gly Thr
            20                  25                  30

Ala Pro Lys Leu Leu Ile Tyr Ser Asp Thr Lys Arg Pro Ser Gly Val
        35                  40                  45

Pro Asp Arg Ile Ser Gly Ser Lys Ser Gly Thr Ser Ala Ser Leu Ala
50                  55                  60

Ile Ser Gly Leu Gln Ser Glu Asp Glu Ala Asp Tyr Tyr Cys Ala Ser
65                  70                  75                  80

Trp Asp Asp Ser Leu Asp Gly Pro Val Phe Gly Cys Gly Thr Lys Leu
                85                  90                  95

Thr Val Leu

<210> SEQ ID NO 58
<211> LENGTH: 61
<212> TYPE: PRT
<213> ORGANISM: Artificial Sequence
<220> FEATURE:
<223> OTHER INFORMATION: Description of Artificial Sequence: Synthetic
      IgG3 hinge for greater accessibility to FcyR sequence

<400> SEQUENCE: 58

Leu Lys Thr Pro Leu Gly Asp Thr Thr His Thr Cys Pro Arg Cys Pro
1               5                   10                  15

Glu Pro Lys Ser Cys Asp Thr Pro Pro Cys Pro Arg Cys Pro Glu
            20                  25                  30

Pro Lys Ser Cys Asp Thr Pro Pro Cys Pro Arg Cys Pro Glu Pro
        35                  40                  45

Lys Ser Cys Asp Thr Pro Pro Cys Pro Arg Cys Pro
50                  55                  60

<210> SEQ ID NO 59
<211> LENGTH: 283
<212> TYPE: PRT
<213> ORGANISM: Artificial Sequence
<220> FEATURE:
<223> OTHER INFORMATION: Description of Artificial Sequence: Synthetic
      IgG1 CH2, CH3 Tm and cytoplasmic tail (T256A) sequence

<400> SEQUENCE: 59

Leu Leu Gly Gly Pro Ser Val Phe Leu Phe Pro Pro Lys Pro Lys Asp
1               5                   10                  15

Thr Leu Met Ile Ser Arg Ala Pro Glu Val Thr Cys Val Val Val Asp
            20                  25                  30

Val Ser His Glu Asp Pro Glu Val Lys Phe Asn Trp Tyr Val Asp Gly
        35                  40                  45

Val Glu Val His Asn Ala Lys Thr Lys Pro Arg Glu Glu Gln Tyr Asn
50                  55                  60

Ser Thr Tyr Arg Val Val Ser Val Leu Thr Val Leu His Gln Asp Trp
65                  70                  75                  80

Leu Asn Gly Lys Glu Tyr Lys Cys Lys Val Ser Asn Lys Ala Leu Pro
```

```
                     85                  90                  95
Ala Pro Ile Glu Lys Thr Ile Ser Lys Ala Lys Gly Gln Pro Arg Glu
                100                 105                 110

Pro Gln Val Tyr Thr Leu Pro Pro Ser Arg Asp Glu Leu Thr Lys Asn
                115                 120                 125

Gln Val Ser Leu Thr Cys Leu Val Lys Gly Phe Tyr Pro Ser Asp Ile
            130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
                180                 185                 190

Ser Val Met His Glu Ala Leu His Asn His Tyr Thr Gln Lys Ser Leu
            195                 200                 205

Ser Leu Ser Pro Glu Leu Gln Leu Glu Glu Ser Cys Ala Glu Ala Gln
        210                 215                 220

Asp Gly Glu Leu Asp Gly Leu Trp Thr Thr Ile Thr Ile Phe Ile Thr
225                 230                 235                 240

Leu Phe Leu Leu Ser Val Cys Tyr Ser Ala Thr Val Thr Phe Phe Lys
                245                 250                 255

Val Lys Trp Ile Phe Ser Ser Val Asp Leu Lys Gln Thr Ile Ile
                260                 265                 270

Pro Asp Tyr Arg Asn Met Ile Gly Gln Gly Ala
            275                 280

<210> SEQ ID NO 60
<211> LENGTH: 598
<212> TYPE: PRT
<213> ORGANISM: Artificial Sequence
<220> FEATURE:
<223> OTHER INFORMATION: Description of Artificial Sequence: Synthetic
      scFv-anti-biotin-G3hinge-IgG1-Tm (598 ORF1) sequence

<400> SEQUENCE: 60

Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
                20                  25                  30

Pro Ser Gln Ser Leu Ser Ile Thr Cys Thr Val Ser Gly Phe Ser Leu
            35                  40                  45

Thr Ala Tyr Gly Val Asp Trp Val Arg Gln Pro Pro Gly Lys Cys Leu
        50                  55                  60

Glu Trp Leu Gly Val Ile Trp Gly Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
                100                 105                 110

Tyr Cys Val Lys His Thr Asn Trp Asp Gly Phe Ala Tyr Trp Gly
            115                 120                 125

Gln Gly Thr Thr Val Thr Val Ser Ser Gly Gly Gly Ser Gly Gly
        130                 135                 140

Gly Gly Ser Gly Gly Gly Ser Gly Ser Pro Gly Gln Ser Val Ser
145                 150                 155                 160
```

-continued

```
Ile Ser Cys Ser Gly Ser Ser Asn Ile Gly Asn Asn Tyr Val Tyr
            165                 170                 175

Trp Tyr Gln His Leu Pro Gly Thr Ala Pro Lys Leu Leu Ile Tyr Ser
        180                 185                 190

Asp Thr Lys Arg Pro Ser Gly Val Pro Asp Arg Ile Ser Gly Ser Lys
        195                 200                 205

Ser Gly Thr Ser Ala Ser Leu Ala Ile Ser Gly Leu Gln Ser Glu Asp
        210                 215                 220

Glu Ala Asp Tyr Tyr Cys Ala Ser Trp Asp Ser Leu Asp Gly Pro
225                 230                 235                 240

Val Phe Gly Cys Gly Thr Lys Leu Thr Val Leu Leu Lys Thr Pro Leu
            245                 250                 255

Gly Asp Thr Thr His Thr Cys Pro Arg Cys Pro Glu Pro Lys Ser Cys
            260                 265                 270

Asp Thr Pro Pro Pro Cys Pro Arg Cys Pro Glu Pro Lys Ser Cys Asp
            275                 280                 285

Thr Pro Pro Pro Cys Pro Arg Cys Pro Glu Pro Lys Ser Cys Asp Thr
            290                 295                 300

Pro Pro Pro Cys Pro Arg Cys Pro Ala Pro Glu Leu Leu Gly Gly Pro
305                 310                 315                 320

Ser Val Phe Leu Phe Pro Pro Lys Pro Lys Asp Thr Leu Met Ile Ser
            325                 330                 335

Arg Ala Pro Glu Val Thr Cys Val Val Val Asp Val Ser His Glu Asp
            340                 345                 350

Pro Glu Val Lys Phe Asn Trp Tyr Val Asp Gly Val Glu Val His Asn
            355                 360                 365

Ala Lys Thr Lys Pro Arg Glu Glu Gln Tyr Asn Ser Thr Tyr Arg Val
            370                 375                 380

Val Ser Val Leu Thr Val Leu His Gln Asp Trp Leu Asn Gly Lys Glu
385                 390                 395                 400

Tyr Lys Cys Lys Val Ser Asn Lys Ala Leu Pro Ala Pro Ile Glu Lys
            405                 410                 415

Thr Ile Ser Lys Ala Lys Gly Gln Pro Arg Glu Pro Gln Val Tyr Thr
            420                 425                 430

Leu Pro Pro Ser Arg Asp Glu Leu Thr Lys Asn Gln Val Ser Leu Thr
            435                 440                 445

Cys Leu Val Lys Gly Phe Tyr Pro Ser Asp Ile Ala Val Glu Trp Glu
            450                 455                 460

Ser Asn Gly Gln Pro Glu Asn Asn Tyr Lys Thr Thr Pro Pro Val Leu
465                 470                 475                 480

Asp Ser Asp Gly Ser Phe Phe Leu Tyr Ser Lys Leu Thr Val Asp Lys
            485                 490                 495

Ser Arg Trp Gln Gln Gly Asn Val Phe Ser Cys Ser Val Met His Glu
            500                 505                 510

Ala Leu His Asn His Tyr Thr Gln Lys Ser Leu Ser Leu Ser Pro Glu
            515                 520                 525

Leu Gln Leu Glu Glu Ser Cys Ala Glu Ala Gln Asp Gly Glu Leu Asp
            530                 535                 540

Gly Leu Trp Thr Thr Ile Thr Ile Phe Ile Thr Leu Phe Leu Leu Ser
545                 550                 555                 560

Val Cys Tyr Ser Ala Thr Val Thr Phe Phe Lys Val Lys Trp Ile Phe
            565                 570                 575

Ser Ser Val Val Asp Leu Lys Gln Thr Ile Ile Pro Asp Tyr Arg Asn
```

```
                    580                 585                 590
Met Ile Gly Gln Gly Ala
        595

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      H7 heavy chain leader sequence

<400> SEQUENCE: 61

Met Glu Phe Gly Leu Ser Trp Val Phe Leu Val Ala Leu Phe Arg Gly
1               5                   10                  15

Val Gln Cys

<210> SEQ ID NO 62
<211> LENGTH: 118
<212> TYPE: PRT
<213> ORGANISM: Artificial Sequence
<220> FEATURE:
<223> OTHER INFORMATION: Description of Artificial Sequence: Synthetic
      anti-biotin vH sequence

<400> SEQUENCE: 62

Gln Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30

Gly Val Asp Trp Val Arg Gln Pro Pro Gly Lys Gly Leu Glu Trp Leu
        35                  40                  45

Gly Val Ile Trp Gly Gly Gly Arg Thr Asn Tyr Asn Ser Gly Leu Met
    50                  55                  60

Ser Arg Leu Ser Ile Arg Lys Asp Asn Ser Lys Ser Gln Val Phe Leu
65                  70                  75                  80

Thr Met Asn Ser Leu Gln Thr Asp Asp Thr Ala Lys Tyr Tyr Cys Val
                85                  90                  95

Lys His Thr Asn Trp Asp Gly Phe Ala Tyr Trp Gly Gln Gly Thr
            100                 105                 110

Thr Val Thr Val Ser Ser
        115

<210> SEQ ID NO 63
<211> LENGTH: 94
<212> TYPE: PRT
<213> ORGANISM: Artificial Sequence
<220> FEATURE:
<223> OTHER INFORMATION: Description of Artificial Sequence: Synthetic
      CH1 sequence

<400> SEQUENCE: 63

Pro Ser Val Phe Pro Leu Ala Pro Ser Ser Lys Ser Thr Ser Gly Gly
1               5                   10                  15

Thr Ala Ala Leu Gly Cys Leu Val Lys Asp Tyr Phe Pro Glu Pro Val
            20                  25                  30

Thr Val Ser Trp Asn Ser Gly Ala Leu Thr Ser Gly Val His Thr Phe
        35                  40                  45

Pro Ala Val Leu Gln Ser Ser Gly Leu Tyr Ser Leu Ser Ser Val Val
    50                  55                  60
```

```
Thr Val Pro Ser Ser Ser Leu Gly Thr Gln Thr Tyr Ile Cys Asn Val
 65                  70                  75                  80

Asn His Lys Pro Ser Asn Thr Lys Val Asp Lys Lys Val Glu
                 85                  90
```

<210> SEQ ID NO 64
<211> LENGTH: 61
<212> TYPE: PRT
<213> ORGANISM: Artificial Sequence
<220> FEATURE:
<223> OTHER INFORMATION: Description of Artificial Sequence: Synthetic
      IgG3 hinge sequence

<400> SEQUENCE: 64

```
Leu Lys Thr Pro Leu Gly Asp Thr Thr His Thr Cys Pro Arg Cys Pro
 1               5                  10                  15

Glu Pro Lys Ser Cys Asp Thr Pro Pro Cys Pro Arg Cys Pro Glu
                 20                  25                  30

Pro Lys Ser Cys Asp Thr Pro Pro Cys Pro Arg Cys Pro Glu Pro
             35                  40                  45

Lys Ser Cys Asp Thr Pro Pro Pro Cys Pro Arg Cys Pro
         50                  55                  60
```

<210> SEQ ID NO 65
<211> LENGTH: 286
<212> TYPE: PRT
<213> ORGANISM: Artificial Sequence
<220> FEATURE:
<223> OTHER INFORMATION: Description of Artificial Sequence: Synthetic
      IgG1 CH2, CH3 Tm and cytoplasmic tail sequence

<400> SEQUENCE: 65

```
Ala Pro Glu Leu Leu Gly Gly Pro Ser Val Phe Leu Phe Pro Pro Lys
 1               5                  10                  15

Pro Lys Asp Thr Leu Met Ile Ser Arg Ala Pro Glu Val Thr Cys Val
                 20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205
```

```
Lys Ser Leu Ser Leu Ser Pro Glu Leu Gln Leu Glu Glu Ser Cys Ala
    210                 215                 220
Glu Ala Gln Asp Gly Glu Leu Asp Gly Leu Trp Thr Thr Ile Thr Ile
225                 230                 235                 240
Phe Ile Thr Leu Phe Leu Ser Val Cys Tyr Ser Ala Thr Val Thr
                245                 250                 255
Phe Phe Lys Val Lys Trp Ile Phe Ser Ser Val Val Asp Leu Lys Gln
                260                 265                 270
Thr Ile Ile Pro Asp Tyr Arg Asn Met Ile Gly Gln Gly Ala
                275                 280                 285

<210> SEQ ID NO 66
<211> LENGTH: 578
<212> TYPE: PRT
<213> ORGANISM: Artificial Sequence
<220> FEATURE:
<223> OTHER INFORMATION: Description of Artificial Sequence: Synthetic
      Summary (578 ORF2a) sequence

<400> SEQUENCE: 66

Met Glu Phe Gly Leu Ser Trp Val Phe Leu Val Ala Leu Phe Arg Gly
1               5                   10                  15
Val Gln Cys Gln Val Lys Leu Gln Glu Ser Gly Pro Gly Leu Val Ala
                20                  25                  30
Pro Ser Gln Ser Leu Ser Ile Thr Cys Thr Val Ser Gly Phe Ser Leu
            35                  40                  45
Thr Ala Tyr Gly Val Asp Trp Val Arg Gln Pro Pro Gly Lys Gly Leu
50                  55                  60
Glu Trp Leu Gly Val Ile Trp Gly Gly Gly Arg Thr Asn Tyr Asn Ser
65                  70                  75                  80
Gly Leu Met Ser Arg Leu Ser Ile Arg Lys Asp Asn Ser Lys Ser Gln
                85                  90                  95
Val Phe Leu Thr Met Asn Ser Leu Gln Thr Asp Asp Thr Ala Lys Tyr
                100                 105                 110
Tyr Cys Val Lys His Thr Asn Trp Asp Gly Gly Phe Ala Tyr Trp Gly
        115                 120                 125
Gln Gly Thr Thr Val Thr Val Ser Ser Pro Ser Val Phe Pro Leu Ala
    130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
                180                 185                 190
Gly Leu Tyr Ser Leu Ser Ser Val Val Thr Val Pro Ser Ser Ser Leu
        195                 200                 205
Gly Thr Gln Thr Tyr Ile Cys Asn Val Asn His Lys Pro Ser Asn Thr
    210                 215                 220
Lys Val Asp Lys Lys Val Glu Leu Lys Thr Pro Leu Gly Asp Thr Thr
225                 230                 235                 240
His Thr Cys Pro Arg Cys Pro Glu Pro Lys Ser Cys Asp Thr Pro Pro
                245                 250                 255
Pro Cys Pro Arg Cys Pro Glu Pro Lys Ser Cys Asp Thr Pro Pro Pro
                260                 265                 270
Cys Pro Arg Cys Pro Glu Pro Lys Ser Cys Asp Thr Pro Pro Pro Cys
        275                 280                 285
```

```
Pro Arg Cys Pro Ala Pro Glu Leu Leu Gly Pro Ser Val Phe Leu
    290                 295                 300

Phe Pro Pro Lys Pro Lys Asp Thr Leu Met Ile Ser Arg Ala Pro Glu
305                 310                 315                 320

Val Thr Cys Val Val Val Asp Val Ser His Glu Asp Pro Glu Val Lys
                325                 330                 335

Phe Asn Trp Tyr Val Asp Gly Val Glu Val His Asn Ala Lys Thr Lys
                340                 345                 350

Pro Arg Glu Glu Gln Tyr Asn Ser Thr Tyr Arg Val Val Ser Val Leu
            355                 360                 365

Thr Val Leu His Gln Asp Trp Leu Asn Gly Lys Glu Tyr Lys Cys Lys
        370                 375                 380

Val Ser Asn Lys Ala Leu Pro Ala Pro Ile Glu Lys Thr Ile Ser Lys
385                 390                 395                 400

Ala Lys Gly Gln Pro Arg Glu Pro Gln Val Tyr Thr Leu Pro Pro Ser
                405                 410                 415

Arg Asp Glu Leu Thr Lys Asn Gln Val Ser Leu Thr Cys Leu Val Lys
                420                 425                 430

Gly Phe Tyr Pro Ser Asp Ile Ala Val Glu Trp Glu Ser Asn Gly Gln
            435                 440                 445

Pro Glu Asn Asn Tyr Lys Thr Thr Pro Pro Val Leu Asp Ser Asp Gly
        450                 455                 460

Ser Phe Phe Leu Tyr Ser Lys Leu Thr Val Asp Lys Ser Arg Trp Gln
465                 470                 475                 480

Gln Gly Asn Val Phe Ser Cys Ser Val Met His Glu Ala Leu His Asn
                485                 490                 495

His Tyr Thr Gln Lys Ser Leu Ser Leu Ser Pro Glu Leu Gln Leu Glu
            500                 505                 510

Glu Ser Cys Ala Glu Ala Gln Asp Gly Glu Leu Asp Gly Leu Trp Thr
        515                 520                 525

Thr Ile Thr Ile Phe Ile Thr Leu Phe Leu Leu Ser Val Cys Tyr Ser
    530                 535                 540

Ala Thr Val Thr Phe Phe Lys Val Lys Trp Ile Phe Ser Ser Val Val
545                 550                 555                 560

Asp Leu Lys Gln Thr Ile Ile Pro Asp Tyr Arg Asn Met Ile Gly Gln
                565                 570                 575

Gly Ala

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ile Arg Glu Ser
1

<210> SEQ ID NO 68
<211> LENGTH: 24
<212> TYPE: PRT
<213> ORGANISM: Artificial Sequence
<220> FEATURE:
<223> OTHER INFORMATION: Description of Artificial Sequence: Synthetic
      L1 Signal sequence
```

<400> SEQUENCE: 68

Met Ala Thr Asp Met Arg Val Pro Ala Gln Leu Leu Gly Leu Leu
1               5                   10                  15

Leu Trp Leu Ser Gly Ala Arg Cys
                20

<210> SEQ ID NO 69
<211> LENGTH: 99
<212> TYPE: PRT
<213> ORGANISM: Artificial Sequence
<220> FEATURE:
<223> OTHER INFORMATION: Description of Artificial Sequence: Synthetic
      LC Variable sequence

<400> SEQUENCE: 69

Gly Ser Pro Gly Gln Ser Val Ser Ile Ser Cys Ser Gly Ser Ser
1               5                   10                  15

Asn Ile Gly Asn Asn Tyr Val Tyr Trp Tyr Gln His Leu Pro Gly Thr
                20                  25                  30

Ala Pro Lys Leu Leu Ile Tyr Ser Asp Thr Lys Arg Pro Ser Gly Val
            35                  40                  45

Pro Asp Arg Ile Ser Gly Ser Lys Ser Gly Thr Ser Ala Ser Leu Ala
50                  55                  60

Ile Ser Gly Leu Gln Ser Glu Asp Glu Ala Asp Tyr Tyr Cys Ala Ser
65                  70                  75                  80

Trp Asp Asp Ser Leu Asp Gly Pro Val Phe Gly Gly Gly Thr Lys Leu
                85                  90                  95

Thr Val Leu

<210> SEQ ID NO 70
<211> LENGTH: 106
<212> TYPE: PRT
<213> ORGANISM: Artificial Sequence
<220> FEATURE:
<223> OTHER INFORMATION: Description of Artificial Sequence: Synthetic
      LC Constant Region 1

<400> SEQUENCE: 70

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Gly Ser Pro
            35                  40                  45

Val Lys Ala Gly Val Glu Thr Thr Lys Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
                100                 105

<210> SEQ ID NO 71
<211> LENGTH: 229
<212> TYPE: PRT
<213> ORGANISM: Artificial Sequence
<220> FEATURE:
<223> OTHER INFORMATION: Description of Artificial Sequence: Synthetic Summary (229 ORF2b) sequence

<400> SEQUENCE: 71

Met Ala Thr Asp Met Arg Val Pro Ala Gln Leu Leu Gly Leu Leu Leu
1               5                   10                  15

Leu Trp Leu Ser Gly Ala Arg Cys Gly Ser Pro Gly Gln Ser Val Ser
            20                  25                  30

Ile Ser Cys Ser Gly Ser Ser Ser Asn Ile Gly Asn Asn Tyr Val Tyr
        35                  40                  45

Trp Tyr Gln His Leu Pro Gly Thr Ala Pro Lys Leu Leu Ile Tyr Ser
    50                  55                  60

Asp Thr Lys Arg Pro Ser Gly Val Pro Asp Arg Ile Ser Gly Ser Lys
65                  70                  75                  80

Ser Gly Thr Ser Ala Ser Leu Ala Ile Ser Gly Leu Gln Ser Glu Asp
                85                  90                  95

Glu Ala Asp Tyr Tyr Cys Ala Ser Trp Asp Asp Ser Leu Asp Gly Pro
            100                 105                 110

Val Phe Gly Gly Gly Thr Lys Leu Thr Val Leu Gly Gln Pro Lys Ala
        115                 120                 125

Asn Pro Thr Val Thr Leu Phe Pro Pro Ser Ser Glu Glu Leu Gln Ala
    130                 135                 140

Asn Lys Ala Thr Leu Val Cys Leu Ile Ser Asp Phe Tyr Pro Gly Ala
145                 150                 155                 160

Val Thr Val Ala Trp Lys Ala Asp Gly Ser Pro Val Lys Ala Gly Val
                165                 170                 175

Glu Thr Thr Lys Pro Ser Lys Gln Ser Asn Asn Lys Tyr Ala Ala Ser
            180                 185                 190

Ser Tyr Leu Ser Leu Thr Pro Glu Gln Trp Lys Ser His Arg Ser Tyr
        195                 200                 205

Ser Cys Gln Val Thr His Glu Gly Ser Thr Val Glu Lys Thr Val Ala
    210                 215                 220

Pro Thr Glu Cys Ser
225

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      GM-CSF signal sequence

<400> SEQUENCE: 72

Met Trp Leu Gln Ser Leu Leu Leu Leu Gly Thr Val Ala Cys Ser Ile
1               5                   10                  15

Ser

<210> SEQ ID NO 73
<211> LENGTH: 127
<212> TYPE: PRT
<213> ORGANISM: Artificial Sequence
<220> FEATURE:
<223> OTHER INFORMATION: Description of Artificial Sequence: Synthetic
      wild type GM-CSF sequence

<400> SEQUENCE: 73

Ala Pro Ala Arg Ser Pro Ser Pro Ser Thr Gln Pro Trp Glu His Val
1               5                   10                  15

```
Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Arg Glu Ser
1

<210> SEQ ID NO 75
<211> LENGTH: 26
<212> TYPE: PRT
<213> ORGANISM: Artificial Sequence
<220> FEATURE:
<223> OTHER INFORMATION: Description of Artificial Sequence: Synthetic
      FLT3L signal sequence

<400> SEQUENCE: 75

Met Ala Thr Val Leu Ala Pro Ala Trp Ser Pro Thr Thr Tyr Leu Leu
1               5                   10                  15

Leu Leu Leu Leu Leu Ser Ser Gly Leu Ser
            20                  25

<210> SEQ ID NO 76
<211> LENGTH: 210
<212> TYPE: PRT
<213> ORGANISM: Artificial Sequence
<220> FEATURE:
<223> OTHER INFORMATION: Description of Artificial Sequence: Synthetic
      FLT3L sequence

<400> SEQUENCE: 76

Gly Thr Gln Asp Cys Ser Phe Gln His Ser Pro Ile Ser Ser Asp Phe
1               5                   10                  15

Ala Val Lys Ile Arg Glu Leu Ser Asp Tyr Leu Leu Gln Asp Tyr Pro
            20                  25                  30

Val Thr Val Ala Ser Asn Leu Gln Asp Glu Glu Leu Cys Gly Gly Leu
        35                  40                  45

Trp Arg Leu Val Leu Ala Gln Arg Trp Met Glu Arg Leu Lys Thr Val
    50                  55                  60

Ala Gly Ser Lys Met Gln Gly Leu Leu Glu Arg Val Asn Thr Glu Ile
65                  70                  75                  80

His Phe Val Thr Lys Cys Ala Phe Gln Pro Pro Pro Ser Cys Leu Arg
```

```
                   85                  90                  95

Phe Val Gln Thr Asn Ile Ser Arg Leu Leu Gln Glu Thr Ser Glu Gln
                100                 105                 110

Leu Val Ala Leu Lys Pro Trp Ile Thr Arg Gln Asn Phe Ser Arg Cys
                115                 120                 125

Leu Glu Leu Gln Cys Gln Pro Asp Ser Ser Thr Leu Pro Pro Pro Trp
            130                 135                 140

Ser Pro Arg Pro Leu Glu Ala Thr Ala Pro Thr Ala Pro Gln Pro Pro
145                 150                 155                 160

Leu Leu Leu Leu Leu Leu Pro Val Gly Leu Leu Leu Leu Ala Ala
                165                 170                 175

Ala Trp Cys Leu His Trp Gln Arg Thr Arg Arg Thr Pro Arg Pro
                180                 185                 190

Gly Glu Gln Val Pro Pro Val Pro Ser Pro Gln Asp Leu Leu Leu Val
                195                 200                 205

Glu His
    210

<210> SEQ ID NO 77
<211> LENGTH: 144
<212> TYPE: PRT
<213> ORGANISM: Artificial Sequence
<220> FEATURE:
<223> OTHER INFORMATION: Description of Artificial Sequence: Synthetic
      Summary (144 ORF3a) sequence

<400> SEQUENCE: 77

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
        130                 135                 140

<210> SEQ ID NO 78
<211> LENGTH: 236
<212> TYPE: PRT
<213> ORGANISM: Artificial Sequence
<220> FEATURE:
<223> OTHER INFORMATION: Description of Artificial Sequence: Synthetic
      Summary (236 ORF3b) sequence

<400> SEQUENCE: 78

Met Ala Thr Val Leu Ala Pro Ala Trp Ser Pro Thr Thr Tyr Leu Leu
1               5                   10                  15

Leu Leu Leu Leu Leu Ser Ser Gly Leu Ser Gly Thr Gln Asp Cys Ser
```

```
            20                  25                  30
Phe Gln His Ser Pro Ile Ser Ser Asp Phe Ala Val Lys Ile Arg Glu
            35                  40                  45
Leu Ser Asp Tyr Leu Leu Gln Asp Tyr Pro Val Thr Val Ala Ser Asn
        50                  55                  60
Leu Gln Asp Glu Glu Leu Cys Gly Gly Leu Trp Arg Leu Val Leu Ala
65                  70                  75                  80
Gln Arg Trp Met Glu Arg Leu Lys Thr Val Ala Gly Ser Lys Met Gln
                85                  90                  95
Gly Leu Leu Glu Arg Val Asn Thr Glu Ile His Phe Val Thr Lys Cys
            100                 105                 110
Ala Phe Gln Pro Pro Ser Cys Leu Arg Phe Val Gln Thr Asn Ile
            115                 120                 125
Ser Arg Leu Leu Gln Glu Thr Ser Glu Gln Leu Val Ala Leu Lys Pro
        130                 135                 140
Trp Ile Thr Arg Gln Asn Phe Ser Arg Cys Leu Glu Leu Gln Cys Gln
145                 150                 155                 160
Pro Asp Ser Ser Thr Leu Pro Pro Pro Trp Ser Pro Arg Pro Leu Glu
                165                 170                 175
Ala Thr Ala Pro Thr Ala Pro Gln Pro Pro Leu Leu Leu Leu Leu Leu
            180                 185                 190
Leu Pro Val Gly Leu Leu Leu Ala Ala Ala Trp Cys Leu His Trp
        195                 200                 205
Gln Arg Thr Arg Arg Arg Thr Pro Arg Pro Gly Glu Gln Val Pro Pro
        210                 215                 220
Val Pro Ser Pro Gln Asp Leu Leu Leu Val Glu His
225                 230                 235

<210> SEQ ID NO 79
<211> LENGTH: 183
<212> TYPE: PRT
<213> ORGANISM: Artificial Sequence
<220> FEATURE:
<223> OTHER INFORMATION: Description of Artificial Sequence: Synthetic
      wild type FLT3L sequence with transmembrane deleted

<400> SEQUENCE: 79

Met Thr Val Leu Ala Pro Ala Trp Ser Pro Thr Thr Tyr Leu Leu Leu
1               5                   10                  15
Leu Leu Leu Leu Ser Ser Gly Leu Ser Gly Thr Gln Asp Cys Ser Phe
            20                  25                  30
Gln His Ser Pro Ile Ser Ser Asp Phe Ala Val Lys Ile Arg Glu Leu
            35                  40                  45
Ser Asp Tyr Leu Leu Gln Asp Tyr Pro Val Thr Val Ala Ser Asn Leu
        50                  55                  60
Gln Asp Glu Glu Leu Cys Gly Gly Leu Trp Arg Leu Val Leu Ala Gln
65                  70                  75                  80
Arg Trp Met Glu Arg Leu Lys Thr Val Ala Gly Ser Lys Met Gln Gly
                85                  90                  95
Leu Leu Glu Arg Val Asn Thr Glu Ile His Phe Val Thr Lys Cys Ala
            100                 105                 110
Phe Gln Pro Pro Pro Ser Cys Leu Arg Phe Val Gln Thr Asn Ile Ser
            115                 120                 125
Arg Leu Leu Gln Glu Thr Ser Glu Gln Leu Val Ala Leu Lys Pro Trp
        130                 135                 140
```

```
Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln
            180
```

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Ile Arg Glu Ser
1
```

<210> SEQ ID NO 81
<211> LENGTH: 26
<212> TYPE: PRT
<213> ORGANISM: Artificial Sequence
<220> FEATURE:
<223> OTHER INFORMATION: Description of Artificial Sequence: Synthetic
      FLT3L signal sequence

<400> SEQUENCE: 81

```
Met Ala Thr Val Leu Ala Pro Ala Trp Ser Pro Thr Thr Tyr Leu Leu
1               5                   10                  15

Leu Leu Leu Leu Leu Ser Ser Gly Leu Ser
            20                  25
```

<210> SEQ ID NO 82
<211> LENGTH: 127
<212> TYPE: PRT
<213> ORGANISM: Artificial Sequence
<220> FEATURE:
<223> OTHER INFORMATION: Description of Artificial Sequence: Synthetic
      wild type GM-CSF sequence

<400> SEQUENCE: 82

```
Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125
```

<210> SEQ ID NO 83
<211> LENGTH: 99
<212> TYPE: PRT

<213> ORGANISM: Artificial Sequence
<220> FEATURE:
<223> OTHER INFORMATION: Description of Artificial Sequence: Synthetic
      CD8alpha transmembrane and cytoplasmic domain

<400> SEQUENCE: 83

Pro Thr Thr Thr Pro Ala Pro Arg Pro Pro Thr Pro Ala Pro Thr Ile
1               5                   10                  15

Ala Ser Gln Pro Leu Ser Leu Arg Pro Glu Ala Cys Arg Pro Ala Ala
                20                  25                  30

Gly Gly Ala Val His Thr Arg Gly Leu Asp Phe Ala Cys Asp Ile Tyr
            35                  40                  45

Ile Trp Ala Pro Leu Ala Gly Thr Cys Gly Val Leu Leu Leu Ser Leu
50                  55                  60

Val Ile Thr Leu Tyr Cys Asn His Arg Asn Arg Arg Val Cys Lys
65                  70                  75                  80

Cys Pro Arg Pro Val Val Lys Ser Gly Asp Lys Pro Ser Leu Ser Ala
                85                  90                  95

Arg Tyr Val

<210> SEQ ID NO 84
<211> LENGTH: 183
<212> TYPE: PRT
<213> ORGANISM: Artificial Sequence
<220> FEATURE:
<223> OTHER INFORMATION: Description of Artificial Sequence: Synthetic
      Summary for CYAGEN (253 ORF4b) sequence

<400> SEQUENCE: 84

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
                20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln
            180

<210> SEQ ID NO 85
<211> LENGTH: 252
<212> TYPE: PRT
<213> ORGANISM: Artificial Sequence
<220> FEATURE:
<223> OTHER INFORMATION: Description of Artificial Sequence: Synthetic
      Summary for CYAGEN (253 ORF4b) sequence

<400> SEQUENCE: 85

Met Ala Thr Val Leu Ala Pro Ala Trp Ser Pro Thr Thr Tyr Leu Leu
1               5                   10                  15

Leu Leu Leu Leu Leu Ser Ser Gly Leu Ser Ala Pro Ala Arg Ser Pro
                20                  25                  30

Ser Pro Ser Thr Gln Pro Trp Glu His Val Asn Ala Ile Gln Glu Ala
            35                  40                  45

Arg Arg Leu Leu Asn Leu Ser Arg Asp Thr Ala Ala Glu Met Asn Glu
        50                  55                  60

Thr Val Glu Val Ile Ser Glu Met Phe Asp Leu Gln Glu Pro Thr Cys
65                  70                  75                  80

Leu Gln Thr Arg Leu Glu Leu Tyr Lys Gln Gly Leu Arg Gly Ser Leu
                85                  90                  95

Thr Lys Leu Lys Gly Pro Leu Thr Met Met Ala Ser His Tyr Lys Gln
            100                 105                 110

His Cys Pro Pro Thr Pro Glu Thr Ser Cys Ala Thr Gln Ile Ile Thr
        115                 120                 125

Phe Glu Ser Phe Lys Glu Asn Leu Lys Asp Phe Leu Leu Val Ile Pro
130                 135                 140

Phe Asp Cys Trp Glu Pro Val Gln Glu Pro Thr Thr Thr Pro Ala Pro
145                 150                 155                 160

Arg Pro Pro Thr Pro Ala Pro Thr Ile Ala Ser Gln Pro Leu Ser Leu
                165                 170                 175

Arg Pro Glu Ala Cys Arg Pro Ala Ala Gly Gly Ala Val His Thr Arg
            180                 185                 190

Gly Leu Asp Phe Ala Cys Asp Ile Tyr Ile Trp Ala Pro Leu Ala Gly
        195                 200                 205

Thr Cys Gly Val Leu Leu Leu Ser Leu Val Ile Thr Leu Tyr Cys Asn
        210                 215                 220

His Arg Asn Arg Arg Arg Val Cys Lys Cys Pro Arg Pro Val Val Lys
225                 230                 235                 240

Ser Gly Asp Lys Pro Ser Leu Ser Ala Arg Tyr Val
                245                 250

<210> SEQ ID NO 86
<211> LENGTH: 261
<212> TYPE: PRT
<213> ORGANISM: Artificial Sequence
<220> FEATURE:
<223> OTHER INFORMATION: Description of Artificial Sequence: Synthetic
      mCD40L sequence modified to stop cleavage

<400> SEQUENCE: 86

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

```
Leu Leu Asn Cys Glu Glu Ile Lys Ser Gln Phe Gly Phe Val Lys
                85                  90                  95

Asp Ile Met Leu Asn Lys Glu Thr Lys Lys Glu Asn Ser Phe Glu
            100                 105                 110

Met Pro Arg Gly Glu Glu Asp Ser Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
            210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
                260

<210> SEQ ID NO 87
<211> LENGTH: 261
<212> TYPE: PRT
<213> ORGANISM: Artificial Sequence
<220> FEATURE:
<223> OTHER INFORMATION: Description of Artificial Sequence: Synthetic
      Summary (261 ORF5) sequence

<400> SEQUENCE: 87

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Gly Phe Val Lys
                85                  90                  95

Asp Ile Met Leu Asn Lys Glu Thr Lys Lys Glu Asn Ser Phe Glu
            100                 105                 110

Met Pro Arg Gly Glu Glu Asp Ser Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
```

165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
                260

<210> SEQ ID NO 88
<211> LENGTH: 221
<212> TYPE: PRT
<213> ORGANISM: Artificial Sequence
<220> FEATURE:
<223> OTHER INFORMATION: Description of Artificial Sequence: Synthetic
      mTNFalpha sequence modified to stop cleavage

<400> SEQUENCE: 88

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Ala His Val
65                  70                  75                  80

Val Ala Asn Pro Gln Ala Glu Gly Gln Leu Gln Trp Leu Asn Arg Arg
                85                  90                  95

Ala Asn Ala Leu Leu Ala Asn Gly Val Glu Leu Arg Asp Asn Gln Leu
            100                 105                 110

Val Val Pro Ser Glu Gly Leu Tyr Leu Ile Tyr Ser Gln Val Leu Phe
        115                 120                 125

Lys Gly Gln Gly Cys Pro Ser Thr His Val Leu Leu Thr His Thr Ile
130                 135                 140

Ser Arg Ile Ala Val Ser Tyr Gln Thr Lys Val Asn Leu Leu Ser Ala
145                 150                 155                 160

Ile Lys Ser Pro Cys Gln Arg Glu Thr Pro Glu Gly Ala Glu Ala Lys
                165                 170                 175

Pro Trp Tyr Glu Pro Ile Tyr Leu Gly Gly Val Phe Gln Leu Glu Lys
            180                 185                 190

Gly Asp Arg Leu Ser Ala Glu Ile Asn Arg Pro Asp Tyr Leu Asp Phe
        195                 200                 205

Ala Glu Ser Gly Gln Val Tyr Phe Gly Ile Ile Ala Leu
        210                 215                 220

<210> SEQ ID NO 89
<211> LENGTH: 221
<212> TYPE: PRT
<213> ORGANISM: Artificial Sequence
<220> FEATURE:

<223> OTHER INFORMATION: Description of Artificial Sequence: Synthetic
      Summary (221 ORF6) sequence

<400> SEQUENCE: 89

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Ala His Val
65                  70                  75                  80

Val Ala Asn Pro Gln Ala Glu Gly Gln Leu Gln Trp Leu Asn Arg Arg
                85                  90                  95

Ala Asn Ala Leu Leu Ala Asn Gly Val Glu Leu Arg Asp Asn Gln Leu
            100                 105                 110

Val Val Pro Ser Glu Gly Leu Tyr Leu Ile Tyr Ser Gln Val Leu Phe
        115                 120                 125

Lys Gly Gln Gly Cys Pro Ser Thr His Val Leu Leu Thr His Thr Ile
    130                 135                 140

Ser Arg Ile Ala Val Ser Tyr Gln Thr Lys Val Asn Leu Leu Ser Ala
145                 150                 155                 160

Ile Lys Ser Pro Cys Gln Arg Glu Thr Pro Glu Gly Ala Glu Ala Lys
                165                 170                 175

Pro Trp Tyr Glu Pro Ile Tyr Leu Gly Gly Val Phe Gln Leu Glu Lys
            180                 185                 190

Gly Asp Arg Leu Ser Ala Glu Ile Asn Arg Pro Asp Tyr Leu Asp Phe
        195                 200                 205

Ala Glu Ser Gly Gln Val Tyr Phe Gly Ile Ile Ala Leu
    210                 215                 220

<210> SEQ ID NO 90
<211> LENGTH: 244
<212> TYPE: PRT
<213> ORGANISM: Artificial Sequence
<220> FEATURE:
<223> OTHER INFORMATION: Description of Artificial Sequence: Synthetic
      wild-type

<400> SEQUENCE: 90

Met Asp Pro Asn Arg Ile Ser Glu Asp Gly Thr His Cys Ile Tyr Arg
1               5                   10                  15

Ile Leu Arg Leu His Glu Asn Ala Asp Phe Gln Asp Thr Thr Leu Glu
            20                  25                  30

Ser Gln Asp Thr Lys Leu Ile Pro Asp Ser Cys Arg Arg Ile Lys Gln
        35                  40                  45

Ala Phe Gln Gly Ala Val Gln Lys Glu Leu Gln His Ile Val Gly Ser
    50                  55                  60

Gln His Ile Arg Ala Glu Lys Ala Met Val Asp Gly Ser Trp Leu Asp
65                  70                  75                  80

Leu Ala Lys Arg Ser Lys Leu Glu Ala Gln Pro Phe Ala His Leu Thr
                85                  90                  95

Ile Asn Ala Thr Asp Ile Pro Ser Gly Ser His Lys Val Ser Leu Ser
            100                 105                 110

```
Ser Trp Tyr His Asp Arg Gly Trp Ala Lys Ile Ser Asn Met Thr Phe
        115                 120                 125

Ser Asn Gly Lys Leu Ile Val Asn Gln Asp Gly Phe Tyr Tyr Leu Tyr
    130                 135                 140

Ala Asn Ile Cys Phe Arg His His Glu Thr Ser Gly Asp Leu Ala Thr
145                 150                 155                 160

Glu Tyr Leu Gln Leu Met Val Tyr Val Thr Lys Thr Ser Ile Lys Ile
                165                 170                 175

Pro Ser Ser His Thr Leu Met Lys Gly Gly Ser Thr Lys Tyr Trp Ser
            180                 185                 190

Gly Asn Ser Glu Phe His Phe Tyr Ser Ile Asn Val Gly Gly Phe Phe
        195                 200                 205

Lys Leu Arg Ser Gly Glu Glu Ile Ser Ile Glu Val Ser Asn Pro Ser
    210                 215                 220

Leu Leu Asp Pro Asp Gln Asp Ala Thr Tyr Phe Gly Ala Phe Lys Val
225                 230                 235                 240

Arg Asp Ile Asp

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ile Arg Glu Ser
1

<210> SEQ ID NO 92
<211> LENGTH: 26
<212> TYPE: PRT
<213> ORGANISM: Artificial Sequence
<220> FEATURE:
<223> OTHER INFORMATION: Description of Artificial Sequence: Synthetic
      FLT3L signal

<400> SEQUENCE: 92

Met Ala Thr Val Leu Ala Pro Ala Trp Ser Pro Thr Thr Tyr Leu Leu
1               5                   10                  15

Leu Leu Leu Leu Leu Ser Ser Gly Leu Ser
            20                  25

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      Linker

<400> SEQUENCE: 93

Gly Gly Gly Gly Ser
1               5

<210> SEQ ID NO 94
<211> LENGTH: 14
<212> TYPE: PRT
<213> ORGANISM: Artificial Sequence
<220> FEATURE:
<223> OTHER INFORMATION: Description of Artificial Sequence: Synthetic
      V5 epitope tag for flow detection
```

```
<400> SEQUENCE: 94

Gly Lys Pro Ile Pro Asn Pro Leu Leu Gly Leu Asp Ser Thr
1               5                   10

<210> SEQ ID NO 95
<211> LENGTH: 118
<212> TYPE: PRT
<213> ORGANISM: Artificial Sequence
<220> FEATURE:
<223> OTHER INFORMATION: Description of Artificial Sequence: Synthetic
      anti-biotin murine vH with inserted Cys for
      intralinkage

<400> SEQUENCE: 95

Gln Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30

Gly Val Asp Trp Val Arg Gln Pro Pro Gly Lys Cys Leu Glu Trp Leu
        35                  40                  45

Gly Val Ile Trp Gly Gly Gly Arg Thr Asn Tyr Asn Ser Gly Leu Met
    50                  55                  60

Ser Arg Leu Ser Ile Arg Lys Asp Asn Ser Lys Ser Gln Val Phe Leu
65                  70                  75                  80

Thr Met Asn Ser Leu Gln Thr Asp Asp Thr Ala Lys Tyr Tyr Cys Val
                85                  90                  95

Lys His Thr Asn Trp Asp Gly Gly Phe Ala Tyr Trp Gly Gln Gly Thr
            100                 105                 110

Thr Val Thr Val Ser Ser
        115

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      Linker

<400> SEQUENCE: 96

Gly Gly Gly Gly Ser Gly Gly Gly Gly Ser Gly Gly Gly Gly Ser
1               5                   10                  15

<210> SEQ ID NO 97
<211> LENGTH: 99
<212> TYPE: PRT
<213> ORGANISM: Artificial Sequence
<220> FEATURE:
<223> OTHER INFORMATION: Description of Artificial Sequence: Synthetic
      LC Variable sequence

<400> SEQUENCE: 97

Gly Ser Pro Gly Gln Ser Val Ser Ile Ser Cys Ser Gly Ser Ser Ser
1               5                   10                  15

Asn Ile Gly Asn Asn Tyr Val Tyr Trp Tyr Gln His Leu Pro Gly Thr
            20                  25                  30

Ala Pro Lys Leu Leu Ile Tyr Ser Asp Thr Lys Arg Pro Ser Gly Val
        35                  40                  45

Pro Asp Arg Ile Ser Gly Ser Lys Ser Gly Thr Ser Ala Ser Leu Ala
    50                  55                  60
```

```
Ile Ser Gly Leu Gln Ser Glu Asp Glu Ala Asp Tyr Tyr Cys Ala Ser
 65                  70                  75                  80

Trp Asp Asp Ser Leu Asp Gly Pro Val Phe Gly Cys Gly Thr Lys Leu
                 85                  90                  95

Thr Val Leu

<210> SEQ ID NO 98
<211> LENGTH: 99
<212> TYPE: PRT
<213> ORGANISM: Artificial Sequence
<220> FEATURE:
<223> OTHER INFORMATION: Description of Artificial Sequence: Synthetic
      CD8alpha transmembrane and cytoplasmic domain

<400> SEQUENCE: 98

Pro Thr Thr Thr Pro Ala Pro Arg Pro Pro Thr Pro Ala Pro Thr Ile
  1               5                  10                  15

Ala Ser Gln Pro Leu Ser Leu Arg Pro Glu Ala Cys Arg Pro Ala Ala
                 20                  25                  30

Gly Gly Ala Val His Thr Arg Gly Leu Asp Phe Ala Cys Asp Ile Tyr
             35                  40                  45

Ile Trp Ala Pro Leu Ala Gly Thr Cys Gly Val Leu Leu Leu Ser Leu
         50                  55                  60

Val Ile Thr Leu Tyr Cys Asn His Arg Asn Arg Arg Arg Val Cys Lys
 65                  70                  75                  80

Cys Pro Arg Pro Val Val Lys Ser Gly Asp Lys Pro Ser Leu Ser Ala
                 85                  90                  95

Arg Tyr Val

<210> SEQ ID NO 99
<211> LENGTH: 244
<212> TYPE: PRT
<213> ORGANISM: Artificial Sequence
<220> FEATURE:
<223> OTHER INFORMATION: Description of Artificial Sequence: Synthetic
      Summary (244 ORF7a) sequence

<400> SEQUENCE: 99

Met Asp Pro Asn Arg Ile Ser Glu Asp Gly Thr His Cys Ile Tyr Arg
  1               5                  10                  15

Ile Leu Arg Leu His Glu Asn Ala Asp Phe Gln Asp Thr Thr Leu Glu
                 20                  25                  30

Ser Gln Asp Thr Lys Leu Ile Pro Asp Ser Cys Arg Arg Ile Lys Gln
             35                  40                  45

Ala Phe Gln Gly Ala Val Gln Lys Glu Leu Gln His Ile Val Gly Ser
         50                  55                  60

Gln His Ile Arg Ala Glu Lys Ala Met Val Asp Gly Ser Trp Leu Asp
 65                  70                  75                  80

Leu Ala Lys Arg Ser Lys Leu Glu Ala Gln Pro Phe Ala His Leu Thr
                 85                  90                  95

Ile Asn Ala Thr Asp Ile Pro Ser Gly Ser His Lys Val Ser Leu Ser
                100                 105                 110

Ser Trp Tyr His Asp Arg Gly Trp Ala Lys Ile Ser Asn Met Thr Phe
            115                 120                 125

Ser Asn Gly Lys Leu Ile Val Asn Gln Asp Gly Phe Tyr Tyr Leu Tyr
        130                 135                 140

Ala Asn Ile Cys Phe Arg His His Glu Thr Ser Gly Asp Leu Ala Thr
145                 150                 155                 160
```

-continued

Glu Tyr Leu Gln Leu Met Val Tyr Val Thr Lys Thr Ser Ile Lys Ile
            165                 170                 175

Pro Ser Ser His Thr Leu Met Lys Gly Gly Ser Thr Lys Tyr Trp Ser
            180                 185                 190

Gly Asn Ser Glu Phe His Phe Tyr Ser Ile Asn Val Gly Gly Phe Phe
            195                 200                 205

Lys Leu Arg Ser Gly Glu Glu Ile Ser Ile Glu Val Ser Asn Pro Ser
        210                 215                 220

Leu Leu Asp Pro Asp Gln Asp Ala Thr Tyr Phe Gly Ala Phe Lys Val
225                 230                 235                 240

Arg Asp Ile Asp

<210> SEQ ID NO 100
<211> LENGTH: 381
<212> TYPE: PRT
<213> ORGANISM: Artificial Sequence
<220> FEATURE:
<223> OTHER INFORMATION: Description of Artificial Sequence: Synthetic
      Summary (381aa ORF7b) sequence

<400> SEQUENCE: 100

Met Ala Thr Val Leu Ala Pro Ala Trp Ser Pro Thr Thr Tyr Leu Leu
1               5                   10                  15

Leu Leu Leu Leu Leu Ser Ser Gly Leu Ser Gly Gly Gly Gly Ser Gly
            20                  25                  30

Lys Pro Ile Pro Asn Pro Leu Leu Gly Leu Asp Ser Thr Gly Gly Gly
            35                  40                  45

Gly Ser Gln Val Lys Leu Gln Glu Ser Gly Pro Gly Leu Val Ala Pro
        50                  55                  60

Ser Gln Ser Leu Ser Ile Thr Cys Thr Val Ser Gly Phe Ser Leu Thr
65                  70                  75                  80

Ala Tyr Gly Val Asp Trp Val Arg Gln Pro Pro Gly Lys Cys Leu Glu
                85                  90                  95

Trp Leu Gly Val Ile Trp Gly Gly Gly Arg Thr Asn Tyr Asn Ser Gly
            100                 105                 110

Leu Met Ser Arg Leu Ser Ile Arg Lys Asp Asn Ser Lys Ser Gln Val
            115                 120                 125

Phe Leu Thr Met Asn Ser Leu Gln Thr Asp Asp Thr Ala Lys Tyr Tyr
        130                 135                 140

Cys Val Lys His Thr Asn Trp Asp Gly Gly Phe Ala Tyr Trp Gly Gln
145                 150                 155                 160

Gly Thr Thr Val Thr Val Ser Ser Gly Gly Gly Gly Ser Gly Gly Gly
                165                 170                 175

Gly Ser Gly Gly Gly Gly Ser Gly Ser Pro Gly Gln Ser Val Ser Ile
            180                 185                 190

Ser Cys Ser Gly Ser Ser Ser Asn Ile Gly Asn Asn Tyr Val Tyr Trp
            195                 200                 205

Tyr Gln His Leu Pro Gly Thr Ala Pro Lys Leu Leu Ile Tyr Ser Asp
        210                 215                 220

Thr Lys Arg Pro Ser Gly Val Pro Asp Arg Ile Ser Gly Ser Lys Ser
225                 230                 235                 240

Gly Thr Ser Ala Ser Leu Ala Ile Ser Gly Leu Gln Ser Glu Asp Glu
                245                 250                 255

Ala Asp Tyr Tyr Cys Ala Ser Trp Asp Asp Ser Leu Asp Gly Pro Val
            260                 265                 270

```
Phe Gly Cys Gly Thr Lys Leu Thr Val Leu Pro Thr Thr Pro Ala
            275                 280                 285

Pro Arg Pro Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
            340                 345                 350

Asn His Arg Asn Arg Arg Val Cys Lys Cys Pro Arg Pro Val Val
            355                 360                 365

Lys Ser Gly Asp Lys Pro Ser Leu Ser Ala Arg Tyr Val
    370                 375                 380

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Met Gln Gly Val Asn Cys Thr Val Ser Ser
1               5                   10

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      CpG sequence

<400> SEQUENCE: 102
ggaaccgtat cggcgatatc ggttgggggg                                    30

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      CpG sequence

<400> SEQUENCE: 103
ggaaccgtat gcggcatatc ggttgggggg                                    30

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Val Arg Ser Ser Ser Arg Thr Pro Ser Asp Lys Pro
1               5                   10

<210> SEQ ID NO 105
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Met Tyr Pro Pro Pro Tyr
1               5

<210> SEQ ID NO 106
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Tyr Met Asn Met
1

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Pro Tyr Ala Pro
1

<210> SEQ ID NO 108
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160
```

```
Asp Asp Phe His Val Asn Gly Gly Glu Leu Ile Leu Ile His Gln Asn
                165                 170                 175

Pro Gly Glu Phe Cys Val Leu
            180
```

<210> SEQ ID NO 109
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
        50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
                100                 105                 110

Ala Ile Cys Ser Ser Thr Thr Ala Ser Arg His His Pro Thr Thr Leu
            115                 120                 125

Ala Val Gly Ile Cys Ser Pro Ala Ser Arg Ser Ile Ser Leu Leu Arg
        130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
                180                 185                 190

Pro
```

<210> SEQ ID NO 110
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
        50                  55                  60
```

Tyr Trp Gln Lys Glu Lys Met Val Leu Thr Met Ser Gly Asp
 65                  70                  75                  80

Met Asn Ile Trp Pro Glu Tyr Lys Asn Arg Thr Ile Phe Asp Ile Thr
                 85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 111
<211> LENGTH: 329
<212> TYPE: PRT
<213> ORGANISM: Homo sapiens

<400> SEQUENCE: 111

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
                20                  25                  30

Asn Glu Thr Ala Asp Leu Pro Cys Gln Phe Ala Asn Ser Gln Asn Gln
            35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

```
His Gly Tyr Pro Glu Pro Lys Lys Met Ser Val Leu Leu Arg Thr Lys
            165                 170                 175

Asn Ser Thr Ile Glu Tyr Asp Gly Val Met Gln Lys Ser Gln Asp Asn
            180                 185                 190

Val Thr Glu Leu Tyr Asp Val Ser Ile Ser Leu Ser Val Ser Phe Pro
            195                 200                 205

Asp Val Thr Ser Asn Met Thr Ile Phe Cys Ile Leu Glu Thr Asp Lys
            210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
            245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
            275                 280                 285

Arg Glu Glu Ser Glu Gln Thr Lys Lys Arg Glu Lys Ile His Ile Pro
            290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
            325
```

<210> SEQ ID NO 112
<211> LENGTH: 7917
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac cctttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggggaga     600 attagatcgc gatgggaaaa aattcggtta aggccagggg gaaagaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa agacaccaa ggaagcttta dacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
```

| | |
|---|---|
| acccaccaag gcaaagagaa gagtggtgca gagagaaaaa agagcagtgg gaataggagc | 1080 |
| tttgttcctt gggttcttgg gagcagcagg aagcactatg ggcgcagcgt caatgacgct | 1140 |
| gacggtacag gccagacaat tattgtctgg tatagtgcag cagcagaaca atttgctgag | 1200 |
| ggctattgag gcgcaacagc atctgttgca actcacagtc tggggcatca agcagctcca | 1260 |
| ggcaagaatc ctggctgtgg aaagatacct aaaggatcaa cagctcctgg ggatttgggg | 1320 |
| ttgctctgga aaactcattt gcaccactgc tgtgccttgg aatgctagtt ggagtaataa | 1380 |
| atctctggaa cagatttgga atcacacgac ctggatggag tgggacagag aaattaacaa | 1440 |
| ttacacaagc ttaatacact ccttaattga agaatcgcaa aaccagcaag aaaagaatga | 1500 |
| acaagaatta ttggaattag ataaatgggc aagtttgtgg aattggttta acataacaaa | 1560 |
| ttggctgtgg tatataaaat tattcataat gatagtagga ggcttggtag gtttaagaat | 1620 |
| agtttttgct gtactttcta tagtgaatag agttaggcag ggatattcac cattatcgtt | 1680 |
| tcagacccac ctcccaaccc cgaggggacc cgacaggccc gaaggaatag aagaagaagg | 1740 |
| tggagagaga gacagagaca gatccattcg attagtgaac ggatctcgac ggtatcgcta | 1800 |
| gcttttaaaa gaaaaggggg gattgggggg tacagtgcag gggaaagaat agtagacata | 1860 |
| atagcaacag acatacaaac taagaatta caaaacaaa ttacaaaaat tcaaaatttt | 1920 |
| actagtgatt atcggatcaa ctttgtatag aaaagttggg ctccggtgcc cgtcagtggg | 1980 |
| cagagcgcac atcgcccaca gtccccgaga agttgggggg aggggtcggc aattgaaccg | 2040 |
| gtgcctagag aaggtggcgc ggggtaaact gggaaagtga tgtcgtgtac tggctccgcc | 2100 |
| tttttcccga gggtgggga gaaccgtata taagtgcagt agtcgccgtg aacgttcttt | 2160 |
| ttcgcaacgg gtttgccgcc agaacacagg taagtgccgt gtgtggttcc cgcgggcctg | 2220 |
| gcctctttac gggttatggc ccttgcgtgc cttgaattac ttccacctgg ctgcagtacg | 2280 |
| tgattcttga tcccgagctt cgggttggaa gtgggtggga gagttcgagg ccttgcgctt | 2340 |
| aaggagcccc ttcgcctcgt gcttgagttg aggcctggcc tgggcgctgg ggccgccgcg | 2400 |
| tgcgaatctg gtggcacctt cgcgcctgtc tcgctgcttt cgataagtct ctagccattt | 2460 |
| aaaatttttg atgacctgct gcgacgcttt ttttctggca agatagtctt gtaaatgcgg | 2520 |
| gccaagatct gcacactggt atttcggttt ttggggccgc gggcggcgac ggggcccgtg | 2580 |
| cgtcccagcg cacatgttcg gcgaggcggg gcctgcgagc gcggccaccg agaatcggac | 2640 |
| gggggtagtc tcaagctggc cggcctgctc tggtgcctgg tctcgcgccg ccgtgtatcg | 2700 |
| ccccgccctg ggcggcaagg ctggcccggt cggcaccagt tgcgtgagcg aaagatggc | 2760 |
| cgcttcccgg ccctgctgca gggagctcaa aatggaggac gcggcgctcg ggagagcggg | 2820 |
| cgggtgagtc acccacacaa aggaaaaggg cctttccgtc ctcagccgtc gcttcatgtg | 2880 |
| actccacgga gtaccgggcg ccgtccaggc acctcgatta gttctcgagc ttttggagta | 2940 |
| cgtcgtcttt aggttggggg gaggggtttt atgcgatgga gtttccccac actgagtggg | 3000 |
| tggagactga agttaggcca gcttggcact tgatgtaatt ctccttggaa tttgcccttt | 3060 |
| ttgagtttgg atcttggttc attctcaagc ctcagacagt ggttcaaagt ttttttcttc | 3120 |
| catttcaggt gtcgtgacaa gtttgtacaa aaaagcaggc tgccaccatg gagagagtgc | 3180 |
| agccctgga ggagaacgtg ggcaacgccg ccagacccag attcgagaga aacaagctgc | 3240 |
| tgctggtggc cagcgtgatc cagggcctgg gcctgctgct gtgcttcacc tacatctgcc | 3300 |
| tgcacttcag cgccctgcag gtgagccaca gatacccag aatccagagc atcaaggtgc | 3360 |
| agttcaccga gtacaagaag gagaagggct tcatcctgac cagccagaag gaggacgaga | 3420 |

-continued

| | |
|---|---|
| tcatgaaggt gcagaacaac agcgtgatca tcaactgcga cggcttctac ctgatcagcc | 3480 |
| tgaagggcta cttcagccag gaggtgaaca tcagcctgca ctaccagaag gacgaggagc | 3540 |
| ccctgttcca gctgaagaag gtgagaagcg tgaacagcct gatggtggcc agcctgacct | 3600 |
| acaaggacaa ggtgtacctg aacgtgacca ccgacaacac cagcctggac gacttccacg | 3660 |
| tgaacggcgg cgagctgatc ctgatccacc agaaccccgg cgagttctgc gtgctgtaaa | 3720 |
| cccagctttc ttgtacaaag tggtgataat cgaattccga taatcaacct ctggattaca | 3780 |
| aaatttgtga agattgact ggtattctta actatgttgc tcctttacg ctatgtggat | 3840 |
| acgctgcttt aatgcctttg tatcatgcta ttgcttcccg tatggctttc attttctcct | 3900 |
| ccttgtataa atcctggttg ctgtctcttt atgaggagtt gtgcccgtt gtcaggcaac | 3960 |
| gtggcgtggt gtgcactgtg tttgctgacg caaccccac tggttgggc attgccacca | 4020 |
| cctgtcagct cctttccggg actttcgctt tcccctccc tattgccacg gcggaactca | 4080 |
| tcgccgcctg ccttgcccgc tgctggacag gggctcggct gttgggcact gacaattccg | 4140 |
| tggtgttgtc ggggaagctg acgtcctttc catggctgct cgcctgtgtt gccacctgga | 4200 |
| ttctgcgcgg gacgtccttc tgctacgtcc cttcggccct caatccagcg gaccttcctt | 4260 |
| cccgcggcct gctgccggct ctgcggcctc ttccgcgtct tcgccttcgc cctcagacga | 4320 |
| gtcggatctc cctttgggcc gcctcccgc atcgggaatt cccgcggttc gctttaagac | 4380 |
| caatgactta caaggcagct gtagatctta gccactttt aaaagaaaag gggggactgg | 4440 |
| aagggctaat tcactcccaa cgaagacaag atctgctttt tgcttgtact gggtctctct | 4500 |
| ggttagacca gatctgagcc tgggagctct ctggctaact agggaaccca ctgcttaagc | 4560 |
| ctcaataaag cttgccttga gtgcttcaag tagtgtgtgc ccgtctgttg tgtgactctg | 4620 |
| gtaactagag atccctcaga cccttttagt cagtgtggaa aatctctagc agtagtagtt | 4680 |
| catgtcatct tattattcag tatttataac ttgcaaagaa atgaatatca gagagtgaga | 4740 |
| ggaacttgtt tattgcagct tataatggtt acaaataaag caatagcatc acaaatttca | 4800 |
| caaataaagc atttttttca ctgcattcta gttgtggttt gtccaaactc atcaatgtat | 4860 |
| cttatcatgt ctggctctag ctatcccgcc cctaactccg cccatcccgc ccctaactcc | 4920 |
| gcccagttcc gcccattctc cgccccatgg ctgactaatt tttttattt atgcagaggc | 4980 |
| cgaggccgcc tcggcctctg agctattcca gaagtagtga ggaggctttt ttggaggcct | 5040 |
| agggacgtac ccaattcgcc ctatagtgag tcgtattacg cgcgctcact ggccgtcgtt | 5100 |
| ttacaacgtc gtgactggga aaaccctggc gttacccaac ttaatcgcct tgcagcacat | 5160 |
| ccccctttcg ccagctggcg taatagcgaa gaggcccgca ccgatcgccc ttcccaacag | 5220 |
| ttgcgcagcc tgaatggcga atgggacgcg ccctgtagcg cgcattaag cgcggcgggt | 5280 |
| gtggtggtta cgcgcagcgt gaccgctaca cttgccagcg ccctagcgcc cgctcctttc | 5340 |
| gctttcttcc cttcctttct cgccacgttc gccggcttc cccgtcaagc tctaaatcgg | 5400 |
| gggctccctt tagggttccg atttagtgct ttacggcacc tcgaccccaa aaaacttgat | 5460 |
| tagggtgatg gttcacgtag tgggccatcg ccctgataga cggttttcg ccctttgacg | 5520 |
| ttggagtcca cgttctttaa tagtggactc ttgttccaaa ctggaacaac actcaaccct | 5580 |
| atctcggtct attcttttga tttataaggg attttgccga tttcggccta ttggttaaaa | 5640 |
| aatgagctga tttaacaaaa atttaacgcg aattttaaca aaatattaac gcttacaatt | 5700 |
| taggtggcac ttttcgggga aatgtgcgcg gaacccctat ttgtttattt ttctaaatac | 5760 |

```
attcaaatat gtatccgctc atgagacaat aaccctgata aatgcttcaa taatattgaa   5820
aaaggaagag tatgagtatt caacatttcc gtgtcgccct tattcccttt tttgcggcat   5880
tttgccttcc tgttttgct cacccagaaa cgctggtgaa agtaaaagat gctgaagatc    5940
agttgggtgc acgagtgggt tacatcgaac tggatctcaa cagcggtaag atccttgaga   6000
gttttcgccc cgaagaacgt tttccaatga tgagcacttt taaagttctg ctatgtggcg   6060
cggtattatc ccgtattgac gccgggcaag agcaactcgg tcgccgcata cactattctc   6120
agaatgactt ggttgagtac tcaccagtca cagaaaagca tcttacggat ggcatgacag   6180
taagagaatt atgcagtgct gccataacca tgagtgataa cactgcggcc aacttacttc   6240
tgacaacgat cggaggaccg aaggagctaa ccgcttttt gcacaacatg ggggatcatg     6300
taactcgcct tgatcgttgg gaaccggagc tgaatgaagc cataccaaac gacgagcgtg   6360
acaccacgat gcctgtagca atggcaacaa cgttgcgcaa actattaact ggcgaactac   6420
ttactctagc ttcccggcaa caattaatag actggatgga ggcggataaa gttgcaggac   6480
cacttctgcg ctcggccctt ccggctggct ggtttattgc tgataaatct ggagccggtg   6540
agcgtgggtc tcgcggtatc attgcagcac tggggccaga tggtaagccc tcccgtatcg   6600
tagttatcta cacgacgggg agtcaggcaa ctatggatga acgaaataga cagatcgctg   6660
agataggtgc ctcactgatt aagcattggt aactgtcaga ccaagtttac tcatatatac   6720
tttagattga tttaaaactt cattttaat ttaaaaggat ctaggtgaag atcctttttg     6780
ataatctcat gaccaaaatc ccttaacgtg agttttcgtt ccactgagcg tcagaccccg   6840
tagaaaagat caaaggatct tcttgagatc ctttttttct gcgcgtaatc tgctgcttgc   6900
aaacaaaaaa accaccgcta ccagcggtgg tttgtttgcc ggatcaagag ctaccaactc   6960
ttttccgaa ggtaactggc ttcagcagag cgcagatacc aaatactgtt cttctagtgt     7020
agccgtagtt aggccaccac ttcaagaact ctgtagcacc gcctacatac ctcgctctgc   7080
taatcctgtt accagtggct gctgccagtg gcgataagtc gtgtcttacc gggttggact   7140
caagacgata gttaccggat aaggcgcagc ggtcgggctg aacggggggt tcgtgcacac   7200
agcccagctt ggagcgaacg acctacaccg aactgagata cctacagcgt gagctatgag   7260
aaagcgccac gcttcccgaa gagagaaagg cggacaggta tccggtaagc ggcagggtcg   7320
gaacaggaga gcgcacgagg gagcttccag ggggaaacgc ctggtatctt tatagtcctg   7380
tcgggtttcg ccacctctga cttgagcgtc gatttttgtg atgctcgtca gggggggcgga   7440
gcctatggaa aaacgccagc aacgcggcct ttttacggtt cctggccttt tgctggcctt   7500
ttgctcacat gttctttcct gcgttatccc ctgattctgt ggataaccgt attaccgcct   7560
ttgagtgagc tgataccgct cgccgcagcc gaacgaccga gcgcagcgag tcagtgagcg   7620
aggaagcgga agagcgccca atacgcaaac cgcctctccc cgcgcgttgg ccgattcatt   7680
aatgcagctg gcacgacagg tttcccgact ggaaagcggg cagtgagcgc aacgcaatta   7740
atgtgagtta gctcactcat taggcacccc aggctttaca ctttatgctt ccggctcgta   7800
tgttgtgtgg aattgtgagc ggataacaat ttcacacagg aaacagctat gaccatgatt   7860
acgccaagcg cgcaattaac cctcactaaa gggaacaaaa gctggagctg caagctt       7917
```

<210> SEQ ID NO 113
<211> LENGTH: 7947
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 113

| | | | | | |
|---|---|---|---|---|---|
| aatgtagtct | tatgcaatac | tcttgtagtc | ttgcaacatg | gtaacgatga | gttagcaaca | 60 |
| tgccttacaa | ggagagaaaa | agcaccgtgc | atgccgattg | gtggaagtaa | ggtggtacga | 120 |
| tcgtgcctta | ttaggaaggc | aacagacggg | tctgacatgg | attggacgaa | ccactgaatt | 180 |
| gccgcattgc | agagatattg | tatttaagtg | cctagctcga | tacataaacg | ggtctctctg | 240 |
| gttagaccag | atctgagcct | gggagctctc | tggctaacta | gggaacccac | tgcttaagcc | 300 |
| tcaataaagc | ttgccttgag | tgcttcaagt | agtgtgtgcc | cgtctgttgt | gtgactctgg | 360 |
| taactagaga | tccctcagac | ccttttagtc | agtgtggaaa | atctctagca | gtggcgcccg | 420 |
| aacagggact | tgaaagcgaa | agggaaacca | gaggagctct | ctcgacgcag | gactcggctt | 480 |
| gctgaagcgc | gcacggcaag | aggcgagggg | cggcgactgg | tgagtacgcc | aaaaattttg | 540 |
| actagcggag | gctagaagga | gagagatggg | tgcgagagcg | tcagtattaa | gcggggggaga | 600 |
| attagatcgc | gatgggaaaa | aattcggtta | aggccagggg | gaaagaaaaa | atataaatta | 660 |
| aaacatatag | tatgggcaag | cagggagcta | gaacgattcg | cagttaatcc | tggcctgtta | 720 |
| gaaacatcag | aaggctgtag | acaaatactg | ggacagctac | aaccatccct | tcagacagga | 780 |
| tcagaagaac | ttagatcatt | atataataca | gtagcaaccc | tctattgtgt | gcatcaaagg | 840 |
| atagagataa | aagacaccaa | ggaagcttta | gacaagatag | aggaagagca | aaacaaaagt | 900 |
| aagaccaccg | cacagcaagc | ggccgctgat | cttcagacct | ggaggaggag | atatgaggga | 960 |
| caattggaga | agtgaattat | ataaatataa | agtagtaaaa | attgaaccat | taggagtagc | 1020 |
| acccaccaag | gcaaagagaa | gagtggtgca | gagagaaaaa | agagcagtgg | gaataggagc | 1080 |
| tttgttcctt | gggttcttgg | gagcagcagg | aagcactatg | ggcgcagcgt | caatgacgct | 1140 |
| gacggtacag | gccagacaat | tattgtctgg | tatagtgcag | cagcagaaca | atttgctgag | 1200 |
| ggctattgag | gcgcaacagc | atctgttgca | actcacagtc | tggggcatca | agcagctcca | 1260 |
| ggcaagaatc | ctggctgtgg | aaagatacct | aaaggatcaa | cagctcctgg | ggatttgggg | 1320 |
| ttgctctgga | aaactcattt | gcaccactgc | tgtgccttgg | aatgctagtt | ggagtaataa | 1380 |
| atctctggaa | cagatttgga | atcacacgac | ctggatggag | tgggacagag | aaattaacaa | 1440 |
| ttacacaagc | ttaatacact | ccttaattga | agaatcgcaa | aaccagcaag | aaaagaatga | 1500 |
| acaagaatta | ttggaattag | ataaatgggc | aagtttgtgg | aattggttta | acataacaaa | 1560 |
| ttggctgtgg | tatataaaat | tattcataat | gatagtagga | ggcttggtag | gtttaagaat | 1620 |
| agttttgct | gtactttcta | tagtgaatag | agttaggcag | ggatattcac | cattatcgtt | 1680 |
| tcagacccac | ctcccaaccc | cgagggggacc | cgacaggccc | gaaggaatag | aagaagaagg | 1740 |
| tggagagaga | gacagagaca | gatccattcg | attagtgaac | ggatctcgac | ggtatcgcta | 1800 |
| gcttttaaaa | gaaaaggggg | gattgggggg | tacagtgcag | gggaagaat | agtagacata | 1860 |
| atagcaacag | acatacaaac | taagaatta | caaaacaaa | ttacaaaaat | tcaaaatttt | 1920 |
| actagtgatt | atcggatcaa | ctttgtatag | aaaagttggg | ctccggtgcc | cgtcagtggg | 1980 |
| cagagcgcac | atcgcccaca | gtccccgaga | agttgggggg | aggggtcggc | aattgaaccg | 2040 |
| gtgcctagag | aaggtggcgc | ggggtaaact | gggaaagtga | tgtcgtgtac | tggctccgcc | 2100 |
| tttttcccga | gggtggggga | gaaccgtata | taagtgcagt | agtcgccgtg | aacgttcttt | 2160 |
| ttcgcaacgg | gtttgccgcc | agaacacagg | taagtgccgt | gtgtggttcc | cgcgggcctg | 2220 |
| gcctctttac | gggttatggc | ccttgcgtgc | cttgaattac | ttccacctgg | ctgcagtacg | 2280 |

-continued

```
tgattcttga tcccgagctt cgggttggaa gtgggtggga gagttcgagg ccttgcgctt    2340
aaggagcccc ttcgcctcgt gcttgagttg aggcctggcc tgggcgctgg ggccgccgcg    2400
tgcgaatctg gtggcacctt cgcgcctgtc tcgctgcttt cgataagtct ctagccattt    2460
aaaattttg atgacctgct gcgacgcttt ttttctggca agatagtctt gtaaatgcgg    2520
gccaagatct gcacactggt atttcggttt ttggggccgc gggcggcgac ggggcccgtg    2580
cgtcccagcg cacatgttcg gcgaggcggg gcctgcgagc gcggccaccg agaatcggac    2640
ggggtagtc tcaagctggc cggcctgctc tggtgcctgg tctcgcgccg ccgtgtatcg    2700
ccccgccctg ggcggcaagg ctggcccggt cggcaccagt tgcgtgagcg gaaagatggc    2760
cgcttcccgg ccctgctgca gggagctcaa aatggaggac gcggcgctcg ggagagcggg    2820
cgggtgagtc acccacacaa aggaaaaggg cctttccgtc ctcagccgtc gcttcatgtg    2880
actccacgga gtaccgggcg ccgtccaggc acctcgatta gttctcgagc ttttggagta    2940
cgtcgtcttt aggttggggg gaggggtttt atgcgatgga gtttccccac actgagtggg    3000
tggagactga agttaggcca gcttggcact tgatgtaatt ctccttggaa tttgcccttt    3060
ttgagtttgg atcttggttc attctcaagc ctcagacagt ggttcaaagt ttttttcttc    3120
catttcaggt gtcgtgacaa gtttgtacaa aaaagcaggc tgccaccatg cccgaggagg    3180
gcagcggctg cagcgtgaga agaagaccct acggctgcgt gctgagagcc gccctggtgc    3240
ccctggtggc cggcctggtg atctgcctgg tggtgtgcat ccagagattc gcccaggccc    3300
agcagcagct gccccctggag agcctgggct gggacgtggc cgagctgcag ctgaaccaca    3360
ccggccccca gcaggacccc agactgtact ggcagggcgg ccccgccctg ggcagaagct    3420
tcctgcacgg ccccgagctg gacaagggcc agctgagaat ccacagagac ggcatctaca    3480
tggtgcacat ccaggtgacc ctggccatct gcagcagcac caccgccagc agacaccacc    3540
ccaccaccct ggccgtgggc atctgcagcc ccgccagcag aagcatcagc ctgctgagac    3600
tgagcttcca ccagggctgc accatcgcca gccagagact gaccccctg gccagaggcg    3660
acaccctgtg caccaacctg accggcaccc tgctgcccag cagaaacacc gacgagacct    3720
tcttcggcgt gcagtgggtg agaccctaaa cccagctttc ttgtacaaag tggtgataat    3780
cgaattccga taatcaacct ctggattaca aatttgtga agattgact ggtattctta    3840
actatgttgc tcctttacg ctatgtggat acgctgcttt aatgccttg tatcatgcta    3900
ttgcttcccg tatggctttc atttctcct ccttgtataa atcctggttg ctgtctcttt    3960
atgaggagtt gtgcccgtt gtcaggcaac gtggcgtggt gtgcactgtg tttgctgacg    4020
caaccccac tggttggggc attgccacca cctgtcagct ccttcccggg actttcgctt    4080
tccccctccc tattgccacg gcggaactca tcgccgcctg ccttgcccgc tgctggacag    4140
gggctcggct gttgggcact gacaattccg tggtgttgtc ggggaagctg acgtcctttc    4200
catggctgct cgcctgtgtt gccacctgga ttctgcgcgg gacgtccttc tgctacgtcc    4260
cttcggccct caatccagcg gaccttcctt cccgcggcct gctgccggct ctgcggcctc    4320
ttccgcgtct tcgccttcgc cctcagacga gtcggatctc cctttgggcc gcctccccgc    4380
atcgggaatt cccgcggttc gctttaagac caatgactta caaggcagct gtagatctta    4440
gccactttt aaagaaag ggggactgg aaggctaat tcactcccaa cgaagacaag    4500
atctgctttt tgcttgtact gggtctctct ggttagacca gatctgagcc tgggagctct    4560
ctggctaact agggaaccca ctgcttaagc ctcaataaag cttgccttga gtgcttcaag    4620
```

```
tagtgtgtgc cgtctgttg tgtgactctg gtaactagag atccctcaga ccctttagt    4680
cagtgtggaa aatctctagc agtagtagtt catgtcatct tattattcag tatttataac   4740
ttgcaaagaa atgaatatca gagagtgaga ggaacttgtt tattgcagct tataatggtt   4800
acaaataaag caatagcatc acaaatttca caaataaagc attttttca ctgcattcta    4860
gttgtggttt gtccaaactc atcaatgtat cttatcatgt ctggctctag ctatcccgcc   4920
cctaactccg cccatcccgc ccctaactcc gcccagttcc gcccattctc cgccccatgg   4980
ctgactaatt ttttttattt atgcagaggc cgaggccgcc tcggcctctg agctattcca   5040
gaagtagtga ggaggctttt ttggaggcct agggacgtac ccaattcgcc ctatagtgag   5100
tcgtattacg cgcgctcact ggccgtcgtt ttacaacgtc gtgactggga aaaccctggc   5160
gttacccaac ttaatcgcct tgcagcacat ccccctttcg ccagctggcg taatagcgaa   5220
gaggcccgca ccgatcgccc ttcccaacag ttgcgcagcc tgaatggcga atgggacgcg   5280
ccctgtagcg gcgcattaag cgcggcgggt gtggtggtta cgcgcagcgt gaccgctaca   5340
cttgccagcg ccctagcgcc cgctcctttc gctttcttcc cttcctttct cgccacgttc   5400
gccggctttc cccgtcaagc tctaaatcgg gggctccctt tagggttccg atttagtgct   5460
ttacggcacc tcgaccccaa aaaacttgat tagggtgatg gttcacgtag tgggccatcg   5520
ccctgataga cggttttcg cccttgacg ttggagtcca cgttctttaa tagtggactc    5580
ttgttccaaa ctggaacaac actcaaccct atctcggtct attctttga tttataaggg    5640
attttgccga tttcggccta ttggttaaaa aatgagctga tttaacaaaa atttaacgcg   5700
aattttaaca aaatattaac gcttacaatt taggtggcac ttttcgggga aatgtgcgcg   5760
gaacccctat ttgtttattt ttctaaatac attcaaatat gtatccgctc atgagacaat   5820
aaccctgata aatgcttcaa taatattgaa aaaggaagag tatgagtatt caacatttcc   5880
gtgtcgccct tattcccttt tttgcggcat tttgccttcc tgtttttgct cacccagaaa   5940
cgctggtgaa agtaaaagat gctgaagatc agttgggtgc acgagtgggt tacatcgaac   6000
tggatctcaa cagcggtaag atccttgaga gttttcgccc cgaagaacgt tttccaatga   6060
tgagcacttt taaagttctg ctatgtggcg cggtattatc ccgtattgac gccgggcaag   6120
agcaactcgg tcgccgcata cactattctc agaatgactt ggttgagtac tcaccagtca   6180
cagaaaagca tcttacggat ggcatgacag taagagaatt atgcagtgct gccataacca   6240
tgagtgataa cactgcggcc aacttacttc tgacaacgat cggaggaccg aaggagctaa   6300
ccgcttttt gcacaacatg ggggatcatg taactcgcct tgatcgttgg gaaccggagc    6360
tgaatgaagc cataccaaac gacgagcgtg acaccacgat gcctgtagca atggcaacaa   6420
cgttgcgcaa actattaact ggcgaactac ttactctagc ttcccggcaa caattaatag   6480
actggatgga ggcggataaa gttgcaggac cacttctgcg ctcggccctt ccggctggct   6540
ggtttattgc tgataaatct ggagccggtg agcgtgggtc tcgcggtatc attgcagcac   6600
tggggccaga tggtaagccc tcccgtatcg tagttatcta cacgacgggg agtcaggcaa   6660
ctatggatga acgaaataga cagatcgctg agataggtgc ctcactgatt aagcattggt   6720
aactgtcaga ccaagtttac tcatatatac tttagattga tttaaaactt catttttaat   6780
ttaaaaggat ctaggtgaag atccttttg ataatctcat gaccaaaatc ccttaacgtg    6840
agttttcgtt ccactgagcg tcagaccccg tagaaaagat caaaggatct tcttgagatc   6900
cttttttct gcgcgtaatc tgctgcttgc aaacaaaaaa accaccgcta ccagcggtgg    6960
tttgtttgcc ggatcaagag ctaccaactc tttttccgaa ggtaactggc ttcagcagag   7020
```

```
cgcagatacc aaatactgtt cttctagtgt agccgtagtt aggccaccac ttcaagaact    7080
ctgtagcacc gcctacatac ctcgctctgc taatcctgtt accagtggct gctgccagtg    7140
gcgataagtc gtgtcttacc gggttggact caagacgata gttaccggat aaggcgcagc    7200
ggtcgggctg aacgggggt tcgtgcacac agcccagctt ggagcgaacg acctacaccg    7260
aactgagata cctacagcgt gagctatgag aaagcgccac gcttcccgaa gagagaaagg    7320
cggacaggta tccggtaagc ggcagggtcg aacaggaga gcgcacgagg gagcttccag    7380
ggggaaacgc ctggtatctt tatagtcctg tcgggtttcg ccacctctga cttgagcgtc    7440 gattttgtg atgctcgtca ggggggcgga gcctatggaa aaacgccagc aacgcggcct    7500
ttttacggtt cctggccttt tgctggcctt ttgctcacat gttctttcct gcgttatccc    7560
ctgattctgt ggataaccgt attaccgcct ttgagtgagc tgataccgct cgccgcagcc    7620
gaacgaccga gcgcagcgag tcagtgagcg aggaagcgga gagcgccca atacgcaaac    7680 cgcctctccc cgcgcgttgg ccgattcatt aatgcagctg gcacgacagg tttcccgact    7740
ggaaagcggg cagtgagcgc aacgcaatta atgtgagtta gctcactcat taggcacccc    7800
aggctttaca ctttatgctt ccggctcgta tgttgtgtgg aattgtgagc ggataacaat    7860
ttcacacagg aaacagctat gaccatgatt acgccaagcg cgcaattaac cctcactaaa    7920
gggaacaaaa gctggagctg caagctt                                        7947

<210> SEQ ID NO 114
<211> LENGTH: 10051
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcgggggaga     600
attagatcgc gatgggaaaa aattcggtta aggccagggg gaagaaaaa atataaatta     660 aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg aataggagc    1080
```

```
tttgttcctt gggttcttgg gagcagcagg aagcactatg ggcgcagcgt caatgacgct   1140
gacggtacag gccagacaat tatttgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaagaatga    1500
acaagaatta ttggaattag ataaatgggc aagtttgtgg aattggttta acataacaaa   1560
ttggctgtgg tatataaaat tattcataat gatagtagga ggcttggtag gtttaagaat   1620
agttttgct gtactttcta tagtgaatag agttaggcag ggatattcac cattatcgtt    1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattgggggg tacagtgcag gggaagaat agtagacata    1860
atagcaacag acatacaaac taagaatta caaaaacaaa ttacaaaaat tcaaaatttt    1920
actagtatca actttgtata gaaaagttgg gctccggtgc ccgtcagtgg gcagagcgca   1980
catcgcccac agtccccgag aagttggggg gaggggtcgg caattgaacc ggtgcctaga   2040
gaaggtggcg cggggtaaac tgggaaagtg atgtcgtgta ctggctccgc ctttttcccg   2100
agggtggggg agaaccgtat ataagtgcag tagtcgccgt gaacgttctt tttcgcaacg   2160
ggtttgccgc cagaacacag gtaagtgccg tgtgtggttc ccgcgggcct ggcctcttta   2220
cgggttatgg cccttgcgtg ccttgaatta cttccacctg gctgcagtac gtgattcttg   2280
atcccgagct tcgggttgga agtgggtggg agagttcgag gccttgcgct taaggagccc   2340
cttcgcctcg tgcttgagtt gaggcctggc ctgggcgctg gggccgccgc gtgcgaatct   2400
ggtggcacct tcgcgcctgt ctcgctgctt tcgataagtc tctagccatt taaaatttt    2460
gatgacctgc tgcgacgctt ttttctggc aagatagtct tgtaaatgcg ggccaagatc    2520
tgcacactgg tatttcggtt tttggggccg cgggcggcga cggggcccgt gcgtcccagc   2580
gcacatgttc ggcgaggcgg ggcctgcgag cgcggccacc gagaatcgga cgggggtagt   2640
ctcaagctgg ccgggctgct ctggtgcctg gtctcgcgcc gccgtgtatc gccccgccct   2700
gggcggcaag gctggcccgg tcggcaccag ttgcgtgagc ggaaagatgg ccgcttcccg   2760
gccctgctgc agggagctca aaatggagga cgcggcgctc gggagagcgg gcgggtgagt   2820
cacccacaca aaggaaaagg gcctttccgt cctcagccgt cgcttcatgt gactccacgg   2880
agtaccgggc gccgtccagg cacctcgatt agttctcgag cttttggagt acgtcgtctt   2940
taggttgggg ggaggggttt tatgcgatgg agtttcccca cactgagtgg gtggagactg   3000
aagttaggcc agcttggcac ttgatgtaat tctccttgga atttgccctt tttgagtttg   3060
gatcttggtt cattctcaag cctcagacag tggttcaaag tttttttctt ccatttcagg   3120
tgtcgtgaca agtttgtaca aaaaagcagg ctgccaccat gggccacacc agaagacagg   3180
gcaccagccc cagcaagtgc ccctacctga acttcttcca gctgctggtg ctggccggcc   3240
tgagccactt ctgcagcggc gtgatccacg tgaccaagga ggtgaaggag gtggccaccc   3300
tgagctgcgg ccacaacgtg agcgtggagg agctggccca gaccagaatc tactggcaga   3360
aggagaagaa gatggtgctg accatgatga gcggcgacat gaacatctgg cccgagtaca   3420
```

```
agaacagaac catcttcgac atcaccaaca acctgagcat cgtgatcctg gccctgagac    3480
ccagcgacga gggcacctac gagtgcgtgg tgctgaagta cgagaaggac gccttcaaga    3540
gagagcacct ggccgaggtg accctgagcg tgaaggccga cttccccacc cccagcatca    3600
gcgacttcga gatccccacc agcaacatca gaagaatcat ctgcagcacc agcggcggct    3660
tccccgagcc ccacctgagc tggctggaga acggcgagga gctgaacgcc atcaacacca    3720
ccgtgagcca ggaccccgag accgagctgt acgccgtgag cagcaagctg gacttcaaca    3780
tgaccaccaa ccacagcttc atgtgcctga tcaagtacgg ccacctgaga gtgaaccaga    3840
ccttcaactg gaacaccacc aagcaggagc acttccccga caacctgctg cccagctggg    3900
ccatcaccct gatcagcgtg aacggcatct tcgtgatctg ctgcctgacc tactgcttcg    3960
cccccagatg cagagagaga agaagaaacg agagactgag aagagagagc gtgagacccg    4020
tgtaaataga tagaacaaca acaattgcat tcattttga tttcaggttc aggggggaggt    4080
gtgggaggtt ttttaaagca agtaaaacct ctacactgac ggtacgcgtt aacaacaaca    4140
attgcattca tttgtagttt caggttcagg gggaggtgtg ggaggttttt taaagcaagt    4200
taaacctcta aaatagtggt acgcgttacc cagctttctt gtacaaagtg gacccagctt    4260
tcttgtacaa agtgggcccc tctccctccc ccccccctaa cgttactggc cgaagccgct    4320
tggaataagg ccggtgtgcg tttgtctata tgttattttc caccatattg ccgtcttttg    4380
gcaatgtgag ggcccggaaa cctggccctg tcttcttgac gagcattcct aggggtcttt    4440
cccctctcgc caaaggaatg caaggtctgt tgaatgtcgt gaaggaagca gttcctctgg    4500
aagcttcttg aagacaaaca acgtctgtag cgacccttg caggcagcgg aacccccac     4560
ctggcgacag gtgcctctgc ggccaaaagc cacgtgtata agatacacct gcaaaggcgg    4620
cacaacccca gtgccacgtt gtgagttgga tagttgtgga aagagtcaaa tggctctcct    4680
caagcgtatt caacaagggg ctgaaggatg cccagaaggt acccccattgt atgggatctg    4740
atctggggcc tcggtgcaca tgctttacat gtgtttagtc gaggttaaaa aaacgtctag    4800
gccccccgaa ccacggggac gtggttttcc tttgaaaaac acgatgataa tatgggccaca   4860
accatggcca ccgtgctggc ccccgcctgg agccccacca cctacctgct gctgctgctg    4920
ctgctgagca gcggcctgag cgccccctg aagatccagg cctacttcaa cgagaccgcc    4980
gacctgccct gccagttcgc caacagccag aaccagagcc tgagcgagct ggtggtgttc    5040
tggcaggacc aggagaacct ggtgctgaac gaggtgtacc tgggcaagga gaagttcgac    5100
agcgtgcaca gcaagtacat gggcagaacc agcttcgaca cgacagctg gaccctgaga     5160
ctgcacaacc tgcagatcaa ggacaagggc ctgtaccagt gcatcatcca ccacaagaag    5220
cccaccggca tgatcagaat ccaccagatg aacagcgagc tgagcgtgct ggccaacttc    5280
agccagcccg agatcgtgcc catcagcaac atcaccgaga acgtgtacat caacctgacc    5340
tgcagcagca tccacggcta ccccgagccc aagaagatga gcgtgctgct gagaaccaag    5400
aacagcacca tcgagtacga cggcgtgatg cagaagagcc aggacaacgt gaccgagctg    5460
tacgacgtga gcatcagcct gagcgtgagc ttccccgacg tgaccagcaa catgaccatc    5520
ttctgcatcc tggagaccga caagaccaga ctgctgagca gccccttcag catcgagctg    5580
gaggaccccc agcccccccc cgaccacatc ccctggatca ccgccgtgct gcccaccgtg    5640
atcatctgcg tgatggtgtt ctgcctgatc ctgtggaagt ggaagaagaa gaagagaccc    5700
agaaacagct acagtgcgg caccaacacc atggagagag aggagagcga gcagaccaag    5760
aagagagaga agatccacat ccccgagaga agcgacgagg cccagagagt gttcaagagc    5820
```

```
agcaagacca gcagctgcga caagagcgac acctgcttct aacaacttta ttatacatag    5880
ttgatcaatt ccgataatca acctctggat tacaaaattt gtgaaagatt gactggtatt    5940
cttaactatg ttgctccttt tacgctatgt ggatacgctg ctttaatgcc tttgtatcat    6000
gctattgctt cccgtatggc tttcattttc tcctccttgt ataaatcctg gttgctgtct    6060
ctttatgagg agttgtggcc cgttgtcagg caacgtggcg tggtgtgcac tgtgtttgct    6120
gacgcaaccc ccactggttg gggcattgcc accacctgtc agctcctttc cgggactttc    6180
gctttccccc tccctattgc cacggcggaa ctcatcgccg cctgccttgc ccgctgctgg    6240 acagggctc ggctgttggg cactgacaat tccgtggtgt tgtcggggaa gctgacgtcc      6300
tttccatggc tgctcgcctg tgttgccacc tggattctgc gcgggacgtc cttctgctac    6360
gtcccttcgg ccctcaatcc agcggacctt ccttcccgcg gcctgctgcc ggctctgcgg    6420
cctcttccgc gtcttcgcct tcgccctcag acgagtcgga tctcccttg ggccgcctcc     6480 ccgcatcgga aattcccgcg gttcgcttta agaccaatga cttacaaggc agctgtagat    6540
cttagccact ttttaaaaga aaggggggga ctggaagggc taattcactc ccaacgaaga    6600
caagatctgc tttttgcttg tactgggtct ctctggttag accagatctg agcctgggag    6660
ctctctggct aactagggaa cccactgctt aagcctcaat aaagcttgcc ttgagtgctt    6720
caagtagtgt gtgcccgtct gttgtgtgac tctggtaact agagatccct cagacccttt    6780
tagtcagtgt ggaaaatctc tagcagtagt agttcatgtc atcttattat tcagtattta    6840
taacttgcaa agaaatgaat atcagagagt gagaggaact tgtttattgc agcttataat    6900
ggttacaaat aaagcaatag catcacaaat ttcacaaata aagcattttt ttcactgcat    6960
tctagttgtg gtttgtccaa actcatcaat gtatcttatc atgtctggct ctagctatcc    7020
cgcccctaac tccgcccatc ccgcccctaa ctccgcccag ttccgcccat tctccgcccc    7080
atggctgact aatttttttt atttatgcag aggccgaggc cgcctcggcc tctgagctat    7140
tccagaagta gtgaggaggc ttttttggag gcctagggac gtacccaatt cgccctatag    7200
tgagtcgtat tacgcgcgct cactggccgt cgttttacaa cgtcgtgact gggaaaaccc    7260
tggcgttacc caacttaatc gccttgcagc acatccccct ttcgccagct ggcgtaatag    7320
cgaagaggcc cgcaccgatc gcccttccca acagttgcgc agcctgaatg gcgaatggga    7380
cgcgccctgt agcggcgcat taagcgcggc gggtgtggtg gttacgcgca gcgtgaccgc    7440
tacacttgcc agcgccctag cgcccgctcc tttcgctttc ttcccttcct ttctcgccac    7500
gttcgccggc tttccccgtc aagctctaaa tcggggctc cctttagggt tccgatttag     7560
tgctttacgg cacctcgacc ccaaaaaact tgattagggt gatggttcac gtagtgggcc    7620
atcgccctga tagacggttt ttcgcccttt gacgttggag tccacgttct ttaatagtgg    7680
actcttgttc caaactggaa caacactcaa ccctatctcg gtctattctt ttgatttata    7740
agggattttg ccgatttcgg cctattggtt aaaaaatgag ctgatttaac aaaaatttaa    7800
cgcgaatttt aacaaaatat taacgcttac aatttaggtg cacttttcg gggaaatgtg     7860 cgcggaaccc ctatttgttt attttttctaa atacattcaa atatgtatcc gctcatgaga    7920
caataaccct gataaatgct tcaataatat tgaaaaagga agagtatgag tattcaacat    7980
ttccgtgtcg cccttattcc cttttttgcg cattttgcc ttcctgtttt tgctcaccca     8040
gaaacgctgg tgaaagtaaa agatgctgaa gatcagttgg gtgcacgagt gggttacatc    8100
gaactggatc tcaacagcgg taagatcctt gagagttttc gccccgaaga acgttttcca    8160
```

```
atgatgagca cttttaaagt tctgctatgt ggcgcggtat tatcccgtat tgacgccggg    8220
caagagcaac tcggtcgccg catacactat tctcagaatg acttggttga gtactcacca    8280
gtcacagaaa agcatcttac ggatggcatg acagtaagag aattatgcag tgctgccata    8340
accatgagtg ataacactgc ggccaactta cttctgacaa cgatcggagg accgaaggag    8400
ctaaccgctt ttttgcacaa catgggggat catgtaactc gccttgatcg ttgggaaccg    8460
gagctgaatg aagccatacc aaacgacgag cgtgacacca cgatgcctgt agcaatggca    8520
acaacgttgc gcaaactatt aactggcgaa ctacttactc tagcttcccg gcaacaatta    8580
atagactgga tggaggcgga taaagttgca ggaccacttc tgcgctcggc ccttccggct    8640
ggctggttta ttgctgataa atctggagcc ggtgagcgtg ggtctcgcgg tatcattgca    8700
gcactgggc cagatggtaa gccctcccgt atcgtagtta tctacacgac ggggagtcag    8760
gcaactatgg atgaacgaaa tagacagatc gctgagatag gtgcctcact gattaagcat    8820
tggtaactgt cagaccaagt ttactcatat atactttaga ttgatttaaa acttcatttt    8880
taatttaaaa ggatctaggt gaagatcctt tttgataatc tcatgaccaa aatcccttaa    8940
cgtgagtttt cgttccactg agcgtcagac cccgtagaaa agatcaaagg atcttcttga    9000
gatccttttt ttctgcgcgt aatctgctgc ttgcaaacaa aaaaaccacc gctaccagcg    9060
gtggtttgtt tgccggatca agagctacca actctttttc cgaaggtaac tggcttcagc    9120
agagcgcaga taccaaatac tgttcttcta gtgtagccgt agttaggcca ccacttcaag    9180
aactctgtag caccgcctac atacctcgct ctgctaatcc tgttaccagt ggctgctgcc    9240
agtggcgata agtcgtgtct taccgggttg gactcaagac gatagttacc ggataaggcg    9300
cagcggtcgg gctgaacggg gggttcgtgc acacagccca gcttggagcg aacgacctac    9360
accgaactga gatacctaca gcgtgagcta tgagaaagcg ccacgcttcc cgaagagaga    9420
aaggcggaca ggtatccggt aagcggcagg gtcggaacag gagagcgcac gagggagctt    9480
ccaggggaa acgcctggta tctttatagt cctgtcgggt ttcgccacct ctgacttgag    9540
cgtcgatttt tgtgatgctc gtcagggggg cggagcctat ggaaaaacgc cagcaacgcg    9600
gccttttttac ggttcctggc cttttgctgg ccttttgctc acatgttctt tcctgcgtta    9660
tcccctgatt ctgtggataa ccgtattacc gcctttgagt gagctgatac cgctcgccgc    9720
agccgaacga ccgagcgcag cgagtcagtg agcgaggaag cggaagagcg cccaatacgc    9780
aaaccgcctc tccccgcgcg ttggccgatt cattaatgca gctggcacga caggtttccc    9840
gactggaaag cgggcagtga gcgcaacgca attaatgtga gttagctcac tcattaggca    9900
ccccaggctt tacactttat gcttccggct cgtatgttgt gtggaattgt gagcggataa    9960
caatttcaca caggaaacag ctatgaccat gattacgcca agcgcgcaat taaccctcac    10020
taaagggaac aaaagctgga gctgcaagct t                                    10051
```